(12) United States Patent
Hoshino et al.

(10) Patent No.: US 10,941,420 B2
(45) Date of Patent: Mar. 9, 2021

(54) LINALOOL COMPOSITION AND METHOD OF PRODUCING THEREFOR

(71) Applicant: AJINOMOTO CO., INC., Tokyo (JP)

(72) Inventors: Yasushi Hoshino, Kanagawa (JP); Yoshiko Inoue, Kanagawa (JP); Mika Moriya, Kanagawa (JP); Akiko Matsudaira, Kanagawa (JP); Yosuke Nishio, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/927,573

(22) Filed: Mar. 21, 2018

(65) Prior Publication Data

US 2018/0291402 A1  Oct. 11, 2018

Related U.S. Application Data

(63) Continuation of application No. PCT/JP2016/078323, filed on Sep. 26, 2016.

(30) Foreign Application Priority Data

Sep. 25, 2015 (JP) .............................. JP2015-188597
Jun. 1, 2016 (JP) .............................. JP2016-110491
Jun. 1, 2016 (JP) .............................. JP2016-110492

(51) Int. Cl.
| | |
|---|---|
| *C12P 7/04* | (2006.01) |
| *C12N 15/74* | (2006.01) |
| *C12N 9/00* | (2006.01) |
| *C12N 15/09* | (2006.01) |

(52) U.S. Cl.
CPC ................. *C12P 7/04* (2013.01); *C12N 9/00* (2013.01); *C12N 15/09* (2013.01); *C12N 15/74* (2013.01); *C12N 2330/51* (2013.01); *C12Y 402/03025* (2013.01); *C12Y 402/03026* (2013.01)

(58) Field of Classification Search
None
See application file for complete search history.

(56) References Cited

U.S. PATENT DOCUMENTS

| 8,658,221 B2 | 2/2014 | Baeuerlein et al. |
| 10,067,130 B2 * | 9/2018 | Meng ................ G01N 33/56983 |
| 2008/0274523 A1 | 11/2008 | Renninger et al. |
| 2018/0291403 A1 * | 10/2018 | Hoshino .................. C12N 9/00 |

FOREIGN PATENT DOCUMENTS

| CN | 102071155 A | 5/2011 |
| JP | 05-170682 A | 7/1993 |
| JP | 09-000278 A | 1/1997 |
| JP | 2005-298580 A | 10/2005 |
| JP | 2006-291007 A | 10/2006 |
| JP | 2011-506713 A | 3/2011 |
| JP | 2011-147432 A | 8/2011 |
| JP | 2013-013406 A | 1/2013 |
| JP | 2013-063063 A | 4/2013 |
| JP | 2013-143944 A | 7/2013 |
| WO | WO2007/139924 A2 | 12/2007 |
| WO | WO2017/051930 A1 | 3/2017 |

OTHER PUBLICATIONS

Accession D12651 (May 12, 2009).*
Wolff et al. (Tetrahedron Letters 43 (2002) 2555-2559).*
Martin et al. (Nat Biotechnol. Jul. 2003;21(7):796-802. Epub Jun. 1, 2003).*
De Werra et al. (Applied & Environ. Microbiol., vol. 75, No. 12, 2009, pp. 4162-4174).*
Nakano, C., et al., "Identification and Characterization of the Linalool/Nerolidol Synthase from Streptomyces clavuligerus," ChemBioChem 2011;12:2403-2407.
Jia, J.-W., et al., "(3R)-Linalool Synthase from Artemisia annua L.: cDNA Isolation, Characterization, and Wound Induction," Arch. Biochem. Biophys. 1999;372(1):143-149.
Landmann, C., et al., "Cloning and functional characterization of three terpene synthases from lavender (Lavandula angustifolia)," Arch. Biochem. Biophys. 2007;465:417-429.
Crowell, A. L., et al., "Molecular cloning and characterization of a new linalool synthase," Arch. Biochem. Biophys. 2002;405:112-121.
Thanasomboon, R., et al., "Construction of synthetic *Escherichia coli* producing s-linalool," Procedia Comput. Sci. 2012;11:88-95.
Iijima, Y., et al., "The Biochemical and Molecular Basis for the Divergent Patterns in the Biosynthesis of Terpenes and Phenylpropenes in the Peltate Glands of Three Cultivars of Basil," Plant Physiol. 2004;136(3):3724-3736.
Dickschat, J. S., et al., "Volatiles Released by a *Streptomyces* Species Isolated from the North Sea," Chem. Biodivers. 2005;2(7):837-865.
Harada, H., et al., "Efficient synthesis of functional isoprenoids from acetoacetate through metabolic pathway-engineered *Escherichia coli*," Appl. Microbiol. Biotechnol. 2009;81:915-925.
Harada, H., et al., "Development of efficient functional analysis of plant terpene biosynthetic genes mainly of saquiterpene biosynthetic genes," NSJ—Review 2011;2:10-17.
Shimada, T., et al., "Characterization of three linalool synthase genes from Citrus unshiu Marc. and analysis of linalool-mediated resistance against *Xanthomonas citri* subsp. *citri* and *Penicilum italicum* in citrus leaves and fruits," Plant Sci. 2014;229:154-166.
Sugiura, M., et al., "Molecular Cloning and Characterization of a Linalool Synthase from Lemon Myrtle," Biosci. Biotechnol. Biochem. 2011;75(7):1245-1248.

(Continued)

*Primary Examiner* — Christian L Fronda
(74) *Attorney, Agent, or Firm* — Cermak Nakajima & McGowan LLP; Shelly Guest Cermak

(57) ABSTRACT

The present invention provides a composition containing linalool, wherein the composition contains a high amount of either enantiomer R-linalool or S-linalool, and has a high content rate of linalool. The present invention also provides a production method for producing the composition. The present invention further provides a composition containing volatile components including linalool, in which a content of linalool in a total content of the volatile components in the composition is 60% or more, and the linalool is present as R-linalool or S-linalool in an amount of 50% or more of the enantiomer, and a production method therefor.

11 Claims, 35 Drawing Sheets

Specification includes a Sequence Listing.

(56) References Cited

OTHER PUBLICATIONS

Carrasco, A., et al., "Lavandula angustifolia and Lavandula latifolia Essential Oils from Spain: Aromatic Profile and Bioactivities," Planta Med. 2016;82:163-170.

Eleni, M. et al., "High Quality Bergamot Oil from Greece: Chemical Analysis Using Chiral Gas Chromatography and Larvicidal Activity against the West Nile Virus," Molecules 2009;14(2):839-849.

Aprotosoaie, A. C., et al., "Linalool: a review on a key odorant molecule with valuable biological properties," Flavour Fragr. J. 2014;29:193-219.

Semikolenov, V. A., et al., "Linalool synthesis from alpha-pinene: kinetic peculiarities of catalytic steps," Appl. Catalysis A: General 2011;211:91-107.

Sun, M. X., et al., "Regulation of isoprenoid pathway for enhanced production of Linalool in *Saccharomyces cerevisiae*," Chinese J. Biotech. 2013;29(6):751-759.

Herrero, O., et al., "Engineering the *Saccharomyces cerevisiae* isoprenoid pathway for de novo production of aromatic monoterpenes in wine," Metabolic Eng. 2008;10:78-86.

Rico, J., et al., "Enhanced Production of a Plant Monoterpene by Overexpression of the 3-Hydroxy-3-Methylglutaryl Coenzyme A Reductase Catalytic Domain in *Saccharoomyces cerevisiae*," Appl. Environmen. Microbiol. 2010;76(19):6449-6454.

Barner, R., et al., "Stereochemical Correlations between (2R,4',8'R)-alpha-Tocopherol, (25S,26)-Dihydroxycholecalciferol, (-)-(1S,5R)-Frontalin and (-)-(R)-Linalol," Helv. Chin. Acta 1983;66(3):880-890.

Ohwa, M., et al., "An Asymmetric Synthesis of Enantiomerically Pure (S)-(+)-Linalool (3,7-Dimethyl-1,6-octadien-3-ol) and a Formal Synthesis of (R)-(-)-Linalool," J. Org. Chem. 1986;51:2599-2601.

Özek, T., et al., "Enantiomeric Distribution of Some Linalool Containing Essential Oils and Their Biological Activities," Rec. Nat. Proc. 2010;4:4:180-192.

International Search Report and Written Opinion for PCT Patent App. No. PCT/JP2016/078323 (dated Nov. 29, 2016) with English translation of the ISR.

Database UniProt [Online], Jul. 22, 2015, retrieved from EBI accession No. UNIPROT:D5SL78, 1 pg.

Siani, A. C., et al., "Linalool from Lippia alba: Study of the Reproducibility of the Essential Oil Profile and the Enantiomeric Purity," J. Agric. Food Chem. 2002;50(12):3518-3521.

Karuppiah, V., et al., "Structural Basis of Catalysis in the Bacterial Monoterpene Synthases Linalool Synthase and 1,8-Cineole Synthase," ACS Catalysis 2017;7(9):6268-6282.

Andreeva, I. G., et al., "Identification of Pantoea ananatis gene encoding membrane pyrroloquinoline quinone (PQQ)-dependent glucose dehydrogenase and pqqABCDEF operon essential for PQQ biosynthesis," FEMS Microbiol. Lett. 2011;318(1):55-60.

Supplementary Partial European Search Report from European Patent App. No. 16848717.1 (dated Feb. 20, 2019).

GenBank Accession No. DS570692.1, Streptomyces clavuligerus ATCC 27064 supercont1.69 genomic scaffold, whole genome shotgun sequence, 2008, pp. 1-12.

GenBank Accession No. AP012032.1, Pantoea ananatis AJ13355 DNA, complete genome, 2011, pp. 1-5.

\* cited by examiner

FIG.29

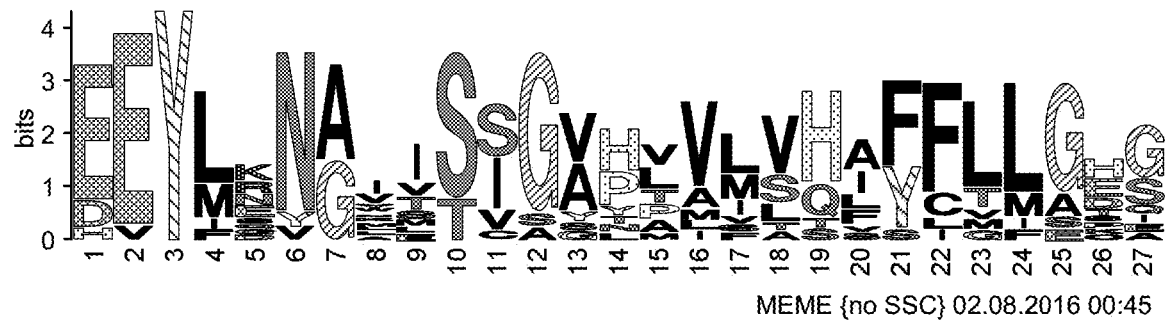

FIG.30

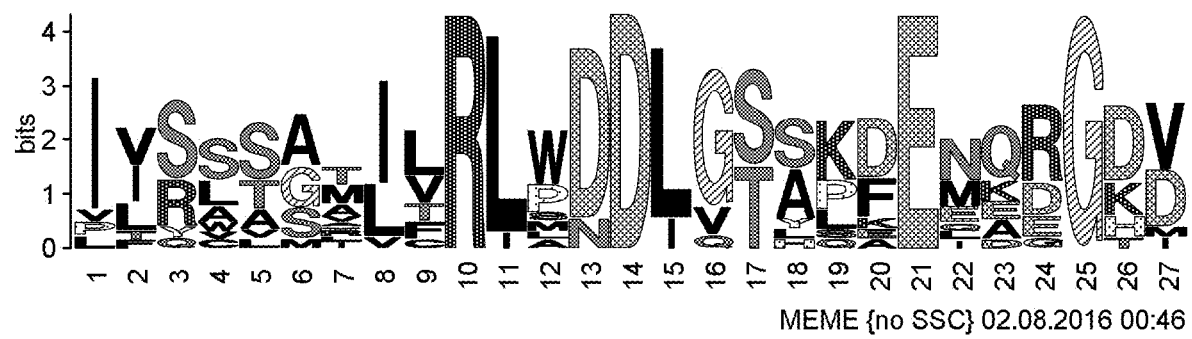

FIG.31

| | |
|---|---|
| M23 | YIDDIFDVYGTLDELILFTETITRWDLAAMGQLPEYMKIC |
| M29 | YIDDIFDVHGTLDELTLFTEAVNRWDIAAFETLPNYMKIC |
| M37 | YVIDDIFDTYGKMDELILFTDAIRRWDLEAMEGLPEYMKIC |
| M25 | YLIDDIFDVYGTLDELTLFTEVVNRWEIGSIEHLPDYMKIC |
| M27 | TSLDDVYDIYGTLDELQLFTDAIQRWDTESISRLPYYMQLF |
| M31 | TAIDDMYDIYGSPDELRRFTDAVNRWDTEALVDLPDYMKIC |
| M21 | YIIDDIFYVCGALDALTLFTEPINRWDLGDIDQLPEYMKIC |
| M17 | TTIDDIYDIYGTLEELQLFTVAFENWDINRLDELPEYMRLC |
| M15 | YVIDDIFDVYGELEELTIFTRVVERWDHKGLKTLPKYMRVC |
| M35 | TALDDVYDIYGTLDELQLFTHVIRRWDTESATQLPYYLQLF |
| M19 | SIIDDIYDAYGTIEELELFATAIERWDLSAIDLLPEYMKLC |
| M33 | TSLDDVYDIYGTLDELQLFTNLFERWDNASIGRLPEYLQLF |
| M39 | TVADDFFDVEGSMVDLEKLTDAVRRWDAEGLGSHSKTIFEA |

FIG.32

| | |
|---|---|
| M25 | DLHEVALRFRLLRQHGYFVSDDVFNNFKN |
| M27 | DLYFTALGFRLLRQHGFQVSQEVFDCFKN |
| M29 | DLYEVALRFRLLRQEGYHVPADVFNNFKN |
| M21 | DLQEVALRFRLLRQQGYYVSADVFNRFRN |
| M33 | DLYFTALGFRLFRQHGFKVSQEVFDRFKN |
| M35 | DLHFTSLGFRLLRQHGFNVSQGVFDCFKN |
| M23 | DLQEVALRFRLLRQEGYYVPADMFNNFRI |
| M31 | DLSTTALRFRLLRQHGYPVSSEVFDQFRS |
| M17 | DLHATALEFRLFRQHGFNVSEDVFDVFME |
| M19 | ELYYISLHFRLLRQNGYKISADVFNSFKD |
| M15 | DLHEIALRFRLLRQEGHYVQENKKGGFKD |
| M37 | DLFTAALRFRLLRHNGIQVTPEIFLKFKD |
| M39 | ELYRDSLAFWLLRVNNHWVSPSIFCWFLD |

FIG.33

| | |
|---|---|
| M23 | EIAKKDFNMVQALHQKEIVQVTKWWKDLGLTK |
| M29 | ELAKADFNMVQSIHQQELLQISKWWQDRGLAE |
| M17 | EFAKIDFNIVQAIHQEELKNVSSWWMETGLGK |
| M27 | ELAKLDFNIIQATQQEELKDLSRWWKSTCLAE |
| M33 | ELAKLNFNIVQATQQEELKALSRWWSSLGLAE |
| M25 | TVAKTDLNMVQSLHQKEVAQVSKWWKELGLCK |
| M37 | ELAILDYNQVQAQHQSELTEITRWWKQLGLVE |
| M35 | ELAKLDFNIIQATQQEELKDLSRWWNDSSLPQ |
| M21 | ELANMDFKLVQSLHQKEIVQISSWWRELGLAK |
| M31 | ELAKLDYNLVQSSYQTELKELTRWWTDLGFKE |
| M19 | TFAMLDFNILQKQHQEELRDIVRWWKNFDVPN |
| M15 | RVAEIDSIRLKSLTQGEMSQTFKWWTELGLEK |
| M39 | QLAVKNYTLRQLVYRDELAEVERWSKERGLCD |

FIG.34

| | |
|---|---|
| M21 | EEYLENGIVSSGVHLVLVHIFFLLGHG |
| M25 | EEYLKNGIISSGVNVVMVHIFFLLGEG |
| M29 | HEYLKNGVISSGVHVVLVHLFFLLGHG |
| M23 | EEYLRNGIESSGVHVALAHFFFLLGHG |
| M15 | EEYMKNGVVSSGVHLVMLHAYILLGEE |
| M37 | EEYIENGASTVGAYMVLVHLFFLIGEG |
| M31 | DEYLSNAWTSVGGPAAMVHAYFLMGCA |
| M33 | EEYFDNAFMTIGAPPVLSQAYFTLGSS |
| M27 | EEYLNNAYISIGATPVISQVFFTLATS |
| M35 | EEYLNYASITIGAPAVISQIYFMLAKS |
| M17 | EEYMQNARISISSPTIFVHFYCVFSDQ |
| M39 | DVYLGNAMTSIAAHTMVLTASCLLGPG |
| M19 | EEYMRVALLSCGYLLLSTSSFLGMEDI |

FIG.35

| | |
|---|---|
| M25 | IISSTAAILRLWDDLGSAKDENQDGDD |
| M29 | IISSTAAILRLWDDLGSAKDENQDGHD |
| M23 | IISSTATILRLWDDLGSAKDENQEGKD |
| M15 | IVSSAATILRLWDDLGSAKDENQDGTD |
| M27 | ILRLSGMLVRLPDDLGTSPFEMKRGDV |
| M35 | IIRLSGMLVRLPDDLGTLPFEMKRGDV |
| M21 | IVSSVATILRIWDDLGSAKDENQGGKD |
| M33 | ILRVSGMLVRLPDDLGTSSFEMERGDV |
| M19 | IVQASSIICRLMDDIVSHKFEQQRGHV |
| M37 | PFSAAGRIFRLWDDLGTSQEEEERGDM |
| M17 | VVRCSSSVFRLANDLVTSPDELARGDV |
| M31 | LLYWSSLITRLSDDLGTSLAEIARGDV |
| M39 | ITSLLMVLTRLLNDIQSYLKEEDEGKI |

FIG. 36

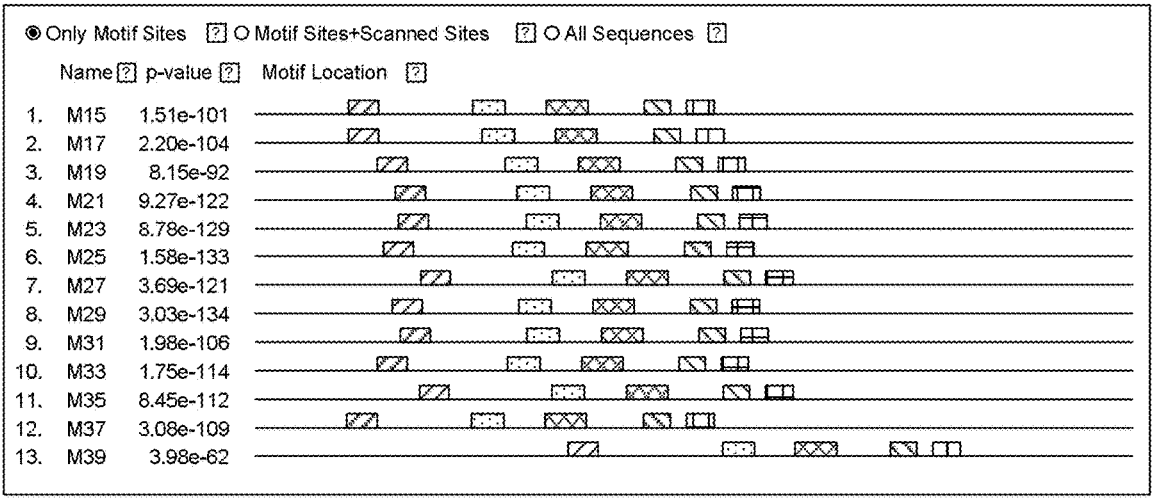

FIG. 37

>At1LINS_M15
MANTAKRSILRNVHASVSNPSKQFHNKTSLEYLHELNIKKIKNILSANVDVPSENLEMIDVIQSLGIDLHFRQEIEQTLH

MIYKEGLQFNGDLHEIALRFRLLRQEGHYVQENKKGGFKDVVKNDVKGLTELFEASELRVEGEETLDGAREFTYSRLNEL

CSGRESHQKQEIMKSLAQPRHKTVRGLTSKRFTSMIKIAGQEDPEWLQSLLRVAEIDSIRLKSLTQGEMSQTFKWWTELG

LEKDVEKARSQPLKWHTWSMKILQDPTLTEQRLDLTKPISLVYVIDDIFDVYGELEELTIFTRVVERWDHKGLKTLPKY

MRVCFEALDMITTEISMKIYKSHGWNPTYALRQSWASLCKAFLVEAKWFNSGYLPTTEEYMKNGVVSSGVHLVMLHAYIL

LGEELTKEKVELIESNPGIVSSAATILRLWDDLGSAKDENQDGTDGSYVECYLNEYKGSTVDEARTHVAQKISRAWKRLN

RECLNPCPFSRSFSKACLNIARTVPLMYSYDDDQRLPDEYLKSLM

FIG.38

>At2LINS_M17

MRRSANYQPSRWDHHHLLSVENKFAKDKRVRERDLLKEKVRKMLNDEQKTYLDQLEFIDDLQKLGVSYHFEAEIDNILTS
SYKKDRTNIQESDLHATALEFRLFRQHGFNVSEDVFDVFMENCGKFDRDDIYGLISLYEASYLSTKLDKNLQIFIRPFAT
QQLRDFVDTHSNEDFGSCDMVEIVVQALDMPYYWQMRRLSTRWYIDVYGKRQNYKNLVVVEFAKIDFNIVQAIHQEELKN
VSSWWMETGLGKQLYFARDRIVENYFWTIGQIQEPQYGYVRQTMTKINALLTTI<u>DDIYDIYG</u>TLEELQLFTVAFENWDI
NRLDELPEYMRLCFLVIYNEVNSIACEILRTKNINVIPFLKKSWTDVSKAYLVEAKWYKSGHKPNLEEYMQNARISISSP
TIFVHFYCVFSDQLSIQVLETLSQHQQNVVRCSSSVFRLANDLVTSPDELARGDVCKSIQCYMSETGASEDKARSHVRQM
INDLWDEMNYEKMAHSSSILHHDFMETVINLARMSQCMYQYGDGHGSPEKAKIVDRVMSLLFNPIPLD

FIG.39

>Cu1LINS_M19

MLFQVSASPNKVIRINAEKESTRRSANFDPTIWGDYFLSYTGDFKESGDASVKHQELKKEIRTMLRADINKPTQTKLDLI
DDIQRLGVSYHFESEIDEILRKMHEANQDCDLGDDENVQELYYISLHFRLLRQNGYKISADVFNSFKDSNGNFKSFLKRD
IRGMLSLYEAAHLRVHGENILNEALTFTVTHLESFTSQSNTQLAAQVNRALNRPIRKSLPRLEAKHYMPIYQKDPSHNKD
LLTFAMLDFNILQKQHQEELRDIVRWWKNFDVPNKLPFIRDRVVEGYFWILGVYFEPKFLLARKILTKVISMASII<u>DDI</u>
<u>YDAYG</u>TIEELELFATAIERWDLSAIDLLPEYMKLCYCALLDAYSEFEKDLASKGILYGLPFAKESMKILVRSYIIEARW
CDQQYVPTMEEYMRVALLSCGYLLLSTSSFLGMEDIVTKEAFEWVSGNPKIVQASSIICRLMDDIVSHKFEQQRGHVASA
VECYMKQHGVSEEEAVKVFREKVGNAWKDINEELMRPPVVPMPLLERVLNLARLMDVLYQNNDSYTNPHLMKDHVAALLK
DPVFFED*

FIG.40

>Cu2LINS_M21

MAFSSKDISSDSSHIHFIPKHISKVGNRNLNNINSLLPNNKKGSINDNIGVSARLKRFTYPSEHSSNFNDDIHIKHAKKL
EVIKHILIKLGDDDSFEGLAMIDVVQRLGIDYYFQDEIELILRRQYSIFFTDGDRYNDLQEVALRFRLLRQQGYYVSADV
FNRFRNKEGEFKQNISEDINGLMSLYEASQLSIGGEDGLDEAGHFSATHLANYDLAGVVEHLLLYPYRKSLSPAKNFFHG
NFQGSEYIWILDLQELANMDFKLVQSLHQKEIVQISSWWRELGLAKKLEFAREQPVKWYVWSMACFTDPNLSWQRIELTK
PISFVYII[DDIFYVCG]ALDALTLFTEPINRWDLGDIDQLPEYMKICFKALNDITNEISKQGVQRSMGITLCTPLRKGVG
EVLCNAFLIEAKWFASGHLPKAEEYLENGIVSSGVHLVLVHIFFLLGHGITNETVQLIDSNPPIVSSVATILRIWDDLGS
AKDENQGGKDGSYIYYYMMEHRDLTAEDAHKHAMDKISDAWKRLNKECLSPNPFSASFTRASFNCARMVPLMYSYDDSQR
LPSLEEYIKSSLFDNLPTQGVY

FIG.41

>Cu3LINS_M23

MAFSSSSRAKLSATSHISKAPDKISKTSRPSLIEFTPSPTIYQKGCITSDNTVASPPLKHFTHTTRHPSFFDHDIQVEHS
RKLKEFKHIFSLVGGNSFEGLVMIDAVQRLRIEYLFKDEIEEILQRQYIISSTCGGHLHDLQEVALRFRLLRQEGYYVPA
DMFNNFRIKEGRFSRINVSEDIGTLMEVYEASQLSIAGEEGLDEAGHFSAKMLNECMTHLDHYHALAIGNTLRHPYHKSL
PRFMAKDVFLSNFQGERRLHVLKEIAKKDFNMVQALHQKEIVQVTKWWKDLGLTKKLPFARDQPLKWYIWSMACLTDPSL
SEQRVELTKPISLIYII[DDIFDVYG]TLDELILFTETITRWDLAAMGQLPEYMKICFKALDDITNEISCKVYKKHGYNPV
QSLRNAWTSLCKAFLVEAKWFASGHMPEAEEYLRNGIESSGVHVALAHFFFLLGHGITKETVELIDGNPAISSTATILR
LWDDLGSAKDENQEGKDGSYIHYYMKEHRYSAAEEAQKSAINKISDAWKRLNKECLCPNPFSASFTRASLNLARMVPLMY
SYDDNQRLPSLEHYIKSLLFESVPTEGVY

FIG.42

>MdLINS_M25

MEFSISQSSFATSSSTPAAPEHLSSQKWSIPEDHSLLSTPLKPLNSKTKYTSSKDGIICFQNEQKLDDLRHALIKVGGEA

VESLDMIDAVQRLGLDYHFEEEIDQILQKQHIISSTTAHGAHHPTDLHEVALRFRLLRQHGYFVSDDVFNNFKNREGNFN

QMLREDIKGLMSLYEASQLSIEGEVVLEEAGKFSGHFLNSSLSHLDHHQARVVGNTLRNPHHKSLAPFMAKNFFVSSFQG

TNNRWLNILQTVAKTDLNMVQSLHQKEVAQVSKWWKELGLCKELKFARDQPIKWYIWSMACLTNPNLSDERIELTKPISF

IYLI[DDIFDVYG]TLDELTLFTEVVNRWEIGSIEHLPDYMKICFKALYDMTNEISCKVYQKHGWNPLHSLKKTWASLCNA

FLVEAKWFKSGHLPMAEEYLKNGIISSGVNVVMVHIFFLLGEGITNQSVEFLNGTPAIISSTAAILRLWDDLGSAKDENQ

DGDDGSYVKLYLNEHQGKTMEEAQEHVTNMISEEWKKLNKELVSPNPLPAAFTKASLNLARMVPLMYSYDDNQCLPSLDE

YMKSMLHA

FIG.43

>PfLINS_M27

MYSLRIYVAIMKKPSAKHVDNVDKKASKPSWRVSLSSSAGLRASSSLQLDVKKPADDEILTARRSGNYQPSLWDFNYLQS

LNTTQYKEVRHLKREAELIEQVKMLLEEEMEAVQQLELVDDLKNLGLSYFFEDQIKQILTFIYNEHKCFHSNSIIEAEEI

RDLYFTALGFRLLRQHGFQVSQEVFDCFKNEEGSDFKARLGDDTKGLLQLYEASFLLREGEDTLELARQYATKFLQKKVD

HELIDDNNLLSWILHSLEIPLHWRIQRLEARWFLDRYATRRDMNQIILELAKLDFNIIQATQQEELKDLSRWWKSTCLAE

KLPFVRDRLVESYFWAIALFEPHQYGYHRKVAAKIITLITSL[DDYYDIYG]TLDELQLFTDAIQRWDTESISRLPYYMQL

FYMVLYNFVSELAYDGLKEKGFITIPYLQRSWADLVEAYLKEAKWFYNGYVPSMEEYLNNAYISIGATPVISQVFFTLAT

SIDKPVIDSLYEYHRILRLSGMLVRLPDDLGTSPFEMKRGDVPKAIQLYMKERNATEIEAQEHVRFLIREAWKEMNTVTT

AADCPFTDDLVAATRNLGRAAQFMYLDGDGNHSQLHQRIACLLFEPYA

FIG.44

>Vv1LINS_M29

MGFSPAFYACSIPPVGPNKFTELGQSKFNNVVLVPTAQKWSIAHDHTLVYKPLRKHNHQSQHLSFTDEFYIKHAQRLDEI

RNVFSEVGEDTLEGLMMIDAIQRLGIDYHFKEEIEAVLQRQYMKASTHGESIQDLYEVALRFRLLRQEGYHVPADVFNNF

KNKEGKFKQNLSKDIKGLLALYEASQLSIEGEDILEEAQRFSSTLLNAGLEHLNHHEATVVGHTLEHPHHKSLPRFMAKS

FLKDFQGPNGWLTVLQELAKADFNMVQSIHQQELLQISKWWQDRGLAEELKFARDQPLKWHMWPMAVLPDPSLSEQRVEL

TKPISMIYII`DDIFDVHG`TLDELTLFTEAVNRWDIAAFETLPNYMKICFKTLDEITNEISNKVYKEHGWNPVDSLRKTW

VSLCNAFLVEAKWFASGHVPKAHEYLKNGVISSGVHVVLVHLFFLLGHGITRGNVDLVDDFPSIISSTAAILRLWDDLGS

AKDENQDGHDGSYIECYIKEHQGSSMENARQNVTYMISDLWKRLNKECLSQHPFSTSFTKGSLNIARMVPLMYSYDDNQS

LPHLEEHMKSLLFEAFPL

FIG.45

>Vv2LINS_M31

MELTLTSLSPLAYGALNCRKNFAMASPRMRIKQGRSELPNLTITSKIDELQVTERRSANYHPSIWDPKFIESLSTPYTNE

GYSNQLEDLKEEAKRVIKDARDTSSRLEFIDSMQRLGVAYHLEEEIKEAIDLVHLDDTTTDDLSTTALRFRLLRQHGYPV

SSEVFDQFRSKDGRFMDGISQDIAGPLSLYEASHLGVEGEDDLEEARRFSTIHLKSLVGNLESDLADQVQQSLEVPLHWR

MPRLEARNFIDIYQRRNTKNSALLELAKLDYNLVQSSYQTELKELTRWWTDLGFKEKLSFSRDRLMENYLWSMGIAPEPH

FSKSRIGLTKFICILTAI`DDMYDIYG`SPDELRRFTDAVNRWDTEALVDLPDYMKICYLAMFNFANEMAYDALRDHDLYI

LPYLKSQWLNLCTSYSMEAQWFYNGYKPSIDEYLSNAWTSVGGPAAMVHAYFLMGCATKGNLNNCLDNASNLLYWSSLIT

RLSDDLGTSLAEIARGDVAKSIQCYMIEKCISEEQARDQVEKLIRYSWKKLNEASTDSSLPKSLINSSLNMARSAQCIFQ

FGDGIGTSVGVTKDRLTSFIIKPILIEPSIKPYLDGMKMSNRR

FIG.46

>LaLINS_M33

MSININMPAAAVLRPFRCSQLHVDETRRSGNYRPSAWDSNYIQSLNSQYKEKKCLTRLEGLIEQVKELKGTKMEAVQQLE
LIDDSQNLGLSYYFQDKIKHILNLIYNDHKYFYDSEAEGMDLYFTALGFRLFRQHGFKVSQEVFDRFKNENGTYFKHDDT
KGLLQLYEASFLVREGEETLEQAREFATKSLQRKLDEDGDGIDANIESWIRHSLEIPLHWRAQRLEARWFLDAYARRPDM
NPVIFELAKLNFNIVQATQQEELKALSRWWSSLGLAEKLPFVRDRLVESYFWAIPLFEPHQYGYQRKVATKIITLITSL
DDVYDIYGTLDELQLFTNLFERWDNASIGRLPEYLQLFYPAIHNFVSEVAYDILKEKGFTSIVYLQRSWVDLLKGYLKE
AKWYNSGYTPSLEEYFDNAFMTIGAPPVLSQAYFTLGSSMEKPIIESMYEYDNILRVSGMLVRLPDDLGTSSFEMERGDV
PKSVQLYMKETNATEEEAVEHVRFLNREAWKKMNTAEAAGDSPLVSDVVAVAANLGRAAQFMYFDGDGNQSSLQQWIVSM
LFEPYA

FIG.47

>McLINS_M35

MCTIISVNHHHVAILSKPKVKLFHTKNKRSASINLPWSLSPSSSAASRPISCSISSKLYTISSAQEETRRSGNYHPSVWD
FDFIQSLDTDHYKEEKQLEREEELIMEVKKLLGAKMEATKQLELIDDLQNLGLSYFFRDEIKNILNSIYKIFQNNNSTKV
GDLHFTSLGFRLLRQHGFNVSQGVFDCFKNEHGSDFEKTLIGEDTKGVLQLYEASFLLREGEDTLEVARKFSTEFLEEKL
KAGIDGDNLSSSIGHSLEIPLHWRIQRLEERWFLDAYSRRKDMNPIIFELAKLDFNIIQATQQEELKDLSRWWNDSSLPQ
KLPFVRDRLVESYYWALGLFEAHKFGYERKTAAKIITLITALDDVYDIYGTLDELQLFTHVIRRWDTESATQLPYYLQL
FYFVLYNFVSEVAYHILKEEGFISIPFLHRAWVDLVEGYLQEAKWYYTKYTPTMEEYLNYASITIGAPAVISQIYFMLAK
SKEKPVIESFYEYDEIIRLSGMLVRLPDDLGTLPFEMKRGDVAKSIQIYMKEQNATREEAEEHVRFMIREAWKEMNTTMA
ANSDLRGDVVMAAANLGRDAQFMYLDGDGNHSQLQHRIANLLFKPYV

FIG.48

>ObLINS_M37

MASAVPLSSTPLINGDNSPLKNTHQHVEERSSKRREYLLEETARKLQRNDTESVEKLKLIDNIQRLGIGYYFEDAIDAVL

RSPFSAEEEEDLFTAALRFRLLRHNGIQVTPEIFLKFKDERGEFDESDTLGLLSLYEASNLGVTGEEILEEAMEFAEPRL

RRSLSELAAPLRSEVAQALDVPRHLRMARLEARRFIEQYGKQSDHDGDLLELAILDYNQVQAQHQSELTEITRWWKQLGL

VEKLGFGRDRALECFMWTMGILPHPKYSSSRIESAKAAALLYVI DDIFDTYGK MDELILFTDAIRRWDLEAMEGLPEYM

KICYMALYNTTNEICYRVLKDTGRIALPYLKSVWIETIEAYMVEVKWFSGGSAPKLEEYIENGASTVGAYMVLVHLFFLI

GEGLTHQNVLFFKQKPYHKPFSAAGRIFRLWDDLGTSQEEEERGDMASSIRLFMKEYKLSTVEEARSCVLEEISRLWKDL

NEGLISIKDALPLTIVKVALNIARTSQVVYKHEQHTYMLSVDNYVEALFFTPLLSS

FIG.49

>CbLINS_M39

MRESLSSSSSSNTQNLFLSTSPYDTAWLALIPHPHHHHHHGRPMFEKCLQWILHNQTPQGFWAAAGDNISDTDDDVTLDCL

LSTLACLVALKRWQLAPDMIHKGLEFVNRNTERLVMKQKPSDVPRWFTIMFPAMLELAGASSLRVDFSENLNRILVELSQ

NRDDILTREEVDEKKQYSPLLLFLEALPAQSYDNDVLKQIIDKNLSNDGSLLQSPSATARAYMITGNTRCLSYLHSLTNS

CSNGGVPSFYPVDDDLHDLVMVNQLTRSGLTEHLIPEIDHLLLKVQKNYKYKKASPKSLYSIAAELYRDSLAFWLLRVNN

HWVSPSIFCWFLDDDEIRDHIETNYEEFAAVLLNVYRATDLMFSGEVQLVEARSFATKNLEKILATGNIHKTNADISSSL

HKMIEHELRVPWTARMDHVENRIWIEEIASSALWFGKSSYLRLSCFHKMSLQQLAVKNYTLRQLVYRDELAEVERWSKER

GLCDMGFCREKTGYCYYAFAASTCLPWSSDVRLVLTKAAVVITVA DDFFDVEG SMVDLEKLTDAVRRWDAEGLGSHSKT

IFEALDDLVNEVRLKCFQQNGQDIKNNLQQLWYETFHSWLMEAKWGKGLTSKPSVDVYLGNAMTSIAAHTMVLTASCLLG

PGFPVHQLWSQRRHQDITSLLMVLTRLLNDIQSYLKEEDEGKINYVWMYMIENNQASIDDSVRHVQTIINVKKQEFIQRV

LSDQHCNLPKSFKQLHFSCLKVFNMFFNSSNIFDTDTDLLLDIHEAFVSPPQVPKFKPHIKPPHQLPATLQPPHQPQQIM

VNKKKVEMVYKSYHHPFKVFTLQKKQSSGHGTMNPRASILAGPNIKLCFS

FIG.50

>Q1XBU5|R-linalool synthase|EC 4.2.3.26|Solanum lycopersicum|TrEMBL

MVSILSNIGMMVVTFKRPSLFTSLRRRSANNIIITKHSHPISTTRRSGNYKPTMWDFQFIQSLHNPYEGDKYMKRLNKLK
KEVKKMMMTVEGSHDEELEKLELIDNLERLGVSYHFKDEIMQIMRSINININIAPPDSLYTTALKFRLLRQHGFHISQDI
LNDFKDENGNLKQSICKDTKDILNSSKDEHDNLKQSTCNNTKGLLKLYEASFLSIENESFLRNTTKSTLAHLMRYVDQNR
CGEEDNMIVELVVHALELPRHWMVPRLETRWYISIYERMSNANPLLLELAKLDFNIVQATHQQDLRILSRWWKNTGLAEK
LPFSRDILVENMFWAVGALFEPQHSYFRRLITKVIVFISII DDIYDVYG TLDELELFTLAIQRWDTKAMEQLPDYMKVC
YLALINIINEVAYEVLKNHDINVLPYLTKSWADLCKSYLQEAKWYHNGYKPNLEEYMDNARISIGVPMVLVHSLFLVTNQ
ITKEALDSLTNYPDIIRWSATIFRLNDDLGTSSDELKRGDVSKSIQCYMNEKGASEEEAIEHIEFLIQETWEAMNTAQSK
NSPLSETFIEVAKNITKASHFMYLHSDVKSSISKILFEPIIISNVAFALK

FIG.51

>gi|211970992|dbj|BAG82825.1| linalool synthase [Backhousia citriodora]

MALPALFGSSLPSSIRHNQPSLFSFRHPRFCSSSSSASFSSQFILCASKTGDQEIVRRSANWQPSVWDYDYVQSLTVDYT
EDKYTKQVQRLKEEVKGLFDREMKQVAKLEFIDVVQRLGLGYHFKTEIKIALSSIHNNTEDAQLSNDLYAASLRFRLLRQ
YGCNVQQDVFQRFMNKTGTFKESLNKDVKGILGLYEASPHGMEGETVLDEAWNFASKHLKDLNLDEVPTNLASNVSHALD
MPIHWRPNRLEARWFMDMYEKQQDLIPSLLRLAKLDFNIVQSIHRKEVSNLARWWVELGANKMTFFRDRLVESYFWSCIL
VFEPQYTDFRELNTRIACMATLI DDVYDIYG TPEELELLTDFILRWDITDIDKLPPTIRNGFMALYNTTNKVGYRTMTK
RGINPIPYLRKLWGDECKADMKEVHWFNNGIKPTLKEYMDVAVDSIGGLILLLNSYFLTTDYLTEEGLNYVSKIPSVMHS
SAQIFRFNDDLSTSSHELARGDNSKALECYMNETGASEEIAREHIRHLVRETWKKMNKEVFEDYPFSGFGPFLSACLNLA
RASHCFYEYGDGYGLPDHQTRDHLASTIFESVSLD

FIG.52

>gi|6469618|gb|AAF13357.1|AF154125_1 (3R)-linalool synthase, partial [Artemisia annua]

GNAYMRIYSTKTTRITANATVNAADTHVRRSANYKPSSWSFDHIQSLSSKYTGDDYVARANTLKDAVKTMIRKSGNSLRT
LELVDELQRLGISYLFEEEISNLLETIYYNYYKFPENWNKINLNLKALGFRLLRQHGYHVPQEIFLNFKDKNQNLNSYLL
NDVVEMLNLYEASYHSFEDESILDDARDITTKYLKESLEKIDGSIFSSVTHALEQPLHWRVPRVEAKWFIELYEKKNGMS
PTLVELAKLDFDMVQAIHLEDLKHASRWWRDTSWDTKLTFARDLIVENFLWTIGFSYLPNFSRGRRTITKVAVMITTLD
DVYDVFGTLGELEQFTDVINRWDIKAIEQLPDYMKICFLGLYKSINDITHETLANKGFLILPYLKKAWADLCKAYLVEA
QWYHRGHIPTLNEYLDNACVSISGPVALMHVHFLTSVSSIEEIHQCIQRTENIVHYVSLIFRLADDLGTSLGEMERGDTL
KSIQLHMHETGATEPEARSYIKLLINKTWKKLNKERATVNSESSQEFIDYATNLVRMAQFMYGEGDEDFGLDVIKSHVLS
LLFTPIQGI

FIG.53

>gi|6469616|gb|AAF13356.1|AF154124_1 (3R)-linalool synthase [Artemisia annua]
MASISLFPYSILKQTSPLARGTAYNRIYSTKTTGITVDVAESHVRRSANYEPSSWSFDHIQSLSSKYTGDDCVARANTLK
ESVKTMIRKEGNLLRTLELVDELQRLGISYLFEGEISNLLETIYYNHYKFPEKWNKFDLNLKALGFRLLRQHGYHVPQEI
FLNFKDKNQNLNSYLLEDVVGMLNLYEASYHSFEDESILTEARDIATKYLKASLEKIDGSILSLVSHALDNRLHWRVPRV
ESKWFIEVYEKRVGASPTLIELAKLDFDMVQAIHLEDLKHASRWWRNTSWDTKLTFARDMLVENFLWTVGFSYLPNFSHG
RRTITKVAAMITTLDDIYDVFGTLGELEQFTDVINRWDIKAIEQLPDYMKICFFGLYNSINDITYETLATKGFLILPYI
KKAWADLCKSYLVEAQWYHRGHIPTLNEYLDNACVSISGPVALMHVHFLTSVSSTKEIHHCIERTQNIVRYVSLIFRLTD
DLGTSLGEMERGDTLKSIQLYMHETGATEPEARSYIKSLIDKTWKKLNKERAIVSSESSREFIDYATNLARMAHFMYGEG
DEDFRLDVIKSHVSSLLFTPIQGI

FIG.54

\>D4N3A0|S-linalool synthase|EC 4.2.3.25|Actinidia arguta|TrEMBL
MASFNRFCVSSLLAPNNSPQISNAPRSTAVPSMPTTQKWSITEDLAFISNPSKQHNHQTGYRIFSDEFYLKHENKLKDVR
RALREVEETPLEGLVMIDTLQRLGIDYHFQGEIGALLQKQQRISTCDYPEHDLFEVSTRFRLLRQEGHNVPADVFNNFRD
KEGRFKSELSRDIRGLMSLYEASQLSIQGEDILDQAADFSSQLLSGWATNLDHHQARLVRNALTHPYHKSLATFMARNFN
YDCKGQNGWVNNLQELAKMDLTMVQSMHQKEVLQVSQWWKGRGLANELKLVRNQPLKWYMWPMAALTDPRFSEERVELTK
PISFIYII DDIFDVYG TLEELTLFTDAVNRWELTAVEQLPDYMKICFKALYDITNEIAYKIYKKHGRNPIDSLRRTWAS
LCNAFLEEAKWFASGNLPKAEEYLKNGIISSGMHVVTVHMFFLLGGCFTEESVNLVDEHAGITSSIATILRLSDDLGSAK
DEDQDGYDGSYLECYLKDHKGSSVENAREEVIRMISDAWKRLNEECLFPNPFSATFRKGSLNIARMVPLMYSYDDNHNLP
ILEEHMKTMLYDSSS

FIG.55

\>D4N3A1|S-linalool synthase|EC 4.2.3.25|Actinidia polygama|TrEMBL
MASFHRFCVSSLLVPNNSPQISNAYRAPAVPSMPTTQKWSITEDLAFISNPSKQHNHQTGYRTFSDEFYVKREKKLKDVR
RALREVEETPLEGLVMIDTLQRLGIDYHFQGEIGALLQKQQRKSKCDYPEHDLFEVSTRFRLLRQEGHNVPADVFNHFRD
KKGRFKSELSRDIRGLMSLYEASQLSIQGEDILDQAADFSSQLLSGWATNPDHHQARLVRNALTHPYHKSLATFTARNFH
YDCKGQNGWVNNLQELAKMDLTVVQSMHQKEVLQVSQWWKDRGLANELKLVRNQPLKWYMWPMAALTDPRFSEERVELTK
PISFIYII DDIFDVYG TLEELTLFTDAVNRWELTAVEQLPDYMKVCFKALYDITNEIAYKIYKKHGWNPIDSLRRMWAS
LCNAFLVEAKWFASGHLPKAEEYLKNGIISSGMHVVTVHMFFLLGGCFTDESVNLVDEHAGITSSIATILRLSDDLGSAK
DEDQDGYDGSYVEYYLKDHKGSSVENAREEVIRMISDAWKRLNEECLSPNPFSATFRKGCLNIARMVPLMYSYDDNHNLP
LLEEHMKAMLYDSSS

FIG.56

>C0KWV5|S-linalool synthase|EC 4.2.3.25|Perilla frutescens var. hirtella|TrEMBL

MSSMRIYVAIMKKPSVKHVDYVDKKASKPSWRVSSSATAGLRASSSLQLDVKKPADEILTARRSGNYQPSLWDFNYLQSL
NTTHYKEERHLKREAELIEQVKMLLDEEMGAVQKLDLVDDLKNLGLSYFFEDQIKQILTFIYNEHECFRSNVEAKERDLY
FTALGFRLLRQHGFQVSQEVFDCFKNEEGSDFKASLGDDTKGLVQLYEASFLLREGEDTLELARQYATKFLQKKVDHELI
DDDSNLLSWIRHSLEIPLHWRIQRLEARWFLDAYATRHDVNPIILELAKLDFNIIQATQQEELKDLSRWWNSTCLVEKLP
FVRDRLVESYFWAIALFEPHQYGYHRKIAAKIITLITSL DDVYDIYG TLDELQLFTDAIQRWDTESISRLAYYMQLFYM
VLYNFVSELAYDGLKEKGFITIPYLQRSWADLVEAYLKEAKWFYNGYTPSMEEYLNNAYISIGATPVISQVFFTLATSID
KPVIESLYEYHRILRLSGMLVRLPDDLGTSPFEMKRGDVPKTIELYMKERNATEIEAQEHVRFLIREAWREMNTATAAAD
CPFTDDLVAAAANLGRAAQFMYLDGDGNHSQLHQRIASLLFEPYA

FIG.57

>C0KWV3|S-linalool synthase|EC 4.2.3.25|Perilla setoyensis|TrEMBL

MSSMRTYVAIMKKPSVEHVDNVDKKASKPSWRVSLSAGLRSSCSLQLEVKPADQILTARRSGNYQPSLWDFNYLQSLNTT
HYKEVRHLKREAELIEQVKMLLEEEMEAVQQLELVDDLKNLGLSYFFEDQIKQILTFIYNEHKCFHSNSIIEAEEIRDLY
FTALGFRLLRQHGFQISQEVFDCFKNEEGSDFKARLGDDTKGLLQLYEASFLLREGEDTLELARQYATKFLQKKVDHELI
DDNNLLSWILHSLEIPLHWRIQRLEARWFLDAYASRRDMNQIILELAKLDFNIIQATQQEELKDLSRWWKSSCLAEKLPF
VRDRLVESYFWAIALFEPHQYGYHRKIAAKIITLITSL DDVYDIYG TLDELQLFTDAIQRWDTESISRLPYYMQLFYMV
LYNFVPRLAYDGLKEKGFITIPYLQRSWADLVEAYLKEAKWYYNGYTPSMEEYLNNAYISIGATPVISQVFFTLATSIDK
PVIDSLYEYHRILRLSGILVRLPDDLGTSPFEMKRGDVPKAIQLYMKERNATEIEAQEHVRFLIREAWKEMNTATAAVDC
PFTDDLVTAAANLGRAAQFMYLDGDGNHSQLHQRIACLLFEPYA

LINALOOL COMPOSITION AND METHOD OF PRODUCING THEREFOR

This application is a Continuation of, and claims priority under 35 U.S.C. § 120 to, International Application No. PCT/JP2016/078323, filed Sep. 26, 2016, and claims priority therethrough under 35 U.S.C. § 119 to Japanese Patent Application No. 2015-188597, filed Sep. 25, 2015, Japanese Patent Application No. 2016-110491, filed Jun. 1, 2016, and Japanese Patent Application No. 2016-110492, filed Jun. 1, 2016, the entireties of which are incorporated by reference herein. Also, the Sequence Listing filed electronically herewith is hereby incorporated by reference (File name: US-577 SL.txt; File size: 358,742 bytes; Date recorded: Jul. 25, 2019).

BACKGROUND OF THE INVENTION

Field of the Invention

The present invention relates to a linalool composition and a method for producing a linalool composition.

Brief Description of the Related Art

The aromatic substance linalool is a monoterpene alcohol that is found in the essential oils of various plants, including lavender and orange. Linalool is used to scent products such as perfumes, cosmetics, shampoos, and soaps, and is also used as an additive to provide flavor to food and beverages. Furthermore, linalool is used as a raw material in other monoterpene-based aromatic materials, and is an important compound as an intermediate of vitamin A or E. Linalool exists as enantiomers, including licareol, or (3R)-(−)-linalool ((3R)-3,7-dimethylocta-1,6-diene-3-ol, R-linalool), and coriandrol, or (3S)-(+)-linalool ((3S)-3,7-dimethylocta-1,6-diene-3-ol, S-linalool). It has been reported that the licareol and the coriandrol each provide distinct odors; licareol smells like woody lavender, and coriandrol smells like a sweet *citrus* similar to petitgrain (see Alejandro Carrasco, Ramiro Martinez-Gutierrez, Virginia Tomas, Jose Tudela, Planta Medica 2016; 82: 163-170 and Melliou Eleni, Michaelakis Antonios, Koliopoulos George, Skaltsounis Alexios-Leandros and Magiatis Prokopios, Molecules 2009, 14(2), 839-849). These two enantiomers also have distinct odor thresholds, and licareol shows a lower threshold by approximately nine times as compared to coriandrol (for example, see Ana Clara Aprotosoaie, Monica Hancianu, Irina-Iuliana Costache Anca Miron, Flavour and Fragrance Journal, 2014, 29, 193-219).

Linalool as a flavor component has been well-studied, revealing relatively many biological activities such as sedative activity, anti-inflammatory activity, and antioxidant activity. In recent years, there has been an increase in health consciousness and a desire for functional food and beverages containing ingredients derived from plants. As a result, the function of linalool has become appealing, and products containing linalool have been developed. The desire for such food and beverages is expected to continue to increase, and therefore the demand for linalool will also increase. For this reason, establishing a method for efficiently producing linalool is in demand.

Linalool is synthesized by linalool synthase with geranyl diphosphate (GPP). GPP, a common precursor of monoterpenes, is produced by condensation of isopentenyl diphosphate (IPP) and dimethylallyl diphosphate (DMAPP). DMAPP is an isomer of isopentenyl diphosphate. The mevalonate pathway and the non-mevalonate pathway (MEP pathway) are known as biosynthetic pathways for IPP and DMAPP. The mevalonate pathway is present in eukaryotes, such as plants, animals, yeasts, and the like, and some actinomycete and archaea. On the other hand, the MEP pathway is present in bacteria and plastids of plants. Conventionally, essential oils of plants including linalool are produced by extraction from plants using various extraction methods, such as, for example, steam distillation and distillation under reduced pressure. (Japanese Patent Application Laid-open No. 2005-298580 A and Japanese Patent Application Laid-open No. 2006-291007 A, respectively). Furthermore, Japanese Patent Application Laid-open No. 2011-506713 W describes a method of extracting a plant component treating a mixture of a plant material and a solvent with an ultra-high-temperature. Meanwhile, a production method by chemical synthesis has also been reported, and for example, V. A. Semikolenov, I. I. Ilyna, and I. L. Simakova, Applied Catalysis A, General, 2001, 211: 91-107 describes a method for producing linalool by chemical synthesis using a catalyst and the raw material α-pinene. Moreover, recently, linalool production in yeast and *Escherichia coli* using a gene recombination technique has been reported (for example, see Chinese Patent Application Laid-open No. 102071155 and Sun M X, Liu J D, Du G C, Zhou J, and Chen J., Chin J Biotech, 2013, 29(6): 751-759, Herrero O, Ramon D, and Orejas M, Metab Eng, 2008, 10, 78-86, Rico J, Pardo E, and Orejas M, Appl Environ Microbiol, 2010, 76, 6449-6454, and Ratana Thanasomboon, Dujduan Waraho, Supapon Cheevadhanarak, and Asawin Meechaia, Procedia Computer Science 11 (2012) 88-95). However, the amount of linalool produced by recombinant yeast is only a trace amount, and thus it cannot necessarily be said that this is an efficient production method.

Linalool exists as enantiomers of R-linalool and S-linalool. R-linalool has an odor of lavender and S-linalool has an odor of orange, and therefore their applications are distinct. For this reason, it is desirable to produce each enantiomer in excess. Linalool produced from α-pinene by chemical synthesis has almost a racemic form. Furthermore, although several chemical synthesis methods for producing optically active linalool are known, they require expensive reagents or complicated processes, and so are not practical (Richard Barner, and Josef Hubscher, Helv. Chim. Acta, Vol. 66, pp. 880-890 (1983) and Masaki Ohwa, Tetsuo Kogure, and Ernes L. Eliel, J. Org. Chem., Vol. 51, pp. 2599-2601 (1986) and Japanese Patent Application Laid-open No. H05-170682 A). An asymmetric hydrolysis method using lipase has been reported, but requires preparing fatty acid ester from linalool in a racemic form, and then a complicated process is required to adjust the matrix (Japanese Patent Application Laid-open No. H09-000278 A). When extracting linalool from plants, generally, it is often extracted as a mixture of R-linalool and S-linalool (Temel Ozek, Nurhayat Tabanca, Fatih Demirci, David E. Wedge and K. Husnu Can Baser, Records of Natural products 2010, 4(4), 180-192). For this reason, in order to obtain purified forms of either R-linalool and S-linalool in excessive amounts, advanced purification technologies such as optical resolution are often required. Furthermore, since many isoprenoid compounds, such as linalyl acetate, limonene, and caryophyllenean, are extracted as impurities from plants, the content of the volatile components (flavor components) is small.

Since large amounts of purified linalool can only be obtained as an asymmetric mixture of R-linalool and S-linalool, it is used as a raw material for chemical synthesis or pharmaceutical products. Furthermore, linalool is widely used as a flavor in food or alcoholic beverages, and in industrial products, including cosmetics, perfumes, and insect repellents.

Hence, linalool obtained by methods described in the art to date is obtained as a mixture of R-linalool and S-linalool, and contains a large amount of other isoprenoid-based impurities. For this reason, a composition containing a large amount of a single enantiomer of linalool, such as a composition containing an excessive amount of either R-linalool or S-linalool, and a production method for such a composition, have not been previously described.

SUMMARY OF THE INVENTION

It is an aspect of the present invention to provide a composition comprising volatile components, wherein said volatile components comprise 60% or more linalool, and linalool consists of R-linalool, S-linalool, or both.

It is a further aspect of the present invention to provide the composition as described above, wherein the volatile components further comprise 3-methyl-2-buten-1-ol.

It is a further aspect of the present invention to provide the composition as described above, wherein said volatile components comprise 40% or less of 3-methyl-2-buten-1-ol.

It is a further aspect of the present invention to provide the composition as described above, wherein said linalool consists of 80% or more of R-linalool or S-linalool.

It is a further aspect of the present invention to provide the composition as described above, wherein a content of R-linalool in the total content of volatile components in the composition is 60% or more.

It is a further aspect of the present invention to provide a composition as described above, wherein said volatile components comprise 60% or more of S-linalool.

It is a further aspect of the present invention to provide the composition as described above, wherein said composition comprises 200 mg/L or more of linalool.

It is a further aspect of the present invention to provide the composition as described above, wherein said volatile components further comprise linalyl acetate, limonene, caryophyllin, 3-methyl-1-butanol, β-citronellol, and/or geraniol.

It is another aspect of the present invention to provide a method for producing the composition as described above, the method comprising culturing a microorganism expressing linalool synthase in a culture medium, and accumulating the composition as described above in the culture medium.

It is a further aspect of the present invention to provide the method as described above, wherein the linalool synthase amino acid sequence has at least one motif represented by the following formula $DDX_1[F/Y][D/Y]X_2X_3G$ (SEQ ID NO: 165), wherein D represents aspartic acid, F represents phenylalanine, Y represents tyrosine, G represents glycine, $X_1$, $X_2$, and $X_3$ each independently represent an arbitrary amino acid, [F/Y] represents F or Y, and [D/Y] represents D or Y.

It is a further aspect of the present invention to provide the method as described above, wherein the linalool synthase is native to actinomycete or a plant belonging to the genus *Arabidopsis*, *Citrus*, *Perilla*, *Vitis*, *Mentha*, *Ocimum*, *Lavandula*, *Picea*, *Solanum*, *Malus*, *Backhousia*, *Actinidia*, *Clarkia*, or *Artemisia*.

It is a further aspect of the present invention to provide the method as described above, wherein the actinomycete is a microorganism belonging to the genus *Streptomyces*.

It is a further aspect of the present invention to provide the method as described above, wherein the plant is *Arabidopsis thaliana*, *Citrus unshiu*, *Malus domestica*, *Perilla frutescens* var. *crispa*, *Vitis vinifera*, *Lavandula angustifolia*, *Mentha citrata*, *Ocimum basilicum*, *Clarkia breweri*, *Actinidia arguta*, *Backhousia citriodora*, *Artemisia annua*, or *Streptomyces clavuligerus*.

It is a further aspect of the present invention to provide the method as described above, wherein the microorganism is selected from the group consisting of the family Enterobacteriaceae, a yeast, a coryneform bacterium, and blue-green algae.

It is a further aspect of the present invention to provide the as described above, wherein the microorganism is a bacterium belonging to the genus *Escherichia*, *Pantoea*, *Synechocystis*, or *Corynebacterium*.

It is a further aspect of the present invention to provide the method as described above, wherein the microorganism is *Escherichia coli*, *Pantoea ananatis*, *Synechocystis* sp., or *Corynebacterium glutamicum*.

It is a further aspect of the present invention to provide the method as described above, wherein the microorganism comprises a heterologous expression unit comprising a polynucleotide encoding linalool synthase and a promoter operably linked thereto.

It is a further aspect of the present invention to provide the method as described above, wherein the polynucleotide is selected from the group consisting of (a1) a polynucleotide that comprises (i1) a nucleotide sequence represented by SEQ ID NO:2 or (ii1) a nucleotide sequence represented by SEQ ID NO:3; (b1) a polynucleotide that comprises a nucleotide sequence having an identity of 90% or more to the nucleotide sequence of (i1) or (ii1), and encodes a protein having a linalool synthase activity; (c1) a polynucleotide that hybridizes under stringent conditions with a polynucleotide comprising a nucleotide sequence complementary to the nucleotide sequence of (i1) or (ii1), and encodes a protein having a linalool synthase activity; (a2) a polynucleotide that comprises (i2) a nucleotide sequence represented by SEQ ID NO:62 or (ii2) a nucleotide sequence represented by SEQ ID NO:63; (b2) a polynucleotide that comprises a nucleotide sequence having an identity of 90% or more to the nucleotide sequence of (i2) or (ii2), and encodes a protein having a linalool synthase activity; (c2) a polynucleotide that hybridizes under stringent conditions with a polynucleotide comprising a nucleotide sequence complementary to the nucleotide sequence of (i2) or (ii2), and encodes a protein having a linalool synthase activity; (a3) a polynucleotide that comprises (i3) a nucleotide sequence represented by SEQ ID NO:65 or (ii3) a nucleotide sequence represented by SEQ ID NO:66; (b3) a polynucleotide that comprises a nucleotide sequence having an identity of 90% or more to the nucleotide sequence of (i3) or (ii3), and encodes a protein having a linalool synthase activity; (c3) a polynucleotide that hybridizes under stringent conditions with a polynucleotide comprising a nucleotide sequence complementary to the nucleotide sequence of (i3) or (ii3), and encodes a protein having a linalool synthase activity; (a4) a polynucleotide that comprises (i4) a nucleotide sequence represented by SEQ ID NO:68 or (ii4) a nucleotide sequence represented by SEQ ID NO:69; (b4) a polynucleotide that comprises a nucleotide sequence having an identity of 90% or more to the nucleotide sequence of (i4) or (ii4), and encodes a protein having a linalool synthase activity; (c4) a polynucleotide that hybridizes under stringent conditions with a polynucleotide comprising a nucleotide sequence complementary to the nucleotide sequence of (i4) or (ii4), and encodes a protein having a linalool synthase activity; (a5) a polynucleotide that comprises (i5) a nucleotide sequence represented by SEQ ID NO:71 or (ii5) a nucleotide sequence represented by SEQ ID NO:72; (b5) a polynucleotide that comprises a nucleotide sequence having an identity of 90% or more to the nucleotide sequence of (i5) or (ii5), and encodes a protein having a linalool synthase activity; (c5) a polynucleotide that hybridizes under stringent conditions with a polynucleotide comprising a nucleotide sequence complementary to the nucleotide sequence of (i5) or (ii5), and encodes a protein having a linalool synthase activity; (a6) a polynucleotide that comprises (i6) a nucleotide sequence represented by SEQ ID NO:74 or (ii6) a nucleotide sequence represented by SEQ ID NO:75; (b6) a polynucleotide that comprises a nucleotide sequence having an identity of 90% or more to the nucleotide sequence of (i6) or (ii6), and encodes a protein having a linalool synthase activity; (c6) a polynucleotide that hybridizes under stringent conditions with a polynucleotide comprising a nucleotide sequence complementary to the nucleotide sequence of (i6) or (ii6), and encodes a protein having a linalool synthase activity; (a7) a polynucleotide that comprises (i7) a nucleotide sequence represented by SEQ ID NO:79, (ii7) a nucleotide sequence comprising nucleotide residues at positions 79 to 1725 in the nucleotide sequence represented by SEQ ID NO:79, or (iii7) a nucleotide sequence represented by SEQ ID NO:80; (b7) a polynucleotide that comprises a nucleotide sequence having an identity of 90% or more to the nucleotide sequence of (i7), (ii7) or (iii7), and encodes a protein having a linalool synthase activity; (c7) a polynucleotide that hybridizes under stringent conditions with a polynucleotide comprising a nucleotide sequence complementary to the nucleotide sequence of (i7), (ii7) or (iii7), and encodes a protein having a linalool synthase activity; (a8) a polynucleotide that comprises (i8) a nucleotide sequence represented by SEQ ID NO:85 (M1) or (ii8) a nucleotide sequence represented by SEQ ID NO:98 (M14); (b8) a polynucleotide that comprises a nucleotide sequence having an identity of 90% or more to the nucleotide sequence of (i8) or (ii8), and encodes a protein having a linalool synthase activity; (c8) a polynucleotide that hybridizes under stringent conditions with a polynucleotide comprising a nucleotide sequence complementary to the nucleotide sequence of (i8) or (ii8), and encodes a protein having a linalool synthase activity; (a9) a polynucleotide that comprises (i9) a nucleotide sequence represented by SEQ ID NO:86 (M2) or (ii9) a nucleotide sequence represented by SEQ ID NO:100 (M16); (b9) a polynucleotide that comprises a nucleotide sequence having an identity of 90% or more to the nucleotide sequence of (i9) or (ii9), and encodes a protein having a linalool synthase activity; (c9) a polynucleotide that hybridizes under stringent conditions with a polynucleotide comprising a nucleotide sequence complementary to the nucleotide sequence of (i9) or (ii9), and encodes a protein having a linalool synthase activity; (a10) a polynucleotide that comprises (i10) a nucleotide sequence represented by SEQ ID NO:87 (M3) or (ii10) a nucleotide sequence represented by SEQ ID NO:102 (M18); (1310) a polynucleotide that comprises a nucleotide sequence having an identity of 90% or more to the nucleotide sequence of (i10) or (ii10), and encodes a protein having a linalool synthase activity; (c10) a polynucleotide that hybridizes under stringent conditions with a polynucleotide comprising a nucleotide sequence complementary to the nucleotide sequence of (i10) or (ii10), and encodes a protein having a linalool synthase activity; (a11) a polynucleotide that comprises (i11) a nucleotide sequence represented by SEQ ID NO:88 (M4) or (ii11) a nucleotide sequence represented by SEQ ID NO:104 (M20); (b11) a polynucleotide that comprises a nucleotide sequence having an identity of 90% or more to the nucleotide sequence of (i11) or (ii11), and encodes a protein having a linalool synthase activity; (c11) a polynucleotide that hybridizes under stringent conditions with a polynucleotide comprising a nucleotide sequence complementary to the nucleotide sequence of (i11) or (ii11), and encodes a protein having a linalool synthase activity; (a12) a polynucleotide that comprises (i12) a nucleotide sequence represented by SEQ ID NO:89 (M5) or (ii12) a nucleotide sequence represented by SEQ ID NO:106 (M22); (b12) a polynucleotide that comprises a nucleotide sequence having an identity of 90% or more to the nucleotide sequence of (i12) or (ii12), and encodes a protein having a linalool synthase activity; (c12) a polynucleotide that hybridizes under stringent conditions with a polynucleotide comprising a nucleotide sequence complementary to the nucleotide sequence of (i12) or (ii12), and encodes a protein having a linalool synthase activity; (a13) a polynucleotide that comprises (i13) a nucleotide sequence represented by SEQ ID NO:90 (M6) or (ii13) a nucleotide sequence represented by SEQ ID NO:108 (M24); (b13) a polynucleotide that comprises a nucleotide sequence having an identity of 90% or more to the nucleotide sequence of (i13) or (ii13), and encodes a protein having a linalool synthase activity; (c13) a polynucleotide that hybridizes under stringent conditions with a polynucleotide comprising a nucleotide sequence complementary to the nucleotide sequence of (i13) or (ii13), and encodes a protein having a linalool synthase activity; (a14) a polynucleotide that comprises (i14) a nucleotide sequence represented by SEQ ID NO:91 (M7) or (ii14) a nucleotide sequence represented by SEQ ID NO:110 (M26); (b14) a polynucleotide that comprises a nucleotide sequence having an identity of 90% or more to the nucleotide sequence of (i14) or (ii14), and encodes a protein having a linalool synthase activity; (c14) a polynucleotide that hybridizes under stringent conditions with a polynucleotide comprising a nucleotide sequence complementary to the nucleotide sequence of (i14) or (ii14), and encodes a protein having a linalool synthase activity; (a15) a polynucleotide that comprises (i15) a nucleotide sequence represented by SEQ ID NO:92 (M8) or (ii15) a nucleotide sequence represented by SEQ ID NO:112 (M28); (b15) a polynucleotide that comprises a nucleotide sequence having an identity of 90% or more to the nucleotide sequence of (i15) or (ii15), and encodes a protein having a linalool synthase activity; (c15) a polynucleotide that hybridizes under stringent conditions with a polynucleotide comprising a nucleotide sequence complementary to the nucleotide sequence of (i15) or (ii15), and encodes a protein having a linalool synthase activity; (a16) a polynucleotide that comprises (i16) a nucleotide sequence represented by SEQ ID NO:93 (M9) or (ii16) a nucleotide sequence represented by SEQ ID NO:114 (M30); (b16) a polynucleotide that comprises a nucleotide sequence having an identity of 90% or more to the nucleotide sequence of (i16) or (ii16), and encodes a protein having a linalool synthase activity; (c16) a polynucleotide that hybridizes under stringent conditions with a polynucleotide comprising a nucleotide sequence complementary to the nucleotide sequence of (i16) or (ii16), and encodes a protein having a linalool synthase activity; (a17) a polynucleotide that comprises (i17) a nucleotide sequence represented by SEQ ID NO:94 (M10) or (ii17) a nucleotide sequence represented by SEQ ID NO:116 (M32); (b17) a polynucleotide that comprises a nucleotide sequence having an identity of 90% or more to the nucleotide sequence of (i17) or (ii17), and encodes a protein having a linalool synthase activity; (c17) a polynucleotide that hybridizes under stringent conditions with a polynucleotide comprising a nucleotide sequence complementary to the nucleotide sequence of (i17) or (ii17), and encodes a protein having a linalool synthase activity; (a18) a polynucleotide that comprises (i18) a nucleotide sequence represented by SEQ ID NO:95 (M11) or (ii18) a nucleotide sequence represented by SEQ ID NO:118 (M34); (b18) a polynucleotide that comprises a nucleotide sequence having an identity of 90% or more to the nucleotide sequence of (i18) or (ii18), and encodes a protein having a linalool synthase activity; (c18) a polynucleotide that hybridizes under stringent conditions with a polynucleotide comprising a nucleotide sequence complementary to the nucleotide sequence of (i18) or (ii18), and encodes a protein having a linalool synthase activity; (a19) a polynucleotide that comprises (i19) a nucleotide sequence represented by SEQ ID NO:96 (M12) or (ii19) a nucleotide sequence represented by SEQ ID NO:120 (M36); (b19) a polynucleotide that comprises a nucleotide sequence having an identity of 90% or more to the nucleotide sequence of (i19) or (ii19), and encodes a protein having a linalool synthase activity; (c19) a polynucleotide that hybridizes under stringent conditions with a polynucleotide comprising a nucleotide sequence complementary to the nucleotide sequence of (i19) or (ii19), and encodes a protein having a linalool synthase activity; (a20) a polynucleotide that comprises (i20) a nucleotide sequence represented by SEQ ID NO:97 (M13) or (ii20) a nucleotide sequence represented by SEQ ID NO:122 (M38); (b20) a polynucleotide that comprises a nucleotide sequence having an identity of 90% or more to the nucleotide sequence of (i20) or (ii20), and encodes a protein having a linalool synthase activity; and (c20) a polynucleotide that hybridizes under stringent conditions with a polynucleotide comprising a nucleotide sequence complementary to the nucleotide sequence of (i20) or (ii20), and encodes a protein having a linalool synthase activity; and (a21) combinations thereof.

It is a further aspect of the present invention to provide the method as described above, wherein the linalool synthase is a protein selected from the group consisting of: (A1) a protein that comprises (in a full-length amino acid sequence represented by SEQ ID NO: 1; (B1) a protein that comprises an amino acid sequence having an identity of 90% or more to the amino acid sequence of (i1'), and has a linalool synthase activity; (C1) a protein that comprises an amino acid sequence having a deletion, substitution, addition, or insertion of one or several amino acids in the amino acid sequence of (i1'), and has a linalool synthase activity; (A2) a protein that comprises (i2') a full-length amino acid sequence represented by SEQ ID NO:61; (B2) a protein that comprises an amino acid sequence having an identity of 90% or more to the amino acid sequence of (i2'), and has a linalool synthase activity; (C2) a protein that comprises an amino acid sequence having a deletion, substitution, addition, or insertion of one or several amino acids in the amino acid sequence of (i2'), and has a linalool synthase activity; (A3) a protein that comprises (i3') a full-length amino acid sequence represented by SEQ ID NO: 64; (B3) a protein that comprises an amino acid sequence having an identity of 90% or more to the amino acid sequence of (i3'), and has a linalool synthase activity; (C3) a protein that comprises an amino acid sequence having a deletion, substitution, addition, or insertion of one or several amino acids in the amino acid sequence of (i3'), and has a linalool synthase activity; (A4) a protein that comprises (i4') a full-length amino acid sequence represented by SEQ ID NO:67; (B4) a protein that comprises an amino acid sequence having an identity of 90% or more to the amino acid sequence of (i4'), and has a linalool synthase activity; (C4) a protein that comprises an amino acid sequence having a deletion, substitution, addition, or insertion of one or several amino acids in the amino acid sequence of (i4'), and has a linalool synthase activity; (A5) a protein that comprises (i5') a full-length amino acid sequence represented by SEQ ID NO: 70; (B5) a protein that comprises an amino acid sequence having an identity of 90% or more to the amino acid sequence of (i5'), and has a linalool synthase activity; (C5) a protein that comprises an amino acid sequence having a deletion, substitution, addition, or insertion of one or several amino acids in the amino acid sequence of (i5'), and has a linalool synthase activity; (A6) a protein that comprises (i6') a full-length amino acid sequence represented by SEQ ID NO: 73; (B6) a protein that comprises an amino acid sequence having an identity of 90% or more to the amino acid sequence of (i6'), and has a linalool synthase activity; (C6) a protein that comprises an amino acid sequence having a deletion, substitution, addition, or insertion of one or several amino acids in the amino acid sequence of (i6'), and has a linalool synthase activity; (A7) a protein that comprises (i7') a full-length amino acid sequence represented by SEQ ID NO:78 or (ii7') an amino acid sequence comprising amino acid residues at positions 27 to 574 in the amino acid sequence represented by SEQ ID NO:1; (B7) a protein that comprises an amino acid sequence having an identity of 90% or more to the amino acid sequence of (i7') or (ii7'), and has a linalool synthase activity; (C7) a protein that comprises an amino acid sequence having a deletion, substitution, addition, or insertion of one or several amino acids in the amino acid sequence of (i7') or (ii7'), and has a linalool synthase activity; (A8) a protein that comprises (i8') a full-length amino acid sequence represented by SEQ ID NO:99 (M15); (B8) a protein that comprises an amino acid sequence having an identity of 90% or more to the amino acid sequence of (i8'), and has a linalool synthase activity; (C8) a protein that comprises an amino acid sequence having a deletion, substitution, addition, or insertion of one or several amino acids in the amino acid sequence of (i8'), and has a linalool synthase activity; (A9) a protein that comprises (i9') a full-length amino acid sequence represented by SEQ ID NO: 101 (M17); (B9) a protein that comprises an amino acid sequence having an identity of 90% or more to the amino acid sequence of (i9'), and has a linalool synthase activity; (C9) a protein that comprises an amino acid sequence having a deletion, substitution, addition, or insertion of one or several amino acids in the amino acid sequence of (i9'), and has a linalool synthase activity; (A10) a protein that comprises (i10') a full-length amino acid sequence represented by SEQ ID NO:103 (M19); (B10) a protein that comprises an amino acid sequence having an identity of 90% or more to the amino acid sequence of (i10'), and has a linalool synthase activity; (C10) a protein that comprises an amino acid sequence having a deletion, substitution, addition, or insertion of one or several amino acids in the amino acid sequence of (i10'), and has a linalool synthase activity; (A11) a protein that comprises (i11') a full-length amino acid sequence represented by SEQ ID NO:105 (M21); (B11) a protein that comprises an amino acid sequence having an identity of 90% or more to the amino acid sequence of (i11'), and has a linalool synthase activity; (C11) a protein that comprises an amino acid sequence having a deletion, substitution, addition, or insertion of one or several amino acids in the amino acid sequence of (i11'), and has a linalool synthase activity; (A12) a protein that comprises (i12') a full-length amino acid sequence represented by SEQ ID NO:107 (M23); (B12) a protein that comprises an amino acid sequence having an identity of 90% or more to the amino acid sequence of (i12'), and has a linalool synthase activity; (C12) a protein that comprises an amino acid sequence having a deletion, substitution, addition, or insertion of one or several amino acids in the amino acid sequence of (i12'), and has a linalool synthase activity; (A13) a protein that comprises (i13') a full-length amino acid sequence represented by SEQ ID NO:109 (M25); (B13) a protein that comprises an amino acid sequence having an identity of 90% or more to the amino acid sequence of (i13'), and has a linalool synthase activity; (C13) a protein that comprises an amino acid sequence having a deletion, substitution, addition, or insertion of one or several amino acids in the amino acid sequence of (i13'), and has a linalool synthase activity; (A14) a protein that comprises (i14') a full-length amino acid sequence represented by SEQ ID NO:111 (M27); (B14) a protein that comprises an amino acid sequence having an identity of 90% or more to the amino acid sequence of (i14'), and has a linalool synthase activity; (C14) a protein that comprises an amino acid sequence having a deletion, substitution, addition, or insertion of one or several amino acids in the amino acid sequence of (i14'), and has a linalool synthase activity; (A15) a protein that comprises (i15') a full-length amino acid sequence represented by SEQ ID NO:113 (M29); (B15) a protein that comprises an amino acid sequence having an identity of 90% or more to the amino acid sequence of (i15'), and has a linalool synthase activity; (C15) a protein that comprises an amino acid sequence having a deletion, substitution, addition, or insertion of one or several amino acids in the amino acid sequence of (i15'), and has a linalool synthase activity; (A16) a protein that comprises (i16') a full-length amino acid sequence represented by SEQ ID NO:115 (M31); (B16) a protein that comprises an amino acid sequence having an identity of 90% or more to the amino acid sequence of (i16'), and has a linalool synthase activity; (C16) a protein that comprises an amino acid sequence having a deletion, substitution, addition, or insertion of one or several amino acids in the amino acid sequence of (i16'), and has a linalool synthase activity; (A17) a protein that comprises (i17') a full-length amino acid sequence represented by SEQ ID NO:117 (M33); (B17) a protein that comprises an amino acid sequence having an identity of 90% or more to the amino acid sequence of (i17'), and has a linalool synthase activity; (C17) a protein that comprises an amino acid sequence having a deletion, substitution, addition, or insertion of one or several amino acids in the amino acid sequence of (i17'), and has a linalool synthase activity; (A18) a protein that comprises (i18') a full-length amino acid sequence represented by SEQ ID NO:119 (M35); (B18) a protein that comprises an amino acid sequence having an identity of 90% or more to the amino acid sequence of (i18'), and has a linalool synthase activity; (C18) a protein that comprises an amino acid sequence having a deletion, substitution, addition, or insertion of one or several amino acids in the amino acid sequence of (i18'), and has a linalool synthase activity; (A19) a protein that comprises (i19') a full-length amino acid sequence represented by SEQ ID NO: 121 (M37); (B19) a protein that comprises an amino acid sequence having an identity of 90% or more to the amino acid sequence of (i19'), and has a linalool synthase activity; (C19) a protein that comprises an amino acid sequence having a deletion, substitution, addition, or insertion of one or several amino acids in the amino acid sequence of (i19'), and has a linalool synthase activity; (A20) a protein that comprises (i20') a full-length amino acid sequence represented by SEQ ID NO: 123 (M39); (B20) a protein that comprises an amino acid sequence having an identity of 90% or more to the amino acid sequence of (i20'), and has a linalool synthase activity; (C20) a protein that comprises an amino acid sequence having a deletion, substitution, addition, or insertion of one or several amino acids in the amino acid sequence of (i20'), and has a linalool synthase activity; (A21) a protein that comprises (i21') a full-length amino acid sequence represented by SEQ ID NO:157; (B21) a protein that comprises an amino acid sequence having an identity of 90% or more to the amino acid sequence of (i21'), and has a linalool synthase activity; (C21) a protein that comprises an amino acid sequence having a deletion, substitution, addition, or insertion of one or several amino acids in the amino acid sequence of (i21'), and has a linalool synthase activity; (A22) a protein that comprises (i22') a full-length amino acid sequence represented by SEQ ID NO:158; (B22) a protein that comprises an amino acid sequence having an identity of 90% or more to the amino acid sequence of (i22'), and has a linalool synthase activity; (C22) a protein that comprises an amino acid sequence having a deletion, substitution, addition, or insertion of one or several amino acids in the amino acid sequence of (i22'), and has a linalool synthase activity; (A23) a protein that comprises (i23') a full-length amino acid sequence represented by SEQ ID NO:159; (B23) a protein that comprises an amino acid sequence having an identity of 90% or more to the amino acid sequence of (i23'), and has a linalool synthase activity; (C23) a protein that comprises an amino acid sequence having a deletion, substitution, addition, or insertion of one or several amino acids in the amino acid sequence of (i23'), and has a linalool synthase activity; (A24) a protein that comprises (i24') a full-length amino acid sequence represented by SEQ ID NO: 160; (B24) a protein that comprises an amino acid sequence having an identity of 90% or more to the amino acid sequence of (i24'), and has a linalool synthase activity; (C24) a protein that comprises an amino acid sequence having a deletion, substitution, addition, or insertion of one or several amino acids in the amino acid sequence of (i24'), and has a linalool synthase activity; (A25) a protein that comprises (i25') a full-length amino acid sequence represented by SEQ ID NO:161; (B25) a protein that comprises an amino acid sequence having an identity of 90% or more to the amino acid sequence of (i25'), and has a linalool synthase activity; (C25) a protein that comprises an amino acid sequence having a deletion, substitution, addition, or insertion of one or several amino acids in the amino acid sequence of (i25'), and has a linalool synthase activity; (A26) a protein that comprises (i26') a full-length amino acid sequence represented by SEQ ID NO: 162; (B26) a protein that comprises an amino acid sequence having an identity of 90% or more to the amino acid sequence of (i26'), and has a linalool synthase activity; (C26) a protein that comprises an amino acid sequence having a deletion, substitution, addition, or insertion of one or several amino acids in the amino acid sequence of (i26'), and has a linalool synthase activity; (A27) a protein that comprises (i27') a full-length amino acid sequence represented by SEQ ID NO: 163; (B27) a protein that comprises an amino acid sequence having an identity of 90% or more to the amino acid sequence of (i27'), and has a linalool synthase activity; (C27) a protein that comprises an amino acid sequence having a deletion, substitution, addition, or insertion of one or several amino acids in the amino acid sequence of (i27'), and has a linalool synthase activity; (A28) a protein that comprises (i28') a full-length amino acid sequence represented by SEQ ID NO:164; (B28) a protein that comprises an amino acid sequence having an identity of 90% or more to the amino acid sequence of (i28'), and has a linalool synthase activity; (C28) a protein that comprises an amino acid sequence having a deletion, substitution, addition, or insertion of one or several amino acids in the amino acid sequence of (i28'), and has a linalool synthase activity; and (A29) combinations thereof.

It is a further aspect of the present invention to provide the method as described above, wherein the microorganism is a bacterium expressing geranyl diphosphate synthase.

It is a further aspect of the present invention to provide the method as described above, wherein the microorganism has an ability to synthesize dimethylallyl diphosphate via a methylerythritol phosphate pathway.

It is a further aspect of the present invention to provide the method as described above, wherein the microorganism has an ability to synthesize dimethylallyl diphosphate via a mevalonate pathway.

It is a further aspect of the present invention to provide the method as described above, wherein a 2-ketogluconate formation pathway is blocked in the microorganism.

It is a further aspect of the present invention to provide the method as described above, wherein the 2-ketogluconate formation pathway is blocked by reducing an activity of glucose dehydrogenase activity.

It is a further aspect of the present invention to provide the method as described above, wherein a glucose dehydrogenase gene is disrupted in the microorganism.

It is a further aspect of the present invention to provide the method as described above, wherein the glucose dehydrogenase gene is a polynucleotide selected from the group consisting of: (x) a polynucleotide that comprises [i] a nucleotide sequence represented by SEQ ID NO:9 or [ii] a nucleotide sequence consisting of nucleotide residues at positions 301 to 2691 in the nucleotide sequence represented by SEQ ID NO: 9; (y) a polynucleotide that comprises a nucleotide sequence having 90% or more of identity to the nucleotide sequence of [i] or [ii], and encodes a protein having a glucose dehydrogenase activity; (z) a polynucleotide that hybridizes under a stringent condition with a polynucleotide comprising a nucleotide sequence complementary to the nucleotide sequence of [i] or [ii], and encodes a protein having a glucose dehydrogenase activity; and (z') combinations thereof.

It is a further aspect of the present invention to provide the method as described above, wherein the glucose dehydrogenase is a protein selected from the group consisting of: (X) a protein that comprises a full-length amino acid sequence represented by SEQ ID NO:10; (Y) a protein that comprises an amino acid sequence having 90% or more of identity to the amino acid sequence represented by SEQ ID NO:10, and has a glucose dehydrogenase activity; (Z) a protein that comprises an amino acid sequence having a deletion, substitution, addition, or insertion of one or several amino acids in the amino acid sequence represented by SEQ ID NO:10, and has a glucose dehydrogenase activity; and (Z') combinations thereof.

A linalool composition is described having an excessive amount of either the R- or S-enantiomer, and a method for producing such a composition is also described. Specifically, a linalool composition containing an excessive amount of R-linalool, a linalool composition containing an excessive amount of S-linalool, a linalool composition having a large amount of linalool, and a production method for these compositions are provided.

BRIEF DESCRIPTION OF DRAWINGS

FIG. 29 shows a diagram illustrating the sequence logo of motif 4.

FIG. 30 shows a diagram illustrating the sequence logo of motif 5.

FIG. 31 shows a diagram illustrating the alignment of motif 1 (SEQ ID NOS 168-180, respectively, in order of appearance).

FIG. 32 shows a diagram illustrating the alignment of motif 2 (SEQ ID NOS 181-193, respectively, in order of appearance).

FIG. 33 shows a diagram illustrating the alignment of motif 3 (SEQ ID NOS 194-206, respectively, in order of appearance).

FIG. 34 shows a diagram illustrating the alignment of motif 4 (SEQ ID NOS 207-219, respectively, in order of appearance).

FIG. 35 shows a diagram illustrating the alignment of motif 5 (SEQ ID NOS 220-232, respectively, in order of appearance).

FIG. 36 shows a diagram illustrating the distribution of input sequences of motifs 1 to 5.

FIG. 37 shows a diagram illustrating the distribution of motif 1 in terpene synthase 14 (SEQ ID NO: 99 (M15)).

FIG. 38 shows a diagram illustrating the distribution of motif 1 in At2g24210 and terpene synthase 10 (TPS10) (SEQ ID NO:101 (M17)).

FIG. 39 shows a diagram illustrating the distribution of motif 1 in linalool synthase (SEQ ID NO: 103 (M19)).

FIG. 40 shows a diagram illustrating the distribution of motif 1 in linalool synthase (SEQ ID NO: 105 (M21)).

FIG. 41 shows a diagram illustrating the distribution of motif 1 in linalool synthase (SEQ ID NO: 107 (M23)).

FIG. 42 shows a diagram illustrating the distribution of motif 1 in linalool synthase (SEQ ID NO: 109 (M25)).

FIG. 43 shows a diagram illustrating the distribution of motif 1 in linalool synthase (SEQ ID NO: 111 (M27)).

FIG. 44 shows a diagram illustrating the distribution of motif 1 in (3 S)-linalool/(E)-nerolidol synthase (SEQ ID NO:113 (M29)).

FIG. 45 shows a diagram illustrating the distribution of motif 1 in (3R)-linalool synthase (SEQ ID NO: 115 (M31)).

FIG. 46 shows a diagram illustrating the distribution of motif 1 in linalool synthase (SEQ ID NO: 117 (M33)).

FIG. 47 shows a diagram illustrating the distribution of motif 1 in linalool synthase (SEQ ID NO: 119 (M35)).

FIG. 48 shows a diagram illustrating the distribution of motif 1 in R-linalool synthase (SEQ ID NO: 121 (M37)).

FIG. 49 shows a diagram illustrating the distribution of motif 1 in S-linalool synthase (SEQ ID NO: 123 (M39)).

FIG. 50 shows a diagram illustrating the distribution of motif 1 in R-linalool synthase (SEQ ID NO: 157).

FIG. 51 shows a diagram illustrating the distribution of motif 1 in linalool synthase (SEQ ID NO: 158).

FIG. 52 shows a diagram illustrating the distribution of motif 1 in (3R)-linalool synthase (SEQ ID NO: 159).

FIG. 53 shows a diagram illustrating the distribution of motif 1 in (3R)-linalool synthase (SEQ ID NO: 160).

FIG. 54 shows a diagram illustrating the distribution of motif 1 in S-linalool synthase (SEQ ID NO: 161).

FIG. 55 shows a diagram illustrating the distribution of motif 1 in S-linalool synthase (SEQ ID NO: 162).

FIG. 56 shows a diagram illustrating the distribution of motif 1 in S-linalool synthase (SEQ ID NO: 163).

FIG. 57 shows a diagram illustrating the distribution of motif 1 in S-linalool synthase (SEQ ID NO: 164).

DESCRIPTION OF THE PREFERRED EMBODIMENTS

Figure 1:
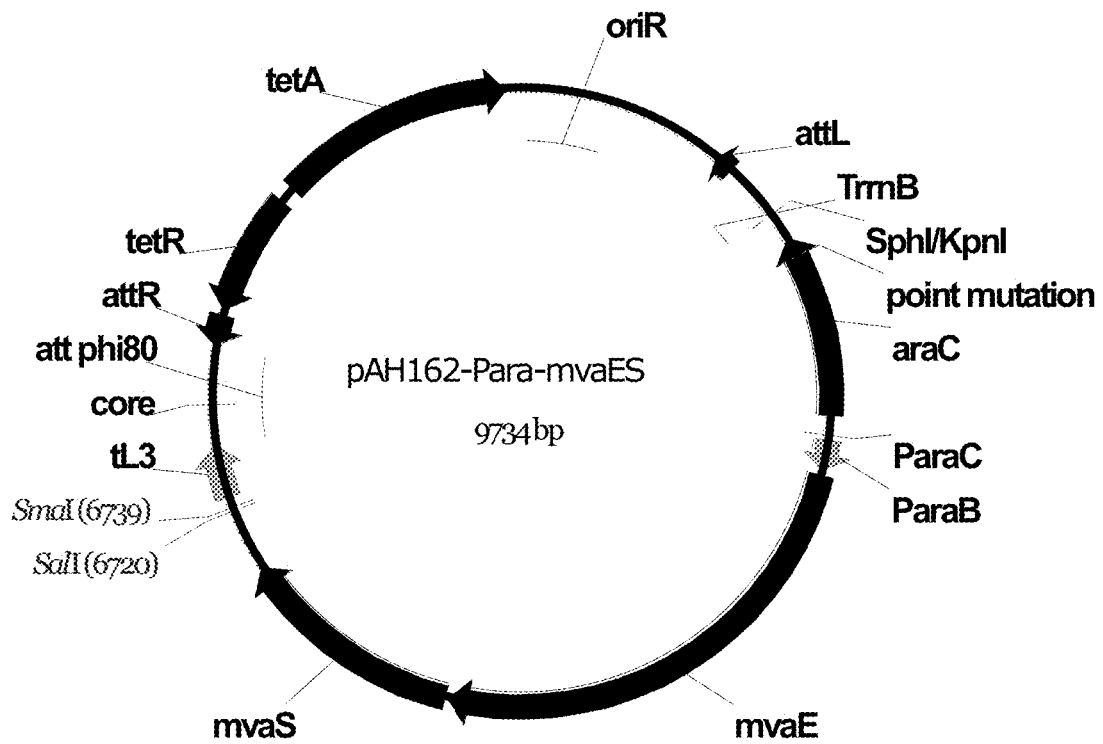
FIG. 1 shows a pAH162-Para-mvaES plasmid possessing an mvaES operon native to E. faecalis under control of E. coli Para promoter and a repressor gene araC.

The present invention provides a linalool composition and a method of producing the composition.

The linalool composition as described herein contains linalool. Linalool is an isoprenoid compound represented by $C_{10}H_{18}O$. Linalool has been assigned CAS number 78-70-6, R-linalool has been assigned CAS number 126-91-0, and S-linalool has been assigned CAS number: 126-90-9. Linalool can exist as enantiomers, and linalool derived from a plant typically exists as R-linalool and S-linalool. The linalool composition as described herein may contain only linalool or may contain components other than linalool. Examples of such other components can include volatile components, such as one or more volatile organic compounds ("VOC"). The volatile organic compound can mean a highly volatile organic compound having a lower limit boiling point of 0° C. to 5° C. and an upper limit boiling point of 100° C., or a lower limit boiling point of 50° C. to 100° C. and an upper limit of boiling point 240° C. to 260° C. The volatile organic compound can have a vapor pressure at 293.15 K of 0.01 kPa or more. The vapor pressure can be measured by a general technique, such as a gas saturation method, a static method, or a boiling-point method ("The Fifth Edition of Experimental Chemistry Course 6. Temperature, Heat, and Pressure, edited by The Chemical Society of Japan, published by MARUZEN Co., Ltd. [ISBN Code] 978-4-621-07305-6 [Publication Date] July, 2005).

Examples of the volatile components can include flavor components such as 3-methyl-1-butanol, 1-pentanol, 3-methyl-2-buten-1-ol, β-citronellol, (R)-(+)-β-citronellol, geraniol, nerol, trans-nerolidol, nerolidyl acetate, linalyl acetate, limonene, and caryophyllin. The linalool composition as described herein can contain one or more of 3-methyl-2-buten-1-ol, linalyl acetate, limonene, caryophyllin, 3-methyl-1-butanol, β-citronellol, and geraniol, and can contain at least 3-methyl-2-buten-1-ol, or 3-methyl-2-buten-1-ol and one or more of linalyl acetate, limonene, caryophyllin, 3-methyl-1-butanol, β-citronellol, and geraniol.

The total content of linalool as a volatile component in the linalool composition can be 60% or more, 70% or more or 80% or more, 85% or more, or 88% or more. The upper limit is not particularly limited, and when the linalool composition does not contain volatile components other than linalool, the content of linalool can be 100%.

The amount of 3-methyl-2-buten-1-ol in the linalool composition can be 40% or less, 10% or less, or 5% or less. The lower limit is not particularly limited, and may be 0% (3-methyl-2-buten-1-ol is not present). When the amount of 3-methyl-2-buten-1-ol in the linalool composition is outside of the above range, the amount may be adjusted. Methods to adjust, including reducing, the amount can include general purification methods such as precision distillation and column chromatography. Implementation conditions, for example, the kind of filler in the column, the weight ratio of the filler, the purification time, in the case of reduction by column chromatography are not particularly limited, but examples can be as follows. Examples of the filler (solid phase) in the column can include activated carbon, activated alumina, silica gel, molecular sieve, and reduced copper. The weight ratio of the filler to linalool can be 0.1 to 2.0, or 0.5 to 1.0. The purification time can be 2 to 8 hours, or 4 to 6 hours.

The amount of linalool in the linalool composition is not particularly limited, but can be 200 mg/L or more, or 500 mg/L or more. Linalool typically is toxic to a microorganism producing linalool, and the microorganism can barely grow once a large amount of linalool accumulates. As described herein, linalool can accumulate in the culture medium, even at amounts of 200 mg/L or 500 mg/L or more, without toxicity to the growth of the host bacterium. In the method as described herein, the amount of accumulating linalool can be 200 mg/L or 500 mg/L or more, or 600 mg/L or more, or even 625 mg/L or 700 mg/L or more. The linalool can be accumulated at a high concentrations. The culture conditions, such as examples of components present in the culture medium, will be described herein.

The total content of volatile components in the linalool composition can mean the total weight of volatile organic compounds contained in the composition. The content of linalool in the linalool composition can mean the content (mg) of linalool per 1 L of the linalool composition. Examples of the identification and quantification methods of the volatile organic compounds and the linalool present in the linalool composition can include gas chromatography and a headspace method.

The headspace method is generally widely used for analyzing volatile components (Yumi Nagai, "Improved Analysis of Flavor Components in Alcoholic Beverages by Headspace Gas Chromatography," Journal of Food Science and Technology, 39(3), 264-270, 1992). When the total content of volatile components in the linalool composition is measured by the headspace method, the measurement may be carried out according to the following procedure, for example. A solution containing a linalool composition is enclosed in a headspace vial and heated under a certain condition, and then the identification of the volatile components is determined by separation and mass analysis by gas chromatography. A standard curve of the identified compound is generated so that the concentration of the compound present in the solution can be calculated and based on this, the total content of the volatile components and the constituent ratio of each component can be determined. In this way, the total content of volatile components in the composition can be measured.

When the total content of volatile components in the linalool composition is measured by gas chromatography, the measurement may be carried out according to the following procedure, for example. A method or the like has been reported in which volatile components are sampled, for example, using a Tenax TA (registered trademark) adsorbent (produced by GL Sciences Inc.) and the total chromatogram peak area, which is eluted and detected in a range of n-hexane and n-hexadecane using a hydrogen flame ionization detector or a mass spectrometer by a non-polar capillary column, is converted into a toluene equivalent amount (Japanese Industrial Standards JIS A 1965).

In the linalool composition as described herein, at least one volatile component other than linalool, or one or more of linalyl acetate, limonene, and caryophyllin are present in a smaller amount as compared to the plant extract, or are present in insubstantial amounts. Incidentally, when two or more volatile components are present, the respective volatile components can be present in a smaller amount as compared to the plant extract or are present in insubstantial amounts. The expression "present in a smaller amount or present in insubstantial amounts" can mean that the content of the components in the composition is smaller than the content of the components corresponding to the plant extract, and in general, the content of the volatile component with respect to the ratio of the content of impurities to the content of linalool is, for example, 40% or less, 30% or less, 20% or less, 10% or less, 7% or less, 6% or less, 5% or less, 4% or less, 3% or less, 2% or less, 1% or less, 0.5% or less, 0.3% or less, 0.1% or less, or non-detectable or 0%. The plant extract is generally an extract obtained by distillation of lavender (*Lavandula angustifolia*), for example, lavender essential oil obtained by the method described in Planta Med 2016; 82(01/02): 163-170, or an extract obtained by distillation of bergamot fruit (*Citrus aurantium* subsp. *Bergamia*), for example, bergamot essential oil described in Molecules 2009, 14(2), 839-849.

The linalool composition as described herein can be used as a flavor and/or a fragrance composition.

The linalool composition as described herein can contain an excess amount of R-linalool, for example, 1% or more (hereinafter, referred to as an R-linalool composition) or a linalool composition containing an excess amount of S-linalool, for example, 1% or more (hereinafter, referred to as an S-linalool composition).

In the R-linalool composition, the enantiomeric excess (e. e.) of R-linalool can be 1% or more. The enantiomeric excess can be, for example, 10% or more, 20% or more, 40% or more, 50% or more, 60% or more, 70% or more, 74% or more, 80% or more, 84% or more, 86% or more, 88% or more, 90% or more, or 100%. Therefore, the composition may be a composition containing R-linalool with a high enantiomeric excess.

The enantiomeric excess (e. e.) of R-linalool is defined by e.e.=(AR−AS)/(AR+AS), wherein AR represents a molar fraction of R-linalool, and AS represents a molar fraction of S-linalool. An area ratio of each peak of R-linalool and S-linalool in gas chromatography using a chiral column can be considered to be almost the same meaning as the molar ratio. The total area is regarded as 100%, and the area ratio of each peak of R-linalool and S-linalool corresponds to a molar fraction.

Regarding the molar ratios of R-linalool and S-linalool in the R-linalool composition, the molar ratio of R-linalool can be higher than that of S-linalool, that is, the composition is not a racemic form. The molar ratio is calculated from the area ratio (percentage) of each peak of R-linalool and S-linalool obtained by gas chromatography using a chiral column. Since the area value of each peak in a chromatogram is proportional to the substance amount, the area ratio of each peak can also be restated as the weight ratios of R-linalool and S-linalool. Furthermore, the molar ratio can also be obtained from an optical rotation of linalool present in the composition.

The ratio of the content of R-linalool to the total content of linalool plus volatile components in the R-linalool composition can be 60% or more, 70% or more, 80% or more, 85% or more, or 88% or more.

In the S-linalool composition, the enantiomeric excess (e. e.) of S-linalool can be 1% or more. The enantiomeric excess can be, for example, 10% or more, 20% or more, 40% or more, 50% or more, 60% or more, 70% or more, 75% or more, 80% or more, 84% or more, 86% or more, 88% or more, 90% or more, or 100%. Therefore, the composition may be a composition containing S-linalool with a high enantiomeric excess.

The enantiomeric excess (e. e.) of S-linalool is defined by e.e.=(AS−AR)/(AR+AS). The symbols are the same as those described in the definition of the enantiomeric excess of R-linalool.

Regarding the molar ratios of R-linalool and S-linalool in the S-linalool composition, the molar ratio of S-linalool can be higher than that of R-linalool, that is, the composition is not a racemic form. The molar ratio is calculated from the area ratio (percentage) of each peak of R-linalool and S-linalool obtained by gas chromatography using a chiral column. Since the area value of each peak in a chromatogram is proportional to the substance amount, the area ratio of each peak can also be restated as the weight ratios of R-linalool and S-linalool. Furthermore, the molar ratio can also be obtained from an optical rotation of linalool present in the composition.

The ratio of the content of S-linalool to the total content of linalool plus volatile components in the S-linalool composition can be 60% or more, 70% or more, 80% or more, 85% or more, or 88% or more.

Examples of measurement methods of the content of R-linalool in the R-linalool composition and the content of S-linalool in the S-linalool composition can include a combination of the methods exemplified above for measuring the content of linalool or measuring the molar ratio.

The "flavor composition" can include a composition containing one or a plurality of compounds, for example, flavor raw materials, which may provide a desired taste when combined with a solvent suitable for oral administration and oral consumption.

The "fragrance composition" can include a mixture of one or a plurality of fragrance components in any form, and one or a plurality of solvents or perfume raw materials. As known to those skilled in the art, one or a plurality of fragrance components, for example, perfume raw materials can provide aromatic odor to a composition, for example, household detergents, perfumes, or other commercially available products.

The linalool composition as described herein can be employed alone or in combination with other components in a fragrance composition, a flavor composition, a solvent, a medium, or the like. For example, the linalool composition as described herein can be employed in combination with the following compositions, for example, candles; air fresheners; perfumes; colognes; personal care products such as soaps, deodorants, shampoos, conditioners, shower gels, and shaving lotions; cosmetics such as lotions and cosmetic cream; detergents; and fabric care products and household detergents/cleaning agents. Such a compound can be widely applied to various products in the flavor industry. Examples of such products can include but are not limited thereto, food such as baked goods, dairy products, and deserts; beverages such as juice, soda water, tea, flavored water, fruit-based "smoothy" drinks, and milk-based drinks; confectionery such as sweets, hard candies, and gums; jelly products, snacks, pharmaceutical products, oral care products.

The linalool composition as described herein can be produced from a microorganism fermentation liquor or may be produced by purification of a microorganism fermentation liquor. The microorganism fermentation liquor is a fermentation product of the microorganism and is usually a liquid. The fermentation can mean that the microorganism utilizes an organic compound, thereby obtaining energy and producing linalool such as R-linalool or S-linalool.

The microorganism may be a microorganism that can produce a microorganism fermentation liquor containing linalool, and may be a bacterium or a fungus. The bacterium may be a gram-positive bacterium or a gram-negative bacterium. Examples of the microorganism can include a microorganism belonging to the family Enterobacteriaceae and a microorganism containing blue-green algae to be described herein.

Examples of the gram-positive bacterium can include bacteria belonging to the genera *Bacillus, Listeria, Staphylococcus, Streptococcus, Enterococcus, Clostridium, Corynebacterium*, and *Streptomyces*. Bacteria belonging to the genera *Bacillus* and *Corynebacterium* are particular examples.

Examples of the bacteria belonging to the genus *Bacillus* can include *Bacillus subtilis, Bacillus anthracis*, and *Bacillus cereus*. *Bacillus subtilis* is a particular example.

Examples of the bacteria belonging to the genus *Corynebacterium* can include *Corynebacterium glutamicum, Corynebacterium efficiens*, and *Corynebacterium callunae*. *Corynebacterium glutamicum* is a particular example.

Examples of the gram-negative bacterium can include bacteria belonging to the genera *Escherichia, Pantoea, Salmonella, Vibrio, Serratia, Enterobacter*, and Cyanobacteria. The bacteria belonging to the genera *Escherichia, Pantoea, Enterobacter*, and Cyanobacteria are particular examples.

*Escherichia coli* is a particular example as the bacterium belonging to the genus *Escherichia*. Examples can include *Escherichia coli* MG1655 and *Escherichia coli* W3110.

Examples of the bacteria belonging to the genus *Pantoea* can include *Pantoea ananatis, Pantoea stewartii, Pantoea agglomerans*, and *Pantoea citrea*. *Pantoea ananatis* and *Pantoea citrea* are particular examples. Strains exemplified in the European Patent Application Publication EP0952221 may be used as the bacteria belonging to the genus *Pantoea*. Examples of representative strains of the bacteria belonging to the genus *Pantoea* can include *Pantoea ananatis* AJ13355 strain (FERM BP-6614) and *Pantoea ananatis* AJ13356 strain (FERM BP-6615) disclosed in the European Patent Application Publication EP0952221, *Pantoea ananatis* SC17 strain (FERM BP-11091), and *Pantoea ananatis* SC17 (0) strain (Katashikina J I et al., BMC Mol Biol 2009; 10:34 VKPM B-9246).

Examples of the bacteria belonging to the genus *Enterobacter* can include *Enterobacter agglomerans* and *Enterobacter aerogenes*. The bacterial strains exemplified in the European Patent Application Publication EP0952221 may be used as the bacteria belonging to the genus *Enterobacter*. Examples of representative strains of the bacteria belonging to the genus *Enterobacter* can include *Enterobacter agglomerans* ATCC12287 strain, *Enterobacter aerogenes* ATCC13048 strain, *Enterobacter aerogenes* NBRC12010 strain (Biotechnol. Bioeng., 2007 Mar. 27; 98(2) 340-348), *Enterobacter aerogenes* AJ110637 (FERM BP-10955), and the like. The *Enterobacter aerogenes* AJ110637 strain was deposited at the International Patent Organism Depositary (IPOD), National Institute of Advanced Industrial Science and Technology (AIST) (Chuo No. 6, Higashi 1-1-1, Tsukuba City, Ibaraki Pref., JP, Postal code 305-8566; currently, International Patent Organism Depositary, National Institute of Technology and Evaluation (NITE-IPOD), #120, 2-5-8 Kazusakamatari, Kisarazu-shi, Chiba, 292-0818, Japan) on Aug. 22, 2007, and was converted to an international deposit under the Budapest Treaty on Mar. 13, 2008, and the assigned deposit number is FERM BP-10955.

Examples of the blue-green algae (Cyanobacteria) can include blue-green algae belonging to the genera *Anabaena, Arthrospira, Cyanothece, Nostoc, Prochlorococcus, Synechococcus,* and *Thermosynechococcus,* and blue-green algae belonging to the genus *Synechocystis* is preferable.

Examples of the bacterium belonging to the genus *Synechocystis* can include *Synechocystis.* sp. (for example, *Synechocystis.* sp. PCC6803, PCC6701, PCC6714, PCC6902, and PCC7008), and *Synechocystis* sp. PCC6803 is a particular example. Examples of representative strains of the bacteria belonging to the genus *Synechocystis* can include *Synechocystis* sp. PCC6803 GT strains (WO 2014/142051 A1).

*Synechocystis* sp. PCC6803 is available from Pasteur Institute, France, and ATCC27184 is available from American Type Culture Collection. The strains such as *Synechocystis* sp. PCC6803 GT can be derived from the PCC6803 strain based on the methods described in Qinglong et al. Int. J. Mol. Sci. 2015, 16, 24081-24093.

Examples of the fungus can include microorganisms belonging to the genera *Saccharomyces, Schizosaccharomyces, Yarrowia, Trichoderma, Aspergillus, Fusarium,* and *Mucor*. The microorganisms belonging to the genus *Saccharomyces, Schizosaccharomyces, Yarrowia,* or *Trichoderma* are particular examples.

Examples of the microorganisms belonging to the genus *Saccharomyces* can include *Saccharomyces carlsbergensis, Saccharomyces cerevisiae, Saccharomyces diastaticus, Saccharomyces douglasii, Saccharomyces kluyveri, Saccharomyces norbensis,* and *Saccharomyces oviformis. Saccharomyces cerevisiae* is a particular example.

*Schizosaccharomyces pombe* is a particular example of the microorganisms belonging to the genus *Schizosaccharomyces*.

*Yarrowia lypolytica* is a particular example of a microorganism belonging to the genus *Yarrowia*.

Examples of the microorganisms belonging to the genus *Trichoderma* can include *Trichoderma harzianum, Trichoderma koningii, Trichoderma longibrachiatum, Trichoderma reesei,* and *Trichoderma viride. Trichoderma reesei* is a particular example.

The aforementioned microorganism can express linalool synthase and can include an amplified linalool synthase gene. Depending on the linalool synthase, as described below, the linalool synthase can be expressed in the microorganism together with another enzyme.

Linalool synthase can refer to one or more enzymes involved in synthesis of linalool from geranyl diphosphate (GPP). When the linalool composition as described herein is an R-linalool composition, the linalool synthase activity can refer to an activity of producing at least R-linalool and/or a mixture of S-linalool and R-linalool. The linalool synthase activity can also refer to an activity of producing linalool with an enantiomeric excess of R-linalool that is, for example, 1% or more, 10% or more, 20% or more, 40% or more, 50% or more, 60% or more, 70% or more, 74% or more, 80% or more, 84% or more, 86% or more, 88% or more, 90% or more, or 100% or more, and the R-linalool synthase activity can be an activity of substantially producing only R-linalool. When the activity substantially produces only R-linalool, the enantiomeric excess of the produced R-linalool can be, usually, 80% or more, 84% or more, 86% or more, 88% or more, or 90% or more.

When the linalool composition as described herein is an S-linalool composition, the linalool synthase activity can refer to an activity of producing at least S-linalool and/or a mixture of S-linalool and R-linalool. The linalool synthase activity can also refer to an activity of producing linalool with an enantiomeric excess of S-linalool that is, for example, 1% or more, 10% or more, 20% or more, 40% or more, 50% or more, 60% or more, 70% or more, 75% or more, 80%. or more, 80% or more, 84% or more, 86% or more, 88% or more, 90% or more, or 100% or more, and the S-linalool synthase activity can be an activity of substantially producing only S-linalool. When the activity substantially produces only S-linalool, the enantiomeric excess of the produced S-linalool can be, usually, 80% or more, 84% or more, 86% or more, 88% or more, or 90% or more.

Linalool synthase may have at least one motif represented by the following formula:

$$DDX_1[F/Y][D/Y]X_2X_3G \qquad \text{(SEQ ID NO: 165)}$$

In the formula, D represents aspartic acid. [F/Y] represents phenylalanine (F) or tyrosine (Y). [D/Y] represents D or Y. $X_1$, $X_2$, X, and $X_3$ each independently represent an arbitrary amino acid. Examples of $X_1$ can include isoleucine (I), valine (V), methionine (M), or F; I or V are particular examples. Examples of $X_2$ can include V, I, alanine (A), or threonine (T); V is a particular example. Examples of $X_3$ can include Y, cysteine (C), histidine (H), glutamic acid (E), or F; and Y is a particular example.

Linalool synthase may have one or a plurality of this motif, but a particular example is having only one motif.

Examples of the motif can include as follows:

a combination in which $X_1$ is I, [F/Y] is F, [D/Y] is D, $X_2$ is V, and $X_3$ is Y;

a combination in which $X_1$ is I, [F/Y] is F, [D/Y] is D, $X_2$ is V, and $X_3$ is Y;

a combination in which $X_1$ is I, [F/Y] is F, [D/Y] is D, $X_2$ is V, and $X_3$ is H;

a combination in which $X_1$ is I, [F/Y] is F, [D/Y] is D, $X_2$ is T, and $X_3$ is Y;

a combination in which $X_1$ is I, [F/Y] is F, [D/Y] is Y, $X_2$ is V, and $X_3$ is C;

a combination in which $X_1$ is I, [F/Y] is Y, [D/Y] is D, $X_2$ is I, and $X_3$ is Y;

a combination in which $X_1$ is I, [F/Y] is Y, [D/Y] is D, $X_2$ is A, and $X_3$ is Y;

a combination in which $X_1$ is I, [F/Y] is Y, [D/Y] is D, $X_2$ is V, and $X_3$ is Y;

a combination in which $X_1$ is V, [F/Y] is Y, [D/Y] is D, $X_2$ is I, and $X_3$ is Y;

a combination in which $X_1$ is V, [F/Y] is Y, [D/Y] is D, $X_2$ is V, and $X_3$ is F;

a combination in which $X_1$ is M, [F/Y] is Y, [D/Y] is D, $X_2$ is I, and $X_3$ is Y; and a combination in which $X_1$ is F, [F/Y] is F, [D/Y] is D, $X_2$ is V, and $X_3$ is E.

Linalool synthase may be derived from any living substance in which it exists natively. Examples of living substances having native linalool synthase can include plants belonging to the genera *Actinidia, Coriandrum, Artemisia, Fragaria, Clarkia, Arabidopsis, Citrus, Perilla, Mentha, Lavandula, Picea, Solanum, Vitis, Malus, Ocimum,* and *Backhousia*, and actinomycete. When the linalool composition as described herein is an R-linalool composition, the linalool synthase can have R-linalool synthase activity (R-linalool synthase), and for example, linalool synthase native to a plant belonging to the genus *Arabidopsis, Perilla, Vitis, Mentha, Solanum, Lavandula,* or *Ocimum*, or actinomycete are particular examples, and linalool synthase native to a plant belonging to the genus *Arabidopsis, Perilla, Vitis, Mentha,* or *Ocimum*, or actinomycete are further particular examples. When the linalool composition as described herein is an S-linalool composition, the linalool synthase can have S-linalool synthase activity (S-linalool synthase), and for example, linalool synthase native to a plant belonging to the genus *Actinidia, Clarkia, Arabidopsis, Malus, Vitis,* or *Perilla* are particular examples, and linalool synthase native to a plant belonging to the genus *Actinidia, Arabidopsis, Perilla, Malus,* or *Clarkia* are further particular examples.

Examples of the plant belonging to the genus *Actinidia* can include hardy kiwifruit (*Actinidia arguta*) and silver vine (*Actinidia polygama*), and hardy kiwifruit is a particular example. Examples of the plant belonging to the genus *Coriandrum* can include coriander (*Coriandrum sativum*). Examples of the plant belonging to the genus *Artemisia* can include annual wormwood (*Artemisia annua*). Examples of the plant belonging to the genus *Backhousia* can include lemon myrtle (*Backhousia citriodora*). Examples of the plant belonging to the genus *Fragaria* can include strawberries (*Fragaria×ananassa*). Examples of the plant belonging to the genus *Clarkia* can include *clarkia* (*Clarkia breweri*). Examples of the plant belonging to the genus *Arabidopsis* can include thale-cress (*Arabidopsis thaliana*). Examples of the plant belonging to the genus *Citrus* can include unshu mikan (*Citrus unshiu*). Examples of the plant belonging to the genus *Perilla* can include Japanese basil (*Perilla hirtella; Perilla setoensis; Perilla frutescens* var. *crispa; Perilla frutescens* var. *hirtella*), and *Perilla frutescens* var. *crispa* is a particular example. Examples of the plant belonging to the genus *Mentha* can include bergamot Mint (*Mentha citrata*) and Water Mint (*Mentha aquatica*), and bergamot Mint is preferable. Examples of the plant belonging to the genus *Lavandula* can include lavender (*Lavandula angustifoha*). Examples of the plant belonging to the genus *Picea* can include Sitka spruce (*Picea sitchensis*) and Norway spruce (*Picea abies*). Examples of the plant belonging to the genus *Solanum* can include tomatoes (*Solanum lycopersicum*). Examples of the plant belonging to the genus *Malta* can include apples (*Malta domestica*). Examples of the plant belonging to the genus *Vitis* can include European grapes (*Vitis vinifera*). Examples of the plant belonging to the genus *Ocimum* can include *Basilico* (*Ocimum basilicum*).

Examples of the actinomycete can include microorganisms belonging to the genera *Streptomyces, Kitasatospora, Streptacidiphilus, Pseudonocardia, Actinoalloteichus, Actinokineospora, Actinomycetospora, Actinophytocola, Actinosynnema, Alloactinosynnema, Allokutzneria, Amycolatopsis, Crossiella, Goodfellowiella, Haloechinothrix, Kibdelosporangium, Kutzneria, Labedaea, Lechevalieria, Lentzea, Longimycelium, Prauserella, Saccharomonospora, Saccharopolyspora, Saccharothrix, Sciscionella, Streptoalloteichus, Tamaricihabitans, Thermobispora, Thermocrispum, Thermotunica, Umezawaea,* and *Yuhushiella*, and microorganisms belonging to the genus *Streptomyces*, for example, *Streptomyces clavuhgerus, Streptomyces griseus, Streptomyces antibioticus, Streptomyces avermitihs, Streptomyces verticillus, Streptomyces peuceticus, Streptomyces tsukubaensis,* or *Stereptomyces hygroscopicus* var. *limoneus* are particular examples.

The microorganism expressing linalool synthase can be obtained, for example, by transforming a microorganism with an expression vector containing a heterologous expression unit that contains a polynucleotide encoding the linalool synthase having a motif, the linalool synthase derived from a living substance in which it exists natively, or the linalool synthase having a motif and derived from a living substance in which it exists natively, and a promoter operably linked to the polynucleotide.

The phrase "derived from" or "native to" or "in which it exists natively" when referring to a nucleic acid sequence such as a gene, a promoter, and the like, or an amino acid sequence such as a protein, can mean a nucleic acid molecule or an amino acid molecule that are naturally or natively synthesized by a microorganism or can be isolated from the natural or wild-type microorganism.

Examples of the polynucleotide encoding the linalool synthase can include one or more polynucleotides designated as (a1) to (c20). When the linalool composition as described herein is an R-linalool composition, particular examples of the polynucleotide encoding linalool synthase include one or more of the polynucleotides designated as (a1) to (c6), (a9) to (c9), (a14) to (c14), (a16) to (c16), and (a18) to (c19), and even further particular examples include one or more polynucleotides designated as (a1) to (c1), (a8) to (a8), (a13) to (c13), (a15) to (c16), and (a18) to (c18). When the linalool composition as described herein is an S-linalool composition, particular examples of the polynucleotide encoding linalool synthase include one or more polynucleotides designated as (a7) to (c8), (a13) to (c13), (a15) to (c15), and (a20) to (c20).

The polynucleotides designated as (a1) to (c20) are as follows:

(a1) a polynucleotide having (i1) the nucleotide sequence represented by SEQ ID NO: 2, or (i11) the nucleotide sequence represented by SEQ ID NO: 3;

(131) a polynucleotide that has a nucleotide sequence having 90% or more identity to the nucleotide sequence of (i1) or (ii1) above, and encodes a protein having a linalool synthase activity;

(c1) a polynucleotide that hybridizes under stringent conditions with a polynucleotide having a nucleotide sequence complementary to the nucleotide sequence of (i1) or (ii1), and encodes a protein having a linalool synthase activity;

(a2) a polynucleotide having (i2) the nucleotide sequence represented by SEQ ID NO: 62, or (ii2) the nucleotide sequence represented by SEQ ID NO: 63;

(b2) a polynucleotide that has a nucleotide sequence having 90% or more identity to the nucleotide sequence of (i2) or (ii2) above, and encodes a protein having a linalool synthase activity;

(c2) a polynucleotide that hybridizes under stringent conditions with a polynucleotide having a nucleotide sequence complementary to the nucleotide sequence of (i2) or (ii2) above, and encodes a protein having a linalool synthase activity;

(a3) a polynucleotide having (i3) the nucleotide sequence represented by SEQ ID NO: 65, or (ii3) the nucleotide sequence represented by SEQ ID NO: 66;

(b3) a polynucleotide that has a nucleotide sequence having 90% or more identity to the nucleotide sequence of (i3) or (ii3) above, and encodes a protein having a linalool synthase activity;

(c3) a polynucleotide that hybridizes under stringent conditions with a polynucleotide having a nucleotide sequence complementary to the nucleotide sequence of (i3) or (ii3) above, and encodes a protein having a linalool synthase activity;

(a4) a polynucleotide having (i4) the nucleotide sequence represented by SEQ ID NO: 68, or (ii4) the nucleotide sequence represented by SEQ ID NO: 69;

(b4) a polynucleotide that has a nucleotide sequence having 90% or more identity to the nucleotide sequence of (i4) or (ii4) above, and encodes a protein having a linalool synthase activity;

(c4) a polynucleotide that hybridizes under stringent conditions with a polynucleotide having a nucleotide sequence complementary to the nucleotide sequence of (i4) or (ii4) above, and encodes a protein having a linalool synthase activity;

(a5) a polynucleotide having (i5) the nucleotide sequence represented by SEQ ID NO: 71, or (ii5) the nucleotide sequence represented by SEQ ID NO: 72;

(b5) a polynucleotide that has a nucleotide sequence having 90% or more identity to the nucleotide sequence of (i5) or (ii5) above, and encodes a protein having a linalool synthase activity;

(c5) a polynucleotide that hybridizes under stringent conditions with a polynucleotide having a nucleotide sequence complementary to the nucleotide sequence of (i5) or (ii5) above, and encodes a protein having a linalool synthase activity;

(a6) a polynucleotide having (i6) the nucleotide sequence represented by SEQ ID NO: 74, or (ii6) the nucleotide sequence represented by SEQ ID NO: 75;

(b6) a polynucleotide that has a nucleotide sequence having 90% or more identity to the nucleotide sequence of (i6) or (ii6) above, and encodes a protein having a linalool synthase activity;

(c6) a polynucleotide that hybridizes under stringent condition with a polynucleotide having a nucleotide sequence complementary to the nucleotide sequence of (i6) or (ii6) above, and encodes a protein having a linalool synthase activity;

(a7) a polynucleotide having (i7) the nucleotide sequence represented by SEQ ID NO:79, (ii7) the nucleotide sequence having the nucleotide residues at positions 79 to 1725 in the nucleotide sequence represented by SEQ ID NO: 79, or (iii7) the nucleotide sequence represented by SEQ ID NO: 80;

(b7) a polynucleotide that has a nucleotide sequence having 90% or more identity to the nucleotide sequence of (i7), (ii7) or (iii7) above, and encodes a protein having a linalool synthase activity;

(c7) a polynucleotide that hybridizes under stringent conditions with a polynucleotide having a nucleotide sequence complementary to the nucleotide sequence of (i7), (ii7), or (iii7) above, and encodes a protein having a linalool synthase activity;

(a8) a polynucleotide having (i8) the nucleotide sequence represented by SEQ ID NO: 85 (M1), or (ii8) the nucleotide sequence represented by SEQ ID NO: 98 (M14);

(b8) a polynucleotide that has a nucleotide sequence having 90% or more identity to the nucleotide sequence of (i8) or (ii8) above, and encodes a protein having a linalool synthase activity;

(c8) a polynucleotide that hybridizes under stringent conditions with a polynucleotide having a nucleotide sequence complementary to the nucleotide sequence of (i8) or (ii8) above, and encodes a protein having a linalool synthase activity;

(a9) a polynucleotide having (i9) the nucleotide sequence represented by SEQ ID NO: 86 (M2), or (ii9) the nucleotide sequence represented by SEQ ID NO: 100 (M16);

(b9) a polynucleotide that has a nucleotide sequence having 90% or more identity to the nucleotide sequence of (i9) or (ii9) above, and encodes a protein having a linalool synthase activity;

(c9) a polynucleotide that hybridizes under stringent conditions with a polynucleotide having a nucleotide sequence complementary to the nucleotide sequence of (i9) or (ii9) above, and encodes a protein having a linalool synthase activity;

(a10) a polynucleotide having (i10) the nucleotide sequence represented by SEQ ID NO: 87 (M3), or (ii10) the nucleotide sequence represented by SEQ ID NO: 102 (M18);

(b10) a polynucleotide that has a nucleotide sequence having 90% or more identity to the nucleotide sequence of (i10) or (ii10) above, and encodes a protein having a linalool synthase activity;

(c10) a polynucleotide that hybridizes under stringent conditions with a polynucleotide having a nucleotide sequence complementary to the nucleotide sequence of (i10) or (ii10) above, and encodes a protein having a linalool synthase activity;

(a11) a polynucleotide having (i11) the nucleotide sequence represented by SEQ ID NO: 88 (M4), or (ii11) the nucleotide sequence represented by SEQ ID NO: 104 (M20);

(b11) a polynucleotide that has a nucleotide sequence having 90% or more identity to the nucleotide sequence of (i11) or (ii11) above, and encodes a protein having a linalool synthase activity;

(c11) a polynucleotide that hybridizes under stringent conditions with a polynucleotide having a nucleotide sequence complementary to the nucleotide sequence of (i11) or (ii11) above, and encodes a protein having a linalool synthase activity;

(a12) a polynucleotide having (i12) the nucleotide sequence represented by SEQ ID NO: 89 (M5), or (ii12) the nucleotide sequence represented by SEQ ID NO: 106 (M22);

(b12) a polynucleotide that has a nucleotide sequence having 90% or more identity to the nucleotide sequence of (i12) or (ii12) above, and encodes a protein having a linalool synthase activity;

(c12) a polynucleotide that hybridizes under stringent conditions with a polynucleotide having a nucleotide sequence complementary to the nucleotide sequence of (i12) or (ii12) above, and encodes a protein having a linalool synthase activity;

(a13) a polynucleotide having (i13) the nucleotide sequence represented by SEQ ID NO: 90 (M6), or (ii13) the nucleotide sequence represented by SEQ ID NO: 108 (M24);

(b13) a polynucleotide that has a nucleotide sequence having 90% or more identity to the nucleotide sequence of (i13) or (ii13) above, and encodes a protein having a linalool synthase activity;

(c13) a polynucleotide that hybridizes under stringent conditions with a polynucleotide having a nucleotide sequence complementary to the nucleotide sequence of (i13) or (ii13) above, and encodes a protein having a linalool synthase activity;

(a14) a polynucleotide having (i14) the nucleotide sequence represented by SEQ ID NO: 91 (M7), or (ii14) the nucleotide sequence represented by SEQ ID NO: 110 (M26);

(b14) a polynucleotide that has a nucleotide sequence having 90% or more identity to the nucleotide sequence of (i14) or (ii14) above, and encodes a protein having a linalool synthase activity;

(c14) a polynucleotide that hybridizes under stringent conditions with a polynucleotide having a nucleotide sequence complementary to the nucleotide sequence of (i14) or (ii14) above, and encodes a protein having a linalool synthase activity;

(a15) a polynucleotide having (i15) the nucleotide sequence represented by SEQ ID NO: 92 (M8), or (ii15) the nucleotide sequence represented by SEQ ID NO: 112 (M28);

(b15) a polynucleotide that has a nucleotide sequence having 90% or more identity to the nucleotide sequence of (i15) or (ii15) above, and encodes a protein having a linalool synthase activity;

(c15) a polynucleotide that hybridizes under a stringent condition with a polynucleotide having a nucleotide sequence complementary to the nucleotide sequence of (i15) or (ii15) above, and encodes a protein having a linalool synthase activity;

(a16) a polynucleotide having (i16) the nucleotide sequence represented by SEQ ID NO: 93 (M9), or (ii16) the nucleotide sequence represented by SEQ ID NO: 114 (M30);

(b16) a polynucleotide that has a nucleotide sequence having 90% or more identity to the nucleotide sequence of (i16) or (ii16) above, and encodes a protein having a linalool synthase activity;

(c16) a polynucleotide that hybridizes under stringent conditions with a polynucleotide having a nucleotide sequence complementary to the nucleotide sequence of (i16) or (ii16) above, and encodes a protein having a linalool synthase activity;

(a17) a polynucleotide having (i17) the nucleotide sequence represented by SEQ ID NO: 94 (M10), or (ii17) the nucleotide sequence represented by SEQ ID NO: 116 (M32);

(b17) a polynucleotide that has a nucleotide sequence having 90% or more identity to the nucleotide sequence of (i17) or (ii17) above, and encodes a protein having a linalool synthase activity;

(c17) a polynucleotide that hybridizes under stringent conditions with a polynucleotide having a nucleotide sequence complementary to the nucleotide sequence of (i17) or (ii17) above, and encodes a protein having a linalool synthase activity;

(a18) a polynucleotide having (i18) the nucleotide sequence represented by SEQ ID NO: 95 (M11), or (ii18) the nucleotide sequence represented by SEQ ID NO: 118 (M34);

(b18) a polynucleotide that has a nucleotide sequence having 90% or more identity to the nucleotide sequence of (i18) or (ii18) above, and encodes a protein having a linalool synthase activity;

(c18) a polynucleotide that hybridizes under stringent conditions with a polynucleotide having a nucleotide sequence complementary to the nucleotide sequence of (i18) or (ii18) above, and encodes a protein having a linalool synthase activity;

(a19) a polynucleotide having (i19) the nucleotide sequence represented by SEQ ID NO: 96 (M12), or (ii19) the nucleotide sequence represented by SEQ ID NO: 120 (M36);

(b19) a polynucleotide that has a nucleotide sequence having 90% or more identity to the nucleotide sequence of (i19) or (ii19) above, and encodes a protein having a linalool synthase activity;

(c19) a polynucleotide that hybridizes under stringent conditions with a polynucleotide having a nucleotide sequence complementary to the nucleotide sequence of (i19) or (ii19) above, and encodes a protein having a linalool synthase activity;

(a20) a polynucleotide having (i20) the nucleotide sequence represented by SEQ ID NO: 97 (M13), or (ii20) the nucleotide sequence represented by SEQ ID NO: 122 (M38);

(b20) a polynucleotide that has a nucleotide sequence having 90% or more identity to the nucleotide sequence of (i20) or (ii20) above, and encodes a protein having a linalool synthase activity; and (c20) a polynucleotide that hybridizes under stringent conditions with a polynucleotide having a nucleotide sequence complementary to the nucleotide sequence of (i20) or (ii20) above, and encodes a protein having a linalool synthase activity.

The nucleotide sequence represented by SEQ ID NO: 2 is the full-length linalool synthase gene native to *Streptomyces clavuligerus*. The nucleotide sequence represented by SEQ ID NO: 2 may encode the amino acid sequence represented by SEQ ID NO: 1 and can include a coding region of the amino acid sequence of mature linalool synthase. The nucleotide sequence represented by SEQ ID NO: 3 has a nucleotide sequence in which codons in the nucleotide sequence represented by SEQ ID NO: 2 are modified. Incidentally, in the linalool synthase of *Streptomyces clavuligerus*, a putative chloroplast localization signal does not exist.

The nucleotide sequence represented by SEQ ID NO: 62 is a full-length linalool synthase gene native to *Arabidopsis thaliana* (thale-cress). The nucleotide sequence represented by SEQ ID NO: 62 may encode the amino acid sequence represented by SEQ ID NO: 61 and can include a coding region of the amino acid sequence of mature linalool synthase. The nucleotide sequence represented by SEQ ID NO: 63 has a nucleotide sequence in which codons in the nucleotide sequence represented by SEQ ID NO: 62 are modified. Incidentally, in the respective sequences represented by SEQ ID NOs: 61 to 63, a portion of the sequence corresponding to a putative chloroplast localization signal is absent.

The nucleotide sequence represented by SEQ ID NO: 65 is a full-length linalool synthase gene native to *Perilla frutescens* var *crispa* (shiso). The nucleotide sequence represented by SEQ ID NO: 65 may encode the amino acid sequence represented by SEQ ID NO: 64 and can include a coding region of the amino acid sequence of mature linalool synthase. The nucleotide sequence represented by SEQ ID NO: 66 has a nucleotide sequence in which codons in the nucleotide sequence represented by SEQ ID NO: 65 are modified. Incidentally, in the sequences represented by SEQ ID NOs: 64 to 66, a portion of the sequence corresponding to a putative chloroplast localization signal is absent.

The nucleotide sequence represented by SEQ ID NO:68 is a full-length linalool synthase gene native to *Vitis vinifera* (European grape). The nucleotide sequence represented by SEQ ID NO: 68 may encode the amino acid sequence represented by SEQ ID NO: 67 and can include a coding region of the amino acid sequence of mature linalool synthase. The nucleotide sequence represented by SEQ ID NO: 69 has a nucleotide sequence in which codons in the nucleotide sequence represented by SEQ ID NO: 68 are modified. Incidentally, in the sequences represented by SEQ ID NOs: 67 to 69, a portion of the sequence corresponding to a putative chloroplast localization signal is absent.

The nucleotide sequence represented by SEQ ID NO: 71 is a full-length linalool synthase gene native to *Mentha citrata* (bergamot Mint). The nucleotide sequence represented by SEQ ID NO: 71 may encode the amino acid sequence represented by SEQ ID NO: 70 and can include a coding region of the amino acid sequence of mature linalool synthase. The nucleotide sequence represented by SEQ ID NO: 72 has a nucleotide sequence in which codons in the nucleotide sequence represented by SEQ ID NO: 71 are modified. Incidentally, in the sequences represented by SEQ ID NOs: 70 to 72, a portion of the sequence corresponding to a putative chloroplast localization signal is absent.

The nucleotide sequence represented by SEQ ID NO: 74 is a full-length linalool synthase gene native to *Ocimum Basilicum* (Basilico). The nucleotide sequence represented by SEQ ID NO: 74 may encode the amino acid sequence represented by SEQ ID NO: 73 and can include a coding region of the amino acid sequence of mature linalool synthase. The nucleotide sequence represented by SEQ ID NO: 75 has a nucleotide sequence in which codons in the nucleotide sequence represented by SEQ ID NO: 74 are modified. Incidentally, in the sequences represented by SEQ ID NOs: 73 to 75, a portion of the sequence corresponding to a putative chloroplast localization signal is absent.

The nucleotide sequence represented by SEQ ID NO: 79 is a full-length nucleotide sequence of a linalool synthase gene native to hardy kiwifruit. The nucleotide sequence represented by SEQ ID NO: 79 may encode the amino acid sequence represented by SEQ ID NO: 78, the nucleotide sequence having nucleotide residues at positions 1 to 78 may encode a putative chloroplast localization signal, and the nucleotide sequence having nucleotide residues at positions 79 to 1725 (1722) may encode an amino acid sequence of mature linalool synthase. The nucleotide sequence represented by SEQ ID NO: 80 has a nucleotide sequence in which codons in the nucleotide sequence having nucleotide residues at positions 79 to 1725 (1722) in the nucleotide sequence represented by SEQ ID NO: 79 are modified and methionine codons are further added at the 5' terminus thereof.

The nucleotide sequence represented by SEQ ID NO: 85 (M1) is a full-length linalool synthase gene native to thalecress. The nucleotide sequence represented by SEQ ID NO: 85 (M1) may encode an amino acid sequence of mature linalool synthase represented by SEQ ID NO: 99 (M15). The nucleotide sequence represented by SEQ ID NO: 98 (M14) has a nucleotide sequence in which codons in the nucleotide sequence having nucleotide residues at positions 70 to 1644 (1641) in the nucleotide sequence represented by SEQ ID NO: 85 (M1) are modified.

The nucleotide sequence represented by SEQ ID NO: 86 (M2) is a full-length linalool synthase gene native to thalecress. The nucleotide sequence represented by SEQ ID NO: 86 (M2) may encode an amino acid sequence of mature linalool synthase represented by SEQ ID NO: 101 (M17). The nucleotide sequence represented by SEQ ID NO: 100 (M16) has a nucleotide sequence in which codons in the nucleotide sequence represented by SEQ ID NO: 86 (M2) are modified.

The nucleotide sequence represented by SEQ ID NO: 87 (M3) is a full-length linalool synthase gene native to *Citrus unshiu* (unshu mikan). The nucleotide sequence represented by SEQ ID NO: 87 (M3) may encode an amino acid sequence of mature linalool synthase represented by SEQ ID NO: 103 (M19). The nucleotide sequence represented by SEQ ID NO: 102 (M18) has a nucleotide sequence in which codons in the nucleotide sequence represented by SEQ ID NO: 87 (M3) are modified.

The nucleotide sequence represented by SEQ ID NO: 88 (M4) is a full-length linalool synthase gene native to *Citrus unshiu* (unshu mikan). The nucleotide sequence represented by SEQ ID NO: 88 (M4) may encode an amino acid sequence of mature linalool synthase represented by SEQ ID NO: 105 (M21). The nucleotide sequence represented by SEQ ID NO: 104 (M20) has a nucleotide sequence in which codons in the nucleotide sequence represented by SEQ ID NO: 88 (M4) are modified.

The nucleotide sequence represented by SEQ ID NO: 89 (M5) is a full-length of a linalool synthase gene native to *Citrus unshiu* (unshu mikan). The nucleotide sequence represented by SEQ ID NO: 89 (M5) may encode an amino acid sequence of mature linalool synthase represented by SEQ ID NO: 107 (M23). The nucleotide sequence represented by SEQ ID NO: 106 (M22) has a nucleotide sequence in which codons in the nucleotide sequence represented by SEQ ID NO: 89 (M5) are modified.

The nucleotide sequence represented by SEQ ID NO: 90 (M6) is a full-length linalool synthase gene native to apple. The nucleotide sequence represented by SEQ ID NO: 90 (M6) may encode an amino acid sequence of mature linalool synthase represented by SEQ ID NO: 109 (M25). The nucleotide sequence represented by SEQ ID NO: 108 (M24) has a nucleotide sequence in which codons in the nucleotide sequence represented by SEQ ID NO: 90 (M6) are modified.

The nucleotide sequence represented by SEQ ID NO: 91 (M7) is a full-length linalool synthase gene native to shiso. The nucleotide sequence represented by SEQ ID NO: 91 (M7) may encode an amino acid sequence of mature linalool synthase represented by SEQ ID NO: 111 (M27). The nucleotide sequence represented by SEQ ID NO: 110 (M26) has a nucleotide sequence in which codons in the nucleotide sequence represented by SEQ ID NO: 91 (M7) are modified.

The nucleotide sequence represented by SEQ ID NO: 92 (M8) is a full-length linalool synthase gene native to European grape. The nucleotide sequence represented by SEQ ID NO: 92 (M8) may encode an amino acid sequence of mature linalool synthase represented by SEQ ID NO: 113 (M29). The nucleotide sequence represented by SEQ ID NO: 112 (M28) has a nucleotide sequence in which codons in the nucleotide sequence represented by SEQ ID NO: 92 (M8) are modified.

The nucleotide sequence represented by SEQ ID NO: 93 (M9) is a full-length linalool synthase gene native to European grape. The nucleotide sequence represented by SEQ ID NO: 93 (M9) may encode an amino acid sequence of mature linalool synthase represented by SEQ ID NO: 115 (M31). The nucleotide sequence represented by SEQ ID NO: 114 (M30) has a nucleotide sequence in which codons in the nucleotide sequence represented by SEQ ID NO: 93 (M9) are modified.

The nucleotide sequence represented by SEQ ID NO: 94 (M10) is a full-length linalool synthase gene native to lavender. The nucleotide sequence represented by SEQ ID NO: 94 (M10) may encode an amino acid sequence of mature linalool synthase represented by SEQ ID NO: 117 (M33). The nucleotide sequence represented by SEQ ID NO: 116 (M32) has a nucleotide sequence in which codons in the nucleotide sequence represented by SEQ ID NO: 94 (M10) are modified.

The nucleotide sequence represented by SEQ ID NO: 95 (M11) is a full-length linalool synthase gene native to bergamot mint. The nucleotide sequence represented by SEQ ID NO: 95 (M11) may encode an amino acid sequence of mature linalool synthase represented by SEQ ID NO: 119 (M35). The nucleotide sequence represented by SEQ ID NO: 118 (M34) has a nucleotide sequence in which codons in the nucleotide sequence represented by SEQ ID NO: 95 (M11) are modified.

The nucleotide sequence represented by SEQ ID NO: 96 (M12) is a full-length linalool synthase gene native to *basilico*. The nucleotide sequence represented by SEQ ID NO: 96 (M12) may encode an amino acid sequence of mature linalool synthase represented by SEQ ID NO: 121 (M37). The nucleotide sequence represented by SEQ ID NO: 120 (M36) has a nucleotide sequence in which codons in the nucleotide sequence represented by SEQ ID NO: 96 (M12) are modified.

The nucleotide sequence represented by SEQ ID NO: 97 (M13) is a full-length linalool synthase gene native to clarkia. The nucleotide sequence represented by SEQ ID NO: 97 (M13) may encode an amino acid sequence of mature linalool synthase represented by SEQ ID NO: 123 (M39). The nucleotide sequence represented by SEQ ID NO: 122 (M38) has a nucleotide sequence in which codons in the nucleotide sequence represented by SEQ ID NO: 97 (M13) are modified.

The percent identity to the nucleotide sequence may be 90%, 91%, 92%, 93%, 94%, 95%, 96%, 97%, 98%, or 99% or more.

The percent identity of the nucleotide sequences, and the percent identity of the amino acid sequences as described herein can be determined using algorithm BLAST (Pro. Natl. Acad. Sci. USA, 90, 5873 (1993)) by Karlin and Altschul, and FASTA (Methods Enzymol., 183, 63 (1990)) by Pearson. The programs referred to as BLASTP and BLASTN were developed based on this algorithm BLAST (see ncbi.nlm.nih.gov). Thus, the percent identity of the nucleotide sequences and the amino acid sequences may be calculated using these programs with their default settings. Also, for example, a numerical value obtained by calculating similarity as a percentage at a setting of "unit size to compare=2" using the full-length of a polypeptide portion encoded in ORF with the software GENETYX Ver. 7.0.9 from Genetyx Corporation employing Lipman-Pearson method may be used as the homology value of the amino acid sequences. The lowest value among the values derived from these calculations may be employed as the percent identity of the nucleotide sequences and the amino acid sequences.

The "stringent conditions" can refer to conditions where a so-called specific hybrid is formed and a non-specific hybrid is not formed. It is difficult to clearly quantify such a condition. However, these conditions can be when substantially the same polynucleotides having high identity, for example, the polynucleotides having the percent identity described above, hybridize with each other and polynucleotides having lower identity than above do not hybridize with each other. Specifically, such conditions can include hybridization in 6×SCC (sodium chloride/sodium citrate) at about 45° C. followed by one or two or more washings in 0.2×SCC and 0.1% SDS at 50 to 65° C. DNAs that hybridize with each other may have identity of more than 90%, 91%, 92%, 93%, 94%, 95%, 96%, 97%, 98%, or 99%.

The (a1) to (c20) polynucleotides may be DNA or RNA obtained from the corresponding DNA by substituting a thymine base with a uracil base, but are preferably DNA.

Linalool synthase can be one or more of the proteins designated as (A1) to (C28). When the linalool composition as described herein is an R-linalool composition, particular examples of the linalool synthase include one or more proteins designated as (A1) to (C6), (A9) to (C9), (A14) to (C14), (A16) to (C16), (A18) to (C19), (A21) to (C21), and (A23) to (C24), and even further particular examples include one or more proteins designated as (A1) to (C6), (A9) to (C9), (A14) to (C14), (A16) to (C16), and (A18) to (C19). When the linalool composition as described herein is an S-linalool composition, particular examples of the linalool synthase include one or more proteins designated as (A7) to (C7), (A8) to (C8), (A13) to (C13), (A15) to (C15), (A20) to (C20), and (A25) to (C28); and even further particular examples include one or more proteins designated as (A7) to (C7), (A8) to (C8), (A13) to (C13), (A15) to (C15), and (A20) to (C20).

The proteins designated as (A1) to (c20) are as follows (A1) a protein having (i1') the full-length amino acid sequence represented by SEQ ID NO: 1;

(B1) a protein that has an amino acid sequence having 90% or more identity to the amino acid sequence of (i1'), and has a linalool synthase activity;

(C1) a protein that has an amino acid sequence having a deletion, substitution, addition, or insertion of one or several amino acids in the amino acid sequence of (i1'), and has a linalool synthase activity;

(A2) a protein having (i2') the full-length amino acid sequence represented by SEQ ID NO: 61;

(B2) a protein that has an amino acid sequence having 90% or more identity to the amino acid sequence of (i2'), and has a linalool synthase activity;

(C2) a protein that has an amino acid sequence having a deletion, substitution, addition, or insertion of one or several amino acids in the amino acid sequence of (i2'), and has a linalool synthase activity;

(A3) a protein having (i3') the full-length amino acid sequence represented by SEQ ID NO: 64;

(B3) a protein that has an amino acid sequence having 90% or more identity to the amino acid sequence of (i3'), and has a linalool synthase activity;

(C3) a protein that has an amino acid sequence having a deletion, substitution, addition, or insertion of one or several amino acids in the amino acid sequence of (i3'), and has a linalool synthase activity;

(A4) a protein having (i4') the full-length amino acid sequence represented by SEQ ID NO: 67;

(B4) a protein that has an amino acid sequence having 90% or more identity to the amino acid sequence of (i4'), and has a linalool synthase activity;

(C4) a protein that has an amino acid sequence having a deletion, substitution, addition, or insertion of one or several amino acids in the amino acid sequence of (i4'), and has a linalool synthase activity;

(A5) a protein having (i5') the full-length amino acid sequence represented by SEQ ID NO: 70;

(B5) a protein that has an amino acid sequence having 90% or more identity to the amino acid sequence of (i5'), and has a linalool synthase activity;

(C5) a protein that has an amino acid sequence having a deletion, substitution, addition, or insertion of one or several amino acids in the amino acid sequence of (i5'), and has a linalool synthase activity;

(A6) a protein having (i6') the full-length amino acid sequence represented by SEQ ID NO: 73;

(B6) a protein that has an amino acid sequence having 90% or more identity to the amino acid sequence of (i6'), and has a linalool synthase activity;

(C6) a protein that has an amino acid sequence having a deletion, substitution, addition, or insertion of one or several amino acids in the amino acid sequence of (i6'), and has a linalool synthase activity;

(A7) a protein having (i7') the full-length amino acid sequence represented by SEQ ID NO: 78, or (ii7') the amino acid sequence having the amino acid residues at positions 27 to 574 in the amino acid sequence represented by SEQ ID NO:78;

(B7) a protein that has an amino acid sequence having 90% or more identity to the amino acid sequence of (i7') or (ii7'), and has a linalool synthase activity;

(C7) a protein that has an amino acid sequence having a deletion, substitution, addition, or insertion of one or several amino acids in the amino acid sequence of (i7') or (ii7'), and has a linalool synthase activity;

(A8) a protein having (i8') the full-length amino acid sequence represented by SEQ ID NO: 99 (M15);

(B8) a protein that has an amino acid sequence having 90% or more identity to the amino acid sequence of (i8'), and has a linalool synthase activity;

(C8) a protein that has an amino acid sequence having a deletion, substitution, addition, or insertion of one or several amino acids in the amino acid sequence of (i8'), and has a linalool synthase activity;

(A9) a protein having (i9') the full-length amino acid sequence represented by SEQ ID NO: 101 (M17);

(B9) a protein that has an amino acid sequence having 90% or more identity to the amino acid sequence of (i9'), and has a linalool synthase activity;

(C9) a protein that has an amino acid sequence having a deletion, substitution, addition, or insertion of one or several amino acids in the amino acid sequence of (i9'), and has a linalool synthase activity;

(A10) a protein having (i10') the full-length amino acid sequence represented by SEQ ID NO: 103 (M19);

(B10) a protein that has an amino acid sequence having 90% or more identity to the amino acid sequence of (i10'), and has a linalool synthase activity;

(C10) a protein that has an amino acid sequence having a deletion, substitution, addition, or insertion of one or several amino acids in the amino acid sequence of (i10'), and has a linalool synthase activity;

(A11) a protein having (i11') the full-length amino acid sequence represented by SEQ ID NO: 105 (M21);

(B11) a protein that has an amino acid sequence having 90% or more identity to the amino acid sequence of (i11), and has a linalool synthase activity;

(C11) a protein that has an amino acid sequence having a deletion, substitution, addition, or insertion of one or several amino acids in the amino acid sequence of (i11'), and has a linalool synthase activity;

(A12) a protein having (i12') the full-length amino acid sequence represented by SEQ ID NO: 107 (M23);

(B12) a protein that has an amino acid sequence having 90% or more identity to the amino acid sequence of (i12'), and has a linalool synthase activity;

(C12) a protein that has an amino acid sequence having a deletion, substitution, addition, or insertion of one or several amino acids in the amino acid sequence of (i12'), and has a linalool synthase activity;

(A13) a protein having (i13') the full-length amino acid sequence represented by SEQ ID NO: 109 (M25);

(B13) a protein that has an amino acid sequence having 90% or more identity to the amino acid sequence of (i13'), and has a linalool synthase activity;

(C13) a protein that has an amino acid sequence having a deletion, substitution, addition, or insertion of one or several amino acids in the amino acid sequence of (i13'), and has a linalool synthase activity;

(A14) a protein having (i14') the full-length amino acid sequence represented by SEQ ID NO: 111 (M27);

(B14) a protein that has an amino acid sequence having 90% or more identity to the amino acid sequence of (i14'), and has a linalool synthase activity;

(C14) a protein that has an amino acid sequence having a deletion, substitution, addition, or insertion of one or several amino acids in the amino acid sequence of (i14'), and has a linalool synthase activity;

(A15) a protein having (i15') the full-length amino acid sequence represented by SEQ ID NO: 113 (M29);

(B15) a protein that has an amino acid sequence having 90% or more identity to the amino acid sequence of (i15'), and has a linalool synthase activity;

(C15) a protein that has an amino acid sequence having a deletion, substitution, addition, or insertion of one or several amino acids in the amino acid sequence of (i15'), and has a linalool synthase activity;

(A16) a protein having (i16') the full-length amino acid sequence represented by SEQ ID NO: 115 (M31);

(B16) a protein that has an amino acid sequence having 90% or more identity to the amino acid sequence of (i16'), and has a linalool synthase activity;

(C16) a protein that has an amino acid sequence having a deletion, substitution, addition, or insertion of one or several amino acids in the amino acid sequence of (i16'), and has a linalool synthase activity;

(A17) a protein having (i17') the full-length amino acid sequence represented by SEQ ID NO: 117 (M33);

(B17) a protein that has an amino acid sequence having 90% or more identity to the amino acid sequence of (i17'), and has a linalool synthase activity;

(C17) a protein that has an amino acid sequence having a deletion, substitution, addition, or insertion of one or several amino acids in the amino acid sequence of (i17'), and has a linalool synthase activity;

(A18) a protein having (i18') the full-length amino acid sequence represented by SEQ ID NO: 119 (M35);

(B18) a protein that has an amino acid sequence having 90% or more identity to the amino acid sequence of (i18'), and has a linalool synthase activity;

(C18) a protein that has an amino acid sequence having a deletion, substitution, addition, or insertion of one or several amino acids in the amino acid sequence of (i18'), and has a linalool synthase activity;

(A19) a protein having (i19') the full-length amino acid sequence represented by SEQ ID NO: 121 (M37);

(B19) a protein that has an amino acid sequence having 90% or more identity to the amino acid sequence of (i19'), and has a linalool synthase activity;

(C19) a protein that has an amino acid sequence having a deletion, substitution, addition, or insertion of one or several amino acids in the amino acid sequence of (i19'), and has a linalool synthase activity;

(A20) a protein having (i20') the full-length amino acid sequence represented by SEQ ID NO: 123 (M39);

(B20) a protein that has an amino acid sequence having 90% or more identity to the amino acid sequence of (i20'), and has a linalool synthase activity;

(C20) a protein that has an amino acid sequence having a deletion, substitution, addition, or insertion of one or several amino acids in the amino acid sequence of (i20'), and has a linalool synthase activity;

(A21) a protein having (i21') the full-length amino acid sequence represented by SEQ ID NO: 157;

(B21) a protein that has an amino acid sequence having 90% or more identity to the amino acid sequence of (i21'), and has a linalool synthase activity;

(C21) a protein that has an amino acid sequence having a deletion, substitution, addition, or insertion of one or several amino acids in the amino acid sequence of (i21'), and has a linalool synthase activity;

(A22) a protein having (i22') the full-length amino acid sequence represented by SEQ ID NO: 158;

(B22) a protein that has an amino acid sequence having 90% or more identity to the amino acid sequence of (i22'), and has a linalool synthase activity;

(C22) a protein that has an amino acid sequence having a deletion, substitution, addition, or insertion of one or several amino acids in the amino acid sequence of (i22'), and has a linalool synthase activity;

(A23) a protein having (i23') the full-length amino acid sequence represented by SEQ ID NO: 159;

(B23) a protein that has an amino acid sequence having 90% or more identity to the amino acid sequence of (i23'), and has a linalool synthase activity;

(C23) a protein that has an amino acid sequence having a deletion, substitution, addition, or insertion of one or several amino acids in the amino acid sequence of (i23'), and has a linalool synthase activity;

(A24) a protein having (i24') the full-length amino acid sequence represented by SEQ ID NO: 160;

(B24) a protein that has an amino acid sequence having 90% or more identity to the amino acid sequence of (i24'), and has a linalool synthase activity;

(C24) a protein that has an amino acid sequence having a deletion, substitution, addition, or insertion of one or several amino acids in the amino acid sequence of (i24'), and has a linalool synthase activity;

(A25) a protein having (i25') the full-length amino acid sequence represented by SEQ ID NO: 161;

(B25) a protein that has an amino acid sequence having 90% or more identity to the amino acid sequence of (i25'), and has a linalool synthase activity;

(C25) a protein that has an amino acid sequence having a deletion, substitution, addition, or insertion of one or several amino acids in the amino acid sequence of (i25'), and has a linalool synthase activity;

(A26) a protein having (i26') the full-length amino acid sequence represented by SEQ ID NO: 162;

(B26) a protein that has an amino acid sequence having 90% or more identity to the amino acid sequence of (i26'), and has a linalool synthase activity;

(C26) a protein that has an amino acid sequence having a deletion, substitution, addition, or insertion of one or several amino acids in the amino acid sequence of (i26'), and has a linalool synthase activity;

(A27) a protein having (i27') the full-length amino acid sequence represented by SEQ ID NO: 163;

(B27) a protein that has an amino acid sequence having 90% or more identity to the amino acid sequence of (i27'), and has a linalool synthase activity;

(C27) a protein that has an amino acid sequence having a deletion, substitution, addition, or insertion of one or several amino acids in the amino acid sequence of (i27'), and has a linalool synthase activity;

(A28) a protein having (i28') the full-length amino acid sequence represented by SEQ ID NO: 164;

(B28) a protein that has an amino acid sequence having 90% or more identity to the amino acid sequence of (i28'), and has a linalool synthase activity; and (C28) a protein that has an amino acid sequence having a deletion, substitution, addition, or insertion of one or several amino acids in the amino acid sequence of (i28'), and has a linalool synthase activity.

The full-length amino acid sequences represented by SEQ ID NOs: 1, 61, 64, 67, 70, and 73 can include mature linalool synthases native to *Streptomyces clavuligerus* (actinomycete), *Arabidopsis thaliana* (thale-cress), *Perilla frutescens* var. *crispa* (Japanese basil), *Vitis vinifera* (European grape), *Mentha citrata* (bergamot Mint), and *Ocimum basilicum* (*basilico*), respectively.

The amino acid sequence having amino acid residues at positions 1 to 26 in the amino acid sequence represented by SEQ ID NO: 78 can include a putative chloroplast localization signal. The amino acid sequence having amino acid residues at positions 27 to 574 can include mature linalool synthase. When mature linalool synthase is expressed by the microorganism, usually, a sequence with methionine residues at the N terminus can be used.

The full-length amino acid sequences represented by SEQ ID NOs: 99 and 101 (M15 and M17) each can include mature linalool synthase native to *Arabidopsis thaliana* (thale-cress) (SEQ ID NO: M15 is terpene synthase 14 and SEQ ID NO: M17 is terpene synthase 10). The amino acid sequences represented by SEQ ID NOs: 103, 105, and 107 (M19, M21, and M23) each can include mature linalool synthase native to *Citrus unshiu*. The amino acid sequence represented by SEQ ID NO: 109 (M25) can include mature linalool synthase native to *Mahis domestica* (apple). The amino acid sequence represented by SEQ ID NO: 111 (M27) can include mature linalool synthase native to *Perilla frutescens* var. *crispa* (shiso). The amino acid sequences represented by SEQ ID NOs: 113 and 115 (M29 and M31) each can include mature amino acid sequences of mature linalool synthases native to *Vitis vinifera* (European grape) (respectively, (3S)-linalool/(E)-nerolidol synthase and (3R)-linalool synthase). The amino acid sequence represented by SEQ ID NO: 117 (M33) can include mature linalool synthase of *Lavandula angustifoha* (lavender). The amino acid sequence represented by SEQ ID NO: 119 (M35) can include mature linalool synthase native to *Mentha citrata* (bergamot Mint). The amino acid sequence represented by SEQ ID NO: 121 (M37) can include mature linalool synthase (R-linalool synthase) of *Ocimum basilicum* (*basilico*). The amino acid sequence represented by SEQ ID NO: 123 (M39) can include mature linalool synthase (S-linalool synthase) of *Clarkia breweri* (*clarkia*). The amino acid sequence of SEQ ID NO: 157 can include mature linalool synthase (R-linalool synthase) of *Solanum lycopersicum* (tomato). The amino acid sequence of SEQ ID NO: 158 can include mature linalool synthase of *Backhousia citriodora* (lemon myrtle). The amino acid sequences of SEQ ID NOs: 159 and 160 can include mature linalool synthase of *Artemisia annua* (annual wormwood). The amino acid sequences of SEQ ID NO: 161 can include mature linalool synthase (S-linalool synthase) of *Actinidia arguta* (hardy kiwifruit). The amino acid sequences of SEQ ID NO: 162 can include mature linalool synthase (S-linalool synthase) of *Actinidia polygama* (silver vine). The amino acid sequences of SEQ ID NO: 163 can include mature amino acid synthase (S-linalool synthase) of *Perilla frutescens* var. *hirtella* (shiso). The amino acid sequence of SEQ ID NO: 164 can include mature amino acid synthase (S-linalool synthase) of *Perilla setoensis* (shiso).

The amino acid sequences of SEQ ID NOs: 99, 101, 103, 105, 107, 109, 111, 113, 115, 117, 119, 121, 123 (M15, M17, M19, M21, M23, M25, M27, M29, M31, M33, M35, M37, M39, respectively), and 157 to 164 each have a motif represented by the formula: $DDX_1[F/Y][D/Y]X_2X_3G$ (SEQ ID NO: 165).

The percent identity to the amino acid sequence may be 90%, 91%, 92%, 93%, 94%, 95%, 96%, 97%, 98%, or 99% or more.

Examples of a mutation can include deletion, substitution, addition, and insertion of amino acid residues. The mutation of one or several amino acids may be introduced into one region or multiple different regions in the amino acid sequence. The term "one or several" can indicate a range in which a three-dimensional structure and an activity of the protein are not greatly impaired. In these proteins, the number represented by "one or several" can be, for example, 1 to 100, 1 to 80, 1 to 50, 1 to 30, 1 to 20, 1 to 10, or 1 to 5. The above protein may have a methionine residue at the N-terminus. The above protein may have a tag at the C-terminus for purification, such as a histidine tag.

The proteins designated as (B1) and (C1) can have a linalool synthase activity that is 50% or more, 60% or more, 70% or more, 80% or more, 90% or more, or 95% or more of the linalool synthase activity of the protein that includes the amino acid sequence designated as (A1) when measured under the same conditions. The proteins designated as (B2) and (C2) can have a linalool synthase activity that is 50% or more, 60% or more, 70% or more, 80% or more, 90% or more, or 95% or more of the linalool synthase activity of the protein that includes the amino acid sequence designated as (A2) above when measured under the same conditions. The proteins designated as (B3) or (C3) can have a linalool synthase activity that is 50% or more, 60% or more, 70% or more, 80% or more, 90% or more, or 95% or more of the linalool synthase activity of the protein that includes the amino acid sequence designated as (A3) when measured under the same conditions. The proteins designated as (B4) and (C4) can have a linalool synthase activity that is 50% or more, 60% or more, 70% or more, 80% or more, 90% or more, or 95% or more of the linalool synthase activity of the protein that includes the amino acid sequence designated as (A4) when measured under the same conditions. The proteins of (B5) and (C5) can have a linalool synthase activity that is 50% or more, 60% or more, 70% or more, 80% or more, 90% or more, or 95% or more of the linalool synthase activity of the protein that includes the amino acid sequence designated as (A5) when measured under the same conditions. The proteins designated as (B6) and (C6) can have a linalool synthase activity that is 50% or more, 60% or more, 70% or more, 80% or more, 90% or more, or 95% or more of the linalool synthase activity of the protein that includes the amino acid sequence designated as (A6) when measured under the same conditions.

The proteins designated as (B2) and (C2) can have a linalool synthase activity that is 50% or more, 60% or more, 70% or more, 80% or more, 90% or more, or 95% or more of the linalool synthase activity of the protein that includes the amino acid sequence designated as either (i2') or (ii2') when measured under the same conditions.

The proteins designated as (B7) and (C7) can have a linalool synthase activity that is 50% or more, 60% or more, 70% or more, 80% or more, 90% or more, or 95% or more of the linalool synthase activity of the protein that includes the amino acid sequence designated as (A7) when measured under the same conditions. The proteins designated as (B8) and (C8) can have a linalool synthase activity that is 50% or more, 60% or more, 70% or more, 80% or more, 90% or more, or 95% or more of the linalool synthase activity of the protein that includes the amino acid sequence designated as (A8) when measured under the same conditions. The proteins designated as (B9) and (C9) can have a linalool synthase activity that is 50% or more, 60% or more, 70% or more, 80% or more, 90% or more, or 95% or more of the linalool synthase activity of the protein that includes the amino acid sequence designated as (A9) when measured under the same conditions. The proteins designated as (B10) and (C10) can have a linalool synthase activity that is 50% or more, 60% or more, 70% or more, 80% or more, 90% or more, or 95% or more of the linalool synthase activity of the protein that includes the amino acid sequence designated as (A10) when measured under the same conditions. The proteins designated as (B11) and (C11) can have a linalool synthase activity that is 50% or more, 60% or more, 70% or more, 80% or more, 90% or more, or 95% or more of the linalool synthase activity of the protein that includes the amino acid sequence designated as (A11) when measured under the same conditions. The proteins designated as (B12) and (C12) can have a linalool synthase activity that is 50% or more, 60% or more, 70% or more, 80% or more, 90% or more, or 95% or more of the linalool synthase activity of the protein that includes the amino acid sequence designated as (A12) above when measured under the same conditions. The proteins designated as (B13) and (C13) can have a linalool synthase activity that is 50% or more, 60% or more, 70% or more, 80% or more, 90% or more, or 95% or more of the linalool synthase activity of the protein that includes the amino acid sequence designated as (A13) when measured under the same conditions. The proteins designated as (B14) and (C14) can have a linalool synthase activity that is 50% or more, 60% or more, 70% or more, 80% or more, 90% or more, or 95% or more of the linalool synthase activity of the protein that includes the amino acid sequence designated as (A14) above when measured under the same conditions. The proteins designated as (B15) and (C15) can have a linalool synthase activity that is 50% or more, 60% or more, 70% or more, 80% or more, 90% or more, or 95% or more of the linalool synthase activity of the protein that includes the amino acid sequence designated as (A15) when measured under the same conditions. The proteins designated as (B16) and (C16) can have a linalool synthase activity that is 50% or more, 60% or more, 70% or more, 80% or more, 90% or more, or 95% or more of the linalool synthase activity of the protein that includes the amino acid sequence designated as (A16) when measured under the same conditions. The proteins designated as (B17) and (C17) can have a linalool synthase activity that is 50% or more, 60% or more, 70% or more, 80% or more, 90% or more, or 95% or more of the linalool synthase activity of the protein that includes the amino acid sequence designated as (A17) when measured under the same conditions. The proteins designated as (B18) and (C18) can have a linalool synthase activity that is 50% or more, 60% or more, 70% or more, 80% or more, 90% or more, or 95% or more of the linalool synthase activity of the protein that includes the amino acid sequence designated as (A18) when measured under the same conditions. The proteins designated as (B19) and (C19) can have a linalool synthase activity that is 50% or more, 60% or more, 70% or more, 80% or more, 90% or more, or 95% or more of the linalool synthase activity of the protein that includes the amino acid sequence designated as (A19) when measured under the same conditions. The proteins designated as (B20) and (C20) can have a linalool synthase activity that is 50% or more, 60% or more, 70% or more, 80% or more, 90% or more, or 95% or more of the linalool synthase activity of the protein that includes the amino acid sequence designated as (A20) when measured under the same conditions. The proteins designated as (B21) and (C21) can have a linalool synthase activity that is 50% or more, 60% or more, 70% or more, 80% or more, 90% or more, or 95% or more of the linalool synthase activity of the protein that includes the amino acid sequence designated as (A21) when measured under the same conditions. The proteins designated as (B22) and (C22) can have a linalool synthase activity that is 50% or more, 60% or more, 70% or more, 80% or more, 90% or more, or 95% or more of the linalool synthase activity of the protein that includes the amino acid sequence designated as (A22) when measured under the same conditions. The proteins designated as (B23) and (C23) can have a linalool synthase activity that is 50% or more, 60% or more, 70% or more, 80% or more, 90% or more, or 95% or more of the linalool synthase activity of the protein that includes the amino acid sequence designated as (A23) when measured under the same conditions. The proteins designated as (B24) and (C24) can have a linalool synthase activity that is 50% or more, 60% or more, 70% or more, 80% or more, 90% or more, or 95% or more of the linalool synthase activity of the protein that includes the amino acid sequence designated as (A24) when measured under the same conditions. The proteins designated as (B25) and (C25) can have a linalool synthase activity that is 50% or more, 60% or more, 70% or more, 80% or more, 90% or more, or 95% or more of the linalool synthase activity of the protein that includes the amino acid sequence designated as (A25) when measured under the same conditions. The proteins designated as (B26) and (C26) can have a linalool synthase activity that is 50% or more, 60% or more, 70% or more, 80% or more, 90% or more, or 95% or more of the linalool synthase activity of the protein that includes the amino acid sequence designated as (A26) when measured under the same conditions.

In the protein, the mutation may be introduced into sites in a catalytic domain and sites other than the catalytic domain as long as an objective activity is retained. The positions of amino acid residues to be mutated in the protein, which is capable of retaining the objective activity, would be understood by a person of ordinary skill in the art. Specifically, the person ordinary skill in the art would be able to recognize the correlation between structure and function, since a person skilled in the art can 1) compare the amino acid sequences of multiple proteins having the same type of activity, for example, the amino acid sequence represented by SEQ ID NO: 1 or 4 and the amino acid sequences of other linalool synthases, 2) determine regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, a person skilled in the art would be able to identify the positions of the amino acid residues that can be mutated in the amino acid sequence of the linalool synthase.

When the amino acid residue is mutated by substitution, the substitution of the amino acid residue may be conservative substitution. The term "conservative substitution" can refer to substitution of a certain amino acid residue with an amino acid residue having a similar side chain. Families of amino acid residues having similar side chains are well-known in the art. Examples of such families can include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group-containing side chain (e.g., alkoxy, phenoxy group-containing side chain) (e.g., serine, threonine, tyrosine), and amino acids having a sulfur-containing side chain (e.g., cysteine, methionine). The conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

The microorganism expressing linalool synthase may also express geranyl diphosphate synthase, and the microorganism can express geranyl diphosphate synthase depending on the linalool synthase to be introduced. Dimethylallyl diphosphate (DMAPP) is known as a precursor of peptide glycan and an electron acceptor, such as menaquinone and the like, and is essential for growth of microorganisms (Fujisaki et al., J. Biochem., 1986; 99: 1137-1146). The geranyl diphosphate synthase activity can refer to an activity to produce geranyl diphosphate from IPP and DMAPP. Examples of the geranyl diphosphate synthase and farnesyl diphosphate synthase can include farnesyl diphosphate synthase native to *Escherichia coli*. Alternatively, examples thereof can include geranyl diphosphate synthase native to microorganisms such as *Bacillus stearothermophilus* (e.g., JP2000-245482), *Pantoea ananatis* (e.g., WO 2007/029577 A1), actinomycete (*Streptomyces* sp) (e.g., WO2007/029577A1), and *Geobacillus stearothermophilus*. Examples thereof also can include geranyl diphosphate synthases native to plants such as grand fir (*Abies grandis*), peppermint (*Mentha× piperita*), Norway spruce (*Picea abies*), Madagascar periwinkle (*Catharanthus roseus*), thale-cress (*Arabidopsis thaliana*), snapdragon (*Antirrhinum majus*) or hop (*Humulus lupulus*).

The polynucleotide encoding geranyl diphosphate synthase can be one or more of the polynucleotide designated as [p], [q], or [r]:

[p] a polynucleotide having:

[xi] the nucleotide sequence represented by SEQ ID NO: 7, or

[xii] the nucleotide sequence represented by SEQ ID NO: 8;

[q] a polynucleotide that has a nucleotide sequence having 90% or more identity to the nucleotide sequence of [xi] or [xii] above, and encodes a protein having a geranyl diphosphate synthase activity; or

[r] a polynucleotide that hybridizes under stringent conditions with a polynucleotide having a nucleotide sequence complementary to the nucleotide sequence of [xi], or [xii] above, and encodes a protein having a geranyl diphosphate synthase activity.

The nucleotide sequence represented by SEQ ID NO: 7 is a nucleotide sequence of a farnesyl diphosphate/geranyl diphosphate synthase gene native to *Escherichia coli*. The nucleotide sequence represented by SEQ ID NO: 7 may encode the amino acid sequence represented by SEQ ID NO: 76 and can include a coding region of a mature farnesyl diphosphate/geranyl diphosphate synthase gene. In the nucleotide sequence represented by SEQ ID NO: 8, codons in the nucleotide sequence represented by SEQ ID NO: 7 are modified and codons encoding serine at position 80 in the protein represented by SEQ ID NO: 73 are mutated into codons encoding phenylalanine (S80F mutation). That is, the nucleotide sequence represented by SEQ ID NO: 8 encodes the amino acid sequence represented by SEQ ID NO: 77 and the protein represented by SEQ ID NO: 77 is a (S80F) mutated protein in which the serine residue at position 80 in the protein represented by SEQ ID NO: 76 is substituted with a phenylalanine residue. It is known that the farnesyl diphosphate synthase having S80F mutation has improved function as a geranyl diphosphate synthase (Reiling K K et al. (2004) Biotechnol Bioeng. 87(2) 200-212). The polynucleotide encoding geranyl diphosphate synthase can be the above-designated [q] or [r]. For this reason, the polynucleotide may have one or more mutations, which may obtain the same effect as the S80F mutation, although it is not limited to the S80F mutation, and mutation is not limited to the S80F mutation. Furthermore, derivation of the farnesyl diphosphate synthase gene is not limited to *Escherichia coli*, and for example, mutation to increase the concentration of geranyl diphosphate in the microbial cell is clearly known in farnesyl diphosphate synthase native to *Bacillus stearothermophilus* (Narita K., et al. (1999) J Biochem 126(3) 566-571.). Furthermore, although not limited to geranyl diphosphate synthase obtained by introducing mutation to the farnesyl diphosphate synthase gene, a gene functioning as the original geranyl diphosphate synthase may be used. For example, a geranyl diphosphate synthase gene native to periwinkle (Rai A., et al. (2013) Mol Plant. 6(5) 1531-49), a geranyl diphosphate synthase gene native to thale-cress (Camara B., (2000) Plant J. 24(2), 241-252), a geranyl diphosphate synthase gene native to actinomycete (WO 2007/029577 A1), and the like may be used. The farnesyl diphosphate synthase activity can refer to an activity of producing farnesyl diphosphate from geranyl diphosphate (GPP) and IPP. The identity of the nucleotide sequence, the stringent conditions, and the definition of polynucleotide are the same as those described in the polynucleotides designated (a1) to (c20).

The geranyl diphosphate synthase can be one or more proteins designated as [P]-[R]:

[P] a protein having the full-length amino acid sequence represented by SEQ ID NO:76 or 77;

[Q] a protein that has an amino acid sequence having 90% or more identity to the above amino acid sequence, and has a geranyl diphosphate synthase activity; and

[R] a protein that has an amino acid sequence having a deletion, substitution, addition, or insertion of one or several amino acids in the amino acid sequence, and has a geranyl diphosphate synthase activity.

The amino acid sequence represented by SEQ ID NO: 76 can include mature farnesyl diphosphate/geranyl diphosphate synthase. The amino acid sequence represented by SEQ ID NO: 77 can include mutated mature farnesyl diphosphate/geranyl diphosphate synthase. The [Q] and [R] proteins can have an activity of 50% or more, 60% or more, 70% or more, 80% or more, 90% or more, or 95% or more of the geranyl diphosphate synthase activity of the protein having the amino acid sequence represented by SEQ ID NO: 76 or 77; the geranyl diphosphate synthase activity and the farnesyl diphosphate synthase activity when they are measured under the same conditions. The definition of deletion, substitution, addition, or insertion, the identity of amino acid, and the like are the same as those described for the proteins designated (A1) to (C28).

Neither the polynucleotide encoding the desired protein nor the promoter operably linked thereto, which make up an expression unit, are necessarily inherent to the microorganism chosen as the host cell. Therefore, the entire expression unit may be a heterologous expression unit. Also, both the polynucleotide encoding linalool synthase and the promoter may not be inherent to the chosen host cell. The promoter may be homologous or heterologous relative to the polynucleotide encoding the desired protein. The expression unit may further include elements such as a terminator, a ribosomal binding site, and a drug resistance gene. The expression unit may be DNA or RNA, but is preferably DNA. The heterologous expression unit can include a gene encoding a protein other than a polynucleotide encoding linalool synthase. Examples of such a protein can include one or more enzymes involved in the mevalonate pathway and one or more enzymes involved in the methylerythritol phosphate pathway, but are not limited thereto.

The microorganism can be obtained, for example, by transformation with the following expression vectors: an expression vector having an expression unit including a polynucleotide encoding linalool synthase and a promoter operably linked to the polynucleotide; an expression vector having an expression unit including a polynucleotide encoding linalool synthase, polynucleotide encoding geranyl diphosphate synthase, and a promoter operably linked to the polynucleotide; an expression vector having a first expression unit including a polynucleotide encoding linalool synthase and a promoter operably linked to the polynucleotide and a second expression unit including a polynucleotide encoding geranyl diphosphate synthase and a promoter operably linked to the polynucleotide; and a combination of a first expression vector having a polynucleotide encoding linalool synthase and a promoter operably linked to the polynucleotide and a second expression vector having an expression unit including a polynucleotide encoding geranyl diphosphate synthase and a promoter operably linked to the polynucleotide. The expression vector may be an integrative vector or a non-integrative vector. In the expression vector, the gene encoding linalool synthase may be placed under the control of a constitutive promoter or inducible promoter. Examples of the constitutive promoter can include the tac promoter, the lac promoter, the trp promoter, the trc promoter, the T7 promoter, the T5 promoter, the T3 promoter, and the SP6 promoter. Examples of the inducible promoter can include a promoter which is inversely dependent on the growth-promoting agent to be described herein. The term "operably linked" can mean that a nucleotide sequence in the regulatory region is linked to a nucleotide sequence of a nucleic acid molecule or gene (that is, a polynucleotide) in the form capable of expressing the polynucleotide, and thus an expression product of the polynucleotide encoded by the nucleotide sequence is produced.

The microorganism expressing linalool synthase can have an ability to synthesize dimethyl diphosphate via a dimethylallyl diphosphate supply pathway from the viewpoint of supplying IPP and DMAPP for efficient production of linalool. Examples of the dimethylallyl diphosphate supply pathway can include a methylerythritol phosphate (MEP) pathway and a mevalonate (MVA) pathway.

The methylerythritol phosphate (MEP) pathway, also called non-mevalonate pathway, is a biosynthesis pathway of isopentenyldiphosphate (IPP) and dimethylallyl pyrophosphate (DMAPP), which are precursors of linalool. Examples of the enzymes involved in the methylerythritol phosphate (MEP) pathway may include 1-deoxy-D-xylulose-5-phosphate synthase (EC: 2.2.1.7, example 1, Dxs, ACCESSION ID NP_414954; example 2, AT3G21500, ACCESSION ID NP_566686; example 3, AT4G15560, ACCESSION ID NP_193291; example 4, AT5G11380, ACCESSION ID NP_001078570), 1-deoxy-D-xylulose-5-phosphate reductoisomerase (EC: 1.1.1.267; example 1, Dxr, ACCESSION ID NP_414715; example 2, AT5G62790, ACCESSION ID NP_001190600), 4-diphosphocytidyl-2-C-methyl-D-erythritol synthase (EC: 2.7.7.60; example 1, IspD, ACCESSION ID NP_417227; example 2, AT2G02500, ACCESSION ID NP_565286), 4-diphosphocytidyl-2-C-methyl-D-erythritol kinase (EC: 2.7.1.148; example 1, IspE, ACCESSION ID NP_415726; example 2, AT2G26930, ACCESSION ID NP_180261), 2-C-methyl-D-erythritol-2,4-cyclodiphosphate synthase (EC: 4.6.1.12; example 1, IspF, ACCESSION ID NP_417226; example 2, AT1G63970, ACCESSION ID NP_564819), 1-hydroxy-2-methyl-2-(E)-butenyl-4-diphosphate synthase (EC: 1.17.7.1; example 1, IspG, ACCESSION ID NP_417010; example 2, AT5G60600, ACCESSION ID NP_001119467), and 4-hydroxy-3-methyl-2-butenyl diphosphate reductase (EC: 1.17.1.2; example 1, IspH, ACCESSION ID NP_414570; example 2, AT4G34350, ACCESSION ID NP_567965).

Examples of the enzymes involved in the mevalonate (MVA) pathway may include mevalonate kinase (EC: 2.7.1.36; example 1, Erg12p, ACCESSION ID NP_013935; example 2, AT5G27450, ACCESSION ID NP_001190411), phosphomevalonate kinase (EC: 2.7.4.2; example 1, Erg8p, ACCESSION ID NP_013947; example 2, AT1G31910, ACCESSION ID NP_001185124), diphosphomevalonate decarboxylase (EC: 4.1.1.33; example 1, Mvd1p, ACCESSION ID NP_014441; example 2, AT2G38700, ACCESSION ID NP_181404; example 3, AT3G54250, ACCESSION ID NP_566995), acetyl-CoA-C-acetyltransferase (EC: 2.3.1.9; example 1, Erg10p, ACCESSION ID NP_015297; example 2, AT5G47720, ACCESSION ID NP_001032028; example 3, AT5G48230, ACCESSION ID NP_568694), hydroxymethylglutaryl-CoA synthase (EC: 2.3.3.10; example 1, Erg13p, ACCESSION ID NP_013580; example 2, AT4G11820, ACCESSION ID NP_192919; example 3, MvaS, ACCESSION ID AAG02438), hydroxymethylglutaryl-CoA reductase (EC: 1.1.1.34; example 1, Hmg2p, ACCESSION ID NP_013555; example 2, Hmg1p, ACCESSION ID NP_013636; example 3, AT1G76490, ACCESSION ID NP_177775; example 4, AT2G17370, ACCESSION ID NP_179329, EC: 1.1.1.88, example, MvaA, ACCESSION ID P13702), and acetyl-CoA-C-acetyltransferase/hydroxymethylglutaryl-CoA reductase (EC: 2.3.1.9/1.1.1.34, example, MvaE, ACCESSION ID AAG02439).

IPP and DMAPP, which are the building blocks of linalool, are typically biosynthesized via either a methylerythritol phosphate pathway or a mevalonate pathway inherent or native to a microorganism, as described above. Therefore, for supplying IPP and DMAPP for efficiently producing R-linalool or S-linalool, the methylerythritol phosphate pathway and/or the mevalonate pathway may be enhanced in the chosen microorganism, as described herein.

To enhance these pathways, the chosen microorganism may further express an enzyme of a mevalonate pathway or a methylerythritol phosphate pathway, for example, mevalonate kinase in addition to the linalool synthase. Therefore, one or more enzymes involved in the mevalonate pathway or the methylerythritol phosphate pathway may also be introduced into the microorganism expressing linalool synthase. In other words, the microorganism expressing linalool synthase can include an expression unit containing a gene that encodes one or more enzymes involved in the mevalonate pathway or the methylerythritol phosphate pathway and a promoter operably linked to the gene. Examples of the mevalonate kinase gene can include genes from microorganisms belonging to the genus *Methanosarcina* such as *Methanosarcina mazei*, the genus *Methanocella* such as *Methanocella paludicola*, the genus *Corynebacterium* such as *Corynebacterium variabile*, the genus *Methanosaeta* such as *Methanosaeta concilii*, and the genus *Nitrosopumilus* such as *Nitrosopumilus maritimus*.

The microorganism expressing linalool synthase may be transformed with one or more expression vectors encoding enzymes involved in the mevalonate pathway or the methylerythritol phosphate pathway. The expression vector may be an integrative vector or a non-integrative vector. In the expression vector, the gene encoding the mevalonate kinase may be placed under the control of a constitutive promoter or inducible promoter (e.g., the promoter which is inversely dependent on the growth-promoting agent). Specifically, the gene encoding the mevalonate kinase may be placed under the control of the constitutive promoter. Examples of the constitutive promoter can include the tac promoter, the lac promoter, the trp promoter, the trc promoter, the T7 promoter, the T5 promoter, the T3 promoter, and the SP6 promoter. Examples of the inducible promoter can include the promoter which is inversely dependent on the growth-promoting agent described below.

The expression vector for such an enzyme may express further a plurality of enzymes, for example, one or more, two or more, three or more or four or more, involved in the mevalonate pathway and/or the methylerythritol phosphate pathway, and may be, for example, an expression vector for polycistronic mRNA.

The one or more enzymes involved in the mevalonate pathway and/or the methylerythritol phosphate pathway may be homologous or heterologous relative to the host. When the origin of the enzyme involved in the mevalonate pathway and/or the methylerythritol phosphate pathway is heterologous relative to the host, for example, the host may be a bacterium as described above (e.g., *Escherichia coli*) and the enzyme involved in the mevalonate pathway may be native to a fungus (e.g., *Saccharomyces cerevisiae*). In addition, when the host inherently produces the enzyme involved in the methylerythritol phosphate pathway, an expression vector to be introduced into the host may express an enzyme involved in the mevalonate pathway.

In the expression vector, the gene encoding one or more enzymes involved in the mevalonate (MVA) pathway or the methylerythritol phosphate (MEP) pathway may be placed under the control of the promoter which is inversely dependent on the growth-promoting agent.

To enhance the mevalonate pathway and/or methylerythritol phosphate pathway, an isopentenyl-diphosphate delta isomerase having an ability to convert isopentenyl diphosphate (IPP) into dimethylallyl diphosphate (DMAPP) may be introduced into the microorganism.

Examples of the isopentenyl-diphosphate delta isomerase (EC: 5.3.3.2) can include Idi1p (ACCESSION ID NP_015208), AT3G02780 (ACCESSION ID NP_186927), AT5G16440 (ACCESSION ID NP_197148) and Idi (ACCESSION ID NP_417365). In the expression vector, the gene encoding the isopentenyl-diphosphate delta isomerase may be placed under the control of the promoter which is inversely dependent on the growth-promoting agent.

The transformation of a host with an expression vector containing the gene(s) described above can be carried out using one or more known methods. Examples of such methods can include a competent cell method using a microbial cell treated with calcium, an electroporation method, and the like. The gene may also be introduced by infecting the microbial cell with a phage vector other than the plasmid vector.

The microorganism expressing linalool synthase (for example, linalool synthase native to a plant belonging to the genus *Arabidopsis, Perilla, Vitis, Mentha, Ocimum, Lavandula, Picea, Solanum, Malus, Backhousia, Actinidia,* or *Clarkia,* or native to actinomycete) can have a dimethylallyl diphosphate supply pathway, and the 2-ketogluconate formation pathway can be blocked.

The microorganism can be a microorganism in which a 2-ketogluconate formation pathway is blocked. In the 2-ketogluconate formation pathway, glucose is oxidized by glucose dehydrogenase to produce gluconate and then the gluconate is oxidized by 2-keto gluconate dehydrogenase to produce NADPH and 2-ketogluconate. Thus, the microorganism in which the 2-ketogluconate formation pathway is blocked can be obtained by reducing the activity of one or more of glucose dehydrogenase (GCD) and 2-keto gluconate dehydrogenase. The 2-ketogluconate formation pathway can be blocked by reduction of the enzyme activity. That is, in the microorganism, the enzyme activity of one or more of glucose dehydrogenase and 2-ketogluconate dehydrogenase can be reduced and thus the 2-ketogluconate formation pathway is blocked in the microorganism.

Reduced enzymatic activity in a microorganism can mean a decrease and/or a complete loss of the activity of the enzyme. Also, the reduced enzymatic activity in a microorganism can include a decrease and/or a complete loss of the expression amount of an enzyme in a microorganism since such a decrease or a complete loss leads to a decrease or a complete loss of the enzymatic activity possessed by the microorganism. Reduction of enzymatic activity in a microorganism can be accomplished by, for example, disrupting one or more of the following: a gene encoding the enzyme, a gene encoding a factor capable of regulating an expression or activity of the enzyme, an expression regulatory region such as a transcriptional regulatory region located upstream to these genes and a translational regulatory region (e.g. promoter and Shine-Dalgarno (SD) sequence), or an untranslated region. The disruption of the above gene or region can be performed by modifying a genomic region corresponding to the gene or region so as to decrease or completely eliminate expression or activity of the enzyme. Examples of such a modification can include, but are not limited to, deletion of a part or all of the genomic region, insertion of a polynucleotide into the genomic region, and replacement of the genomic region with another polynucleotide.

The microorganism expressing linalool synthase can be a microorganism that is capable of synthesizing pyrroloquinoline quinone (PQQ), or using PQQ supplied in culture environment.

The microorganism expressing linalool synthase can be a microorganism having reduced activity of glucose dehydrogenase, and also can be a microorganism having reduced activity of glucose dehydrogenase that uses PQQ as a coenzyme.

When the microorganism expressing linalool synthase is a microorganism obtained by transforming a host microorganism originally having the 2-ketogluconate formation pathway with an expression vector having the gene encoding an isoprenoid compound-synthetic enzyme, the microorganism can be modified to block the 2-ketogluconate formation pathway.

For example, a microorganism belonging to the family Enterobacteriaceae such as *Escherichia coli* has a gene encoding glucose dehydrogenase and produces GCD apoenzyme, but since the microorganism does not have production ability of PQQ, it does not have GCD activity in the absence of PQQ. However, it is known that if a foreign gene is expressed in a microbial cell, an alternative substance of PQQ is generated and the substance exhibits GCD activity (WO2006/183898). The above host microorganism "originally having 2-ketogluconate formation pathway" can include microorganisms such as the microorganism belonging to the family Enterobacteriaceae that acquire GCD activity.

The modification to block the 2-ketogluconate formation pathway can be a modification to reduce the activity of the glucose dehydrogenase, and more preferably, a modification to reduce the activity of the glucose dehydrogenase that uses PQQ as coenzyme. The modification can be performed so that GCD activity per cell of the modified microorganism is lower than that of an unmodified strain such as a wild-type strain belonging to the family Enterobacteriaceae. For example, it may be confirmed that a molecular weight of GCD per cell or GCD activity per molecule of the modified strain is lower than those of the wild-type strain. The GCD activity per cell of the modified strain and the wild-type strain can be compared, for example, by comparing GCD activity contained in a cell extract composition of both strains cultured under the same conditions. Examples of the wild-type of the microorganism belonging to the family Enterobacteriaceae that can be used as comparison (control) can include *Pantoea ananatis* AJ13355 (FERM BP-6614), *Pantoea ananatis* SC17 strain (FERM BP-11091), and *Pantoea ananatis* SC17 (0) strain (Katashkina J I et al., BMC Mol Biol., 2009; 10:34 VKPM B-9246).

The activity of the glucose dehydrogenase that uses PQQ as a coenzyme can refer to an activity catalyzing the following reaction:

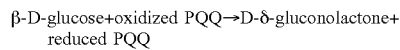
β-D-glucose+oxidized PQQ→D-δ-gluconolactone+ reduced PQQ

The GCD activity can be measured, for example, on the basis of detection of generation of the reduced DCPIP through the following reactions by measuring absorbance in 600 nm (JP2007-129965):

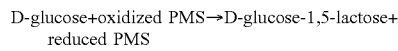
D-glucose+oxidized PMS→D-glucose-1,5-lactose+ reduced PMS

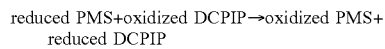
reduced PMS+oxidized DCPIP→oxidized PMS+ reduced DCPIP

PMS: phenazine methosulfate
DCPIP: 2,6-dichlorophenol-indophenol

The activity of the glucose dehydrogenase can be reduced by disrupting a gene encoding a glucose dehydrogenase (gcd gene), a gene encoding a factor capable of regulating an expression or activity of GCD, or a transcriptional regulatory region located upstream to these genes.

The gcd gene can be one or more polynucleotides designated as (x)-(z):

(x) a polynucleotide having:

[i] the nucleotide sequence represented by SEQ ID NO: 9, or

[ii] the nucleotide sequence consisting of the nucleotide residues at positions 301 to 2691 in the nucleotide sequence represented by SEQ ID NO: 9;

(y) a polynucleotide that has a nucleotide sequence having 90% or more identity to the nucleotide sequence of [i] or [ii] above, and encodes a protein having a GCD activity; and (z) a polynucleotide that hybridizes under stringent conditions with a polynucleotide having a nucleotide sequence complementary to the nucleotide sequence of [i] or [ii] above, and encodes a protein having a GCD activity.

The nucleotide sequence represented by SEQ ID NO: 9 can include a full-length nucleotide sequence of the gcd gene from *Pantoea ananatis*. The nucleotide sequence represented by SEQ ID NO: 9 can encode the amino acid sequence represented by SEQ ID NO: 10, and the nucleotide sequence having the nucleotide residues at positions 301 to 2691 (2688) can encode an amino acid sequence of mature GCD. The identity of the gene, the stringent conditions and polynucleotide are the same as the corresponding definitions of the polynucleotides designated as (a1) to (c20) described below.

GCD can be one or more proteins designated as (X)-(Z):

(X) a protein having the full-length amino acid sequence represented by SEQ ID NO: 10;

(Y) a protein that has an amino acid sequence having 90% or more identity to the amino acid sequence represented by SEQ ID NO: 10, and has a GCD activity; or (Z) a protein that has an amino acid sequence having a deletion, substitution, addition, or insertion of one or several amino acids in the amino acid sequence represented by SEQ ID NO: 10, and has a GCD activity.

The amino acid sequence represented by SEQ ID NO: 10 can include the mature GCD. The protein of (Y) or (Z) can have GCD activity that is 50% or more, 60% or more, 70% or more, 80% or more, 90% or more, or 95% or more of the GCD activity of the protein having the amino acid sequence represented by SEQ ID NO: 10 when measured under the same conditions. The deletion, substitution, addition, or insertion, and the identity of the amino acid are the same as the corresponding definitions of the proteins designated as (A1) to (C28) described below.

The gcd gene can be cloned by synthesizing an oligonucleotide based on these sequences, and carrying out PCR reaction using a chromosome of *Pantoea ananatis* as a template. The gcd gene may be disrupted by homologous recombination. In this case, a gene having, for example, 80% or more, 90% or more, or 95% or more identity to the gcd gene on a chromosome may be used. Also, a gene that hybridizes under stringent conditions with the gcd gene on the chromosome may be used. Example of the stringent conditions can include washing once, or 2-3 times, at salt concentrations corresponding to 1×SCC and 0.1% SDS, or 0.1×SCC and 0.1% SDS, at 60° C.

The gcd gene may be disrupted, for example, by deletion of an entire target gene and a upstream and downstream portion of the target gene on a chromosome; introducing a substitution of an amino acid (missense mutation) or a insertion of a terminating codon (nonsense mutation); or introducing a frame shift mutation of addition or deletion of one or two nucleotide (Journal of Biological Chemistry 272:8611-8617 (1997) Proceedings of the National Academy of Sciences, USA 95 5511-5515 (1998), Journal of Biological Chemistry 266, 20833-20839 (1991)).

The disruption of each gene can be performed by genetic recombination. Examples of the method using gene recombination can include deleting all or part of an expression regulatory region, such as the promoter region, coding region, or non-coding region, or insertion a polynucleotide into the region by utilizing homologous recombination.

Disruption of the expression regulatory region can be performed for one or more, two or more, or three or more, times. In the deletion of the coding region, the region to be deleted may be an N-terminal region, an internal region, or a C-terminal region, or even the entire coding region, so long as the function of the protein to be produced by the gene is reduced. Generally, deletion of a longer region will more certainly disrupt a target gene. It is preferable that reading frames upstream and downstream of the region to be deleted are not the same.

When a polynucleotide is inserted into a coding region, the polynucleotide may be inserted into any region of a target gene. However, insertion of a longer polynucleotide will more certainly disrupt the target gene. It is preferable that reading frames upstream and downstream of the region to be deleted are not the same. The polynucleotide is not limited so long as the polynucleotide reduces a function of the protein encoded by the target gene. However, examples of it can include a transposon carrying an antibiotic-resistant gene or a gene useful for L-amino acid production.

Examples of method for mutating the target gene on the chromosome can include the following method. First, a part of the target gene is deleted to produce a mutated gene that cannot produce a functional protein. Next, a microorganism is transformed by the DNA containing the mutated gene to cause a homologous recombination between the mutated gene and the target gene on the chromosome, and thereby, replace the target gene on the chromosome with the mutated gene. The protein encoded by the obtained mutated target gene, even if it is produced, has a stereostructure different from that of a wild-type protein, and thus, the function thereof is reduced. Such gene disruption based on gene replacement utilizing homologous recombination has been already reported. Examples of this method can include: methods using linear DNA such as the method called Red-driven integration (Datsenko, K. A, and Wanner, B. L. Proc. Natl. Acad. Sci. USA. 97: 6640-6645 (2000)), a method utilizing Red-driven integration in combination with the delivering system derived from λ phage (Cho, E. H., Gumport, R. I., Gardner, J. F. J. Bacteriol. 184: 5200-5203 (2002)) (WO2005/010175); a method using a plasmid having thermosensitive replication origin or a plasmid capable having conjugation transfer ability; or a method utilizing a suicide vector having no replication origin in a host (U.S. Pat. No. 6,303,383 or Japanese Patent Laid Open No. H5-007491).

Decrease in transcription amount of a target gene can be confirmed by comparing amount of mRNA transcribed from the target gene with that in a wild-type strain or unmodified strain. Examples of the method for evaluating the amount of mRNA can include northern hybridization and RT-PCR (Molecular cloning (Cold spring Harbor Laboratory Press, Cold spring Harbor (USA), 2001)). The transcription amount may be decreased to any extent so long as it is decreased compared with that observed in a wild-type strain or unmodified strain, and, for example, can be decreased to at least 75% or less, 50% or less, 25% or less, or 10% or less, of that observed in a wild-type strain or unmodified strain, and it is more preferable that the gene is not expressed at all.

Decrease in amount of a protein encoded by a target gene can be confirmed by Western blotting using an antibody that binds to the protein (Molecular cloning (Cold spring Harbor Laboratory Press, Cold spring Harbor (USA), 2001). The amount of protein may be decreased to any extent so long as it is decreased compared with that observed in a wild-type strain or unmodified strain, for example, it can be decreased to at least 75% or less, 50% or less, 25% or less, or 10% or less of that observed in a wild-type strain or unmodified strain, and it is more preferable that the protein is not produced at all (the activity is completely eliminated).

Examples of the method for decreasing the activity of GCD can include, besides the aforementioned genetic manipulation techniques, a method of treating a microorganism belonging to the family Enterobacteriaceae, such as a bacteria belonging to the genus *Pantoea*, with ultraviolet irradiation or a mutagen used for a typical mutagenesis treatment such as N-methyl-N'-nitro-N-nitrosoguanidine (NTG) or nitrous acid, and selecting a strain having decreased GCD activity.

The activity of GCD can also be reduced by reducing PQQ biosynthesis. The PQQ biosynthesis can be reduced, for example, by deleting part or all of pqqABCDEF that is operon required for PQQ biosynthesis (J. S. Velterop, P. W. Postma, J. Bacteriology 177(17): 5088-5098 (1995)).

The method as described herein can include one or more of the following steps:

1) culturing a microorganism expressing linalool synthase in the presence of a growth-promoting agent at a sufficient concentration to grow the linalool-producing microorganism;

2) decreasing the concentration of the growth-promoting agent to induce production of linalool by the microorganism; and 3) culturing the microorganism to produce linalool.

From the view point of efficient production of linalool composition, for example, R-linalool composition and S-linalool composition, the above step 1), which corresponds to a growth phase of a microorganism, and the above step 3), which corresponds to a formation phase of linalool, can be conducted separately. The above step 2), which corresponds to an induction phase of linalool formation, functions to move the microorganism from the growth phase to the formation phase of linalool.

The growth-promoting agent can refer to a factor essential for the growth of a microorganism or a factor having an activity of promoting the growth of the microorganism, which can be consumed by the microorganism, the consumption of which causes reduction of its amount in a culture medium, and consequent loss or reduction of the growth of the microorganism. For example, when the growth-promoting agent in a certain amount is used, a microorganism continues to grow until the growth-promoting agent in that amount is consumed, but once the growth-promoting agent is entirely consumed, the microorganism cannot grow or the growth rate decreases. Therefore, the degree of the growth of the microorganism can be regulated by the growth-promoting agent. Examples of such a growth-promoting agent can include, but are not limited to, substances such as oxygen (gas); minerals such as ions of iron, magnesium, potassium and calcium; phosphorus compounds such as monophosphoric acid, diphosphoric acid, and polyphosphoric acid, or salt thereof; nitrogen compounds such as ammonia, nitrate, nitrite, nitrogen (gas), and urea; sulfur compounds such as ammonium sulfate and thiosulfuric acid; and nutrients such as vitamins (e.g., vitamin A, vitamin D, vitamin E, vitamin K, vitamin B1, vitamin B2, vitamin B6, vitamin B12, niacin, pantothenic acid, biotin, ascorbic acid), and amino acids (e.g., alanine, arginine, asparagine, aspartic acid, cysteine, glutamine, glutamic acid, glycine, histidine, leucine, isoleucine, lysine, methionine, phenylalanine, proline, serine, threonine, tryptophan, tyrosine, valine, selenocysteine). One kind of growth-promoting agent may be used, or two or more kinds of growth-promoting agents may be used in combination.

When the method as described herein includes the above steps 1) to 3), the microorganism expressing linalool synthase can have an ability to grow depending on the growth-promoting agent and an ability to produce linalool depending on a promoter that is inversely dependent on the growth-promoting agent, and to which an ability to synthesize linalool by an enzymatic reaction has been conferred. Such an microorganism can grow in the presence of the growth-promoting agent at a concentration sufficient for the growth of the microorganism. Here, the "sufficient concentration" of the growth-promoting agent can refer to a concentration that is effective for the growth of the microorganism. The expression "ability to produce linalool depending on a promoter that is inversely depending on the growth-promoting agent" can mean that linalool cannot be produced at all or a at very low efficiency in the presence of a relatively high concentration of the growth-promoting agent; whereas, linalool can be produced or R-linalool or S-linalool can be produced at a high efficiency in the presence of the growth-promoting agent at a relatively low concentration or in the absence of the growth-promoting agent. Therefore, the chosen microorganism can grow well but cannot produce linalool or produces linalool at a low efficiency in the presence of the growth-promoting agent at the sufficient concentration. The chosen microorganism cannot grow well but can produce linalool and can produce linalool at a high efficiency in the presence of the growth-promoting agent at an insufficient concentration or in the absence of the growth-promoting agent. The chosen microorganism can produce R-linalool and can produce R-linalool at a high efficiency, or can produce S-linalool and can produce S-linalool at a high efficiency, in the absence of the growth-promoting agent.

When the method as described herein includes the above steps 1) to 3), a gene encoding linalool synthase and expressing linalool synthase can be under the control of a promoter that is inversely dependent on the growth-promoting agent. The expression "promoter that is inversely dependent on the growth-promoting agent" can mean a promoter that does not induce transcription of the gene at all, or only at very low amounts, in the presence of a relatively high concentration of the growth-promoting agent; but is able to induce transcription of the gene at a medium to high rate in the presence of the growth-promoting agent at relatively low concentration or in the absence of the growth-promoting agent. Therefore, the promoter that is inversely dependent on the growth-promoting agent can suppress the expression of the gene encoding linalool synthase in the presence of the growth-promoting agent at a concentration sufficient for the growth of the microorganism; whereas, the promoter can promote the expression of the gene encoding linalool synthase in the presence of the growth-promoting agent at a concentration insufficient for the growth of the microorganism. Specifically, the growth of the microorganism is under the control of the promoter which is inversely dependent on the growth-promoting agent.

For example, when the growth-promoting agent is a phosphorus compound, a phosphorus deficiency-inducible promoter can be utilized. The expression "phosphorus deficiency-inducible promoter" can refer to a promoter that can promote the expression of a downstream gene at a low concentration of the phosphorus compound. The low concentration of the phosphorus compound can mean 100 mg/L or less. The expression "phosphorus" is synonymous to the expression "phosphorus compound", and they can be used interchangeably. The concentration of total phosphorus can be quantified by decomposing all of the phosphorus compounds in the liquid to orthophosphoric acid by a strong acid or oxidizing agent. The total phosphorus concentration under phosphorus-deficient conditions may be 100 mg/L or less, 50 mg/L or less, 10 mg/L or less, 5 mg/L or less, 1 mg/L or less, 0.1 mg/L or less, or 0.01 mg/L or less. Examples of the phosphorus deficiency-inducible promoter can include a promoter of the gene encoding alkali phosphatase, for example, phoA, a promoter of the gene encoding an acid phosphatase, for example, phoC, a promoter of the gene encoding a sensor histidine kinase, for example, phoR, a promoter of the gene encoding a response regulator, for example, phoB, and a promoter of the gene encoding a phosphorus uptake carrier, for example, pstS.

In the above step 1), the microorganism expressing linalool synthase can be grown in the presence of the growth-promoting agent at the sufficient concentration. More specifically, the microorganism expressing linalool synthase can be grown by culturing the isoprenoid compound-producing microorganism in a culture medium in the presence of the growth-promoting agent at the sufficient concentration.

For example, when a phosphorus compound is used as the growth-promoting agent, the microorganism expressing linalool synthase can grow well in the presence of the phosphorus compound at a sufficient concentration, and thus, the phosphorus compound can act as the growth-promoting agent. When the growth-promoting agent is the phosphorus compound, the concentration of the phosphorus compound that is sufficient for the growth in step 1) is not particularly limited, and may be, for example, 200 mg/L or more, 300 mg/L or more, 500 mg/L or more, 1000 mg/L or more, or 2000 mg/L or more. The concentration of the phosphorus compound for the growth may be, for example, 20 g/L or less, 10 g/L or less, or 5 g/L or less.

In the above step 2), the production of the isoprenoid compound by the microorganism is induced by decreasing the concentration of the growth-promoting agent. More specifically, the concentration of the growth-promoting agent can be decreased by decreasing the amount of the growth-promoting agent supplied to the culture medium. Even if the amount of the growth-promoting agent supplied to the culture medium is kept constant throughout steps 1) and 2), the concentration of the growth-promoting agent can be decreased by utilizing the growth of the microorganism. In the early phase of the growth of the microorganism in step 1), the microorganism does not grow sufficiently and the cell number in the culture medium is small. Thus, consumption of the growth-promoting agent by the microorganism is relatively low. Therefore, the concentration of the growth-promoting agent in the culture medium is relatively high in the early phase of the growth. On the other hand, in the late phase of the growth of the microorganism in step 1), the microorganism grows sufficiently and the cell number is large, and thus, the consumption of the growth-promoting agent by the microorganism is relatively high. Therefore, the concentration of the growth-promoting agent in the culture medium becomes relatively low in the late phase of the growth. As described above, when a constant amount of the growth-promoting agent is supplied to the culture medium throughout steps 1) and 2), the concentration of the growth-promoting agent in the culture medium decreases in inverse proportion to the growth of the microorganism. This decreased concentration can be used as a trigger to induce the production of linalool by the microorganism.

For example, when a phosphorus compound or an amino acid is used as the growth-promoting agent, the concentration of the phosphorus compound or the amino acid in the culture medium, which can induce the production of linalool by the microorganism, can be, for example, 100 mg/L or less, 50 mg/L or less, or 10 mg/L or less.

In the above step 3), linalool is produced by culturing the microorganism. More specifically, R-linalool or S-linalool can be produced by culturing the microorganism in the culture medium under the conditions described in step 2) where the concentration of the growth-promoting agent is decreased. The concentration of the growth-promoting agent in the culture medium can be maintained at the concentration described in step 2) in order to make the production of R-linalool or S-linalool by the microorganism possible.

In the method as described herein, it is also possible that the period of time for culturing the microorganism in step 3) is set so that it is longer than the period of time for culturing in step 1). In conventional methods, an inducer is used to obtain linalool in a higher amount, and it is necessary to culture a microorganism for a longer period of time using the inducer in the formation phase of linalool. However, when the cultivation is continued for a long period of time, the inducer decomposes, and the microorganism fails to maintain the ability to produce R-linalool or S-linalool. Thus, it is necessary to continuously add the inducer into culture medium. As the inducer may be expensive, the cost for producing linalool possibly is prohibitive. Therefore, culturing a microorganism for a long period of time using the inducer in the formation phase of linalool is problematic in that the cost for producing linalool is increased depending on the duration of the cultivation period. On the other hand, in the method as described herein that does not use a particular substance such as the inducer in step 3), the decomposition of the particular substance is not an issue, and the prohibitive cost issue that occurs in conventional method due to long cultivation times in the formation phase of linalool is avoided. Therefore, in the method as described herein, the period of time for step 3) can easily be longer, in contrast to the conventional methods that utilize the inducer. In the method as described herein, the longer the period of time in step 3), the more R-linalool or S-linalool that can be produced.

The method as described herein may be combined with another method in terms of enhancing the amount of produced linalool. Examples of such a method can include a method of utilizing an environmental factor such as light (Pia Lindberg, Sungsoon Park, Anastasios Melis, Metabolic Engineering 12 (2010): 70-79) or temperature (Norma A Valdez-Cruz, Luis Caspeta, Nestor O Pérez, Octavio T Ramirez, Mauricio A Trujillo-Roldán, Microbial Cell Factories 2010, 9:1), change of pH (EP 1233068 A2), addition of surfactant (JP H11-009296 A), and auto-inducible expression system (WO2013/151174).

The culture medium used in the method as described herein may contain a carbon source for producing linalool. The carbon source can include carbohydrates such as monosaccharides, disaccharides, oligosaccharides and polysaccharides; invert sugars obtained by hydrolyzing sucrose; glycerol; compounds having one carbon atom (hereinafter referred to as a C1 compound) such as methanol, formaldehyde, formate, carbon monoxide and carbon dioxide; oils such as corn oil, palm oil and soybean oil; acetate; animal fats; animal oils; fatty acids such as saturated fatty acids and unsaturated fatty acids; lipids; phospholipids; glycerolipids; glycerol fatty acid esters such as monoglyceride, diglyceride and triglyceride; polypeptides such as microbial proteins and plant proteins; renewable carbon sources such as hydrolyzed biomass carbon sources; yeast extracts, or combinations thereof. For a nitrogen source, inorganic ammonium salts such as ammonium sulfate, ammonium chloride and ammonium phosphate, organic nitrogen such as hydrolyzed soybeans, ammonia gas, ammonia water, and the like can be used. The culture medium can contain required substances such as vitamin B1 and L-homoserine, or yeast extract and the like in an appropriate amount as an organic trace nutrient source. In addition thereto, potassium phosphate, magnesium sulfate, iron ion, manganese ion, and the like can be added in a small amount if necessary. The culture medium employed in the method as described herein can be a natural medium or a synthesized medium as long as it contains a carbon source, a nitrogen source, inorganic ions, and optionally other organic trace ingredients.

Examples of the monosaccharide can include triose such as ketotriose (dihydroxyacetone) and aldotriose (glyceraldehyde); tetrose such as ketotetrose (erythrulose) and aldotetrose (erythrose, threose); pentose such as ketopentose (ribulose, xylulose), aldopentose (ribose, arabinose, xylose, lyxose) and deoxysaccharide (deoxyribose); hexose such as ketohexose (psichose, fructose, sorbose, tagatose), aldohexose (allose, altrose, glucose, mannose, gulose, idose, galactose, talose), and deoxysaccharide (fucose, fuculose, rhamnose); and heptose such as sedoheptulose. C6 sugars such as fructose, mannose, galactose and glucose; and C5 sugars such as xylose and arabinose are particular examples.

Examples of the disaccharide can include sucrose, lactose, maltose, trehalose, turanose, and cellobiose. Sucrose and lactose are particular examples.

Examples of the oligosaccharide can include trisaccharides such as raffinose, melezitose and maltotriose; tetrasaccharides such as acarbose and stachyose; and other oligosaccharides such as fructooligosaccharide (FOS), galactooligosaccharide (GOS) and mannan-oligosaccharide (MOS).

Examples of the polysaccharide can include glycogen, starch (amylose, amylopectin), cellulose, dextrin, and glucan (β-1,3-glucan), and starch and cellulose are particular examples.

Examples of the microbial protein can include polypeptides native to a yeast or bacterium.

Examples of the plant protein can include polypeptides native to soybean, corn, canola, Jatropha, palm, peanut, sunflower, coconut, mustard, cotton seed, palm kernel oil, olive, safflower, sesame, and linseed.

Examples of the lipid can include substances containing one or more saturated or unsaturated fatty acids of C4 or more.

The oil can be a lipid that contains one or more saturated or unsaturated fatty acids of C4 or more and is liquid at room temperature, and examples of the oil can include lipids derived from soybean, corn, canola, Jatropha, palm, peanut, sunflower, coconut, mustard, cotton seed, palm kernel oil, olive, safflower, sesame, linseed, oily microbial cells, Chinese tallow tree, and a combination of two or more thereof.

Examples of the fatty acid can include compounds represented by a formula RCOOH ("R" represents a hydrocarbon group having two or more carbon atoms).

The unsaturated fatty acid can be a compound having at least one double bond between two carbon atoms in the group "R" as described above, and examples of the unsaturated fatty acid can include oleic acid, vaccenic acid, linoleic acid, palmitelaidic acid, and arachidonic acid.

The saturated fatty acid is a compound where the "R" is a saturated aliphatic group, and examples of the saturated fatty acid can include docosanoic acid, eicosanoic acid, octadecanoic acid, hexadecanoic acid, tetradecanoic acid, and dodecanoic acid. Of these, saturated fatty acids containing one or more C2 to C22 fatty acids are particular examples, and C12 fatty acid, C14 fatty acid, C16 fatty acid, C18 fatty acid, C20 fatty acid, and C22 fatty acid are even more particular examples.

The carbon source can include salts, such as isopropyl myristate, and derivatives of these fatty acids and salts of these derivatives. Examples of the salt can include lithium salts, potassium salts, sodium salts, and so forth.

Examples of the carbon source can also include combinations of carbohydrates such as glucose with lipids, oils, fats, fatty acids, and glycerol fatty acid esters.

Examples of the renewable carbon source can include hydrolyzed biomass carbon sources.

Examples of the biomass carbon source can include cellulose-based substrates such as waste materials of woods, papers and pulps, leafy plants, and fruit pulps; and partial plants such as stalks, grain particles, roots, and tubers.

Examples of the plant employed as the biomass carbon source can include corn, wheat, rye, sorghum, triticale, rice, millet, barley, cassava, legume such as pea, potato, sweet potato, banana, sugar cane, and tapioca.

When a renewable carbon source such as biomass is added to the culture medium, the carbon source can be pretreated. Examples of the pretreatment can include an enzymatic pretreatment, a chemical pretreatment, and a combination of the enzymatic pretreatment and the chemical pretreatment.

It is preferred that the renewable carbon source is entirely or partially hydrolyzed before being added to the culture medium.

Examples of the carbon source can also include a yeast extract and a combination of a yeast extract with another carbon source such as glucose. The combination of the yeast extract with a C1 compound such as carbon dioxide and methanol is a particular example.

In the method as described herein, a particular example is to culture the microorganism expressing linalool synthase in a standard culture medium containing saline and nutrients.

The culture medium is not particularly limited, and examples of the culture medium can include ready-made general media that is commercially available such as Luria Bertani (LB) broth, Sabouraud dextrose (SD) broth, and yeast medium (YM) broth. A medium suitable for the cultivation of a specific host can be selected appropriately.

The cell medium can contain appropriate minerals, salts, supplemental elements, buffers, and ingredients known to those of ordinary skill in the art that are suitable for the cultivation and to facilitate the production of linalool in addition to the appropriate carbon source.

The standard cell culture conditions are regulated as described above and can be used as the culture conditions for the microorganism.

The culture temperature can be 20 to 40° C., and the pH value can be about 4.5 to about 9.5.

The microorganism as described herein can be cultured under aerobic, oxygen-free, or anaerobic conditions depending on a nature of the chosen host for the isoprenoid compound-producing microorganism. A known fermentation method such as a batch cultivation method, a feeding cultivation method, or a continuous cultivation method can appropriately be used as the cultivation method.

Incidentally, R-linalool and S-linalool have low solubility with respect to water and can be dissolved in an organic layer to be recovered by forming an organic layer in a culture medium and culturing with two phases. As a material to be added in order to form an organic layer, for example, dodecane, methyl oleate, oleyl alcohol, dibutyl phthalate, isopropyl myristate, or the like can be used.

The linalool composition as described herein contains an abundant amount of linalool and thus can be used as a flavor and/or a fragrance composition without any change or by being purified as necessary.

EXAMPLES

Hereinafter, the present invention will be described in detail with reference to the following non-limiting Examples.

Example 1: Construction of Linalool Synthase-Expressing Plasmid 1-1) Obtaining a Linalool Synthase Gene Native to *Streptomyces clavuligerus*

The nucleotide sequence (GenBank accession number: DS570692) and the amino acid sequence (GenPept accession number: EDY52263) of a linalool synthase (ScLINS) gene/protein native to *Streptomyces clavuligerus* have been reported (Nakano al. (2011) ChemBiochem.; 12(16): 2403-2407). The amino acid sequence of a linalool synthase protein and the nucleotide sequence of its gene native to *Streptomyces clavuligerus* are shown in SEQ ID NO: 1 and SEQ ID NO: 2, respectively. In order to efficiently express the ScLINS gene, codons of the ScLINS gene were optimized, and this was designated as opt_ScLINS. The nucleotide sequence of opt_ScLINS is shown in SEQ ID NO: 3. DNA in which a tac promoter region (deBoer et al., (1983) Proc. Natl. Acad. Sci. U.S.A., 80: 21-25) had been added to the opt_ScLINS gene was chemically synthesized, cloned into pMW119 (produced by NIPPON GENE CO., LTD.) and the resulting plasmid was designated as pMW119-Ptac-opt_ScLINS.

1-2) Obtaining a Mutated Farnesyl Diphosphate Synthase Gene Native to *Escherichia coli*

Farnesyl diphosphate synthase native to is encoded by an ispA gene (SEQ ID NO: 7) (Fujisaki et al. (1990) J. Biochem. (Tokyo) 108:995-1000). A mutation that increases the concentration of geranyl diphosphate in microbial cells has been demonstrated in farnesyl diphosphate synthase native to *Bacillus stearothemophilus* (Narita et al. (1999) J Biochem 126(3):566-571). Based on this finding, the similar mutant has been also produced in farnesyl diphosphate synthase native to *Escherichia coli* (Reiling K K et al. (2004) Biotechnol Bioeng. 87(2) 200-212). In order to efficiently express an ispA mutant (S80F) gene having a high activity for producing geranyl diphosphate, a sequence in which the codons were optimized was designed and designated as ispA*. A nucleotide sequence of ispA* is shown in SEQ ID NO: 8. The ispA* gene was chemically synthesized, subsequently cloned into pMW119 (produced by NIPPON GENE CO., LTD.), and the resulting plasmid was designated as pMW119-ispA*.

1-3) Construction of Co-Expression Plasmid for Opt_ScLINS and the ispA* Gene

PCR with pMW119-Ptac-opt_ScLINS as a template was carried out using primers shown in SEQ ID NO: 14 and SEQ ID NO: 11 to obtain a Ptac-opt_ScLINS fragment. Furthermore, PCR with pMW119-ispA* as a template was carried out using primers shown in SEQ ID NO: 12 and SEQ ID NO: 15 to obtain an ispA* fragment. The purified Ptac-opt_ScLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_ScLINS-ispA*.

1-4) Obtaining a Linalool Synthase Gene Native to *Coriandrum sativum* (Coriander)

The nucleotide sequence (GenBank accession number: KF700700) and the amino acid sequence (GenPept accession number: AHC54051) of a linalool synthase (CsLINS) gene and protein native to *Coriandrum sativum* have been reported (Galata M et al., (2014) Phytochemistry, 102, 64-73). The amino acid sequence of a linalool synthase protein and the nucleotide sequence of its gene native to *Coriandrum sativum* are shown in SEQ ID NO: 4 and SEQ ID NO: 5. In order to efficiently express the CsLINS gene, codons were optimized, a CsLINS gene in which the chloroplast localization signal had been cleaved was designed, and this was designated as opt_CsLINS. The nucleotide sequence of opt_CsLINS is shown in SEQ ID NO: 6. DNA in which the tac promoter region (deBoer et al., (1983) Proc. Natl. Acad. Sci. U.S.A., 80: 21-25) had been added to the opt_CsLINS gene was chemically synthesized, cloned into pMW119 (produced by NIPPON GENE CO., LTD.), and the resulting plasmid was designated as pMW119-Ptac-opt_CsLINS.

1-5) Construction of Co-Expression Plasmid for Opt_CsLINS and ispA* Genes

PCR with pMW119-Ptac-opt_CsLINS as a template was carried out using primers shown in SEQ ID NO: 14 and SEQ ID NO: 16 to obtain a Ptac-opt_CsLINS fragment. Furthermore, PCR with pMW119-ispA* as a template was carried out using primers shown in SEQ ID NO: 17 and SEQ ID NO: 15 to obtain an ispA* fragment. The purified Ptac-opt_CsLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_CsLINS-ispA*.

1-6) Construction of Co-Expression Plasmid for Opt_CsLINS and ispA* Genes in which the Expression Amount is Optimized PCR with pACYC177-Ptac-opt_CsLINS-ispA* constructed in 1-5 as a template was carried out using a primer shown in SEQ ID NO: 13 and a primer shown in SEQ ID NO: 15 to obtain an opt_CsLINS-ispA* fragment in which a part of the sequence of the upstream of CsLINS had been changed. The purified opt_CsLINS-ispA* fragment in which a part of the sequence of the upstream of CsLINS had been changed was ligated to pACYC177 (produced by NIPPON GENE CO., LTD.) and digested with restriction enzymes PstI and ScaI using In-Fusion HD cloning kit (produced by Clontech Laboratories, Inc.), and the resulting opt_CsLINS-ispA* expression plasmid was designated as pACYC177-Ptac2-opt_CsLINS-ispA*.

Reference Practical Example 1

Construction of microaerobically inducible isoprenoid compound-producing microorganism (SWITCH-PlId/IspSM), phosphate deficiency-inducible isoprenoid compound-producing microorganism (SWITCH-PphoC/IspSM, SWITCH-PpstS/IspSM) and arabinose-inducible isoprenoid compound-producing microorganism (SWITCH-Para/IspSM)

1-1) Construction of pMW-Para-mvaES-Ttrp 1-1-1) Chemical Synthesis of mvaE Gene Native to *Enterococcus faecalis*

A nucleotide sequence and an amino acid sequence of mvaE encoding acetyl-CoA acetyltransferase and hydroxymethylglutaryl-CoA reductase and native to *Enterococcus faecalis* have been reported (Accession number of nucleotide sequence: AF290092.1,(1479 . . . 3890), Accession number of amino acid sequence: AAG02439) (J. Bacteriol. 182 (15): 4319-4327 (2000)). The amino acid sequence of the mvaE protein native to *Enterococcus faecalis* and the nucleotide sequence of its gene are shown as SEQ ID NO: 22 and SEQ ID NO: 23, respectively. In order to efficiently express the mvaE gene in *E. coli*, an mvaE gene in which codon usage in *E. coli* had been optimized was designed, and this was designated as EFmvaE. This nucleotide sequence is shown as SEQ ID NO: 24. The mvaE gene was chemically synthesized, then was cloned into pUC57 (produced by GenScript), and the resulting plasmid was designated as pUC57-EFmvaE.

1-1-2) Chemical Synthesis of mvaS Gene Native to *Enterococcus faecalis*

A nucleotide sequence of mvaS native to *Enterococcus faecalis* encoding hydroxymethylglutaryl-CoA synthase, and its amino acid sequence have been reported (Accession number of nucleotide sequence: AF290092.1, complement (142 . . . 1293), Accession number of amino acid sequence: AAG02438) (J. Bacteriol. 182(15): 4319-4327 (2000)). The amino acid sequence of the mvaS protein native to *Enterococcus faecalis* and the nucleotide sequence of its gene are shown as SEQ ID NO: 25 and SEQ ID NO: 26, respectively. In order to efficiently express the mvaS gene in *E. coli*, an mvaS gene optimized to the codon usage in *E. coli* was designed, and this was designated as EFmvaS. This nucleotide sequence is shown as SEQ ID NO: 27. The mvaS gene was chemically synthesized, then was cloned into pUC57 (produced by GenScript), and the resulting plasmid was designated as pUC57-EFmvaS.

1-1-3) Construction of Expression Vector for Arabinose-Inducible mvaES

An expression vector for an arabinose-inducible gene upstream of the mevalonate pathway was constructed by the following procedure. PCR with plasmid pKD46 as the template was carried out using synthesized oligonucleotides shown as SEQ ID NO: 28 and SEQ ID NO: 29 as primers to obtain a PCR fragment containing Para composed of araC and an araBAD promoter native to *E. coli*. PCR with plasmid pUC57-EFmvaE as the template was carried out using synthesized oligonucleotides shown as SEQ ID NO: 30 and SEQ ID NO: 31 as primers to obtain a PCR fragment containing the EFmvaE gene. PCR with plasmid pUC57-EFmvaS as the template was carried out using synthesized oligonucleotides shown as SEQ ID NO: 32 and SEQ ID NO: 33 as primers to obtain a PCR fragment containing the EFmvaS gene. PCR with plasmid pSTV-Ptac-Ttrp (WO 2013/069634 A1) as the template was carried out using synthesized oligonucleotides shown as SEQ ID NO: 34 and SEQ ID NO: 35 as primers to obtain a PCR fragment containing a Ttrp sequence. Prime Star polymerase (produced by Takara Bio Inc.) was used for PCR to obtain these four PCR fragments. A reaction solution was prepared according to a composition attached to a kit, and DNA was amplified through 30 cycles of reactions at 98° C. for 10 seconds, 55° C. for 5 seconds and 72° C. for one minute per kb. PCR with the purified PCR product containing Para and PCR product containing the EFmvaE gene as the template was carried out using synthesized oligonucleotides shown as SEQ ID NO: 28 and SEQ ID NO: 31 as primers, and PCR with the purified PCR product containing the EFmvaS gene and PCR product containing Ttrp as the template was carried out using synthesized oligonucleotides shown in SEQ ID NO: 32 and SEQ ID NO: 35 as primers. As a result, a PCR product containing Para and the EFmvaE gene and a PCR product containing the EFmvaS gene and Ttrp were obtained. A plasmid pMW219 (produced by NIPPON GENE CO., LTD.) was digested with SmaI according to a standard method. pMW219 digested with SmaI was ligated to the purified PCR product containing Para and the EFmvaE gene and the purified PCR product containing the EFmvaS gene and Ttrp using In-Fusion HD Cloning Kit (produced by Clontech Laboratories, Inc.). The resulting plasmid was designated as pMW-Para-mvaES-Ttrp.

1-2) Construction of the Integrative Conditionally Replicated Plasmids Carrying Upstream and Downstream Genes in Mevalonate Pathways 1-2-1) Construction of Plasmids Containing the mvaES Gene Under the Control of a Different Promoter To construct integrative plasmids carrying upstream and downstream genes of mevalonate pathways, the pAH162-λattL-TcR-λattR vector (Minaeva et al., BMC Biotechnol., 2008; 8: 63) was used.

KpnI-SalI fragment of pMW-Para-mvaES-Ttrp was cloned into SphI-SalI recognition sites of pAH162-2attL-TcR-2attR. As a result, the pAH162-Para-mvaES plasmid carrying mvaES operon from *E. faecalis* under control of the *E. coli* Para promoter and repressor gene araC have been constructed (FIG. 1).

Figure 2:
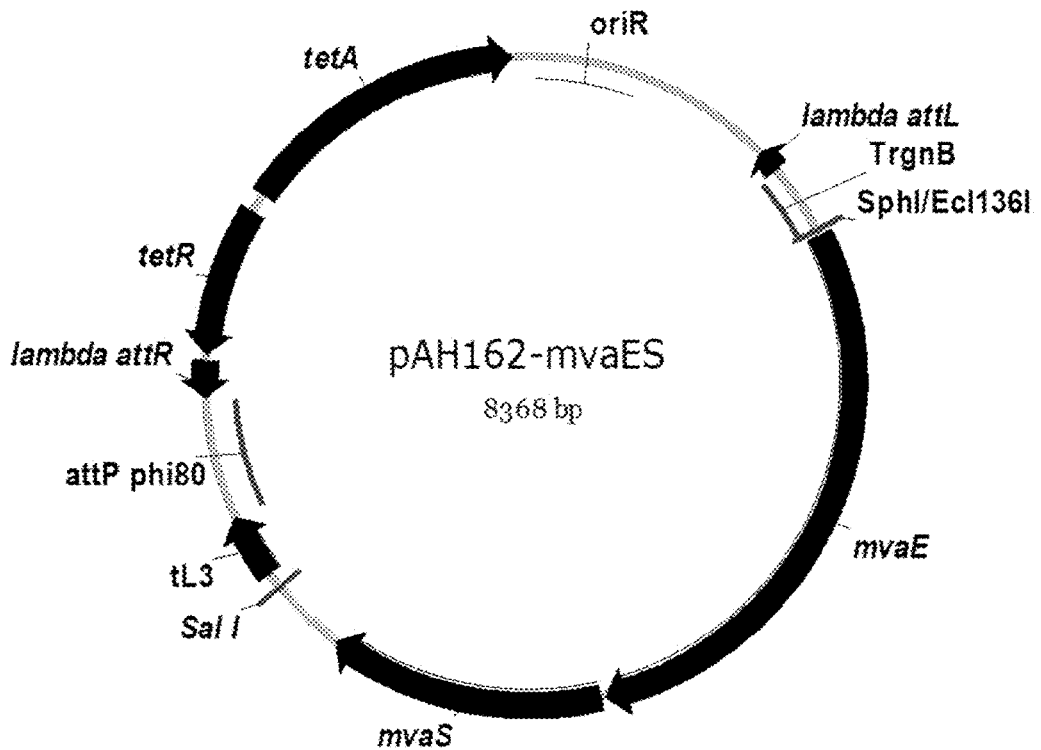
FIG. 2 shows a map of pAH162-mvaES.

In order to obtain a variant of promoter-deficient operon, an Ecl136II-SalI fragment of pMW219-Para-mvaES-Ttrp was subcloned into the same integrative vector. A map of the resulting plasmid is shown in FIG. 2.

Figure 3:
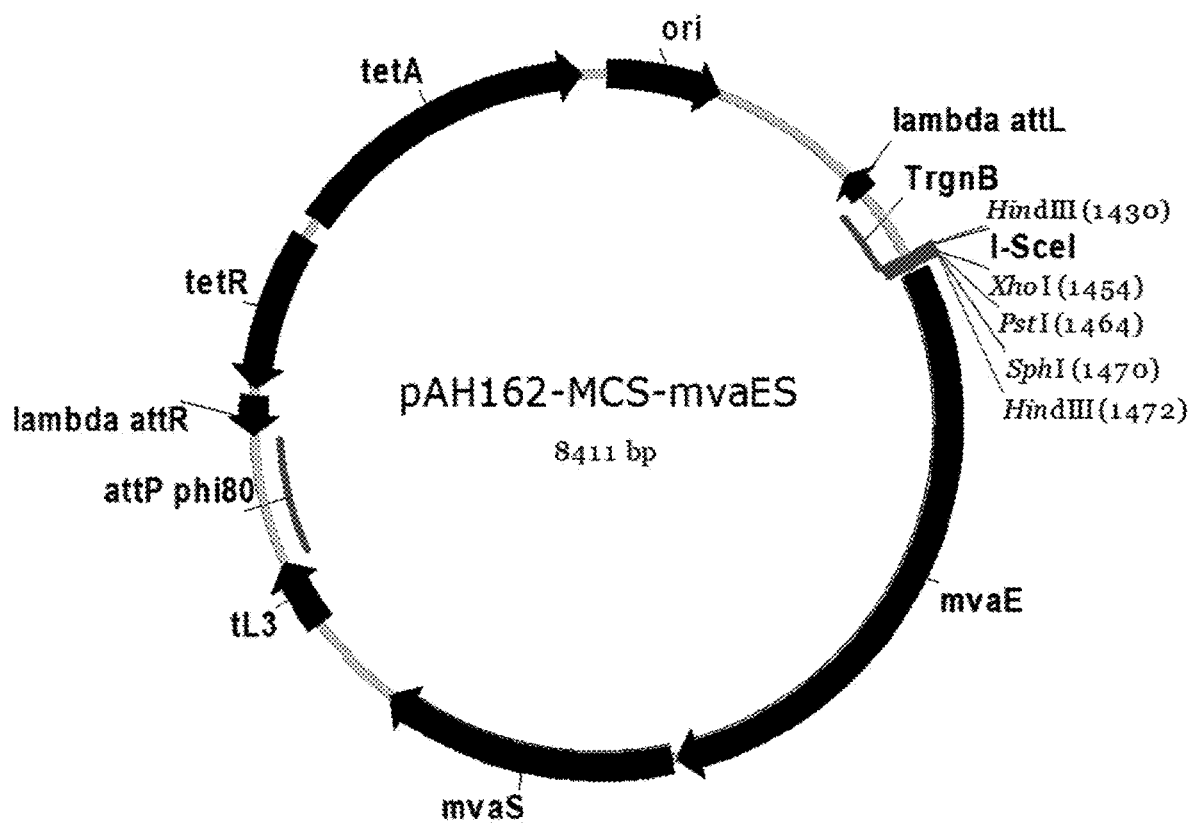
FIG. 3 shows a plasmid for chromosome fixation of pAH162-MCS-mvaES.
Figure 4A:
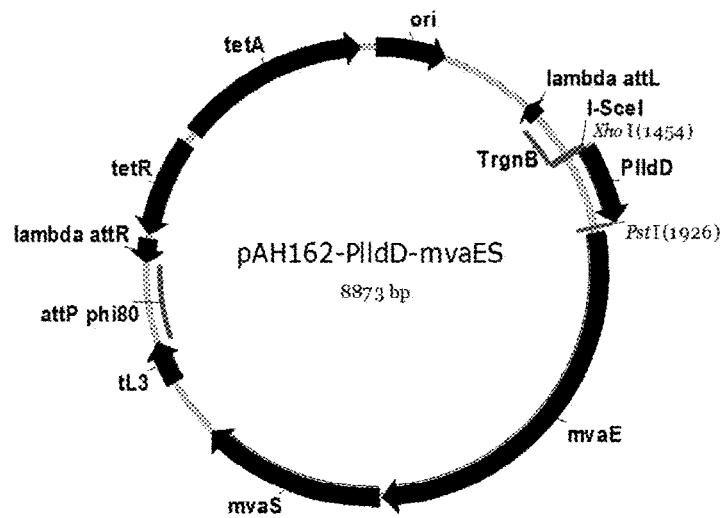
FIGS. 4A, 4B, and 4C show a set of plasmids for chromosome fixation which possess an mvaES gene under transcription control of (A) $P_{lldD}$, (B) $P_{phoC}$, or (C) $P_{pstS}$.
Figure 4B:
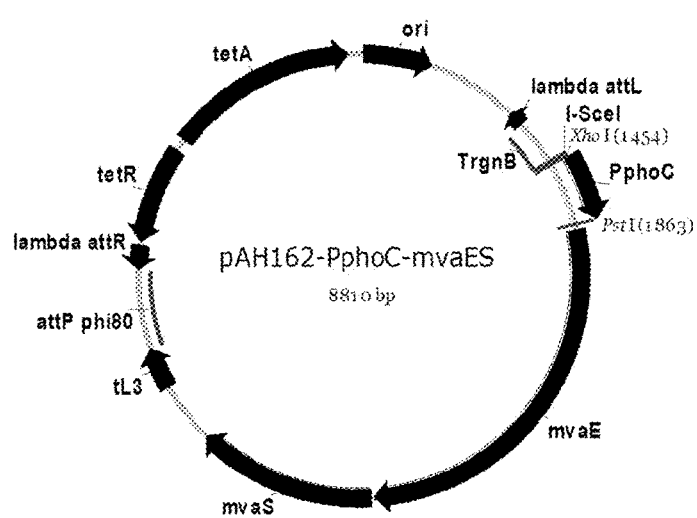
Figure 4C:
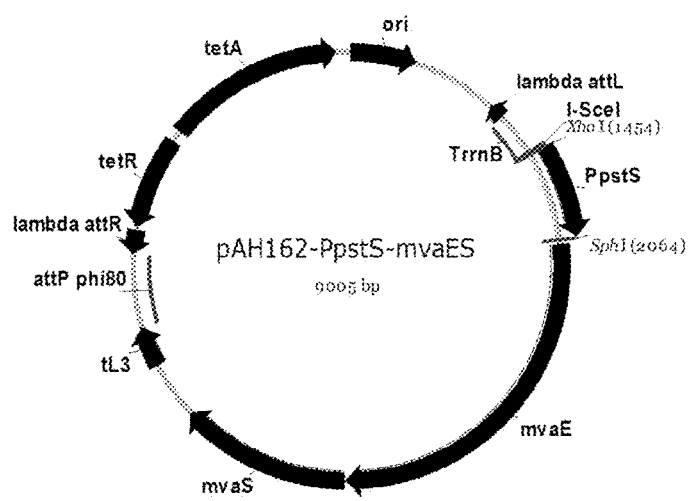

A set of plasmids for chromosome fixation, which retains the mvaES gene under the control of a different promoter, was constructed. For this purpose, a polylinker containing I-SceI, XhoI, PstI and SphI recognition sites was inserted into the unique HindIII recognition site located upstream of the mvaES gene. In order to accomplish this purpose, annealing was carried out using the primers 1, 2 (Table 1) and polynucleotide kinase. After that, the resulting double-stranded DNA fragment was 5' phosphorylated with polynucleotide kinase and the resulting phosphorylated fragment was inserted into a pAH162-mvaES plasmid cleaved with HindIII by a ligation reaction. The resulting pAH162-MCS-mvaES plasmid (FIG. 3) is convenient for cloning of a promoter with a desired orientation before the mvaES gene. DNA fragments retaining a regulatory region of a 11dD, phoC and pstS genes were generated by PCR with genomic DNA from *P. ananatis* SC17(0) strain (Katashkina et al., BMC Mol Biol., 2009; 10: 34) as the template using primers 3 and 4, primers 5 and 6, and primers 7 and 8 (Table 1), respectively, and cloned into an appropriate restriction enzyme recognition site of pAH162-MCS-mvaES. The resulting plasmids are shown in FIG. 4. The cloned promoter fragments were sequenced and confirmed to exactly correspond to predicted nucleotide sequences.

1-2-2) Construction of pAH162-Km-Ptac-KDyI Plasmid for Chromosome Fixation

Figure 5:
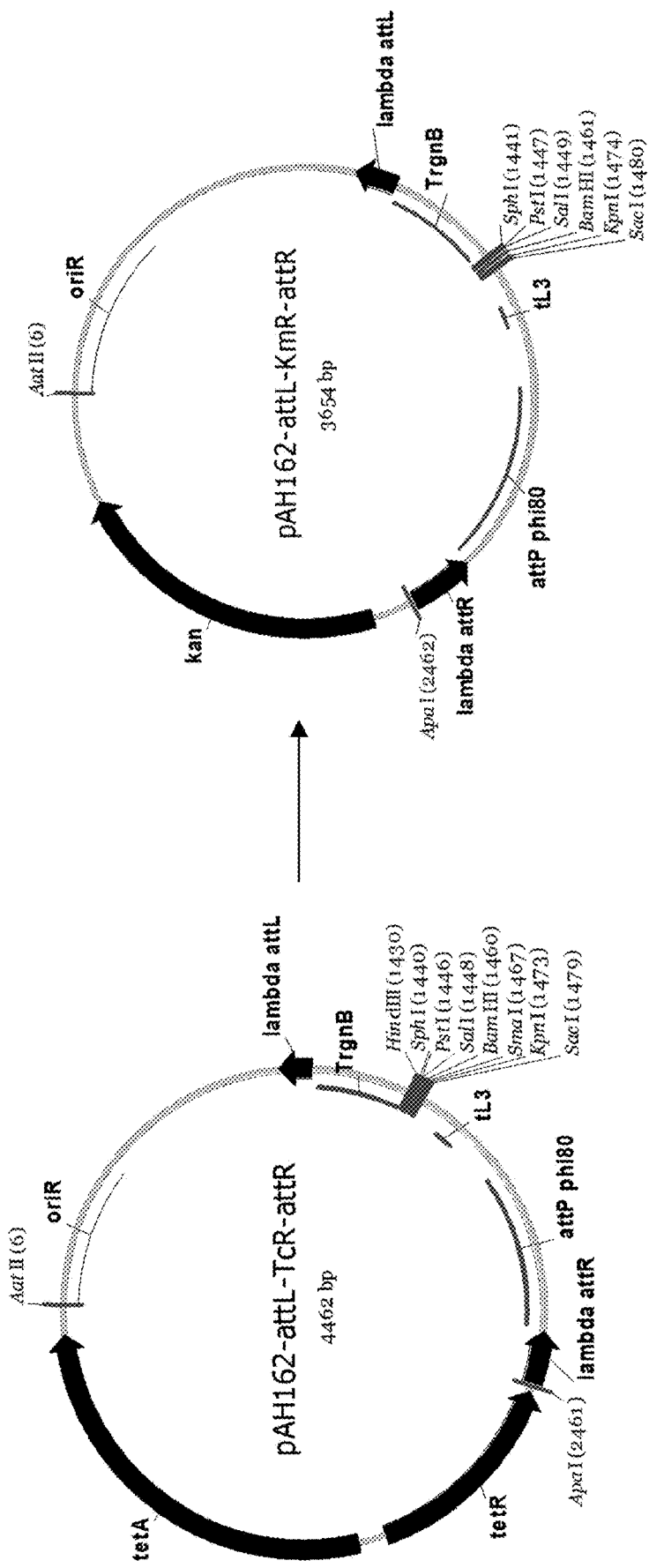
FIG. 5 shows an outline for construction of a pAH162-λattL-Km$^R$-λattR vector.

An AatII-ApaI fragment of pAH162-λattL-Tc$^R$-λattR containing a tetAR gene (Minaeva et al., BMC Biotechnol., 2008; 8: 63) was replaced with a DNA fragment obtained by PCR with a pUC4K plasmid (Taylor L A and Rose R E., Nucleic Acids Res., 16: 358, 1988) as the template using the primers 9 and 10 (Table 1). As a result, pAH162-λattL-Km$^R$-λattR was obtained (FIG. 5).

Figure 6:
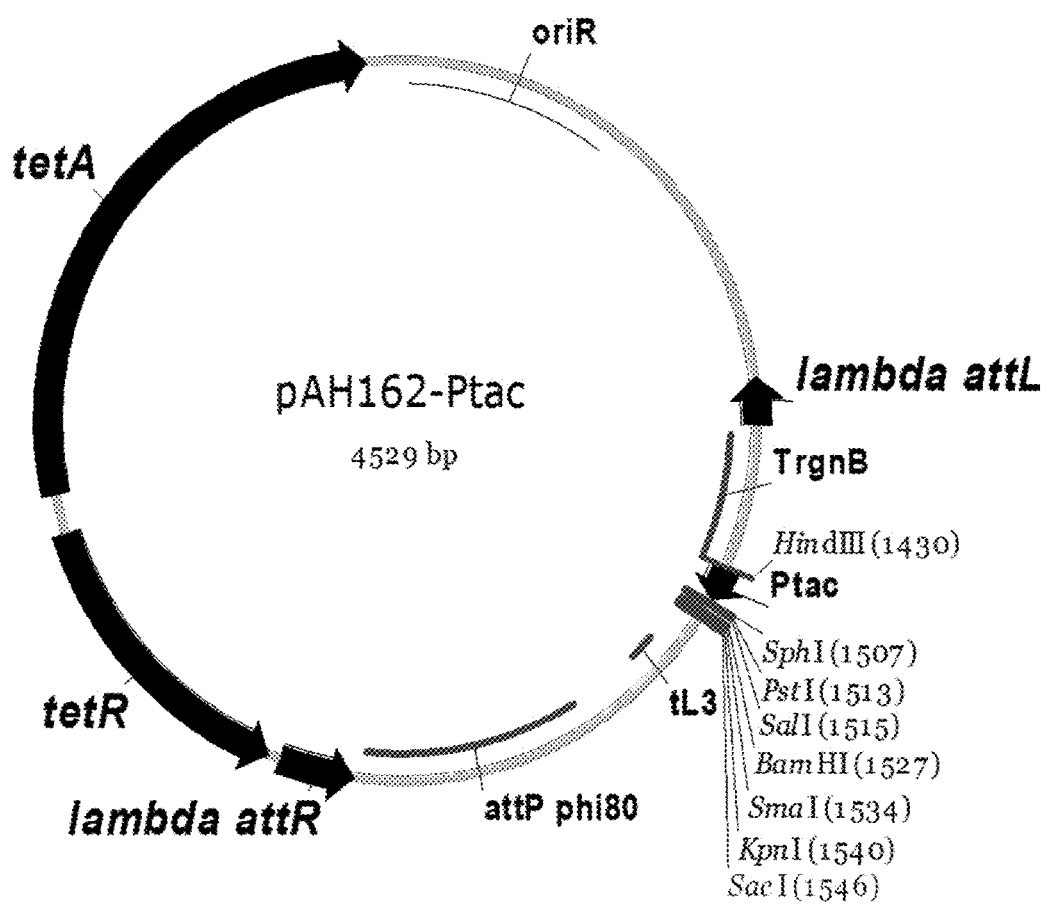
FIG. 6 shows a pAH162-Ptac expression vector for chromosome fixation.

A Ptac promoter was inserted into a HindIII-SphI recognition site of the pAH162-λattL-Tc$^R$-λattR vector (Minaeva N I et al., BMC Biotechnol., 2008; 8: 63). As a result, the expression vector pAH162-Ptac for chromosome fixation was constructed. The cloned promoter fragment was sequenced and confirmed to be the sequence as designed. A map of pAH162-Ptac is shown in FIG. 6.

Figure 7:
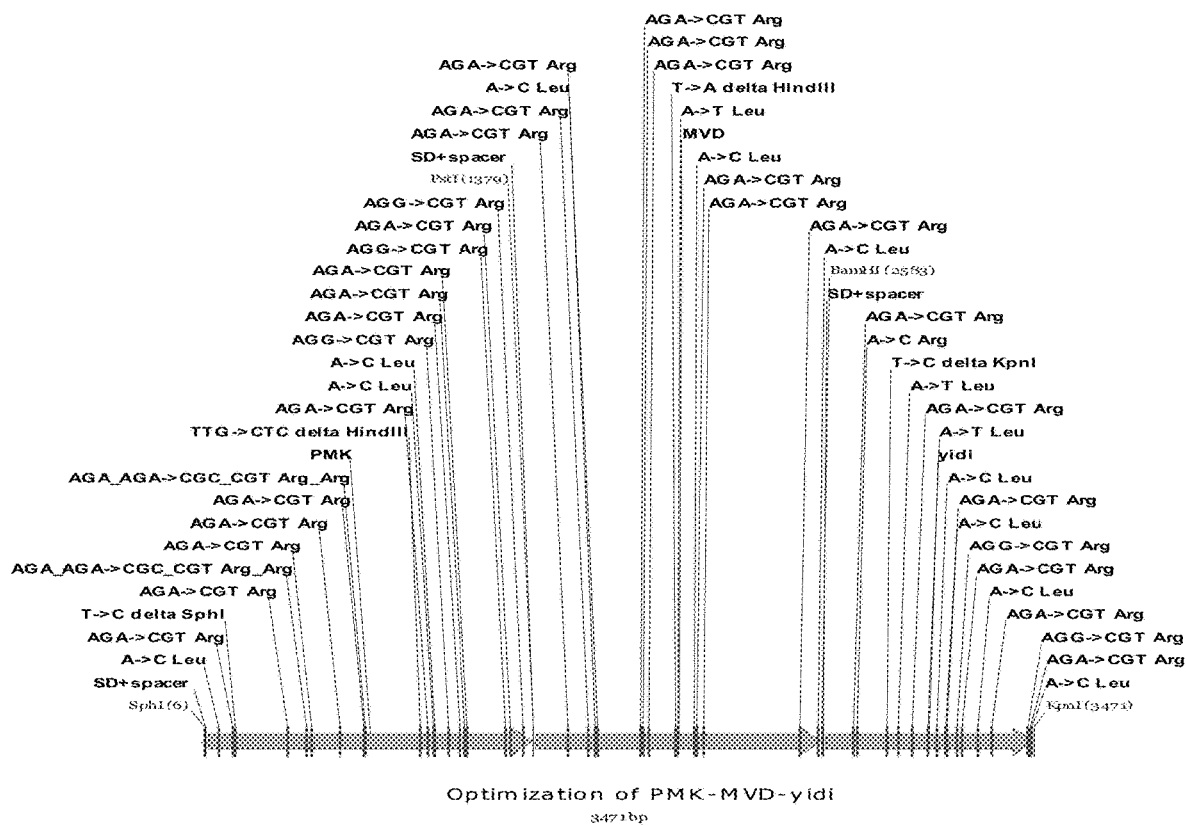
FIG. 7 shows codon optimization in a KDyI operon obtained by chemical synthesis.
Figure 8A:
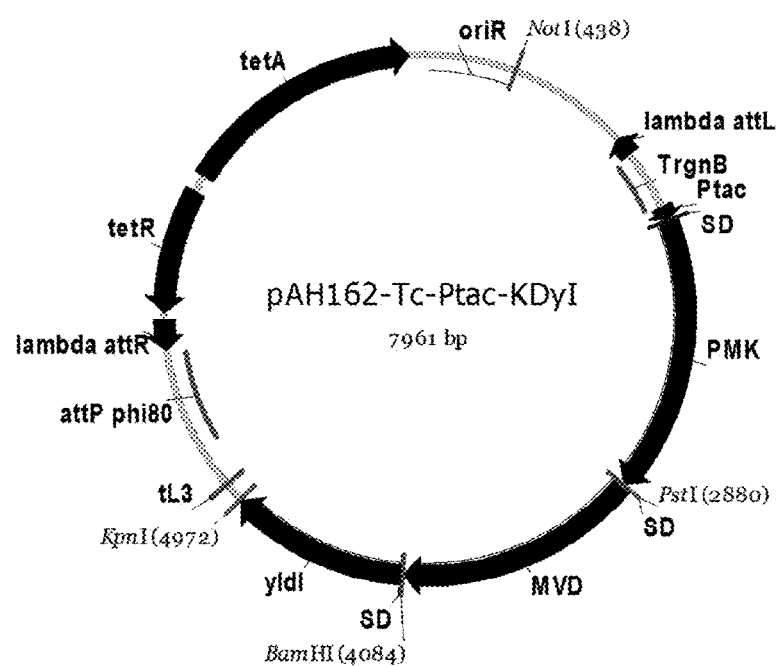
FIGS. 8A and 8B shows plasmids (A) pAH162-Tc-Ptac-KDyI and (B) pAH162-Km-Ptac-KDyI for chromosome fixation, which retain the KDyI operon with codon optimization.
Figure 8B:
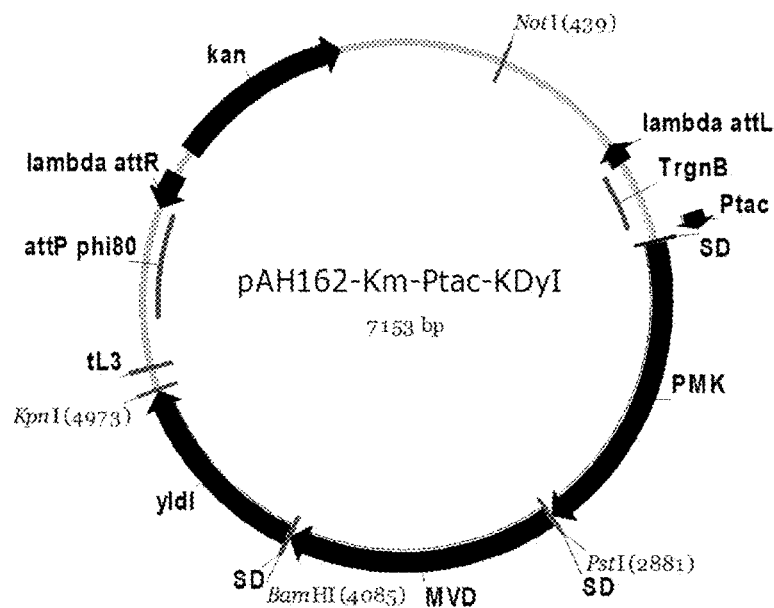

A DNA fragment that retained the PMK, MVD and yldI genes native to *S. cerevisiae*, in which rare codons had been replaced with synonymous codons, and had been chemically synthesized by ATG Service Gene (Russia) (FIG. 7) was subcloned into a SphI-KpnI restriction enzyme recognition site of the vector pAH162-Ptac for the chromosome fixation. The DNA sequence including the chemically synthesized KDyI operon is shown in SEQ ID NO: 60. The resulting plasmid pAH162-Tc-Ptac-KDyI retaining a Ptac-KDyI expression cassette is shown in FIG. 8(A). Subsequently, for the purpose of replacing a drug resistant marker gene, a NotI-KpnI fragment of pAH162-Tc-Ptac-KDyI retaining the tetAR gene was replaced with a corresponding fragment of pAH162-λattL-Km$^R$-λattR. As a result, a plasmid pAH162-Km-Ptac-KDyI having a kanamycin resistant gene, kan, as a marker was obtained (FIG. 8(B)).

Figure 9:
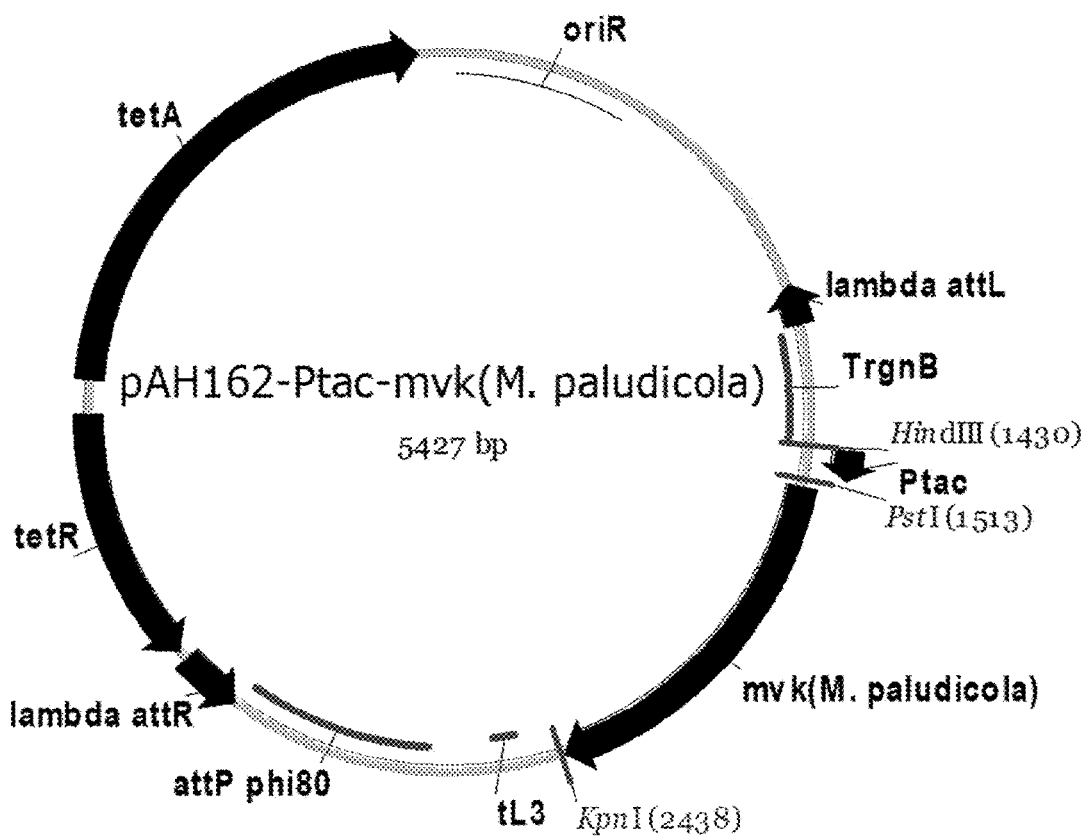
FIG. 9 shows a plasmid for chromosome fixation, which retains a mevalonate kinase gene native to M. paludicola.

A chemically synthesized DNA fragment containing a coding region of a putative mvk gene native to SANAE (for full-length genomic sequence, see GenBank Accession Number AP011532) that is strain of *Methanocella paludicola*, which had been ligated to a classical SD sequence, was cloned into a PstI-KpnI recognition site of the above integrative expression vector pAH162-Ptac. A map of the plasmid for the chromosome fixation retaining the mvk gene is shown in FIG. 9.

1-3) Construction of Recipient Strain SC17(0) ΔampC::attB$_{phi80}$ ΔampH::attB$_{phi80}$ ΔCrt::Ptac-Mvk (*M. paludicola*)

Using a two-stage technique of λ-Red dependent integration of a PCR amplified DNA fragment containing the kan gene flanked by attL$_{phi80}$ and attR$_{phi80}$ and 40 bp sequences homologous to a target chromosome site (Katashkina et al., BMC Mol Biol., 2009; 10: 34), and subsequent phage phi80 Int/Xis-dependent removal of the kanamycin resistant marker (Andreeva et al., FEMS Microbiol Lett., 2011; 318(1): 55-60), chromosomal modifications of ΔampH::attB$_{phi80}$ and ΔampC::attB$_{phi80}$ were introduced into *P. ananatis* SC17(0) strain in a stepwise fashion. SC17(0) is a 2-Red resistant derivative of *P. ananatis* AJ13355 (Katashkina et al., BMC Mol Biol., 2009; 10: 34); an annotated full-length genomic sequence of *P. ananatis* AJ13355 is available as PRJDA162073 or GenBank Accession Numbers AP012032.1 and AP012033.1. Using pMWattphi plasmid (Minaeva et al., BMC Biotechnol., 2008; 8:63) as the template, and using primers 11 and 12, and primers 13 and 14 (Table 1), DNA fragments used for integration into an ampH and ampC gene regions, respectively, were generated. The primers 15 and 16, and the primers 17 and 18 (Table 1) were used to verify the resulting chromosome modifications by PCR.

Figure 10A:
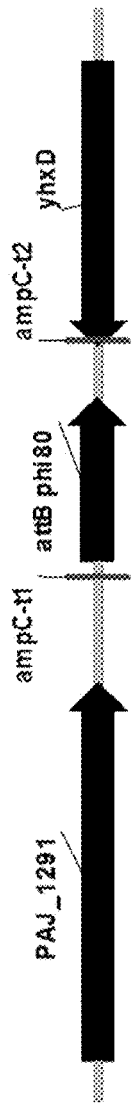
FIGS. 10A, 10B, and 10C show maps of genome modifications of (A) ΔampC::attB$_{phi80}$, (B) ΔampH::attB$_{phi80}$, and (C) Δcrt::attB$_{phi80}$.
Figure 10B:
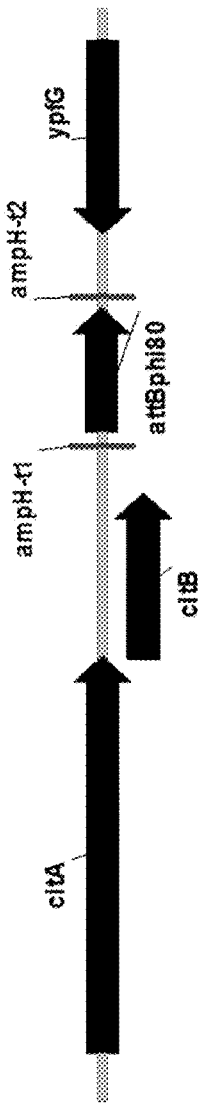
Figure 10C:

In parallel, a derivative of *P. ananatis* SC17(0) retaining the attB site of phi80 phage in place of the crt operon located on the pEA320 320 kb megaplasmid, which is a part of *P. ananatis* AJ13355 genome, was constructed. In order to obtain this strain, 2-Red dependent integration of a PCR-amplified DNA fragment retaining attL$_{phi80}$-kan-attR$_{phi80}$ flanked by a 40 bp region homologous to a target site in the genome was carried out according to the previously described technique (Katashkina et al., BMC Mol Biol., 2009; 10: 34). Therefore, a DNA fragment to be used in the replacement of the crt operon with attL$_{phi80}$-kan-attR$_{phi80}$ was amplified in the reaction using the primers 19 and 20 (Table 1). The pMWattphi plasmid (Minaeva et al., BMC Biotechnol., 2008; 8: 63) was used as the template in this reaction. The resulting integrated product was designated as SC17(0) Δcrt::attL$_{phi80}$-kan-attR$_{phi80}$. The primers 21 and 22 (Table 1) were used to verify the chromosome structure of SC17(0) Δcrt::attL$_{phi80}$-kan-attR$_{phi80}$ by PCR. The kanamycin resistance marker was removed from the constructed strain according to the reported technique using a pAH129-cat helper plasmid (Andreeva et al., FEMS Microbiol Lett., 2011; 318(1): 55-60). The primers 21 and 22 were used to verify the resulting SC17(0) Δcrt::attB$_{phi80}$ strain by PCR. Maps of the resulting genome-modified products, ΔampC::attB$_{phi80}$, ΔampH::attB$_{phi80}$ and Δcrt::attB$_{phi80}$ are shown in FIGS. 10 (A), (B) and (C), respectively.

Figure 11A:
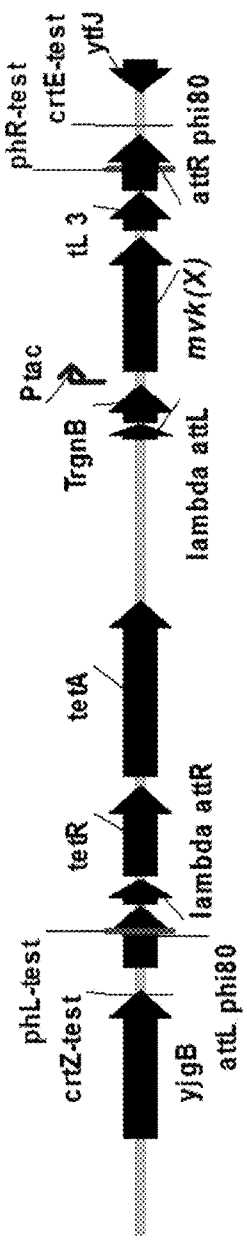
FIGS. 11A and 11B show maps of genome modifications of (A) Δcrt::pAH162-Ptac-mvk(X) and (B) Δcrt::Ptac-mvk(X).

The aforementioned pAH162-Ptac-mvk (*M. paludicola*) plasmid was integrated into an attB$_{phi80}$ site of SC17(0) Δcrt::attB$_{phi80}$ according to the reported protocol (Andreeva et al., FEMS Microbiol Lett., 2011; 318(1): 55-60). The integration of the plasmid was confirmed by PCR using the primers 21 and 23 and the primers 22 and 24 (Table 1). As a result, the SC17(0) Δcrt::pAH162-Ptac-mvk (*M. paludicola*) strain was obtained. A map of the modified genome of Δcrt::pAH162-Ptac-mvk (*M. paludicola*) is shown in FIG. 11(A).

Figure 11B:
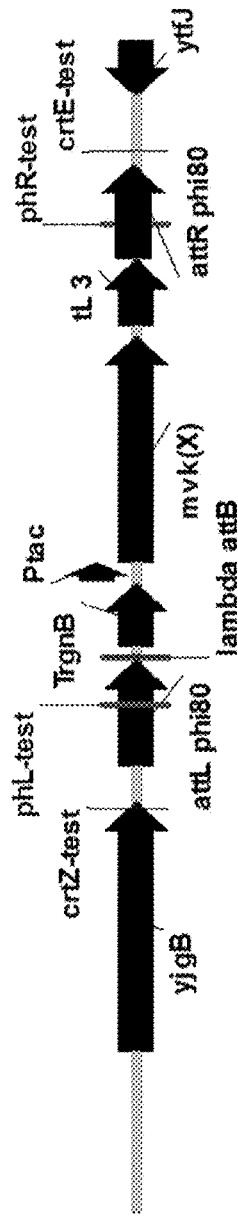

Subsequently, a genetic trait of SC17(0) Δcrt::pAH162-Ptac-mvk (*M. paludicola*) was transferred to SC17(0) ΔampC::attB$_{phi80}$ ΔampH::attB$_{phi80}$ via a genome DNA electroporation method (Katashkina et al., BMC Mol Biol., 2009; 10: 34). The resulting strain utilizes a tetracycline resistant gene, tetRA as the marker. The vector part of the pAH162-Ptac-mvk (*M. paludicola*) integrative plasmid including tetRA marker genes was eliminated using the reported pMW-intxis-cat helper plasmid (Katashkina J I et al., BMC Mol Biol., 2009; 10: 34). As a result, a marker gene deficient strain, SC17(0) ΔampH::attB$_{φ80}$ ΔampC::attB$_{φ80}$ Δcrt::Ptac-mvk (*M. paludicola*) was obtained. A map of the modified genome of Δcrt::Ptac-mvk (*M. paludicola*) is shown in FIG. 11(B).

1-4) Construction of Set of SWITCH Strains

Figure 12A:
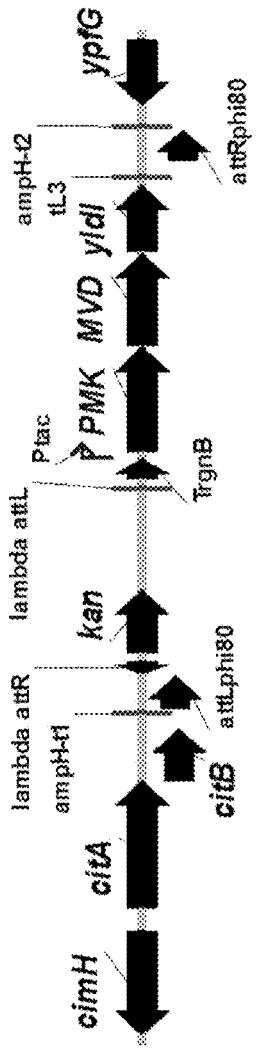
FIGS. 12A, 12B, and 12C show maps of chromosome modifications of (A) ΔampH::pAH162-Km-Ptac-KDyI, (B) ΔampC::pAH162-Km-Ptac-KDyI and (C) ΔampC::Ptac-KDyI.
Figure 12B:
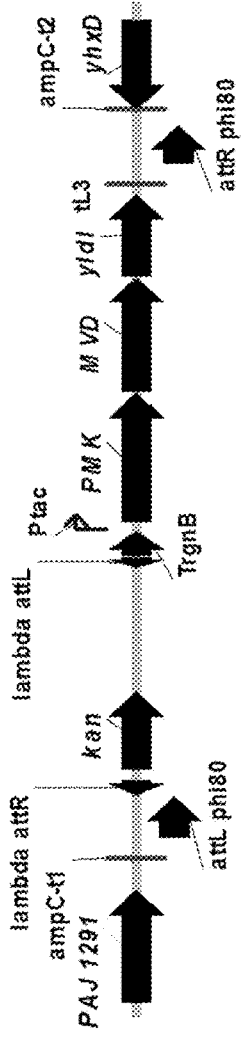
Figure 12C:
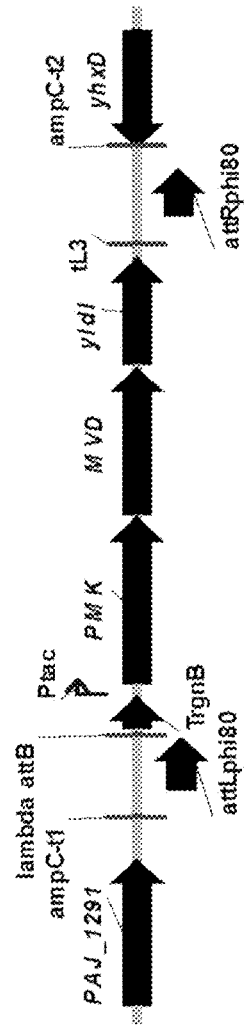
Figure 13A:
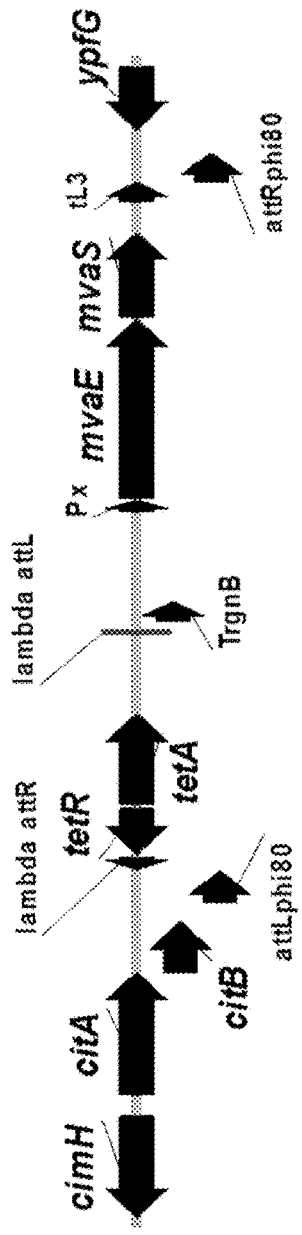
FIGS. 13A and 13B show maps of chromosome modifications of (A) ΔampH::pAH162-Px-mvaES and (B) ΔampC::pAH162-Px-mvaES.
Figure 13B:
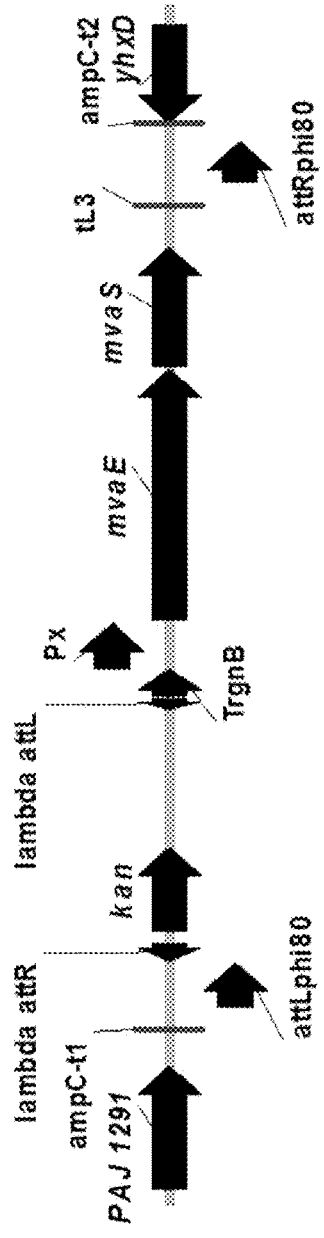

The pAH162-Km-Ptac-KDyI plasmid was integrated into the chromosome of SC17(0) ΔampH::attB$_{φ80}$ ΔampC::attB$_{φ80}$ Δcrt::Ptac-mvk (*M. paludicola*)/pAH123-cat strain according to the reported protocol (Andreeva et al., FEMS Microbiol Lett. 2011; 318(1): 55-60). The cells were seeded on LB agar containing 50 mg/L of kanamycin. A grown Km$^R$ clone was examined by PCR reaction using the primers 11 and 15 and the primers 11 and 17 (Table 1). Strains retaining the pAH162-Km-Ptac-KDyI plasmid integrated into ΔampH::attB$_{φ80}$ or ΔampC::attB$_{φ80}$m were chosen. Maps of the modified chromosomes of ΔampH::pAH162-Km-Ptac-KDyI, ΔampC::pAH162-Km-Ptac-KDyI and ΔampC::Ptac-KDyI are shown in FIGS. 12(A), (B) and (C).

pAH162-Px-mvaES (Px is one of the following regulatory regions: araC-P$_{ara}$ (*E. coli*), P$_{lldD}$, P$_{phoC}$, P$_{pstS}$) was inserted into the attB$_{phi80}$ site of SC17(0) ΔampC::pAH162-Km-Ptac-KDyI ΔampH::attB$_{phi80}$ Δcrt::Ptac-mvk (*M. paludicola*) and SC17(0) ΔampC::attB$_{phi80}$ ΔampH::pAH162-Km-Ptac-KDyI Δcrt::Ptac-mvk (*M. paludicola*) recipient strains using a pAH123-cat helper plasmid according to the reported protocol (Andreeva et al., FEMS Microbiol Lett., 2011; 318(1): 55-60). As a result, two sets of strains designated as SWITCH-Px-1 and SWITCH-Px-2 were obtained. Maps of the modified chromosomes of ΔampH::pAH162-Px-mvaES and ΔampC::pAH162-Px-mvaES are shown in FIG. 13.

TABLE 1

Primer sequences utilized in Reference Practical Example 1

| No | Name | Sequence 5'->3' |
|---|---|---|
| 1 | Linker-F | AGCTTTAGGGATAACAGGGTAATCTCGAGCTGCAGGCA TGCA (SEQ ID NO: 36) |
| 2 | Linker-R | AGCTTGCATGCCTGCAGCTCGAGATTACCCTGTTATCCC TAA (SEQ ID NO: 37) |
| 3 | lldD5' CAS | TTTTTAAGCTTTAGGGATAACAGGGTAATCTCGAGATTT AAAGCGGCTGCTTTAC (SEQ ID NO: 38) |
| 4 | lldD3' CAS | TTTTTAAGCTTGCATGCCTGCAGTATTTAATAGAATCAG GTAG (SEQ ID NO: 39) |
| 5 | phoC5' SCA | TTTTTAAGCTTTAGGGATAACAGGGTAATCTCGAGTGG ATAACCTCATGTAAAC (SEQ ID NO: 40) |
| 6 | phoC3' CAS | TTTTTAAGCTTGCATGCCTGCAGTTGATGTCTGATTATC TCTGA (SEQ ID NO: 41) |

TABLE 1-continued

Primer sequences utilized in Reference Practical Example 1

| No | Name | Sequence 5'->3' |
|---|---|---|
| 7 | pstS5' CAS | TTTTTAAGCTTTAGGGATAACAGGGTAATCTCGAGAGC CTCTCACGCGTGAATC (SEQ ID NO: 42) |
| 8 | pstS3' CAS | TTTTTAAGCTTGCATGCCTGCAGAGGGGAGAAAAGTCA GGCTAA (SEQ ID NO: 43) |
| 9 | n67 | TGCGAAGACGTCCTCGTGAAGAAGGTGTTGCTG (SEQ ID NO: 44) |
| 10 | n68 | TGCGAAGGGCCCCGTTGTGTCTCAAAATCTCTGATG (SEQ ID NO: 45) |
| 11 | ampH-attL-phi80 | ATGCGCACTCCTTACGTACTGGCTCTACTGGTTTCTTTG CGAAAGGTCATTTTTCCTGAATATGCTCACA (SEQ ID NO: 46) |
| 12 | ampH-attR-phi80 | TTAAGGAATCGCCTGGACCATCATCGGCGAGCCGTTCT GACGTTTGTTGACAGCTGGTCCAATG (SEQ ID NO: 47) |
| 13 | DampC-phL | CTGATGAACTGTCACCTGAATGAGTGCTGATGAAAATA TAGAAAGGTCATTTTTCCTGAATATGCTCA (SEQ ID NO: 48) |
| 14 | DampC-PhR | ATTCGCCAGCATAACGATGCCGCTGTTGAGCTGAGGAA CACGTTTGTTGACAGCTGGTCCAATG (SEQ ID NO: 49) |
| 15 | ampH-t1 | GCGAAGCCCTCTCCGTTG (SEQ ID NO: 50) |
| 16 | ampH-t2 | AGCCAGTCAGCCTCATCAGCG (SEQ ID NO: 51) |
| 17 | ampC-t1 | GATTCCCACTTCACCGAGCCG (SEQ ID NO: 52) |
| 18 | ampC-t2 | GGCAGGTATGGTGCTCTGACG (SEQ ID NO: 53) |
| 19 | crtE-attR-phi80 | ATGACGGTCTGCGCAAAAAAACACGTTCATCTCACTCG CGCGTTTGTTGACAGCTGGTCCAATG (SEQ ID NO: 54) |
| 20 | crtZ-attL-phi80 | ATGTTGTGGATTTGGAATGCCCTGATCGTTTTCGTTACC GGAAAGGTCATTTTTCCTGAATATGCTCA (SEQ ID NO: 55) |
| 21 | crtZ-test | CCGTGTGGTTCTGAAAGCCGA (SEQ ID NO: 56) |
| 22 | crtE-test | CGTTGCCGTAAATGTATCCGT (SEQ ID NO: 57) |
| 23 | phL-test | GGATGTAAACCATAACACTCTGCGAAC (SEQ ID NO: 58) |

Example 2: Construction of SC17(0)Δgcd and SWITCH-PphoC Δgcd

The gcd gene in *P. ananatis* codes for glucose dehydrogenase, and it has been reported that *P. ananatis* produces gluconate during aerobic growth (Andreeva et al., FEMS Microbiol Lett. 2011 May; 318(1):55-60).

The SC17(0)Δgcd strain in which the gcd gene is disrupted is constructed using λRed-dependent integration of DNA fragments obtained in PCRs with the primers gcd-attL and gcd-attR (Table 2) and the pMW118-attL-kan-attR plasmid (Minaeva et al., BMC Biotechnol. 2008; 8:63) as the template. To verify the integrant, the primers gcd-t1 and gcd-t2 (Table 2) are used.

Genomic DNA of the SC17(0)Δgcd strain is isolated using the Wizard Genomic DNA Purification Kit (Promega) and electro-transformed into the marker-less derivative of the SWITCH-PphoC strain according to the previously described method (Katashkina et al., BMC Mol Biol. 2009; 10:34]. As a result, the SWITCH-PphoC-Δgcd ($Km^R$) strain is obtained. The primers gcd-t1 and gcd-t2 (Table 2) are used for PCR analysis of the obtained integrant. The kanamycin resistant marker gene is obtained according to the standard λInt/Xis-mediated procedure (Katashkina et al., BMC Mol Biol. 2009; 10:34). The obtained strain is designated as SWITCH-PphoC Δgcd strain.

TABLE 2

Primer List

| Primer | Nucleotide sequence (SEQ ID NO:) |
|---|---|
| gcd-attL | GGTCAACATTATGGGGAAAAACTCCTCATCCTTTAGCGTGtga agcctgattttttatactaagttgg (SEQ ID NO: 18) |
| gcd-attR | TTACTTCTGGTCGGGCAGCGCATAGGCAATCACGTAATCGcgc tcaagttagtataaaaaagctgaac (SEQ ID NO: 19) |
| gcd-t1 | TGACAACAATCTATCTGATT (SEQ ID NO: 20) |
| gcd-t2 | tgcgcctggttaagctggcg (SEQ ID NO: 21) |

Example 3: Evaluation of Ability to Produce Linalool by Linalool Synthase-Expressing Strains Derived from the SWITCH-PphoC Δgcd Strain 3-1) Introduction of the Linalool Synthase Expression Plasmid into SWITCH-PphoC Δgcd Competent cells of SWITCH-PphoC Δgcd strain obtained in Example 2 were prepared, and pACYC177-Ptac-opt_ScLINS-ispA*, or pACYC177-Ptac2-opt_CsLINS-ispA* constructed in Example 1 or pACYC177 were introduced into the cells by an electroporation method. Resulting strains were designated as SWITCH-PphoC Δgcd/ScLINS-ispA*, SWITCH-PphoC Δgcd/Ptac2-CsLINS-ispA*, and SWITCH-PphoC Δgcd/pACYC177 strains, respectively.

The strains obtained above were cultured on an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

3-2) Evaluation of Ability to Produce Linalool by Linalool Synthase-Expressing Strains Derived from the SWITCH-PphoC Δgcd Strain The glycerol stocks of SWITCH-PphoC Δgcd/ScLINS-ispA*, SWITCH-PphoC Δgcd/Ptac2-CsLINS-ispA*, and SWITCH-PphoC Δgcd/pACYC177 strains were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated into 5 mL of fermentation medium (Table 3) described below containing 50 mg/L of kanamycin in a test tube produced by AGC Techno Glass Co., Ltd. (diameter×length×thickness=25× 200×1.2 mm), and cultured at 30° C. on a reciprocal shaking culture apparatus at 120 rpm for 24 hours. The fermentation medium with addition of isopropyl myristate is presented in Table 3, and the fermentation medium composition without addition of isopropyl myristate is presented in Table 4.

TABLE 3

Fermentation medium for SWITCH-PphoC Δgcd, linalool-producing host strain (with addition of isopropyl myristate)

| Group A | |
|---|---|
| D-Glucose | 40 g/L |
| MgSO$_4$•7H$_2$O | 1 g/L |
| Not adjusted pH, AC 115° C., 10 minutes | |
| Group B | |
| (NH$_4$)$_2$SO$_4$ | 20 J g/L |
| KH$_2$PO$_4$ | 0.5 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |

Dry-heat sterilization 180° C., 2 hours

TABLE 4

Fermentation medium for SWITCH-PphoC Δgcd, linalool-producing host strain (without addition of isopropyl myristate)

| Group A | |
|---|---|
| D-Glucose | 40 g/L |
| MgSO$_4$•7H$_2$O | 1 g/L |
| Not adjusted pH, AC 115° C., 10 minutes | |
| Group B | |
| (NH$_4$)$_2$SO$_4$ | 20 g/L |
| KH$_2$PO$_4$ | 0.3 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |

Dry-heat sterilization 180° C., 2 hours

After the completion of sterilization, the above Groups A, B and C were mixed. Then, 1 mL of isopropyl myristate (produced by Tokyo Chemical Industry Co., Ltd.) was added to 5 mL of the fermentation medium in the test tube. Meanwhile, cultivation was also performed without addition of isopropyl myristate.

24 hours after starting the cultivation, the concentrations of isopropyl myristate and linalool in the culture supernatant were measured under the following conditions using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd.). A sample for measurement was appropriately diluted with ethanol (supplid from Wako Pure Chemical Industries, Ltd.).

| | |
|---|---|
| Temperature in vaporization chamber | 360.0° C. |
| Injection amount | 1.0 μL |

-continued

| | |
|---|---|
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

Linalool is shown in terms of accumulated concentration in the fermentation liquor. A mean value obtained from two test tubes with addition of isopropyl myristate is shown in Table 5, and results obtained from two test tubes without addition of isopropyl myristate is shown in Table 6.

TABLE 5

Accumulation of linalool when linalool synthase native to *S. clavuligerus*, linalool synthase native to *C. sativum*, and mutated ispA were introduced in SWITCH-PphoC Δgcd (with addition of isopropyl myristate)

| Strain | O.D.620 nm | Linalool (mg/L) |
|---|---|---|
| SWITCH-PphoC Δgcd/pACYC177 | 8.9 | 0.0 |
| SWITCH-PphoC Δgcd/ScLINS-ispA* | 14.9 | 1179.0 |
| SWITCH-PphoC Δgcd/Ptac2-CsLINS-ispA* | 21.5 | 1108.1 |

TABLE 6

Accumulation of linalool when linalool synthase native to *S. clavuligerus*, linalool synthase native to *C. sativum* and mutated ispA were introduced in SWITCH-PphoC Δgcd (without addition of isopropyl myristate)

| Strain | O.D.620 nm | Linalool (mg/L) |
|---|---|---|
| SWITCH-PphoCΔgcd/pACYC177 | 12.2 | 0.0 |
| SWITCH-PphoCΔgcd/ScLINS-ispA* | 8.3 | 255.9 |
| SWITCH-PphoCΔgcd/Ptac2-CsLINS-ispA* | 10.3 | 511.7 |

Example 4: GC Analysis of Linalool Produced by Linalool Synthase-Expressing Strain Derived from SWITCH-PphoC Δgcd Strain Using Optical Isomer Separation Column Analysis of the enantiomer of linalool produced by the SWITCH-PphoC Δgcd/ScLINS-ispA* strain and the SWITCH-PphoC Δgcd/Ptac2-CsLINS-ispA* strain obtained in Example 3 was carried out. A cultivated sample with addition of isopropyl myristate was used in the analysis. Measurement was carried out under the following conditions using gas chromatograph GC-2025AF (produced by SHIMADZU CORPORATION). Rt (registered trademark)-bDEXsm (produced by Restek Corporation, length 30 m, internal diameter 0.25 mm, thickness 0.25 μm) that is an optical isomer separation column was used as a column, a reagent Linalool (Catalogue code: 126-00993) produced by Wako Pure Chemical Industries, Ltd. was used as a mixed linalool standard solution of R-linalool and S-linalool, and a reagent Linalool (Catalogue code: 62139-25ML) produced by Sigma-Aldrich Co. LLC. was used as a standard solution of R-linalool. Since an available product as a reagent of S-linalool did not exist, the peak of S-linalool was identified by comparing chromatograms of the mixed linalool standard solution of R-linalool and S-linalool and the standard solution of R-linalool. A sample for measurement was appropriately diluted with ethanol (produced by Wako Pure Chemical Industries, Ltd.).

| Temperature in vaporization chamber | 350.0° C. |
|---|---|
| Injection amount | 1.0 μL |
| Injection mode | Split 1:10 |
| Carrier gas | He |
| Control mode | Line velocity |
| Pressure | 153.3 kPa |
| Total flow | 21.5 mL/minute |
| Column flow | 1.68 mL/minute |
| Line velocity | 40 cm/sec |
| Purge flow | 3.0 mL/minute |
| Column oven temperature program Total time | 30.0 minutes |

| Rate (° C./minute) | Temperature (° C.) | Hold time (min) |
|---|---|---|
|  | 115.0 | 10.0 |
| 10.0 | 225.0 | 9.0 |

| Detector temperature | 365.0° C. |
|---|---|
| Detector | FID |
| Make-up gas | He (30.0 mL/min) |
| Hydrogen flow | 40.0 mL/min |
| Air | 400.0 mL/min |

Figure 14:
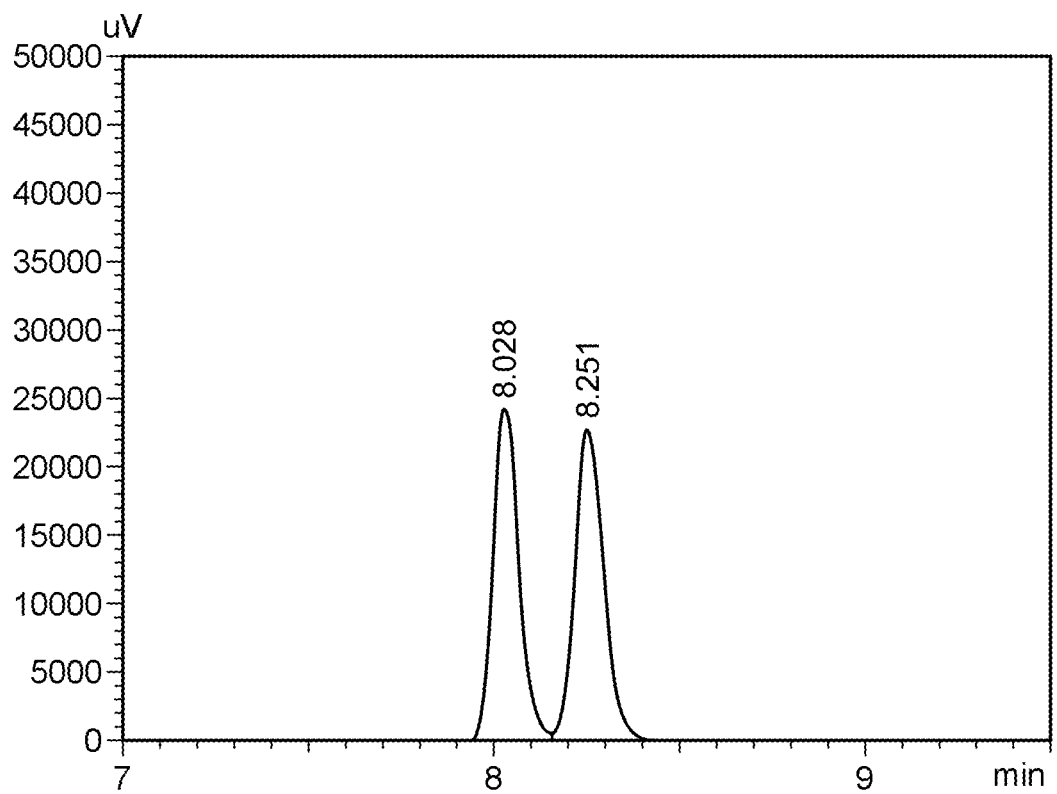
FIG. 14 shows a diagram illustrating chromatogram of a mixed linalool standard solution of R-linalool and S-linalool.
Figure 15:
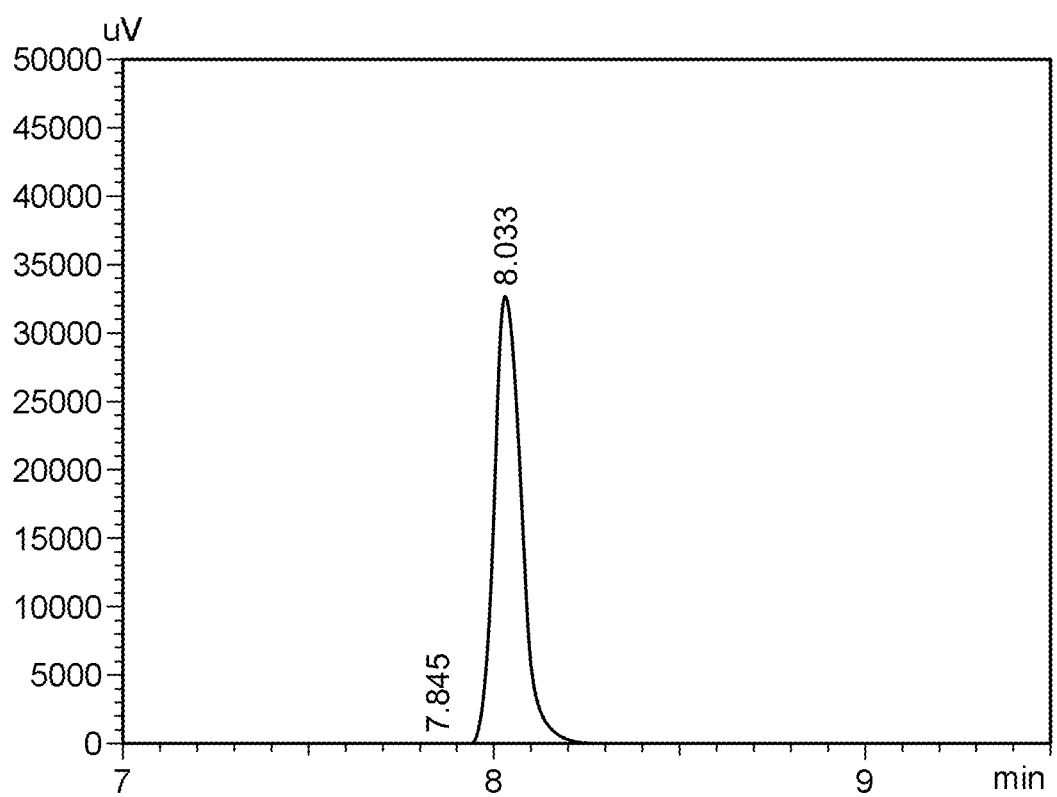
FIG. 15 shows a diagram illustrating chromatogram of a standard solution of R-linalool.
Figure 16:
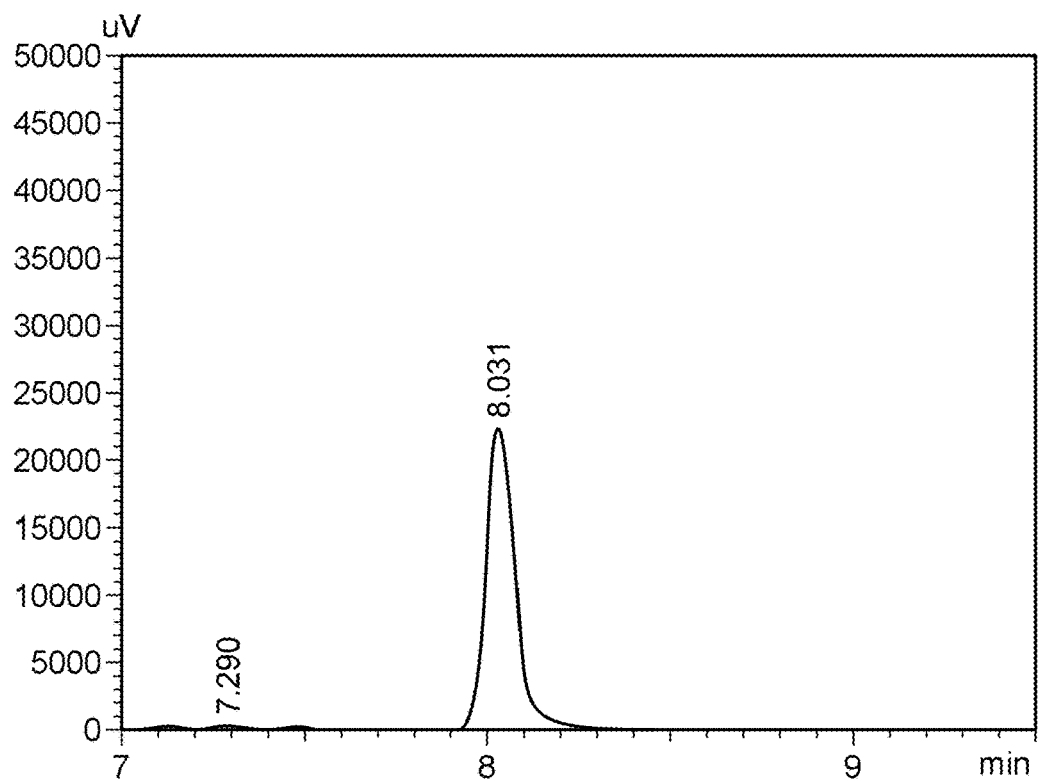
FIG. 16 shows a diagram illustrating chromatogram of a linalool sample produced by a linalool synthase-expressing strain native to S. clavuligerus.
Figure 17:
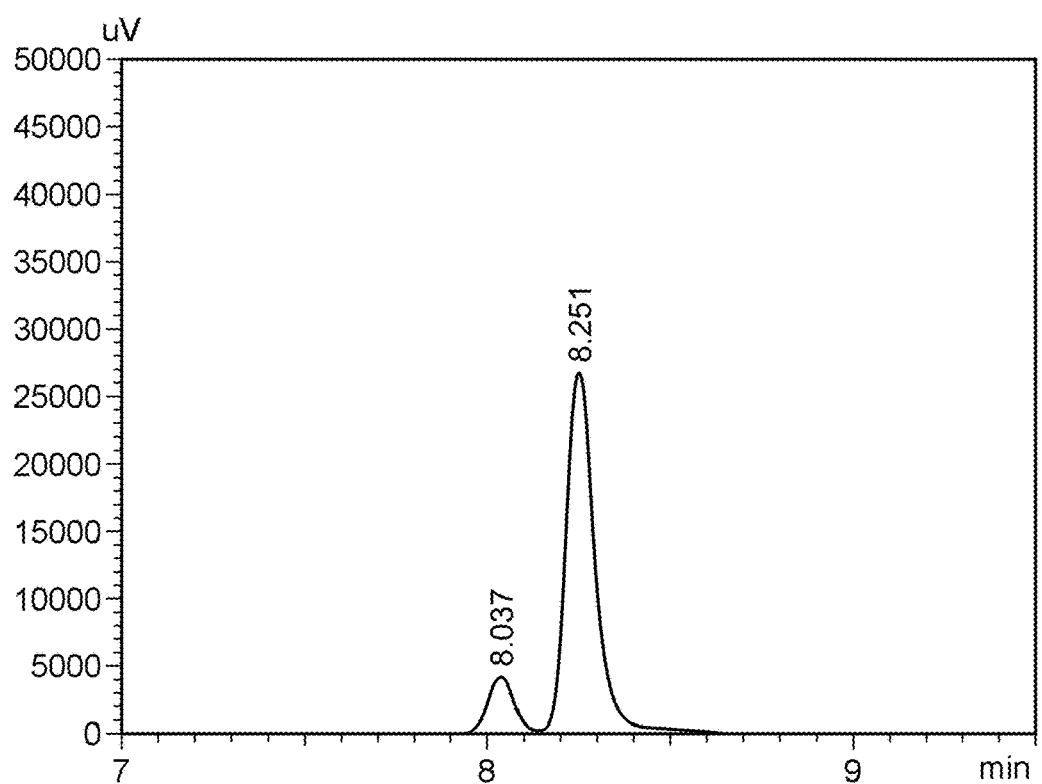
FIG. 17 shows a diagram illustrating chromatogram of a linalool sample produced by a linalool synthase-expressing strain native to C. sativum.

Chromatograms of the mixed linalool standard solution of R-linalool and S-linalool and the standard solution of R-linalool are illustrated in FIGS. 14 and 15, respectively. Chromatograms of the linalool samples produced from linalool synthase-expressing strains native to *S. clavuligerus* and *C. sativum* are illustrated in FIGS. 16 and 17, respectively.

Only the peak of R-linalool was detected in the linalool produced by the linalool synthase native to *S. clavuligerus*. It was shown that by using the linalool synthase native to *S. clavuligerus*, only R-linalool was obtained as linalool. The enantiomeric excess of R-linalool at this time was 100% e. e. On the other hand, both the peaks of R-linalool and S-linalool were detected in the linalool produced by the linalool synthase native to *C. sativum*. When a rough production ratio was calculated from each peak area, the production ratio was R-linalool:S-linalool=1:7 in the linalool synthase native to *C. sativum*.

Example 5: Headspace (HS)-GC/MS Analysis of Linalool Produced by Linalool Synthase-Expressing Strain Derived from SWITCH-PphoC Δgcd Strain Linalool purities in volatile components in each culture solution were measured by HS-GC/MS using cultivated samples of the SWITCH-PphoC Δgcd/ScLINS-ispA* strain obtained in Example 3 without addition of isopropyl myristate. Cultivated samples without addition of isopropyl myristate were used for analysis. Measurement was carried out under the following conditions using a gas chromatograph mass spectrometer GCMS-TQ8030 (produced by SHIMADZU CORPORATION). HP-5 ms (produced by Agilent Technologies, length 30 m, internal diameter 0.25 mm, thickness 0.25 μm) was used as a column, and a linalool standard solution was prepared using a reagent Linalool (Catalogue code: 126-00993). The HS vial was used by being substituted with nitrogen, and the reagent standard solution for measurement and the cultivated samples were appropriately diluted with ultrapure water.

| GC condition: | |
|---|---|
| Temperature in vaporization room | 200.0° C. |
| Injection amount | 1 mL |
| Injection mode | Split 1:30 |
| Carrier gas | He |
| Control mode | Line velocity |
| Pressure | 53.5 kPa |
| Total flow rate | 34.0 mL/min |
| Column flow rate | 1.0 mL/min |
| Line velocity | 36.3 cm/sec |
| Purge flow rate | 3.0 mL/min |
| Equilibrium time | 3.0 min |
| Column oven temperature program Total time | 33.0 min |

| Rate (° C./min) | Temperature (° C.) | Hold time (min) |
|---|---|---|
|  | 50.0 | 10.0 |
| 10.0 | 230.0 | 5.0 |

| MS condition: | |
|---|---|
| Temperature in ion source | 250.0° C. |
| Temperature in interface | 280° C. |
| Solvent elution time | 2.0 min |
| Starting m/z | 50 |
| Finishing m/z | 200 |

| HS condition: | |
|---|---|
| Vial warming temperature | 80.0° C. |
| Vial warming time | 1800 sec |
| Syringe warming temperature | 95.0° C. |
| Syringe conditioning | 240 sec |
| Cycle time | 2580 sec |

Figure 18:
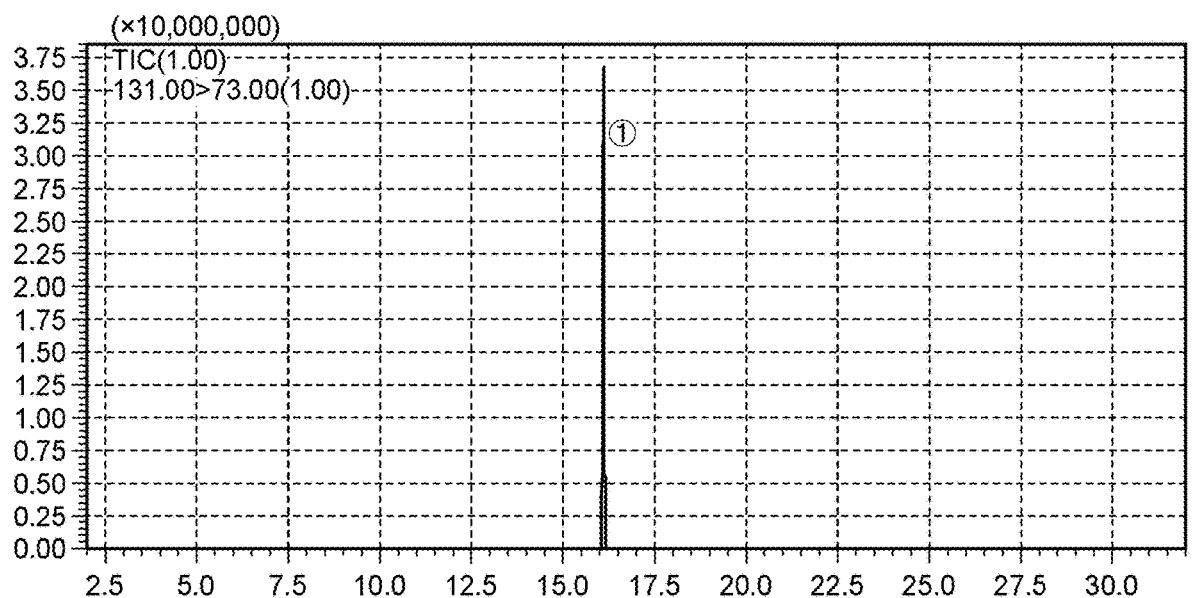
FIG. 18 shows a diagram illustrating total ion chromatogram of a mixed linalool standard solution of R-linalool and S-linalool.
Figure 19:
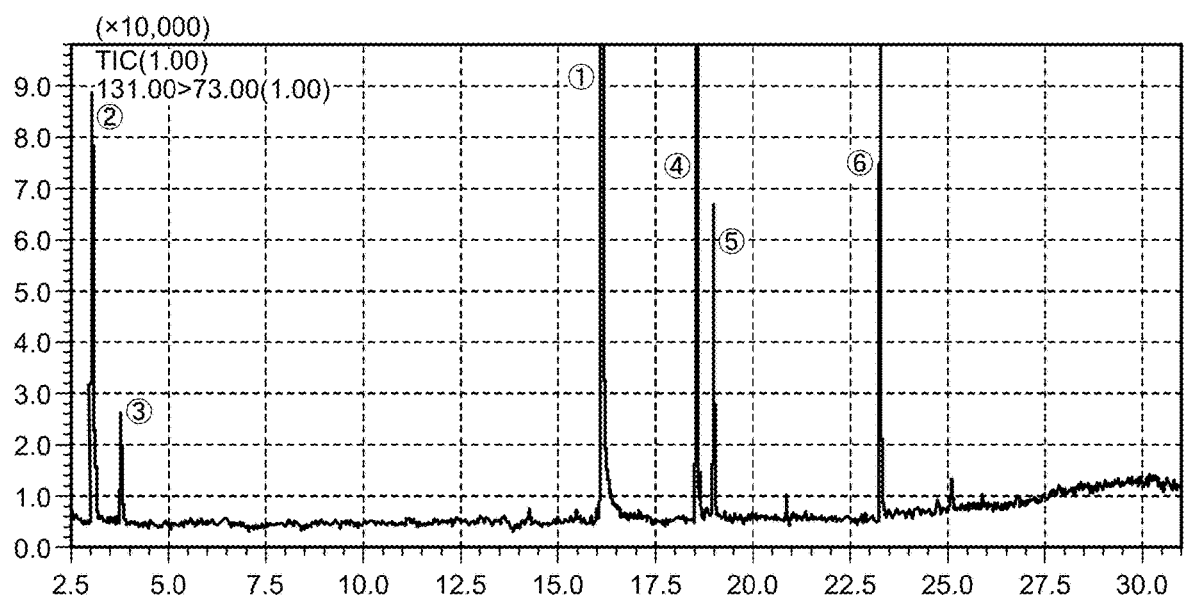
FIG. 19 shows a diagram illustrating total ion chromatogram of a linalool sample produced by a linalool synthase-expressing strain native to S. clavuligerus.

The total ion chromatogram (TIC) of the mixed linalool standard solution of R-linalool and S-linalool is illustrated in FIG. 18, and the identified substance is presented in Table 7. Other than linalool in which an authentic sample is analyzed, substance names estimated from fragment ion peaks are shown. Furthermore, the TIC of the cultivated sample of *S. clavuligerus* is illustrated in FIG. 19, and the identified compounds are presented in Table 8. As comparative targets, proportions of linalool in essential oil components native to lavender (Planta Med 2016; 82(01/02): 163-170) and derived from bergamot (Molecules 2009, 14(2), 839-849) and substances, which are contained in a relatively large amount, other than linalool in the essential oil components are presented in Table 9.

TABLE 7

Identification result of volatile components in reagent linalool (HS-GC/MS)

| | CAS No. | Compound name | Molecular formula | Similarity | Retention time (min) | Area |
|---|---|---|---|---|---|---|
| 1 | 78-70-6 | Linalool | $C_{10}H_{18}O$ | 95 | 16.122 | 117,804,749 |

TABLE 8

Identification result of volatile components produced by linalool synthase-expressing strain native to *S. clavuligerus* (HS-GC/MS)

| | CAS No. | Compound name | Molecular formula | Similarity | Retention time (min) | Area | Area proportion |
|---|---|---|---|---|---|---|---|
| 1 | 78-70-6 | Linalool | $C_{10}H_{18}O$ | 95 | 16.078 | 9,784,391 | 89.5% |
| 2 | 123-51-3 | 3-Methyl-1-butanol | $C_5H_{12}O$ | 96 | 3.009 | 290,174 | 2.7% |
|  | 71-41-0 | 1-Pentanol | $C_5H_{12}O$ | 94 |  |  |  |
| 3 | 556-82-1 | 3-Methyl-2-butene-1-ol | $C_5H_{10}O$ | 94 | 3.732 | 62,736 | 0.6% |
| 4 | 106-22-9 | β-Citronellol | $C_{10}H_{20}O$ | 96 | 18.516 | 455,497 | 4.2% |
|  | 1117-61-9 | (R)-(+)-β-Citronellol | $C_{10}H_{20}O$ | 94 |  |  |  |
| 5 | 106-24-1 | Geraniol | $C_{10}H_{18}O$ | 95 | 18.95 | 103,505 | 0.9% |
|  | 106-25-2 | Nerol | $C_{10}H_{18}O$ | 94 |  |  |  |
| 6 | 40716-66-3 | trans-Nerolidol | $C_{15}H_{26}O$ | 93 | 23.232 | 237,498 | 2.2% |
|  | 2306-78-7 | Nerolidyl acetate | $C_{17}H_{28}O_2$ | 93 |  |  |  |
|  |  |  |  |  | Total | 10,933,801 | 100.0% |

TABLE 9

Comparison table of linalool and other main components contained in linalool fermentation liquor and plant extract (essential oil)

| | Area (%) | | |
|---|---|---|---|
| | Fermentation liquor | [a] Lavender EO | [b] Bergamot fruit EO |
| R-Linalool | 89.5 | 38.0 | 31.8 |
| Linalyl acetate | — | 37.0 | 10.7 |
| Limonene | — | 0.5 | 31.7 |
| Caryophyllene | — | 3.5 | 0.2 |

[a] Extract derived from *Lavandula angustifolia* (Planta Med 2016; 82(01/02): 163-170)
[b] Extract derived from *Citrus aurantium* subsp. *Bergamia* (Molecules 2009, 14(2), 839-849)

From the above results, it was demonstrated that the content of R-linalool obtained by the area percentage method of volatile components (flavor components) contained in the fermentation liquor was 89.5%, that is, extremely high. Furthermore, it is known that linalyl acetate, limonene, and caryophyllin are contained in extracts derived from plants including linalool. The production of linalyl acetate, limonene, and caryophyllin was not detected as volatile components (flavor components) contained in the fermentation liquor. From these points of view, it was demonstrated that by using the production method as described herein, a linalool composition with a high purity of R-linalool in volatile components (flavor components) can be produced.

From this result, it is shown that the linalool synthase-expressing strain native to *S. clavuligerus* produces linalool at a high ratio of 85% or more in terms of area proportion in volatile components thereof. Furthermore, this result shows that by cultivating a microorganism expressing linalool synthase derived from actinomycete, it is possible to obtain R-linalool with a high enantiomeric excess and a high linalool purity in volatile components of the fermentation liquor.

Example 6: Construction of Linalool Synthase-Expression Plasmid 6-1) Obtaining a Linalool Synthase Gene Native to *Actinidia arguta* (Hardy Kiwifruit)

A nucleotide sequence (GenBank accession number: GQ338153) and an amino acid sequence (GenPept accession number: ADD81294) of a linalool synthase (AaLINS) gene and protein native to *Actinidia arguta* have been reported (Chen, X. et al., (2010) Functional Plant Biology, 37: 232-243). The amino acid sequence of a linalool synthase protein and the nucleotide sequence of its gene native to *Actinidia arguta* are shown in SEQ ID NO: 78 and SEQ ID NO: 79. In order to efficiently express the AaLINS gene, codons were optimized, an AaLINS gene in which a chloroplast localization signal had been cleaved was designed, and this was designated as opt_AaLINS. A nucleotide sequence of opt_AaLINS is shown in SEQ ID NO: 3. DNA in which a tac promoter region (deBoer et al., (1983) Proc. Natl. Acad. Sci. U.S.A., 80, 21-25) had been added to the opt_AaLINS gene was chemically synthesized, cloned into pMW119 (produced by NIPPON GENE CO., LTD.), and the resulting plasmid was designated as pMW119-Ptac-opt_AaLINS.

6-2) Construction of Co-Expression Plasmid for Opt_AaLINS and ispA* Genes

PCR with pMW119-Ptac-opt_AaLINS as a template was carried out using primers shown in SEQ ID NO: 81 and SEQ ID NO: 82 to obtain a Ptac-opt_AaLINS fragment. Furthermore, PCR with pMW119-ispA* as a template was carried out using primers shown in SEQ ID NO: 83 and SEQ ID NO: 84 to obtain an ispA* fragment. The purified Ptac-opt_AaLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_AaLINS-ispA*.

Example 7: Evaluation of Ability to Produce Linalool by Linalool Synthase-Expressing Strains Derived from SWITCH-PphoC ΔGcd Strain 7-1) Introduction of Linalool Synthase Expression Plasmid into SWITCH-PphoC ΔGcd Strain Competent cells of SWITCH-PphoC Δgcd obtained in Example 2 were prepared, and pACYC177-Ptac-opt_Aa-LINS-ispA* constructed in Example 6, pACYC177-Ptac2-opt_CsLINS-ispA* or pACYC177-Ptac2-opt_CsLINS constructed in Example 1, or pACYC177 were introduced into the cells by an electroporation method. The resulting strains were designated as SWITCH-PphoC Δgcd/AaLINS-ispA*, SWITCH-PphoC Δgcd/Ptac2-CsLINS-ispA*, and SWITCH-PphoC Δgcd/pACYC177 strains, respectively.

The strains obtained above were cultured on an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

7-2) Evaluation of Ability to Produce Linalool by Linalool Synthase-Expressing Strains Derived from SWITCH-PphoC Δgcd Strain The glycerol stocks of SWITCH-PphoC Δgcd/AaLINS-ispA*, SWITCH-PphoC Δgcd/Ptac2-CsLINS-ispA*, SWITCH-PphoC Δgcd/Ptac2-CsLINS, and SWITCH-PphoC Δgcd/pACYC177 strains were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium (its composition was described in Table 3) containing 50 mg/L of kanamycin in a test tube produced by AGC Techno Glass Co., Ltd. (diameter×length×thickness=25× 200×1.2 mm), and cultured at 30° C. on a reciprocal shaking culture apparatus at 120 rpm for 24 hours, as Example 3.

After 24 hours from starting the cultivation, the concentrations of isopropyl myristate and linalool in the culture supernatant were measured under the following conditions using gas chromatograph GC-2025AF (produced by SHIMADZU CORPORATION) under the condition described in Example 3.

Linalool is shown in terms of accumulated concentration in the fermentation liquor. A mean value obtained from two test tubes with addition of isopropyl myristate is shown in Table 10, and results obtained from two test tubes without addition of isopropyl myristate is shown in Table 11.

TABLE 10

Accumulation of linalool when linalool synthase native to *A. arguta*, linalool synthase native to *C. sativum*, and mutated ispA were introduced into SWITCH-PphoC Δgcd (with addition of isopropyl myristate)

| Strain | O.D.620 nm | Linalool (mg/L) |
|---|---|---|
| SWITCH-PphoC Δgcd/pACYC177 | 8.9 | 0.0 |
| SWITCH-PphoC Δgcd/AaLINS-ispA* | 17.4 | 1575.7 |
| SWITCH-PphoC Δgcd/Ptac2-CsLINS-ispA* | 21.5 | 1108.1 |

TABLE 11

Accumulation of linalool when linalool synthase native to *A. arguta*, linalool synthase native to *C. sativum*, and mutated ispA were introduced into SWITCH-PphoC Δgcd (without addition of isopropyl myristate)

| Strain | O.D.620 nm | Linalool (mg/L) |
|---|---|---|
| SWITCH-PphoC Δgcd/pACYC177 | 12.2 | 0.0 |
| SWITCH-PphoC Δgcd/AaLINS-ispA* | 9.3 | 530.3 |
| SWITCH-PphoC Δgcd/Ptac2-CsLINS-ispA* | 10.3 | 511.7 |

Example 8: GC Analysis of Linalool Produced by Linalool Synthase-Expressing Strain Native to SWITCH-PphoC Δgcd Strain Using Optical Isomer Separation Column Analysis of the enantiomer of linalool produced by the SWITCH-PphoC Δgcd/AaLINS-ispA* strain and the SWITCH-PphoC Δgcd/Ptac2-CsLINS-ispA* strain obtained in Example 7 was carried out. A cultivated sample with addition of isopropyl myristate was used in the analysis. Measurement was carried out under the conditions described in Example 4 using gas chromatograph GC-2025AF (produced by SHIMADZU CORPORATION).

Figure 20:
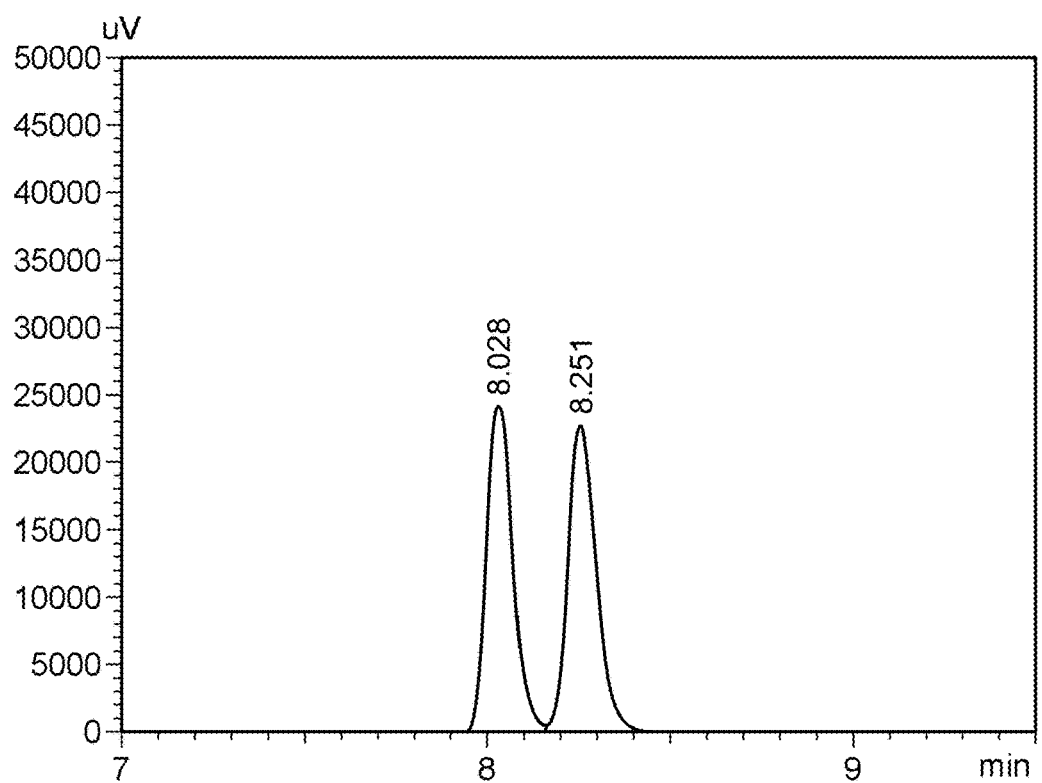
FIG. 20 shows a diagram illustrating chromatogram of a mixed linalool standard solution of R-linalool and S-linalool.
Figure 21:
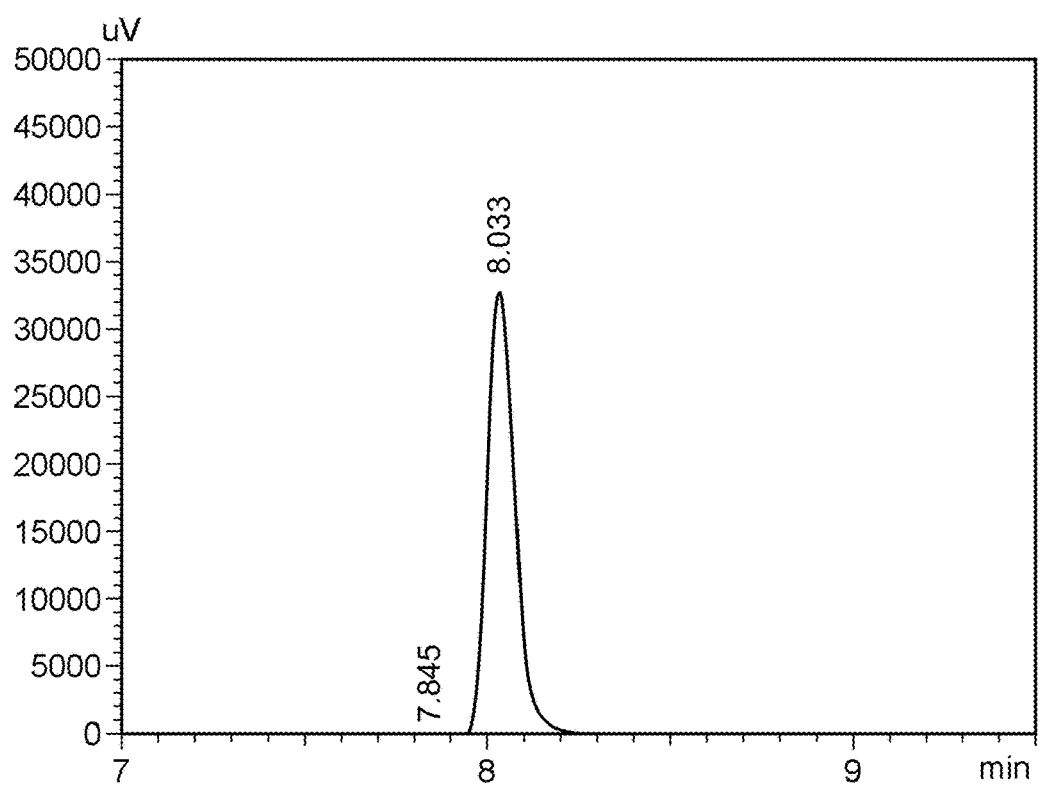
FIG. 21 shows a diagram illustrating chromatogram of a standard solution of R-linalool.
Figure 22:
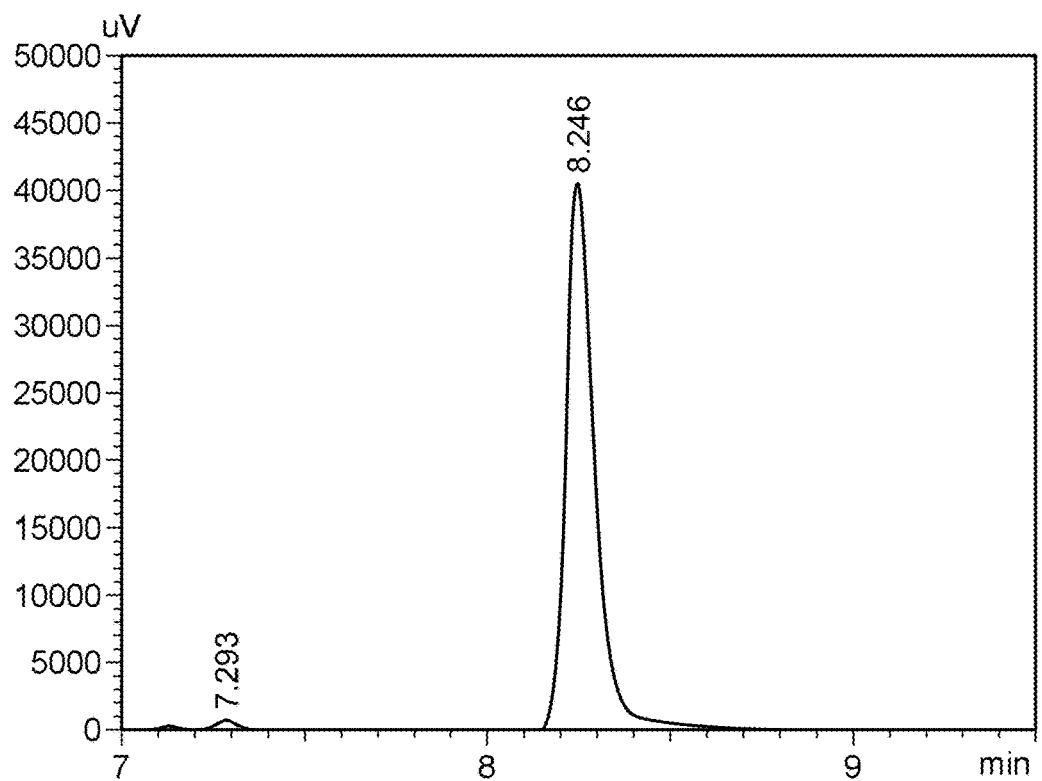
FIG. 22 shows a diagram illustrating chromatogram of a linalool sample produced by a linalool synthase-expressing strain native to A. arguta.
Figure 23:
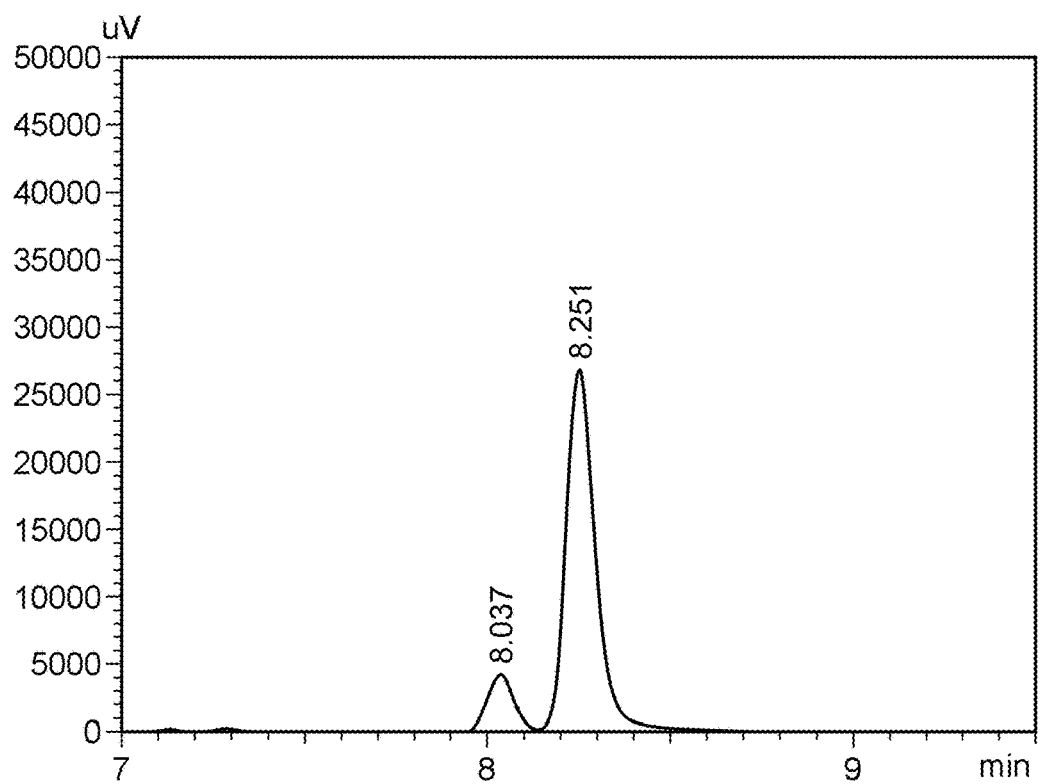
FIG. 23 shows a diagram illustrating chromatogram of a linalool sample produced by a linalool synthase-expressing strain native to C. sativum.

Chromatograms of the mixed linalool standard solution of R-linalool and S-linalool and the standard solution of R-linalool are illustrated in FIGS. 20 and 21, respectively. Chromatograms of the linalool samples produced from linalool synthase-expressing strains native to *A. arguta* and *C. sativum* are illustrated in FIGS. 22 and 23, respectively.

Only the peak of S-linalool was detected in the linalool produced by the linalool synthase native to *A. arguta*. It was shown that by using the linalool synthase native to *A. arguta*, only S-linalool was obtained as linalool. The enantiomeric excess of S-linalool at this time was 100% e. e. On the other hand, both the peaks of R-linalool and S-linalool were detected in the linalool produced by the linalool synthase native to *C. sativum*. When a rough production ratio was calculated from each peak area, the production ratio was R-linalool:S-linalool=1:7 in the linalool synthase native to *C. sativum*.

Example 9: Headspace (HS)-GC/MS Analysis of Linalool Produced by Linalool Synthase-Expressing Strain Derived from SWITCH-PphoC Δgcd Strain Linalool purities in volatile components in each culture solution were measured by HS-GC/MS using cultivated samples of the SWITCH-PphoC Δgcd/AaLINS-ispA* strain obtained in Example 7 without addition of isopropyl myristate. Measurement was carried out under the following conditions using a gas chromatograph mass spectrometer GCMS-TQ8030 (produced by SHIMADZU CORPORATION) under the conditions described in Example 5. HP-5 ms (produced by Agilent Technologies, length 30 m, internal diameter 0.25 mm, thickness 0.25 μm) was used as a column, and a linalool standard solution was prepared using a reagent Linalool (Catalogue code: 126-00993). The HS vial was used by being substituted with nitrogen, and the reagent standard solution for measurement and the cultivated samples were appropriately diluted with ultrapure water.

Figure 24:
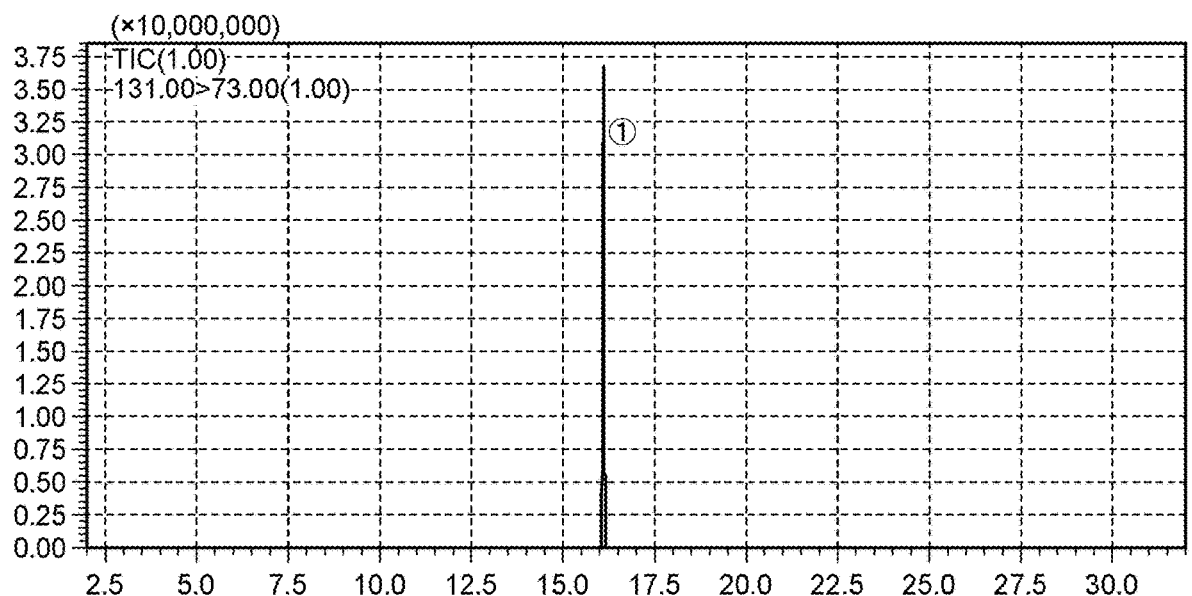
FIG. 24 shows a diagram illustrating total ion chromatogram of a mixed linalool standard solution of R-linalool and S-linalool.
Figure 25:
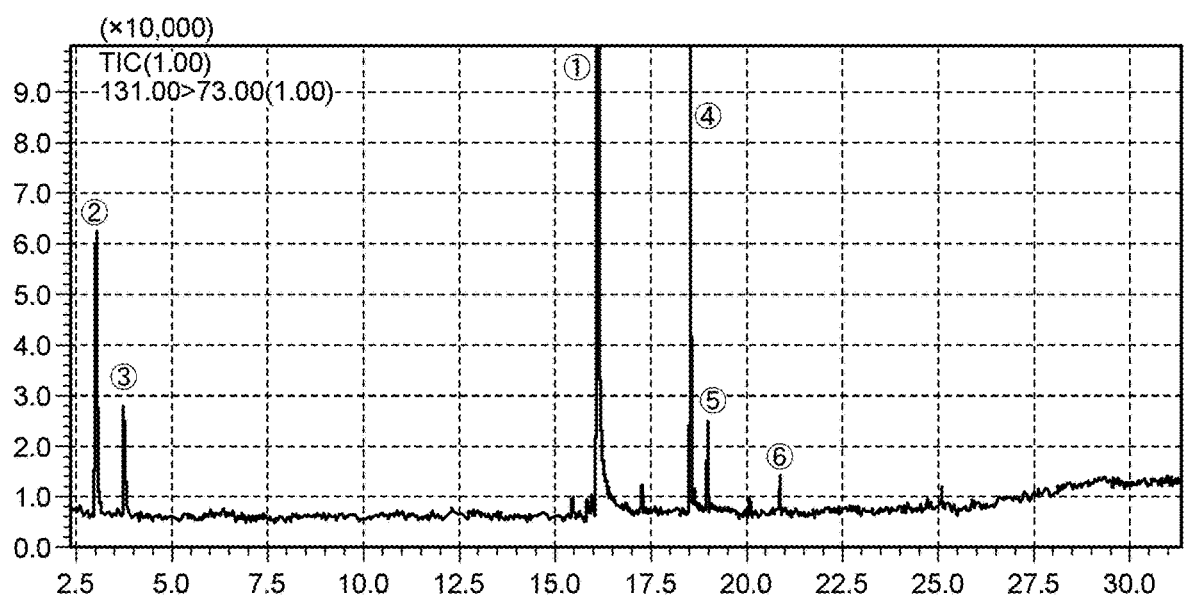
FIG. 25 shows a diagram illustrating total ion chromatogram of a linalool sample produced by a linalool synthase-expressing strain native to A. arguta.
Figure 26:
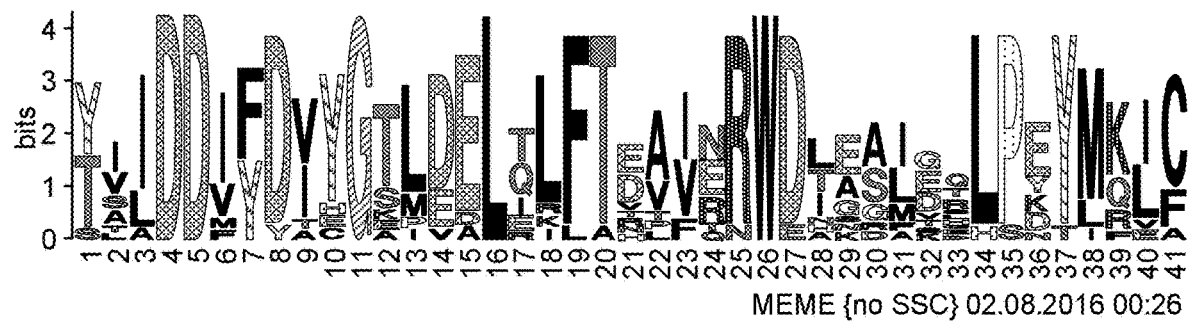
FIG. 26 shows a diagram illustrating the sequence logo of motif 1.
Figure 27:
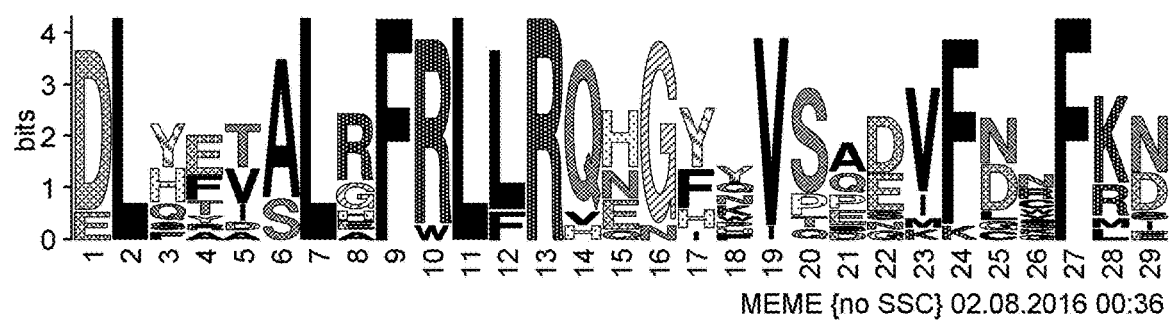
FIG. 27 shows a diagram illustrating the sequence logo of motif 2.
Figure 28:
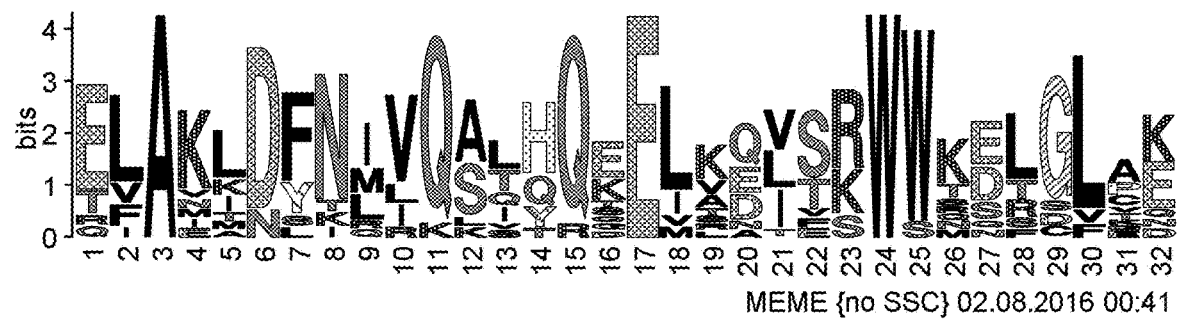
FIG. 28 shows a diagram illustrating the sequence logo of motif 3.

The total ion chromatogram (TIC) of the mixed linalool standard solution of R-linalool and S-linalool is illustrated in FIG. 24, and the identified substance is presented in Table 12. Other than linalool in which an authentic sample is analyzed, substance names estimated from fragment ion peaks are shown. Furthermore, the TIC of the cultivated sample of *A. arguta* is illustrated in FIG. 25, and the identified compounds are presented in Table 13. As comparative targets, proportions of linalool in essential oil components derived from lavender (Planta Med 2016; 82(01/02): 163-170) and derived from bergamot (Molecules 2009, 14(2), 839-849;) and substances, which are contained in a relatively large amount, other than linalool in the essential oil components are presented in Table 14.

TABLE 12

Identification of volatile components in reagent linalool (HS-GC/MS)

| | CAS No. | Compound name | Molecular formula | Similarity | Retention time (min) | Area |
|---|---|---|---|---|---|---|
| 1 | 78-70-6 | Linalool | $C_{10}H_{18}O$ | 95 | 16.122 | 117,804,749 |

TABLE 13

Identification result of volatile components produced by linalool synthase-expressing strain native to *A. arguta* (HS-GC/MS)

| | CAS No. | Compound name | Molecular formula | Similarity | Retention time (min) | Area | Area proportion |
|---|---|---|---|---|---|---|---|
| 1 | 78-70-6 | Linalool | $C_{10}H_{18}O$ | 95 | 16.08 | 12,097,400 | 96.45% |
| 2 | 123-51-3 | 3-Methyl-1-butanol | $C_5H_{12}O$ | 95 | 3.011 | 175,957 | 1.40% |
|   | 71-41-0 | 1-Pentanol | $C_5H_{12}O$ | 93 | | | |
| 3 | 556-82-1 | 3-Methyl-2-buten-1-ol | $C_5H_{10}O$ | 94 | 3.744 | 53,842 | 0.43% |
| 4 | 106-22-9 | β-Citronellol | $C_{10}H_{20}O$ | 96 | 18.518 | 173,794 | 1.39% |
|   | 1117-61-9 | (R)-(+)-β-Citronellol | $C_{10}H_{20}O$ | 93 | | | |
| 5 | 106-25-2 | Nerol | $C_{10}H_{18}O$ | 92 | 18.954 | 31,268 | 0.25% |
|   | 106-24-1 | Geraniol | $C_{10}H_{18}O$ | 92 | | | |
| 6 | 57576-09-7 | Isopulegol acetate | $C_{12}H_{20}O_2$ | 82 | 20.855 | 10,795 | 0.09% |
| | | | | | Total | 12,543,056 | 100.00% |

TABLE 14

Comparison table of linalool and other main components contained in linalool fermentation liquor and plant extract (essential oil)

| | Area (%) | | |
|---|---|---|---|
| | Fermentation liquor | [a]Lavender EO | [b]Bergamot fruit EO |
| S-Linalool | 96.5 | 38.0 | 31.8 |
| Linalyl acetate | — | 37.0 | 10.7 |
| Limonene | — | 0.5 | 31.7 |
| Caryophyllene | — | 3.5 | 0.2 |

[a]Extract derived from *Lavandula angustifolia* (Planta Med 2016; 82(01/02): 163-170)

[b]Extract derived from *Citrus aurantium* subsp. *Bergamia* ((Molecules 2009, 14(2), 839-849;)

From the above results, it was demonstrated that the content of S-linalool obtained by the area percentage method of volatile components (flavor components) contained in the fermentation liquor was 96.45%, that is, extremely high. Furthermore, it is known that linalyl acetate, limonene, and caryophyllin are contained in extracts derived from plants including linalool. The production of linalyl acetate, limonene, and caryophyllin was not detected as volatile components (flavor components) contained in the fermentation liquor. From these points of view, it was demonstrated that by using the production method as described herein, a linalool composition with a high purity of S-linalool in volatile components (flavor components) can be produced.

From this result, it is shown that the linalool synthase-expressing strain native to *A. arguta* produces linalool at a high ratio of 95% or more in terms of area proportion in volatile components thereof. Furthermore, this result shows that by cultivating a microorganism expressing linalool synthase native to *A. arguta*, it is possible to obtain S-linalool with a high enantiomeric excess and a high linalool purity in volatile components of the fermentation liquor.

TABLE 15

Sequence information (Part 1)

| SEQ ID NO | Sequence |
|---|---|
| 1 | Amino acid sequence of *S. clavuligerus* linalool synthase |
| 2 | Nucleotide sequence of *S. clavuligerus*-derived linalool synthase |
| 3 | Nucleotide sequence of codon-modified *S. clavuligerus*-derived linalool synthase |
| 4 | Amino acid sequence of *C. sativum* linalool synthase |

TABLE 15-continued

Sequence information (Part 1)

| SEQ ID NO | Sequence |
|---|---|
| 5 | Nucleotide sequence of T C. sativum-derived linalool synthase |
| 6 | Nucleotide sequence of codon-modified C. sativum-derived linalool synthase |
| 7 | Nucleotide sequence of E. Coli-derived farnesyl diphosphate synthase (ispA) |
| 8 | Nucleotide sequence of codon-modified E. coli-derived farnesyl diphosphate synthase (ispA*) |
| 9 | Nucleotide sequence of P. ananatis-derived GCD |
| 10 | Amino acid sequence of P. ananatis-derived GCD |
| 11 | GTGTGAAATTAGCCAGAGCTGCGGGCCACC |
| 12 | TGGCTAATTTCACACAGGAGACTGCCatggatttttccccagcag |
| 13 | ACGTTGTTGCCATTGCCCTGTTTGCAATTAATCATCG |
| 14 | ACGTTGTTGCCATTGCCCTGTTGACAATTAATCATCG |
| 15 | ATGACTTGGTTGAGTCTATTTGTTGCGCTGGATGATG |
| 16 | TGTGAAATTATAAGGGAATGGGTTCAAC |
| 17 | CCTTATAATTTCACACAGGAGACTGCCATGGATTTTCCCCAGCAG |
| 18-21 | See Table 2 |
| 22 | Amino acid sequence of E. faecalis-derived mvaE protein |
| 23 | Nucleotide sequence of E. faecalis-derived mvaE |
| 24 | Nucleotide sequence of codon-modified E. faecalis dericed mvaE (EFmvaE) |
| 25 | Amino acid sequence of E. faecalis-derived mvaS protein |
| 26 | Nucleotide sequence of E. faecalis-derived mvaS |
| 27 | Nucleotide sequence of codon-modified E. faecalis-derived mvaS (EFmvaS) |
| 28-35 | Primer used in Reference Practical Example 1 |
| 36-59 | See Table 5 |
| 60 | Nucleotide sequence including Kdyl operon |
| 61 | Amino acid sequence of A. thaliana-derived linalool synthase |
| 62 | Nucleotide sequence of A. thaliana-derived linalool synthase |
| 63 | Nucleotide sequence of codon-modified A. thaliana-derived linalool synthase |
| 64 | Amino acid sequence of P. frutescens var. crispa-derived linalool synthase |
| 65 | Nucleotide sequence of P. frutescens var. crispa-derived linalool synthase |
| 66 | Nucleotide sequence of codon-modified P. frutescens var. crispa-derived linalool synthase |
| 67 | Amino acid sequence of V. vinifera-derived linalool synthase |
| 68 | Nucleotide sequence of V. vinifera-derived linalool synthase |
| 69 | Nucleotide sequence of codon-modified V. vinifera-derived linalool synthase |
| 70 | Amino acid sequence of M. citrata-derived linalool synthase |
| 71 | Nucleotide sequence of M. citrata-derived linalool synthase |
| 72 | Nucleotide sequence of codon-modified M. citrata-derived linalool synthase |
| 73 | Amino acid sequence of O. basilicum-derived linalool synthase |
| 74 | Nucleotide sequence of O. basilicum-derived linalool synthase |
| 75 | Nucleotide sequence of codon-modified O. basilicum-derived linalool synthase |
| 76 | Amino acid sequence of E. Coli-derived linalool synthase (ispA) |
| 77 | Amino acid sequence of codon-modified E. Coli-derived farnesyl diphosphate synthase (ispA*) |

TABLE 16

Sequence information (Part 2)

| SEQ ID NO | Sequence |
|---|---|
| 78 | Amino acid sequence of A. arguta-derived linalool synthase |
| 79 | Nucleotide sequence of A. arguta-derived linalool synthase |
| 80 | Nucleotide sequence of codon-modified A. arguta-derived linalool synthase |
| 81 | ACGTTGTTGCCATTGCCCTGTTGACAATTAATCATCG |
| 82 | TGTGAAATTAGCTACTGGAATCATACAAC |
| 83 | GTAGCTAATTTCACACAGGAGACTGCCATGGATTTTCCCCAGCAG |
| 84 | ATGACTTGGTTGAGTCTATTTGTTGCGCTGGATGATG |

Example 10: Database Search of Linalool Synthase

A homology search on a non-redundant database was carried out using the amino acid sequence of linalool synthase (GenPept accession number ADD81294.1) native to hardy kiwifruit as a query sequence and by the BLASTP program (Altschul et al., "Basic local alignment search tool." J. Mol. Biol. 215, 403-410, 1990). Furthermore, plant names which are reported to produce linalool were searched by Essential oil database (Kumari et al., "EssOilDB: a database of essential oils reflecting terpene composition and variability in the plant kingdom" Database, 2014, 1-12 doi: 10. 1093/database/bau120). By comparing these results, candidates of linalool synthase were extracted from plants which are known to have an ability to produce linalool. Furthermore, literature references disclosing candidate sequences were reviewed and 13 distinct enzymes that are expected to have linalool synthase function were chosen (Table 17). Regarding the amino acid sequences of these 13 distinct enzymes, chloroplast localization signal sequences were investigated according to SignalP or literature information described in Table 18. Regarding those in which the presence of the signal sequence is indicated, the predicted signal sequence was eliminated to obtain mature amino acid sequences. The sequences of genes encoding these amino acid sequences are shown in SEQ ID NOs: 85 to 97 (M1 to M13) (Table 17). As for these, gene synthesis was carried out on the based on sequences optimized for use of codons in *Pantoea ananatis*. The DNA sequences after the codon optimization are shown in SEQ ID NOs: 98, 100, 102, 104, 106, 108, 110, 112, 114, 116, 118, 120, and 122 (M14, M16, M18, M20, M22, M24, M26, M28, M30, M32, M34, M36, and M38) (Table 18). Gene names presented in Table 18 are applied to these DNA sequences. The amino acid sequences encoded by these DNA sequences are shown in SEQ ID NOs: 99, 101, 103, 105, 107, 109, 111, 113, 115, 117, 119, 121, and 123 (M15, M17, M19, M21, M23, M25, M27, M29, M31, M33, M35, M37, and M39) (Table 18). The DNA of each gene after the codon optimization was obtained by chemical synthesis and then cloned into pUC57. The names of the resulting plasmids are described in Table 19.

TABLE 17

Extracted linalool synthase candidates

| # | Origin | GenPept accession number | DDBJ/EMBL/ Genbank accession number | SEQ ID NO. |
|---|--------|--------------------------|--------------------------------------|------------|
| 1 | *Arabidopsis thaliana* | NP_001185286 | NM_001198357 | 85 (M1) |
| 2 | *Arabidopsis thaliana* | ACF41947 | BT033153 | 86 (M2) |
| 3 | *Citrus unshiu* | BAP75561 | AB857232 | 87 (M3) |
| 4 | *Citrus unshiu* | BAP75560 | AB857231 | 88 (M4) |
| 5 | *Citrus unshiu* | BAP75559 | AB857230 | 89 (M5) |
| 6 | *Malus domestica* | AGB14629 | JX848734 | 90 (M6) |
| 7 | *Perilla frutescens* var. *crispa* | AAL38029 | AF444798 | 91 (M7) |
| 8 | *Vitis vinifera* | AEY82696 | JQ062931 | 92 (M8) |
| 9 | *Vitis vinifera* | ADR74209 | HM807390 | 93 (M9) |
| 10 | *Lavandula angustifolia* | ABB73045 | DQ263741 | 94 (M10) |
| 11 | *Mentha citrata* | AAL99381 | AY083653 | 95 (M11) |
| 12 | *Ocimum basilicum* | AAV63789 | AY693647 | 96 (M12) |
| 13 | *Clarkia breweri* | AAC49395 | U58314 | 97 (M13) |

TABLE 18

Literatures of linalool synthase candidates described in Table 17 and annotation information

| # | Definition | literature | DNA sequence number[1] | Amino acid sequence number[2] |
|---|------------|------------|------------------------|-------------------------------|
| 1 | terpene synthase 14 | Nature 408, 816-820 (2000) | 98 (M14) | 99 (M15) |
| 2 | At2g24210, terpene synthase 10, TPS10 | Plant Cell. 25, 4640-4657 (2013), Arch Biochem Biophys. 375, 261-269 (2000) | 100 (M16) | 101 (M17) |
| 3 | linalool synthase | Plant Sci. 229, 154-166 (2014) | 102 (M18) | 103 (M19) |
| 4 | linalool synthase | Plant Sci. 229, 154-166 (2014) | 104 (M20) | 105 (M21) |
| 5 | linalool synthase | Plant Sci. 229, 154-166 (2014) | 106 (M22) | 107 (M23) |
| 6 | linalool synthase | Plant Physiol. 161, 787-804 (2013) | 108 (M24) | 109 (M25) |
| 7 | linalool synthase | Phytochemistry 71, 1068-1075 (2010) | 110 (M26) | 111 (M27) |
| 8 | (3S)-linalool/(E)-nerolidol synthase | Int J Mol Sci 15, 21992-22010 (2014) | 112 (M28) | 113 (M29) |
| 9 | (3R)-linalool synthase | BMC Plant Biol. 10, 226 (2010) | 114 (M30) | 115 (M31) |
| 10 | linalool synthase | Arch. Biochem. Biophys. 465, 417-429 (2007) | 116 (M32) | 117 (M33) |
| 11 | linalool synthase | Arch. Biochem. Biophys. 405, 112-121 (2002) | 118 (M34) | 119 (M35) |
| 12 | R-linalool synthase | Plant Physiol. 136, 3724-3736 (2004) | 120 (M36) | 121 (M37) |
| 13 | S-linalool synthase | Plant Cell 8, 1137-1148 (1996) | 122 (M38) | 123 (M39) |

[1]sequence number in the sequence listing corresponding to DNA sequence after codon optimization
[2]sequence number in the sequence listing corresponding to the amino acid sequence of linalool synthase used in test

TABLE 19

Vectors obtained by cloning sequences after codon optimization of Table 18 into pUC57

| # | Insert DNA sequence number | Gene name after codon optimization | Vector name |
|---|-----------------------------|-------------------------------------|-------------|
| 1 | 98 (M14) | At1LINS | pUC57-At1LINS |
| 2 | 100 (M16) | At2LINS | pUC57-At2LINS |

TABLE 19-continued

Vectors obtained by cloning sequences after codon optimization of Table 18 into pUC57

| # | Insert DNA sequence number | Gene name after codon optimization | Vector name |
|---|---|---|---|
| 3 | 102 (M18) | Cu1LINS | pUC57-Cu1LINS |
| 4 | 104 (M20) | Cu2LINS | pUC57-Cu2LINS |
| 5 | 106 (M22) | Cu3LINS | pUC57-Cu3LINS |
| 6 | 108 (M24) | MdLINS | pUC57-MdLINS |
| 7 | 110 (M26) | PfLINS | pUC57-PfLINS |
| 8 | 112 (M28) | Vv1LINS | pUC57-Vv1LINS |
| 9 | 114 (M30) | Vv2LINS | pUC57-Vv2LINS |
| 10 | 116 (M32) | LaLINS | pUC57-LaLINS |
| 11 | 118 (M34) | McLINS | pUC57-McLINS |
| 12 | 120 (M36) | ObLINS | pUC57-ObLINS |
| 13 | 122 (M38) | CbLINS | pUC57-CbLINS |

Example 11: Construction of Various Linalool Synthase-Expressing Plasmids 11-1) Construction of co-expression plasmid for At1LINS and ispA* genes PCR with pUC57-At1LINS described in Table 19 as a template was carried out using primer Q28 (SEQ ID NO:124) and primer Q29 (SEQ ID NO:125) to obtain At1LINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-At1LINS-ispA*.

11-2) Construction of Co-Expression Plasmid for At2LINS and ispA* Genes

PCR with pUC57-At2LINS described in Table 19 as a template was carried out using primer Q30 (SEQ ID NO:126) and primer Q31 (SEQ ID NO:127) to obtain At2LINS fragment. Furthermore, PCR with pACYC177-Ptac-opt_AaLINS-ispA* constructed in Example 1 as a template was carried out using primer Q46 (SEQ ID NO:142) and primer Q47 (SEQ ID NO:143) to obtain a DNA fragment including pACYC177, tac promoter region (deBoer, et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-At2LINS-ispA*.

11-3) Construction of Co-Expression Plasmid for MdLINS and ispA* Genes

PCR with pUC57-MdLINS described in Table 19 as a template was carried out using primer Q32 (SEQ ID NO:128) and primer Q33 (SEQ ID NO:129) to obtain MdLINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-MdLINS-ispA*.

11-4) Construction of Co-Expression Plasmid for PfLINS and ispA* Genes

PCR with pUC57-PfLINS described in Table 19 as a template was carried out using primer Q34 (SEQ ID NO:130) and primer Q35 (SEQ ID NO:131) to obtain NUNS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-PfLINS-ispA*.

11-5) Construction of Co-Expression Plasmid for Vv1LINS and ispA* Genes

PCR with pUC57-Vv1LINS described in Table 19 as a template was carried out using primer Q36 (SEQ ID NO:132) and primer Q37 (SEQ ID NO:133) to obtain Vv1LINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-Vv1LINS-ispA*.

11-6) Construction of Co-Expression Plasmid for Vv2LINS and ispA* Genes

PCR with pUC57-Vv2LINS described in Table 19 as a template was carried out using primer Q38 (SEQ ID NO:134) and primer Q39 (SEQ ID NO:135) to obtain Vv2LINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-Vv2LINS-ispA*.

11-7) Construction of Co-Expression Plasmid for McLINS and ispA* Genes

PCR with pUC57-McLINS described in Table 19 as a template was carried out using primer Q40 (SEQ ID NO:136) and primer Q41 (SEQ ID NO:137) to obtain McLINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-McLINS-ispA*.

11-8) Construction of Co-Expression Plasmid for ObLINS and ispA* Genes

PCR with pUC57-ObLINS described in Table 19 as a template was carried out using primer Q42 (SEQ ID NO:138) and primer Q43 (SEQ ID NO:139) to obtain ObLINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-ObLINS-ispA*.

11-9) Construction of Co-Expression Plasmid for ObLINS and ispA* Genes

PCR with pUC57-ObLINS described in Table 19 as a template was carried out using primer Q44 (SEQ ID NO:140) and primer Q45 (SEQ ID NO:141) to obtain ObLINS fragment. Furthermore, PCR with pACYC177-Ptac-opt_AaLINS-ispA* constructed in Example 6 as a template was carried out using primer Q46 (SEQ ID NO:142) and primer Q47 (SEQ ID NO:143) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-CbLINS-ispA*.

Example 12: Evaluation of Ability to Produce Linalool by Linalool Synthase-Expressing Strains Derived from SWITCH-PphoC Δgcd Strain 12-1) Introduction of Linalool Synthase Expression Plasmid into SWITCH-PphoC Δgcd Strain Competent cells of SWITCH-PphoC Δgcd obtained in Example 2 were prepared, and pACYC177-At1LINS-ispA*, pACYC177-At2LINS-ispA*, pACYC177-MdLINS-ispA*, pACYC177-PfLINS-ispA*, pACYC177-Vv1LINS-ispA*, pACYC177-Vv2LINS-ispA*, pACYC177-McLINS-ispA*, pACYC177-ObLINS-ispA*, and pACYC177-CbLINS-ispA* constructed in Example 11, and pACYC177 were introduced into the cells by an electroporation method. Resulting strains were designated as SWITCH-PphoC Δgcd/At1LINS-ispA*, SWITCH-PphoC Δgcd/At2LINS-ispA*, SWITCH-PphoC Δgcd/MdLINS-ispA*, SWITCH-PphoC Δgcd/PfLINS-ispA*, SWITCH-PphoC Δgcd/Vv1LINS-ispA*, SWITCH-PphoC Δgcd/Vv2LINS-ispA*, SWITCH-PphoC Δgcd/McLINS-ispA*, SWITCH-PphoC Δgcd/ObLINS-ispA*, SWITCH-PphoC Δgcd/CbLINS-ispA*, and SWITCH-PphoC Δgcd/pACYC177 strains, respectively.

The strains obtained above were cultured on an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

12-2) Evaluation of Ability to Produce Linalool by Linalool Synthase-Expressing Strains Derived from SWITCH-PphoC Δgcd Strain The glycerol stocks of SWITCH-PphoC Δgcd/At1LINS-ispA*, SWITCH-PphoC Δgcd/At2LINS-ispA*, SWITCH-PphoC Δgcd/MdLINS-ispA*, SWITCH-PphoC Δgcd/PfLINS-ispA*, SWITCH-PphoC Δgcd/Vv1LINS-ispA*, SWITCH-PphoC Δgcd/Vv2LINS-ispA*, SWITCH-PphoC Δgcd/McLINS-ispA*, SWITCH-PphoC Δgcd/ObLINS-ispA*, SWITCH-PphoC Δgcd/CbLINS-ispA*, and SWITCH-PphoC Δgcd/pACYC177 strains were thawed. Subsequently, 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated into 5 mL of fermentation medium used in Example 3 (Table 3) containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours. After the completion of sterilization, the Groups A, B and C were mixed. Then, 1 mL of isopropyl myristate (produced by Tokyo Chemical Industry Co., Ltd.) was added to 5 mL of the fermentation medium dispensed in the test tube.

After 24 hours from starting the cultivation, the concentrations of isopropyl myristate and linalool in the culture supernatant were measured under the following conditions using gas chromatograph GC-2025AF (produced by SHIMADZU CORPORATION) under the conditions described in Example 3.

Linalool is shown in terms of accumulated concentration in the fermentation liquor. A mean value obtained from two test tubes with addition of isopropyl myristate is shown in Table 20.

TABLE 20

Accumulation of linalool when various linalool synthases, and mutated ispA were introduced in SWITCH-PphoC Δgcd (with addition of isopropyl myristate)

| Strain | O.D. 620 nm | Linalool (mg/L) |
| --- | --- | --- |
| SWITCH-PphoCΔgcd/pACYC177 | 13.6 | 0.0 |
| SWITCH-PphoCΔgcd/At1LINS-ispA* | 20.2 | 13.3 |
| SWITCH-PphoCΔgcd/At2LINS-ispA* | 18.9 | 30.8 |
| SWITCH-PphoCΔgcd/MdLINS-ispA* | 11.5 | 116.7 |
| SWITCH-PphoCΔgcd/PfLINS-ispA* | 14.6 | 29.2 |
| SWITCH-PphoCΔgcd/Vv1LINS-ispA* | 16.5 | 37.3 |
| SWITCH-PphoCΔgcd/Vv2LINS-ispA* | 16.6 | 2.6 |
| SWITCH-PphoCΔgcd/McLINS-ispA* | 16.4 | 19.0 |
| SWITCH-PphoCΔgcd/ObLINS-ispA* | 21.7 | 519.8 |

Example 13: GC Analysis of Linalool Produced by Linalool Synthase-Expressing Strain Derived from SWITCH-PphoC Δgcd Strain Using Optical Isomer Separation Column Analysis of the enantiomer of linalool produced by the SWITCH-PphoC Δgcd/At1LINS-ispA* strain, the SWITCH-PphoC Δgcd/At2LINS-ispA* strain, the SWITCH-PphoC Δgcd/MdLINS-ispA* strain, the SWITCH-PphoC Δgcd/PfLINS-ispA* strain, the SWITCH-PphoC Δgcd/Vv1LINS-ispA* strain, the SWITCH-PphoC Δgcd/Vv2LINS-ispA* strain, the SWITCH-PphoC Δgcd/McLINS-ispA* strain, the SWITCH-PphoC Δgcd/ObLINS-ispA* strain, and the SWITCH-PphoC Δgcd/CbLINS-ispA* strain obtained in Example 12 was carried out. A sample cultivated under the same conditions as in Example 12 was used in the analysis. Measurement was carried out under the same conditions as in Example 4 using gas chromatograph GC-2025AF (produced by SHIMADZU CORPORATION).

The ratio of the peak area of S-linalool or the peak area of R-linalool to the sum of the peak area of S-linalool and the peak area of R-linalool detected in the cultivated samples of respective strains is presented in Table 21.

TABLE 21

Production ratio of S enantiomer linalool and R enantiomer linalool
when various linalool synthases and mutated ispA were introduced
in SWITCH-PphoC Δgcd (with addition of isopropyl myristate)

| Strain | Ratio (%) of R-linalool to sum of peak area of S-linalool and peak area of R-linalool (%) | Ratio (%) of S-linalool to sum of peak area of S-linalool and peak area of R-linalool (%) |
|---|---|---|
| SWITCH-PphoCΔgcd/At1LINS-ispA* | 1.5 | 98.5 |
| SWITCH-PphoCΔgcd/At2LINS-ispA* | 97.8 | 2.2 |
| SWITCH-PphoCΔgcd/MdLINS-ispA* | 0.0 | 100.0 |
| SWITCH-PphoCΔgcd/PfLINS-ispA* | 96.6 | 3.4 |
| SWITCH-PphoCΔgcd/Vv1LINS-ispA* | 0.6 | 99.4 |
| SWITCH-PphoCΔgcd/Vv2LINS-ispA* | 92.4 | 7.6 |
| SWITCH-PphoCΔgcd/McLINS-ispA* | 97.6 | 2.4 |
| SWITCH-PphoCΔgcd/ObLINS-ispA* | 100.0 | 0.0 |
| SWITCH-PphoCΔgcd/CbLINS-ispA* | 0.3 | 99.7 |

Only the peak of the S enantiomer was detected in the linalool produced by the linalool synthase native to *Malus×domestica*. It was shown that by using the linalool synthase native to *Malus×domestica*, linalool having an enantiomeric excess of the S enantiomer of 100% was obtained. Only the peak of the R enantiomer was detected in the linalool produced by the linalool synthase native to *Ocimum basilicum*. It was shown that by using the linalool synthase native to *Ocimum basilicum*, linalool having an enantiomeric excess of the R enantiomer of 100% was obtained. Both the peaks of the R enantiomer and the S enantiomer were also detected in linalool produced by linalool synthase other than the above-described linalool synthase.

Example 14: Construction of Linalool Synthase-Expressing Plasmid

A *Corynebacterium glutamicum* (i) 2256 strain (ATCC13869) was used as a coryneform bacterium (Okumura et al., 1962, Santamaria et al., 1984, Tsuchida et al., 1986). A plasmid for expressing an opt_AaLINS gene and an ispA gene in *C. glutamicum* was constructed by the following procedure. PCR with pACYC177-Ptac-optAaLINS-ispA* obtained in Example 1 as a template was carried out using primers 814 and 815 shown in SEQ ID NOs: 144 and 145 to obtain an optAaLINS-ispA* fragment. Then, PCR with chromosomal DNA of the *C. glutamicum* 2256 strain as a template was carried out using primers 812 and 813 shown in SEQ ID NOs: 146 and 147 for the purpose of obtaining a promoter sequence of Elongation Factor Tu (hereinafter, described as P0480) (WO 2013/179722 A1) to obtain a P0480 fragment. Subsequently, a shuttle vector pVK9 of *C. glutamicum* and *E. coli* (WO 2013/179722 A1) was digested with a restriction enzyme XbaI (produced by Takara Bio Inc.) (Miwa et al., 1985). The purified optAaLINS-ispA* fragment, the PCR product of P0480, and pVK9 digested with XbaI and then purified were ligated using In-Fusion HD cloning kit (produced by Clontech Laboratories, Inc.). The resulting plasmid for expressing an optAaLINS-ispA* gene was designated as pVK9-P0480-optAaLINS-ispA* and the sequence information of this plasmid was shown in SEQ ID NO: 148.

Example 15: Linalool Production in *C. glutamicum* 2256 Strain 15-1) Introduction of Opt_AaLINS-ispA* Gene-Expressing Plasmid to *C. glutamicum* 2256 Strain The transformation of the *C. glutamicum* 2256 strain was carried our according to the previously described method (WO 2013/179722 A1). The respective plasmid DNAs of pVK9 and pVK9-P0480-optAaLINS-ispA* were introduced, applied onto a CM-Dex plate culture medium containing 25 μg/ml of kanamycin (WO 2013/179722 A1), and cultured at 30° C. for 48 hours. The transformant exhibiting kanamycin resistance was obtained from the plate after cultivation, and a strain in which pVK9 is introduced into the *C. glutamicum* 2256 strain was designated as a 2256/pVK9 strain and a strain in which pVK9-P0480-optAaLINS-ispA* is introduced into the *C. glutamicum* 2256 strain was designated as 2256/pVK9-P0480-optAaLINS-ispA*.

15-2) Evaluation of Ability to Produce Linalool by Linalool Synthase-Expressing Strains Derived from *C. glutamicum* 2256 Strain The 2256/pVK9 strain and the 2256/pVK9-P0480-optAaLINS-ispA* strain were uniformly applied onto a CM-Dex plate containing 25 (mg/L) of kanamycin and cultured at 30° C. for about 18 hours. The microbial cells corresponding to ⅙ part of the plate were inoculated from the plate after the cultivation to a large diameter test tube containing 5 ml of the culture medium for coryne_linalool production (Table 22) containing 25 (mg/L) of kanamycin, and cultured at 30° C. for 24 hours.

TABLE 22

| Culture medium for coryne_linalool production | |
|---|---|
| Glucose | 80 g/L |
| $(NH_4)_2SO_4$ | 30 g/L |

TABLE 22-continued

Culture medium for coryne_linalool production

| | |
|---|---|
| $KH_2PO_4$ | 1 g/L |
| $MgSO_4 \cdot 7H_2O$ | 0.4 g/L |
| $FeSO_4 \cdot 7H_2O$ | 0.01 g/L |
| $MnSO_4 \cdot 4\text{-}5H_2O$ | 0.01 g/L |
| VB1•HCl | 200 µg/L |
| Biotin | 60 µg/L |
| Mameno | 0.48 g/L |
| pH 8.0(KOH) | |
| Autoclave 115° C. 10 min | |
| $CaCO_3$ | 50 g/L |
| 180° C. 90 min | |

1 mL of isopropyl myristate (produced by Tokyo Chemical Industry Co., Ltd.) was added to 5 mL of a culture medium for coryne_linalool production (Table 22) dispensed in the large diameter test tube.

24 hours after starting the cultivation, the concentrations of isopropyl myristate and linalool contained in the culture solution and linalool contained in were measured under the same conditions as in Example 3 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries, Ltd.).

The concentration of linalool is shown in terms of medium. An average value obtained from three large diameter test tubes is presented in Table 23. Linalool production was not observed in the control 2256/pVK9 strain, whereas the linalool production was confirmed in the 2256/pVK9-P0480-optAaLINS-ispA* strain (Table 23).

TABLE 23

Accumulation of linalool when linalool synthase native to *A. arguta* and mutant ispA were introduced

| Strain | O.D. 620 nm | Linalool (mg/L) |
|---|---|---|
| 2256/pVK9 | 73.4 | 0.00 |
| 2256/pVK9-$P_{0480}$-sLINS2-ispA* | 86.3 | 4.32 |

Example 16: Construction of Linalool Synthase-Expressing Plasmid 16-1) Plasmid that can be Transformed into *Synechocystis* sp. PCC6803 GT Strain It is known that *Synechocystis* sp. PCC6803 can be subjected to natural transformation. The plasmids pTKHT0846-slr0846 and pUC57-slr0846 contain the sequences of parts of coding regions of sll0822, slr0846, and sll0821, the sequence of a kanamycin resistance gene, and the like, and when the coding regions of slr0846 and sll0821 are set to homologous sequences, the genomic recombination of the *Synechocystis* sp. PCC6803 strain can be carried out (Midorikawa et al. (2012) Plant Cell Physiol. 53(1): 164-172). The plasmid of pTKHT0846-slr0846 was furnished by Prof. Masahiko Ikeuchi, Graduate School of Arts and Sciences, the University of Tokyo, and the total synthesis of pUC57-slr0846 was entrusted to GenScript.

16-2) Construction of Opt_AaLINS Gene-Expressing Plasmid

PCR with pMW119-Ptac-opt_AaLINS obtained in Example 6 as a template was carried out using a primer 671 shown in SEQ ID NO: 149 and a primer 691 shown in SEQ ID NO: 150 to obtain a Ptac-opt_AaLINS fragment. The purified Ptac-opt_AaLINS fragment was ligated to pTKHT0846-slr0846 digested with restriction enzymes AatII and HpaI using In-Fusion HD cloning kit (produced by Clontech Laboratories, Inc.) to construct pTKHT0846-Ptac-opt_AaLINS.

16-3) Construction of Opt_AaLINS-ispA* Gene-Expressing Plasmid

PCR with pACYC177-Ptac-opt_AaLINS-ispA* obtained in Example 6 as a template was carried out using a primer 719 shown in SEQ ID NO: 151 and a primer 721 shown in SEQ ID NO: 152 to obtain an opt_AaLINS-ispA* fragment. The purified opt_AaLINS-ispA* fragment was ligated to pUC57-slr0846-PpsbA2 digested with a restriction enzyme NheI using In-Fusion HD cloning kit (produced by Clontech Laboratories, Inc.) to construct pUC57-slr0846-PpsbA2-opt_AaLINS-ispA*.

Example 17: Linalool Production in *Synechocystis* sp. PCC6803 GT Strain 17-1) Introduction of Opt_AaLINS Gene-Expressing Plasmid into *Synechocystis* Sp. PCC6803 GT Strain The *Synechocystis* sp. PCC6803 GT strain was transformed according to the previously described method (WO 2015/115520 A1). 1 to 2 µg of the constructed plasmid pTKHT0846-Ptac-opt_AaLINS was mixed to 1 mL of the culture solution of the *Synechocystis* sp. PCC6803 GT strain (O.D 730=0.5 to 1.0) and the resulting solution was used as a cell-DNA mixture solution. The O.D. value was measured by a 96-well plate reader (Molecular Devices Spectra Max M2e) at 720 nm. Hereinafter, the O.D. value of cultivation using the *Synechocystis* sp. PCC6803 GT strain was measured by this instrument. A nitrocellulose membrane (Millipore Corporation, surfactant free, pore size 0.2 µm, model number: HATF08250) was placed on a BG-11 agar medium (Table 24) without addition of a drug, and then the cell-DNA mixture solution was applied thereto. After cultivation under conditions of 18 to 24 hours, 34° C., $CO_2$ concentration 1%, and light intensity 50 µE/m²/s, the nitrocellulose membrane was transferred to the BG-11 agar medium (Table 24) containing 20 mg/L of kanamycin. Thereafter, cultivation was carried out under conditions of 2 to 4 weeks, 34° C., $CO_2$ concentration 1%, and light intensity 50 µE/m²/s, and then emerging colonies were subcultured to a new BG-11 agar medium (Table 24) containing 20 mg/L of kanamycin. This subculturing operation was repeated three to four times, and colony PCR was carried out to resulting colonies using a primer 683 shown in SEQ ID NO: 153 and a primer 684 shown in SEQ ID NO: 154. It was confirmed that a DNA fragment having a target size was inserted to a target position in genome, and the resulting strain was designated as a GT0846K-Ptac-AaLINS strain.

The strain obtained above was grown on the BG-11 agar medium (Table 24) containing 20 mg/L of kanamycin. Cultivation was carried out for about 3 days under conditions of 60 rpm, 34° C., $CO_2$ concentration 1%, and light intensity 50 µE/m2/s with a whirl shaking culture apparatus provided with an LED light emitting unit (LC-LED 450W (white)) (TAITEC CORPORATION NR-20 or NR-30). Cells were collected by centrifugation of about 1 mL of this culture solution at 7,000 rpm, for 5 min, and at room temperature, a stocked solution prepared by removing the supernatant and adding dimethylsulfoxide to the BG-11 liquid culture medium (Table 24) to have a final concentration of 5% was added and suspended, and the resulting solution was dispensed in each appropriate amount and then stored as a frozen stock at −80° C.

TABLE 24

BG-11 culture Medium for cultivation

Stock solution
Solution I

| | |
|---|---|
| Citric acid (anhydride) | 0.3 g/100 mL |
| Ferric Ammonium Citrate | 0.3 g/100 mL |
| Na$_2$ EDTA | 0.05 g/100 mL |

Not adjusted pH; adjusted to 100 mL by using water treated with reverse osmosis membrane (RO water)
Solution II

| | |
|---|---|
| NaNO$_3$ | 30 g/L |
| K$_2$HPO$_4$ | 0.78 g/L |
| MgSO$_4$·7H$_2$O | 1.5 g/L |

Not adjusted pH; adjusted to 1 L by RO water
Solution III

| | |
|---|---|
| CaCl$_2$·2H$_2$O | 1.9 g/100 mL |

Not adjusted pH; adjusted to 100 mL by RO water
Solution IV

| | |
|---|---|
| Na$_2$CO$_3$ | 2 g/100 mL |

Not adjusted pH; after adjusted to 100 mL by RO water, sterilized by filter pHRO100 mL
Solution A6

| | |
|---|---|
| H$_3$BO$_3$ | 2.86 g/L |
| MnCl$_2$·4H$_2$O | 1.81 g/L |
| ZnSO$_4$·7H$_2$O | 0.22 g/L |
| CuSO$_4$·5H$_2$O | 0.08 g/L |
| Na$_2$MoO4 | 0.021 g/L |
| Concentrated sulfuric acid one droplet/L | |
| Co(No3)$_2$·6H$_2$O | 0.0494 g/L |

Not adjusted pH; adjusted to 1 L by RO water

As for the liquid culture medium, 50 mL of Solution II, 2 mL of Solution III, 1 mL of Solution IV, 1 mL of Solution A6, 20 mL of 1 M TES-KOH (pH 8.2), and 926 mL of RO water were mixed and subjected to treatment at AC 121° C./20 min, and 2 mL of Solution I similarly subjected to treatment at AC 121° C./20 min was mixed thereto.

As for the agar medium, 1 mL of Solution I, 25 mL of Solution II, 1 mL of Solution III, 0.5 mL of Solution IV, 0.5 mL of Solution A6, 1.5 g of sodium thiosulfate (anhydride), 10 mL of 1 M TES-KOH (pH 7.8), and 261 mL of RO water were mixed, and a solution subjected to treatment at AC 121° C./20 min and the total amount of a mixed solution of 7.5 g of BactoAgar (produced by Nippon Becton, Dickinson and Company) similarly subjected to treatment at AC 121° C./20 min and 200 mL of RO water were mixed thereto.

17-2) Introduction of Opt_AaLINS-ispA* Gene-Expressing Plasmid into *Synechocystis* sp. PCC6803 GT Strain The transformation was carried out by the same method as in 17-1. As a drug for selecting a transformant into which pUC57-slr0846-PpsbA2-opt_AaLINS-ispA* is introduced, a culture medium containing 20 mg/L of kanamycin (Table 24) was used. Colony PCR was carried out to resulting colonies using a primer 683 shown in SEQ ID NO: 153 and a primer 684 shown in SEQ ID NO: 154. It was confirmed that a DNA fragment having a target size was inserted to a target position in genome, and the resulting strain was designated as a GT0846K-PpsbA2-AaLINS-ispA* strain.

The strain obtained above was grown on the BG-11 agar medium (Table 24) containing 20 mg/L of kanamycin. The frozen stock was prepared by the method described in 17-1 and stored at −80° C.

17-3) Evaluation of Ability to Produce Linalool by Linalool Synthase-Expressing Strain Derived from *Synechocystis* sp. PCC6803 GT Strain The ability to produce linalool was evaluated in the *Synechocystis* sp. PCC6803 GT strain, the GT0846K-Ptac-AaLINS strain, and the GT0846K-PpsbA2-AaLINS-ispA* strain. That is, the frozen stocks were thawed, 50 μL of a microbial cell suspension from each strain was uniformly applied onto a BG-11 agar medium (Table 24) containing a necessary drug, and cultivation was carried out for about 7 days under conditions of 34° C., $CO_2$ concentration 1%, and light intensity 50 μE/m$^2$/s. The *Synechocystis* sp. PCC6803 GT strain was cultured without addition of a drug, and the GT0846K-Ptac-AaLINS strain and the GT0846K-PpsbA2-AaLINS-ispA* strain were cultured with addition of 20 mg/L of kanamycin. The resulting microbial cells on the agar medium were scraped in an appropriate amount using a 1 μL inoculating loop (produced by Thermo Fisher Scientific Inc.) and inoculated into 5 mL of a BG-11 liquid culture medium (Table 24) containing a necessary drug in a 6-well plate (produced by Corning Incorporated, model number: 351146). Cultivation was carried out for about 3 days under culture conditions of 60 rpm, 30° C., $CO_2$ concentration 1%, and light intensity 50 μE/m$^2$/s with a whirl shaking culture apparatus provided with an LED light emitting unit (LC-LED 450W (white)) (TAITEC CORPORATION NR-20 or NR-30). The microbial cells were inoculated into 10 mL of a BG-11 liquid culture medium for cultivation (Table 24) containing a necessary drug in an Erlenmeyer flask (HARIO) having a capacity of 50 mL to satisfy O.D 730=0.05 using the culture solution, and cultivation was carried out for about 6 days under conditions of 60 rpm, 30° C., $CO_2$ concentration 1%, and light intensity 100 μE/m$^2$/s with a whirl shaking culture apparatus provided with an LED light emitting unit (LC-LED 450W (white)) (TAITEC CORPORATION NR-20 or NR-30).

Two mL of isopropyl myristate (produced by Tokyo Chemical Industry Co., Ltd.) was added to 10 mL of BG-11 liquid culture medium for cultivation (Table 24) dispensed in the Erlenmeyer flask.

About 6 days after starting the cultivation, the concentration of linalool in isopropyl myristate was measured under the conditions described in Example 3 using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries, Ltd.).

Linalool is shown in terms of accumulated concentration in the culture solution. An average value obtained from three Erlenmeyer flasks is presented in Table 25. Linalool production was not recognized in the control *Synechocystis* sp. PCC6803 GT strain, whereas the linalool production was confirmed in the GT0846K-Ptac-AaLINS strain and the GT0846K-PpsbA2-AaLINS-ispA* strain.

TABLE 25

Accumulation of linalool when linalool synthase native to *A. arguta* and mutant ispA were introduced

| Strain | O.D 730 nm | Linalool (mg/L) |
|---|---|---|
| *Synechocystis* sp. PCC6803 GT strain | 8.2 | 0.0 |
| GT0846K-Ptac-AaLINS strain | 8.7 | 11.4 |
| GT0846K-PpsbA2-AaLINS-ispA* strain | 3.4 | 11.6 |

Example 18: Construction of Linalool Synthase-Expressing Plasmid-Introduced Strain Derived from *Actinidia arguta* (Hardy Kiwifruit) from Yeast 18-1) Construction of Plasmid Expressing Linalool Synthase Native to *Actinidia arguta* by Yeast PCR with the plasmid pACYC177-Ptac-opt_AaLINS-ispA* constructed in Example 6 as a template was carried out using primer Q48 (SEQ ID NO: 155) and a primer Q49 (SEQ ID NO: 156) to obtain an AaLINS-ispA* fragment. The purified AaLINS-ispA* fragment was ligated to vector pYES2 (produced by Invitrogen) digested with restriction enzymes KpnI and BamHI using In-Fusion HD cloning kit (produced by Clontech Laboratories, Inc.) to construct pYES2-Ptac-opt_AaLINS-ispA*.

18-2) Introduction of Linalool Expression Plasmid Derived from *Actinidia arguta* into Yeast The pYES2-Ptac-opt_AaLINS-ispA* was introduced into the i S288C ura3Δ0 strain described in JP 5857973 B2.

The S288C ura3Δ0 strain was inoculated to a YPD liquid culture medium and cultured at 30° C. for 16 hours, and then 0.6 ml of the culture solution was transferred to 10 ml of the culture medium. Furthermore, cultivation was carried out at 30° C. for 2 hours and then the total amount of cells was collected to prepare competent cells using Frozen-EZ Yeast Transformation II™ kit (produced by ZYMO RESEARCH CORP.). The prepared competent cells were transformed with pYES2-Ptac-opt_AaLINS-ispA*, uniformly applied onto an SD-Ura plate, and then cultured at 30° C. for 3 days to obtain a transformant. The resulting strain was designated as S288C ura3A0/pYES2-Ptac-opt_AaLINS-ispA*. The composition of the YPD culture medium is presented in Table 26 and the composition of the SD-Ura culture medium is presented in Table 27.

TABLE 26

| YPD culture medium | |
| --- | --- |
| Group A | |
| Polypeptone | 10 g/L |
| Yeast Extract | 10 g/L |
| Not adjusted pH, AC 120° C., 15 minutes | |
| Group B | |
| Glucose | 20 g/L |
| Not adjusted pH, AC 120° C., 20 minutes | |
| Group A and Group B were mixed after sterilization | |
| In the case of the plate, Agar was added to a concentration of 20 g/L. | |

TABLE 27

| Ura culture medium | |
| --- | --- |
| Group A | |
| Difco Yeast Nitrogen Base W/O AA (Becton Dickinson Cat. No. 291940) | 6.7 g/L |
| Ura DO supplement (Clontech Cat. No. 630416) | 0.77 g/L |
| After adjusting pH to 5.7 with KOH, AC 120° C., 15 minutes | |
| Group B | |
| Glucose | 20 g/L |
| Not adjusted pH, AC 120° C., 20 minutes | |
| Group A and Group B were mixed after sterilization | |
| In the case of the plate, Agar was added to a concentration of 20 g/L. | |

Example 19: Linalool Production in Yeast

The S288C ura3Δ0/pYES2-Ptac-opt_AaLINS-ispA* strain obtained in Example 18 is uniformly applied onto an SD-Ura plate having the composition presented in Table 33 and cultured at 30° C. for about 24 hours. The resulting microbial cells on the plate are scraped in an amount corresponding to about ½ of a 10 μL inoculating loop (produced by Thermo Fisher Scientific Inc.). The scraped microbial cells are inoculated into 5 mL of SD-Ura-Gal culture medium in a test tube produced by AGC Techno Glass Co., Ltd. (diameter×length×thickness (mm)=25×200× 1.2), and cultured at 30° C. on a reciprocal shaking culture apparatus at 120 rpm for 48 hours so that linalool can be obtained. The composition of the SD-Ura-Gal culture medium is presented in Table 28.

TABLE 28

| SD-Ura-Gal culuture medium | |
| --- | --- |
| Group A | |
| Difco Yeast Nitrogen Base W/O AA (Becton Dickinson Cat. No. 291940) | 6.7 g/L |
| Ura DO supplement (Clontech Cat. No. 630416) | 0.77 g/L |
| After adjusting pH to 5.8 with KOH, filter sterilization | |
| Group B | |
| Galactose | 20 g/L |
| Not adjusted pH, filter sterilization | |
| Group A and Group B were mixed after sterilization | |
| 1 mL of isopropyl myristate (produced by Tokyo Chemical Industry Co., Ltd.) was added to 5 mL of the SD-Ura-Gal culture medium dispensed in the test tube after inoculation | |

Example 20: Percentage (%) of Linalool in Volatile Components Contained in Culture Solution of Linalool Synthase-Expressing Strain Derived from SWITCH-PphoC Δgcd The SWITCH-PphoC Δgcd/AaLINS-ispA* strain constructed in Example 7, the SWITCH-PphoC Δgcd/Ptac2-CsLINS-ispA* strain constructed in Example 3, and the SWITCH-PphoC Δgcd/ScLINS-ispA* strain constructed in Example 3 were cultured without addition of isopropyl myristate and the conditions described in Table 4 in Example 3. Analysis was carried out using the cultivated sample after the filter sterilization and a reagent standard solution presented in Table 29 under the conditions described in Example 5, and then a standard curve was generated using peak area values of the obtained reagent standard solution. The peak detected in the cultivated sample was quantified using the standard curve made by the reagent standard solution. The contents of the detected linalool and components having a large peak area and considered as a main component among volatile by-products other than linalool in the cultivated sample are respectively represented by % relative to the entire volatile components, and the results thereof are presented in Table 30.

TABLE 29

Standard reagents used in HS-GC/MS analysis Compound name

| CAS No. | Compound name | Manufacturer name | Product Code |
|---|---|---|---|
| 556-82-1 | 3-Methyl-2-buten-1-ol | Tokyo Chemical Industry Co., Ltd. | M0714 |
| 123-51-3 | 3-Methyl-1-butanol | Sigma-Aldrich | 309435 |
| 106-22-9 | β-Citronellol | Sigma-Aldrich | C83201 |
| 40716-66-3 | trans-Nerolidol | EXTRASYNTHESE S.A. | 5212S |
| 106-24-1 | Geraniol | Wako Pure Chemical Industries, Ltd. | 076-01383 |
| 78-70-6 | Linalool | Wako Pure Chemical Industries, Ltd. | 126-00993 |

TABLE 30

Presence ratio of volatile components Compound name

| Compound name | Presence ratio (%) | | |
|---|---|---|---|
| | Coriander | Hardy kiwifruit | Actinomycete |
| 3-Methyl-2-buten-1-ol | 11.3 | 8.3 | 7.5 |
| 3-Methyl-1-butanol | 7.6 | 6.1 | 8.2 |
| β-Citronellol | 3.7 | 4.2 | 5.7 |
| trans-Nerolidol | — | — | 1.9 |
| Geraniol | 9.5 | 9.2 | 11.1 |
| Non-identified peak[Note] | — | — | 4.5 |
| Linalool | 68.0 | 72.3 | 61.1 |

[Note] A non-identified peak was quantified using the standard curve of linalool and then the presence ratio thereof was calculated.

Example 21: Searching for an Amino Acid Sequence Motif Locally Stored in Linalool Synthase 13 distinct linalool synthase genes were synthesized and used as input sequences, and motif searching was carried out using MEME capable of finding locally stored sequences (Timothy L. Bailey and Charles Elkan, "Fitting a mixture model by expectation maximization to discover motifs in biopolymers", Proceedings of the Second International Conference on Intelligent Systems for Molecular Biology, pp. 28-36, AAAI Press, Menlo Park, Calif., 1994, meme-suite.org.). As the searching option of MEME, as for the site distribution condition, a condition that one similar motif is present in each sequence (One occurrence of a contributing motif site per sequence) was employed, and other than that condition, the default conditions were used. As a result, five motifs were obtained as output (FIGS. 26 to 30). The alignments configuring respective motif sequences are illustrated in FIGS. 31 to 35. The distribution positions of respective motifs in the 13 linalool synthases are illustrated in FIG. 36.

Subsequently, in order to define the found motifs as character strings, unique amino acid residues in the motif are determined, or that only appear twice, and residues other than those residues were classified. Thereafter, the motif length was defined as 8 to 20 amino acids, and the six amino acid sequence motifs are presented in Table 31.

The detection sensitivity of these six amino acid sequence motifs was examined. As a false-negative examination, the preserved properties of the six amino acid motif sequences as compared to the 168 amino acid sequences found using the keyword search "linalool synthase" from GenPept database were examined with fuzzpro. As a false-positive examination, whether the six amino acid motif-like sequences as compared to the 151 amino acid sequences found using the keyword search "limonene synthase" from GenPept database are found was examined with fuzzpro (Table 31).

TABLE 31

Detection of linalool synthase and limonene synthase by amino acid sequence motif

| Amino acid motif | With respect to linalool synthase | With respect to limonene synthase |
|---|---|---|
| DDx[F/Y][D/Y] xxG | 140/168, 83% | 86/151, 57% |
| Lxx[FL][TA]x(4)[RN]W[DE] | 117/168, 70% | 75/151, 50% |
| [DE]Lx(4)LxF[RW]L[LF]R | 65/168, 39% | 55/151, 36% |
| Axx[DN]x(4)[QK]xxx[QR]xEx(6)W[WS] | 72/168, 43% | 50/151, 33% |
| [EV]Yxxx[AG]xx[ST] | 121/168, 72% | 60/151, 40% |
| R[LI]x[DN]D[LI]x[ST]xxxExxxG | 103/168, 61% | 70/151, 46% |

Some of the sequences extracted by keyword search "linalool synthase" contain about 10 to 20 enzymes having an extremely short sequence, or are practically different from linalool synthase. On the other hand, it was found that each linalool synthase presented in Table 18 contains the DDx[F/Y][D/Y]xxG (SEQ ID NO: 165) motif (FIGS. 37 to 49). Also, in other linalool synthases (Table 32) not presented in Table 18, the DDx[F/Y][D/Y]xxG (SEQ ID NO: 165) motif was observed (FIGS. 50 to 57). From these points, it was found that DDx[F/Y][D/Y]xxG (SEQ ID NO: 165) is an amino acid sequence motif capable of detecting linalool synthase. On the other hand, with a high false positive of 86/161 (57%), linalool synthase cannot be accurately detected using only the DDx[F/Y][D/Y]xxG (SEQ ID NO: 165) motif. It was found that Lxx[FL][TA]x(4)[RN]W[DE], [EV]Yxxx[AG]xx[ST], and R[LI]x[DN]D[LI]x[ST]xxxExxxG (SEQ ID NO: 167) also have the same feature as DDx[F/Y][D/Y]xxG (SEQ ID NO: 165) in terms of generating a large number of false positives.

As motifs found in terpene synthase, DDxxD motif, NSE motif, and DxDD motif have been reported (Chen et al., The Plant Journal (2011) 66, 212-229). The DDx[F/Y][D/Y]xxG (SEQ ID NO: 165) motif includes the DDxxD motif, but is not limited thereto, and is a motif which can more specifically define sequences.

TABLE 32

Linalool synthase having DDx[F/Y] [D/Y] xxG motif

| SEQ ID NO | Microorganism name and accession number |
|---|---|
| 157 | Q1XBU5\|R-linalool synthase\|EC 4.2.3.26\|*Solanum lycopersicum*\|TrEMBL |
| 158 | gi\|211970992\|dbj\|BAG82825.1\| linalool synthase [*Backhousia citriodora*] |
| 159 | gi\|6469618\|gb\|AAF13357.1\|AF154125_1 (3R)-linalool synthase, partial [*Artemisia annua*] |
| 160 | gi\|6469616\|gb\|AAF13356.1\|AF154124_1 (3R)-linalool synthase [*Artemisia annua*] |
| 161 | D4N3A0\|S-linalool synthase\|EC 4.2.3.25\|*Actinidia arguta*\|TrEMBL |
| 162 | D4N3A1\|S-linalool synthase\|EC 4.2.3.25\|*Actindia polygama*\|TrEMBL |
| 163 | C0KWV5\|S-linalool synthase\|EC 4.2.3.25\|*Perilla frutescens* var. *hirtella*\|TrEMBL |
| 164 | C0KWV3\|S-linalool synthase\|EC 4.2.3.25\|*Perilla setoyensis*\|TrEMBL |

TABLE 33

Sequences of primer used in Example 10 and later Examples (Part 1)

| SEQ ID NO. | NO. | Microorganism name and accession number |
|---|---|---|
| 124 | Q28 | CACAAGGAGACTGCCATGGCGAACACGGCGAAGCGTAGTATCC |
| 125 | Q29 | GTCTCCTGTGTGAAATTACATCAGGCTTTTCAGATACTCATCGG |
| 126 | Q30 | CACAAGGAGACTGCCATGCGTCGTAGTGCGAATTACCAGCCGAG |
| 127 | Q31 | GTCTCCTGTGTGAAATTAGTCCAGCGGGATAGGGTTAAACAGC |
| 128 | Q32 | CACAAGGAGACTGCCATGGAGTTTAGCATTAGCCAGAGTAGTTTTGCG |
| 129 | Q33 | GTCTCCTGTGTGAAATTAGGCGTGCAGCATACTCTTCATGTACTC |
| 130 | Q34 | CACAAGGAGACTGCCATGTATAGCCTGCGTATTTATGTGGCG |
| 131 | Q35 | GTCTCCTGTGTGAAATTAGGCATAGGGTTCAAACAGCAGGCAGGCG |
| 132 | Q36 | CACAAGGAGACTGCCATGGGTTTTAGTCCTGCCTTTTATGCGTG |
| 133 | Q37 | GTCTCCTGTGTGAAATTACAGGGGAAACGCTTCAAACAGCAGACTC |
| 134 | Q38 | CACAAGGAGACTGCCATGGAACTGACCCTGACGAGTCTGAGCCCG |
| 135 | Q39 | GTCTCCTGTGTGAAATTAGCGGCGGTTACTCATCTTCATGCCATCC |
| 136 | Q40 | CACAAGGAGACTGCCATGTGTACCATCATTAGCGTCAATCATC |
| 137 | Q41 | GTCTCCTGTGTGAAATTAGACGTAGGGCTTAAACAGCAGATTGGC |
| 138 | Q42 | CACAAGGAGACTGCCATGGCGAGTGCGGTCCCCCTGAGTAGTACG |
| 139 | Q43 | GTCTCCTGTGTGAAATTAACTACTCAGCAGGGGCGTAAAAAACAGGG |
| 140 | Q44 | CACAAGGAGACTGCCATGCGTGAGAGCCTGAGCAGTAGCAGTAGC |
| 141 | Q45 | GTCTCCTGTGTGAAATTAACTAAAGCACAGTTTGATATTCGGAC |
| 142 | Q46 | GGCAGTCTCCTTGTGTGAAATTGTTATCCGCTCA |
| 143 | Q47 | TTTCACACAGGAGACTGCCATGGATTTTCCCCAGC |
| 144 | 814 | ATGTCCACCGCCGTGCCCTCTATGCCCACTACCCAAAAATG |
| 145 | 815 | gcaggtcgactctagCTATTTGTTGCGCTGGATGATGTAATC |
| 146 | 812 | ggtacccggggatcctctagAGATCGTTTAGATCCGAAGG |
| 147 | 813 | CACGGCGGTGGACATTGTATGTCCTCCTGGACTTCGTGGT |
| 148 | xx | pVK9-P0480-optAaLINS-ispA* 4363-4724: P0480; 4725-6374: optAaLINS; 6375-6393: spacer; 6394-7293: ispA* |

TABLE 34

Sequences of primer used in Example 10 and later Examples (Part 2)

| SEQ ID NO. | NO. | Microorganism name and accession number |
|---|---|---|
| 149 | 671 | tctagagtcgacgtcCCCTGTTGACAATTAATCATCGGCTCGTATAATGTGTGGA |
| 150 | 691 | tccaatgtgaggaTTAGCTACTGGAATCATACAACATGGTTTTCATGTGTTCT |
| 151 | 719 | aaggaattataaccaaATGTCCACCGCCGTGCCCTCTATCCGCCCACTACAAAAATG |
| 152 | 721 | gatggggaagtttaggctagcCTATTTGTTGCGCTGGATGATGTAATCGGCCAGG |
| 153 | 683 | ggaggattgggttaccctcagtgtg |
| 154 | 684 | cgccatatcaatcccaacgctctgg |
| 155 | Q48 | GGAATATTAAGCTTGGTACCATGTCCACCGCCGTGCCCTCTATG |
| 156 | Q49 | GTGGATCCGAGCTCGGTACCCTATTTGTTGCGCTGGATGATG |

Reference Example 1: Linalool Addition Test

The glycerol stock of the SWITCH-PphoC Δgcd/pSTV28 strain obtained by transforming the SWITCH-PphoC Δgcd strain constructed in Example 2 with the commercially available plasmid vector pSTV28 (produced by Takara Bio Inc.) was thawed, and 50 μL of a microbial cell suspension was uniformly applied onto an LB plate containing 60 mg/L of chloramphenicol and cultured at 34° C. for 18 hours while left to stand (without agitation). The resulting microbial cells on the plate were recovered and inoculated into a small-sized L-type culture tube (model type: TV100030, produced by Advantec Toyo Kaisha, Ltd.) injected with 4 mL of a culture medium described below containing 60 mg/L of chloramphenicol such that the initial O.D. was within a range of 0.01 to 0.02, and cap-type SILICOSEN was used as a culture plug. The minimum culture medium was used as a growing medium, 10 mL of 20% (w/v) glucose, 0.05 mL of 1 M $CaCl_2$), and 1.0 mL of 1 M $MgSO_4$ separately sterilized (AC 120° C., 20 minutes, 1 M $CaCl_2$) was subjected to filtration) were added after being cooled (50° C. or lower) to 50 mL of the 10×M9 Salts described in Table 35 and mixed with sterilized water to prepare 500 mL. The culture temperature was set to 34° C. and the shaking speed was set to 70 rpm. Cultivation was carried out using a small-sized shaking culture apparatus TVS062CA (produced by Advantec Toyo Kaisha, Ltd.) for 23 hours, the shaking of 5.0 sec was stopped every 15 minutes, and the O.D. values were automatically measured.

TABLE 35

| 10×M9 salts | |
|---|---|
| $Na_2HPO_4 \cdot 7H_2O$ | 128 g/L |
| $KH_2PO_4$ | 30 g/L |
| NaCl | 5.0 g/L |
| $NH_4Cl$ | 10 g/L |
| Not adjusted pH, AC 120° C., 15 minutes | |

After the start of the cultivation, at the time point when the O.D. value reached 0.6 to 0.7, a linalool solution was added to each small-sized L-type culture tube such that concentrations of the reagent Linalool in respective culture mediums became 1251 mg/L, 837 mg/L, 626 mg/L, and 417 mg/L. The linalool solution was diluted with ethanol (produced by Wako Pure Chemical Industries, Ltd.) such that volumes of the reagent Linalool (produced by Wako Pure Chemical Industries, Ltd.) present was 15%, 10%, 7.5%, 5.0%, and 0.0% (v/v), and then 40 µL of the resulting solution was added to each small-sized L-type culture tube. The concentration of linalool in the culture medium was calculated from the specific gravity of the reagent Linalool (0.86 (20/4° C.)) (reference literature: actual values supplied from Wako Pure Chemical Industries, Ltd.).

Figure 58:
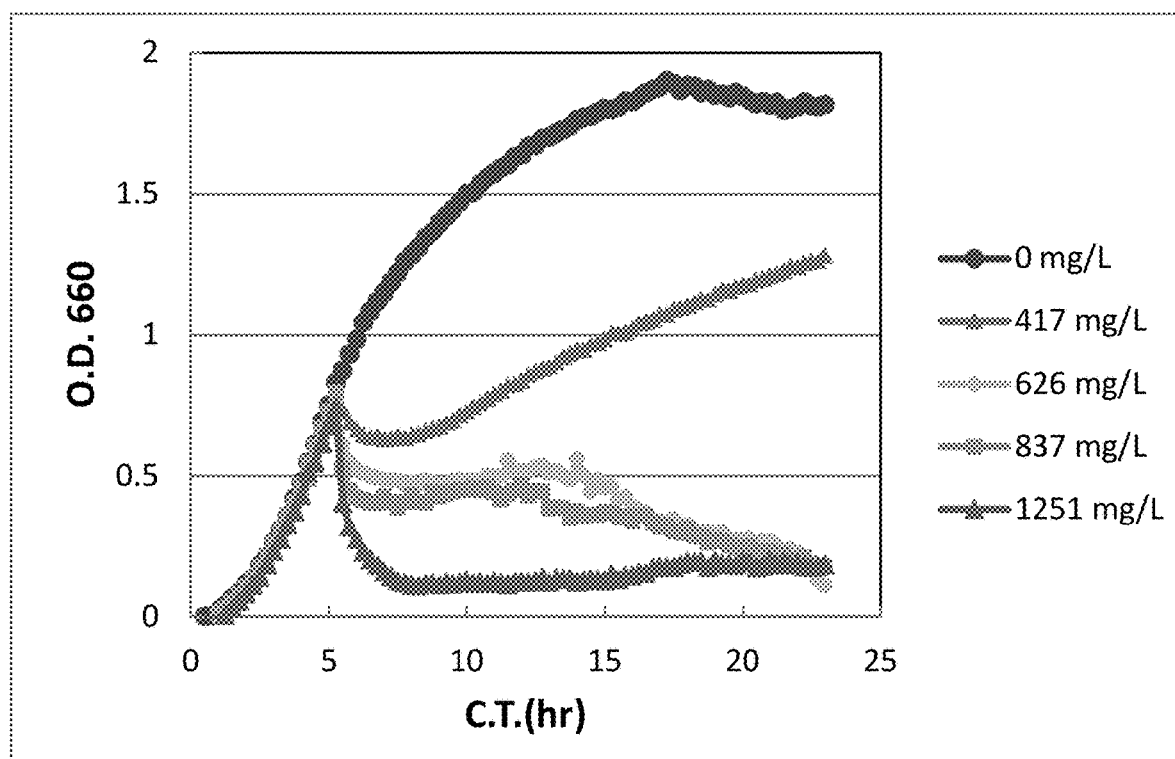
FIG. 58 shows a diagram illustrating a result of a linalool addition test.

The graph showing changes of the O.D. value over time measured using TVS062CA communication software (TV100070, produced by Advantec Toyo Kaisha, Ltd.) is illustrated in FIG. 58.

In general, it is known that a plurality of kinds of monoterpenoid including linalool exhibit antibiotic properties (Park et al., Anaerobe, 18(3), 369-372, 2012). It was recognized that by adding 626 mg/L or more of linalool to the culture medium in the case of the SWITCH-PphoC Δgcd/pSTV28 strain, the O.D. value is decreased (FIG. 58). These results show that in order to suppress microbial cell growth inhibition, the concentration of linalool in the culture medium is preferably less than 626 mg/L.

Example 22: Linalool Fermentation without Addition of Isopropyl Myristate (Under Single Phase Condition) Using Jar Fermenter The SWITCH-PphoC Δgcd/pACYC177 constructed in Example 3, SWITCH-PphoC Δgcd/AaLINS-ispA* strains constructed in Example 7, and the SWITCH-PphoC Δgcd/ScLINS-ispA* strain constructed in Example 3 were used in a test. The glycerol stocks were thawed, 50 µL of a microbial cell suspension from each strain was uniformly applied onto an LB plate containing 50 mg/L of kanamycin, and cultured at 34° C. for 18 hours. The resulting microbial cells were recovered from the plate. Subsequently, 300 mL of a fermentation medium (Table 20) described below containing 50 mg/L of kanamycin was injected into a jar fermenter having a capacity of 1 L. Then, inoculation was carried out such that the initial O.D. was 0.1. As for the fermentation medium, Group A and Group B described in Table 36 were mixed after the completion of sterilization. Cultivation was carried out for 30 hours while the culture temperature was set to 30° C., the ventilation volume was set to 1 vvm, the dissolved oxygen level was adjusted to 6% or more by stirring, and the culture pH was controlled to 6.5 using ammonia gas.

TABLE 36

| Linalool fermentation medium for jar fermenter cultivation | |
|---|---|
| Group A | |
| D-Glucose | 100 g/L |
| $MgSO_4 \cdot 7H_2O$ | 1 g/L |
| Not adjusted pH, AC 120° C., 20 minutes | |
| Group B | |
| Citato 3Na·2H₂O | 1 g/L |
| $(NH_4)_2SO_4$ | 1 g/L |
| $KH_2PO_4$ | 1.25 g/L |
| Betaine anhydride | 2 g/L |
| $FeSO_4 \cdot 7H_2O$ | 30 mg/L |
| $MnSO_4 \cdot 5H_2O$ | 30 mg/L |
| Yeast Extract | 2 g/L |
| Disfoam GD-113K | 0.01 mL/L |
| Not adjusted pH, AC 120° C., 20 minutes | |

After the start of the cultivation, sampling was appropriately carried out, and then analysis of the O.D. value and linalool was carried out. The concentration of linalool was measured under the conditions described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries, Ltd.). A sample for measurement was appropriately diluted with ethanol (produced by Wako Pure Chemical Industries, Ltd.).

Figure 59:
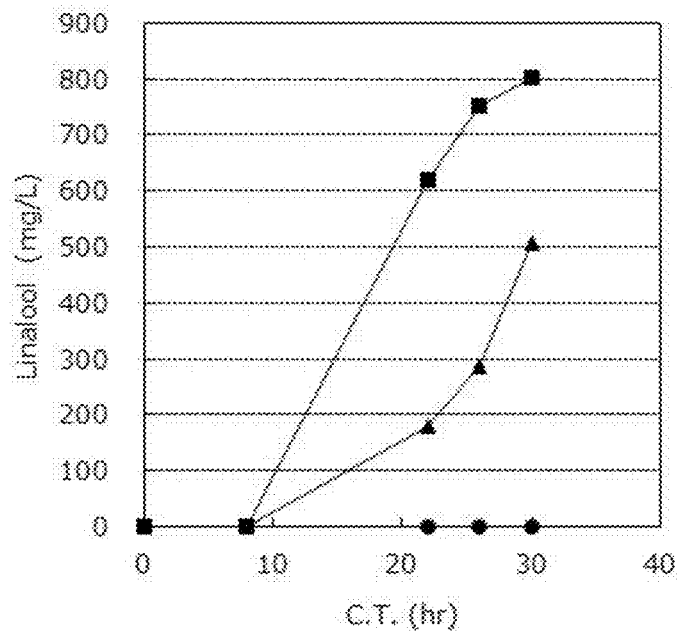
FIG. 59 shows a diagram illustrating a result of changes in linalool accumulation over time.
Figure 60:
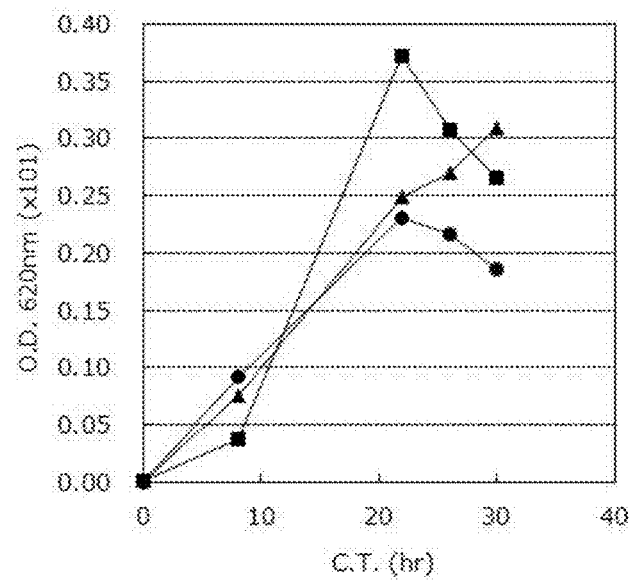
FIG. 60 shows a diagram illustrating a result of changes at O.D. 620 nm over time.

The concentration of linalool and the O.D. value at the time of the completion of cultivation are presented in Table 37, and graphs showing changes over time are illustrated in FIGS. 59 and 60, respectively.

TABLE 37

| Fermentation result of SWITCH-PphoC Δgcd strain native to S. clavuligerus, linalool synthase native to A. arguta, and mutated ispA-introduced strain under the single phase condition using jar fermenter | | | |
|---|---|---|---|
| Strain | Symbol | O.D. 620 nm (x101) | Linalool (mg/L) |
| SWITCH-PphoC Δgcd/pACYC177 | ● | 0.19 | 0.0 |
| SWITCH-PphoC Δgcd/ScLINS-ispA* | ▲ | 0.31 | 507.3 |
| SWITCH-PphoC Δgcd/AaLINS-ispA* | ■ | 0.27 | 801.0 |

From Table 37 and FIGS. 59 and 60 (results of jar cultivation), it was shown that linalool fermentation can be carried out even when the concentration of linalool reaches 626 mg/L, which typically can inhibit growth inhibition of the SWITCH-PphoC Δgcd strain. While Reference Example 1 suggests that the concentration of linalool in the culture medium should be kept to 625 mg/L or less, the SWITCH-PphoC Δgcd/AaLINS-ispA* strain allows for linalool accumulation up to a concentration equal to or more than a typically toxic concentration, which allows for sufficient growth during cultivation. These results show that growth inhibition hardly occurs regardless of culture conditions and efficient linalool fermentation can be carried out.

While the invention has been described in detail with reference to preferred embodiments thereof, it will be apparent to the person skilled in the art that various changes can be made, and equivalents employed, without departing from the scope of the invention. All the cited references herein are incorporated by reference as a part of this application.

INDUSTRIAL APPLICABILITY

According to the present invention, linalool compositions with high enantiomeric excess, in particular, linalool compositions containing R-linalool with high enantiomeric excess and linalool compositions containing S-linalool with high enantiomeric excess can be produced. Therefore, it is useful in fields using linalool, in particular, R-linalool or S-linalool, for example, chemical industry fields such as flavor, cosmetics, foods, and pharmaceuticals.

The invention claimed is:

1. A method for producing a composition comprising volatile components, wherein said volatile components comprise 60% or more linalool, and linalool consists of R-linalool, S-linalool, or both, the method comprising:
A) culturing a microorganism expressing linalool synthase in a culture medium, and
B) accumulating the composition in the culture medium,
C) collecting the composition from the culture medium or the microorganism;
wherein the microorganism has an ability to synthesize dimethylallyl diphosphate via a methylerythritol phosphate pathway and/or an ability to synthesize dimethylallyl diphosphate via a mevalonate pathway, and
wherein the microorganism is a bacterium belonging to the genus *Pantoea*, and
wherein a 2-ketogluconate formation pathway is blocked in the bacterium, and
wherein said linalool synthase has a property selected from the group consisting of:
(a) an amino acid sequence comprising at least one motif of the following formula: $DDX_1[F/Y][D/Y]X_2X_3G$ (SEQ ID No: 165), wherein D represents aspartic acid, F represents phenylalanine, Y represents tyrosine, G represents glycine, $X_1$, $X_2$, and $X_3$ each independently represent an arbitrary amino acid, [F/Y] represents F or Y, and [D/Y] represents D or Y, and wherein the at least one motif is selected from the group consisting of:
(i) a combination in which $X_1$ is I, [F/Y] is F, [D/Y] is D, $X_2$ is V, and $X_3$ is Y,
(ii) a combination in which $X_1$ is I, [F/Y] is F, [D/Y] is D, $X_2$ is V, and $X_3$ is Y,
(iii) a combination in which $X_1$ is I, [F/Y] is F, [D/Y] is D, $X_2$ is V, and $X_3$ is H,
(iv) a combination in which $X_1$ is I, [F/Y] is F, [D/Y] is D, $X_2$ is T, and $X_3$ is Y,
(v) a combination in which $X_1$ is I, [F/Y] is F, [D/Y] is Y, $X_2$ is V, and $X_3$ is C,
(vi) a combination in which $X_1$ is I, [F/Y] is Y, [D/Y] is D, $X_2$ is I, and $X_3$ is Y,
(vii) a combination in which $X_1$ is I, [F/Y] is Y, [D/Y] is D, $X_2$ is A, and $X_3$ is Y,
(viii) a combination in which $X_1$ is I, [F/Y] is Y, [D/Y] is D, $X_2$ is V, and $X_3$ is Y,
(ix) a combination in which $X_1$ is V, [F/Y] is Y, [D/Y] is D, $X_2$ is I, and $X_3$ is Y,
(x) a combination in which $X_1$ is V, [F/Y] is Y, [D/Y] is D, $X_2$ is V, and $X_3$ is F,
(xi) a combination in which $X_1$ is M, [F/Y] is Y, [D/Y] is D, $X_2$ is I, and $X_3$ is Y, and
(xii) a combination in which $X_1$ is F, [F/Y] is F, [D/Y] is D, $X_2$ is V, and $X_3$ is E;
(b) said linalool synthase is native to a microorganism belonging to the genus *Streptomyces*; and
(c) combinations thereof.

2. The method of claim 1, wherein the microorganism belonging to the genus *Streptomyces* is *Streptomyces clavuligerus*.

3. The method according to claim 1, wherein the bacterium belonging to the genus *Pantoea* is *Pantoea ananatis*.

4. The method of claim 1, wherein the microorganism comprises a heterologous expression unit comprising a polynucleotide encoding linalool synthase and a promoter operably linked thereto.

5. The method of claim 4, wherein the polynucleotide is selected from the group consisting of:
(a1) a polynucleotide that comprises:
  (i1) a nucleotide sequence of SEQ ID NO:2 or
  (ii1) a nucleotide sequence of SEQ ID NO:3;
(b1) a polynucleotide that comprises a nucleotide sequence having an identity of 90% or more to the nucleotide sequence of (i1) or (ii1), and encodes a protein having a linalool synthase activity;
(c1) a polynucleotide that hybridizes under stringent conditions with a polynucleotide comprising a nucleotide sequence complementary to the nucleotide sequence of (i1) or (ii1), and encodes a protein having a linalool synthase activity;
(a2) a polynucleotide that comprises:
  (i2) a nucleotide sequence of SEQ ID NO:62 or
  (ii2) a nucleotide sequence of SEQ ID NO:63;
(b2) a polynucleotide that comprises a nucleotide sequence having an identity of 90% or more to the nucleotide sequence of (i2) or (ii2), and encodes a protein having a linalool synthase activity;
(c2) a polynucleotide that hybridizes under stringent conditions with a polynucleotide comprising a nucleotide sequence complementary to the nucleotide sequence of (i2) or (ii2), and encodes a protein having a linalool synthase activity;
(a3) a polynucleotide that comprises:
  (i3) a nucleotide sequence of SEQ ID NO:65 or
  (ii3) a nucleotide sequence of SEQ ID NO:66;

(b3) a polynucleotide that comprises a nucleotide sequence having an identity of 90% or more to the nucleotide sequence of (i3) or (ii3), and encodes a protein having a linalool synthase activity;
(c3) a polynucleotide that hybridizes under stringent conditions with a polynucleotide comprising a nucleotide sequence complementary to the nucleotide sequence of (i3) or (ii3), and encodes a protein having a linalool synthase activity;
(a4) a polynucleotide that comprises:
  (i4) a nucleotide sequence of SEQ ID NO:68 or
  (ii4) a nucleotide sequence of SEQ ID NO:69;
(b4) a polynucleotide that comprises a nucleotide sequence having an identity of 90% or more to the nucleotide sequence of (i4) or (ii4), and encodes a protein having a linalool synthase activity;
(c4) a polynucleotide that hybridizes under stringent conditions with a polynucleotide comprising a nucleotide sequence complementary to the nucleotide sequence of (i4) or (ii4), and encodes a protein having a linalool synthase activity;
(a5) a polynucleotide that comprises:
  (i5) a nucleotide sequence of SEQ ID NO:71 or
  (ii5) a nucleotide sequence of SEQ ID NO:72;
(b5) a polynucleotide that comprises a nucleotide sequence having an identity of 90% or more to the nucleotide sequence of (i5) or (ii5), and encodes a protein having a linalool synthase activity;
(c5) a polynucleotide that hybridizes under stringent conditions with a polynucleotide comprising a nucleotide sequence complementary to the nucleotide sequence of (i5) or (ii5), and encodes a protein having a linalool synthase activity;
(a6) a polynucleotide that comprises:
  (i6) a nucleotide sequence of SEQ ID NO:74 or
  (ii6) a nucleotide sequence of SEQ ID NO:75;
(b6) a polynucleotide that comprises a nucleotide sequence having an identity of 90% or more to the nucleotide sequence of (i6) or (ii6), and encodes a protein having a linalool synthase activity;
(c6) a polynucleotide that hybridizes under stringent conditions with a polynucleotide comprising a nucleotide sequence complementary to the nucleotide sequence of (i6) or (ii6), and encodes a protein having a linalool synthase activity;
(a7) a polynucleotide that comprises:
  (i7) a nucleotide sequence of SEQ ID NO:79,
  (ii7) a nucleotide sequence consisting of nucleotide residues at positions 79 to 1725 in the nucleotide sequence of SEQ ID NO:79, or
  (iii7) a nucleotide sequence of SEQ ID NO:80;
(b7) a polynucleotide that comprises a nucleotide sequence having an identity of 90% or more to the nucleotide sequence of (i7), (ii7) or (iii7), and encodes a protein having a linalool synthase activity;
(c7) a polynucleotide that hybridizes under stringent conditions with a polynucleotide comprising a nucleotide sequence complementary to the nucleotide sequence of (i7), (ii7) or (iii7), and encodes a protein having a linalool synthase activity;
(a8) a polynucleotide that comprises:
  (i8) a nucleotide sequence of SEQ ID NO:85 (M1) or
  (ii8) a nucleotide sequence of SEQ ID NO:98 (M14);
(b8) a polynucleotide that comprises a nucleotide sequence having an identity of 90% or more to the nucleotide sequence of (i8) or (ii8), and encodes a protein having a linalool synthase activity;
(c8) a polynucleotide that hybridizes under stringent conditions with a polynucleotide comprising a nucleotide sequence complementary to the nucleotide sequence of (i8) or (ii8), and encodes a protein having a linalool synthase activity;
(a9) a polynucleotide that comprises:
  (i9) a nucleotide sequence of SEQ ID NO:86 (M2) or
  (ii9) a nucleotide sequence of SEQ ID NO:100 (M16);
(b9) a polynucleotide that comprises a nucleotide sequence having an identity of 90% or more to the nucleotide sequence of (i9) or (ii9), and encodes a protein having a linalool synthase activity;
(c9) a polynucleotide that hybridizes under stringent conditions with a polynucleotide comprising a nucleotide sequence complementary to the nucleotide sequence of (i9) or (ii9), and encodes a protein having a linalool synthase activity;
(a10) a polynucleotide that comprises:
  (i10) a nucleotide sequence of SEQ ID NO:87 (M3) or
  (ii10) a nucleotide sequence of SEQ ID NO:102 (M18);
(b10) a polynucleotide that comprises a nucleotide sequence having an identity of 90% or more to the nucleotide sequence of (i10) or (ii10), and encodes a protein having a linalool synthase activity;
(c10) a polynucleotide that hybridizes under stringent conditions with a polynucleotide comprising a nucleotide sequence complementary to the nucleotide sequence of (i10) or (ii10), and encodes a protein having a linalool synthase activity;
(a11) a polynucleotide that comprises:
  (i11) a nucleotide sequence of SEQ ID NO:88 (M4) or
  (ii11) a nucleotide sequence of SEQ ID NO:104 (M20);
(b11) a polynucleotide that comprises a nucleotide sequence having an identity of 90% or more to the nucleotide sequence of (i11) or (ii11), and encodes a protein having a linalool synthase activity;
(c11) a polynucleotide that hybridizes under stringent conditions with a polynucleotide comprising a nucleotide sequence complementary to the nucleotide sequence of (i11) or (ii11), and encodes a protein having a linalool synthase activity;
(a12) a polynucleotide that comprises:
  (i12) a nucleotide sequence of SEQ ID NO:89 (M5) or
  (ii12) a nucleotide sequence of SEQ ID NO:106 (M22);
(b12) a polynucleotide that comprises a nucleotide sequence having an identity of 90% or more to the nucleotide sequence of (i12) or (ii12), and encodes a protein having a linalool synthase activity;
(c12) a polynucleotide that hybridizes under stringent conditions with a polynucleotide comprising a nucleotide sequence complementary to the nucleotide sequence of (i12) or (ii12), and encodes a protein having a linalool synthase activity;
(a13) a polynucleotide that comprises:
  (i13) a nucleotide sequence of SEQ ID NO:90 (M6) or
  (ii13) a nucleotide sequence of SEQ ID NO:108 (M24);
(b13) a polynucleotide that comprises a nucleotide sequence having an identity of 90% or more to the nucleotide sequence of (i13) or (ii13), and encodes a protein having a linalool synthase activity;
(c13) a polynucleotide that hybridizes under stringent conditions with a polynucleotide comprising a nucleotide sequence complementary to the nucleotide sequence of (i13) or (ii13), and encodes a protein having a linalool synthase activity;

(a14) a polynucleotide that comprises:
(i14) a nucleotide sequence of SEQ ID NO:91 (M7) or
(ii14) a nucleotide sequence of SEQ ID NO:110 (M26);
(b14) a polynucleotide that comprises a nucleotide sequence having an identity of 90% or more to the nucleotide sequence of (i14) or (ii14), and encodes a protein having a linalool synthase activity;
(c14) a polynucleotide that hybridizes under stringent conditions with a polynucleotide comprising a nucleotide sequence complementary to the nucleotide sequence of (i14) or (ii14), and encodes a protein having a linalool synthase activity;
(a15) a polynucleotide that comprises:
(i15) a nucleotide sequence of SEQ ID NO:92 (M8) or
(ii15) a nucleotide sequence of SEQ ID NO:112 (M28);
(b15) a polynucleotide that comprises a nucleotide sequence having an identity of 90% or more to the nucleotide sequence of (i15) or (ii15), and encodes a protein having a linalool synthase activity;
(c15) a polynucleotide that hybridizes under stringent conditions with a polynucleotide comprising a nucleotide sequence complementary to the nucleotide sequence of (i15) or (ii15), and encodes a protein having a linalool synthase activity;
(a16) a polynucleotide that comprises:
(i16) a nucleotide sequence of SEQ ID NO:93 (M9) or
(ii16) a nucleotide sequence of SEQ ID NO:114 (M30);
(b16) a polynucleotide that comprises a nucleotide sequence having an identity of 90% or more to the nucleotide sequence of (i16) or (ii16), and encodes a protein having a linalool synthase activity;
(c16) a polynucleotide that hybridizes under stringent conditions with a polynucleotide comprising a nucleotide sequence complementary to the nucleotide sequence of (i16) or (ii16), and encodes a protein having a linalool synthase activity;
(a17) a polynucleotide that comprises:
(i17) a nucleotide sequence of SEQ ID NO:94 (M10) or
(ii17) a nucleotide sequence of SEQ ID NO:116 (M32);
(b17) a polynucleotide that comprises a nucleotide sequence having an identity of 90% or more to the nucleotide sequence of (i17) or (ii17), and encodes a protein having a linalool synthase activity;
(c17) a polynucleotide that hybridizes under stringent conditions with a polynucleotide comprising a nucleotide sequence complementary to the nucleotide sequence of (i17) or (ii17), and encodes a protein having a linalool synthase activity;
(a18) a polynucleotide that comprises:
(i18) a nucleotide sequence of SEQ ID NO:95 (M11) or
(ii18) a nucleotide sequence of SEQ ID NO:118 (M34);
(b18) a polynucleotide that comprises a nucleotide sequence having an identity of 90% or more to the nucleotide sequence of (i18) or (ii18), and encodes a protein having a linalool synthase activity;
(c18) a polynucleotide that hybridizes under stringent conditions with a polynucleotide comprising a nucleotide sequence complementary to the nucleotide sequence of (i18) or (ii18), and encodes a protein having a linalool synthase activity;
(a19) a polynucleotide that comprises:
(i19) a nucleotide sequence of SEQ ID NO: 96 (M12) or
(ii19) a nucleotide sequence of SEQ ID NO:120 (M36);
(b19) a polynucleotide that comprises a nucleotide sequence having an identity of 90% or more to the nucleotide sequence of (i19) or (ii19), and encodes a protein having a linalool synthase activity;
(c19) a polynucleotide that hybridizes under stringent conditions with a polynucleotide comprising a nucleotide sequence complementary to the nucleotide sequence of (i19) or (ii19), and encodes a protein having a linalool synthase activity;
(a20) a polynucleotide that comprises:
(i20) a nucleotide sequence of SEQ ID NO:97 (M13) or
(ii20) a nucleotide sequence of SEQ ID NO:122 (M38);
(b20) a polynucleotide that comprises a nucleotide sequence having an identity of 90% or more to the nucleotide sequence of (i20) or (ii20), and encodes a protein having a linalool synthase activity;
(c20) a polynucleotide that hybridizes under stringent conditions with a polynucleotide comprising a nucleotide sequence complementary to the nucleotide sequence of (i20) or (ii20), and encodes a protein having a linalool synthase activity; and
(a21) combinations thereof;
wherein the stringent conditions comprise hybridization in 6×SCC (sodium chloride/sodium citrate) at about 45° C. followed by one or two or more washings in 0.2×SSC and 0.1% SDS at 50° C. to 65° C.

6. The method of claim 1, wherein the linalool synthase is a protein selected from the group consisting of:
(A1) a protein that comprises (in a full-length amino acid sequence of SEQ ID NO: 1;
(B1) a protein that comprises an amino acid sequence having an identity of 90% or more to the amino acid sequence of (i1'), and has a linalool synthase activity;
(C1) a protein that comprises an amino acid sequence having a deletion, substitution, addition, or insertion of one or several amino acids in the amino acid sequence of (i1'), and has a linalool synthase activity;
(A2) a protein that comprises (i2') a full-length amino acid sequence of SEQ ID NO:61;
(B2) a protein that comprises an amino acid sequence having an identity of 90% or more to the amino acid sequence of (i2'), and has a linalool synthase activity;
(C2) a protein that comprises an amino acid sequence having a deletion, substitution, addition, or insertion of one or several amino acids in the amino acid sequence of (i2'), and has a linalool synthase activity;
(A3) a protein that comprises (i3') a full-length amino acid sequence of SEQ ID NO: 64;
(B3) a protein that comprises an amino acid sequence having an identity of 90% or more to the amino acid sequence of (i3'), and has a linalool synthase activity;
(C3) a protein that comprises an amino acid sequence having a deletion, substitution, addition, or insertion of one or several amino acids in the amino acid sequence of (i3'), and has a linalool synthase activity;
(A4) a protein that comprises (i4') a full-length amino acid sequence of SEQ ID NO:67;
(B4) a protein that comprises an amino acid sequence having an identity of 90% or more to the amino acid sequence of (i4'), and has a linalool synthase activity;
(C4) a protein that comprises an amino acid sequence having a deletion, substitution, addition, or insertion of one or several amino acids in the amino acid sequence of (i4'), and has a linalool synthase activity;
(A5) a protein that comprises (i5') a full-length amino acid sequence of SEQ ID NO: 70;
(B5) a protein that comprises an amino acid sequence having an identity of 90% or more to the amino acid sequence of (i5'), and has a linalool synthase activity;

(C5) a protein that comprises an amino acid sequence having a deletion, substitution, addition, or insertion of one or several amino acids in the amino acid sequence of (i5'), and has a linalool synthase activity;
(A6) a protein that comprises (i6') a full-length amino acid sequence of SEQ ID NO: 73;
(B6) a protein that comprises an amino acid sequence having an identity of 90% or more to the amino acid sequence of (i6'), and has a linalool synthase activity;
(C6) a protein that comprises an amino acid sequence having a deletion, substitution, addition, or insertion of one or several amino acids in the amino acid sequence of (i6'), and has a linalool synthase activity;
(A7) a protein that comprises:
  (i7') a full-length amino acid sequence of SEQ ID NO:78 or
  (ii7') an amino acid sequence consisting of amino acid residues at positions 27 to 574 in the amino acid sequence of SEQ ID NO:1;
(B7) a protein that comprises an amino acid sequence having an identity of 90% or more to the amino acid sequence of (i7') or (ii7'), and has a linalool synthase activity;
(C7) a protein that comprises an amino acid sequence having a deletion, substitution, addition, or insertion of one or several amino acids in the amino acid sequence of (i7') or (ii7'), and has a linalool synthase activity;
(A8) a protein that comprises (i8') a full-length amino acid sequence of SEQ ID NO:99 (M15);
(B8) a protein that comprises an amino acid sequence having an identity of 90% or more to the amino acid sequence of (i8'), and has a linalool synthase activity;
(C8) a protein that comprises an amino acid sequence having a deletion, substitution, addition, or insertion of one or several amino acids in the amino acid sequence of (i8'), and has a linalool synthase activity;
(A9) a protein that comprises (i9') a full-length amino acid sequence of SEQ ID NO: 101 (M17);
(B9) a protein that comprises an amino acid sequence having an identity of 90% or more to the amino acid sequence of (i9'), and has a linalool synthase activity;
(C9) a protein that comprises an amino acid sequence having a deletion, substitution, addition, or insertion of one or several amino acids in the amino acid sequence of (i9'), and has a linalool synthase activity;
(A10) a protein that comprises (i10') a full-length amino acid sequence of SEQ ID NO:103 (M19);
(B10) a protein that comprises an amino acid sequence having an identity of 90% or more to the amino acid sequence of (i10'), and has a linalool synthase activity;
(C10) a protein that comprises an amino acid sequence having a deletion, substitution, addition, or insertion of one or several amino acids in the amino acid sequence of (i10'), and has a linalool synthase activity;
(A11) a protein that comprises (i11') a full-length amino acid sequence of SEQ ID NO:105 (M21);
(B11) a protein that comprises an amino acid sequence having an identity of 90% or more to the amino acid sequence of (i11'), and has a linalool synthase activity;
(C11) a protein that comprises an amino acid sequence having a deletion, substitution, addition, or insertion of one or several amino acids in the amino acid sequence of (i11'), and has a linalool synthase activity;
(A12) a protein that comprises (i12') a full-length amino acid sequence of SEQ ID NO:107 (M23);
(B12) a protein that comprises an amino acid sequence having an identity of 90% or more to the amino acid sequence of (i12'), and has a linalool synthase activity;
(C12) a protein that comprises an amino acid sequence having a deletion, substitution, addition, or insertion of one or several amino acids in the amino acid sequence of (i12'), and has a linalool synthase activity;
(A13) a protein that comprises (i13') a full-length amino acid sequence of SEQ ID NO:109 (M25);
(B13) a protein that comprises an amino acid sequence having an identity of 90% or more to the amino acid sequence of (i13'), and has a linalool synthase activity;
(C13) a protein that comprises an amino acid sequence having a deletion, substitution, addition, or insertion of one or several amino acids in the amino acid sequence of (i13'), and has a linalool synthase activity;
(A14) a protein that comprises (i14') a full-length amino acid sequence of SEQ ID NO:111 (M27);
(B14) a protein that comprises an amino acid sequence having an identity of 90% or more to the amino acid sequence of (i14'), and has a linalool synthase activity;
(C14) a protein that comprises an amino acid sequence having a deletion, substitution, addition, or insertion of one or several amino acids in the amino acid sequence of (i14'), and has a linalool synthase activity;
(A15) a protein that comprises (i15') a full-length amino acid sequence of SEQ ID NO:113 (M29);
(B15) a protein that comprises an amino acid sequence having an identity of 90% or more to the amino acid sequence of (i15'), and has a linalool synthase activity;
(C15) a protein that comprises an amino acid sequence having a deletion, substitution, addition, or insertion of one or several amino acids in the amino acid sequence of (i15'), and has a linalool synthase activity;
(A16) a protein that comprises (i16') a full-length amino acid sequence of SEQ ID NO:115 (M31);
(B16) a protein that comprises an amino acid sequence having an identity of 90% or more to the amino acid sequence of (i16'), and has a linalool synthase activity;
(C16) a protein that comprises an amino acid sequence having a deletion, substitution, addition, or insertion of one or several amino acids in the amino acid sequence of (i16'), and has a linalool synthase activity;
(A17) a protein that comprises (i17') a full-length amino acid sequence of SEQ ID NO:117 (M33);
(B17) a protein that comprises an amino acid sequence having an identity of 90% or more to the amino acid sequence of (i17'), and has a linalool synthase activity;
(C17) a protein that comprises an amino acid sequence having a deletion, substitution, addition, or insertion of one or several amino acids in the amino acid sequence of (i17'), and has a linalool synthase activity;
(A18) a protein that comprises (i18') a full-length amino acid sequence of SEQ ID NO:119 (M35);
(B18) a protein that comprises an amino acid sequence having an identity of 90% or more to the amino acid sequence of (i18'), and has a linalool synthase activity;
(C18) a protein that comprises an amino acid sequence having a deletion, substitution, addition, or insertion of one or several amino acids in the amino acid sequence of (i18'), and has a linalool synthase activity;
(A19) a protein that comprises (i19') a full-length amino acid sequence of SEQ ID NO: 121 (M37);
(B19) a protein that comprises an amino acid sequence having an identity of 90% or more to the amino acid sequence of (i19'), and has a linalool synthase activity;

(C19) a protein that comprises an amino acid sequence having a deletion, substitution, addition, or insertion of one or several amino acids in the amino acid sequence of (i19'), and has a linalool synthase activity;
(A20) a protein that comprises (i20') a full-length amino acid sequence of SEQ ID NO: 123 (M39);
(B20) a protein that comprises an amino acid sequence having an identity of 90% or more to the amino acid sequence of (i20'), and has a linalool synthase activity;
(C20) a protein that comprises an amino acid sequence having a deletion, substitution, addition, or insertion of one or several amino acids in the amino acid sequence of (i20'), and has a linalool synthase activity;
(A21) a protein that comprises (i21') a full-length amino acid sequence of SEQ ID NO:157;
(B21) a protein that comprises an amino acid sequence having an identity of 90% or more to the amino acid sequence of (i21'), and has a linalool synthase activity;
(C21) a protein that comprises an amino acid sequence having a deletion, substitution, addition, or insertion of one or several amino acids in the amino acid sequence of (i21'), and has a linalool synthase activity;
(A22) a protein that comprises (i22') a full-length amino acid sequence of SEQ ID NO:158;
(B22) a protein that comprises an amino acid sequence having an identity of 90% or more to the amino acid sequence of (i22'), and has a linalool synthase activity;
(C22) a protein that comprises an amino acid sequence having a deletion, substitution, addition, or insertion of one or several amino acids in the amino acid sequence of (i22'), and has a linalool synthase activity;
(A23) a protein that comprises (i23') a full-length amino acid sequence of SEQ ID NO:159;
(B23) a protein that comprises an amino acid sequence having an identity of 90% or more to the amino acid sequence of (i23'), and has a linalool synthase activity;
(C23) a protein that comprises an amino acid sequence having a deletion, substitution, addition, or insertion of one or several amino acids in the amino acid sequence of (i23'), and has a linalool synthase activity;
(A24) a protein that comprises (i24') a full-length amino acid sequence of SEQ ID NO: 160;
(B24) a protein that comprises an amino acid sequence having an identity of 90% or more to the amino acid sequence of (i24'), and has a linalool synthase activity;
(C24) a protein that comprises an amino acid sequence having a deletion, substitution, addition, or insertion of one or several amino acids in the amino acid sequence of (i24'), and has a linalool synthase activity;
(A25) a protein that comprises (i25') a full-length amino acid sequence of SEQ ID NO:161;
(B25) a protein that comprises an amino acid sequence having an identity of 90% or more to the amino acid sequence of (i25'), and has a linalool synthase activity;
(C25) a protein that comprises an amino acid sequence having a deletion, substitution, addition, or insertion of one or several amino acids in the amino acid sequence of (i25'), and has a linalool synthase activity;
(A26) a protein that comprises (i26') a full-length amino acid sequence of SEQ ID NO: 162;
(B26) a protein that comprises an amino acid sequence having an identity of 90% or more to the amino acid sequence of (i26'), and has a linalool synthase activity;
(C26) a protein that comprises an amino acid sequence having a deletion, substitution, addition, or insertion of one or several amino acids in the amino acid sequence of (i26'), and has a linalool synthase activity;
(A27) a protein that comprises (i27') a full-length amino acid sequence of SEQ ID NO: 163;
(B27) a protein that comprises an amino acid sequence having an identity of 90% or more to the amino acid sequence of (i27'), and has a linalool synthase activity;
(C27) a protein that comprises an amino acid sequence having a deletion, substitution, addition, or insertion of one or several amino acids in the amino acid sequence of (i27'), and has a linalool synthase activity;
(A28) a protein that comprises (i28') a full-length amino acid sequence of SEQ ID NO:164;
(B28) a protein that comprises an amino acid sequence having an identity of 90% or more to the amino acid sequence of (i28'), and has a linalool synthase activity;
(C28) a protein that comprises an amino acid sequence having a deletion, substitution, addition, or insertion of one or several amino acids in the amino acid sequence of (i28'), and has a linalool synthase activity; and
(A29) combinations thereof.

7. The method of claim 1, wherein the microorganism is a bacterium expressing geranyl diphosphate synthase.

8. The method of claim 1, wherein the 2-ketogluconate formation pathway is blocked by reducing an activity of glucose dehydrogenase.

9. The method of claim 8, wherein said reducing comprises disrupting a glucose dehydrogenase gene.

10. The method of claim 9, wherein the glucose dehydrogenase gene is a polynucleotide selected from the group consisting of:
(x) a polynucleotide that comprises:
[i] a nucleotide sequence of SEQ ID NO:9 or
[ii] a nucleotide sequence consisting of nucleotide residues at positions 301 to 2691 in the nucleotide sequence of SEQ ID NO: 9;
(y) a polynucleotide that comprises a nucleotide sequence having an identity of 90% or more to the nucleotide sequence of [i] or [ii], and encodes a protein having a glucose dehydrogenase activity;
(z) a polynucleotide that hybridizes under stringent conditions with a polynucleotide comprising a nucleotide sequence complementary to the nucleotide sequence of [i] or [ii], and encodes a protein having a glucose dehydrogenase activity,
wherein the stringent conditions comprise hybridization in 6×SCC (sodium chloride/sodium citrate) at about 45° C. followed by one or two or more washings in 0.2×SSC and 0.1% SDS at 50° C. to 65° C.; and
(z') combinations thereof.

11. The method of claim 8, wherein the glucose dehydrogenase is a protein selected from the group consisting of:
(X) a protein that comprises a full-length amino acid sequence of SEQ ID NO:10;
(Y) a protein that comprises an amino acid sequence having an identity of 90% or more to the amino acid sequence of SEQ ID NO:10, and has a glucose dehydrogenase activity;
(Z) a protein that comprises an amino acid sequence having a deletion, substitution, addition, or insertion of one or several amino acids in the amino acid sequence of SEQ ID NO:10, and has a glucose dehydrogenase activity; and
(Z') combinations thereof.

* * * * *

SEQUENCE LISTING

<160> NUMBER OF SEQ ID NOS: 232

<210> SEQ ID NO 1
<211> LENGTH: 333
<212> TYPE: PRT
<213> ORGANISM: Streptomyces clavuligerus

<400> SEQUENCE: 1

```
Met Gly Ser Leu Met Gln Glu Phe Glu Phe Ala Val Pro Ala Pro Ser
1               5                   10                  15

Arg Val Ser Pro Asp Leu Ala Arg Ala Arg Ala Arg His Leu Asp Trp
            20                  25                  30

Val His Ala Met Asp Leu Val Arg Gly Glu Glu Ala Arg Arg Arg Tyr
        35                  40                  45

Glu Phe Ser Cys Val Ala Asp Ile Gly Ala Tyr Gly Tyr Pro His Ala
    50                  55                  60

Thr Gly Ala Asp Leu Asp Leu Cys Val Asp Val Leu Gly Trp Thr Phe
65                  70                  75                  80

Leu Phe Asp Asp Gln Phe Asp Ala Gly Asp Gly Arg Glu Arg Asp Ala
                85                  90                  95

Leu Ala Val Cys Ala Glu Leu Thr Asp Leu Leu Trp Lys Gly Thr Ala
            100                 105                 110

Ala Thr Ala Ala Ser Pro Pro Ile Val Val Ala Phe Ser Asp Cys Trp
        115                 120                 125

Glu Arg Met Arg Ala Gly Met Ser Asp Ala Trp Arg Arg Arg Thr Val
    130                 135                 140

His Glu Trp Val Asp Tyr Leu Ala Gly Trp Pro Thr Lys Leu Ala Asp
145                 150                 155                 160

Arg Ala His Gly Ala Val Leu Asp Pro Ala Ala His Leu Arg Ala Arg
                165                 170                 175

His Arg Thr Ile Cys Cys Arg Pro Leu Phe Ala Leu Ala Glu Arg Val
            180                 185                 190

Gly Gly Tyr Glu Val Pro Arg Arg Ala Trp His Ser Ser Arg Leu Asp
        195                 200                 205

Gly Met Arg Phe Thr Thr Ser Asp Ala Val Ile Gly Met Asn Glu Leu
    210                 215                 220

His Ser Phe Glu Lys Asp Arg Ala Gln Gly His Ala Asn Leu Val Leu
225                 230                 235                 240

Ser Leu Val His His Gly Gly Leu Thr Gly Pro Glu Ala Val Thr Arg
                245                 250                 255

Val Cys Asp Leu Val Gln Gly Ser Ile Glu Ser Phe Leu Arg Leu Arg
```

```
                260                 265                 270
Ser Gly Leu Pro Glu Leu Gly Arg Ala Leu Gly Val Glu Gly Ala Val
                275                 280                 285

Leu Asp Arg Tyr Ala Asp Ala Leu Ser Ala Phe Cys Arg Gly Tyr His
            290                 295                 300

Asp Trp Gly Arg Gly Ala Ser Arg Tyr Thr Thr Arg Asp His Pro Gly
305                 310                 315                 320

Asp Leu Gly Leu Glu Asn Leu Val Ala Arg Ser Ser Gly
                325                 330
```

<210> SEQ ID NO 2
<211> LENGTH: 1002
<212> TYPE: DNA
<213> ORGANISM: Streptomyces clavuligerus

<400> SEQUENCE: 2

```
ttggggtcat tgatgcagga attcgaattc gcggtgcccg cgccgagccg tgtcagtccg    60
gatctcgccc gcgcgagggc ccgtcatctc gactgggtcc acgccatgga cctggtgcgc   120
ggcgaggagg ccaggcggcg ttacgagttc tcctgtgtgg ccgacatcgg cgcctatgga   180
tatccgcacg cgaccggtgc ggacctggat ctctgcgtcg acgtcctcgg gtggaccttc   240
ctcttcgacg atcaattcga cgccggggac gggcgggagc gggacgcttt ggcggtctgc   300
gcggagctga cggacctgtt gtggaagggg acggcggcca cggcggcctc gccgccgatc   360
gtggtggcgt tcagcgactg ctgggagcgg atgcgggcgg catgtcgga cgcgtggcgg   420 cggcggacgt ccatgagtg gtggactat ctggcgggct ggcccaccaa gctcgccgac   480
cgcgcgcacg cgccgtcct ggacccggcc gcgcatctgc gcgcgcggca ccggacgatc   540
tgctgccgcc cgctcttcgc cctggcggaa cgggtcgggg ggtacgaggt cccgcggcgg   600
gcctggcact ccagccggct cgacgggatg cggttcacca cgtccgatgc ggtgatcggc   660
atgaacgagc tccactcgtt cgagaaggac cgggcgcagg ccacgccaa cctcgtcctg   720 agcctcgtgc accacggcgg actcaccggg ccggaggccg tcacccgggt gtgcgacctg   780
gtccagggct cgatcgagtc cttcctgcga ctgcggtccg ggctgccgga gctgggccgg   840
gccctcggtg tcgaggggc cgtgctcgac cggtacgccg acgcgctgtc cgcgttctgc   900
cgcgggtacc acgactgggg tcgcggcgcc tcgcggtaca ccacccgcga tcaccccggc   960
gatctcggac tggagaatct cgtcgcccgg tcgtcgggct ga                    1002
```

<210> SEQ ID NO 3
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Streptomyces clavuligerus
      (opt_ScLINS)

<400> SEQUENCE: 3

```
atgggttctc tgatgcagga atttgaattt gctgtgcccg ctccctctcg cgttagcccc    60
gatttagccc gtgctcgtgc tcgtcatctg gattgggttc atgccatgga cttagttcgg   120
ggtgaagaag cccggcgccg ttatgaattt agctgtgtgg ctgatattgg cgcctatggt   180
tacccccatg ccaccggcgc tgatctggac ttgtgcgtgg atgtttgggg ttggaccttt   240
```

```
ttatttgatg accaatttga tgctggagac ggtcgtgaac gtgatgctct ggctgtgtgt    300
gccgaattga ccgacttgtt atggaaagga accgctgcta ctgctgctag ccccccatt    360
gtggttgcct tttctgattg ctgggaacgg atgcgggctg gtatgagtga cgcttggcgg    420
cgccgtaccg tgcatgaatg ggttgattat ttggccgggt ggcccactaa attagccgat    480
cgtgctcacg gagctgtgtt agaccccgct gctcatctgc gtgctcgtca ccgtaccatt    540
tgttgccgcc ccctgtttgc cttggctgaa cgtgtgggag gttacgaagt tcccccgtcgt    600
gcttggcatt ccagtcgttt ggatggtatg cggtttacca cttccgacgc cgtgattggt    660
atgaacgaac tgcatagttt tgaaaaagat cgtgctcaag ggcacgccaa cttagtgctg    720
tccttggttc atcacggagg attgaccgga cccgaagctg tgactcgtgt ttgtgattta    780
gttcagggct ccattgaatc cttttttgcgg ctgcgcagtg ggttacccga actgggacgt    840
gctctgggag tggaaggagc tgttttggat cggtacgccg acgctttaag cgcttttttgc    900
cgcgggtatc atgattgggg gcgtggagcc tctcggtaca ccactcgcga tcaccccggc    960
gacttgggtt tagaaaattt ggtggcccgc agctctggct aa                     1002
```

<210> SEQ ID NO 4
<211> LENGTH: 590
<212> TYPE: PRT
<213> ORGANISM: Coriandrum sativum

<400> SEQUENCE: 4

```
Met Ala Ala Ile Thr Ile Phe Pro Leu Ser Tyr Ser Ile Lys Phe Arg
1               5                   10                  15

Arg Ser Ser Pro Cys Asn Pro Lys Asp Val Thr Ala Cys Lys Ser Val
            20                  25                  30

Ile Lys Ser Val Thr Gly Met Thr Lys Val Pro Val Pro Val Pro Glu
        35                  40                  45

Pro Ile Val Arg Arg Ser Gly Asn Tyr Lys Pro Cys Met Trp Asp Asn
    50                  55                  60

Asp Phe Leu Gln Ser Leu Lys Thr Glu Tyr Thr Gly Glu Ala Ile Asn
65                  70                  75                  80

Ala Arg Ala Ser Glu Met Lys Glu Glu Val Arg Met Ile Phe Asn Asn
                85                  90                  95

Val Val Glu Pro Leu Asn Gln Leu Glu Leu Ile Asp Gln Leu Gln Arg
            100                 105                 110

Leu Gly Leu Asp Tyr His Phe Arg Asp Glu Ile Asn His Thr Leu Lys
        115                 120                 125

Asn Val His Asn Gly Gln Lys Ser Glu Thr Trp Glu Lys Asp Leu His
    130                 135                 140

Ala Thr Ala Leu Glu Phe Arg Leu Leu Arg Gln His Gly His Tyr Ile
145                 150                 155                 160

Ser Pro Glu Gly Phe Lys Arg Phe Thr Glu Asn Gly Ser Phe Asn Lys
                165                 170                 175

Gly Ile Arg Ala Asp Val Arg Gly Leu Leu Ser Leu Tyr Glu Ala Ser
            180                 185                 190

Tyr Phe Ser Ile Glu Gly Glu Ser Leu Met Glu Glu Ala Trp Ser Phe
        195                 200                 205

Thr Ser Asn Ile Leu Lys Glu Cys Leu Glu Asn Thr Ile Asp Leu Asp
    210                 215                 220

Leu Gln Met Gln Val Arg His Ala Leu Glu Leu Pro Leu Gln Trp Arg
225                 230                 235                 240
```

```
Ile Pro Arg Phe Asp Ala Lys Trp Tyr Ile Asn Leu Tyr Gln Arg Ser
                245                 250                 255
Gly Asp Met Ile Pro Ala Val Leu Glu Phe Ala Lys Leu Asp Phe Asn
            260                 265                 270
Ile Arg Gln Ala Leu Asn Gln Glu Glu Leu Lys Asp Leu Ser Arg Trp
        275                 280                 285
Trp Ser Arg Leu Asp Met Gly Glu Lys Leu Pro Phe Ala Arg Asp Arg
290                 295                 300
Leu Val Thr Ser Phe Phe Trp Ser Leu Gly Ile Thr Gly Glu Pro His
305                 310                 315                 320
His Arg Tyr Cys Arg Glu Val Leu Thr Lys Ile Ile Glu Phe Val Gly
                325                 330                 335
Val Tyr Asp Asp Val Tyr Asp Val Tyr Gly Thr Leu Asp Glu Leu Glu
            340                 345                 350
Leu Phe Thr Asn Val Val Lys Arg Trp Asp Thr Asn Ala Met Lys Glu
        355                 360                 365
Leu Pro Asp Tyr Met Lys Leu Cys Phe Leu Ser Leu Ile Asn Met Val
370                 375                 380
Asn Glu Thr Thr Tyr Asp Ile Leu Lys Asp His Asn Ile Asp Thr Leu
385                 390                 395                 400
Pro His Gln Arg Lys Trp Phe Asn Asp Leu Phe Glu Arg Tyr Ile Val
                405                 410                 415
Glu Ala Arg Trp Tyr Asn Ser Gly Tyr Gln Pro Thr Leu Glu Glu Tyr
            420                 425                 430
Leu Lys Asn Gly Phe Val Ser Ile Gly Gly Pro Ile Gly Val Leu Tyr
        435                 440                 445
Ser Tyr Ile Cys Thr Glu Asp Pro Ile Lys Lys Glu Asp Leu Glu Phe
450                 455                 460
Ile Glu Asp Leu Pro Asp Ile Val Arg Leu Thr Cys Glu Ile Phe Arg
465                 470                 475                 480
Leu Thr Asp Asp Tyr Gly Thr Ser Ser Ala Glu Leu Lys Arg Gly Asp
                485                 490                 495
Val Pro Ser Ser Ile Tyr Cys Tyr Met Ser Asp Thr Gly Val Thr Glu
            500                 505                 510
Glu Val Ser Arg Lys His Met Met Asn Leu Ile Arg Lys Lys Trp Ala
        515                 520                 525
Gln Ile Asn Lys Leu Arg Phe Ser Lys Glu Tyr Asn Asn Pro Leu Ser
530                 535                 540
Trp Ser Phe Val Asp Ile Met Leu Asn Ile Ile Arg Ala Ala His Phe
545                 550                 555                 560
Leu Tyr Asn Thr Gly Asp Asp Gly Phe Gly Val Glu Asp Val Ala Val
                565                 570                 575
Glu Ala Thr Leu Val Ser Leu Leu Val Glu Pro Ile Pro Leu
            580                 585                 590

<210> SEQ ID NO 5
<211> LENGTH: 1773
<212> TYPE: DNA
<213> ORGANISM: Coriandrum sativum

<400> SEQUENCE: 5
atggcagcga taactatatt tccactttct tattcgatca aatttaggag atcctcccca      60
tgcaatccta aagatgtgac agcctgcaag tctgtaatta aatccgtcac tggaatgact     120
aaggttcctg ttccagtacc agagcctatc gtaaggcgat cagggaacta caaaccttgc     180
```

```
atgtgggaca acgatttctt gcagtctttg aaaactgaat acaccgggga agcaatcaat      240
gcacgagctt ctgagatgaa ggaagagtg aggatgatat ttaataatgt ggtcgaacca       300
ttgaatcagc ttgagctgat tgatcagttg cagagacttg ggttggatta tcattttcgt      360
gatgaaatca accatacttt gaagaacgta cataatggtc agaagagtga gacttgggag      420
aaggacttgc atgctactgc tcttgaattt aggcttctta gacaacatgg acattatata      480
tcccctgagg gcttcaagag atttacagag aatgggagct tcaataaagg tatccgtgca      540
gatgtccggg gactattaag tttatatgaa gcctcgtact tttctattga aggagagtcc      600
ctgatggagg aggcttggtc ctttacaagt aacatcctta agagtgcct cgaaaatact       660 attgatttgg atctccagat gcaagtgaga catgctttgg aacttccact acaatggagg      720
atcccgagat ttgatgcaaa gtggtacata aatttgtatc aaagaagtgg tgacatgatc      780
ccagcggttc tggaatttgc aaagttggac ttcaacatta ggcaagcgtt gaaccaagaa      840
gagcttaaag atttgtcgag gtggtggagt agattagaca tgggagagaa acttcccttt      900
gccagagata ggttggtaac atcatttttc tggagtttgg ggattactgg cgagcctcat      960
cacagatatt gcagagagt tttaaccaaa ataatagagt ttgttggtgt atacgatgat       1020
gtttatgatg tatatggtac acttgatgaa cttgaactct ttacaaatgt cgtgaagagg      1080
tgggatacaa atgcaatgaa agagctccca gactacatga agttgtgctt cctgtcattg     1140
atcaacatgg tcaatgaaac gacttacgac atcctcaagg accataacat cgatacttta     1200
ccacaccaaa gaaaatggtt caatgattta ttcgagcgtt acatagtgga ggcgaggtgg     1260
tataacagtg ataccagcc aacactagaa gaatacttga aaaatggatt tgtgtcaata     1320
ggaggcccca ttggagtgct ttactcttac atctgtactg aggatccaat caagaaagaa     1380
gatttagagt ttatcgagga ccttcctgat atagtacgat tgacatgtga aatttttcgg     1440
ttaactgatg attatggaac atcttcggct gagttaaaga gaggagatgt tccatcttct     1500
atatattgct acatgtcgga tactggtgtt acggaagaag tttcccgtaa gcacatgatg     1560
aacttgatca ggaagaagtg ggcacaaatt aacaaactca gattttcaaa ggagtataat     1620
aatcctttat cgtggtcttt tgttgatatt atgttgaata taatcagggc agcccatttt    1680
ttgtataata ctggagacga tggctttggt gttgaagatg ttgcagttga agctacatta    1740
gtttcgcttc ttgtcgagcc cattcctctc taa                                   1773

<210> SEQ ID NO 6
<211> LENGTH: 1659
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Coriandrum sativum
      (opt_CsLINS)

<400> SEQUENCE: 6
atgactaaag tgcccgtgcc cgtgcccgaa cccattgtgc ggcggagcgg taactataaa       60
ccctgtatgt gggataacga ttttctgcaa agcttaaaaa ccgaatatac tggcgaagcc      120
attaatgccc gtgcttctga aatgaaagaa gaagtgcgga tgattttaa caacgtggtt       180 gaaccctga ccaattggga actgattgat caactgcagc gctgggggtt ggactaccat       240
tttcgtgatg aaattaacca taccttgaaa aacgtgcaca acggacaaaa atccgaaacc      300
```

```
tgggaaaaag atttacacgc cactgctctg gaatttcgtt tgttacggca gcatggccac    360
tatattagcc ccgaaggttt taaacggttt accgaaaatg ggtcttttaa caaaggcatt    420
cgggccgatg tgcggggcct gttgtccctg tacgaagcta gctactttc tattgaaggt     480 gaaagtttga tggaagaagc ctggtccttt actagtaaca ttttgaaaga atgtctggaa    540
aacaccattg atttagacct gcaaatgcag gtgcgccatg ccttggaatt acccctgcaa    600
tggcgcattc cccgttttga tgctaaatgg tacattaacc tgtaccagcg cagtggggac    660
atgattcccg ccgtgttgga atttgctaaa ctggatttta acattcgtca gccttgaac    720 caggaagaat taaagacct gagccgctgg tggtctcgtc tggatatggg cgaaaaattg     780 cccttgctc gggatcgctt ggtgacttcc tttttctgga gtttaggcat taccggtgaa    840
ccccatcacc ggtactgtcg cgaagttctg accaaaatta ttgaatttgt ggggttac     900 gatgacgtgt atgacgttta cggaaccttg gatgaattgg aactgtttac taacgtggtt    960
aaacgttggg acaccaacgc catgaaagaa ttacccgatt atatgaaact gtgctttctg   1020
tccttgatta atatggtgaa cgaaaccact tacgatattc tgaaagacca taacattgat   1080
accttgcccc accaacgcaa atggtttaac gatctgtttg aacggtacat tgtgaagcc    1140 cgctggtata atagtggtta ccagcccacc ctggaagaat acttgaaaaa tgggtttgtg   1200
tccattggcg gtcccattgg agttttgtac agttacattt gtactgaaga ccccatcaaa   1260
aaagaagatt tggaatttat tgaagattta cccgacattg tgcgtctgac ctgcgaaatt   1320
tttcggctga ccgatgacta tggcacttcc agtgccgaat tgaaacgggg tgacgttccc   1380 agctctatt attgctacat gagcgatacc ggtgtgactg aagaagtttc tcggaaacat   1440
atgatgaacc tgattcgcaa aaaatggggcc caaattaaca aactgcggtt tagcaaagaa   1500
tataataacc ccttgtcctg gagttttgtg gatattatgc tgaacattat tcgcgccgct   1560
cattttctgt acaacactgg ggatgacggg tttggagttg aagatgtggc cgttgaagct   1620
accttagtga gtttactggt tgaacccatt cccttataa                           1659

<210> SEQ ID NO 7
<211> LENGTH: 900
<212> TYPE: DNA
<213> ORGANISM: Escherichia coli

<400> SEQUENCE: 7
atggactttc gcagcaact cgaagcctgc gttaagcagg ccaaccaggc gctgagccgt     60
tttatcgccc cactgcccctt tcagaacact cccgtggtcg aaaccatgca gtatggcgca    120
ttattaggtg gtaagcgcct gcgacccttc ctggtttatg ccaccggtca tatgttcggc    180
gttagcacaa acacgctgga cgcacccgct gccgccgttg agtgtatcca cgcttactca    240
ttaattcatg atgatttacc ggcaatggat gatgacgatc tgcgtcgcgg tttgccaacc    300
tgccatgtga gtttggcga agcaaacgcg attctcgctg cgacgctt acaaacgctg      360 gcgttctcga tttttaagcga tgccgatatg ccggaagtgt cggaccgcga cagaatttcg    420
atgatttctg aactggcgag cgccagtggt attgccggaa tgtgcggtgg tcaggcatta   480
gatttagacg cggaaggcaa acacgtacct ctggacgcgc ttgagcgtat tcatcgtcat   540
aaaaccggcg cattgattcg cgccgccgtt cgccttggtg cattaagcgc cggagataaa   600
ggacgtcgtg ctctgccggt actcgacaag tatgcagaga gcatcggcct tgccttccag   660
gttcaggatg acatcctgga tgtggtggga gatactgcaa cgttgggaaa acgccagggt   720
```

```
gccgaccagc aacttggtaa aagtacctac cctgcacttc tgggtcttga gcaagcccgg    780
aagaaagccc gggatctgat cgacgatgcc cgtcagtcgc tgaaacaact ggctgaacag    840
tcactcgata cctcggcact ggaagcgcta gcggactaca tcatccagcg taataaataa    900
```

<210> SEQ ID NO 8
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      farnesyl diphosphate synthase gene derived from Escherichia coli
      (ispA gene)

<400> SEQUENCE: 8

```
atggattttc cccagcagct ggaagcctgc gtgaaacagg ccaaccaggc cctgagccgc     60
tttatcgccc ccctgccctt cagaacaccc ccgtggtgg aaaccatgca gtacggcgcc    120
ctgctgggcg gcaaacgcct cgccccttt ctggtgtacg ccaccggcca catgtttggc    180
gtgagcacca cacccctgga tgcccccgcc gcgccgtgg aatgcatcca cgcctacttt    240
ctgatccacg atgatctgcc cgccatggat gatgatgatc tgcgccgcgg cctgcccacc    300
tgccacgtga atttggcga agccaacgcc atcctggccg cgatgccct gcagaccctg    360 gcctttagca tcctgagcga tgccgatatg cccgaagtga gcgatcgcga tcgcatcagc    420
atgatcagcg aactggccag cgccagcggc atcgccggca tgtgcggcgg ccaggccctg    480
gatctggatg ccgaaggcaa acacgtgccc ctggatgccc tggaacgcat ccaccgccac    540
aaaaccggcg ccctgatccg cgccgccgtg cgcctgggcg ccctgagcgc cggcgataaa    600
ggccgccgcg ccctgcccgt gctggataaa tacgccgaaa gcatcggcct ggcctttcag    660
gtgcaggatg atatcctgga tgtggtgggc gataccgcca ccctgggcaa acgccagggc    720
gccgatcagc agctgggcaa aagcacctac cccgccctgc tgggcctgga acaggcccgc    780
aaaaaagccc gcgatctgat cgatgatgcc cgcagagcc tgaaacagct ggccgaacag    840
agcctggata ccagcgccct ggaagccctg gccgattaca tcatccagcg caacaaatag    900
```

<210> SEQ ID NO 9
<211> LENGTH: 2931
<212> TYPE: DNA
<213> ORGANISM: Pantoea anantis
<220> FEATURE:
<221> NAME/KEY: CDS
<222> LOCATION: (301)..(2691)

<400> SEQUENCE: 9

```
gcgtctggcg atctcattcc ctttacgctt taacctttct tatctcctgg cactattgaa     60
tcatatcggc aaggccccat taacaccctc taaagtattg ccttagatgc gttgttaaga    120
gctttaagcc aaaaaaatca aaactcatac caatttttgct ataacattta acagatatgg    180
atcatcacgc ttcagggaag agcgaaataa gaatgccttt catcttttgt actttatgac    240
tgacaacaat ctatctgatt gttttcctga gttttctggc aacgaaatga ggtcaacatt    300
```

```
atg ggg aaa aac tcc tca tcc ttt agc gtg gtc cgt ttt tta acg gtg    348
Met Gly Lys Asn Ser Ser Ser Phe Ser Val Val Arg Phe Leu Thr Val
1               5                   10                  15 ctg ttc gcc gtg cta acg ggt gcg ttc atg tta att ggt ggt atc tgg    396
Leu Phe Ala Val Leu Thr Gly Ala Phe Met Leu Ile Gly Gly Ile Trp
            20                  25                  30
```

```
ctg gcc acg atc ggt ggt tcc tgg tac tac atc atc ggc ggt gca gcc    444
Leu Ala Thr Ile Gly Gly Ser Trp Tyr Tyr Ile Ile Gly Gly Ala Ala
        35                  40                  45 atg ctg ctt acc gct ttc ctg ctg tgg cga cgt aac agc gct gcc ctg    492
Met Leu Leu Thr Ala Phe Leu Leu Trp Arg Arg Asn Ser Ala Ala Leu
 50                  55                  60 gtt gtc tat gcg ctc tta ctg ctg gct acg ctg gcc tgg ggc gtt tgg    540
Val Val Tyr Ala Leu Leu Leu Leu Ala Thr Leu Ala Trp Gly Val Trp
 65                  70                  75                  80 gaa gtc ggc acc gac ttc tgg gca ctg gca ccg cgt acc gac gta ctg    588
Glu Val Gly Thr Asp Phe Trp Ala Leu Ala Pro Arg Thr Asp Val Leu
                85                  90                  95 gtg atc ttt ggc gtc tgg ctg gtg ttg ccc ttt gtc tat cgc ggc tta    636
Val Ile Phe Gly Val Trp Leu Val Leu Pro Phe Val Tyr Arg Gly Leu
            100                 105                 110 tac cag ccg ggt aaa ggc gca ctg ggt gcc atg ggc gta gcg ctg gtt    684
Tyr Gln Pro Gly Lys Gly Ala Leu Gly Ala Met Gly Val Ala Leu Val
        115                 120                 125 gcc agt gca gcg gtg tta acc tat tcc gtc ttt aat gat ccg caa gtg    732
Ala Ser Ala Ala Val Leu Thr Tyr Ser Val Phe Asn Asp Pro Gln Val
    130                 135                 140 gtt aac ggt gca tta ccg gca aca gcg gat aat gcg cct cag gca cag    780
Val Asn Gly Ala Leu Pro Ala Thr Ala Asp Asn Ala Pro Gln Ala Gln
145                 150                 155                 160 ccg ttg agc aat att gct gat ggt gac tgg ccg gcc tat gcg cgc gat    828
Pro Leu Ser Asn Ile Ala Asp Gly Asp Trp Pro Ala Tyr Ala Arg Asp
                165                 170                 175 cag caa ggg acg cgc ttc tcg ccg ctc aag cag atc aac cac gac aat    876
Gln Gln Gly Thr Arg Phe Ser Pro Leu Lys Gln Ile Asn His Asp Asn
            180                 185                 190 gtg aaa gaa ctg cag gtt gcc tgg caa ttc cag acc ggt gat atg aaa    924
Val Lys Glu Leu Gln Val Ala Trp Gln Phe Gln Thr Gly Asp Met Lys
        195                 200                 205 cgc cca agc gat ccg ggc gaa att acc gat gaa gtg acg cca atc aag    972
Arg Pro Ser Asp Pro Gly Glu Ile Thr Asp Glu Val Thr Pro Ile Lys
    210                 215                 220 att cgc gac acg ctg tat ctt tgc acg cca cat cag att tta ttt gct   1020
Ile Arg Asp Thr Leu Tyr Leu Cys Thr Pro His Gln Ile Leu Phe Ala
225                 230                 235                 240 ctg gat gcg gcc acc ggc aag caa aag tgg aag ttt gat ccc ggc ctg   1068
Leu Asp Ala Ala Thr Gly Lys Gln Lys Trp Lys Phe Asp Pro Gly Leu
                245                 250                 255 aaa acc aac cca acc ttc cag cac gtg acc tgt cgt ggt gtg tca tac   1116
Lys Thr Asn Pro Thr Phe Gln His Val Thr Cys Arg Gly Val Ser Tyr
            260                 265                 270 cac gaa ttc cct gca gcg aag gat gcg tcc aat acc cag cct gcg ctg   1164
His Glu Phe Pro Ala Ala Lys Asp Ala Ser Asn Thr Gln Pro Ala Leu
        275                 280                 285 tgc tcg cgt cgt atc tac ctg cca gtc aat gac ggg cgt ttg ttc gcg   1212
Cys Ser Arg Arg Ile Tyr Leu Pro Val Asn Asp Gly Arg Leu Phe Ala
    290                 295                 300 ctg gat gcg gaa acc ggt gaa cgc tgc ccg gcc ttt ggt aac aac ggt   1260
Leu Asp Ala Glu Thr Gly Glu Arg Cys Pro Ala Phe Gly Asn Asn Gly
305                 310                 315                 320 gag ctg gat ctg cag cac aag cag ccg gtc aca acg cca ggc atg tat   1308
Glu Leu Asp Leu Gln His Lys Gln Pro Val Thr Thr Pro Gly Met Tyr
                325                 330                 335 gag cca acc tcg cca ccg gtg att act gac acc acc att gtg atg gct   1356
Glu Pro Thr Ser Pro Pro Val Ile Thr Asp Thr Thr Ile Val Met Ala
```

-continued

|     | 340 |     |     |     | 345 |     |     |     | 350 |     |     |     |     |      |
|-----|-----|-----|-----|-----|-----|-----|-----|-----|-----|-----|-----|-----|-----|------|
| ggc | gcg | gta | acc | gat | aac | ttt | tca | acc | cgt | gaa | cct | tca | ggc | gcc atc | 1404 |
| Gly | Ala | Val | Thr | Asp | Asn | Phe | Ser | Thr | Arg | Glu | Pro | Ser | Gly | Ala Ile |
|     |     | 355 |     |     |     | 360 |     |     |     | 365 |     |     |     |      |

```
ggc gcg gta acc gat aac ttt tca acc cgt gaa cct tca ggc gcc atc    1404
Gly Ala Val Thr Asp Asn Phe Ser Thr Arg Glu Pro Ser Gly Ala Ile
            355                 360                 365 cgt ggc ttt gat gtg aac acc ggt aag ctg ttg tgg gtg ttc gat ccg    1452
Arg Gly Phe Asp Val Asn Thr Gly Lys Leu Leu Trp Val Phe Asp Pro
370                 375                 380 ggc gcg aaa gat cct aac gcg att ccg gcg gat gaa cac acg ttc acc    1500
Gly Ala Lys Asp Pro Asn Ala Ile Pro Ala Asp Glu His Thr Phe Thr
385                 390                 395                 400 atg aac tcc cct aac tcg tgg gca cct gcg gtt tac gat ccg aag ctg    1548
Met Asn Ser Pro Asn Ser Trp Ala Pro Ala Val Tyr Asp Pro Lys Leu
                405                 410                 415 gat atc gtt tac ctg cca atg ggg gtg acc acg ccg gat atc tgg ggc    1596
Asp Ile Val Tyr Leu Pro Met Gly Val Thr Thr Pro Asp Ile Trp Gly
            420                 425                 430 ggc aac cgc aca cct gag cag gaa cgt tat gcc agc agc gtg ctg gcg    1644
Gly Asn Arg Thr Pro Glu Gln Glu Arg Tyr Ala Ser Ser Val Leu Ala
            435                 440                 445 ctg aac gcg acg acc ggt aag ctg gtg tgg tca tat cag act gtg cat    1692
Leu Asn Ala Thr Thr Gly Lys Leu Val Trp Ser Tyr Gln Thr Val His
450                 455                 460 cac gat ctg tgg gat atg gac ctg cct tcg cag ccg acg ctg gcg gat    1740
His Asp Leu Trp Asp Met Asp Leu Pro Ser Gln Pro Thr Leu Ala Asp
465                 470                 475                 480 att acc gat aaa gac ggt aat acc gtg ccg gtt atc tat gcc cct gcc    1788
Ile Thr Asp Lys Asp Gly Asn Thr Val Pro Val Ile Tyr Ala Pro Ala
                485                 490                 495 aaa acc ggg aac atc ttt gtt ctg gat cgc cgc aca ggt aaa act gtg    1836
Lys Thr Gly Asn Ile Phe Val Leu Asp Arg Arg Thr Gly Lys Thr Val
                500                 505                 510 gtt ccg gcc ccg gaa acc cct gtt ccg cag ggc gca gct aag ggc gac    1884
Val Pro Ala Pro Glu Thr Pro Val Pro Gln Gly Ala Ala Lys Gly Asp
            515                 520                 525 cat gtc tca gct aca cag cct tac tct gaa ctg acc ttc cgt ccg aaa    1932
His Val Ser Ala Thr Gln Pro Tyr Ser Glu Leu Thr Phe Arg Pro Lys
530                 535                 540 cag aac ctg acg gat aag gac atg tgg ggc gcg acg atg tat gac cag    1980
Gln Asn Leu Thr Asp Lys Asp Met Trp Gly Ala Thr Met Tyr Asp Gln
545                 550                 555                 560 ctg gtg tgc cgc gtg att ttc aaa cgt ctg cgc tac gaa ggt ccg ttc    2028
Leu Val Cys Arg Val Ile Phe Lys Arg Leu Arg Tyr Glu Gly Pro Phe
                565                 570                 575 acg cca cct tct gag cag ggc acc ctg gtc ttc ccg ggc aac ctg ggc    2076
Thr Pro Pro Ser Glu Gln Gly Thr Leu Val Phe Pro Gly Asn Leu Gly
                580                 585                 590 atg ttt gaa tgg ggc ggc att tcc gtt gat ccg cat cgt cag att gcg    2124
Met Phe Glu Trp Gly Gly Ile Ser Val Asp Pro His Arg Gln Ile Ala
            595                 600                 605 att gct aac cca atg gcg ctg ccg ttc gtg tct aag ctg atc cca cgc    2172
Ile Ala Asn Pro Met Ala Leu Pro Phe Val Ser Lys Leu Ile Pro Arg
610                 615                 620 ggt ccg ggt aat ccg gaa gag cca cca aaa ggc gca acg ggc ggt tca    2220
Gly Pro Gly Asn Pro Glu Glu Pro Pro Lys Gly Ala Thr Gly Gly Ser
625                 630                 635                 640 ggt act gaa acc ggt att cag ccg cag tac ggt gtg cca tat ggc gtt    2268
Gly Thr Glu Thr Gly Ile Gln Pro Gln Tyr Gly Val Pro Tyr Gly Val
                645                 650                 655 gaa ctg aat ccg ttc ctg tca cct ttt ggt ctg ccg tgt aaa caa cct    2316
```

```
Glu Leu Asn Pro Phe Leu Ser Pro Phe Gly Leu Pro Cys Lys Gln Pro
            660                 665                 670 gca tgg ggt tat gtt tct gct gtt gac ctg aaa acc aac gaa gtg gtg      2364
Ala Trp Gly Tyr Val Ser Ala Val Asp Leu Lys Thr Asn Glu Val Val
            675                 680                 685 tgg aaa caa cgt att ggt acc gtt cgt gac agc tca cct gta ccg ctg      2412
Trp Lys Gln Arg Ile Gly Thr Val Arg Asp Ser Ser Pro Val Pro Leu
690                 695                 700 ccc ttt aaa atg ggt atg cca atg ctg ggc gga ccg gtt gcc acc gca      2460
Pro Phe Lys Met Gly Met Pro Met Leu Gly Gly Pro Val Ala Thr Ala
705                 710                 715                 720 ggc aaa gtg ttc ttt att ggc gca acg gct gat aac tac ctg cgc gct      2508
Gly Lys Val Phe Phe Ile Gly Ala Thr Ala Asp Asn Tyr Leu Arg Ala
                725                 730                 735 ttc agc acc gac acc ggt gaa ctc ttg tgg cag gcg cgc ctg cca gcc      2556
Phe Ser Thr Asp Thr Gly Glu Leu Leu Trp Gln Ala Arg Leu Pro Ala
                740                 745                 750 ggt ggt cag gca acg cca atg acc tat gaa gtt aac ggc aag caa tac      2604
Gly Gly Gln Ala Thr Pro Met Thr Tyr Glu Val Asn Gly Lys Gln Tyr
            755                 760                 765 gtt gtg att gct gcc ggt ggc cat ggt tca ttc ggc acc aag ctg ggc      2652
Val Val Ile Ala Ala Gly Gly His Gly Ser Phe Gly Thr Lys Leu Gly
770                 775                 780 gat tac gtg att gcc tat gcg ctg ccc gac cag aag taa ttaacacctg      2701
Asp Tyr Val Ile Ala Tyr Ala Leu Pro Asp Gln Lys
785                 790                 795 aacagaggcg gactccggtc cgcctttttt tatgcctgct atctgccctg tgcttttgcg    2761
cgtggggagc gccagcttaa ccaggcgcac agccccatga ccatgcaggt ggccagaaat    2821
actggccgca ttccccacgc gccaccaatc accccaccaa aaaggggacc actgacctgg    2881
ccgatatact gcgccgacgt cgaatagccg agcatgcgcc ccacctgcac               2931

<210> SEQ ID NO 10
<211> LENGTH: 796
<212> TYPE: PRT
<213> ORGANISM: Pantoea anantis

<400> S

```
            145                 150                 155                 160
        Pro Leu Ser Asn Ile Ala Asp Gly Asp Trp Pro Ala Tyr Ala Arg Asp
                        165                 170                 175
        Gln Gln Gly Thr Arg Phe Ser Pro Leu Lys Gln Ile Asn His Asp Asn
                        180                 185                 190
        Val Lys Glu Leu Gln Val Ala Trp Gln Phe Gln Thr Gly Asp Met Lys
                        195                 200                 205
        Arg Pro Ser Asp Pro Gly Glu Ile Thr Asp Glu Val Thr Pro Ile Lys
                        210                 215                 220
        Ile Arg Asp Thr Leu Tyr Leu Cys Thr Pro His Gln Ile Leu Phe Ala
        225                 230                 235                 240
        Leu Asp Ala Ala Thr Gly Lys Gln Lys Trp Lys Phe Asp Pro Gly Leu
                        245                 250                 255
        Lys Thr Asn Pro Thr Phe Gln His Val Thr Cys Arg Gly Val Ser Tyr
                        260                 265                 270
        His Glu Phe Pro Ala Ala Lys Asp Ala Ser Asn Thr Gln Pro Ala Leu
                        275                 280                 285
        Cys Ser Arg Arg Ile Tyr Leu Pro Val Asn Asp Gly Arg Leu Phe Ala
                        290                 295                 300
        Leu Asp Ala Glu Thr Gly Glu Arg Cys Pro Ala Phe Gly Asn Asn Gly
        305                 310                 315                 320
        Glu Leu Asp Leu Gln His Lys Gln Pro Val Thr Thr Pro Gly Met Tyr
                        325                 330                 335
        Glu Pro Thr Ser Pro Pro Val Ile Thr Asp Thr Thr Ile Val Met Ala
                        340                 345                 350
        Gly Ala Val Thr Asp Asn Phe Ser Thr Arg Glu Pro Ser Gly Ala Ile
                        355                 360                 365
        Arg Gly Phe Asp Val Asn Thr Gly Lys Leu Leu Trp Val Phe Asp Pro
                        370                 375                 380
        Gly Ala Lys Asp Pro Asn Ala Ile Pro Ala Asp Glu His Thr Phe Thr
        385                 390                 395                 400
        Met Asn Ser Pro Asn Ser Trp Ala Pro Ala Val Tyr Asp Pro Lys Leu
                        405                 410                 415
        Asp Ile Val Tyr Leu Pro Met Gly Val Thr Thr Pro Asp Ile Trp Gly
                        420                 425                 430
        Gly Asn Arg Thr Pro Glu Gln Glu Arg Tyr Ala Ser Ser Val Leu Ala
                        435                 440                 445
        Leu Asn Ala Thr Thr Gly Lys Leu Val Trp Ser Tyr Gln Thr Val His
                        450                 455                 460
        His Asp Leu Trp Asp Met Asp Leu Pro Ser Gln Pro Thr Leu Ala Asp
        465                 470                 475                 480
        Ile Thr Asp Lys Asp Gly Asn Thr Val Pro Val Ile Tyr Ala Pro Ala
                        485                 490                 495
        Lys Thr Gly Asn Ile Phe Val Leu Asp Arg Arg Thr Gly Lys Thr Val
                        500                 505                 510
        Val Pro Ala Pro Glu Thr Pro Val Pro Gln Gly Ala Ala Lys Gly Asp
                        515                 520                 525
        His Val Ser Ala Thr Gln Pro Tyr Ser Glu Leu Thr Phe Arg Pro Lys
                        530                 535                 540
        Gln Asn Leu Thr Asp Lys Asp Met Trp Gly Ala Thr Met Tyr Asp Gln
        545                 550                 555                 560
        Leu Val Cys Arg Val Ile Phe Lys Arg Leu Arg Tyr Glu Gly Pro Phe
                        565                 570                 575
```

```
Thr Pro Pro Ser Glu Gln Gly Thr Leu Val Phe Pro Gly Asn Leu Gly
            580                 585                 590

Met Phe Glu Trp Gly Gly Ile Ser Val Asp Pro His Arg Gln Ile Ala
            595                 600                 605

Ile Ala Asn Pro Met Ala Leu Pro Phe Val Ser Lys Leu Ile Pro Arg
            610                 615                 620

Gly Pro Gly Asn Pro Glu Glu Pro Pro Lys Gly Ala Thr Gly Gly Ser
625                 630                 635                 640

Gly Thr Glu Thr Gly Ile Gln Pro Gln Tyr Gly Val Pro Tyr Gly Val
                645                 650                 655

Glu Leu Asn Pro Phe Leu Ser Pro Phe Gly Leu Pro Cys Lys Gln Pro
            660                 665                 670

Ala Trp Gly Tyr Val Ser Ala Val Asp Leu Lys Thr Asn Glu Val Val
            675                 680                 685

Trp Lys Gln Arg Ile Gly Thr Val Arg Asp Ser Ser Pro Val Pro Leu
            690                 695                 700

Pro Phe Lys Met Gly Met Pro Met Leu Gly Gly Pro Val Ala Thr Ala
705                 710                 715                 720

Gly Lys Val Phe Phe Ile Gly Ala Thr Ala Asp Asn Tyr Leu Arg Ala
                725                 730                 735

Phe Ser Thr Asp Thr Gly Glu Leu Leu Trp Gln Ala Arg Leu Pro Ala
            740                 745                 750

Gly Gly Gln Ala Thr Pro Met Thr Tyr Glu Val Asn Gly Lys Gln Tyr
            755                 760                 765

Val Val Ile Ala Ala Gly His Gly Ser Phe Gly Thr Lys Leu Gly
            770                 775                 780

Asp Tyr Val Ile Ala Tyr Ala Leu Pro Asp Gln Lys
785                 790                 795

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 11
gtgtgaaatt agccagagct gcgggccacc                                    30

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 12
tggctaattt cacacaggag actgccatgg attttcccca gcag                    44

<210> SEQ ID NO 13
<211> LENGTH: 37
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Primer

<400> SEQUENCE: 13
acgttgttgc cattgccctg tttgcaatta atcatcg                              37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 14
acgttgttgc cattgccctg ttgacaatta atcatcg                              37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 15
atgacttggt tgagtctatt tgttgcgctg gatgatg                              37

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 16
tgtgaaatta taagggaatg ggttcaac                                        28

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 17
ccttataatt tcacacagga gactgccatg gattttcccc agcag                     45

<210> SEQ ID NO 18
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (gcd-attL)

-continued

<400> SEQUENCE: 18
ggtcaacatt atggggaaaa actcctcatc ctttagcgtg tgaagcctgc ttttttatac    60
taagttgg                                                             68

<210> SEQ ID NO 19
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (gcd-attR)

<400> SEQUENCE: 19
ttacttctgg tcgggcagcg cataggcaat cacgtaatcg cgctcaagtt agtataaaaa    60
agctgaac                                                             68

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (gcd-t1)

<400> SEQUENCE: 20
tgacaacaat ctatctgatt                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (gcd-t2)

<400> SEQUENCE: 21
tgcgcctggt taagctggcg                                                20

<210> SEQ ID NO 22
<211> LENGTH: 803
<212> TYPE: PRT
<213> ORGANISM: Enterococcus faecalis

<400> SEQUENCE: 22

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
                20                  25                  30

Val Thr Thr Gln Leu Leu Lys Arg His Ser Thr Ile Ser Glu Glu Ile
            35                  40                  45

Asp Gln Val Ile Phe Gly Asn Val Leu Gln Ala Gly Asn Gly Gln Asn
        50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

```
Leu Ala Lys Gln Leu Ile Gln Leu Gly Glu Ala Glu Val Leu Ile Ala
            100                 105                 110
Gly Gly Ile Glu Asn Met Ser Gln Ala Pro Lys Leu Gln Arg Phe Asn
            115                 120                 125
Tyr Glu Thr Glu Ser Tyr Asp Ala Pro Phe Ser Met Met Tyr Asp
        130                 135                 140
Gly Leu Thr Asp Ala Phe Ser Gly Gln Ala Met Gly Leu Thr Ala Glu
145                 150                 155                 160
Asn Val Ala Glu Lys Tyr His Val Thr Arg Glu Gln Asp Gln Phe
                165                 170                 175
Ser Val His Ser Gln Leu Lys Ala Ala Gln Ala Gln Ala Glu Gly Ile
            180                 185                 190
Phe Ala Asp Glu Ile Ala Pro Leu Glu Val Ser Gly Thr Leu Val Glu
            195                 200                 205
Lys Asp Glu Gly Ile Arg Pro Asn Ser Ser Val Glu Lys Leu Gly Thr
210                 215                 220
Leu Lys Thr Val Phe Lys Glu Asp Gly Thr Val Thr Ala Gly Asn Ala
225                 230                 235                 240
Ser Thr Ile Asn Asp Gly Ala Ser Ala Leu Ile Ile Ala Ser Gln Glu
            245                 250                 255
Tyr Ala Glu Ala His Gly Leu Pro Tyr Leu Ala Ile Ile Arg Asp Ser
        260                 265                 270
Val Glu Val Gly Ile Asp Pro Ala Tyr Met Gly Ile Ser Pro Ile Lys
        275                 280                 285
Ala Ile Gln Lys Leu Leu Ala Arg Asn Gln Leu Thr Thr Glu Glu Ile
290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
            325                 330                 335
Gly Ile Ser Leu Gly His Ala Ile Gly Ala Thr Gly Ala Arg Leu Leu
            340                 345                 350
Thr Ser Leu Ser Tyr Gln Leu Asn Gln Lys Glu Lys Tyr Gly Val
        355                 360                 365
Ala Ser Leu Cys Ile Gly Gly Gly Leu Gly Leu Ala Met Leu Leu Glu
        370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
            405                 410                 415
Lys Lys Glu Phe Glu Asn Thr Ala Leu Ser Ser Gln Ile Ala Asn His
            420                 425                 430
Met Ile Glu Asn Gln Ile Ser Glu Thr Glu Val Pro Met Gly Val Gly
        435                 440                 445
Leu His Leu Thr Val Asp Glu Thr Asp Tyr Leu Val Pro Met Ala Thr
        450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
            485                 490                 495
Val Phe Tyr Asp Val Ala Asp Ala Glu Ser Leu Ile Asp Glu Leu Gln
        500                 505                 510
```

Val Arg Glu Thr Glu Ile Phe Gln Gln Ala Glu Leu Ser Tyr Pro Ser
            515                 520                 525

Ile Val Lys Arg Gly Gly Leu Arg Asp Leu Gln Tyr Arg Ala Phe
        530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
            565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
            595                 600                 605

Ser Arg Leu Ser Lys Gly Ser Asn Gly Arg Glu Ile Ala Glu Lys Ile
            610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
            645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
            675                 680                 685

Gln Leu Ile Gly Glu Ile Ser Val Pro Leu Ala Leu Ala Thr Val Gly
            690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
            725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
            755                 760                 765

Gly Ala Thr Gly Lys Glu Val Glu Ala Val Ala Gln Gln Leu Lys Arg
            770                 775                 780

Gln Lys Thr Met Asn Gln Asp Arg Ala Leu Ala Ile Leu Asn Asp Leu
785                 790                 795                 800

Arg Lys Gln

<210> SEQ ID NO 23
<211> LENGTH: 2412
<212> TYPE: DNA
<213> ORGANISM: Enterococcus faecalis

<400> SEQUENCE: 23

```
atgaaaacag tagttattat tgatgcatta cgaacaccaa ttggaaaata taaaggcagc      60
ttaagtcaag taagtgccgt agacttagga acacatgtta caacacaact tttaaaagaa     120
cattccacta tttctgaaga aattgatcaa gtaatctttg gaaatgtttt acaagctgga     180
aatggccaaa atcccgcacg acaaatagca ataaacagcg gtttgtctca tgaaattccc     240
gcaatgacgg ttaatgaggt ctgcggatca ggaatgaagg ccgttatttt ggcgaaacaa     300
ttgattcaat taggagaagc ggaagtttta attgctggcg ggattgagaa tatgtcccaa     360
gcacctaaat tacaacgttt taattacgaa acagaaagct acgatgcgcc ttttctagt     420 atgatgtatg atggattaac ggatgccttt agtggtcagg caatgggctt aactgctgaa     480
```

```
aatgtggccg aaaagtatca tgtaactaga gaagagcaag atcaattttc tgtacattca      540
caattaaaag cagctcaagc acaagcagaa gggatattcg ctgacgaaat agccccatta      600
gaagtatcag gaacgcttgt ggagaaagat gaagggattc gccctaattc gagcgttgag      660
aagctaggaa cgcttaaaac agttttaaa gaagacggta ctgtaacagc agggaatgca       720
tcaaccatta atgatggggc ttctgcttg attattgctt cacaagaata tgccgaagca       780
cacggtcttc cttatttagc tattattcga gacagtgtgg aagtcggtat tgatccagcc      840
tatatgggaa tttcgccgat taaagccatt caaaaactgt tagcgcgcaa tcaacttact      900
acggaagaaa ttgatctgta tgaaatcaac gaagcatttg cagcaacttc aatcgtggtc      960
caaagagaac tggctttacc agaggaaaag gtcaacattt atggtggcgg tatttcatta     1020
ggtcatgcga ttggtgccac aggtgctcgt ttattaacga gtttaagtta tcaattaaat     1080 caaaagaaa agaaatatgg agtggcttct ttatgtatcg gcggtggctt aggactcgct      1140
atgctactag agagacctca gcaaaaaaaa aacagccgat tttatcaaat gagtcctgag     1200
gaacgcctgg cttctcttct taatgaaggc cagatttctg ctgatacaaa aaaagaattt     1260
gaaaatacgg ctttatcttc gcagattgcc aatcatatga ttgaaaatca aatcagtgaa     1320
acagaagtgc cgatgggcgt tggcttacat ttaacagtgg acgaaactga ttatttggta     1380
ccaatggcga cagaagagcc ctcagttatt gcggctttga gtaatggtgc aaaaatagca     1440
caaggattta aaacagtgaa tcaacaacgc ttaatgcgtg acaaatcgt tttttacgat      1500 gttgcagatc ccgagtcatt gattgataaa ctacaagtaa gagaagcgga agtttttcaa     1560
caagcagagt taagttatcc atctatcgtt aaacggggcg gcggcttaag agatttgcaa     1620
tatcgtactt ttgatgaatc atttgtatct gtcgacttt tagtagatgt taaggatgca      1680
atgggggcaa atatcgttaa cgctatgttg gaaggtgtgg ccgagttgtt ccgtgaatgg     1740
tttgcggagc aaaagatttt attcagtatt ttaagtaatt atgccacgga gtcggttgtt    1800
acgatgaaaa cggctattcc agtttcacgt ttaagtaagg ggagcaatgg ccgggaaatt     1860
gctgaaaaaa ttgttttagc ttcacgctat gcttcattag atccttatcg ggcagtcacg     1920
cataacaaag gaatcatgaa tggcattgaa gctgtagttt tagctacagg aaatgataca     1980
cgcgctgtta gcgcttcttg tcatgcttt gcggtgaagg aaggtcgcta ccaaggcttg      2040
actagttgga cgctggatgg cgaacaacta attggtgaaa tttcagttcc gcttgcttta     2100
gccacggttg gcggtgccac aaaagtctta cctaaatctc aagcagctgc tgatttgtta    2160
gcagtgacgg atgcaaaaga actaagtcga gtagtagcgg ctgttggttt ggcacaaaat     2220
ttagcggcgt tacgggcctt agtctctgaa ggaattcaaa aaggacacat ggctctacaa     2280
gcacgttctt tagcgatgac ggtcggagct actggtaaag aagttgaggc agtcgctcaa     2340
caattaaaac gtcaaaaaac gatgaaccaa gaccgagcca tggctatttt aaatgattta    2400
agaaaacaat aa                                                          2412
```

<210> SEQ ID NO 24
<211> LENGTH: 2412
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes mvaE derived from Enterococcus faecalis

<400> SEQUENCE: 24

```
atgaaaaccg tggttattat cgatgcgctg cgcacgccga ttggtaaata taaaggcagc      60
ctgtctcaag tgagcgccgt tgatctgggt acgcatgtga ccacgcagct gctgaaacgt     120
cacagcacca tctctgaaga aattgatcag gtgatctttg gtaacgttct gcaagccggt     180
aatggtcaga atccggcacg tcagattgca atcaacagtg gcctgagcca tgaaattccg     240
gcgatgaccg tgaatgaagt ttgcggtagc ggcatgaaag cggttattct ggccaaacag     300
ctgatccagc tgggtgaagc ggaagtgctg attgccggcg gtatcgaaaa catgagtcag     360
gcaccgaaac tgcaacgttt taattatgaa accgaaagct acgatgcccc gttcagctct     420
atgatgtatg atggcctgac cgatgcattt agcggtcagg cgatgggcct gacggcagaa     480
aacgtggcgg aaaaatacca tgttacccgc gaagaacagg atcagttttc tgttcacagt     540
cagctgaaag cggcccaggc ccaggcagaa ggtattttcg ccgatgaaat cgcaccgctg     600
gaagtgtctg gtacgctggt tgaaaaagat gaaggcattc gtccgaatag tagcgtggaa     660
aaactgggca ccctgaaaac ggtgttcaaa gaagatggca ccgttacggc gggcaatgca     720
agcaccatca tgatggtgc gagtgccctg attatcgcga ccaggaata tgcagaagcg     780
catggcctgc cgtacctggc cattatccgc gattctgtgg aagttggtat tgatccggca     840
tatatgggca ttagtccgat caaagcgatt cagaaactgc tggcccgtaa ccagctgacc     900
accgaagaaa ttgatctgta cgaaatcaat gaagcgtttg cagcgaccag tattgtggtt     960
cagcgcgaac tggccctgcc ggaagaaaaa gttaacattt atggcggtgg catcagcctg    1020
ggtcacgcaa ttggtgccac cggtgcacgt ctgctgacca gtctgagcta tcagctgaat    1080
cagaaagaga aaaatacgg tgtggcaagc ctgtgtattg gtggcggtct gggtctggcc    1140
atgctgctgg aacgtccgca gcagaagaaa aactctcgtt tttaccagat gagtccggaa    1200
gaacgtctgg ccagtctgct gaacgaaggc cagattagcg cagataccaa aaaagaattc    1260
gaaaatacgg cactgtctag tcagatcgcg aaccatatga ttgaaaatca gatcagcgaa    1320
accgaagtgc cgatgggtgt tggcctgcac ctgaccgtgg atgaaacgga ttatctggtt    1380
ccgatggcga cggaagaacc gagcgttatt gccgcactgt ctaacggtgc aaaaatcgcg    1440
cagggctta aaaccgtgaa tcagcagcgt ctgatgcgcg ccagattgt gttctacgat    1500
gttgcggatc cggaaagcct gatcgataaa ctgcaagtgc gcgaagccga agttttttcag    1560
caggcagaac tgagctatcc gtctattgtg aaacgtggcg gtggcctgcg cgatctgcaa    1620
taccgtacct ttgatgaaag tttcgtgagc gttgatttcc tggtggatgt taaagatgcc    1680
atgggtgcaa acatcgtgaa tgcgatgctg gaaggcgttg ccgaactgtt tcgtgaatgg    1740
ttcgcggaac agaaaatcct gttttctatc ctgagtaact acgcgaccga aagcgtggtt    1800
accatgaaaa cggccattcc tgtgagccgc ctgtctaaag gtagtaatgg ccgtgaaatt    1860
gcggaaaaaa tcgttctggc gagccgctat gcctctctgg atccgtaccg tgccgtgacc    1920
cataacaaag gtattatgaa tggcatcgaa gcagtggttc tggcgaccgg taacgatacc    1980
cgtgccgtgt ctgcaagttg ccatgcattc gcagttaaag aaggtcgtta tcagggcctg    2040
accagctgga cgctggatgg tgaacagctg atcggcgaaa tttctgtgcc gctgccctg    2100
gcaaccgtgg gtggcgcgac gaaagttctg ccgaaaagcc aggcggccgc agatctgctg    2160
gcggtgaccg atgcaaaaga actgtctcgc gtggttgcgg ccgttggtct ggcacagaat    2220
ctggcagcgc tgcgtgcgct ggtgtctgaa ggtattcaga aaggccacat ggcactgcaa    2280
gcccgtagtc tggccatgac cgtgggtgca acgggcaaag aagtggaagc agttgcgcag    2340
```

```
cagctgaaac gccagaaaac catgaaccag gatcgtgcca tggcaatcct gaatgatctg    2400
cgcaaacagt aa                                                        2412
```

<210> SEQ ID NO 25
<211> LENGTH: 383
<212> TYPE: PRT
<213> ORGANISM: Enterococcus faecalis

<400> SEQUENCE: 25

```
Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350
```

Glu Thr Leu Asp Thr Asp Ile Asp Gln Thr Leu Glu Asp Glu Leu Lys
            355                 360                 365

Tyr Ser Ile Ser Ala Ile Asn Asn Thr Val Arg Ser Tyr Arg Asn
        370                 375                 380

<210> SEQ ID NO 26
<211> LENGTH: 1152
<212> TYPE: DNA
<213> ORGANISM: Enterococcus faecalis

<400> SEQUENCE: 26

| | | | | |
|---|---|---|---|---|
| atgacaattg | ggattgataa | aattagtttt | tttgtgcccc | cttattatat | tgatatgacg | 60 |
| gcactggctg | aagccagaaa | tgtagaccct | ggaaaatttc | atattggtat | tgggcaagac | 120 |
| caaatggcgg | tgaacccaat | cagccaagat | attgtgacat | tgcagccaa | tgccgcagaa | 180 |
| gcgatcttga | ccaagaaga | taaagaggcc | attgatatgg | tgattgtcgg | gactgagtcc | 240 |
| agtatcgatg | agtcaaaagc | ggccgcagtt | gtcttacatc | gtttaatggg | gattcaacct | 300 |
| ttcgctcgct | ctttcgaaat | caaggaagct | tgttacggag | caacagcagg | cttacagtta | 360 |
| gctaagaatc | acgtagcctt | acatccagat | aaaaaagtct | tggtcgtagc | ggcagatatt | 420 |
| gcaaaatatg | gcttaaattc | tggcggtgag | cctacacaag | gagctgggc | ggttgcaatg | 480 |
| ttagttgcta | gtgaaccgcg | cattttggct | taaaagagg | ataatgtgat | gctgacgcaa | 540 |
| gatatctatg | acttttggcg | tccaacaggc | cacccgtatc | ctatggtcga | tggtccttg | 600 |
| tcaaacgaaa | cctacatcca | atcttttgcc | caagtctggg | atgaacataa | aaaacgaacc | 660 |
| ggtcttgatt | ttgcagatta | tgatgcttta | gcgttccata | ttccttacac | aaaaatgggc | 720 |
| aaaaaagcct | tattagcaaa | aatctccgac | caaactgaag | cagaacagga | acgaattta | 780 |
| gcccgttatg | aagaaagtat | cgtctatagt | cgtcgcgtag | aaacttgta | tacgggttca | 840 |
| ctttatctgg | gactcatttc | cctttagaa | aatgcaacga | ctttaaccgc | aggcaatcaa | 900 |
| attggtttat | tcagttatgg | ttctggtgct | gtcgctgaat | ttttcactgg | tgaattagta | 960 |
| gctggttatc | aaaatcattt | acaaaaagaa | actcatttag | cactgctgga | taatcggaca | 1020 |
| gaactttcta | tcgctgaata | tgaagccatg | tttgcagaaa | ctttagacac | agacattgat | 1080 |
| caaacgttag | aagatgaatt | aaaatatagt | atttctgcta | ttaataatac | cgttcgttct | 1140 |
| tatcgaaact | aa | | | | | 1152 |

<210> SEQ ID NO 27
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes mvaS
      derived from Enterococcus faecalis

<400> SEQUENCE: 27

| | | | | |
|---|---|---|---|---|
| atgaccattg | gtatcgataa | aattagctttt | ttcgtgccgc | cgtattacat | cgatatgacg | 60 |
| gcgctggccg | aagcacgtaa | cgttgatccg | ggcaaatttc | atattggcat | cggtcaggat | 120 |
| cagatggcgg | tgaacccgat | ttctcaggat | atcgttacct | tcgcggccaa | tgcagcggaa | 180 |
| gcaattctga | cgaaagaaga | taaagaagcg | attgatatgg | tgatcgttgg | caccgaaagc | 240 |
| tctatcgatg | aaagtaaagc | cgcagcggtg | gttctgcacc | gtctgatggg | cattcagccg | 300 |
| tttgcgcgca | gcttcgaaat | caaagaagcc | tgctatggcg | cgaccgccgg | tctgcaactg | 360 |

```
gccaaaaacc atgtggcact gcacccggat aaaaaagttc tggtggttgc cgcagatatt    420
gcgaaatacg gtctgaatag cggcggtgaa ccgacccagg gtgcaggtgc cgtggcaatg    480
ctggttgcat ctgaaccgcg tattctggcg ctgaaagaag ataacgtgat gctgacccag    540
gatatctatg atttttggcg tccgaccggt catccgtacc cgatggtgga tggcccgctg    600
agtaatgaaa cctatattca gagcttcgcc caggtttggg atgaacataa aaaacgtacg    660
ggtctggatt ttgcggatta tgatgcactg gcgttccaca ttccgtacac caaaatgggc    720
aaaaaagcgc tgctggccaa aatcagcgat cagacggaag ccgaacagga acgtattctg    780
gcacgctatg aagaaagcat cgtgtactct cgtcgcgttg caacctgta taccggttct    840 ctgtacctgg gcctgattag tctgctggaa aacgcgacca cgctgacggc cggcaatcag    900
atcggtctgt tttcttatgg cagtggtgcc gtggcagaat ttttcaccgg tgaactggtt    960
gccggctacc agaaccatct gcaaaaagaa acccacctgg ccctgctgga taatcgcacg    1020
gaactgtcta ttgcagaata tgaagcaatg tttgcggaaa ccctggatac ggatatcgat    1080
cagaccctgg aagatgaact gaaatatagt attagcgcga tcaacaatac ggtgcgtagt    1140
taccgcaatt aa                                                         1152
```

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      Para composed of araC and ara BAD promoters from E.coli

<400> SEQUENCE: 28
tgaattcgag ctcggtaccc actcttcctt tttcaatatt                           40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      Para composed of araC and ara BAD promoters from E.coli

<400> SEQUENCE: 29
ataataacca cggttttcat tttttataac ctccttagag                           40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      EFmvaE gene

<400> SEQUENCE: 30
ctctaaggag gttataaaaa atgaaaaccg tggttattat                           40

<210> SEQ ID NO 31

```
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      EFmvaE gene

<400> SEQUENCE: 31
ttatcgatac caatggtcat gttttttac ctcctttact gtttgcgcag atcat          55

<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      EFmvaS gene

<400> SEQUENCE: 32
atgatctgcg caaacagtaa aggaggtaaa aaaacatgac cattggtatc gataa          55

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      EFmvaS gene

<400> SEQUENCE: 33
cagcggaact ggcggctccc ttaattgcgg taactacgca                           40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      Ttrp

<400> SEQUENCE: 34
tgcgtagtta ccgcaattaa gggagccgcc agttccgctg                           40

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for amplifying a fragment comprising
      Ttrp

<400> SEQUENCE: 35
gtcgactcta gaggatccct aatgagaatt agtcaaat                             38
```

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (Linker-F)

<400> SEQUENCE: 36
agctttaggg ataacagggt aatctcgagc tgcaggcatg ca                           42

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (Linker-R)

<400> SEQUENCE: 37
agcttgcatg cctgcagctc gagattaccc tgttatccct aa                           42

<210> SEQ ID NO 38
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (lldD5' CAS)

<400> SEQUENCE: 38
tttttaagct ttagggataa cagggtaatc tcgagattta aagcggctgc tttac            55

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (lldD3' CAS)

<400> SEQUENCE: 39
tttttaagct tgcatgcctg cagtatttaa tagaatcagg tag                          43

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (phoC5' CAS)

<400> SEQUENCE: 40
tttttaagct ttagggataa cagggtaatc tcgagtggat aacctcatgt aaac              54

<210> SEQ ID NO 41
<211> LENGTH: 44
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Primer (phoC3' CAS)

<400> SEQUENCE: 41
tttttaagct tgcatgcctg cagttgatgt ctgattatct ctga                       44

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (pstS5' CAS)

<400> SEQUENCE: 42
tttttaagct ttagggataa cagggtaatc tcgagagcct ctcacgcgtg aatc            54

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (pstS3' CAS)

<400> SEQUENCE: 43
tttttaagct tgcatgcctg cagaggggag aaaagtcagg ctaa                       44

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (n67)

<400> SEQUENCE: 44
tgcgaagacg tcctcgtgaa gaaggtgttg ctg                                   33

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (n68)

<400> SEQUENCE: 45
tgcgaagggc cccgttgtgt ctcaaaatct ctgatg                                36

<210> SEQ ID NO 46
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Primer (ampH-attL-phi80)

<400> SEQUENCE: 46
atgcgcactc cttacgtact ggctctactg gtttctttgc gaaaggtcat ttttcctgaa    60
tatgctcaca    70

<210> SEQ ID NO 47
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (ampH-attR-phi80)

<400> SEQUENCE: 47
ttaaggaatc gcctggacca tcatcggcga gccgttctga cgtttgttga cagctggtcc    60
aatg    64

<210> SEQ ID NO 48
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (DampC-phL)

<400> SEQUENCE: 48
ctgatgaact gtcacctgaa tgagtgctga tgaaaatata gaaaggtcat ttttcctgaa    60
tatgctca    68

<210> SEQ ID NO 49
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (DampC-phR)

<400> SEQUENCE: 49
attcgccagc ataacgatgc cgctgttgag ctgaggaaca cgtttgttga cagctggtcc    60
aatg    64

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (ampH-t1)

<400> SEQUENCE: 50
gcgaagccct ctccgttg    18

<210> SEQ ID NO 51
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Primer (ampH-t2)

<400> SEQUENCE: 51
agccagtcag cctcatcagc g                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (ampC-t1)

<400> SEQUENCE: 52
gattcccact tcaccgagcc g                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (ampC-t2)

<400> SEQUENCE: 53
ggcaggtatg gtgctctgac g                                              21

<210> SEQ ID NO 54
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (crtE-attRphi80)

<400> SEQUENCE: 54
atgacggtct gcgcaaaaaa acacgttcat ctcactcgcg cgtttgttga cagctggtcc    60
aatg                                                                 64

<210> SEQ ID NO 55
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (crtZ-attLphi80)

<400> SEQUENCE: 55
atgttgtgga tttggaatgc cctgatcgtt ttcgttaccg gaaaggtcat ttttcctgaa    60
tatgctca                                                             68

<210> SEQ ID NO 56
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Primer (crtZ-test)

<400> SEQUENCE: 56
ccgtgtggtt ctgaaagccg a                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (crtE-test)

<400> SEQUENCE: 57
cgttgccgta aatgtatccg t                                              21

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (phL-test)

<400> SEQUENCE: 58
ggatgtaaac cataacactc tgcgaac                                        27

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer (phR-test)

<400> SEQUENCE: 59
gattggtggt tgaattgtcc gtaac                                          25

<210> SEQ ID NO 60
<211> LENGTH: 3471
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence of the chemically synthesized DNA
      fragment retaining artificial KDyI operon with optimized codons

<400> SEQUENCE: 60
gcatgcagga ggtatgaatg tcagagttgc gtgccttcag tgccccaggg aaagcgttac     60
tcgctggtgg atatttagtt ttagatacaa aatatgaagc atttgtagtc ggattatcgg    120
cacgtatgca cgctgtagcc catccttacg gttcattgca agggtctgat aagtttgaag    180
tgcgtgtgaa aagtaaacaa tttaaagatg gggagtggct gtaccatata agtcctaaaa    240
gtggcttcat tcctgtttcg ataggcggat ctaagaaccc tttcattgaa aaagttatcg    300
```

```
ctaacgtatt tagctacttt aaacctaaca tggacgacta ctgcaatcgt aacttgttcg    360
ttattgatat tttctctgat gatgcctacc attctcagga ggatagcgtt accgaacatc    420
gtggcaaccg ccgtttgagt tttcattcgc accgtattga agaagttccc aaaacagggc    480
tgggctcctc ggcaggttta gtcacagttt taactacagc tttggcctcc ttttttgtat    540
cggacctgga aaataatgta gacaaatatc gtgaagttat tcataattta gcacaagttg    600
ctcattgtca agctcagggt aaaattggaa gcgggtttga tgtagcggcg gcagcatatg    660
gatctatccg ttatcgccgt tcccacccg cattaatctc taatttgcca gatattggaa     720
gtgctactta cggcagtaaa ctggcgcatt tggttgatga agaagactgg aatattacga    780
ttaaaagtaa ccatttacct tcgggattaa ctttatggat gggcgatatt aagaatggtt    840
cagaaacagt aaaactggtc cagaaggtaa aaaattggta tgattcgcat atgccagaaa    900
gcctcaaaat atatacagaa ctcgatcatg caaattctcg ttttatggat ggactctcta    960
aactcgatcg cttacacgag actcatgacg attacagcga tcagatattt gagtctcttg   1020
agcgtaatga ctgtacctgt caaaagtatc ctgaaatcac agaagttcgt gatgcagttg   1080
ccacaattcg tcgttccttt cgtaaaataa ctaaagaatc tggtgccgat atcgaacctc   1140
ccgtacaaac tagcttattg gatgattgcc agaccttaaa aggagttctt acttgcttaa   1200
tacctggtgc tggtggttat gacgccattg cagtgattac taagcaagat gttgatcttc   1260
gtgctcaaac cgctaatgac aaacgttttt ctaaggttca atggctggat gtaactcagg   1320
ctgactgggg tgttcgtaaa gaaaaagatc cggaaactta tcttgataaa taactgcaga   1380
ggaggtatga atgaccgttt acacagcatc cgttaccgca cccgtcaaca tcgcaaccct   1440
taagtattgg gggaaacgtg acacgaagtt gaatctgccc accaattcgt ccatatcagt   1500
gactttatcg caagatgacc tccgtacgtt gacctctgcg gctactgcac ctgagtttga   1560
acgcgacact ttgtggttaa atggagaacc acacagcatc gacaatgaac gtactcaaaa   1620
ttgtctgcgc gacctccgcc aattacgtaa ggaaatggaa tcgaaggacg cctcattgcc   1680
cacattatct caatggaaac tccacattgt ctccgaaaat aactttccta cagcagctgg   1740
tttagcttcc tccgctgctg gctttgctgc attggtctct gcaattgcta agttatacca   1800
attaccacag tcaacttcag aaatatctcg tatagcacgt aaggggtctg gttcagcttg   1860
tcgttcgttg tttggcggat acgtggcctg ggaaatggga aaagctgaag atggtcatga   1920
ttccatggca gtacaaatcg cagacagctc tgactggcct cagatgaaag catgtgtcct   1980
tgttgtcagc gatattaaaa aggatgtgag ttccactcag ggtatgcaat tgaccgtggc   2040
aacctccgaa ctctttaaag aacgtattga acatgtcgta ccaaagcgtt ttgaagtcat   2100
gcgtaaagcc attgttgaaa agatttcgc caccttgca aaggaaacaa tgatggattc      2160
caactctttc catgccacat gtttggactc tttccctcca atattctaca tgaatgacac   2220
ttccaagcgt atcatcagtt ggtgccacac cattaatcag tttacggag aaacaatcgt    2280 tgcatacacg tttgatgcag gtccaaatgc tgtgttgtac tacttagctg aaaatgagtc   2340
gaaactcttt gcatttatct ataaattgtt tggctctgtt cctggatggg acaagaaatt   2400
tactactgag cagcttgagg cttttcaacca tcaatttgaa tcatctaact ttactgcacg   2460
tgaattggat cttgagttgc aaaaggatgt tgcccgtgtg attttaactc aagtcggttc   2520
aggcccacaa gaaacaaacg aatctttgat tgacgcaaag actggtctcc caaaggaata   2580
aggatccagg aggtatgaat gactgccgac aacaatagta tgccccatgg tgcagtatct   2640
agttacgcca aattagtgca aaaccaaaca cctgaagaca ttttggaaga gtttcctgaa   2700
```

```
attattccat tacaacaacg tcctaatacc cgctctagtg agacgtcaaa tgacgaaagc   2760
ggagaaacat gttttctgg tcatgatgag gagcaaatta agttaatgaa tgaaaattgt   2820
attgttttgg attgggacga taatgctatt ggtgccggca ccaagaaagt ttgtcattta   2880
atggaaaata ttgaaaaggg tttacttcat cgtgcattct ccgtctttat tttcaatgaa   2940
caaggtgaat tacttttaca acaacgtgcc actgaaaaaa taactttccc tgatctttgg   3000
actaacacat gctgctctca tccactttgt attgatgacg aattaggttt gaagggtaag   3060
ctcgacgata agattaaggg cgctattact gcggcggtgc gtaaactcga tcatgaatta   3120
ggtattccag aagatgaaac taagacacgt ggtaagtttc acttttttaaa ccgtatccat   3180 tacatggcac caagcaatga accatggggt gaacatgaaa ttgattacat cctctttat   3240 aagatcaacg ctaaagaaaa cttgactgtc aacccaaacg tcaatgaagt tcgtgacttc   3300
aaatgggttt caccaaatga tttgaaaact atgtttgctg acccaagtta caagtttacg   3360
ccttggttta agattatttg cgagaattac ttattcaact ggtgggagca attagatgac   3420
ctttctgaag tggaaaatga ccgtcaaatt catcgtatgc tctaaggtac c            3471
```

<210> SEQ ID NO 61
<211> LENGTH: 547
<212> TYPE: PRT
<213> ORGANISM: Arabidopsis thaliana

<400> SEQUENCE: 61

```
Met Arg Arg Ser Ala Asn Tyr Gln Pro Ser Arg Trp Asp His His His
1               5                   10                  15

Leu Leu Ser Val Glu Asn Lys Phe Ala Lys Asp Lys Arg Val Arg Glu
                20                  25                  30

Arg Asp Leu Leu Lys Glu Lys Val Arg Lys Met Leu Asn Asp Glu Gln
            35                  40                  45

Lys Thr Tyr Leu Asp Gln Leu Glu Phe Ile Asp Asp Leu Gln Lys Leu
        50                  55                  60

Gly Val Ser Tyr His Phe Glu Ala Glu Ile Asp Asn Ile Leu Thr Ser
65                  70                  75                  80

Ser Tyr Lys Lys Asp Arg Thr Asn Ile Gln Glu Ser Asp Leu His Ala
                85                  90                  95

Thr Ala Leu Glu Phe Arg Leu Phe Arg Gln His Gly Phe Asn Val Ser
                100                 105                 110

Glu Asp Val Phe Asp Val Phe Met Glu Asn Cys Gly Lys Phe Asp Arg
            115                 120                 125

Asp Asp Ile Tyr Gly Leu Ile Ser Leu Tyr Glu Ala Ser Tyr Leu Ser
        130                 135                 140

Thr Lys Leu Asp Lys Asn Leu Gln Ile Phe Ile Arg Pro Phe Ala Thr
145                 150                 155                 160

Gln Gln Leu Arg Asp Phe Val Asp Thr His Ser Asn Glu Asp Phe Gly
                165                 170                 175

Ser Cys Asp Met Val Glu Ile Val Gln Ala Leu Asp Met Pro Tyr
                180                 185                 190

Tyr Trp Gln Met Arg Arg Leu Ser Thr Arg Trp Tyr Ile Asp Val Tyr
            195                 200                 205

Gly Lys Arg Gln Asn Tyr Lys Asn Leu Val Val Val Glu Phe Ala Lys
        210                 215                 220

Ile Asp Phe Asn Ile Val Gln Ala Ile His Gln Glu Glu Leu Lys Asn
225                 230                 235                 240
```

```
Val Ser Ser Trp Trp Met Glu Thr Gly Leu Gly Lys Gln Leu Tyr Phe
            245                 250                 255

Ala Arg Asp Arg Ile Val Glu Asn Tyr Phe Trp Thr Ile Gly Gln Ile
            260                 265                 270

Gln Glu Pro Gln Tyr Gly Tyr Val Arg Gln Thr Met Thr Lys Ile Asn
            275                 280                 285

Ala Leu Leu Thr Thr Ile Asp Asp Ile Tyr Asp Ile Tyr Gly Thr Leu
            290                 295                 300

Glu Glu Leu Gln Leu Phe Thr Val Ala Phe Glu Asn Trp Asp Ile Asn
305                 310                 315                 320

Arg Leu Asp Glu Leu Pro Glu Tyr Met Arg Leu Cys Phe Leu Val Ile
            325                 330                 335

Tyr Asn Glu Val Asn Ser Ile Ala Cys Glu Ile Leu Arg Thr Lys Asn
            340                 345                 350

Ile Asn Val Ile Pro Phe Leu Lys Lys Ser Trp Thr Asp Val Ser Lys
            355                 360                 365

Ala Tyr Leu Val Glu Ala Lys Trp Tyr Lys Ser Gly His Lys Pro Asn
            370                 375                 380

Leu Glu Glu Tyr Met Gln Asn Ala Arg Ile Ser Ile Ser Ser Pro Thr
385                 390                 395                 400

Ile Phe Val His Phe Tyr Cys Val Phe Ser Asp Gln Leu Ser Ile Gln
            405                 410                 415

Val Leu Glu Thr Leu Ser Gln His Gln Gln Asn Val Val Arg Cys Ser
            420                 425                 430

Ser Ser Val Phe Arg Leu Ala Asn Asp Leu Val Thr Ser Pro Asp Glu
            435                 440                 445

Leu Ala Arg Gly Asp Val Cys Lys Ser Ile Gln Cys Tyr Met Ser Glu
450                 455                 460

Thr Gly Ala Ser Glu Asp Lys Ala Arg Ser His Val Arg Gln Met Ile
465                 470                 475                 480

Asn Asp Leu Trp Asp Glu Met Asn Tyr Glu Lys Met Ala His Ser Ser
            485                 490                 495

Ser Ile Leu His His Asp Phe Met Glu Thr Val Ile Asn Leu Ala Arg
            500                 505                 510

Met Ser Gln Cys Met Tyr Gln Tyr Gly Asp Gly His Gly Ser Pro Glu
            515                 520                 525

Lys Ala Lys Ile Val Asp Arg Val Met Ser Leu Leu Phe Asn Pro Ile
            530                 535                 540

Pro Leu Asp
545
```

<210> SEQ ID NO 62
<211> LENGTH: 1644
<212> TYPE: DNA
<213> ORGANISM: Arabidopsis thaliana

<400> SEQUENCE: 62

| | | | | | |
|---|---|---|---|---|---|
| atgcgtcgtt | ctgcgaacta | tcagccttct | cgttgggacc | atcaccatct | cctctcggtc | 60 |
| gaaataaat | ttgcgaaaga | taaagggta | cgagagagag | atttgttgaa | ggaaaaagtg | 120 |
| agaaagatgc | tcaatgatga | gcaaaagact | tatcttgacc | aattggagtt | cattgacgat | 180 |
| ctacaaaaac | tcggggtttc | ttatcatttt | gaagcggaaa | tcgacaacat | tttaacatct | 240 |
| tcttataaaa | aagatagaac | aaacatccag | gagagtgacc | tacatgccac | cgcactcgag | 300 |

```
ttccgactttt tcaggcaaca tggtttcaat gtttcagaag atgtattcga tgttttcatg      360
gaaaattgtg ggaagtttga ccgtgatgat atatatggtt taatatctct ttacgaagca      420
tcatatcttt cgacaaaatt ggataaaaac ctgcaaatat tcatcagacc ttttgctaca      480
caacaactca gagactttgt tgatactcat agtaatgaag attttgggtc gtgtgacatg      540
gtggaaattg tggtccaagc gttggatatg ccctactatt ggcaaatgag aaggctatcc      600
accagatggt acatagatgt gtatggaaaa agacaaaatt ataagaacct tgtcgtcgtt      660
gaatttgcca agattgattt caacatcgta caagctattc atcaagagga actcaaaaac      720
gtttccagct ggtggatgga gacaggttta ggtaagcaac tctactttgc aagagacaga      780
atagtggaga attatttctg gacgattgga caaatccaag agcctcaata cggatacgtt      840
cgacaaacaa tgacgaaaat aaatgcactc cttactacaa ttgatgatat ctacgatatc      900
tatggcactc ttgaagaact tcagcttttc actgtcgcgt ttgaaaactg ggatataaat      960
cgtcttgatg aactccccga gtacatgagg ttgtgttttc ttgttatata caatgaagtc     1020
aatagcattg catgtgagat tctcagaact aaaaatatca acgtgatccc attcctcaaa     1080
aaatcttgga cagatgtatc caaagcgtat ttagtagaag caaagtggta caaaagtggt     1140
cacaaaccaa atttggaaga gtacatgcaa aatgctcgga tttcaatctc gtccccaacg     1200
atatttgttc acttctactg cgtattctcc gaccagctct ctattcaggt cttggagact     1260
ttgtcccaac accaacaaaa cgtcgtccga tgctcctcct cagtgttccg tctagccaac     1320
gaccttgtaa cctcaccgga tgaattggcg agaggagacg tctgcaaatc catccaatgt     1380
tacatgagtg aaactggagc atcagaggat aaggcgcgtt cgcatgttcg acagatgatc     1440
aatgacttgt gggatgaaat gaattatgag aaaatggcac atagctcttc gatactccat     1500
catgatttta tggaaacagt gataaatttg gcacgcatgt ctcaatgcat gtatcaatat     1560
ggcgatggcc atggctctcc cgaaaaagcc aaaatcgttg atcgtgtcat gtccttactc     1620
ttcaatccga ttcctttaga ttga                                             1644
```

<210> SEQ ID NO 63
<211> LENGTH: 1644
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Arabidopsis thaliana

<400> SEQUENCE: 63

```
atgcgtcgta gtgcgaatta ccagccgagt cgttgggacc atcatcacct gctgagtgtg       60
gagaataagt ttgcgaagga caagcgtgtc cgcgaacgcg acctgctgaa agaaaaggtt      120
cgcaaaatgc tgaatgacga acagaagacc tacctggatc agctggaatt tattgatgac      180
ctgcagaaac tgggcgtcag ctaccatttt gaagccgaaa tgataatat cctgaccagc       240 agctacaaaa aggaccgcac gaatatccag gaaagcgatc tgcatgccac ggcgctggaa      300
tttcgcctgt ttcgccagca cggctttaat gttagcgaag atgtgtttga cgtctttatg      360
gaaaattgtg gcaagtttga ccgcgatgac atctacggcc tgattagcct gtacgaagcc      420
agctacctga gcaccaaact ggataagaat ctgcagattt ttattcgtcc ctttgccacc      480
cagcagctgc gtgattttgt tgacacgcat agcaatgaag attttggcag ctgcgacatg      540
gtggaaattg ttgtgcaggc cctggacatg ccctactact ggcagatgcg ccgcctgagc      600
```

-continued

```
acccgttggt acatcgatgt gtacggcaaa cgccagaatt acaagaatct ggtcgttgtg      660
gaatttgcca aaatcgactt taatattgtg caggcgatcc accaggaaga actgaaaaat      720
gtcagcagtt ggtggatgga aaccggcctg gcaagcagc  tgtactttgc gcgcgatcgc      780
attgtcgaaa attactttg  gacgattggc cagatccagg aaccgcagta cggctacgtt      840
cgccagacca tgacgaagat caatgccctg ctgaccacga ttgatgacat ctacgatatt      900
tacggcaccc tggaagaact gcagctgttt acggttgcgt ttgaaaattg ggatattaat      960
cgcctggacg aactgccgga atacatgcgc ctgtgttttc tggttatcta caatgaagtg     1020
aatagcattg cctgcgaaat cctgcgcacc aagaacatca acgtgatccc ctttctgaaa     1080
aagagctgga cggacgtgag caaagcctac ctggtcgaag cgaaatggta caagagcggc     1140
cataagccga atctggaaga atacatgcag aatgcgcgca ttagcatcag cagccccacc     1200
atctttgtcc attttactg  tgttttagc  gatcagctga gcatccaggt gctggaaacg     1260
ctgagccagc accagcagaa tgtcgttcgc tgcagcagca gcgttttttcg cctggccaat    1320 gatctggtga ccagccccga tgaactggcc cgcggcgatg tgtgtaaaag cattcagtgc     1380
tacatgagcg aaacgggtgc cagcgaagat aaggcccgca gccatgtccg ccagatgatc     1440
aatgatctgt gggacgaaat gaattacgaa aaaatggccc acagcagcag cattctgcat     1500
cacgacttta tggaaaccgt tatcaatctg gcgcgcatga gccagtgtat gtaccagtac     1560
ggtgatggtc atggcagccc cgaaaaagcc aaaatcgtgg accgtgtgat gagcctgctg     1620
tttaacccta tcccgctgga ctaa                                            1644
```

<210> SEQ ID NO 64
<211> LENGTH: 607
<212> TYPE: PRT
<213> ORGANISM: Perilla frutescens

<400> SEQUENCE: 64

```
Met Tyr Ser Leu Arg Ile Tyr Val Ala Ile Met Lys Lys Pro Ser Ala
1               5                   10                  15

Lys His Val Asp Asn Val Asp Lys Lys Ala Ser Lys Pro Ser Trp Arg
            20                  25                  30

Val Ser Leu Ser Ser Ser Ala Gly Leu Arg Ala Ser Ser Ser Leu Gln
        35                  40                  45

Leu Asp Val Lys Lys Pro Ala Asp Asp Glu Ile Leu Thr Ala Arg Arg
    50                  55                  60

Ser Gly Asn Tyr Gln Pro Ser Leu Trp Asp Phe Asn Tyr Leu Gln Ser
65                  70                  75                  80

Leu Asn Thr Thr Gln Tyr Lys Glu Val Arg His Leu Lys Arg Glu Ala
                85                  90                  95

Glu Leu Ile Glu Gln Val Lys Met Leu Leu Glu Glu Met Glu Ala
            100                 105                 110

Val Gln Gln Leu Glu Leu Val Asp Asp Leu Lys Asn Leu Gly Leu Ser
        115                 120                 125

Tyr Phe Phe Glu Asp Gln Ile Lys Gln Ile Leu Thr Phe Ile Tyr Asn
    130                 135                 140

Glu His Lys Cys Phe His Ser Asn Ser Ile Ile Glu Ala Glu Ile
145                 150                 155                 160

Arg Asp Leu Tyr Phe Thr Ala Leu Gly Phe Arg Leu Leu Arg Gln His
                165                 170                 175

Gly Phe Gln Val Ser Gln Glu Val Phe Asp Cys Phe Lys Asn Glu Glu
```

```
                180              185              190
Gly Ser Asp Phe Lys Ala Arg Leu Gly Asp Asp Thr Lys Gly Leu Leu
            195              200              205
Gln Leu Tyr Glu Ala Ser Phe Leu Leu Arg Glu Gly Glu Asp Thr Leu
        210              215              220
Glu Leu Ala Arg Gln Tyr Ala Thr Lys Phe Leu Gln Lys Lys Val Asp
225              230              235              240
His Glu Leu Ile Asp Asp Asn Asn Leu Leu Ser Trp Ile Leu His Ser
            245              250              255
Leu Glu Ile Pro Leu His Trp Arg Ile Gln Arg Leu Glu Ala Arg Trp
            260              265              270
Phe Leu Asp Arg Tyr Ala Thr Arg Arg Asp Met Asn Gln Ile Ile Leu
            275              280              285
Glu Leu Ala Lys Leu Asp Phe Asn Ile Ile Gln Ala Thr Gln Gln Glu
            290              295              300
Glu Leu Lys Asp Leu Ser Arg Trp Trp Lys Ser Thr Cys Leu Ala Glu
305              310              315              320
Lys Leu Pro Phe Val Arg Asp Arg Leu Val Glu Ser Tyr Phe Trp Ala
            325              330              335
Ile Ala Leu Phe Glu Pro His Gln Tyr Gly Tyr His Arg Lys Val Ala
            340              345              350
Ala Lys Ile Ile Thr Leu Ile Thr Ser Leu Asp Asp Val Tyr Asp Ile
            355              360              365
Tyr Gly Thr Leu Asp Glu Leu Gln Leu Phe Thr Asp Ala Ile Gln Arg
            370              375              380
Trp Asp Thr Glu Ser Ile Ser Arg Leu Pro Tyr Tyr Met Gln Leu Phe
385              390              395              400
Tyr Met Val Leu Tyr Asn Phe Val Ser Glu Leu Ala Tyr Asp Gly Leu
            405              410              415
Lys Glu Lys Gly Phe Ile Thr Ile Pro Tyr Leu Gln Arg Ser Trp Ala
            420              425              430
Asp Leu Val Glu Ala Tyr Leu Lys Glu Ala Lys Trp Phe Tyr Asn Gly
            435              440              445
Tyr Val Pro Ser Met Glu Glu Tyr Leu Asn Asn Ala Tyr Ile Ser Ile
            450              455              460
Gly Ala Thr Pro Val Ile Ser Gln Val Phe Phe Thr Leu Ala Thr Ser
465              470              475              480
Ile Asp Lys Pro Val Ile Asp Ser Leu Tyr Glu Tyr His Arg Ile Leu
            485              490              495
Arg Leu Ser Gly Met Leu Val Arg Leu Pro Asp Asp Leu Gly Thr Ser
            500              505              510
Pro Phe Glu Met Lys Arg Gly Asp Val Pro Lys Ala Ile Gln Leu Tyr
            515              520              525
Met Lys Glu Arg Asn Ala Thr Glu Ile Glu Ala Gln Glu His Val Arg
530              535              540
Phe Leu Ile Arg Glu Ala Trp Lys Glu Met Asn Thr Val Thr Thr Ala
545              550              555              560
Ala Asp Cys Pro Phe Thr Asp Asp Leu Val Ala Ala Thr Arg Asn Leu
            565              570              575
Gly Arg Ala Ala Gln Phe Met Tyr Leu Asp Gly Asp Gly Asn His Ser
            580              585              590
Gln Leu His Gln Arg Ile Ala Cys Leu Leu Phe Glu Pro Tyr Ala
            595              600              605
```

<210> SEQ ID NO 65
<211> LENGTH: 1824
<212> TYPE: DNA
<213> ORGANISM: Perilla frutescens

<400> SEQUENCE: 65

| | | | | | |
|---|---|---|---|---|---|
| atgtatagct | tgagaatata | tgtagcgatc | atgaaaaagc | catcagctaa | acatgttgac | 60 |
| aacgtcgaca | agaaagcttc | aaagccgtcg | tggcgtgtct | cactctcttc | gagtgcggt | 120 |
| ctccgagctt | cttcctcctt | acaactcgat | gtaaaaaagc | ccgctgatga | tgaaattctg | 180 |
| acggcccgac | gctctggcaa | ctaccagcct | tcccttggg | atttcaacta | ccttcaatct | 240 |
| ctcaacacta | ctcagtataa | ggaagtgagg | cacttgaaaa | gggaagcaga | gctgattgag | 300 |
| caagtgaaga | tgctgctgga | agaagaaatg | gaggcagttc | aacaattgga | gttggttgat | 360 |
| gacttgaaaa | atctgggatt | gtcttatttt | tttgaagacc | aaattaagca | gatcttaacg | 420 |
| tttatatata | atgagcataa | atgtttccac | agtaatagta | ttattgaagc | ggaggaaatt | 480 |
| agggattgt | atttcacagc | tcttggattc | agactcctca | gacaacatgg | tttccaagtc | 540 |
| tctcaagagg | tatttgattg | tttcaagaac | gaggagggta | gtgatttcaa | agcaaggctt | 600 |
| ggtgacgata | caaaaggatt | gctgcaactc | tacgaagcct | ctttcctatt | gagagaaggt | 660 |
| gaagatacac | tggagctagc | aaggcaatat | gccaccaaat | ttctccagaa | aaaagttgat | 720 |
| catgaattaa | ttgacgacaa | taatctatta | tcatggattc | tccattcttt | ggagatcccg | 780 |
| cttcactgga | ggattcagag | gctggaggca | agatggttct | tagatcgtta | cgcgacgaga | 840 |
| cgagacatga | atcaaatcat | tcttgagctc | gccaaactcg | acttcaatat | tattcaagca | 900 |
| acacaacagg | aagaactcaa | agatctctca | aggtggtgga | agagtacatg | tctggctgag | 960 |
| aaacttccat | tcgtgaggga | taggcttgtg | aaaagctact | tttgggccat | tgctctcttt | 1020 |
| gaacctcatc | aatatggata | tcacagaaaa | gttgctgcca | agattattac | actaataaca | 1080 |
| tctttagatg | atgtttacga | tatctatggt | acattagacg | aactcaaact | atttacagac | 1140 |
| gcgattcaaa | gatgggatac | tgaatcaata | agccgccttc | catattatat | gcaattattt | 1200 |
| tatatggtac | tctacaactt | tgtttcggag | ctggcttacg | atggtctcaa | ggagaagggt | 1260 |
| ttcatcacca | tcccatattt | acagagatcg | tgggcagatt | tggttgaagc | atatttaaaa | 1320 |
| gaggcaaagt | ggttctacaa | tggatatgta | ccaagcatgg | aagaatatct | caacaacgcc | 1380 |
| tacatttcaa | taggggctac | tcccgtaatt | tctcaagttt | tcttcacatt | agcaacctcc | 1440 |
| attgacaaac | cagtgatcga | cagcttgtac | gaataccacc | gcatacttcg | cctctctgga | 1500 |
| atgcttgtaa | ggcttcctga | tgatttagga | acatcaccgt | ttgagatgaa | gagaggcgac | 1560 |
| gtgccgaaag | caatccagtt | gtacatgaag | gaaagaaatg | ctaccgagat | agaggctcaa | 1620 |
| gaacacgtga | ggtttctgat | tcgtgaggcg | tggaaggaga | tgaacacggt | aacgacggcg | 1680 |
| gccgattgtc | cgtttacgga | tgatttggtt | gcagcgacac | gtaatcttgg | tagggcggca | 1740 |
| cagtttatgt | atctcgacgg | agatggtaac | cactctcaat | tacatcagcg | gattgcgtgc | 1800 |
| ctactgttcg | agccatatgc | atga | | | | 1824 |

<210> SEQ ID NO 66
<211> LENGTH: 1824
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Pereilla frutescens var. crispa

<400> SEQUENCE: 66

```
atgtatagcc tgcgtattta tgtggcgatt atgaaaaagc ccagtgcgaa gcatgttgac      60
aatgtggaca agaaagcgag taagcctagc tggcgcgtta gcctgagcag cagcgcgggc     120
ctgcgtgcca gcagcagcct gcagctggat gtgaaaaagc cggcggatga tgaaatcctg     180
acggcccgcc gcagcggtaa ttaccagccc agcctgtggg actttaatta cctgcagagc     240
ctgaatacca cgcagtacaa agaagtgcgc catctgaagc gcgaagcgga actgattgaa     300
caggtcaaaa tgctgctgga agaagaaatg gaagccgtcc agcagctgga actggttgat     360
gacctgaaga atctgggcct gagctacttt ttcgaagatc agattaaaca gatcctgacg     420
tttatctaca cgaacataa gtgttttcac agcaatagca ttatcgaagc ggaagaaatt     480
cgcgacctgt actttacggc cctgggtttt cgtctgctgc gtcagcatgg ctttcaggtt     540
agccaggaag tgtttgattg ctttaagaat gaagaaggca gcgactttaa agcccgtctg     600
ggtgatgaca ccaagggcct gctgcagctg tacgaagcca gctttctgct gcgcgaaggc     660
gaagatacgc tggaactggc ccgccagtac gcgaccaaat tcctgcagaa aaaggtggac     720
cacgaactga tcgatgacaa taatctgctg agctggattc tgcatagcct ggaaatcccg     780
ctgcactggc gcattcagcg cctggaagcg cgctggtttc tggatcgcta cgccacgcgt     840
cgcgacatga atcagattat cctggaactg gcgaaactgg attttaatat tatccaggcc     900
acgcagcagg aagaactgaa agacctgagc cgttggtgga gagcacctg tctggcggaa     960
aaactgccgt tgtgcgcga tcgcctggtc gaaagctact tttgggccat gcgctgttt    1020
gaaccccatc agtacggcta ccaccgcaaa gtcgccgcga agattatcac cctgatcacg    1080
agcctggatg acgtttacga tatttacggc accctggacg aactgcagct gtttacggat    1140
gcgatccagc gctgggacac cgaaagcatt agccgcctgc cctactacat gcagctgttt    1200
tacatggttc tgtacaattt tgtgagcgaa ctggcctacg atggcctgaa agaaaagggc    1260
tttattacca ttccctacct gcagcgtagc tgggcggacc tggtggaagc gtacctgaaa    1320
gaagccaagt ggttttacaa tggctacgtc cccagcatgg aagaatacct gaataatgcg    1380
tacattagca ttggtccac cccggtcatc agccaggttt ctttaccct ggccacgagc    1440
attgataaac ccgtcatcga cagcctgtac gaataccatc gcattctgcg tctgagcggt    1500
atgctggttc gcctgcccga tgacctgggt acgagcccct ttgaaatgaa acgcggcgat    1560
gttccgaagg cgatccagct gtacatgaaa gaacgcaatg cgacggaaat cgaagcccag    1620
gaacacgttc gctttctgat cgcgaagcc tggaaggaaa tgaataccgt taccacggcc    1680
gcggattgcc cctttaccga tgacctggtt gcggccaccc gtaatctggg tcgtgccgcg    1740
cagtttatgt acctggatgg cgacggtaac cacagtcagc tgcaccagcg tatcgcctgc    1800
ctgctgtttg aaccctatgc ctaa                                           1824
```

<210> SEQ ID NO 67
<211> LENGTH: 602
<212> TYPE: PRT
<213> ORGANISM: Vitis vinifera

<400> SEQUENCE: 67

```
Met Glu Leu Thr Leu Thr Ser Leu Ser Pro Leu Ala Tyr Gly Ala Leu
1               5                   10                  15
```

```
Asn Cys Arg Lys Asn Phe Ala Met Ala Ser Pro Arg Met Arg Ile Lys
             20                  25                  30

Gln Gly Arg Ser Glu Leu Pro Asn Leu Thr Ile Thr Ser Lys Ile Asp
         35                  40                  45

Glu Leu Gln Val Thr Glu Arg Ser Ala Asn Tyr His Pro Ser Ile
 50                  55                  60

Trp Asp Pro Lys Phe Ile Glu Ser Leu Ser Thr Pro Tyr Thr Asn Glu
 65                  70                  75                  80

Gly Tyr Ser Asn Gln Leu Glu Asp Leu Lys Glu Ala Lys Arg Val
             85                  90                  95

Ile Lys Asp Ala Arg Asp Thr Ser Ser Arg Leu Glu Phe Ile Asp Ser
             100                 105                 110

Met Gln Arg Leu Gly Val Ala Tyr His Leu Glu Glu Ile Lys Glu
         115                 120                 125

Ala Ile Asp Leu Val His Leu Asp Asp Thr Thr Asp Asp Leu Ser
 130                 135                 140

Thr Thr Ala Leu Arg Phe Arg Leu Leu Arg Gln His Gly Tyr Pro Val
145              150                 155                 160

Ser Ser Glu Val Phe Asp Gln Phe Arg Ser Lys Asp Gly Arg Phe Met
             165                 170                 175

Asp Gly Ile Ser Gln Asp Ile Ala Gly Pro Leu Ser Leu Tyr Glu Ala
             180                 185                 190

Ser His Leu Gly Val Glu Gly Glu Asp Asp Leu Glu Glu Ala Arg Arg
         195                 200                 205

Phe Ser Thr Ile His Leu Lys Ser Leu Val Gly Asn Leu Glu Ser Asp
         210                 215                 220

Leu Ala Asp Gln Val Gln Gln Ser Leu Glu Val Pro Leu His Trp Arg
225              230                 235                 240

Met Pro Arg Leu Glu Ala Arg Asn Phe Ile Asp Ile Tyr Gln Arg Arg
             245                 250                 255

Asn Thr Lys Asn Ser Ala Leu Leu Glu Leu Ala Lys Leu Asp Tyr Asn
             260                 265                 270

Leu Val Gln Ser Ser Tyr Gln Thr Glu Leu Lys Glu Leu Thr Arg Trp
         275                 280                 285

Trp Thr Asp Leu Gly Phe Lys Glu Lys Leu Ser Phe Ser Arg Asp Arg
 290                 295                 300

Leu Met Glu Asn Tyr Leu Trp Ser Met Gly Ile Ala Pro Glu Pro His
305              310                 315                 320

Phe Ser Lys Ser Arg Ile Gly Leu Thr Lys Phe Ile Cys Ile Leu Thr
             325                 330                 335

Ala Ile Asp Asp Met Tyr Asp Ile Tyr Gly Ser Pro Asp Glu Leu Arg
             340                 345                 350

Arg Phe Thr Asp Ala Val Asn Arg Trp Asp Thr Glu Ala Leu Val Asp
             355                 360                 365

Leu Pro Asp Tyr Met Lys Ile Cys Tyr Leu Ala Met Phe Asn Phe Ala
         370                 375                 380

Asn Glu Met Ala Tyr Asp Ala Leu Arg Asp His Asp Leu Tyr Ile Leu
385              390                 395                 400

Pro Tyr Leu Lys Ser Gln Trp Leu Asn Leu Cys Thr Ser Tyr Ser Met
             405                 410                 415

Glu Ala Gln Trp Phe Tyr Asn Gly Tyr Lys Pro Ser Ile Asp Glu Tyr
             420                 425                 430
```

| | | | | | | | | | | | | | |
|---|---|---|---|---|---|---|---|---|---|---|---|---|---|
|Leu|Ser|Asn|Ala|Trp|Thr|Ser|Val|Gly|Gly|Pro|Ala|Ala|Met|Val|His|
| |435| | | | |440| | | | |445| | | | |

Ala Tyr Phe Leu Met Gly Cys Ala Thr Lys Gly Asn Leu Asn Asn Cys
    450                 455                 460

Leu Asp Asn Ala Ser Asn Leu Leu Tyr Trp Ser Ser Leu Ile Thr Arg
465                 470                 475                 480

Leu Ser Asp Asp Leu Gly Thr Ser Leu Ala Glu Ile Ala Arg Gly Asp
                485                 490                 495

Val Ala Lys Ser Ile Gln Cys Tyr Met Ile Glu Lys Cys Ile Ser Glu
                500                 505                 510

Glu Gln Ala Arg Asp Gln Val Glu Lys Leu Ile Arg Tyr Ser Trp Lys
            515                 520                 525

Lys Leu Asn Glu Ala Ser Thr Asp Ser Ser Leu Pro Lys Ser Leu Ile
530                 535                 540

Asn Ser Ser Leu Asn Met Ala Arg Ser Ala Gln Cys Ile Phe Gln Phe
545                 550                 555                 560

Gly Asp Gly Ile Gly Thr Ser Val Gly Val Thr Lys Asp Arg Leu Thr
                565                 570                 575

Ser Phe Ile Ile Lys Pro Ile Leu Ile Glu Pro Ser Ile Lys Pro Tyr
                580                 585                 590

Leu Asp Gly Met Lys Met Ser Asn Arg Arg
            595                 600

<210> SEQ ID NO 68
<211> LENGTH: 1809
<212> TYPE: DNA
<213> ORGANISM: Vitis vinifera

<400> SEQUENCE: 68

```
atggaactaa ccctcacatc cctctcaccc ttggcctatg gtgccctcaa ttgtcgtaaa      60
aattttgcca tggcatcccc aagaatgaga atcaagcaag ggagatcaga attgcccaac     120
ctcacaatca cttcgaagat tgatgagtta caagtgaccg aaaggcgatc ggctaattac     180
catcctagca tttgggaccc caaatttatt gagtccttaa gcactcccta tacgaatgag     240
ggctattcca accaattaga ggacttgaag gaagaagcta aagggtaat taaggacgct      300 agagacactt cctcccgatt agagttcatt gattcgatgc aacggttggg agtggcttac     360
catttggagg aggagatcaa agaggctatt gatcttgttc atttggatga taccactacc     420
gatgatcttt ccacaactgc actccgattt agacttctac gacaacacgg ctatccagtt     480
agctcagagg tgtttgatca attcagaagt aaagatggga gattcatgga tggcatcagc     540
caggatattg ctgggccttt gagtttgtat gaagcttccc atcttggagt cgagggagaa     600
gatgacttgg aagaagccag gaggttcagt actatacatt tgaagtcact ggttgggaat     660
ttggagagtg atttagctga ccaagtgcag cagtccctgg aagttccctt acactggaga     720
atgccaaggc tagaagcccg aaacttcatc gatatctacc aaaggcgcaa tacgaagaac     780
tctgctctcc ttgagctagc caagctggac tacaatctag tgcaatcatc atatcagacg     840
gagttgaagg agctaacaag gtggtggacg gacttgggat ttaaggagaa gctaagtttt     900
tctcgggatc gattgatgga gaactatttg tggtcaatgg ggatcgctcc tgagccccac     960
ttctccaaaa gcaggatagg actcaccaaa ttcatatgca tattaacagc catagatgac    1020
atgtatgaca tatatggatc accgatgag cttcgacgtt ttacagatgc tgtgaatcga    1080
tgggatactg aggcactggt ggaccttcca gattacatga agatatgtta cttggccatg    1140
```

```
ttcaactttg ctaatgaaat ggcctacgat gcattaagag atcacgacct atatatttta    1200
ccctatctta aaagtcagtg gctaaatctc tgtacatcct actcaatgga agctcaatgg    1260
ttttacaatg ggtataagcc aagcatcgat gaatacttaa gcaatgcctg gacttccgta    1320
gggggtcctg cagccatggt ccatgcctat tttctaatgg gttgtgccac caagggaaac    1380
ttgaacaatt gtttagacaa tgcctctaat ctactttatt ggtcatctct tattactcga    1440
cttagcgatg atttgggaac ttctttagcc gagattgcga gaggcgacgt ggcaaaatct    1500
atccaatgtt acatgattga aaatgtata tccgaagaac aagctcgaga tcaagtagag    1560
aagcttatac gttactcatg gaaaaagttg aatgaagcaa gtactgatag ctctctccca    1620
aagtccttaa taaattcatc attgaacatg gcgcgatcag ctcaatgtat tttcaattt    1680 ggagatggaa tcggtacatc agttggggtg accaaagatc gattgacatc attcattatc    1740
aagccaatat tgatagaacc aagcattaaa ccctatcttg atggcatgaa gatgagcaac    1800
agaagatga                                                            1809
```

<210> SEQ ID NO 69
<211> LENGTH: 1809
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Vitis vinifera

<400> SEQUENCE: 69

```
atggaactga ccctgacgag tctgagcccg ctggcgtatg tgccctgaa ctgccgtaag     60 aactttgcga tggcgagtcc ccgtatgcgc attaagcagg gccgcagcga actgccgaat    120
ctgacgatta ccagcaaaat cgacgaactg caggtgaccg aacgccgcag cgcgaattac    180
cacccgagca tttgggatcc caaatttatc gaaagcctga gcacgcccta caccaatgaa    240
ggctacagca atcagctgga agatctgaaa gaagaagcca agcgcgtcat taagatgcg    300 cgcgacacga gcagccgcct ggaatttatc gacagcatgc agcgcctggg cgtggcctac    360
catctggaag aagaaattaa ggaagcgatc gatctggtcc acctggatga caccacgacc    420
gatgacctga gcaccacggc cctgcgtttt cgtctgctgc gtcagcatgg ttacccggtc    480
agcagcgaag ttttttgatca gtttcgcagc aaagatggcc gctttatgga cggcattagc    540
caggatattg cgggtcctct gagcctgtac gaagccagcc atctgggcgt tgaaggcgaa    600
gatgacctgg aagaagcccg ccgctttagc accatccacc tgaagagcct ggtgggcaat    660
ctggaaagcg atctggcgga ccaggtgcag cagagcctgg aagtccccct gcactggcgt    720
atgcctcgtc tggaagcccg caattttatt gacatctacc agcgtcgcaa taccaagaat    780
agcgccctgc tggaactggc gaaactggat tacaatctgg ttcagagcag ctaccagacg    840
gaactgaaag aactgacgcg ttggtggacc gacctgggct taaagaaaa gctgagcttt    900 agccgcgatc gcctgatgga aaattacctg tggagcatgg cattgcgcc ggaaccccat    960 tttagcaaga gccgcatcgg cctgaccaaa tttatttgta tcctgacggc cattgatgac    1020
atgtacgaca tctacggcag ccccggatgaa ctgcgccgct ttaccgacgc cgtcaatcgc    1080
tgggatacgg aagcgctggt tgatctgccc gactacatga agatttgtta cctggccatg    1140
tttaactttg cgaatgaaat ggcctacgat gcgctgcgcg atcatgacct gtacatcctg    1200
ccgtacctga agagccagtg gctgaatctg tgcaccagct acagcatgga agcccagtgg    1260
```

```
ttttacaatg gctacaaacc gagcattgat gaatacctga gcaatgcctg gaccagcgtt   1320
ggcggcccgg cggccatggt gcacgcctac tttctgatgg gctgtgcgac gaagggcaat   1380
ctgaataatt gcctggacaa tgcgagcaat ctgctgtact ggagcagcct gatcacgcgt   1440
ctgagcgatg acctgggtac gagcctggcg gaaattgccc gcggcgatgt cgccaagagc   1500
atccagtgtt acatgattga aaatgcatc agcgaagaac aggcgcgcga ccaggttgaa   1560
aagctgattc gctacagctg gaaaaagctg aatgaagcca gcacggatag cagcctgccg   1620
aaaagcctga tcaatagcag cctgaatatg gcccgcagcg cgcagtgcat ttttcagttt   1680
ggtgatggta ttggtacgag cgttggcgtg accaaggatc gcctgacgag ctttattatc   1740
aaacccattc tgattgaacc gagcattaag ccctacctgg atggcatgaa gatgagtaac   1800
cgccgctaa                                                          1809
```

<210> SEQ ID NO 70
<211> LENGTH: 606
<212> TYPE: PRT
<213> ORGANISM: Mentha citrata

<400> SEQUENCE: 70

```
Met Cys Thr Ile Ile Ser Val Asn His His Val Ala Ile Leu Ser
1               5                   10                  15

Lys Pro Lys Val Lys Leu Phe His Thr Lys Asn Lys Arg Ser Ala Ser
            20                  25                  30

Ile Asn Leu Pro Trp Ser Leu Ser Pro Ser Ser Ala Ala Ser Arg
        35                  40                  45

Pro Ile Ser Cys Ser Ile Ser Ser Lys Leu Tyr Thr Ile Ser Ser Ala
    50                  55                  60

Gln Glu Glu Thr Arg Arg Ser Gly Asn Tyr His Pro Ser Val Trp Asp
65                  70                  75                  80

Phe Asp Phe Ile Gln Ser Leu Asp Thr Asp His Tyr Lys Glu Glu Lys
                85                  90                  95

Gln Leu Glu Arg Glu Glu Glu Leu Ile Met Glu Val Lys Lys Leu Leu
            100                 105                 110

Gly Ala Lys Met Glu Ala Thr Lys Gln Leu Glu Leu Ile Asp Asp Leu
        115                 120                 125

Gln Asn Leu Gly Leu Ser Tyr Phe Phe Arg Asp Glu Ile Lys Asn Ile
    130                 135                 140

Leu Asn Ser Ile Tyr Lys Ile Phe Gln Asn Asn Asn Ser Thr Lys Val
145                 150                 155                 160

Gly Asp Leu His Phe Thr Ser Leu Gly Phe Arg Leu Leu Arg Gln His
                165                 170                 175

Gly Phe Asn Val Ser Gln Gly Val Phe Asp Cys Phe Lys Asn Glu His
            180                 185                 190

Gly Ser Asp Phe Glu Lys Thr Leu Ile Gly Glu Asp Thr Lys Gly Val
        195                 200                 205

Leu Gln Leu Tyr Glu Ala Ser Phe Leu Leu Arg Glu Gly Glu Asp Thr
    210                 215                 220

Leu Glu Val Ala Arg Lys Phe Ser Thr Glu Phe Leu Glu Glu Lys Leu
225                 230                 235                 240

Lys Ala Gly Ile Asp Gly Asp Asn Leu Ser Ser Ser Ile Gly His Ser
                245                 250                 255

Leu Glu Ile Pro Leu His Trp Arg Ile Gln Arg Leu Glu Glu Arg Trp
            260                 265                 270
```

Phe Leu Asp Ala Tyr Ser Arg Arg Lys Asp Met Asn Pro Ile Ile Phe
         275                 280                 285

Glu Leu Ala Lys Leu Asp Phe Asn Ile Ile Gln Ala Thr Gln Gln Glu
         290                 295                 300

Glu Leu Lys Asp Leu Ser Arg Trp Trp Asn Asp Ser Ser Leu Pro Gln
305                 310                 315                 320

Lys Leu Pro Phe Val Arg Asp Arg Leu Val Glu Ser Tyr Tyr Trp Ala
                 325                 330                 335

Leu Gly Leu Phe Glu Ala His Lys Phe Gly Tyr Glu Arg Lys Thr Ala
             340                 345                 350

Ala Lys Ile Ile Thr Leu Ile Thr Ala Leu Asp Asp Val Tyr Asp Ile
         355                 360                 365

Tyr Gly Thr Leu Asp Glu Leu Gln Leu Phe Thr His Val Ile Arg Arg
     370                 375                 380

Trp Asp Thr Glu Ser Ala Thr Gln Leu Pro Tyr Tyr Leu Gln Leu Phe
385                 390                 395                 400

Tyr Phe Val Leu Tyr Asn Phe Val Ser Glu Val Ala Tyr His Ile Leu
                 405                 410                 415

Lys Glu Glu Gly Phe Ile Ser Ile Pro Phe Leu His Arg Ala Trp Val
             420                 425                 430

Asp Leu Val Glu Gly Tyr Leu Gln Glu Ala Lys Trp Tyr Tyr Thr Lys
         435                 440                 445

Tyr Thr Pro Thr Met Glu Glu Tyr Leu Asn Tyr Ala Ser Ile Thr Ile
     450                 455                 460

Gly Ala Pro Ala Val Ile Ser Gln Ile Tyr Phe Met Leu Ala Lys Ser
465                 470                 475                 480

Lys Glu Lys Pro Val Ile Glu Ser Phe Tyr Glu Tyr Asp Glu Ile Ile
                 485                 490                 495

Arg Leu Ser Gly Met Leu Val Arg Leu Pro Asp Asp Leu Gly Thr Leu
             500                 505                 510

Pro Phe Glu Met Lys Arg Gly Asp Val Ala Lys Ser Ile Gln Ile Tyr
         515                 520                 525

Met Lys Glu Gln Asn Ala Thr Arg Glu Glu Ala Glu Glu His Val Arg
     530                 535                 540

Phe Met Ile Arg Glu Ala Trp Lys Glu Met Asn Thr Thr Met Ala Ala
545                 550                 555                 560

Asn Ser Asp Leu Arg Gly Asp Val Val Met Ala Ala Ala Asn Leu Gly
                 565                 570                 575

Arg Asp Ala Gln Phe Met Tyr Leu Asp Gly Asp Gly Asn His Ser Gln
             580                 585                 590

Leu Gln His Arg Ile Ala Asn Leu Leu Phe Lys Pro Tyr Val
         595                 600                 605

<210> SEQ ID NO 71
<211> LENGTH: 1821
<212> TYPE: DNA
<213> ORGANISM: Mentha citrata

<400> SEQUENCE: 71
atgtgtacta ttattagcgt aaatcatcat catgtggcga tccttagcaa gcctaaagta    60
aaacttttcc acaccaaaaa caagagatca gcttcaatta atctcccatg gagtctctct   120
ccttcttcat ccgccgcctc tcgccccatc agttgttcta tctcctcaaa actatatacc   180
atcagttcgg ctcaggagga aacccgacgt tccggaaact accacccttc agtttgggat   240

```
tttgatttca ttcaatctct cgacactgat cactataagg aggagaagca gttagagagg    300
gaggaagagc tgatcatgga ggtgaagaag ttgttggggg caaaaatgga ggcaactaag    360
cagttggagt tgattgatga cttgcagaat ttgggattgt cttattttt ccgagacgag     420 attaagaata tcttgaattc tatatataaa attttccaaa ataataatag tactaaagta    480
ggggatttgc atttcacgtc tcttggattc aggctcctcc ggcagcatgg tttcaacgtt    540
tcacaaggag tatttgattg cttcaagaac gagcatggta gcgatttcga gaaaccccta    600
attggggaag atacgaaagg agtgctgcaa ctttacgaag catcattcct tttgagagaa    660
ggtgaagata cattggaggt agctagaaaa ttctccaccg aatttctcga ggaaaaactc    720
aaagccggaa tcgatggtga taatctatca tcatcgattg ccattctt ggagatccct      780 cttcactgga ggattcaaag actagaggaa agatggttct tagatgctta ctcaaggagg    840
aaagacatga accctatcat tttcgagctc gccaaactcg acttcaatat tattcaagca    900
acgcagcaag aagaactcaa agatctctca aggtggtgga atgattcaag cctacctcaa    960
aaactcccat ttgtgaggga taggctggtg aaagctact attgggccct tgggttgttt    1020
gaggctcaca aatttggata tgaaagaaaa actgctgcaa agattattac cctaattaca    1080
gctcttgatg atgtttatga tatttatggc acactcgacg agctccaact atttacacac    1140
gtcattcgaa gatgggatac tgaatcagcc acccaacttc cttattactt gcaattattc    1200
tatttcgtac tatacaactt tgtttccgag gtggcgtacc acattctaaa ggaagagggt    1260
ttcatcagca tcccatttct acacagagcg tgggtggatt tggttgaagg atatttacaa    1320
gaggcaaagt ggtactacac taaatataca ccaaccatgg aagaatattt gaactatgcc    1380
agcatcacaa tagggctcc tgcagtaata tcccaaattt attttatgct agccaaatcg     1440
aaagagaaac cggtgatcga gagtttttac gaatacgacg aaataattcg cctttcggga    1500
atgctcgtga ggcttcccga tgacctagga acactaccgt ttgagatgaa gagaggcgac    1560
gtggcgaaat caatccagat ttacatgaag gaacagaatg caacacggga agaagcagaa    1620
gaacacgtga ggtttatgat tagggaggcg tggaaggaga tgaacacaac tatggcggcg    1680
aattctgatt tgagaggtga tgtggttatg gctgcagcta atcttggaag ggatgcacag    1740
tttatgtatc tcgacggaga cggtaaccac tctcagttac aacaccggat tgcgaacttg    1800
ctgttcaagc catatgtctg a                                              1821
```

<210> SEQ ID NO 72
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Mentha citrata

<400> SEQUENCE: 72

```
atgtgtacca tcattagcgt caatcatcat catgtcgcca tcctgagcaa gccgaaggtc     60
aagctgtttc ataccaagaa taagcgcagc gccagcatca atctgccgtg gagcctgagc    120
cctagcagca gcgcggccag ccgcccgatt agctgtagca tcagcagcaa actgtacacc    180
atcagcagcg cccaggaaga aacgcgccgc agcggcaatt accatcccag cgtttgggat    240
tttgacttta ttcagagcct ggataccgac cactacaagg aagaaaaaca gctggaacgc    300
```

```
gaagaagaac tgatcatgga agtgaaaaag ctgctgggcg cgaagatgga agccacgaaa      360
cagctggaac tgattgatga cctgcagaat ctgggcctga gctactttt ccgcgacgaa       420
atcaagaaca tcctgaacag catctacaag atctttcaga caacaatag caccaaggtt      480
ggcgatctgc attttacgag cctgggtttt cgtctgctgc gtcagcacgg ctttaatgtt     540
agccagggcg tgtttgattg ctttaaaaat gaacatggca gcgactttga aaagaccctg     600
atcggcgaag atacgaaagg cgtgctgcag ctgtacgaag cgagcttct gctgcgcgaa      660
ggcgaagata ccctggaagt cgcccgcaaa tttagcacgg aatttctgga gaaaaactg     720
aaggcgggca ttgatggcga caatctgagc agcagcattg ccatagcct ggaaatcccg      780
ctgcactggc gcattcagcg cctggaagaa cgctggttc tggatgccta cagccgtcgc      840
aaggacatga atcccattat ctttgaactg gcgaaactgg actttaatat tatccaggcc    900
acccagcagg aagaactgaa ggatctgagc cgttggtgga tgacagcag cctgccgcag     960
aaactgccct tgtccgcga tcgcctggtt gaaagctact actgggcgct gggcctgttt     1020
gaagcccata agtttggcta cgaacgcaag acggccgcga aaattatcac cctgatcacg    1080
gcgctggatg acgtgtacga tatttacggc accctggacg aactgcagct gtttacgcac    1140
gtcattcgcc gctgggacac ggaaagcgcc acccagctgc cgtactacct gcagctgttt    1200
tactttgtcc tgtacaattt tgtcagcgaa gttgcgtacc atattctgaa gaagaaggc    1260
tttattagca tcccctttct gcaccgcgcg tgggtggatc tggtcgaagg ctacctgcag    1320
gaagccaagt ggtactacac caaatacacc ccgacgatgg aagaatacct gaattacgcc   1380
agcattacca ttggtgcccc ggccgttatt agccagatct actttatgct ggcgaaaagc    1440
aaggaaaaac cggtgatcga agcttttac gaatacgacg aaattattcg tctgagcggt     1500
atgctggttc gcctgcccga tgacctgggt accctgccct tgaaatgaa gcgcggcgat    1560
gttgccaaaa gcattcagat ctacatgaag gaacagaatg cgacgcgcga agaagccgaa   1620
gaacacgtgc gctttatgat tcgcgaagcg tggaaagaaa tgaataccac gatggccgcg   1680
aatagcgatc tgcgcggcga cgttgtgatg gcggccgcca atctgggtcg tgatgcccag    1740
tttatgtacc tggatggcga cggtaatcat agtcagctgc agcaccgcat cgccaatctg    1800
ctgtttaagc cctacgtcta a                                              1821
```

<210> SEQ ID NO 73
<211> LENGTH: 535
<212> TYPE: PRT
<213> ORGANISM: Ocimum basilicum

<400> SEQUENCE: 73

Met Ala Ser Ala Val Pro Leu Ser Ser Thr Pro Leu Ile Asn Gly Asp
1               5                   10                  15

Asn Ser Pro Leu Lys Asn Thr His Gln His Val Glu Glu Arg Ser Ser
            20                  25                  30

Lys Arg Arg Glu Tyr Leu Leu Glu Glu Thr Ala Arg Lys Leu Gln Arg
        35                  40                  45

Asn Asp Thr Glu Ser Val Glu Lys Leu Lys Leu Ile Asp Asn Ile Gln
    50                  55                  60

Arg Leu Gly Ile Gly Tyr Tyr Phe Glu Asp Ala Ile Asp Ala Val Leu
65                  70                  75                  80

Arg Ser Pro Phe Ser Ala Glu Glu Glu Glu Asp Leu Phe Thr Ala Ala
                85                  90                  95

Leu Arg Phe Arg Leu Leu Arg His Asn Gly Ile Gln Val Thr Pro Glu

-continued

```
              100                 105                 110
Ile Phe Leu Lys Phe Lys Asp Glu Arg Gly Glu Phe Asp Glu Ser Asp
            115                 120                 125
Thr Leu Gly Leu Leu Ser Leu Tyr Glu Ala Ser Asn Leu Gly Val Thr
            130                 135                 140
Gly Glu Glu Ile Leu Glu Glu Ala Met Glu Phe Ala Glu Pro Arg Leu
145                 150                 155                 160
Arg Arg Ser Leu Ser Glu Leu Ala Ala Pro Leu Arg Ser Glu Val Ala
                165                 170                 175
Gln Ala Leu Asp Val Pro Arg His Leu Arg Met Ala Arg Leu Glu Ala
                180                 185                 190
Arg Arg Phe Ile Glu Gln Tyr Gly Lys Gln Ser Asp His Asp Gly Asp
            195                 200                 205
Leu Leu Glu Leu Ala Ile Leu Asp Tyr Asn Gln Val Gln Ala Gln His
            210                 215                 220
Gln Ser Glu Leu Thr Glu Ile Thr Arg Trp Trp Lys Gln Leu Gly Leu
225                 230                 235                 240
Val Glu Lys Leu Gly Phe Gly Arg Asp Arg Ala Leu Glu Cys Phe Met
                245                 250                 255
Trp Thr Met Gly Ile Leu Pro His Pro Lys Tyr Ser Ser Arg Ile
                260                 265                 270
Glu Ser Ala Lys Ala Ala Ala Leu Leu Tyr Val Ile Asp Asp Ile Phe
            275                 280                 285
Asp Thr Tyr Gly Lys Met Asp Glu Leu Ile Leu Phe Thr Asp Ala Ile
            290                 295                 300
Arg Arg Trp Asp Leu Glu Ala Met Glu Gly Leu Pro Glu Tyr Met Lys
305                 310                 315                 320
Ile Cys Tyr Met Ala Leu Tyr Asn Thr Thr Asn Glu Ile Cys Tyr Arg
                325                 330                 335
Val Leu Lys Asp Thr Gly Arg Ile Ala Leu Pro Tyr Leu Lys Ser Val
                340                 345                 350
Trp Ile Glu Thr Ile Glu Ala Tyr Met Val Glu Val Lys Trp Phe Ser
            355                 360                 365
Gly Gly Ser Ala Pro Lys Leu Glu Glu Tyr Ile Glu Asn Gly Ala Ser
            370                 375                 380
Thr Val Gly Ala Tyr Met Val Leu Val His Leu Phe Phe Leu Ile Gly
385                 390                 395                 400
Glu Gly Leu Thr His Gln Asn Val Leu Phe Phe Lys Gln Lys Pro Tyr
                405                 410                 415
His Lys Pro Phe Ser Ala Ala Gly Arg Ile Phe Arg Leu Trp Asp Asp
                420                 425                 430
Leu Gly Thr Ser Gln Glu Glu Glu Arg Gly Asp Met Ala Ser Ser
            435                 440                 445
Ile Arg Leu Phe Met Lys Glu Tyr Lys Leu Ser Thr Val Glu Glu Ala
            450                 455                 460
Arg Ser Cys Val Leu Glu Glu Ile Ser Arg Leu Trp Lys Asp Leu Asn
465                 470                 475                 480
Glu Gly Leu Ile Ser Ile Lys Asp Ala Leu Pro Leu Thr Ile Val Lys
                485                 490                 495
Val Ala Leu Asn Ile Ala Arg Thr Ser Gln Val Val Tyr Lys His Glu
                500                 505                 510
Gln His Thr Tyr Met Leu Ser Val Asp Asn Tyr Val Glu Ala Leu Phe
            515                 520                 525
```

```
Phe Thr Pro Leu Leu Ser Ser
    530             535
```

<210> SEQ ID NO 74
<211> LENGTH: 1608
<212> TYPE: DNA
<213> ORGANISM: Ocimum basilicum

<400> SEQUENCE: 74

| | | | | | |
|---|---|---|---|---|---|
| atggcatccg | cagtgcctct | aagttcaact | cctctcatca | acggggataa | ctctccgctt | 60 |
| aaaaacacac | atcaacacgt | ggaggagagg | agcagcaaga | ggagagaata | tctgctggag | 120 |
| gaaacggcgc | gaaaactgca | gagaaacgac | accgaatcgg | tggagaaact | caagctcatc | 180 |
| gacaacatcc | aacggctggg | aatcggctac | tattttgagg | atgccatcga | cgccgtactc | 240 |
| cgctcgcctt | tctccgccga | agaagaagaa | gacctcttca | ccgctgctct | gcgcttccgc | 300 |
| ttgctccgcc | acaatggcat | ccaagtcacc | cctgaaatat | tcctaaaatt | caaggacgag | 360 |
| agaggagaat | tcgacgaatc | ggacacgcta | gggttactga | gcttgtacga | agcgtcaaat | 420 |
| ttggggggtta | caggagaaga | gatactggag | gaggctatgg | agttcgcgga | gcctcgcctg | 480 |
| agacgatcac | tgtcagagct | ggcggcgccg | cttcgtagtg | aggtggcgca | agccctagat | 540 |
| gtgccgaggc | atctgagaat | ggcgaggttg | gaagccagac | gattcatcga | gcagtatggt | 600 |
| aaacagagcg | atcatgatgg | agacctttg | gagctagcaa | ttttggatta | taatcaagtt | 660 |
| caggctcaac | accaatccga | actcactgaa | attaccaggt | ggtggaagca | actgggtttg | 720 |
| gtggaaaagt | tgggtttcgg | tagagacaga | gcgttggagt | gctttatgtg | gaccatgggg | 780 |
| atcctacctc | accctaaata | ctcttcttct | agaatagaat | cagccaaggc | agctgctctt | 840 |
| ctgtacgtca | tcgatgatat | tttcgatacc | tatggcaaaa | tggacgaact | catcctcttc | 900 |
| accgacgcaa | ttcgaagatg | ggatttggaa | gcaatggagg | gtctaccga | gtacatgaaa | 960 |
| atatgctaca | tggcgttgta | caacaccacc | aatgaaatat | gctacagagt | gctcaaggat | 1020 |
| actggacgga | tcgccctccc | atacctcaaa | tctgtgtgga | tagagactat | tgaagcttat | 1080 |
| atggtggagg | tgaagtggtt | cagtggtgga | agtgccccaa | agttggaaga | atacattgag | 1140 |
| aatgggcat | caactgtagg | ggcatacatg | gttcttgtcc | acctattctt | tctcattgga | 1200 |
| gaaggtctca | cccaccaaaa | tgtcctattt | ttcaaacaaa | aaccctatca | caagcctttc | 1260 |
| tccgccgccg | gccggatttt | tcgcctttgg | gacgatcttg | gaacttctca | ggaggaggaa | 1320 |
| gaacgaggag | atatggcgtc | aagtatacgg | ttatttatga | aagagtacaa | gttgtcgacg | 1380 |
| gtagaggagg | ctagaagttg | cgttttggaa | gagatatccc | gtttatggaa | ggatcttaat | 1440 |
| gaagggctca | tcagtataaa | ggacgccttg | ccattaacca | tagtcaaagt | cgcacttaac | 1500 |
| attgcacgaa | cttctcaagt | tgtatacaag | cacgaacaac | atacatatat | gttgagtgtt | 1560 |
| gataattacg | tggaagccct | cttcttcact | cctcttcttt | cttcttag | | 1608 |

<210> SEQ ID NO 75
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Ocimum basilicum

<400> SEQUENCE: 75

-continued

```
atggcgagtg cggtcccct gagtagtacg cccctgatta acggcgacaa tagtcccctg    60 aaaaatacc accagcatgt tgaggagcgc agcagcaaac gtcgcgaata cctgctggaa   120
gaaaccgcgc gcaagctgca gcgcaatgac acggaaagcg ttgaaaaact gaagctgatt   180
gataatatcc agcgcctggg cattggctac tactttgaag atgccattga tgcggtgctg   240
cgcagcccct ttagcgccga agaagaagaa gacctgttta ccgcggccct gcgttttcgt   300
ctgctgcgtc ataatggcat tcaggtcacc ccggaaatct ttctgaaatt taaggatgaa   360
cgcggcgaat ttgacgaaag cgatacgctg ggcctgctga gcctgtacga agcgagcaat   420
ctgggcgtga ccggcgaaga aatcctggaa gaagcgatgg aatttgcgga accccgtctg   480
cgccgcagcc tgagcgaact ggccgcgccc ctgcgcagcg aagtcgccca ggccctggat   540
gttccccgtc acctgcgcat ggcccgtctg gaagcccgcc gctttattga acagtacggc   600
aaacagagcg atcatgacgg cgatctgctg gaactggcga ttctggacta caatcaggtc   660
caggcccagc accagagcga actgaccgaa atcacgcgtt ggtggaaaca gctgggcctg   720
gttgaaaaac tgggttttgg tcgcgatcgc gccctggaat gttttatgtg gacgatgggc   780
attctgccgc atcccaaata cagcagcagc cgtattgaaa cgccaaggc ggccgccctg   840 ctgtacgtta ttgatgacat cttttgacacc tacggcaaaa tggatgaact gattctgttt   900
acggacgcga tccgccgctg ggatctggaa gccatggaag gcctgcccga atacatgaag   960
atttgttaca tggcgctgta caataccacg aatgaaattt gctaccgcgt tctgaaagat  1020
accggtcgta ttgccctgcc ttacctgaag agcgtgtgga ttgaaaccat cgaagcgtac  1080
atggtcgaag ttaaatggtt tagcggcggc agcgccccca gctggaaga atacattgaa  1140 aatggtgcca gcaccgtggg tgcctacatg gtgctggtcc acctgttttt cctgatcggc  1200
gaaggcctga cccaccagaa tgtcctgttt ttcaaacaga gccgtacca caaacccttt  1260 agcgccgcgg tcgtatttt tcgtctgtgg gatgacctgg gcacgagcca ggaagaagaa  1320
gaacgcggcg atatggcgag cagcatccgc ctgtttatga aagaatacaa gctgagcacc  1380
gtggaagaag cccgcagctg cgtcctggaa gaaattagcc gcctgtggaa agacctgaat  1440
gaaggcctga ttagcatcaa agatgccctg ccgctgacca ttgttaaggt ggcgctgaat  1500
atcgcccgca cgagccaggt tgtgtacaag catgaacagc acacctacat gctgagtgtt  1560
gacaattatg tggaagcct gttttttacg cccctgctga gtagttaa              1608
```

<210> SEQ ID NO 76
<211> LENGTH: 299
<212> TYPE: PRT
<213> ORGANISM: Escherichia coli

<400> SEQUENCE: 76

```
Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Ser
65                  70                  75                  80

Leu Ile His Asp Asp Leu Pro Ala Met Asp Asp Asp Leu Arg Arg
```

```
                    85                  90                  95
Gly Leu Pro Thr Cys His Val Lys Phe Gly Glu Ala Asn Ala Ile Leu
                100                 105                 110

Ala Gly Asp Ala Leu Gln Thr Leu Ala Phe Ser Ile Leu Ser Asp Ala
            115                 120                 125

Asp Met Pro Glu Val Ser Arg Asp Arg Ile Ser Met Ile Ser Glu
        130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
                180                 185                 190

Gly Ala Leu Ser Ala Gly Asp Lys Gly Arg Arg Ala Leu Pro Val Leu
            195                 200                 205

Asp Lys Tyr Ala Glu Ser Ile Gly Leu Ala Phe Gln Val Gln Asp Asp
        210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
                260                 265                 270

Ser Leu Lys Gln Leu Ala Glu Gln Ser Leu Asp Thr Ser Ala Leu Glu
            275                 280                 285

Ala Leu Ala Asp Tyr Ile Ile Gln Arg Asn Lys
        290                 295

<210> SEQ ID NO 77
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant farnesyl diphosphate synthase derived
      from Escherichia coli whose 80th serine residue of the enzyme is
      substituted with a phenilalanine  (ispA* (S80F))

<400> SEQUENCE: 77

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Phe
65                  70                  75              80

Leu Ile His Asp Asp Leu Pro Ala Met Asp Asp Asp Asp Leu Arg Arg
                85                  90                  95

Gly Leu Pro Thr Cys His Val Lys Phe Gly Glu Ala Asn Ala Ile Leu
                100                 105                 110

Ala Gly Asp Ala Leu Gln Thr Leu Ala Phe Ser Ile Leu Ser Asp Ala
            115                 120                 125
```

```
Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
                260                 265                 270

Ser Leu Lys Gln Leu Ala Glu Gln Ser Leu Asp Thr Ser Ala Leu Glu
            275                 280                 285

Ala Leu Ala Asp Tyr Ile Ile Gln Arg Asn Lys
        290                 295

<210> SEQ ID NO 78
<211> LENGTH: 574
<212> TYPE: PRT
<213> ORGANISM: Actinidia arguta

<400> SEQUENCE: 78

Met Ala Ser Phe Asn Arg Phe Cys Val Ser Ser Leu Leu Ala Pro Asn
1               5                   10                  15

Asn Ser Pro Gln Ile Ser Asn Ala Pro Arg Ser Thr Ala Val Pro Ser
            20                  25                  30

Met Pro Thr Thr Gln Lys Trp Ser Ile Thr Glu Asp Leu Ala Phe Ile
        35                  40                  45

Ser Asn Pro Ser Lys Gln His Asn His Gln Thr Gly Tyr Arg Ile Phe
50                  55                  60

Ser Asp Glu Phe Tyr Leu Lys His Glu Asn Lys Leu Lys Asp Val Arg
65                  70                  75                  80

Arg Ala Leu Arg Glu Val Glu Glu Thr Pro Leu Glu Gly Leu Val Met
                85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Gln Arg Ile Ser Thr Cys Asp Tyr
        115                 120                 125

Pro Glu His Asp Leu Phe Glu Val Ser Thr Arg Phe Arg Leu Leu Arg
    130                 135                 140

Gln Glu Gly His Asn Val Pro Ala Asp Val Phe Asn Asn Phe Arg Asp
145                 150                 155                 160

Lys Glu Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
```

```
            195                 200                 205
Thr Asn Leu Asp His His Gln Ala Arg Leu Val Arg Asn Ala Leu Thr
210                 215                 220
His Pro Tyr His Lys Ser Leu Ala Thr Phe Met Ala Arg Asn Phe Asn
225                 230                 235                 240
Tyr Asp Cys Lys Gly Gln Asn Gly Trp Val Asn Asn Leu Gln Glu Leu
                245                 250                 255
Ala Lys Met Asp Leu Thr Met Val Gln Ser Met His Gln Lys Glu Val
            260                 265                 270
Leu Gln Val Ser Gln Trp Trp Lys Gly Arg Gly Leu Ala Asn Glu Leu
        275                 280                 285
Lys Leu Val Arg Asn Gln Pro Leu Lys Trp Tyr Met Trp Pro Met Ala
290                 295                 300
Ala Leu Thr Asp Pro Arg Phe Ser Glu Glu Arg Val Glu Leu Thr Lys
305                 310                 315                 320
Pro Ile Ser Phe Ile Tyr Ile Ile Asp Asp Ile Phe Asp Val Tyr Gly
                325                 330                 335
Thr Leu Glu Glu Leu Thr Leu Phe Thr Asp Ala Val Asn Arg Trp Glu
            340                 345                 350
Leu Thr Ala Val Glu Gln Leu Pro Asp Tyr Met Lys Ile Cys Phe Lys
        355                 360                 365
Ala Leu Tyr Asp Ile Thr Asn Glu Ile Ala Tyr Lys Ile Tyr Lys Lys
370                 375                 380
His Gly Arg Asn Pro Ile Asp Ser Leu Arg Arg Thr Trp Ala Ser Leu
385                 390                 395                 400
Cys Asn Ala Phe Leu Glu Glu Ala Lys Trp Phe Ala Ser Gly Asn Leu
                405                 410                 415
Pro Lys Ala Glu Glu Tyr Leu Lys Asn Gly Ile Ile Ser Ser Gly Met
            420                 425                 430
His Val Val Thr Val His Met Phe Phe Leu Leu Gly Gly Cys Phe Thr
        435                 440                 445
Glu Glu Ser Val Asn Leu Val Asp Glu His Ala Gly Ile Thr Ser Ser
450                 455                 460
Ile Ala Thr Ile Leu Arg Leu Ser Asp Asp Leu Gly Ser Ala Lys Asp
465                 470                 475                 480
Glu Asp Gln Asp Gly Tyr Asp Gly Ser Tyr Leu Glu Cys Tyr Leu Lys
                485                 490                 495
Asp His Lys Gly Ser Ser Val Glu Asn Ala Arg Glu Glu Val Ile Arg
            500                 505                 510
Met Ile Ser Asp Ala Trp Lys Arg Leu Asn Glu Glu Cys Leu Phe Pro
        515                 520                 525
Asn Pro Phe Ser Ala Thr Phe Arg Lys Gly Ser Leu Asn Ile Ala Arg
530                 535                 540
Met Val Pro Leu Met Tyr Ser Tyr Asp Asp Asn His Asn Leu Pro Ile
545                 550                 555                 560
Leu Glu Glu His Met Lys Thr Met Leu Tyr Asp Ser Ser Ser
                565                 570

<210> SEQ ID NO 79
<211> LENGTH: 1725
<212> TYPE: DNA
<213> ORGANISM: Actinidia arguta

<400> SEQUENCE: 79
```

```
atggccagct tcaacaggtt ttgtgtctct tctcttcttg ctccaaacaa cagcccacaa      60
attagcaatg ctccccgctc caccgctgta ccctctatgc ctaccaccca aaaatggagc     120
atcaccgaag acctagcatt catttctaat ccctcgaaac aacacaacca tcaaaccgga     180
tatcgcattt tctctgatga gttttaccta aagcacgaaa acaaattgaa ggacgttagg     240
agagcgttaa gggaagtgga ggaaacccca ttagaaggtc tggtcatgat cgacaccctc     300
caacggctag gcattgacta ccacttccag ggggagattg gagccctact acagaaacaa     360
cagagaatat ctacttgtga ttatcccgag catgatcttt ttgaggtctc tactcgcttt     420
cggctgttaa ggcaagaagg tcacaatgtg cctgcagatg tgtttaacaa cttcagagac     480
aaggagggaa ggttcaaatc agaactaagc agagacatca gggggttgat gagtttgtat     540
gaagcttcac agttaagcat acaaggagaa gacatacttg atcaagccgc agattttagt     600
tcccaactcc ttagcgggtg ggcgacaaat ctcgatcatc atcaagctag gcttgtgcgt     660
aatgcactga cacatcccta tcacaagagc ctagcgacat tcatggcaag aaacttcaat     720
tatgattgca agggccaaaa tggatgggtc aataacttgc aagaactagc aaaaatggac     780
ttaactatgg ttcagtccat gcatcaaaaa gaagtccttc aagtttccca atggtggaaa     840
ggcaggggtt tggccaatga attgaagctt gtgagaaatc agccacttaa atggtacatg     900
tggccaatgg cagccctcac agatccaaga ttctcagagg aaagagttga actcacaaaa     960
ccaatctctt ttatctatat catagatgac attttttgatg tttatgggac attagaagaa    1020
ctcactctct tcacagatgc tgtcaataga tgggaactta ctgctgttga gcaactaccc    1080
gactacatga agatttgctt taaggctctt tatgacatca caaatgaaat cgcctacaag    1140
atctacaaaa agcatggacg gaaccccata gattctctgc ggagaacgtg ggcaagtttg    1200
tgcaacgcgt tcttagaaga agcaaaatgg tttgcttctg ggaacttgcc aaaggcagaa    1260
gagtacttga agaatgggat catcagttca gggatgcatg tggttacggt tcacatgttc    1320
tttctcttgg gcggttgttt caccgaagaa agtgtcaatc ttgtggatga acatgcggga    1380
attacatctt ctatagcaac aatccttcgt ctttcggatg acttgggaag tgccaaggat    1440
gaggatcaag atggctacga tggatcctat ttagaatgct atctgaagga ccacaagggc    1500
tcttcggtag agaatgcaag agaagaagtt attcgcatga tttcagatgc atggaagcgc    1560
ctcaacgagg aatgcctatt tccgaatcca ttttcagcaa cttttcaggaa gggttctctt    1620 aatatcgcaa ggatggttcc tttgatgtac agctatgatg acaatcataa cctcccaatc    1680
cttgaggagc acatgaagac aatgctctat gatagttctt cttga                    1725
```

<210> SEQ ID NO 80
<211> LENGTH: 1650
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Actinidia arguta (opt_AaLINS)

<400> SEQUENCE: 80

```
atgtccaccg ccgtgccctc tatgcccact acccaaaaat ggtctattac cgaagactta      60
gcctttatta gcaatcccag caaacaacat aatcaccaaa ccggctaccg gattttagt     120 gacgaatttt acctgaaaca tgaaaacaaa ttgaaagatg tgcggcgcgc cttgcgtgaa     180
gttgaagaaa cccccctgga aggcttggtg atgattgaca ctttacagcg gctgggtatt     240
```

```
gattaccact ttcaaggcga aattggtgcc ttgttacaga aacaacagcg cattagtacc    300
tgtgactatc ccgaacatga tttgtttgaa gtgagcactc gctttcgtct gttgcgtcaa    360
gaaggtcaca atgtgcccgc cgacgttttt aataactttc gcgataaaga agggcgtttt    420
aaatctgaac tgtcccggga tattcgcgga ttgatgtcct tatacgaagc cagtcaactg    480
agcattcagg gggaagacat tttggatcaa gccgctgact tttccagtca gttactgtct    540
ggatgggcca ccaatttaga tcatcaccaa gcccgtctgg tgcggaacgc tttgacccat    600
ccctaccaca aaagtctggc acttttatg gctcgcaact ttaactacga ttgcaaaggg     660
caaaacggat gggtgaataa cctgcaggaa ttggccaaaa tggatttaac catggttcaa    720
agtatgcatc agaaagaagt gctgcaagtt agccagtggt ggaaagggcg gggattggcc    780
aatgaactga aattggtgcg caaccaaccc ttgaaatggt atatgtggcc catggccgct    840
ttaaccgatc cccggttttc tgaagaacgc gtggaattga ctaaacccat ttcctttatt    900
tacattattg atgacttttt tgacgtttat ggcaccttag aagaattaac cctgtttact    960
gatgccgtga tcggtggga attaactgct gttgaacagc tgcccgacta catgaaaatt    1020
tgttttaaag ccttgtacga tattaccaac gaaattgctt acaaaattta caaaaaacat   1080
gggcgcaacc ccattgatag tttacgtcgg acttgggcca gcttatgcaa tgcttttctg   1140
gaagaagcca atggtttgc tagtggcaat ttgcccaaag ccgaagaata cctgaaaaac    1200
gggattatta gctctggaat gcatgtggtt accgtgcaca tgttttttctt gttaggcggt   1260 tgttttactg aagaatccgt gaatttggtt gatgaacatg ccggcattac ctccagtatt   1320
gctactattt tgcgtttatc tgatgactta ggttccgcca aagatgaaga ccaagatggc   1380
tatgacggta gctacttgga atgttacctg aaagatcata aaggtagctc tgtgaaaaat   1440
gcccgtgaag aagttattcg gatgatttcc gatgcttgga aacgcttgaa tgaagaatgc   1500
ttatttccca acccctttc tgccaccttt cgcaaagggt ccttaaatat tgctcgtatg    1560
gtgcccctga tgtacagtta cgatgacaac cataacctgc ccattctgga agaacacatg   1620
aaaaccatgt tgtatgattc cagtagctaa                                    1650
```

<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Primer

<400> SEQUENCE: 81

```
acgttgttgc cattgccctg ttgacaatta atcatcg                              37
```

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Primer

<400> SEQUENCE: 82

```
tgtgaaatta gctactggaa tcatacaac                                       29
```

```
<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 83
gtagctaatt tcacacagga gactgccatg gattttcccc agcag              45

<210> SEQ ID NO 84
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 84
atgacttggt tgagtctatt tgttgcgctg gatgatg                       37

<210> SEQ ID NO 85
<211> LENGTH: 1575
<212> TYPE: DNA
<213> ORGANISM: Arabidopsis thaliana

<400> SEQUENCE: 85
atggcaaata ctgctaaaag atcgatcttg agaaacgtcc atgcttcagt ttctaaccct    60
tcgaagcagt ttcataataa gacatcctta gaatatttac acgagttgaa tatcaagaag   120
atcaagaata tactaagtgc aaacgtagat gttccatccg agaacctgga gatgatcgat   180
gtcattcaaa gtttaggcat tgatctccat tttcgacaag agatcgagca aacccttcac   240
atgatttaca agaaggcct ccaattcaac ggtgatctcc atgagatagc gcttcgcttt   300
cgattgctga caagagggg tcactatgtt caagaaaaca agaagggtgg atttaaagac   360
gtagtaaaaa atgacgtcaa gggtctaaca gaattgtttg aagcttctga gctccgtgta   420
gaaggtgaag aaacactcga cggtgcgaga gaattcacat atagccgcct taatgaactt   480
tgctcaggta gagaaagtca tcaaaagcaa gagataatga agtctttggc gcaacctcgc   540
cacaaaaccg taagaggatt aacgtccaag aggttcacaa gcatgatcaa atcgcgggt   600 caagaagatc cagaatggtt acagtctcta ttacgagtgg cggagatcga ttccattagg   660
ctaaagtcat tgactcaagg agaaatgtct caaacattta aatggtggac agaacttggt   720
ttagaaaaag atgtggagaa ggcaagaagc cagccgttaa aatggcatac gtggtccatg   780
aaaattcttc aagatccgac cttaaccgaa caaaggcttg atcttaccaa accaatatcg   840
cttgtttatg ttatagatga cattttcgat gtctatgggg agctagaaga actaaccatc   900
ttcacacgag ttgttgagag atgggatcat aagggctta agacgctacc caaatacatg   960
agggtttgtt ttgaagctct agatatgatc acaacggaga ttagcatgaa gatctacaaa  1020
tcacatggtt ggaacccgac atacgctctt cgacaatcgt gggcaagttt gtgtaaagca  1080
ttcttggtag aagcaaagtg gtttaattcg ggttacttac ccaccactga agagtatatg  1140
aagaatgggg ttgtgagttc aggtgttcat ttagtgatgc ttcatgccta tatcttgtta  1200
ggcgaagaac taacaaaaga gaaagtcgaa ctaatagaga gtaacccggg gattgtatca  1260
```

```
tctgcagcta caattctcag gctctgggat gatctcggaa gtgccaagga tgagaaccaa    1320
gatggaactg atggatcata tgtagagtgt tacctgaacg agtacaaggg atcaactgtt    1380
gatgaagcaa gaacacatgt tgcccagaag atatctagag catggaaacg cttgaacagg    1440
gagtgtctga atccatgtcc attctcaaga tcattctcaa aagcttgtct caacattgca    1500
agaacagttc ctttaatgta cagctatgat gatgatcaac gacttcccga cgaatatctc    1560
aagtctctaa tgtaa                                                    1575

<210> SEQ ID NO 86
<211> LENGTH: 1644
<212> TYPE: DNA
<213> ORGANISM: Arabidopsis thaliana

<400> SEQUENCE: 86
atgcgtcgtt ctgcgaacta tcagccttct cgttgggacc atcaccatct cctctcggtc      60
gaaaataaat ttgcgaaaga taaagggta cgagagagag atttgttgaa ggaaaaagtg     120
agaaagatgc tcaatgatga gcaaaagact tatcttgacc aattggagtt cattgacgat     180
ctacaaaaac tcggggtttc ttatcatttt gaagcggaaa tcgacaacat tttaacatct     240
tcttataaaa aagatagaac aaacatccag gagagtgacc tacatgccac cgcactcgag     300
ttccgacttt tcaggcaaca tggtttcaat gtttcagaag atgtattcga tgttttcatg     360
gaaaattgtg gaagtttga ccgtgatgat atatatggtt taatatctct ttacgaagca     420
tcatatcttt cgacaaaatt ggataaaaac ctgcaaatat tcatcagacc ttttgctaca     480
caacaactca gagactttgt tgatactcat agtaatgaag attttgggtc gtgtgacatg     540
gtggaaattg tggtccaagc gttggatatg ccctactatt ggcaaatgag aaggctatcc     600
accagatggt acatagatgt gtatggaaaa agacaaaatt ataagaacct tgtcgtcgtt     660
gaatttgcca agattgattt caacatcgta caagctattc atcaagagga actcaaaaac     720
gtttccagct ggtggatgga gacaggttta ggtaagcaac tctactttgc aagagacaga     780
atagtggaga attatttctg gacgattgga caaatccaag agcctcaata cggatacgtt     840
cgacaaacaa tgacgaaaat aaatgcactc cttactacaa ttgatgatat ctacgatatc     900
tatggcactc ttgaagaact tcagcttttc actgtcgcgt ttgaaaactg ggatataaat     960
cgtcttgatg aactccccga gtacatgagg ttgtgttttc ttgttatata caatgaagtc    1020
aatagcattg catgtgagat tctcagaact aaaaatatca acgtgatccc attcctcaaa    1080
aaatcttgga cagatgtatc caaagcgtat ttagtagaag caaagtggta caaagtggt    1140 cacaaaccaa atttggaaga gtacatgcaa aatgctcgga tttcaatctc gtccccaacg    1200
atatttgttc acttctactg cgtattctcc gaccagctct ctattcaggt cttggagact    1260
ttgtcccaac accaacaaaa cgtcgtccga tgctcctcct cagtgttccg tctagccaac    1320
gaccttgtaa cctcaccgga tgaattggcg agaggagacg tctgcaaatc catccaatgt    1380
tacatgagtg aaactggagc atcagaggat aaggcgcgtt cgcatgttcg acagatgatc    1440
aatgacttgt gggatgaaat gaattatgag aaaatggcac atagctcttc gatactccat    1500
catgatttta tggaaacagt gataaatttg gcacgcatgt ctcaatgcat gtatcaatat    1560
ggcgatggcc atggctctcc cgaaaaagcc aaaatcgttg atcgtgtcat gtccttactc    1620
ttcaatccga ttcctttaga ttga                                         1644

<210> SEQ ID NO 87
```

<211> LENGTH: 1698
<212> TYPE: DNA
<213> ORGANISM: Citrus unshiu

<400> SEQUENCE: 87

```
atgttgtttc aagtttcagc ctctcctaat aaagttatcc gaataaatgc cgagaaagaa      60
tctactcgtc gttcggcaaa ttttgatcct accatttggg gggattattt cctttcatat     120
actggtgact tcaaggaaag tggtgatgct agcgtgaagc atcaagagct gaagaaagaa     180
attagaacga tgctaagagc tgatatcaac aagcctacgc agactaaact ggatttgatt     240
gatgacattc agcgtttagg agtgtcttat cattttgaaa gtgagattga tgaaatcttg     300
cgaaaaatgc atgaggctaa ccaagattgt gatcttggcg atgatgaaaa tgttcaggag     360
ctctattata tctctcttca ttttcgatta cttagacaaa atggctataa aatttctgct     420
gatgtctttta acagcttcaa ggatagcaat gggaacttca agtctttcct taaaagagat     480
attcggggaa tgttaagcct gtatgaagcg gcacatctca gggtacatgg agaaaatata     540
ctcaacgaag cacttacttt cactgtcact caccttgagt catttacaag ccaatccaac     600
actcaacttg cggctcaagt caatcgtgcc ctcaatcgac ctattcgcaa aagcttacca     660
aggctagagg caaacacta catgccaatc tatcagaaag acccttcaca caacaaagat     720
ctattaacct tgccatgtt agatttcaac atacttcaga acaacacca gaagaactc      780
agagatatcg taaggtggtg gaaaaatttt gatgttccca ataagctacc tttcataaga     840
gacagagtgg tggagggcta tttctggatt ttgggagtat attttgagcc aaaattttta     900
ttggctagaa aaattctaac caagtgata tcaatggctt caattattga tgacattat      960
gatgcttatg gtacaataga gaacttgag cttttttgcca cagcaattga gaggtgggat    1020
ctcagtgcca tagatctgct tcctgagtac atgaagttgt gctattgcgc tctcctggat    1080
gcttacagcg aatttgagaa agatttggcc agcaaaggaa tattgtacgg cctacctttt    1140
gctaaagaat cgatgaagat tttggtgaga agttacatca tcgaagctag atggtgtgac    1200
caacaatatg taccgacaat ggaggaatac atgcgcgttg cactactttc atgtggctac    1260
ttactgttat caacatcttc atttctggga atggaagata ttgtaacaaa agaagccttt    1320
gaatgggtat ccggcaaccc taaaatcgtt caggcttcct caataatttg cagactcatg    1380
gatgacattg tctctcataa gtttgagcaa cagagaggac atgtggcctc agctgttgaa    1440
tgctacatga agcagcatgg agtttctgag gaagaggcag ttaaagtgtt tcgggagaaa    1500
gttgggaatg cgtggaaaga tataaatgag gagctcatga gaccacctgt tgttcctatg    1560
cctttgctcg aacgggttct taatcttgct cgtttaatgg atgtgctgta ccaaaataat    1620
gattcctata caaatcctca cttgatgaaa gatcatgtag ccgcattgct taaggatcct    1680
gttttctttg aagactag                                                 1698
```

<210> SEQ ID NO 88
<211> LENGTH: 1746
<212> TYPE: DNA
<213> ORGANISM: Citrus unshiu

<400> SEQUENCE: 88

```
atggctttct cttccaaaga tatttcgtct gattcatccc acattcactt tattccaaaa      60
cacatatcaa aagttggcaa ccgaaacctc aataacatta attctttgct gcctaataat     120
aaaaagggca gcattaatga taacataggt gtttctgccc ggttgaaacg tttcacttat     180
cccagtgaac actccagtaa ttttaatgac gacattcaca ttaagcatgc gaaaaaactg     240
```

```
gaggtaatca agcacatact tatcaaacta ggagatgacg attcttttga aggattggcc      300
atgattgatg tcgttcaacg cctagggatt gattactatt tcaagatga gattgaacta       360 attctacgaa ggcagtatag catattttc actgatggtg atcgctataa tgaccttcaa       420
gaggttgccc ttcgctttcg actgttgaga caacaaggtt actatgtgtc tgcagatgtt      480
tttaacaggt tcagaaacaa agaagggag tttaaacaga atataagtga agacatcaat      540
ggattgatga gcttatacga ggcctcacag ctaagtattg gaggagaaga tgggcttgat      600
gaagctggac actttagtgc gacacatctt gctaattatg atctagcggg agtagttgag      660
catctgttgc tgtatccta tcgcaaaagc ttgtccccgg ccaaaaactt tttccatggc       720
aattttcaag gcagtgaata tatttggata ctggatttgc aagaactagc gaatatggat      780
ttcaaattgg tccaatcctt acaccaaaag gaaattgtgc aaatatccag ttggtggaga      840
gagctcggtt tggctaagaa gttggaattt gcaagagagc aaccagttaa atggtatgtg      900
tggtcaatgg catgtttcac ggatccaaac ttgtcgtggc aaaggataga gctcacaaaa      960
cccatctcct tcgtctacat tattgacgac attttttatg tttgtggagc actcgatgcc     1020
ctcacccttt tcacagaacc cattaataga tgggatcttg gggacattga tcaattgcca     1080
gagtacatga agatatgttt caaggctctt aacgatatca ctaatgaaat cagcaaacaa     1140
ggtgtacaaa ggagcatggg tataaaccctg tgcactcctt tgcgaaaggg cgtgggggaa     1200
gttttgtgca acgcgttcct aatagaggca aaatggtttg cttccgggca cttgcctaag     1260
gctgaagagt acttgaaaaa tgggattgtt agttcagggg tacacttggt acttgtgcac     1320
attttctttc tcctgggtca tggcatcacc aatgaaacag tgcaactcat tgacagcaac     1380
ccacccattg tatcatccgt cgcaacaatt cttcgaattt gggatgactt gggaagtgct     1440
aaggatgaaa atcaaggcgg caaagatgga tcatatatat attactacat gatggaacac     1500
cgagacttaa cggctgaaga tgcacacaag catgccatgg ataagatttc agatgcatgg     1560
aagcgcctaa acaaggaatg cctctccca aatccatttt cagcatcttt cacaagggct     1620
tcttttaact gtgccagaat ggttcctttg atgtacagct atgatgacag ccaacggctt     1680
ccgagcctcg aggagtatat taagtcctcc ctttttgata atttgcctac tcaaggagtg     1740
tactag                                                                1746
```

<210> SEQ ID NO 89
<211> LENGTH: 1767
<212> TYPE: DNA
<213> ORGANISM: Citrus unshiu

<400> SEQUENCE: 89

```
atggctttct cttccagttc tagagctaag ttgtctgcta cctcccacat ttcaaaggct       60
ccagataaga tttcaaaaac tagcaggcct agcctcattg aatttactcc ttcgcctact      120
atctatcaaa aagggtgcat tactagtgac aatacagtcg cttctcctcc ccttaaacac      180
ttcacccaca caactagaca ccccagcttc ttcgatcatg atattcaagt cgaacattct      240
cggaaattga aggaattcaa gcatatattt agcctagtcg ggggaaattc ttttgaagga      300
ttagtcatga ttgatgctgt tcaacggcta cgcattgagt accttttcaa agatgagatt      360
gaagaaattt tacaaaggca atatatcata tcttccactt gtggtggtca cctccatgat      420
cttcaagagg ttgccttcg ctttcggttg ctgagacaag aaggttacta cgtgcctgcg      480
gatatgttta caactttag gatcaaggaa gggagattca gccggatcaa cgtaagtgaa      540
```

| gacataggga cattgatgga agtatatgaa gcttcgcagc taagtatagc aggcgaagaa | 600 |
| gggcttgacg aagccggaca ctttagtgcg aagatgctca atgagtgcat gacacatctt | 660 |
| gatcactatc atgctctagc tatcgggaat actttgaggc atccatacca caaaagcttg | 720 |
| cccagattta tggccaaaga cgttttcctt agcaatttcc aaggtgaacg cagattgcat | 780 |
| gttttaaaag aaatagcgaa aaaagatttc aacatggtac aggccttaca ccaaaaagag | 840 |
| attgttcaag taaccaaatg gtggaaagac ctcggtttga ctaagaagtt gccgtttgca | 900 |
| agagaccaac cacttaaatg gtacatttgg tctatggctt gcctcacaga tccaagcttg | 960 |
| tcagagcaaa gagttgagct cacaaaaccc atatccctca tctacattat tgacgacata | 1020 |
| tttgatgttt atgggacgct tgatgaactt attctcttca cagaaactat tactagatgg | 1080 |
| gatcttgccg ctatgggtca attgcctgag tacatgaaga tatgtttcaa agctcttgac | 1140 |
| gatattacta acgaaatcag ctgcaaggtc tataagaagc atgggtataa cccagtacag | 1200 |
| tccctccgaa atgcgtggac aagtttgtgc aaagcatttc tagtggaagc gaaatggttt | 1260 |
| gcttctggac acatgcctga ggctgaagaa tacttgagga atgggattga gagttcagga | 1320 |
| gtacatgtgg cactggcgca cttttttttt ctcctaggtc atggtataac taaggaaacg | 1380 |
| gtggagctta ttgacggtaa cccggccata atatcatcaa ccgcaacaat tcttcggctc | 1440 |
| tgggatgact tgggaagtgc aaaggatgag aatcaagaag gtaaggatgg atcttacatc | 1500 |
| cattactaca tgaaggaaca ccgatattct gccgccgaag aggcacaaaa aagtgctatc | 1560 |
| aataaaattt cagacgcatg gaagcggctc aacaagaat gcctctgccc aaatccattc | 1620 |
| tcagcatctt tcacgagggc ttctctcaat cttgcaagaa tggtccccctt gatgtacagt | 1680 |
| tacgatgaca accaacgcct accaagcctc gaacattaca ttaagtccct actctttgaa | 1740 |
| agcgtaccta ctgaaggagt ttattaa | 1767 |

<210> SEQ ID NO 90
<211> LENGTH: 1704
<212> TYPE: DNA
<213> ORGANISM: Malus domestica

<400> SEQUENCE: 90

| atggaatttt ctatttccca gtcctccttt gcgacctcgt cttctactcc agctgctccg | 60 |
| gaacaccttta gttctcaaaa atggagcatc cccgaagatc acagtttgct ttctactccc | 120 |
| ttaaaaccgc ttaactccaa aacgaagtat acttcatcta aggatggcat aatttgtttc | 180 |
| cagaatgaac aaaaactgga cgacttaagg catgcattga taaagtggg aggagaagca | 240 |
| gttgaaagtt tggacatgat cgatgcggtt caacggctag gtctagacta ccactttgaa | 300 |
| gaagaaattg accaaattct ccaaaagcaa catataatat ctagtactac tgctcatggt | 360 |
| gctcaccatc ccaccgacct acatgaagtc gctctccgct ttcgactact caggcagcat | 420 |
| ggttacttcg tctctgatga tgtgtttaac aacttcaaga acagagaagg aaatttcaat | 480 |
| caaatgttaa gggaagacat caaggggttg atgagtttgt atgaagcttc acagctaagt | 540 |
| atagagggtg aagttgtact tgaagaagct ggaaagttta gtggccattt cctaaattca | 600 |
| tcactgtcac atctcgatca tcaccaggcc agagttgttg aaacacatt gagaaatcct | 660 |
| catcacaaaa gcttggcccc attcatggcc aagaactttt tgtctctag cttccaagga | 720 |
| acaaataata gatggctaaa tatattacaa actgtagcaa aaacagattt aaatatggtc | 780 |
| cagtcccttc accagaaaga agttgctcaa gtttccaaat ggtggaaaga gctgggattg | 840 |
| tgtaaggagt tgaagtttgc aagagaccaa cctattaaat ggtacatttg gtccatggct | 900 |

```
tgcctaacaa atccaaactt gtcagatgag aggattgagc tcacaaaacc tatctcattt      960
atctatttga ttgatgacat ttttgacgtt tacgggacgc ttgatgaact cactcttttc     1020
acggaggttg tcaatagatg ggaaattggt tctatagagc acttaccgga ctacatgaag     1080
atatgcttca aggctctta cgatatgacg aatgaaatca gctgtaaggt ctatcaaaag     1140
cacggatgga acccattgca ttcgctaaag aagacgtggg ctagtctgtg caatgcattt     1200
ttagtggaag caaaatggtt caaatctggg cacttgccta tggctgaaga gtacttgaag     1260
aatggaatta tttcttctgg ggtgaatgtg gtgatggtcc acattttctt tctgttgggt     1320
gaaggtataa ccaatcaaag tgtggagttc ttgaatggca ctccagccat tatatcttca     1380
acggcagcaa ttcttcggct ttgggacgac ttgggaagtg ccaaggatga aatcaagat      1440 ggggacgacg ggtcatatgt aaagttgtat ttaaatgaac atcaaggcaa gaccatggag     1500
gaagcacaag aacatgttac aaatatgatt tcagaagaat ggaagaagct gaacaaagaa     1560
ttggtgtctc ctaatccact tcccgcggca ttcacaaagg cttccctaaa tctcgcaaga     1620
atggtgccat tgatgtatag ctacgacgac aaccagtgcc ttccatctct tgacgagtac     1680
atgaaatcga tgcttcatgc atga                                            1704
```

<210> SEQ ID NO 91
<211> LENGTH: 1824
<212> TYPE: DNA
<213> ORGANISM: Perilla frutescens

<400> SEQUENCE: 91

```
atgtatagct tgagaatata tgtagcgatc atgaaaaagc catcagctaa acatgttgac       60
aacgtcgaca agaaagcttc aaagccgtcg tggcgtgtct cactctcttc gagtgcgggt      120
ctccgagctt cttcctcctt acaactcgat gtaaaaaagc ccgctgatga tgaaattctg      180
acggcccgac gctctggcaa ctaccagcct tccctttggg atttcaacta ccttcaatct      240
ctcaacacta ctcagtataa ggaagtgagg cacttgaaaa gggaagcaga gctgattgag      300
caagtgaaga tgctgctgga agaagaaatg gaggcagttc aacaattgga gttggttgat      360
gacttgaaaa atctgggatt gtcttatttt tttgaagacc aaattaagca gatcttaacg      420
tttatatata tgagcataa atgtttccac agtaatagta ttattgaagc ggaggaaatt      480
agggatttgt atttcacagc tcttggattc agactcctca gacaacatgg tttccaagtc      540
tctcaagagg tatttgattg tttcaagaac gaggagggta gtgatttcaa agcaaggctt      600
ggtgacgata caaaaggatt gctgcaactc tacgaagcct cttttcctatt gagagaaggt     660 gaagatacac tggagctagc aaggcaatat gccaccaaat ttctccagaa aaaagttgat     720
catgaattaa ttgacgacaa taatctatta tcatggattc tccattcttt ggagatcccg     780
cttcactgga ggattcagag gctggaggca agatggttct tagatcgtta cgcgacgaga     840
cgagacatga atcaaatcat tcttgagctc gccaaactcg acttcaatat tattcaagca     900
acacaacagg aagaactcaa agatctctca aggtggtgga gagtacatg tctggctgag     960 aaacttccat tcgtgaggga taggcttgtg gaaagctact tttgggccat tgctctcttt    1020
gaacctcatc aatatggata tcacagaaaa gttgctgcca agattattac actaataaca    1080
tctttagatg atgtttacga tatctatggt acattagacg aactacaact atttacagac    1140
gcgattcaaa gatgggatac tgaatcaata agccgcctc catattatat gcaattattt    1200
tatatggtac tctacaactt tgtttcggag ctggcttacg atggtctcaa ggagaagggt    1260
```

```
ttcatcacca tcccatattt acagagatcg tgggcagatt tggttgaagc atatttaaaa    1320
gaggcaaagt ggttctacaa tggatatgta ccaagcatgg aagaatatct caacaacgcc    1380
tacatttcaa tagggctac tcccgtaatt tctcaagttt tcttcacatt agcaacctcc     1440
attgacaaac cagtgatcga cagcttgtac gaataccacc gcatacttcg cctctctgga    1500
atgcttgtaa ggcttcctga tgatttagga acatcaccgt ttgagatgaa gagaggcgac    1560
gtgccgaaag caatccagtt gtacatgaag gaaagaaatg ctaccgagat agaggctcaa    1620
gaacacgtga ggtttctgat tcgtgaggcg tggaaggaga tgaacacggt aacgacggcg    1680
gccgattgtc cgtttacgga tgatttggtt gcagcgacac gtaatcttgg tagggcggca    1740
cagtttatgt atctcgacgg agatggtaac cactctcaat acatcagcg gattgcgtgc     1800 ctactgttcg agccatatgc atga                                           1824

<210> SEQ ID NO 92
<211> LENGTH: 1734
<212> TYPE: DNA
<213> ORGANISM: Vitis vinifera

<400> SEQUENCE: 92
atgggattct ctcctgcctt ttacgcttgc tccattcctc cagttggtcc taacaaattc      60
acagagctag ccagtccaa attcaacaat gttgtgcttg tgcctactgc tcagaaatgg     120
agcattgccc acgaccacac cttggtttat aagcccttaa gaaagcataa tcatcaatct    180
caacatctca gctttactga tgaatttac atcaagcatg cacaaagatt ggatgaaatt    240
agaaacgtat tcagtgaagt tggagaggat acgctgaaag gtttgatgat gattgatgcc    300
atacaaaggt tgggcattga ctaccacttc aaagaggaaa ttgaagcagt tctacagaga    360
cagtatatga aagccagcac tcacggtgag agcattcagg atctctacga ggttgctctt    420
cgttttcggc tattgagaca agaaggttac catgtgcctg cagatgtgtt taacaacttc    480
aagaacaagg aggggaagtt taaacaaaat ctcagcaaag acatcaaggg attgttggct    540
ttatatgaag cttcacaact gagtatagaa ggagaagata tcctcgagga agcccaaaga    600
ttcagcagca cgctccttaa cgcagggttg aacatctta atcaccacga agctacagtt    660
gttgggcata cactggagca tccccatcat aagagcttgc caaggttcat ggccaaaagc    720
ttccttaagg acttccaggg accaaatgga tggctgactg tcttgcaaga acttgcaaaa    780
gcggatttca atatggttca atccatacat cagcaggaat tacttcaaat ttcgaaatgg    840 tgcaagacc gaggtttggc tgaggagttg aaatttgcaa gagaccaacc actgaaatgg    900
cacatgtggc ccatggcagt actccccgat ccaagcttgt cagagcaaag ggttgagctc    960
acaaaaccca tctctatgat ctatataatc gatgacattt tgatgttca tggaacgctt   1020 gatgagctca ctctctttac agaagctgtc aatagatggg atatagctgc tttcgagacg   1080 ctaccaaaact acatgaagat atgcttcaag actctagatg aaatcacaaa tgaaatcagc   1140
aacaaggtct acaaagagca cgggtggaac ccagtagact cgctacggaa gacgtgggtg   1200
agtttatgca atgcgtttct agtagaagcc aaatggtttg cctctgggca tgtgccaaag   1260
gcccacgagt acttgaaaaa cggggtcatc agttcagggg tacatgtggt gcttgttcac   1320
ttgttctttc tcttgggcca tggcataacc aggggaaatg tggatcttgt ggatgacttc   1380
cccagcatca tatcttccac agctgccatt cttcgtcttt gggacgacct gggaagcgcc   1440
aaggatgaga tcaagatgg ccacgacggg tcatacatcg agtgctacat taaggaacac    1500
caaggctctt ccatggaaaa tgcacggcaa aatgtgacct atatgatttc agacttatgg   1560
```

| | | |
|---|---|---|
| aagcgcctca acaaggagtg cctctctcag catccatttt caacttcttt tacaaagggt | | 1620 |
| tcccttaaca ttgcaaggat ggttcctttg atgtacagtt atgatgacaa tcagagtctt | | 1680 |
| ccacaccttg aggaacatat gaagtccctc ctctttgaag catttcccct gtag | | 1734 |

<210> SEQ ID NO 93
<211> LENGTH: 1809
<212> TYPE: DNA
<213> ORGANISM: Vitis vinifera

<400> SEQUENCE: 93

| | | |
|---|---|---|
| atggaactaa ccctcacatc cctctcaccc ttggcctatg gtgccctcaa ttgtcgtaaa | | 60 |
| aattttgcca tggcatcccc aagaatgaga atcaagcaag ggagatcaga attgcccaac | | 120 |
| ctcacaatca cttcgaagat tgatgagtta caagtgaccg aaaggcgatc ggctaattac | | 180 |
| catcctagca tttgggaccc caaatttatt gagtccttaa gcactcccta tacgaatgag | | 240 |
| ggctattcca accaattaga ggacttgaag gaagaagcta aaagggtaat taaggacgct | | 300 |
| agagacactt cctcccgatt agagttcatt gattcgatgc aacggttggg agtggcttac | | 360 |
| catttggagg aggagatcaa agaggctatt gatcttgttc atttggatga taccactacc | | 420 |
| gatgatcttt ccacaactgc actccgattt agacttctac gacaacacgg ctatccagtt | | 480 |
| agctcagagt gtttgatca attcagaagt aaagatggga gattcatgga tggcatcagc | | 540 |
| caggatattg ctgggccttt gagtttgtat gaagcttccc atcttggagt cgagggagaa | | 600 |
| gatgacttgg aagaagccag gaggttcagt actatacatt tgaagtcact ggttgggaat | | 660 |
| ttggagagtg atttagctga ccaagtgcag cagtccctgg aagttcccct tacactggaga | | 720 |
| atgccaaggc tagaagcccg aaacttcatc gatatctacc aaaggcgcaa tacgaagaac | | 780 |
| tctgctctcc ttgagctagc caagctggac tacaatctag tgcaatcatc atatcagacg | | 840 |
| gagttgaagg agctaacaag gtggtggacg gacttgggat ttaaggagaa gctaagtttt | | 900 |
| tctcgggatc gattgatgga gaactatttg tggtcaatgg ggatcgctcc tgagccccac | | 960 |
| ttctccaaaa gcaggatagg actcaccaaa ttcatatgca tattaacagc catagatgac | | 1020 |
| atgtatgaca tatatggatc accggatgag cttcgacgtt ttacagatgc tgtgaatcga | | 1080 |
| tgggatactg aggcactggt ggaccttcca gattacatga agatatgtta cttggccatg | | 1140 |
| ttcaactttg ctaatgaaat ggcctacgat gcattaagag atcacgacct atatatttta | | 1200 |
| ccctatctta aaagtcagtg gctaaatctc tgtacatcct actcaatgga agctcaatgg | | 1260 |
| ttttacaatg ggtataagcc aagcatcgat gaatacttaa gcaatgcctg gcttccgta | | 1320 |
| gggggtcctg cagccatggt ccatgcctat tttctaatgg ttgtgccac caagggaaac | | 1380 |
| ttgaacaatt gtttagacaa tgcctctaat ctacttatt ggtcatctct tattactcga | | 1440 |
| cttagcgatg atttgggaac ttctttagcc gagattgcga gaggcgacgt ggcaaaatct | | 1500 |
| atccaatgtt acatgattga aaaatgtata tccgaagaac aagctcgaga tcaagtagag | | 1560 |
| aagcttatac gttactcatg gaaaaagttg aatgaagcaa gtactgatag ctctctccca | | 1620 |
| aagtccttaa taaattcatc attgaacatg gcgcgatcag ctcaatgtat ttttcaattt | | 1680 |
| ggagatggaa tcggtacatc agttggggtg accaaagatc gattgacatc attcattatc | | 1740 |
| aagccaatat tgatagaacc aagcattaaa ccctatcttg atggcatgaa gatgagcaac | | 1800 |
| agaagatga | | 1809 |

<210> SEQ ID NO 94

<211> LENGTH: 1695
<212> TYPE: DNA
<213> ORGANISM: Lavandula angustifolia

<400> SEQUENCE: 94

```
atgtcgatca atatcaacat gcctgcagcc gccgtcctcc gcccttttcg ctgctcacaa      60
ctacatgtcg atgaaacccg acgctccgga aactaccgcc cctcggcttg ggattccaac     120
tacatccaat ctctcaattc tcagtataag gaaaagaagt gcttgacaag gctagaaggg     180
ctgattgagc aagtgaagga actgaagggg acaaaaatgg aggctgttca acaattggag     240
ttgattgatg actcgcagaa tctgggatta tcatattatt ttcaagataa aattaaacat     300
atcttgaatt tgatatataa tgatcacaaa tattttacg atagtgaagc tgaaggaatg      360
gatttgtatt ttacagctct tggatttaga ctctttagac aacatggttt taaagtctcc     420
caagaagtat ttgatcgttt caagaacgag aatggtacgt atttcaagca cgacgataca     480
aagggattgt tgcagctcta cgaagcatca ttcctagtgc gagaaggcga agagacactc     540
gaacaagcac gagaatttgc caccaaatcc ctacaaagaa aacttgatga ggatggtgat     600
ggaattgacg ccaatatcga atcatggatc cgccactctc tggagatccc acttcattgg     660
agggctcaga ggctagaggc gagatggttc ctagatgctt atgcgagaag gcccgacatg     720
aaccccgtta tcttcgagct tgctaaactc aacttcaata ttgtccaagc aacacaacaa     780
gaagaattga aagctctctc gaggtggtgg agtagtttag gctagctga aaaactccca      840
tttgtgaggg ataggcttgt ggaaagctac ttttgggcta ttccactctt tgagcctcat     900
caatatggat atcaaagaaa agtggccacc aagatcataa ccctaatcac atctttagac     960
gatgtttacg atatctatgg cacgttagat gaattgcaac tatttacgaa cttatttgaa    1020
agatgggata atgcatcaat cggccgactt cctgaatact tgcaattgtt ctatttcgca    1080
atccacaact ttgtttccga ggtggcttac gacattctca agaaaaggg tttcactagt    1140
attgtatatt tacagagatc gtgggtggat ttgctaaaag gatacctaaa agaggcaaag    1200
tggtacaata gtggatacac gccaagcctc gaggaatatt tcgacaacgc attcatgaca    1260
ataggggccc ctccggtact atcgcaagct tatttcacat taggaagctc gatggagaaa    1320
ccgatcatcg agagcatgta cgaatatgac aacatacttc gcgtttcggg aatgctcgtg    1380
aggcttcccg atgacctagg aacatcatcg ttcgagatgg agagaggcga cgtgccgaaa    1440
tcggtccagc tatacatgaa ggaaacaaat gctacggagg aggaggcggt ggagcacgtg    1500
aggttttga tcgggaggc gtggaagaag atgaacacgg cggaggcggc cggtgattct     1560
ccgttagtga gtgacgtggt ggcggtggcg gcgaatcttg aagggcggc gcagtttatg     1620
tatttcgacg gagatggtaa ccagtctagt ttgcagcagt ggattgtgag catgctgttc    1680
gagccgtacg catga                                                    1695
```

<210> SEQ ID NO 95
<211> LENGTH: 1821
<212> TYPE: DNA
<213> ORGANISM: Mentha citrata

<400> SEQUENCE: 95

```
atgtgtacta ttattagcgt aaatcatcat catgtggcga tccttagcaa gcctaaagta      60
aaactttttcc acaccaaaaa caagagatca gcttcaatta atctcccatg gagtctctct     120
ccttcttcat ccgccgcctc tcgccccatc agttgttcta tctcctcaaa actatatacc     180
atcagttcgg ctcaggagga aacccgacgt tccggaaact accacccttc agtttgggat     240
```

| | |
|---|---|
| tttgatttca ttcaatctct cgacactgat cactataagg aggagaagca gttagagagg | 300 |
| gaggaagagc tgatcatgga ggtgaagaag ttgttggggg caaaaatgga ggcaactaag | 360 |
| cagttggagt tgattgatga cttgcagaat ttgggattgt cttattttt ccgagacgag | 420 |
| attaagaata tcttgaattc tatatataaa attttccaaa ataataatag tactaaagta | 480 |
| ggggatttgc atttcacgtc tcttggattc aggctcctcc ggcagcatgg tttcaacgtt | 540 |
| tcacaaggag tatttgattg cttcaagaac gagcatggta gcgatttcga gaaaccccta | 600 |
| attggggaag atacgaaagg agtgctgcaa ctttacgaag catcattcct tttgagagaa | 660 |
| ggtgaagata cattggaggt agctagaaaa ttctccaccg aatttctcga ggaaaaactc | 720 |
| aaagccggaa tcgatggtga taatctatca tcatcgattg gccattcttt ggagatccct | 780 |
| cttcactgga ggattcaaag actagaggaa agatggttct tagatgctta ctcaaggagg | 840 |
| aaagacatga accctatcat tttcgagctc gccaaactcg acttcaatat tattcaagca | 900 |
| acgcagcaag aagaactcaa agatctctca aggtggtgga atgattcaag cctacctcaa | 960 |
| aaactcccat tgtgaggga taggctggtg aaagctact attgggccct tgggttgttt | 1020 |
| gaggctcaca aatttggata tgaaagaaaa actgctgcaa agattattac cctaattaca | 1080 |
| gctcttgatg atgtttatga tatttatggc acactcgacg agctccaact atttacacac | 1140 |
| gtcattcgaa gatgggatac tgaatcagcc acccaacttc cttattactt gcaattattc | 1200 |
| tatttcgtac tatacaactt tgtttccgag gtggcgtacc acattctaaa ggaagagggt | 1260 |
| ttcatcagca tcccatttct acacagacg tgggtggatt tggttgaagg atatttacaa | 1320 |
| gaggcaaagt ggtactacac taaatataca ccaaccatgg aagaatattt gaactatgcc | 1380 |
| agcatcacaa taggggctcc tgcagtaata tcccaaattt attttatgct agccaaatcg | 1440 |
| aaagagaaac cggtgatcga gagttttac gaatacgacg aaataattcg cctttcggga | 1500 |
| atgctcgtga ggcttcccga tgacctagga cactaccgt ttgagatgaa gagaggcgac | 1560 |
| gtggcgaaat caatccagat ttacatgaag gaacagaatg caacacggga agaagcagaa | 1620 |
| gaacacgtga ggtttatgat tagggaggcg tggaaggaga tgaacacaac tatggcggcg | 1680 |
| aattctgatt tgagaggtga tgtggttatg gctgcagcta atcttggaag ggatgcacag | 1740 |
| tttatgtatc tcgacggaga cggtaaccac tctcagttac aacaccggat tgcgaacttg | 1800 |
| ctgttcaagc catatgtctg a | 1821 |

<210> SEQ ID NO 96
<211> LENGTH: 1608
<212> TYPE: DNA
<213> ORGANISM: Ocimum basilicum

<400> SEQUENCE: 96

| | |
|---|---|
| atggcatccg cagtgcctct aagttcaact cctctcatca acgggataaa ctctccgctt | 60 |
| aaaaacacac atcaacacgt ggaggagagg agcagcaaga ggagagaata tctgctggag | 120 |
| gaaacggcgc gaaaactgca gagaaacgac accgaatcgg tggagaaact caagctcatc | 180 |
| gacaacatcc aacggctggg aatcggctac tattttgagg atgccatcga cgccgtactc | 240 |
| cgctcgcctt tctccgccga agaagaagaa gacctcttca ccgctgctct gcgcttccgc | 300 |
| ttgctccgcc acaatggcat ccaagtcacc cctgaaatat tcctaaaatt caaggacgag | 360 |
| agaggagaat tcgacgaatc ggacacgcta gggttactga gcttgtacga agcgtcaaat | 420 |
| ttgggggtta caggagaaga gatactggag gaggctatgg agttcgcgga gcctcgcctg | 480 |

| | |
|---|---|
| agacgatcac tgtcagagct ggcggcgccg cttcgtagtg aggtggcgca agccctagat | 540 |
| gtgccgaggc atctgagaat ggcgaggttg aagccagac gattcatcga gcagtatggt | 600 |
| aaacagagcg atcatgatgg agacctttg gagctagcaa ttttggatta taatcaagtt | 660 |
| caggctcaac accaatccga actcactgaa attaccaggt ggtggaagca actgggtttg | 720 |
| gtggaaaagt tgggtttcgg tagagacaga gcgttggagt gctttatgtg gaccatgggg | 780 |
| atcctacctc accctaaata ctcttcttct agaatagaat cagccaaggc agctgctctt | 840 |
| ctgtacgtca tcgatgatat tttcgatacc tatggcaaaa tggacgaact catcctcttc | 900 |
| accgacgcaa ttcgaagatg ggatttggaa gcaatggagg gtctacccga gtacatgaaa | 960 |
| atatgctaca tggcgttgta caacaccacc aatgaaatat gctacagagt gctcaaggat | 1020 |
| actggacgga tcgccctccc atacctcaaa tctgtgtgga tagagactat tgaagcttat | 1080 |
| atggtggagg tgaagtggtt cagtggtgga agtgccccaa agttggaaga atacattgag | 1140 |
| aatgggcat caactgtagg ggcatacatg gttcttgtcc acctattctt tctcattgga | 1200 |
| gaaggtctca cccaccaaaa tgtcctattt ttcaaacaaa accctatca caagcctttc | 1260 |
| tccgccgccg gccggatttt tcgcctttgg gacgatcttg gaacttctca ggaggaggaa | 1320 |
| gaacgaggag atatggcgtc aagtatacgg ttatttatga aagagtacaa gttgtcgacg | 1380 |
| gtagaggagg ctagaagttg cgttttggaa gagatatccc gtttatggaa ggatcttaat | 1440 |
| gaagggctca tcagtataaa ggacgccttg ccattaacca tagtcaaagt cgcacttaac | 1500 |
| attgcacgaa cttctcaagt tgtatacaag cacgaacaac atacatatat gttgagtgtt | 1560 |
| gataattacg tggaagccct cttcttcact cctcttcttt cttcttag | 1608 |

<210> SEQ ID NO 97
<211> LENGTH: 2550
<212> TYPE: DNA
<213> ORGANISM: Clarkia breweri

<400> SEQUENCE: 97

| | |
|---|---|
| atgagagaat cattgtcttc ttcatcatct aatactcaga atttgtttct ctcaacttca | 60 |
| ccttatgaca ctgcttggct cgcccttatc cctcatcctc atcatcacca tcaccatggc | 120 |
| cgacccatgt ttgaaaaatg tctgcaatgg attctccata accagacacc acaaggtttc | 180 |
| tgggcagcag ctggtgacaa tatttccgac accgacgatg acgtcaccct ggattgtctt | 240 |
| ctatcaacct tggcttgctt agttgcactc aaaaggtggc agcttgctcc cgacatgatt | 300 |
| cataaaggat tggaatttgt aaatagaaac acagagagac ttgtaatgaa gcagaagccg | 360 |
| agcgacgttc ctcgttggtt caccatcatg ttcccggcga tgctcgagct tgccggagct | 420 |
| tccagtctcc gagtcgattt cagcgagaat cttaacagaa tcttggtgga actatctcaa | 480 |
| aatagggatg atattctcac aagggaggaa gttgatgaga agaagcaata ctcaccattg | 540 |
| ctactatttc tagaagcatt gcctgcacaa tcctatgaca atgatgttct aaagcaaatt | 600 |
| atagacaaga acttgagcaa tgatggttct ttattgcaat cgccttctgc tacagcaaga | 660 |
| gcatacatga taacaggaaa taccagatgc ttatcgtatc tacactcttt aacaaatagc | 720 |
| tgctctaatg gaggagtacc atcattctat cctgttgacg acgacctcca tgatcttgtc | 780 |
| atggtgaatc aactgacaag gtcgggtttg actgaacatc tcatcccgga gattgaccac | 840 |
| cttctactca aagttcaaaa gaactacaaa tacaaaaaag catcaccaaa atcattgtat | 900 |
| agcattgctg cggaactata cagggattca ttagcatttt ggttgcttcg agtcaataat | 960 |
| cactgggtat caccatcaat ttttttgttgg ttttttagatg acgacgaaat ccgtgatcac | 1020 |

-continued

```
atcgaaacaa actacgagga atttgctgcc gtgcttctta atgtgtatcg agctaccgat      1080
cttatgttct ccggcgaagt ccaacttgtc gaagcaagat ctttcgctac caagaatctt      1140
gagaaaatat tagcaacagg aaacatacat aaaactaatg cagatatctc atctagtttg      1200
cataagatga tcgaacacga actaagagtt ccttggaccg caagaatgga ccatgttgaa      1260
aatcgaattt ggatcgaaga aatagcttcc agtgctttat ggtttggaaa atcatcctac      1320
cttaggttat cttgctttca caagatgagt ttacagcaac tcgcggtgaa aaattatacg      1380
cttcgacaat tggtttaccg agacgagctt gcggaagttg agaggtggtc taaagaaaga      1440
gggctatgtg acatgggatt tgtagagag aaaaccgggt attgttacta cgcatttgcg      1500
gcaagtactt gtctgccgtg gagttccgac gtgaggctgg tcctgaccaa ggcggcagtt      1560
gtcattacag tggccgatga tttctttgat gtcgaaggat ctatggttga tctcgaaaaa      1620
ttaacggatg cagttcggag gtgggatgcg aagggttag cagccacag caagacaata      1680 tttgaagccc tggatgatct tgtaaatgaa gttagactca agtgtttcca acaaaatgga      1740
caagacatca aaacaatct ccaacaatta tggtatgaaa cattccattc atggcttatg      1800
gaagctaagt ggggaaaggg gttaacaagt aaaccatctg tagatgtgta tcttggaaat      1860
gcaatgacat ccatagcagc tcacaccatg gtccttacag catcctgtct tctaggtccc      1920
ggtttcccgg ttcaccaact atggtcgcaa aggcgccacc aggacattac atccttgctc      1980
atggtcttga ctcgcttgct aaatgacatt caatcctact tgaaagaaga agacgaagga      2040
aaaataaact atgtatggat gtacatgatc gagaacaatc aagcgtcgat agatgactcg      2100
gttcgacacg tccagacgat aatcaatgta aaaaagcaag aattcatcca acgtgttcta      2160
tcggatcaac attgcaatct cccaaagtca ttcaagcagc tccatttctc ctgcctcaaa      2220
gtattcaaca tgttcttcaa ctcctccaac attttcgaca ctgataccga ccttcttctt      2280
gacattcacg aagcttttgt ttctccacca caagttccca aattcaaacc ccacatcaag      2340
ccacctcatc agcttccagc aacacttcag ccacctcatc agccccaaca ataatggtc      2400 aataagaaga aggtggaaat ggtttacaaa agctatcatc atccattcaa ggttttcacc      2460
ttgcagaaga aacaaagttc gggacatggt acaatgaatc caagggctag tatcttagca      2520
ggacccaaca tcaaactatg tttcagttaa                                      2550
```

<210> SEQ ID NO 98
<211> LENGTH: 1575
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Arabitopsis thaliana (At1LINS)

<400> SEQUENCE: 98

```
atggcgaaca cggcgaagcg tagtatcctg cgtaatgtcc atgcgagcgt tagcaacccg       60
agtaagcagt tcataataa gacgagtctg gaataccctgc atgaactgaa cattaaaaag      120
atcaagaaca ttctgagcgc caatgttgac gtgccgagcg aaaatctgga atgatcgat      180 gtgattcaga gcctgggcat tgacctgcat tttcgccagg aaattgaaca gaccctgcac      240
atgatctaca agaaggcct gcagtttaat ggcgatctgc atgaaattgc ctgcgttttt      300
cgtctgctgc gtcaggaagg ccactacgtc caggaaaata aaaagggcgg ctttaaagat      360
```

```
gttgtgaaga atgacgtgaa aggcctgacg gaactgtttg aagcgagcga actgcgcgtc    420
gaaggcgaag aaacgctgga cggcgcccgc gaatttacct acagccgcct gaatgaactg    480
tgtagcggcc gcgaaagcca tcagaagcag gaaattatga aaagcctggc ccagccccgt    540
cacaaaacgg ttcgcggcct gacgagcaag cgctttacca gcatgattaa atcgcgggc     600 caggaagatc ccgaatggct gcagagcctg ctgcgcgtgg ccgaaatcga cagcattcgc    660
ctgaagagcc tgacccaggg cgaaatgagc cagacgttta atggtggac  cgaactgggc    720 ctggaaaagg atgttgaaaa agcgcgcagc cagccgctga gtggcatac  gtggagcatg    780 aaaattctgc aggatccgac cctgacggaa cagcgcctgg acctgaccaa gcccatcagc    840
ctggtctacg ttatcgatga cattttttgat gtctacggcg aactggaaga actgaccatc    900
tttacgcgcg tcgttgaacg ctgggaccat aaaggcctga gaccctgcc  caaatacatg    960 cgcgtttgtt ttgaagcgct ggatatgatc accacggaaa ttagcatgaa aatctacaag   1020
agccacggct ggaatcccac ctacgccctg cgccagagct gggccagcct gtgcaaggcg   1080
tttctggtgg aagccaaatg gtttaatagc ggctacctgc ccaccacgga gaatacatg    1140 aagaatggcg tggtcagcag cggcgtgcat ctggtcatgc tgcacgcgta cattctgctg   1200
ggcgaagaac tgacgaaaga aaaggtcgaa ctgattgaaa gcaatccggg catcgttagc   1260
agcgcggcca ccattctgcg tctgtgggat gacctgggta gcgccaagga cgaaaatcag   1320
gatggcacgg acggcagcta cgttgaatgt tacctgaatg aatacaaagg cagcacggtt   1380
gatgaagcgc gcacccacgt ggcccagaag attagccgcg cgtggaaacg cctgaatcgc   1440
gaatgtctga atccgtgccc ctttagccgc agctttagca aagcgtgcct gaatatcgcc   1500
cgcacggtgc ccctgatgta tagttatgat gatgaccagc gtctgcccga tgagtatctg   1560
aaaagcctga tgtaa                                                    1575
```

<210> SEQ ID NO 99
<211> LENGTH: 524
<212> TYPE: PRT
<213> ORGANISM: Arabidopsis thaliana

<400> SEQUENCE: 99

Met Ala Asn Thr Ala Lys Arg Ser Ile Leu Arg Asn Val His Ala Ser
1               5                   10                  15

Val Ser Asn Pro Ser Lys Gln Phe His Asn Lys Thr Ser Leu Glu Tyr
            20                  25                  30

Leu His Glu Leu Asn Ile Lys Lys Ile Lys Asn Ile Leu Ser Ala Asn
        35                  40                  45

Val Asp Val Pro Ser Glu Asn Leu Glu Met Ile Asp Val Ile Gln Ser
    50                  55                  60

Leu Gly Ile Asp Leu His Phe Arg Gln Glu Ile Gln Thr Leu His
65                  70                  75                  80

Met Ile Tyr Lys Glu Gly Leu Gln Phe Asn Gly Asp Leu His Glu Ile
                85                  90                  95

Ala Leu Arg Phe Arg Leu Leu Arg Gln Glu Gly His Tyr Val Gln Glu
            100                 105                 110

Asn Lys Lys Gly Gly Phe Lys Asp Val Val Lys Asn Asp Val Lys Gly
        115                 120                 125

Leu Thr Glu Leu Phe Glu Ala Ser Glu Leu Arg Val Glu Gly Glu Glu
    130                 135                 140

Thr Leu Asp Gly Ala Arg Glu Phe Thr Tyr Ser Arg Leu Asn Glu Leu
145                 150                 155                 160

```
Cys Ser Gly Arg Glu Ser His Gln Lys Gln Glu Ile Met Lys Ser Leu
            165                 170                 175

Ala Gln Pro Arg His Lys Thr Val Arg Gly Leu Thr Ser Lys Arg Phe
        180                 185                 190

Thr Ser Met Ile Lys Ile Ala Gly Gln Glu Asp Pro Glu Trp Leu Gln
    195                 200                 205

Ser Leu Leu Arg Val Ala Glu Ile Asp Ser Ile Arg Leu Lys Ser Leu
210                 215                 220

Thr Gln Gly Glu Met Ser Gln Thr Phe Lys Trp Trp Thr Glu Leu Gly
225                 230                 235                 240

Leu Glu Lys Asp Val Glu Lys Ala Arg Ser Gln Pro Leu Lys Trp His
            245                 250                 255

Thr Trp Ser Met Lys Ile Leu Gln Asp Pro Thr Leu Thr Glu Gln Arg
        260                 265                 270

Leu Asp Leu Thr Lys Pro Ile Ser Leu Val Tyr Val Ile Asp Asp Ile
    275                 280                 285

Phe Asp Val Tyr Gly Glu Leu Glu Glu Leu Thr Ile Phe Thr Arg Val
290                 295                 300

Val Glu Arg Trp Asp His Lys Gly Leu Lys Thr Leu Pro Lys Tyr Met
305                 310                 315                 320

Arg Val Cys Phe Glu Ala Leu Asp Met Ile Thr Thr Glu Ile Ser Met
            325                 330                 335

Lys Ile Tyr Lys Ser His Gly Trp Asn Pro Thr Tyr Ala Leu Arg Gln
        340                 345                 350

Ser Trp Ala Ser Leu Cys Lys Ala Phe Leu Val Glu Ala Lys Trp Phe
    355                 360                 365

Asn Ser Gly Tyr Leu Pro Thr Thr Glu Glu Tyr Met Lys Asn Gly Val
370                 375                 380

Val Ser Gly Val His Leu Val Met Leu His Ala Tyr Ile Leu Leu
385                 390                 395                 400

Gly Glu Glu Leu Thr Lys Glu Lys Val Glu Leu Ile Glu Ser Asn Pro
            405                 410                 415

Gly Ile Val Ser Ser Ala Ala Thr Ile Leu Arg Leu Trp Asp Asp Leu
        420                 425                 430

Gly Ser Ala Lys Asp Glu Asn Gln Asp Gly Thr Asp Gly Ser Tyr Val
    435                 440                 445

Glu Cys Tyr Leu Asn Glu Tyr Lys Gly Ser Thr Val Asp Glu Ala Arg
450                 455                 460

Thr His Val Ala Gln Lys Ile Ser Arg Ala Trp Lys Arg Leu Asn Arg
465                 470                 475                 480

Glu Cys Leu Asn Pro Cys Pro Phe Ser Arg Ser Phe Ser Lys Ala Cys
            485                 490                 495

Leu Asn Ile Ala Arg Thr Val Pro Leu Met Tyr Ser Tyr Asp Asp Asp
        500                 505                 510

Gln Arg Leu Pro Asp Glu Tyr Leu Lys Ser Leu Met
    515                 520

<210> SEQ ID NO 100
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: DNA having modified codons, which encodes linalool synthase gene derived from Arabitopsis thaliana (At2LINS)

<400> SEQUENCE: 100

```
atgcgtcgta gtgcgaatta ccagccgagt cgttgggacc atcatcacct gctgagtgtg      60
gagaataagt ttgcgaagga caagcgtgtc cgcgaacgcg acctgctgaa agaaaaggtt     120
cgcaaaatgc tgaatgacga acagaagacc tacctggatc agctggaatt tattgatgac     180
ctgcagaaac tgggcgtcag ctaccatttt gaagccgaaa ttgataatat cctgaccagc     240
agctacaaaa aggaccgcac gaatatccag gaaagcgatc tgcatgccac ggcgctggaa     300
tttcgcctgt tcgccagca cggctttaat gttagcgaag atgtgtttga cgtctttatg     360
gaaaattgtg gcaagtttga ccgcgatgac atctacggcc tgattagcct gtacgaagcc     420
agctacctga gcaccaaact ggataagaat ctgcagattt ttattcgtcc ctttgccacc     480
cagcagctgc gtgattttgt tgacacgcat agcaatgaag attttggcag ctgcgacatg     540
gtggaaattg ttgtgcaggc cctggacatg ccctactact ggcagatgcg ccgcctgagc     600
acccgttggt acatcgatgt gtacggcaaa cgccagaatt acaagaatct ggtcgttgtg     660
gaatttgcca aaatcgactt taatattgtg caggcgatcc accaggaaga actgaaaaat     720
gtcagcagtt ggtggatgga accggcctg gcaagcagc tgtactttgc gcgcgatcgc      780
attgtcgaaa attacttttg gacgattggc cagatccagg aaccgcagta cggctacgtt     840
cgccagacca tgacgaagat caatgccctg ctgaccacga ttgatgacat ctacgatatt     900
tacggcaccc tggaagaact gcagctgttt acggttgcgt ttgaaaattg ggatattaat     960
cgcctggacg aactgccgga atacatgcgc ctgtgttttc tggttatcta caatgaagtg    1020
aatagcattg cctgcgaaat cctgcgcacc aagaacatca acgtgatccc ctttctgaaa    1080
aagagctgga cggacgtgag caaagcctac ctggtcgaag cgaaatggta caagagcggc    1140
cataagccga atctgaaga atacatgcag aatgcgcgca ttagcatcag cagccccacc    1200
atctttgtcc attttttactg tgtttttagc gatcagctga gcatccaggt gctggaaacg    1260
ctgagccagc accagcagaa tgtcgttcgc tgcagcagca gcgttttttcg cctggccaat    1320
gatctggtga ccagccccga tgaactggcc cgcggcgatg tgtgtaaaag cattcagtgc    1380
tacatgagcg aaacgggtgc cagcgaagat aaggcccgca gccatgtccg ccagatgatc    1440
aatgatctgt gggacgaaat gaattacgaa aaaatggccc acagcagcag cattctgcat    1500
cacgacttta tggaaaccgt tatcaatctg gcgcgcatga ccagtgtat gtaccagtac    1560
ggtgatggtc atggcagccc cgaaaaagcc aaaatcgtgg accgtgtgat gagcctgctg    1620
tttaacccta tcccgctgga ctaa                                            1644
```

<210> SEQ ID NO 101
<211> LENGTH: 547
<212> TYPE: PRT
<213> ORGANISM: Arabidopsis thaliana

<400> SEQUENCE: 101

```
Met Arg Arg Ser Ala Asn Tyr Gln Pro Ser Arg Trp Asp His His His
1               5                   10                  15

Leu Leu Ser Val Glu Asn Lys Phe Ala Lys Asp Lys Arg Val Arg Glu
                20                  25                  30

Arg Asp Leu Leu Lys Glu Lys Val Arg Lys Met Leu Asn Asp Glu Gln
            35                  40                  45

Lys Thr Tyr Leu Asp Gln Leu Glu Phe Ile Asp Asp Leu Gln Lys Leu
```

```
                50                  55                  60
Gly Val Ser Tyr His Phe Glu Ala Glu Ile Asp Asn Ile Leu Thr Ser
 65                  70                  75                  80

Ser Tyr Lys Lys Asp Arg Thr Asn Ile Gln Glu Ser Asp Leu His Ala
                     85                  90                  95

Thr Ala Leu Glu Phe Arg Leu Phe Arg Gln His Gly Phe Asn Val Ser
                100                 105                 110

Glu Asp Val Phe Asp Val Phe Met Glu Asn Cys Gly Lys Phe Asp Arg
                115                 120                 125

Asp Asp Ile Tyr Gly Leu Ile Ser Leu Tyr Glu Ala Ser Tyr Leu Ser
            130                 135                 140

Thr Lys Leu Asp Lys Asn Leu Gln Ile Phe Ile Arg Pro Phe Ala Thr
145                 150                 155                 160

Gln Gln Leu Arg Asp Phe Val Asp Thr His Ser Asn Glu Asp Phe Gly
                165                 170                 175

Ser Cys Asp Met Val Glu Ile Val Val Gln Ala Leu Asp Met Pro Tyr
                180                 185                 190

Tyr Trp Gln Met Arg Arg Leu Ser Thr Arg Trp Tyr Ile Asp Val Tyr
                195                 200                 205

Gly Lys Arg Gln Asn Tyr Lys Asn Leu Val Val Glu Phe Ala Lys
                210                 215                 220

Ile Asp Phe Asn Ile Val Gln Ala Ile His Gln Glu Leu Lys Asn
225                 230                 235                 240

Val Ser Ser Trp Trp Met Glu Thr Gly Leu Gly Lys Gln Leu Tyr Phe
                    245                 250                 255

Ala Arg Asp Arg Ile Val Glu Asn Tyr Phe Trp Thr Ile Gly Gln Ile
                260                 265                 270

Gln Glu Pro Gln Tyr Gly Tyr Val Arg Gln Thr Met Thr Lys Ile Asn
                275                 280                 285

Ala Leu Leu Thr Thr Ile Asp Asp Ile Tyr Asp Ile Tyr Gly Thr Leu
                290                 295                 300

Glu Glu Leu Gln Leu Phe Thr Val Ala Phe Glu Asn Trp Asp Ile Asn
305                 310                 315                 320

Arg Leu Asp Glu Leu Pro Glu Tyr Met Arg Leu Cys Phe Leu Val Ile
                325                 330                 335

Tyr Asn Glu Val Asn Ser Ile Ala Cys Glu Ile Leu Arg Thr Lys Asn
                340                 345                 350

Ile Asn Val Ile Pro Phe Leu Lys Lys Ser Trp Thr Asp Val Ser Lys
                355                 360                 365

Ala Tyr Leu Val Glu Ala Lys Trp Tyr Lys Ser Gly His Lys Pro Asn
                370                 375                 380

Leu Glu Glu Tyr Met Gln Asn Ala Arg Ile Ser Ile Ser Ser Pro Thr
385                 390                 395                 400

Ile Phe Val His Phe Tyr Cys Val Phe Ser Asp Gln Leu Ser Ile Gln
                405                 410                 415

Val Leu Glu Thr Leu Ser Gln His Gln Asn Val Val Arg Cys Ser
                420                 425                 430

Ser Ser Val Phe Arg Leu Ala Asn Asp Leu Val Thr Ser Pro Asp Glu
                435                 440                 445

Leu Ala Arg Gly Asp Val Cys Lys Ser Ile Gln Cys Tyr Met Ser Glu
450                 455                 460

Thr Gly Ala Ser Glu Asp Lys Ala Arg Ser His Val Arg Gln Met Ile
465                 470                 475                 480
```

```
Asn Asp Leu Trp Asp Glu Met Asn Tyr Glu Lys Met Ala His Ser Ser
            485                 490                 495

Ser Ile Leu His His Asp Phe Met Glu Thr Val Ile Asn Leu Ala Arg
            500                 505                 510

Met Ser Gln Cys Met Tyr Gln Tyr Gly Asp Gly His Gly Ser Pro Glu
            515                 520                 525

Lys Ala Lys Ile Val Asp Arg Val Met Ser Leu Leu Phe Asn Pro Ile
            530                 535                 540

Pro Leu Asp
545

<210> SEQ ID NO 102
<211> LENGTH: 1698
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Citrus unshiu (Cu1LINS)

<400> SEQUENCE: 102
atgctgtttc aggtgagcgc cagtcccaat aaggtgatcc gtattaacgc cgagaaggag      60
agtacccgtc gtagtgccaa ctttgacccg acgatttggg gcgattactt tctgagctac     120
accggcgatt ttaaagaaag cggcgacgcc agcgtcaagc atcaggaact gaaaaaggaa     180
attcgcacga tgctgcgcgc ggatatcaat aaacccaccc agacgaagct ggacctgatt     240
gatgacatcc agcgcctggg cgtgagctac catttgaaaa gcgaaattga cgaaatcctg     300
cgcaaaatgc acgaagccaa tcaggattgt gacctgggcg atgacgaaaa tgtgcaggaa     360
ctgtactaca ttagcctgca ttttcgcctg ctgcgccaga tggctacaa atcagcgcg     420 gatgtcttta tagctttaa ggacagcaat ggcaatttta aaagctttct gaagcgcgat     480
attcgcggca tgctgagcct gtacgaagcc gcgcatctgc gcgttcacgg cgaaaatatc     540
ctgaatgaag ccctgacctt tacggtgacc cacctggaaa gctttacgag ccagagcaat     600
acgcagctgg cggcccaggt taatcgtgcc ctgaatcgcc cgattcgcaa agcctgccc     660 cgcctggaag cgaagcatta catgccgatc taccagaaag atcccagcca aataaggac     720 ctgctgacgt ttgcgatgct ggattttaat attctgcaga acagcacca ggaagaactg     780 cgcgatatcg tgcgttggtg gaaaaatttt gacgtcccga ataagctgcc ctttattcgc     840
gaccgcgttg tggaaggcta cttttggatc ctgggcgtct actttgaacc gaagtttctg     900
ctggcccgca aaattctgac caaggttatc agcatggcca gcattatcga tgacattac     960 gatgcgtacg gcacgatcga agaactggaa ctgtttgcca ccgcgattga acgctgggat    1020
ctgagcgcga tcgacctgct gcccgaatac atgaaactgt gttactgcgc cctgctggat    1080
gcgtacagcg aatttgaaaa agacctgcc agcaagggca ttctgtacgg cctgccgttt    1140
gcgaaagaaa gcatgaagat cctggtgcgc agctacatta tcgaagcccg ctggtgtgat    1200
cagcagtacg ttcccacgat ggaagaatac atgcgtgtgg ccctgctgag ctgtggttac    1260
ctgctgctga gcacgagcag ctttctgggc atggaagaca ttgttaccaa gaagccttt    1320 gaatgggtca gcggcaatcc gaagattgtt caggcgagca gcattatctg tcgcctgatg    1380
gatgacatcg tgagccataa atttgaacag cagcgcggtc atgttgccag cgccgtggaa    1440
tgctacatga gcagcatgg cgtgagcgaa gaagaagccg tgaaagtctt cgcgaaaag    1500
```

```
gtcggcaatg cgtggaaaga tatcaatgaa gaactgatgc gcccgcccgt tgttcccatg   1560
cctctgctgg aacgcgtcct gaatctggcc cgcctgatgg atgttctgta ccagaataat   1620
gacagctaca ccaatccgca cctgatgaag gaccatgttg ccgccctgct gaaagaccct   1680
gtgttttttg aggactaa                                                 1698
```

<210> SEQ ID NO 103
<211> LENGTH: 565
<212> TYPE: PRT
<213> ORGANISM: Citrus unshiu

<400> SEQUENCE: 103

```
Met Leu Phe Gln Val Ser Ala Ser Pro Asn Lys Val Ile Arg Ile Asn
1               5                   10                  15

Ala Glu Lys Glu Ser Thr Arg Arg Ser Ala Asn Phe Asp Pro Thr Ile
            20                  25                  30

Trp Gly Asp Tyr Phe Leu Ser Tyr Thr Gly Asp Phe Lys Glu Ser Gly
        35                  40                  45

Asp Ala Ser Val Lys His Gln Glu Leu Lys Lys Glu Ile Arg Thr Met
    50                  55                  60

Leu Arg Ala Asp Ile Asn Lys Pro Thr Gln Thr Lys Leu Asp Leu Ile
65                  70                  75                  80

Asp Asp Ile Gln Arg Leu Gly Val Ser Tyr His Phe Glu Ser Glu Ile
                85                  90                  95

Asp Glu Ile Leu Arg Lys Met His Glu Ala Asn Gln Asp Cys Asp Leu
            100                 105                 110

Gly Asp Asp Glu Asn Val Gln Glu Leu Tyr Tyr Ile Ser Leu His Phe
        115                 120                 125

Arg Leu Leu Arg Gln Asn Gly Tyr Lys Ile Ser Ala Asp Val Phe Asn
    130                 135                 140

Ser Phe Lys Asp Ser Asn Gly Asn Phe Lys Ser Phe Leu Lys Arg Asp
145                 150                 155                 160

Ile Arg Gly Met Leu Ser Leu Tyr Glu Ala Ala His Leu Arg Val His
                165                 170                 175

Gly Glu Asn Ile Leu Asn Glu Ala Leu Thr Phe Thr Val Thr His Leu
            180                 185                 190

Glu Ser Phe Thr Ser Gln Ser Asn Thr Gln Leu Ala Ala Gln Val Asn
        195                 200                 205

Arg Ala Leu Asn Arg Pro Ile Arg Lys Ser Leu Pro Arg Leu Glu Ala
    210                 215                 220

Lys His Tyr Met Pro Ile Tyr Gln Lys Asp Pro Ser His Asn Lys Asp
225                 230                 235                 240

Leu Leu Thr Phe Ala Met Leu Asp Phe Asn Ile Leu Gln Lys Gln His
                245                 250                 255

Gln Glu Glu Leu Arg Asp Ile Val Arg Trp Trp Lys Asn Phe Asp Val
            260                 265                 270

Pro Asn Lys Leu Pro Phe Ile Arg Asp Arg Val Val Glu Gly Tyr Phe
        275                 280                 285

Trp Ile Leu Gly Val Tyr Phe Glu Pro Lys Phe Leu Leu Ala Arg Lys
    290                 295                 300

Ile Leu Thr Lys Val Ile Ser Met Ala Ser Ile Ile Asp Asp Ile Tyr
305                 310                 315                 320

Asp Ala Tyr Gly Thr Ile Glu Glu Leu Glu Leu Phe Ala Thr Ala Ile
                325                 330                 335
```

Glu Arg Trp Asp Leu Ser Ala Ile Asp Leu Pro Glu Tyr Met Lys
            340                 345                 350

Leu Cys Tyr Cys Ala Leu Leu Asp Ala Tyr Ser Glu Phe Glu Lys Asp
        355                 360                 365

Leu Ala Ser Lys Gly Ile Leu Tyr Gly Leu Pro Phe Ala Lys Glu Ser
370                 375                 380

Met Lys Ile Leu Val Arg Ser Tyr Ile Ile Glu Ala Arg Trp Cys Asp
385                 390                 395                 400

Gln Gln Tyr Val Pro Thr Met Glu Glu Tyr Met Arg Val Ala Leu Leu
            405                 410                 415

Ser Cys Gly Tyr Leu Leu Leu Ser Thr Ser Ser Phe Leu Gly Met Glu
            420                 425                 430

Asp Ile Val Thr Lys Glu Ala Phe Glu Trp Val Ser Gly Asn Pro Lys
            435                 440                 445

Ile Val Gln Ala Ser Ser Ile Ile Cys Arg Leu Met Asp Asp Ile Val
        450                 455                 460

Ser His Lys Phe Glu Gln Gln Arg Gly His Val Ala Ser Ala Val Glu
465                 470                 475                 480

Cys Tyr Met Lys Gln His Gly Val Ser Glu Glu Ala Val Lys Val
                485                 490                 495

Phe Arg Glu Lys Val Gly Asn Ala Trp Lys Asp Ile Asn Glu Glu Leu
            500                 505                 510

Met Arg Pro Pro Val Val Pro Met Pro Leu Leu Glu Arg Val Leu Asn
            515                 520                 525

Leu Ala Arg Leu Met Asp Val Leu Tyr Gln Asn Asn Asp Ser Tyr Thr
530                 535                 540

Asn Pro His Leu Met Lys Asp His Val Ala Ala Leu Leu Lys Asp Pro
545                 550                 555                 560

Val Phe Phe Glu Asp
            565

<210> SEQ ID NO 104
<211> LENGTH: 1746
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Citrus unshiu (Cu2LINS)

<400> SEQUENCE: 104
atggcgttta gcagcaagga catcagtagc gacagcagtc acattcattt tatcccgaag      60
cacatcagta aggttggtaa tcgtaacctg aataatatta atagcctgct gccgaacaac     120
aaaaagggca gcatcaacga taacatcggc gtcagcgccc gcctgaaacg ctttacctac     180
cccagcgaac atagcagcaa ctttaacgat gacatccata tcaagcacgc caaaaagctg     240
gaagttatta acacattgct gatcaagctg ggcgatgacg atagctttga aggcctggcg     300
atgattgacg ttgtgcagcg cctgggcatc gactactact tcaggatga aattgaactg      360 atcctgcgtc gccagtacag cattttcttt acggacggcg atcgctacaa tgatctgcag     420
gaagttgcgc tgcgtttttcg tctgctgcgt cagcagggct actacgtgag cgcggacgtc     480
tttaatcgct ttcgcaacaa agaaggcgaa tttaagcaga acatcagcga agatatcaat     540
ggcctgatga gcctgtacga agcgagccag ctgagcatcg gcggcgaaga tggcctggat     600

-continued

```
gaagccggcc attttagcgc cacccacctg gcgaattacg atctggcggg cgtcgttgaa    660
catctgctgc tgtacccgta ccgcaaaagc ctgagccccg ccaagaattt ctttcacggc    720
aattttcagg gcagcgaata catttggatc ctggacctgc aggaactggc gaatatggat    780
tttaaactgg tgcagagcct gcatcagaag gaaattgtcc agatcagcag ttggtggcgc    840
gaactgggcc tggcgaaaaa gctggaattt gcccgcgaac agccggttaa atggtacgtt    900
tggagcatgg cctgttttac cgacccgaat ctgagctggc agcgcattga actgacgaaa    960
cccatcagct ttgtttacat catcgacgat atctttttacg tgtgtggtgc cctggatgcc   1020
ctgaccctgt ttacggaacc gattaatcgc tgggatctgg cgacatcga tcagctgccc   1080 gaatacatga agatttgttt taaggcgctg aacgatatca ccaatgaaat cagcaaacag   1140
ggcgtgcagc gcagcatggg cattaccctg tgtacgccgc tgcgtaaggg cgttggcgaa   1200
gtgctgtgca atgcctttct gatcgaagcc aaatggtttg cgagcggcca tctgcccaag   1260
gcggaagaat acctgaaaaa tggcattgtc agcagcggcg ttcatctggt gctggtccac   1320
attttctttc tgctgggcca cggcatcacc aatgaaacgg tccagctgat tgatagcaat   1380
ccgcccatcg tcagcagcgt tgcgacgatt ctgcgcatct gggacgatct gggcagcgcc   1440
aaagacgaaa atcagggcgg caaggatggc agctacattt actactacat gatggaacac   1500
cgcgacctga ccgccgaaga tgcgcataaa cacgcgatgg acaagatcag cgatgcctgg   1560
aaacgcctga ataaggaatg tctgagcccg aatcccttta gcgccagctt tacgcgcgcg   1620
agctttaatt gcgcccgcat ggtgccgctg atgtacagct acgacgatag ccagcgcctg   1680
cccagcctgg aagaatacat taagagcagt ctgtttgaca atctgcctac gcagggtgtt   1740
tactaa                                                              1746
```

<210> SEQ ID NO 105
<211> LENGTH: 581
<212> TYPE: PRT
<213> ORGANISM: Citrus unshiu

<400> SEQUENCE: 105

```
Met Ala Phe Ser Ser Lys Asp Ile Ser Ser Asp Ser His Ile His
1               5                   10                  15

Phe Ile Pro Lys His Ile Ser Lys Val Gly Asn Arg Asn Leu Asn Asn
                20                  25                  30

Ile Asn Ser Leu Leu Pro Asn Asn Lys Lys Gly Ser Ile Asn Asp Asn
            35                  40                  45

Ile Gly Val Ser Ala Arg Leu Lys Arg Phe Thr Tyr Pro Ser Glu His
        50                  55                  60

Ser Ser Asn Phe Asn Asp Asp Ile His Ile Lys His Ala Lys Lys Leu
65                  70                  75                  80

Glu Val Ile Lys His Ile Leu Ile Lys Leu Gly Asp Asp Ser Phe
                85                  90                  95

Glu Gly Leu Ala Met Ile Asp Val Val Gln Arg Leu Gly Ile Asp Tyr
                100                 105                 110

Tyr Phe Gln Asp Glu Ile Glu Leu Ile Leu Arg Arg Gln Tyr Ser Ile
            115                 120                 125

Phe Phe Thr Asp Gly Asp Arg Tyr Asn Asp Leu Gln Glu Val Ala Leu
        130                 135                 140

Arg Phe Arg Leu Leu Arg Gln Gln Gly Tyr Tyr Val Ser Ala Asp Val
145                 150                 155                 160
```

```
Phe Asn Arg Phe Arg Asn Lys Glu Gly Glu Phe Lys Gln Asn Ile Ser
            165                 170                 175

Glu Asp Ile Asn Gly Leu Met Ser Leu Tyr Glu Ala Ser Gln Leu Ser
        180                 185                 190

Ile Gly Gly Glu Asp Gly Leu Asp Glu Ala Gly His Phe Ser Ala Thr
            195                 200                 205

His Leu Ala Asn Tyr Asp Leu Ala Gly Val Val Glu His Leu Leu Leu
        210                 215                 220

Tyr Pro Tyr Arg Lys Ser Leu Ser Pro Ala Lys Asn Phe Phe His Gly
225                 230                 235                 240

Asn Phe Gln Gly Ser Glu Tyr Ile Trp Ile Leu Asp Leu Gln Glu Leu
                245                 250                 255

Ala Asn Met Asp Phe Lys Leu Val Gln Ser Leu His Gln Lys Glu Ile
            260                 265                 270

Val Gln Ile Ser Ser Trp Trp Arg Glu Leu Gly Leu Ala Lys Lys Leu
        275                 280                 285

Glu Phe Ala Arg Glu Gln Pro Val Lys Trp Tyr Val Trp Ser Met Ala
    290                 295                 300

Cys Phe Thr Asp Pro Asn Leu Ser Trp Gln Arg Ile Glu Leu Thr Lys
305                 310                 315                 320

Pro Ile Ser Phe Val Tyr Ile Ile Asp Asp Ile Phe Tyr Val Cys Gly
                325                 330                 335

Ala Leu Asp Ala Leu Thr Leu Phe Thr Glu Pro Ile Asn Arg Trp Asp
            340                 345                 350

Leu Gly Asp Ile Asp Gln Leu Pro Glu Tyr Met Lys Ile Cys Phe Lys
        355                 360                 365

Ala Leu Asn Asp Ile Thr Asn Glu Ile Ser Lys Gln Gly Val Gln Arg
    370                 375                 380

Ser Met Gly Ile Thr Leu Cys Thr Pro Leu Arg Lys Gly Val Gly Glu
385                 390                 395                 400

Val Leu Cys Asn Ala Phe Leu Ile Glu Ala Lys Trp Phe Ala Ser Gly
                405                 410                 415

His Leu Pro Lys Ala Glu Glu Tyr Leu Glu Asn Gly Ile Val Ser Ser
            420                 425                 430

Gly Val His Leu Val Leu Val His Ile Phe Phe Leu Leu Gly His Gly
        435                 440                 445

Ile Thr Asn Glu Thr Val Gln Leu Ile Asp Ser Asn Pro Pro Ile Val
    450                 455                 460

Ser Ser Val Ala Thr Ile Leu Arg Ile Trp Asp Asp Leu Gly Ser Ala
465                 470                 475                 480

Lys Asp Glu Asn Gln Gly Gly Lys Asp Gly Ser Tyr Ile Tyr Tyr Tyr
                485                 490                 495

Met Met Glu His Arg Asp Leu Thr Ala Glu Asp Ala His Lys His Ala
            500                 505                 510

Met Asp Lys Ile Ser Asp Ala Trp Lys Arg Leu Asn Lys Glu Cys Leu
        515                 520                 525

Ser Pro Asn Pro Phe Ser Ala Ser Phe Thr Arg Ala Ser Phe Asn Cys
    530                 535                 540

Ala Arg Met Val Pro Leu Met Tyr Ser Tyr Asp Asp Ser Gln Arg Leu
545                 550                 555                 560

Pro Ser Leu Glu Glu Tyr Ile Lys Ser Ser Leu Phe Asp Asn Leu Pro
                565                 570                 575

Thr Gln Gly Val Tyr
```

<210> SEQ ID NO 106
<211> LENGTH: 1767
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Citrus unshiu (Cu3LINS)

<400> SEQUENCE: 106

```
atggcgttta gtagcagtag ccgtgcgaag ctgagtgcga cgagtcacat tagcaaagcc      60
cctgataaga ttagcaagac gagccgtccg agcctgattg aatttacgcc gagccccacc     120
atttaccaga aaggctgtat cacgagcgat aataccgtcg cgagcccgcc cctgaagcat     180
tttacgcaca ccacgcgcca tcccagcttt ttcgatcacg acattcaggt cgaacatagc     240
cgcaagctga aggaatttaa gcatatcttt agcctggttg cggcaatag ctttgaaggc      300
ctggtgatga ttgatgccgt ccagcgcctg cgcatcgaat acctgtttaa ggacgaaatt     360
gaagaaatcc tgcagcgcca gtacattatc agcagcacgt gtggtggcca tctgcacgat     420
ctgcaggaag ttgcgctgcg ctttcgcctg ctgcgccagg aaggctacta cgtgccggcc     480
gatatgttta caactttcg catcaaagaa ggccgcttta ccgcattaa tgtcagcgaa       540
gacatcggca ccctgatgga gtttacgaa gcgagccagc tgagcatcgc cggcgaagaa      600
ggcctggatg aagccggcca ctttagcgcg aagatgctga tgaatgcat gacgcatctg      660
gaccattacc acgccctggc gatcggcaat accctgcgcc atccgtacca caaaagcctg    720
ccccgcttta tggccaagga tgtgtttctg agcaattttc agggcgaacg ccgcctgcac     780
gtgctgaagg aaatcgcgaa aaaggacttt aacatggtcc aggccctgca tcagaaggaa    840
atcgttcagg tgacgaaatg gtggaaggat ctgggcctga ccaaaaagct gccgtttgcg     900
cgcgaccagc ccctgaaatg gtacatttgg agcatggcct gtctgacgga tccgagcctg    960
agcgaacagc gcgtggaact gaccaagccc attagcctga tctacattat cgatgacatc   1020
tttgatgtct acggcacgct ggacgaactg attctgttta ccgaaacgat cacgcgttgg   1080
gacctggcgg ccatgggtca gctgccggaa tacatgaaaa tttgtttta ggcgctggat    1140
gacattacga atgaaatcag ctgcaaagtt tacaaaaagc acggctacaa tccggtgcag   1200
agcctgcgca tgcgtggac cagcctgtgc aaagcctttc tggttgaagc caagtggttt    1260
gcgagcggcc atatgcccga agccgaagaa tacctgcgca tggcatcga aagcagcggc    1320
gtccatgttg ccctggcgca cttttctctt ctgctgggcc acggcattac gaaagaaacc   1380
gtggaactga tcgatggcaa tcccgcgatt atcagcagca cggccaccat tctgcgtctg   1440
tgggatgacc tgggtagcgc caaagatgaa aatcaggaag gcaaggacgg cagctacatc   1500
cactactaca tgaaagaaca tcgctacagc gccgcgaaag aagcccagaa aagcgcgatt   1560
aataagatca gcgacgcctg gaaacgcctg aataaggaat gtctgtgccc gaatccttt    1620
agcgccagct ttacgcgtgc cagcctgaat ctggcccgta tggttccgct gatgtacagc   1680
tacgatgaca atcagcgcct gcccagcctg gaacattaca ttaagagcct gctgtttgag   1740
agcgtgccta cggagggcgt ctactaa                                       1767
```

<210> SEQ ID NO 107
<211> LENGTH: 588

<212> TYPE: PRT
<213> ORGANISM: Citrus unshiu

<400> SEQUENCE: 107

```
Met Ala Phe Ser Ser Ser Arg Ala Lys Leu Ser Ala Thr Ser His
1               5                   10                  15

Ile Ser Lys Ala Pro Asp Lys Ile Ser Lys Thr Ser Arg Pro Ser Leu
                20                  25                  30

Ile Glu Phe Thr Pro Ser Pro Thr Ile Tyr Gln Lys Gly Cys Ile Thr
            35                  40                  45

Ser Asp Asn Thr Val Ala Ser Pro Pro Leu Lys His Phe Thr His Thr
        50                  55                  60

Thr Arg His Pro Ser Phe Phe Asp His Asp Ile Gln Val Glu His Ser
65              70                  75                  80

Arg Lys Leu Lys Glu Phe Lys His Ile Phe Ser Leu Val Gly Gly Asn
                85                  90                  95

Ser Phe Glu Gly Leu Val Met Ile Asp Ala Val Gln Arg Leu Arg Ile
            100                 105                 110

Glu Tyr Leu Phe Lys Asp Glu Ile Glu Glu Ile Leu Gln Arg Gln Tyr
        115                 120                 125

Ile Ile Ser Ser Thr Cys Gly Gly His Leu His Asp Leu Gln Glu Val
130                 135                 140

Ala Leu Arg Phe Arg Leu Leu Arg Gln Glu Gly Tyr Tyr Val Pro Ala
145                 150                 155                 160

Asp Met Phe Asn Asn Phe Arg Ile Lys Glu Gly Arg Phe Ser Arg Ile
                165                 170                 175

Asn Val Ser Glu Asp Ile Gly Thr Leu Met Glu Val Tyr Glu Ala Ser
            180                 185                 190

Gln Leu Ser Ile Ala Gly Glu Gly Leu Asp Glu Ala Gly His Phe
        195                 200                 205

Ser Ala Lys Met Leu Asn Glu Cys Met Thr His Leu Asp His Tyr His
210                 215                 220

Ala Leu Ala Ile Gly Asn Thr Leu Arg His Pro Tyr His Lys Ser Leu
225                 230                 235                 240

Pro Arg Phe Met Ala Lys Asp Val Phe Leu Ser Asn Phe Gln Gly Glu
                245                 250                 255

Arg Arg Leu His Val Leu Lys Glu Ile Ala Lys Lys Asp Phe Asn Met
            260                 265                 270

Val Gln Ala Leu His Gln Lys Glu Ile Val Gln Val Thr Lys Trp Trp
        275                 280                 285

Lys Asp Leu Gly Leu Thr Lys Lys Leu Pro Phe Ala Arg Asp Gln Pro
290                 295                 300

Leu Lys Trp Tyr Ile Trp Ser Met Ala Cys Leu Thr Asp Pro Ser Leu
305                 310                 315                 320

Ser Glu Gln Arg Val Glu Leu Thr Lys Pro Ile Ser Leu Ile Tyr Ile
                325                 330                 335

Ile Asp Asp Ile Phe Asp Val Tyr Gly Thr Leu Asp Glu Leu Ile Leu
            340                 345                 350

Phe Thr Glu Thr Ile Thr Arg Trp Asp Leu Ala Ala Met Gly Gln Leu
        355                 360                 365

Pro Glu Tyr Met Lys Ile Cys Phe Lys Ala Leu Asp Asp Ile Thr Asn
370                 375                 380

Glu Ile Ser Cys Lys Val Tyr Lys Lys His Gly Tyr Asn Pro Val Gln
385                 390                 395                 400
```

```
Ser Leu Arg Asn Ala Trp Thr Ser Leu Cys Lys Ala Phe Leu Val Glu
            405                 410                 415

Ala Lys Trp Phe Ala Ser Gly His Met Pro Glu Ala Glu Tyr Leu
        420                 425                 430

Arg Asn Gly Ile Glu Ser Ser Gly Val His Val Ala Leu Ala His Phe
            435                 440                 445

Phe Phe Leu Leu Gly His Gly Ile Thr Lys Glu Thr Val Glu Leu Ile
        450                 455                 460

Asp Gly Asn Pro Ala Ile Ile Ser Ser Thr Ala Thr Ile Leu Arg Leu
465                 470                 475                 480

Trp Asp Asp Leu Gly Ser Ala Lys Asp Glu Asn Gln Glu Gly Lys Asp
                485                 490                 495

Gly Ser Tyr Ile His Tyr Tyr Met Lys Glu His Arg Tyr Ser Ala Ala
            500                 505                 510

Glu Glu Ala Gln Lys Ser Ala Ile Asn Lys Ile Ser Asp Ala Trp Lys
        515                 520                 525

Arg Leu Asn Lys Glu Cys Leu Cys Pro Asn Pro Phe Ser Ala Ser Phe
            530                 535                 540

Thr Arg Ala Ser Leu Asn Leu Ala Arg Met Val Pro Leu Met Tyr Ser
545                 550                 555                 560

Tyr Asp Asp Asn Gln Arg Leu Pro Ser Leu Glu His Tyr Ile Lys Ser
                565                 570                 575

Leu Leu Phe Glu Ser Val Pro Thr Glu Gly Val Tyr
            580                 585
```

<210> SEQ ID NO 108
<211> LENGTH: 1704
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA having modified codons, which encodes linalool synthase gene derived from Malus domestica (MdLINS)

<400> SEQUENCE: 108

```
atggagttta gcattagcca gagtagtttt gcgaccagta gcagcacgcc cgccgcccct    60
gagcacctga gcagccagaa gtggagtatt cccgaagatc atagcctgct gagcaccccg   120
ctgaaaccgc tgaatagcaa aaccaagtac acgagcagca aggacggcat catttgtttt   180
cagaacgaac agaagctgga tgacctgcgc catgcgctga ttaaggttgg cggcgaagcc   240
gtggaaagcc tggatatgat cgacgcggtt cagcgcctgg gcctggatta ccactttgaa   300
gaagaaattg accagatcct gcagaaacag catattatca gcagcacgac cgcccatggt   360
gcccatcacc ccaccgatct gcatgaagtt gccctgcgtt ttcgtctgct cgtcagcac    420 ggctactttg tgagcgatga cgtctttaac aactttaaga accgcgaagg caactttaat   480
cagatgctgc gcgaagacat taagggcctg atgagcctgt acgaagcgag ccagctgagc   540
atcgaaggcg aagttgtgct ggaagaagcc ggcaaattta gcggccattt tctgaatagc   600
agcctgagcc acctggatca tcaccaggcg cgcgtcgttg caatacccct gcgcaatccc   660
catcacaaaa gcctggcccc gtttatggcg aagaatttct tgtcagcag  cttcagggc    720 acgaataatc gctggctgaa tattctgcag accgtggcga aacgggatct gaatatggtc   780
cagagcctgc atcagaagga agtcgcccag gttagcaaat ggtggaagga actgggcctg   840
```

```
tgtaaagaac tgaagtttgc gcgcgatcag cccattaaat ggtacatctg gagcatggcc    900
tgcctgacca atcccaatct gagcgacgaa cgcatcgaac tgacgaagcc gattagcttt    960
atctacctga ttgatgacat ctttgatgtg tacggcaccc tggacgaact gaccctgttt   1020
acggaagtgg tcaatcgctg ggaaattggc agcatcgaac acctgccgga ttacatgaaa   1080
atttgtttta aggcgctgta cgacatgacc aatgaaatca gctgcaaagt ctaccagaag   1140
catggctgga atcccctgca cagcctgaaa aagacgtggg ccagcctgtg caatgcgttt   1200
ctggttgaag ccaaatggtt taagagcggc catctgccga tggccgaaga atacctgaaa   1260
aatggcatta tcagcagcgg cgtcaatgtt gtgatggttc acattttctt tctgctgggc   1320
gaaggcatca ccaatcagag cgtggaattt ctgaatggca ccccggcgat tatcagcagc   1380
accgcggcca ttctgcgcct gtgggatgac ctgggtagcg ccaaggatga aaatcaggac   1440
ggcgatgacg gcagctacgt caaactgtac ctgaatgaac atcagggcaa gaccatggaa   1500
gaagcccagg aacacgttac gaatatgatc agcgaagaat ggaaaaagct gaataaagaa   1560
ctggtgagcc ccaatcccct gcccgcggcc tttaccaagg ccagcctgaa tctggcccgc   1620
atggttccgc tgatgtacag ctacgacgat aatcagtgtc tgccgagtct ggatgagtac   1680
atgaagagta tgctgcacgc ctaa                                          1704
```

<210> SEQ ID NO 109
<211> LENGTH: 567
<212> TYPE: PRT
<213> ORGANISM: Malus domestica

<400> SEQUENCE: 109

```
Met Glu Phe Ser Ile Ser Gln Ser Ser Phe Ala Thr Ser Ser Ser Thr
1               5                   10                  15

Pro Ala Ala Pro Glu His Leu Ser Ser Gln Lys Trp Ser Ile Pro Glu
            20                  25                  30

Asp His Ser Leu Leu Ser Thr Pro Leu Lys Pro Leu Asn Ser Lys Thr
        35                  40                  45

Lys Tyr Thr Ser Ser Lys Asp Gly Ile Ile Cys Phe Gln Asn Glu Gln
    50                  55                  60

Lys Leu Asp Asp Leu Arg His Ala Leu Ile Lys Val Gly Gly Glu Ala
65                  70                  75                  80

Val Glu Ser Leu Asp Met Ile Asp Ala Val Gln Arg Leu Gly Leu Asp
                85                  90                  95

Tyr His Phe Glu Glu Glu Ile Asp Gln Ile Leu Gln Lys Gln His Ile
            100                 105                 110

Ile Ser Ser Thr Thr Ala His Gly Ala His Pro Thr Asp Leu His
        115                 120                 125

Glu Val Ala Leu Arg Phe Arg Leu Leu Arg Gln His Gly Tyr Phe Val
    130                 135                 140

Ser Asp Asp Val Phe Asn Asn Phe Lys Asn Arg Glu Gly Asn Phe Asn
145                 150                 155                 160

Gln Met Leu Arg Glu Asp Ile Lys Gly Leu Met Ser Leu Tyr Glu Ala
                165                 170                 175

Ser Gln Leu Ser Ile Glu Gly Glu Val Val Leu Glu Glu Ala Gly Lys
            180                 185                 190

Phe Ser Gly His Phe Leu Asn Ser Ser Leu Ser His Leu Asp His His
        195                 200                 205

Gln Ala Arg Val Val Gly Asn Thr Leu Arg Asn Pro His His Lys Ser
    210                 215                 220
```

Leu Ala Pro Phe Met Ala Lys Asn Phe Phe Val Ser Ser Phe Gln Gly
225                 230                 235                 240

Thr Asn Asn Arg Trp Leu Asn Ile Leu Gln Thr Val Ala Lys Thr Asp
            245                 250                 255

Leu Asn Met Val Gln Ser Leu His Gln Lys Glu Val Ala Gln Val Ser
        260                 265                 270

Lys Trp Trp Lys Glu Leu Gly Leu Cys Lys Glu Leu Lys Phe Ala Arg
    275                 280                 285

Asp Gln Pro Ile Lys Trp Tyr Ile Trp Ser Met Ala Cys Leu Thr Asn
290                 295                 300

Pro Asn Leu Ser Asp Glu Arg Ile Glu Leu Thr Lys Pro Ile Ser Phe
305                 310                 315                 320

Ile Tyr Leu Ile Asp Asp Ile Phe Asp Val Tyr Gly Thr Leu Asp Glu
                325                 330                 335

Leu Thr Leu Phe Thr Glu Val Val Asn Arg Trp Glu Ile Gly Ser Ile
            340                 345                 350

Glu His Leu Pro Asp Tyr Met Lys Ile Cys Phe Lys Ala Leu Tyr Asp
        355                 360                 365

Met Thr Asn Glu Ile Ser Cys Lys Val Tyr Gln Lys His Gly Trp Asn
370                 375                 380

Pro Leu His Ser Leu Lys Lys Thr Trp Ala Ser Leu Cys Asn Ala Phe
385                 390                 395                 400

Leu Val Glu Ala Lys Trp Phe Lys Ser Gly His Leu Pro Met Ala Glu
                405                 410                 415

Glu Tyr Leu Lys Asn Gly Ile Ile Ser Ser Gly Val Asn Val Val Met
            420                 425                 430

Val His Ile Phe Phe Leu Leu Gly Glu Gly Ile Thr Asn Gln Ser Val
        435                 440                 445

Glu Phe Leu Asn Gly Thr Pro Ala Ile Ile Ser Ser Thr Ala Ala Ile
450                 455                 460

Leu Arg Leu Trp Asp Asp Leu Gly Ser Ala Lys Asp Glu Asn Gln Asp
465                 470                 475                 480

Gly Asp Asp Gly Ser Tyr Val Lys Leu Tyr Leu Asn Glu His Gln Gly
                485                 490                 495

Lys Thr Met Glu Glu Ala Gln Glu His Val Thr Asn Met Ile Ser Glu
            500                 505                 510

Glu Trp Lys Lys Leu Asn Lys Glu Leu Val Ser Pro Asn Pro Leu Pro
        515                 520                 525

Ala Ala Phe Thr Lys Ala Ser Leu Asn Leu Ala Arg Met Val Pro Leu
530                 535                 540

Met Tyr Ser Tyr Asp Asp Asn Gln Cys Leu Pro Ser Leu Asp Glu Tyr
545                 550                 555                 560

Met Lys Ser Met Leu His Ala
                565

<210> SEQ ID NO 110
<211> LENGTH: 1824
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Perilla frutescens var. crispa
      (PfLINS)

<400> SEQUENCE: 110

```
atgtatagcc tgcgtattta tgtggcgatt atgaaaaagc ccagtgcgaa gcatgttgac    60
aatgtggaca agaaagcgag taagcctagc tggcgcgtta gcctgagcag cagcgcgggc   120
ctgcgtgcca gcagcagcct gcagctggat gtgaaaaagc cggcggatga tgaaatcctg   180
acggcccgcc gcagcggtaa ttaccagccc agcctgtggg actttaatta cctgcagagc   240
ctgaatacca cgcagtacaa agaagtcgcc catctgaagc gcgaagcgga actgattgaa   300
caggtcaaaa tgctgctgga agaagaaatg gaagccgtcc agcagctgga actggttgat   360
gacctgaaga atctgggcct gagctacttt ttcgaagatc agattaaaca gatcctgacg   420
tttatctaca cgaacataa gtgttttcac agcaatagca ttatcgaagc ggaagaaatt   480
cgcgacctgt actttacggc cctgggtttt cgtctgctgc gtcagcatgg ctttcaggtt   540
agccaggaag tgtttgattg ctttaagaat gaagaaggca gcgactttaa agcccgtctg   600
ggtgatgaca ccaagggcct gctgcagctg tacgaagcca gctttctgct gcgcgaaggc   660
gaagatacgc tggaactggc ccgccagtac gcgaccaaat ttctgcagaa aaaggtggac   720
cacgaactga tcgatgacaa taatctgctg agctggattc tgcatagcct ggaaatcccg   780
ctgcactggc gcattcagcg cctggaagcg cgctggtttc tggatcgcta cgccacgcgt   840
cgcgacatga atcagattat cctggaactg gcgaaactgg atttaatat tatccaggcc   900
acgcagcagg aagaactgaa agacctgagc cgttggtgga gagcacctg tctggcggaa   960
aaactgccgt ttgtgcgcga tcgcctggtc gaaagctact tttgggccat gcgctgttt   1020
gaaccccatc agtacggcta ccaccgcaaa gtcgccgcga gattatcac cctgatcacg   1080
agcctggatg acgtttacga tatttacggc accctggacg aactgcagct gtttacggat   1140
gcgatccagc gctgggacac cgaaagcatt agccgcctgc cctactacat gcagctgttt   1200
tacatggttc tgtacaattt tgtgagcgaa ctggcctacg atggcctgaa agaaaagggc   1260
tttattacca ttccctacct gcagcgtagc tgggcggacc tggtggaagc gtacctgaaa   1320
gaagccaagt ggttttacaa tggctacgtc cccagcatgg aagaatacct gaataatgcg   1380
tacattagca ttggtgccac cccggtcatc agccaggttt tctttaccct ggccacgagc   1440
attgataaac ccgtcatcga cagcctgtac gaataccatc gcattctgcg tctgagcggt   1500
atgctggttc gcctgcccga tgacctgggt acgagcccct ttgaaatgaa acgcggcgat   1560
gttccgaagg cgatccagct gtacatgaaa gaacgcaatg cgacggaaat cgaagcccag   1620
gaacacgttc gctttctgat tcgcgaagcc tggaaggaaa tgaataccgt taccacggcc   1680
gcggattgcc cctttaccga tgacctggtt gcggccaccc gtaatctggg tcgtgccgcg   1740
cagtttatgt acctggatgg cgacggtaac cacagtcagc tgcaccagcg tatcgcctgc   1800
ctgctgtttg aaccctatgc ctaa                                          1824
```

<210> SEQ ID NO 111
<211> LENGTH: 607
<212> TYPE: PRT
<213> ORGANISM: Perilla frutescens

<400> SEQUENCE: 111

```
Met Tyr Ser Leu Arg Ile Tyr Val Ala Ile Met Lys Lys Pro Ser Ala
1               5                  10                  15

Lys His Val Asp Asn Val Asp Lys Lys Ala Ser Lys Pro Ser Trp Arg
            20                  25                  30
```

-continued

Val Ser Leu Ser Ser Ser Ala Gly Leu Arg Ala Ser Ser Leu Gln
        35              40              45

Leu Asp Val Lys Lys Pro Ala Asp Glu Ile Leu Thr Ala Arg Arg
50              55              60

Ser Gly Asn Tyr Gln Pro Ser Leu Trp Asp Phe Asn Tyr Leu Gln Ser
65              70              75              80

Leu Asn Thr Thr Gln Tyr Lys Glu Val Arg His Leu Lys Arg Glu Ala
                85              90              95

Glu Leu Ile Glu Gln Val Lys Met Leu Leu Glu Glu Met Glu Ala
                100             105             110

Val Gln Gln Leu Glu Leu Val Asp Asp Leu Lys Asn Leu Gly Leu Ser
        115             120             125

Tyr Phe Phe Glu Asp Gln Ile Lys Gln Ile Leu Thr Phe Ile Tyr Asn
        130             135             140

Glu His Lys Cys Phe His Ser Asn Ser Ile Ile Glu Ala Glu Glu Ile
145             150             155             160

Arg Asp Leu Tyr Phe Thr Ala Leu Gly Phe Arg Leu Leu Arg Gln His
                165             170             175

Gly Phe Gln Val Ser Gln Glu Val Phe Asp Cys Phe Lys Asn Glu Glu
        180             185             190

Gly Ser Asp Phe Lys Ala Arg Leu Gly Asp Asp Thr Lys Gly Leu Leu
        195             200             205

Gln Leu Tyr Glu Ala Ser Phe Leu Leu Arg Glu Gly Glu Asp Thr Leu
        210             215             220

Glu Leu Ala Arg Gln Tyr Ala Thr Lys Phe Leu Gln Lys Lys Val Asp
225             230             235             240

His Glu Leu Ile Asp Asp Asn Asn Leu Leu Ser Trp Ile Leu His Ser
                245             250             255

Leu Glu Ile Pro Leu His Trp Arg Ile Gln Arg Leu Glu Ala Arg Trp
        260             265             270

Phe Leu Asp Arg Tyr Ala Thr Arg Arg Asp Met Asn Gln Ile Ile Leu
        275             280             285

Glu Leu Ala Lys Leu Asp Phe Asn Ile Ile Gln Ala Thr Gln Gln Glu
290             295             300

Glu Leu Lys Asp Leu Ser Arg Trp Trp Lys Ser Thr Cys Leu Ala Glu
305             310             315             320

Lys Leu Pro Phe Val Arg Asp Arg Leu Val Glu Ser Tyr Phe Trp Ala
                325             330             335

Ile Ala Leu Phe Glu Pro His Gln Tyr Gly Tyr His Arg Lys Val Ala
                340             345             350

Ala Lys Ile Ile Thr Leu Ile Thr Ser Leu Asp Asp Val Tyr Asp Ile
        355             360             365

Tyr Gly Thr Leu Asp Glu Leu Gln Leu Phe Thr Asp Ala Ile Gln Arg
        370             375             380

Trp Asp Thr Glu Ser Ile Ser Arg Leu Pro Tyr Tyr Met Gln Leu Phe
385             390             395             400

Tyr Met Val Leu Tyr Asn Phe Val Ser Glu Leu Ala Tyr Asp Gly Leu
                405             410             415

Lys Glu Lys Gly Phe Ile Thr Ile Pro Tyr Leu Gln Arg Ser Trp Ala
                420             425             430

Asp Leu Val Glu Ala Tyr Leu Lys Glu Ala Lys Trp Phe Tyr Asn Gly
        435             440             445

Tyr Val Pro Ser Met Glu Glu Tyr Leu Asn Asn Ala Tyr Ile Ser Ile

| | | | | | | | | | | | | |
|---|---|---|---|---|---|---|---|---|---|---|---|---|
| | | 450 | | | 455 | | | 460 | | | | |
| Gly | Ala | Thr | Pro | Val | Ile | Ser | Gln | Val | Phe | Phe | Thr | Leu | Ala | Thr | Ser |
| 465 | | | | 470 | | | | | 475 | | | | | 480 | |
| Ile | Asp | Lys | Pro | Val | Ile | Asp | Ser | Leu | Tyr | Glu | Tyr | His | Arg | Ile | Leu |
| | | | 485 | | | | | 490 | | | | | 495 | | |
| Arg | Leu | Ser | Gly | Met | Leu | Val | Arg | Leu | Pro | Asp | Asp | Leu | Gly | Thr | Ser |
| | | | 500 | | | | | 505 | | | | | 510 | | |
| Pro | Phe | Glu | Met | Lys | Arg | Gly | Asp | Val | Pro | Lys | Ala | Ile | Gln | Leu | Tyr |
| | | 515 | | | | | 520 | | | | | 525 | | | |
| Met | Lys | Glu | Arg | Asn | Ala | Thr | Glu | Ile | Glu | Ala | Gln | Glu | His | Val | Arg |
| | 530 | | | | | 535 | | | | | 540 | | | | |
| Phe | Leu | Ile | Arg | Glu | Ala | Trp | Lys | Glu | Met | Asn | Thr | Val | Thr | Thr | Ala |
| 545 | | | | | 550 | | | | | 555 | | | | | 560 |
| Ala | Asp | Cys | Pro | Phe | Thr | Asp | Asp | Leu | Val | Ala | Ala | Thr | Arg | Asn | Leu |
| | | | 565 | | | | | 570 | | | | | 575 | | |
| Gly | Arg | Ala | Ala | Gln | Phe | Met | Tyr | Leu | Asp | Gly | Asp | Gly | Asn | His | Ser |
| | | | 580 | | | | | 585 | | | | | 590 | | |
| Gln | Leu | His | Gln | Arg | Ile | Ala | Cys | Leu | Leu | Phe | Glu | Pro | Tyr | Ala | |
| | | 595 | | | | | 600 | | | | | 605 | | | |

```
<210> SEQ ID NO 112
<211> LENGTH: 1734
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Vitis vinifera (VvlLINS)

<400> SEQUENCE: 112
atgggtttta gtcctgcctt ttatgcgtgt agtatccctc ccgttggtcc gaacaagttt      60
accgagctgg gtcagagcaa gtttaacaat gttgtgctgg ttccgaccgc ccagaaatgg     120
agcattgcgc atgatcacac gctggtgtac aaacccctgc gcaagcataa tcaccagagc     180
cagcatctga gctttaccga tgaattttac attaagcacg cgcagcgcct ggacgaaatc     240
cgcaatgtct ttagcgaagt tggcgaagac acgctggaag gcctgatgat gattgatgcc     300
atccagcgcc tgggcatcga ctaccatttt aagaagaaa tcgaagccgt cctgcagcgc     360
cagtacatga aggcgagcac ccacggcgaa agcattcagg atctgtacga agttgccctg     420
cgttttcgtc tgctgcgtca ggaaggctac catgtgccgg ccgatgtctt taacaacttt     480
aagaacaagg aaggcaaatt taagcagaat ctgagcaaag acatcaaggg cctgctggcc     540
ctgtacgaag cgagccagct gagcattgaa ggcgaagata tcctggaaga agcccagcgc     600
tttagcagca ccctgctgaa tgcgggcctg aacacctga tcatcacga gccaccgtc     660 gttggccata cgctgaaca cccgcatcac aaaagcctgc cccgctttat ggcgaaaagc     720
tttctgaagg attttcaggg ccccaatggc tggctgacgg tcctgcagga actggccaaa     780
gcggacttta atatggttca gagcattcat cagcaggaac tgctgcagat cagcaaatgg     840
tggcaggatc gcgcctggc cgaagaactg aaatttgcgc gcgaccagcc gctgaagtgg     900
cacatgtggc cgatggccgt tctgcccgac cctagcctga gcaacagcg tgtggaactg     960 accaaaccga ttagcatgat ctacatcatc gatgacatct ttgatgtgca tggcacgctg    1020
gacgaactga cctgtttac ggaagccgtc aatcgctggg acattgccgc gtttgaaacc    1080
```

-continued

```
ctgcccaact acatgaagat tgttttaag accctggatg aaatcacgaa cgaaatcagc    1140
aacaaggttt acaaggaaca cggctggaat ccggttgata gcctgcgcaa aacgtgggtg    1200
agcctgtgca atgcgtttct ggtcgaagcc aagtggtttg cgagcggcca tgtgcccaaa    1260
gcccacgaat acctgaagaa tggcgttatt agcagcggcg tgcatgtggt cctggtccac    1320
ctgtttttcc tgctgggcca tggcatcacc cgcggcaatg ttgacctggt ggatgacttt    1380
ccgagcatta tcagcagcac cgcggccatt ctgcgtctgt gggatgacct gggtagcgcg    1440
aaagatgaaa atcaggatgg ccatgacggc agctacattg aatgttacat caaggaacac    1500
cagggcagca gcatggaaaa tgcccgccag aatgttacgt acatgattag cgatctgtgg    1560
aaacgcctga ataaggaatg cctgagccag cacccgttta gcaccagctt tacgaaaggc    1620
agcctgaata tcgcccgcat ggtgcccctg atgtacagct acgatgacaa tcagagcctg    1680
ccccatctgg aggagcacat gaagagtctg ctgtttgaag cgtttcccct gtaa          1734
```

<210> SEQ ID NO 113
<211> LENGTH: 577
<212> TYPE: PRT
<213> ORGANISM: Vitis vinifera

<400> SEQUENCE: 113

```
Met Gly Phe Ser Pro Ala Phe Tyr Ala Cys Ser Ile Pro Pro Val Gly
1               5                   10                  15

Pro Asn Lys Phe Thr Glu Leu Gly Gln Ser Lys Phe Asn Asn Val Val
            20                  25                  30

Leu Val Pro Thr Ala Gln Lys Trp Ser Ile Ala His Asp His Thr Leu
        35                  40                  45

Val Tyr Lys Pro Leu Arg Lys His Asn His Gln Ser Gln His Leu Ser
    50                  55                  60

Phe Thr Asp Glu Phe Tyr Ile Lys His Ala Gln Arg Leu Asp Glu Ile
65                  70                  75                  80

Arg Asn Val Phe Ser Glu Val Gly Glu Asp Thr Leu Glu Gly Leu Met
                85                  90                  95

Met Ile Asp Ala Ile Gln Arg Leu Gly Ile Asp Tyr His Phe Lys Glu
            100                 105                 110

Glu Ile Glu Ala Val Leu Gln Arg Gln Tyr Met Lys Ala Ser Thr His
        115                 120                 125

Gly Glu Ser Ile Gln Asp Leu Tyr Glu Val Ala Leu Arg Phe Arg Leu
    130                 135                 140

Leu Arg Gln Glu Gly Tyr His Val Pro Ala Asp Val Phe Asn Asn Phe
145                 150                 155                 160

Lys Asn Lys Glu Gly Lys Phe Lys Gln Asn Leu Ser Lys Asp Ile Lys
                165                 170                 175

Gly Leu Leu Ala Leu Tyr Glu Ala Ser Gln Leu Ser Ile Glu Gly Glu
            180                 185                 190

Asp Ile Leu Glu Glu Ala Gln Arg Phe Ser Ser Thr Leu Leu Asn Ala
        195                 200                 205

Gly Leu Glu His Leu Asn His His Glu Ala Thr Val Val Gly His Thr
    210                 215                 220

Leu Glu His Pro His His Lys Ser Leu Pro Arg Phe Met Ala Lys Ser
225                 230                 235                 240

Phe Leu Lys Asp Phe Gln Gly Pro Asn Gly Trp Leu Thr Val Leu Gln
                245                 250                 255

Glu Leu Ala Lys Ala Asp Phe Asn Met Val Gln Ser Ile His Gln Gln
```

```
                    260                 265                 270
Glu Leu Leu Gln Ile Ser Lys Trp Trp Gln Asp Arg Gly Leu Ala Glu
                275                 280                 285
Glu Leu Lys Phe Ala Arg Asp Gln Pro Leu Lys Trp His Met Trp Pro
        290                 295                 300
Met Ala Val Leu Pro Asp Pro Ser Leu Ser Glu Gln Arg Val Glu Leu
305                 310                 315                 320
Thr Lys Pro Ile Ser Met Ile Tyr Ile Ile Asp Asp Ile Phe Asp Val
                    325                 330                 335
His Gly Thr Leu Asp Glu Leu Thr Leu Phe Thr Glu Ala Val Asn Arg
                340                 345                 350
Trp Asp Ile Ala Ala Phe Glu Thr Leu Pro Asn Tyr Met Lys Ile Cys
            355                 360                 365
Phe Lys Thr Leu Asp Glu Ile Thr Asn Glu Ile Ser Asn Lys Val Tyr
        370                 375                 380
Lys Glu His Gly Trp Asn Pro Val Asp Ser Leu Arg Lys Thr Trp Val
385                 390                 395                 400
Ser Leu Cys Asn Ala Phe Leu Val Glu Ala Lys Trp Phe Ala Ser Gly
                    405                 410                 415
His Val Pro Lys Ala His Glu Tyr Leu Lys Asn Gly Val Ile Ser Ser
                420                 425                 430
Gly Val His Val Val Leu Val His Leu Phe Phe Leu Leu Gly His Gly
            435                 440                 445
Ile Thr Arg Gly Asn Val Asp Leu Val Asp Asp Phe Pro Ser Ile Ile
        450                 455                 460
Ser Ser Thr Ala Ala Ile Leu Arg Leu Trp Asp Asp Leu Gly Ser Ala
465                 470                 475                 480
Lys Asp Glu Asn Gln Asp Gly His Asp Gly Ser Tyr Ile Glu Cys Tyr
                    485                 490                 495
Ile Lys Glu His Gln Gly Ser Ser Met Glu Asn Ala Arg Gln Asn Val
                500                 505                 510
Thr Tyr Met Ile Ser Asp Leu Trp Lys Arg Leu Asn Lys Glu Cys Leu
            515                 520                 525
Ser Gln His Pro Phe Ser Thr Ser Phe Thr Lys Gly Ser Leu Asn Ile
        530                 535                 540
Ala Arg Met Val Pro Leu Met Tyr Ser Tyr Asp Asp Asn Gln Ser Leu
545                 550                 555                 560
Pro His Leu Glu Glu His Met Lys Ser Leu Leu Phe Glu Ala Phe Pro
                    565                 570                 575
Leu

<210> SEQ ID NO 114
<211> LENGTH: 1809
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Vitis vinifera (Vv2LINS)

<400> SEQUENCE: 114
atggaactga ccctgacgag tctgagcccg ctggcgtatg gtgccctgaa ctgccgtaag      60
aactttgcga tggcgagtcc ccgtatgcgc attaagcagg ccgcagcga actgccgaat     120
```

| | |
|---|---|
| ctgacgatta ccagcaaaat cgacgaactg caggtgaccg aacgccgcag cgcgaattac | 180 |
| cacccgagca tttgggatcc caaatttatc gaaagcctga gcacgcccta caccaatgaa | 240 |
| ggctacagca atcagctgga agatctgaaa gaagaagcca agcgcgtcat taaagatgcg | 300 |
| cgcgacacga gcagccgcct ggaatttatc gacagcatgc agcgcctggg cgtggcctac | 360 |
| catctggaag aagaaattaa ggaagcgatc gatctggtcc acctggatga caccacgacc | 420 |
| gatgacctga gcaccacggc cctgcgtttt cgtctgctgc gtcagcatgg ttacccggtc | 480 |
| agcagcgaag ttttgatca gtttcgcagc aaagatggcc gctttatgga cggcattagc | 540 |
| caggatattg cgggtcctct gagcctgtac gaagccagcc atctgggcgt tgaaggcgaa | 600 |
| gatgacctgg aagaagcccg ccgctttagc accatccacc tgaagagcct ggtgggcaat | 660 |
| ctggaaagcg atctggcgga ccaggtgcag cagagcctgg aagtcccct gcactggcgt | 720 |
| atgcctcgtc tggaagcccg caatttatt gacatctacc agcgtcgcaa taccaagaat | 780 |
| agcgccctgc tggaactggc gaaactggat tacaatctgg ttcagagcag ctaccagacg | 840 |
| gaactgaaag aactgacgcg ttggtggacc gacctgggct taaagaaaaa gctgagcttt | 900 |
| agccgcgatc gcctgatgga aaattacctg tggagcatgg gcattgcgcc ggaaccccat | 960 |
| tttagcaaga gccgcatcgg cctgaccaaa tttatttgta tcctgacggc cattgatgac | 1020 |
| atgtacgaca tctacggcag cccggatgaa ctgcgccgct ttaccgacgc cgtcaatcgc | 1080 |
| tgggatacga agcgctggt tgatctgccc gactacatga agatttgtta cctggccatg | 1140 |
| tttaactttg cgaatgaaat ggcctacgat gcgctgcgcg atcatgacct gtacatcctg | 1200 |
| ccgtacctga agagccagtg gctgaatctg tgcaccagct acagcatgga agcccagtgg | 1260 |
| ttttacaatg gctacaaacc gagcattgat gaatacctga gcaatgcctg gaccagcgtt | 1320 |
| ggcggcccgg cggccatggt gcacgcctac tttctgatgg gctgtgcgac gaagggcaat | 1380 |
| ctgaataatt gcctggacaa tgcgagcaat ctgctgtact ggagcagcct gatcacgcgt | 1440 |
| ctgagcgatg acctgggtac gagcctggcg gaaattgccc gcggcgatgt cgccaagagc | 1500 |
| atccagtgtt acatgattga aaatgcatc agcgaagaac aggcgcgcga ccaggttgaa | 1560 |
| aagctgattc gctacagctg gaaaaagctg aatgaagcca gcacggatag cagcctgccg | 1620 |
| aaaagcctga tcaatagcag cctgaatatg gcccgcagcg cgcagtgcat ttttcagttt | 1680 |
| ggtgatggta ttggtacgag cgttggcgtg accaaggatc gcctgacgag ctttattatc | 1740 |
| aaacccattc tgattgaacc gagcattaag ccctacctgg atggcatgaa gatgagtaac | 1800 |
| cgccgctaa | 1809 |

<210> SEQ ID NO 115
<211> LENGTH: 602
<212> TYPE: PRT
<213> ORGANISM: Vitis vinifera

<400> SEQUENCE: 115

Met Glu Leu Thr Leu Thr Ser Leu Ser Pro Leu Ala Tyr Gly Ala Leu
1               5                   10                  15

Asn Cys Arg Lys Asn Phe Ala Met Ala Ser Pro Arg Met Arg Ile Lys
            20                  25                  30

Gln Gly Arg Ser Glu Leu Pro Asn Leu Thr Ile Thr Ser Lys Ile Asp
        35                  40                  45

Glu Leu Gln Val Thr Glu Arg Arg Ser Ala Asn Tyr His Pro Ser Ile
    50                  55                  60

Trp Asp Pro Lys Phe Ile Glu Ser Leu Ser Thr Pro Tyr Thr Asn Glu

```
                65                  70                  75                  80
        Gly Tyr Ser Asn Gln Leu Glu Asp Leu Lys Glu Ala Lys Arg Val
                        85                  90                  95
        Ile Lys Asp Ala Arg Asp Thr Ser Ser Arg Leu Glu Phe Ile Asp Ser
                    100                 105                 110
        Met Gln Arg Leu Gly Val Ala Tyr His Leu Glu Glu Ile Lys Glu
                        115                 120                 125
        Ala Ile Asp Leu Val His Leu Asp Asp Thr Thr Thr Asp Asp Leu Ser
                    130                 135                 140
        Thr Thr Ala Leu Arg Phe Arg Leu Leu Arg Gln His Gly Tyr Pro Val
        145                 150                 155                 160
        Ser Ser Glu Val Phe Asp Gln Phe Arg Ser Lys Asp Gly Arg Phe Met
                        165                 170                 175
        Asp Gly Ile Ser Gln Asp Ile Ala Gly Pro Leu Ser Leu Tyr Glu Ala
                    180                 185                 190
        Ser His Leu Gly Val Glu Gly Glu Asp Asp Leu Glu Glu Ala Arg Arg
                        195                 200                 205
        Phe Ser Thr Ile His Leu Lys Ser Leu Val Gly Asn Leu Glu Ser Asp
                    210                 215                 220
        Leu Ala Asp Gln Val Gln Gln Ser Leu Glu Val Pro Leu His Trp Arg
        225                 230                 235                 240
        Met Pro Arg Leu Glu Ala Arg Asn Phe Ile Asp Ile Tyr Gln Arg Arg
                        245                 250                 255
        Asn Thr Lys Asn Ser Ala Leu Leu Glu Leu Ala Lys Leu Asp Tyr Asn
                    260                 265                 270
        Leu Val Gln Ser Ser Tyr Gln Thr Glu Leu Lys Glu Leu Thr Arg Trp
                    275                 280                 285
        Trp Thr Asp Leu Gly Phe Lys Glu Lys Leu Ser Phe Ser Arg Asp Arg
        290                 295                 300
        Leu Met Glu Asn Tyr Leu Trp Ser Met Gly Ile Ala Pro Glu Pro His
        305                 310                 315                 320
        Phe Ser Lys Ser Arg Ile Gly Leu Thr Lys Phe Ile Cys Ile Leu Thr
                        325                 330                 335
        Ala Ile Asp Asp Met Tyr Asp Ile Tyr Gly Ser Pro Asp Glu Leu Arg
                    340                 345                 350
        Arg Phe Thr Asp Ala Val Asn Arg Trp Asp Thr Glu Ala Leu Val Asp
                    355                 360                 365
        Leu Pro Asp Tyr Met Lys Ile Cys Tyr Leu Ala Met Phe Asn Phe Ala
                    370                 375                 380
        Asn Glu Met Ala Tyr Asp Ala Leu Arg Asp His Asp Leu Tyr Ile Leu
        385                 390                 395                 400
        Pro Tyr Leu Lys Ser Gln Trp Leu Asn Leu Cys Thr Ser Tyr Ser Met
                        405                 410                 415
        Glu Ala Gln Trp Phe Tyr Asn Gly Tyr Lys Pro Ser Ile Asp Glu Tyr
                        420                 425                 430
        Leu Ser Asn Ala Trp Thr Ser Val Gly Gly Pro Ala Ala Met Val His
                    435                 440                 445
        Ala Tyr Phe Leu Met Gly Cys Ala Thr Lys Gly Asn Leu Asn Asn Cys
                    450                 455                 460
        Leu Asp Asn Ala Ser Asn Leu Leu Tyr Trp Ser Ser Leu Ile Thr Arg
        465                 470                 475                 480
        Leu Ser Asp Asp Leu Gly Thr Ser Leu Ala Glu Ile Ala Arg Gly Asp
                        485                 490                 495
```

```
Val Ala Lys Ser Ile Gln Cys Tyr Met Ile Glu Lys Cys Ile Ser Glu
            500                 505                 510

Glu Gln Ala Arg Asp Gln Val Glu Lys Leu Ile Arg Tyr Ser Trp Lys
        515                 520                 525

Lys Leu Asn Glu Ala Ser Thr Asp Ser Ser Leu Pro Lys Ser Leu Ile
    530                 535                 540

Asn Ser Ser Leu Asn Met Ala Arg Ser Ala Gln Cys Ile Phe Gln Phe
545                 550                 555                 560

Gly Asp Gly Ile Gly Thr Ser Val Gly Val Thr Lys Asp Arg Leu Thr
                565                 570                 575

Ser Phe Ile Ile Lys Pro Ile Leu Ile Glu Pro Ser Ile Lys Pro Tyr
                580                 585                 590

Leu Asp Gly Met Lys Met Ser Asn Arg Arg
            595                 600
```

<210> SEQ ID NO 116
<211> LENGTH: 1695
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Lavandula angustifolia
      (LaLINS)

<400> SEQUENCE: 116

```
atgagtatca acattaacat gcccgccgcc gccgttctgc gtccgtttcg ttgtagtcag    60
ctgcacgtcg atgagacccg ccgtagtggc aattaccgcc cgagcgcctg ggacagcaat   120
tacatccaga gcctgaatag ccagtacaag gaaagaaat gtctgacgcg cctggaaggc   180
ctgattgaac aggttaaaga actgaagggc accaaaatgg aagcggtgca gcagctggaa   240
ctgatcgatg acagccagaa tctgggcctg agctactact tcaggataa gatcaagcat   300 atcctgaacc tgatctacaa cgaccacaag tacttttacg atagcgaagc cgaaggcatg   360
gacctgtact ttacggcgct gggctttcgc ctgtttcgcc agcatggctt taaggttagc   420
caggaagtgt ttgatcgctt taagaacgaa acggcacct actttaagca cgatgacacg   480
aaaggcctgc tgcagctgta cgaagccagc tttctggttc gcgaaggcga agaaaccctg   540
gaacaggccc gcgaatttgc gacgaagagc ctgcagcgca actggatga agacggcgat   600 ggcattgatg cgaatatcga aagctggatt cgccatagcc tggaaattcc gctgcattgg   660
cgtgcccagc gtctggaagc ccgttggttt ctggatgcct acgcccgccg ccctgatatg   720
aatcccgtca tctttgaact ggccaagctg aactttaaca tcgttcaggc cacgcagcag   780
gaagaactga agcccctgag ccgttggtgg agcagcctgg gcctggccga aaaactgccc   840
tttgtgcgcg accgcctggt cgaaagttac ttttgggcca tcccgctgtt tgaaccccat   900
cagtacggct accagcgcaa ggtggcgacc aaaattatca ccctgatcac gagcctggat   960
gacgtctacg acatttacgg cacccctgga gaactgcagc tgtttacgaa cctgtttgaa  1020
cgctgggata tgccagcat cggccgcctg ccggaatacc tgcagctgtt ttactttgcc  1080
attcacaatt ttgtcagcga agttgcgtac gacatcctga agaaaaggg ctttaccagc  1140 attgtgtacc tgcagcgcag ctgggtcgat ctgctgaagg ctacctgaa ggaagccaaa  1200 tggtacaata gcggctacac cccgagcctg gaagaatact tgataatgc ctttatgacg  1260
```

```
attggtgccc ctccggtgct gagccaggcc tactttaccc tgggcagcag catggaaaaa    1320
cccattatcg aaagcatgta cgaatacgac aatatcctgc gcgttagcgg tatgctggtt    1380
cgcctgcccg atgacctggg tacgagcagc tttgaaatgg aacgcggcga tgtccccaag    1440
agcgttcagc tgtacatgaa agaaaccaat gccacggaag aagaagccgt ggaacatgtc    1500
cgctttctga atcgcgaagc ctggaaaaag atgaatacgg ccgaagcggc cggtgacagc    1560
cccctggtca gcgatgttgt tgcggttgcg gccaatctgg gtcgtgccgc gcagtttatg    1620
tactttgacg gcgatggtaa ccagagtagc ctgcagcagt ggattgtcag tatgctgttt    1680
gaaccgtatg cctaa                                                     1695
```

<210> SEQ ID NO 117
<211> LENGTH: 564
<212> TYPE: PRT
<213> ORGANISM: Lavandula angustifolia

<400> SEQUENCE: 117

```
Met Ser Ile Asn Ile Asn Met Pro Ala Ala Ala Val Leu Arg Pro Phe
1               5                   10                  15

Arg Cys Ser Gln Leu His Val Asp Glu Thr Arg Arg Ser Gly Asn Tyr
            20                  25                  30

Arg Pro Ser Ala Trp Asp Ser Asn Tyr Ile Gln Ser Leu Asn Ser Gln
        35                  40                  45

Tyr Lys Glu Lys Lys Cys Leu Thr Arg Leu Glu Gly Leu Ile Glu Gln
    50                  55                  60

Val Lys Glu Leu Lys Gly Thr Lys Met Glu Ala Val Gln Gln Leu Glu
65                  70                  75                  80

Leu Ile Asp Asp Ser Gln Asn Leu Gly Leu Ser Tyr Tyr Phe Gln Asp
                85                  90                  95

Lys Ile Lys His Ile Leu Asn Leu Ile Tyr Asn Asp His Lys Tyr Phe
            100                 105                 110

Tyr Asp Ser Glu Ala Glu Gly Met Asp Leu Tyr Phe Thr Ala Leu Gly
        115                 120                 125

Phe Arg Leu Phe Arg Gln His Gly Phe Lys Val Ser Gln Glu Val Phe
    130                 135                 140

Asp Arg Phe Lys Asn Glu Asn Gly Thr Tyr Phe Lys His Asp Asp Thr
145                 150                 155                 160

Lys Gly Leu Leu Gln Leu Tyr Glu Ala Ser Phe Leu Val Arg Glu Gly
                165                 170                 175

Glu Glu Thr Leu Glu Gln Ala Arg Glu Phe Ala Thr Lys Ser Leu Gln
            180                 185                 190

Arg Lys Leu Asp Glu Asp Gly Asp Gly Ile Asp Ala Asn Ile Glu Ser
        195                 200                 205

Trp Ile Arg His Ser Leu Glu Ile Pro Leu His Trp Arg Ala Gln Arg
    210                 215                 220

Leu Glu Ala Arg Trp Phe Leu Asp Ala Tyr Ala Arg Arg Pro Asp Met
225                 230                 235                 240

Asn Pro Val Ile Phe Glu Leu Ala Lys Leu Asn Phe Asn Ile Val Gln
                245                 250                 255

Ala Thr Gln Gln Glu Glu Leu Lys Ala Leu Ser Arg Trp Trp Ser Ser
            260                 265                 270

Leu Gly Leu Ala Glu Lys Leu Pro Phe Val Arg Asp Arg Leu Val Glu
        275                 280                 285

Ser Tyr Phe Trp Ala Ile Pro Leu Phe Glu Pro His Gln Tyr Gly Tyr
```

```
                290                 295                 300
Gln Arg Lys Val Ala Thr Lys Ile Ile Thr Leu Ile Thr Ser Leu Asp
305                 310                 315                 320

Asp Val Tyr Asp Ile Tyr Gly Thr Leu Asp Glu Leu Gln Leu Phe Thr
                325                 330                 335

Asn Leu Phe Glu Arg Trp Asp Asn Ala Ser Ile Gly Arg Leu Pro Glu
                340                 345                 350

Tyr Leu Gln Leu Phe Tyr Phe Ala Ile His Asn Phe Val Ser Glu Val
                355                 360                 365

Ala Tyr Asp Ile Leu Lys Glu Lys Gly Phe Thr Ser Ile Val Tyr Leu
                370                 375                 380

Gln Arg Ser Trp Val Asp Leu Leu Lys Gly Tyr Leu Lys Glu Ala Lys
385                 390                 395                 400

Trp Tyr Asn Ser Gly Tyr Thr Pro Ser Leu Glu Glu Tyr Phe Asp Asn
                405                 410                 415

Ala Phe Met Thr Ile Gly Ala Pro Pro Val Leu Ser Gln Ala Tyr Phe
                420                 425                 430

Thr Leu Gly Ser Ser Met Glu Lys Pro Ile Ile Glu Ser Met Tyr Glu
                435                 440                 445

Tyr Asp Asn Ile Leu Arg Val Ser Gly Met Leu Val Arg Leu Pro Asp
                450                 455                 460

Asp Leu Gly Thr Ser Ser Phe Glu Met Glu Arg Gly Asp Val Pro Lys
465                 470                 475                 480

Ser Val Gln Leu Tyr Met Lys Glu Thr Asn Ala Thr Glu Glu Glu Ala
                485                 490                 495

Val Glu His Val Arg Phe Leu Asn Arg Glu Ala Trp Lys Lys Met Asn
                500                 505                 510

Thr Ala Glu Ala Ala Gly Asp Ser Pro Leu Val Ser Asp Val Val Ala
                515                 520                 525

Val Ala Ala Asn Leu Gly Arg Ala Ala Gln Phe Met Tyr Phe Asp Gly
                530                 535                 540

Asp Gly Asn Gln Ser Ser Leu Gln Gln Trp Ile Val Ser Met Leu Phe
545                 550                 555                 560

Glu Pro Tyr Ala

<210> SEQ ID NO 118
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Mentha citrata (McLINS)

<400> SEQUENCE: 118
atgtgtacca tcattagcgt caatcatcat catgtcgcca tcctgagcaa gccgaaggtc      60
aagctgtttc ataccaagaa taagcgcagc gccagcatca atctgccgtg gagcctgagc     120
cctagcagca gcgcggccag ccgcccgatt agctgtagca tcagcagcaa actgtacacc     180
atcagcagcg cccaggaaga aacgcgccgc agcggcaatt accatcccag cgtttgggat     240 tttgactta ttcagagcct ggataccgac cactacaagg aagaaaaaca gctggaacgc     300
gaagaagaac tgatcatgga agtgaaaaag ctgctgggcg cgaagatgga agccacgaaa     360
cagctggaac tgattgatga cctgcagaat ctgggcctga gctacttttt ccgcgacgaa     420
```

```
atcaagaaca tcctgaacag catctacaag atctttcaga acaacaatag caccaaggtt    480
ggcgatctgc attttacgag cctgggtttt cgtctgctgc gtcagcacgg ctttaatgtt    540
agccagggcg tgtttgattg cttttaaaaat gaacatggca gcgactttga aaagaccctg   600
atcggcgaag atacgaaagg cgtgctgcag ctgtacgaag cgagctttct gctgcgcgaa    660
ggcgaagata ccctggaagt cgcccgcaaa tttagcacgg aatttctgga gaaaaactg    720
aaggcgggca ttgatggcga caatctgagc agcagcattg ccatagcct ggaaatcccg     780
ctgcactggc gcattcagcg cctggaagaa cgctggtttc tggatgccta cagccgtcgc    840
aaggacatga atcccattat ctttgaactg gcgaaactgg actttaatat tatccaggcc    900
acccagcagg aagaactgaa ggatctgagc cgttggtgga atgacagcag cctgccgcag   960
aaactgccct ttgtccgcga tcgcctggtt gaaagctact actgggcgct gggcctgttt    1020
gaagcccata agtttggcta cgaacgcaag acggccgcga aaattatcac cctgatcacg   1080
gcgctggatg acgtgtacga tatttacggc accctggacg aactgcagct gtttacgcac   1140
gtcattcgcc gctgggacac ggaaagcgcc acccagctgc cgtactacct gcagctgttt   1200
tactttgtcc tgtacaattt tgtcagcgaa gttgcgtacc atattctgaa gaagaaggc   1260
tttattagca tcccctttct gcaccgcgcg tgggtggatc tggtcgaagg ctacctgcag   1320
gaagccaagt ggtactacac caaatacacc ccgacgatgg aagaatacct gaattacgcc   1380
agcattacca ttggtgcccc ggccgttatt agccagatct actttatgct ggcgaaaagc   1440
aaggaaaaac cggtgatcga agctttttac gaatacgacg aaattattcg tctgagcggt   1500
atgctggttc gcctgcccga tgacctgggt accctgccct ttgaaatgaa gcgcggcgat   1560
gttgccaaaa gcattcagat ctacatgaag aacagaatg cgacgcgcga agaagccgaa   1620
gaacacgtgc gctttatgat tcgcgaagcg tggaaagaaa tgaataccac gatggccgcg   1680
aatagcgatc tgcgcggcga cgttgtgatg gcggccgcca atctgggtcg tgatgcccag   1740
tttatgtacc tggatggcga cggtaatcat agtcagctgc agcaccgcat cgccaatctg   1800
ctgtttaagc cctacgtcta a                                              1821
```

<210> SEQ ID NO 119
<211> LENGTH: 606
<212> TYPE: PRT
<213> ORGANISM: Mentha citrata

<400> SEQUENCE: 119

Met Cys Thr Ile Ile Ser Val Asn His His Val Ala Ile Leu Ser
1               5                   10                  15

Lys Pro Lys Val Lys Leu Phe His Thr Lys Asn Lys Arg Ser Ala Ser
            20                  25                  30

Ile Asn Leu Pro Trp Ser Leu Ser Pro Ser Ser Ala Ala Ser Arg
        35                  40                  45

Pro Ile Ser Cys Ser Ile Ser Lys Leu Tyr Thr Ile Ser Ser Ala
    50                  55                  60

Gln Glu Glu Thr Arg Arg Ser Gly Asn Tyr His Pro Ser Val Trp Asp
65                  70                  75                  80

Phe Asp Phe Ile Gln Ser Leu Asp Thr Asp His Tyr Lys Glu Glu Lys
                85                  90                  95

Gln Leu Glu Arg Glu Glu Glu Leu Ile Met Glu Val Lys Lys Leu Leu
            100                 105                 110

Gly Ala Lys Met Glu Ala Thr Lys Gln Leu Glu Leu Ile Asp Asp Leu

```
            115                 120                 125
Gln Asn Leu Gly Leu Ser Tyr Phe Arg Asp Glu Ile Lys Asn Ile
            130                 135                 140

Leu Asn Ser Ile Tyr Lys Ile Phe Gln Asn Asn Ser Thr Lys Val
145                 150                 155                 160

Gly Asp Leu His Phe Thr Ser Leu Gly Phe Arg Leu Leu Arg Gln His
                    165                 170                 175

Gly Phe Asn Val Ser Gln Gly Val Phe Asp Cys Phe Lys Asn Glu His
                    180                 185                 190

Gly Ser Asp Phe Glu Lys Thr Leu Ile Gly Asp Thr Lys Gly Val
                    195                 200                 205

Leu Gln Leu Tyr Glu Ala Ser Phe Leu Leu Arg Glu Gly Glu Asp Thr
            210                 215                 220

Leu Glu Val Ala Arg Lys Phe Ser Thr Glu Phe Leu Glu Glu Lys Leu
225                 230                 235                 240

Lys Ala Gly Ile Asp Gly Asp Asn Leu Ser Ser Ser Ile Gly His Ser
                    245                 250                 255

Leu Glu Ile Pro Leu His Trp Arg Ile Gln Arg Leu Glu Glu Arg Trp
                    260                 265                 270

Phe Leu Asp Ala Tyr Ser Arg Arg Lys Asp Met Asn Pro Ile Ile Phe
                    275                 280                 285

Glu Leu Ala Lys Leu Asp Phe Asn Ile Ile Gln Ala Thr Gln Gln Glu
            290                 295                 300

Glu Leu Lys Asp Leu Ser Arg Trp Trp Asn Asp Ser Ser Leu Pro Gln
305                 310                 315                 320

Lys Leu Pro Phe Val Arg Asp Arg Leu Val Glu Ser Tyr Tyr Trp Ala
                    325                 330                 335

Leu Gly Leu Phe Glu Ala His Lys Phe Gly Tyr Glu Arg Lys Thr Ala
                    340                 345                 350

Ala Lys Ile Ile Thr Leu Ile Thr Ala Leu Asp Asp Val Tyr Asp Ile
                    355                 360                 365

Tyr Gly Thr Leu Asp Glu Leu Gln Leu Phe Thr His Val Ile Arg Arg
            370                 375                 380

Trp Asp Thr Glu Ser Ala Thr Gln Leu Pro Tyr Tyr Leu Gln Leu Phe
385                 390                 395                 400

Tyr Phe Val Leu Tyr Asn Phe Val Ser Glu Val Ala Tyr His Ile Leu
                    405                 410                 415

Lys Glu Glu Gly Phe Ile Ser Ile Pro Phe Leu His Arg Ala Trp Val
                    420                 425                 430

Asp Leu Val Glu Gly Tyr Leu Gln Glu Ala Lys Trp Tyr Tyr Thr Lys
            435                 440                 445

Tyr Thr Pro Thr Met Glu Glu Tyr Leu Asn Tyr Ala Ser Ile Thr Ile
            450                 455                 460

Gly Ala Pro Ala Val Ile Ser Gln Ile Tyr Phe Met Leu Ala Lys Ser
465                 470                 475                 480

Lys Glu Lys Pro Val Ile Glu Ser Phe Tyr Glu Tyr Asp Glu Ile Ile
                    485                 490                 495

Arg Leu Ser Gly Met Leu Val Arg Leu Pro Asp Asp Leu Gly Thr Leu
                    500                 505                 510

Pro Phe Glu Met Lys Arg Gly Asp Val Ala Lys Ser Ile Gln Ile Tyr
                    515                 520                 525

Met Lys Glu Gln Asn Ala Thr Arg Glu Glu Ala Glu Glu His Val Arg
            530                 535                 540
```

```
Phe Met Ile Arg Glu Ala Trp Lys Glu Met Asn Thr Thr Met Ala Ala
545                 550                 555                 560

Asn Ser Asp Leu Arg Gly Asp Val Val Met Ala Ala Asn Leu Gly
            565                 570                 575

Arg Asp Ala Gln Phe Met Tyr Leu Asp Gly Asp Gly Asn His Ser Gln
        580                 585                 590

Leu Gln His Arg Ile Ala Asn Leu Leu Phe Lys Pro Tyr Val
        595                 600                 605

<210> SEQ ID NO 120
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Ocimum basilicum (Ob1LINS)

<400> SEQUENCE: 120
atggcgagtg cggtcccccct gagtagtacg cccctgatta acggcgacaa tagtcccctg     60 aaaaatacccc accagcatgt tgaggagcgc agcagcaaac gtcgcgaata cctgctggaa    120
gaaaccgcgc gcaagctgca gcgcaatgac acggaaagcg ttgaaaaact gaagctgatt    180
gataatatcc agcgcctggg cattggctac tactttgaag atgccattga tgcggtgctg    240
cgcagcccct ttagcgccga agaagaagaa gacctgttta ccgcggccct gcgttttcgt    300
ctgctgcgtc ataatggcat tcaggtcacc ccggaaatct ttctgaaatt taaggatgaa    360
cgcggcgaat ttgacgaaag cgatacgctg ggcctgctga gcctgtacga agcgagcaat    420
ctgggcgtga ccggcgaaga atcctggaa gaagcgatgg aatttgcgga ccccgtctg     480 cgccgcagcc tgagcgaact ggccgcgccc ctgcgcagcg aagtcgccca ggccctggat    540
gttccccgtc acctgcgcat ggcccgtctg gaagcccgcc gctttattga acagtacggc    600
aaacagagcg atcatgacgg cgatctgctg gaactggcga ttctggacta caatcaggtc    660
caggcccagc accagagcga actgaccgaa atcacgcgtt ggtggaaaca gctgggcctg    720
gttgaaaaac tgggttttgg tcgcgatcgc gccctggaat gttttatgtg gacgatgggc    780
attctgccgc atcccaaata cagcagcagc cgtattgaaa gcgccaaggc ggccgccctg    840
ctgtacgtta ttgatgacat ctttgacacc tacggcaaaa tggatgaact gattctgttt    900
acggacgcga tccgccgctg ggatctggaa gccatggaag cctgcccgat acatgaag     960 atttgttaca tggcgctgta caataccacg aatgaaattt gctaccgcgt tctgaaagat   1020
accggtcgta ttgccctgcc ttacctgaag agcgtgtgga ttgaaaccat cgaagcgtac   1080
atggtcgaag ttaaatggtt tagcggcggc agcgcccca agctggaaga atacattgaa   1140
aatggtgcca gcaccgtggg tgcctacatg gtgctggtcc acctgttttt cctgatcggc   1200
gaaggcctga cccaccagaa tgtcctgttt ttcaaacaga gccgtacca caaacccttt   1260 agcgccgcgg tcgtattttt tcgtctgtgg gatgacctgg gcacgagcca ggaagaagaa   1320
gaacgcggcg atatggcgag cagcatccgc ctgtttatga agaatacaa gctgagcacc   1380 gtggaagaag cccgcagctg cgtcctggaa gaaattagcc gcctgtggaa agacctgaat   1440
gaaggcctga ttagcatcaa agatgccctg ccgctgacca ttgttaaggt ggcgctgaat   1500
atcgcccgca cgagccaggt tgtgtacaag catgaacagc acacctacat gctgagtgtt   1560
```
gacaattatg tggaagccct gttttttacg cccctgctga gtagttaa                1608

<210> SEQ ID NO 121
<211> LENGTH: 535
<212> TYPE: PRT
<213> ORGANISM: Ocimum basilicum

<400> SEQUENCE: 121

Met Ala Ser Ala Val Pro Leu Ser Ser Thr Pro Leu Ile Asn Gly Asp
1               5                   10                  15

Asn Ser Pro Leu Lys Asn Thr His Gln His Val Glu Glu Arg Ser Ser
                20                  25                  30

Lys Arg Arg Glu Tyr Leu Leu Glu Thr Ala Arg Lys Leu Gln Arg
        35                  40                  45

Asn Asp Thr Glu Ser Val Glu Lys Leu Lys Leu Ile Asp Asn Ile Gln
    50                  55                  60

Arg Leu Gly Ile Gly Tyr Tyr Phe Glu Asp Ala Ile Asp Ala Val Leu
65                  70                  75                  80

Arg Ser Pro Phe Ser Ala Glu Glu Glu Asp Leu Phe Thr Ala Ala
                85                  90                  95

Leu Arg Phe Arg Leu Leu Arg His Asn Gly Ile Gln Val Thr Pro Glu
            100                 105                 110

Ile Phe Leu Lys Phe Lys Asp Glu Arg Gly Glu Phe Asp Glu Ser Asp
        115                 120                 125

Thr Leu Gly Leu Leu Ser Leu Tyr Glu Ala Ser Asn Leu Gly Val Thr
130                 135                 140

Gly Glu Glu Ile Leu Glu Glu Ala Met Glu Phe Ala Glu Pro Arg Leu
145                 150                 155                 160

Arg Arg Ser Leu Ser Glu Leu Ala Ala Pro Leu Arg Ser Glu Val Ala
                165                 170                 175

Gln Ala Leu Asp Val Pro Arg His Leu Arg Met Ala Arg Leu Glu Ala
            180                 185                 190

Arg Arg Phe Ile Glu Gln Tyr Gly Lys Gln Ser Asp His Asp Gly Asp
        195                 200                 205

Leu Leu Glu Leu Ala Ile Leu Asp Tyr Asn Gln Val Gln Ala Gln His
    210                 215                 220

Gln Ser Glu Leu Thr Glu Ile Thr Arg Trp Trp Lys Gln Leu Gly Leu
225                 230                 235                 240

Val Glu Lys Leu Gly Phe Gly Arg Asp Arg Ala Leu Glu Cys Phe Met
                245                 250                 255

Trp Thr Met Gly Ile Leu Pro His Pro Lys Tyr Ser Ser Arg Ile
            260                 265                 270

Glu Ser Ala Lys Ala Ala Ala Leu Leu Tyr Val Ile Asp Asp Ile Phe
        275                 280                 285

Asp Thr Tyr Gly Lys Met Asp Glu Leu Ile Leu Phe Thr Asp Ala Ile
    290                 295                 300

Arg Arg Trp Asp Leu Glu Ala Met Glu Gly Leu Pro Glu Tyr Met Lys
305                 310                 315                 320

Ile Cys Tyr Met Ala Leu Tyr Asn Thr Thr Asn Glu Ile Cys Tyr Arg
                325                 330                 335

Val Leu Lys Asp Thr Gly Arg Ile Ala Leu Pro Tyr Leu Lys Ser Val
            340                 345                 350

Trp Ile Glu Thr Ile Glu Ala Tyr Met Val Glu Val Lys Trp Phe Ser
        355                 360                 365

```
        Gly Gly Ser Ala Pro Lys Leu Glu Glu Tyr Ile Glu Asn Gly Ala Ser
            370                 375                 380

Thr Val Gly Ala Tyr Met Val Leu Val His Leu Phe Phe Leu Ile Gly
        385                 390                 395                 400

Glu Gly Leu Thr His Gln Asn Val Leu Phe Phe Lys Gln Lys Pro Tyr
                        405                 410                 415

His Lys Pro Phe Ser Ala Ala Gly Arg Ile Phe Arg Leu Trp Asp Asp
                    420                 425                 430

Leu Gly Thr Ser Gln Glu Glu Glu Arg Gly Asp Met Ala Ser Ser
                        435                 440                 445

Ile Arg Leu Phe Met Lys Glu Tyr Lys Leu Ser Thr Val Glu Glu Ala
        450                 455                 460

Arg Ser Cys Val Leu Glu Glu Ile Ser Arg Leu Trp Lys Asp Leu Asn
        465                 470                 475                 480

Glu Gly Leu Ile Ser Ile Lys Asp Ala Leu Pro Leu Thr Ile Val Lys
                        485                 490                 495

Val Ala Leu Asn Ile Ala Arg Thr Ser Gln Val Val Tyr Lys His Glu
                    500                 505                 510

Gln His Thr Tyr Met Leu Ser Val Asp Asn Tyr Val Glu Ala Leu Phe
                515                 520                 525

Phe Thr Pro Leu Leu Ser Ser
            530                 535

<210> SEQ ID NO 122
<211> LENGTH: 2550
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA having modified codons, which encodes
      linalool synthase gene derived from Clarkia breweri (CbLINS)

<400> SEQUENCE: 122
atgcgtgaga gcctgagcag tagcagtagc aatacccaga acctgttttct gagtacgagt    60 ccttacgata cggcgtggct ggccctgatt ccgcatcccc atcaccatca ccatcacggc   120
cgccctatgt ttgaaaaatg tctgcagtgg attctgcaca atcagacccc gcagggtttt   180
tgggcggccg cgggtgataa tatcagcgac accgatgacg atgtgacgct ggactgtctg   240
ctgagcaccc tggcctgcct ggttgccctg aaacgttggc agctggcccc ggatatgatt   300
cataagggcc tggaatttgt caatcgcaat accgaacgcc tggttatgaa gcagaaaccg   360
agcgacgtgc cccgctggtt tacgatcatg tttccggcca tgctggaact ggccggtgcc   420
agcagcctgc gcgtcgattt tagcgaaaat ctgaatcgca ttctggttga actgagccag   480
aatcgcgacg atatcctgac ccgcgaagaa gtggatgaaa agaaacagta cagcccgctg   540
ctgctgtttc tggaagccct gcccgcgcag agctacgaca tgatgttcct gaaacagatt   600
atcgataaga atctgagcaa tgacggcagc ctgctgcaga gccccagcgc cacggcccgt   660
gcctacatga tcaccggcaa tacgcgctgt ctgagctacc tgcatagcct gacgaatagc   720
tgcagcaatg gcggcgttcc gagcttttac cccgtggacg atgacctgca cgacctggtc   780
atggttaatc agctgacccg cagcggcctg acggaacatc tgattccgga aatcgatcac   840
ctgctgctga aggtgcagaa aaattacaag tacaaaaagg ccagcccaa aagcctgtac   900 agcattgcgg ccgaactgta ccgcgatagc ctggcgtttt gctgctgcg cgttaataat   960
```

```
cattgggtga gcccgagcat cttttgttgg tttctggatg acgatgaaat tcgcgaccac    1020
atcgaaacca attacgaaga atttgcggcc gtgctgctga atgtctaccg cgccacggat    1080
ctgatgttta gcggcgaagt tcagctggtt gaagcccgca gctttgcgac caaaaatctg    1140
gaaaagattc tggccaccgg caatatccat aaaacgaatg cggacattag cagcagcctg    1200
cataagatga tcgaacatga actgcgtgtg ccttggaccg cccgtatgga tcacgtcgaa    1260
aatcgcattt ggatcgaaga aattgccagc agcgcgctgt ggtttggcaa agcagctac     1320 ctgcgcctga gctgctttca taaaatgagc ctgcagcagc tggccgttaa gaattacacc    1380
ctgcgccagc tggtctaccg cgacgaactg gcggaagttg aacgctggag caaagaacgc    1440
ggcctgtgtg atatgggctt tgccgcgaa aagaccggct actgttacta cgcctttgcc     1500
gccagcacct gtctgccctg gagcagcgat gtccgtctgg ttctgaccaa gcggccgtt    1560 gtgatcacgg tggcggacga tttctttgat gtcgaaggca gcatggttga tctggaaaaa    1620
ctgacggatg cggtccgccg ctgggatgcc gaaggcctgg gcagccacag caagacgatt    1680
tttgaggccc tggacgatct ggtgaatgaa gtccgcctga atgttttca gcagaatggc     1740 caggacatca gaataatct gcagcagctg tggtacgaaa cctttcatag ctggctgatg     1800
gaagcgaaat ggggcaaggg cctgaccagc aaaccgagcg tggatgtcta cctgggcaat    1860
gccatgacga gcattgcggc ccacaccatg gttctgaccg ccagctgtct gctgggtccc    1920
ggttttccgg tgcatcagct gtggagccag cgtcgccacc aggatatcac cagcctgctg    1980
atggtgctga cgcgcctgct gaatgacatt cagagctacc tgaaagaaga agatgaaggc    2040
aagatcaact acgtttggat gtacatgatc gaaaacaatc aggccagcat cgacgatagc    2100
gttcgccatg tgcagacgat catcaacgtt aaaaagcagg aatttatcca gcgcgtgctg    2160
agcgatcagc attgtaatct gccgaaaagc tttaagcagc tgcactttag ctgcctgaaa    2220
gtgtttaaca tgtttttcaa cagcagcaac atctttgaca ccgatacgga cctgctgctg    2280
gatatccatg aagcctttgt gagcccgccc caggtcccga gtttaaacc ccatattaag     2340 ccgcccacc agctgcccgc caccctgcag ccgccccacc agccccagca gatcatggtc     2400
aacaaaaaga agtcgaaat ggtttacaag agctaccatc accccttaa ggttttacg      2460 ctgcagaaga aacagagcag cggccacggc acgatgaatc cccgtgcgag tatcctggcc    2520
ggtccgaata tcaaactgtg ctttagttaa                                     2550
```

<210> SEQ ID NO 123
<211> LENGTH: 849
<212> TYPE: PRT
<213> ORGANISM: Clarkia breweri

<400> SEQUENCE: 123

```
Met Arg Glu Ser Leu Ser Ser Ser Ser Asn Thr Gln Asn Leu Phe
1               5                   10                  15

Leu Ser Thr Ser Pro Tyr Asp Thr Ala Trp Leu Ala Leu Ile Pro His
                20                  25                  30

Pro His His His His His Gly Arg Pro Met Phe Glu Lys Cys Leu
            35                  40                  45

Gln Trp Ile Leu His Asn Gln Thr Pro Gln Gly Phe Trp Ala Ala Ala
        50                  55                  60

Gly Asp Asn Ile Ser Asp Thr Asp Asp Val Thr Leu Asp Cys Leu
65                  70                  75                  80

Leu Ser Thr Leu Ala Cys Leu Val Ala Leu Lys Arg Trp Gln Leu Ala
                85                  90                  95
```

```
Pro Asp Met Ile His Lys Gly Leu Glu Phe Val Asn Arg Asn Thr Glu
            100                 105                 110
Arg Leu Val Met Lys Gln Lys Pro Ser Asp Val Pro Arg Trp Phe Thr
            115                 120                 125
Ile Met Phe Pro Ala Met Leu Glu Leu Ala Gly Ala Ser Ser Leu Arg
            130                 135                 140
Val Asp Phe Ser Glu Asn Leu Asn Arg Ile Leu Val Glu Leu Ser Gln
145                 150                 155                 160
Asn Arg Asp Asp Ile Leu Thr Arg Glu Glu Val Asp Glu Lys Lys Gln
                165                 170                 175
Tyr Ser Pro Leu Leu Leu Phe Leu Glu Ala Leu Pro Ala Gln Ser Tyr
            180                 185                 190
Asp Asn Asp Val Leu Lys Gln Ile Ile Asp Lys Asn Leu Ser Asn Asp
            195                 200                 205
Gly Ser Leu Leu Gln Ser Pro Ser Ala Thr Ala Arg Ala Tyr Met Ile
            210                 215                 220
Thr Gly Asn Thr Arg Cys Leu Ser Tyr Leu His Ser Leu Thr Asn Ser
225                 230                 235                 240
Cys Ser Asn Gly Gly Val Pro Ser Phe Tyr Pro Val Asp Asp Leu
                245                 250                 255
His Asp Leu Val Met Val Asn Gln Leu Thr Arg Ser Gly Leu Thr Glu
            260                 265                 270
His Leu Ile Pro Glu Ile Asp His Leu Leu Lys Val Gln Lys Asn
            275                 280                 285
Tyr Lys Tyr Lys Lys Ala Ser Pro Lys Ser Leu Tyr Ser Ile Ala Ala
            290                 295                 300
Glu Leu Tyr Arg Asp Ser Leu Ala Phe Trp Leu Leu Arg Val Asn Asn
305                 310                 315                 320
His Trp Val Ser Pro Ser Ile Phe Cys Trp Phe Leu Asp Asp Glu
            325                 330                 335
Ile Arg Asp His Ile Glu Thr Asn Tyr Glu Glu Phe Ala Ala Val Leu
            340                 345                 350
Leu Asn Val Tyr Arg Ala Thr Asp Leu Met Phe Ser Gly Glu Val Gln
            355                 360                 365
Leu Val Glu Ala Arg Ser Phe Ala Thr Lys Asn Leu Glu Lys Ile Leu
            370                 375                 380
Ala Thr Gly Asn Ile His Lys Thr Asn Ala Asp Ile Ser Ser Ser Leu
385                 390                 395                 400
His Lys Met Ile Glu His Glu Leu Arg Val Pro Trp Thr Ala Arg Met
            405                 410                 415
Asp His Val Glu Asn Arg Ile Trp Ile Glu Glu Ile Ala Ser Ser Ala
            420                 425                 430
Leu Trp Phe Gly Lys Ser Ser Tyr Leu Arg Leu Ser Cys Phe His Lys
            435                 440                 445
Met Ser Leu Gln Gln Leu Ala Val Lys Asn Tyr Thr Leu Arg Gln Leu
            450                 455                 460
Val Tyr Arg Asp Glu Leu Ala Glu Val Glu Arg Trp Ser Lys Glu Arg
465                 470                 475                 480
Gly Leu Cys Asp Met Gly Phe Cys Arg Glu Lys Thr Gly Tyr Cys Tyr
                485                 490                 495
Tyr Ala Phe Ala Ala Ser Thr Cys Leu Pro Trp Ser Ser Asp Val Arg
            500                 505                 510
```

Leu Val Leu Thr Lys Ala Ala Val Ile Thr Val Ala Asp Asp Phe
            515                 520                 525

Phe Asp Val Glu Gly Ser Met Val Asp Leu Lys Leu Thr Asp Ala
530                 535                 540

Val Arg Arg Trp Asp Ala Glu Gly Leu Gly Ser His Ser Lys Thr Ile
545                 550                 555                 560

Phe Glu Ala Leu Asp Asp Leu Val Asn Glu Val Arg Leu Lys Cys Phe
                565                 570                 575

Gln Gln Asn Gly Gln Asp Ile Lys Asn Asn Leu Gln Gln Leu Trp Tyr
            580                 585                 590

Glu Thr Phe His Ser Trp Leu Met Glu Ala Lys Trp Gly Lys Gly Leu
            595                 600                 605

Thr Ser Lys Pro Ser Val Asp Val Tyr Leu Gly Asn Ala Met Thr Ser
            610                 615                 620

Ile Ala Ala His Thr Met Val Leu Thr Ala Ser Cys Leu Leu Gly Pro
625                 630                 635                 640

Gly Phe Pro Val His Gln Leu Trp Ser Gln Arg Arg His Gln Asp Ile
                645                 650                 655

Thr Ser Leu Leu Met Val Leu Thr Arg Leu Leu Asn Asp Ile Gln Ser
            660                 665                 670

Tyr Leu Lys Glu Glu Asp Glu Gly Lys Ile Asn Tyr Val Trp Met Tyr
            675                 680                 685

Met Ile Glu Asn Asn Gln Ala Ser Ile Asp Asp Ser Val Arg His Val
690                 695                 700

Gln Thr Ile Ile Asn Val Lys Lys Gln Glu Phe Ile Gln Arg Val Leu
705                 710                 715                 720

Ser Asp Gln His Cys Asn Leu Pro Lys Ser Phe Lys Gln Leu His Phe
                725                 730                 735

Ser Cys Leu Lys Val Phe Asn Met Phe Phe Asn Ser Ser Asn Ile Phe
            740                 745                 750

Asp Thr Asp Thr Asp Leu Leu Leu Asp Ile His Glu Ala Phe Val Ser
            755                 760                 765

Pro Pro Gln Val Pro Lys Phe Lys Pro His Ile Lys Pro Pro His Gln
770                 775                 780

Leu Pro Ala Thr Leu Gln Pro Pro His Gln Pro Gln Ile Met Val
785                 790                 795                 800

Asn Lys Lys Lys Val Glu Met Val Tyr Lys Ser Tyr His His Pro Phe
                805                 810                 815

Lys Val Phe Thr Leu Gln Lys Lys Gln Ser Ser Gly His Gly Thr Met
            820                 825                 830

Asn Pro Arg Ala Ser Ile Leu Ala Gly Pro Asn Ile Lys Leu Cys Phe
            835                 840                 845

Ser

<210> SEQ ID NO 124
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 124
cacaaggaga ctgccatggc gaacacggcg aagcgtagta tcc                43

<210> SEQ ID NO 125
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 125
gtctcctgtg tgaaattaca tcaggctttt cagatactca tcgg    44

<210> SEQ ID NO 126
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 126
cacaaggaga ctgccatgcg tcgtagtgcg aattaccagc cgag    44

<210> SEQ ID NO 127
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 127
gtctcctgtg tgaaattagt ccagcgggat agggttaaac agc    43

<210> SEQ ID NO 128
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 128
cacaaggaga ctgccatgga gtttagcatt agccagagta gttttgcg    48

<210> SEQ ID NO 129
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 129
gtctcctgtg tgaaattagg cgtgcagcat actcttcatg tactc    45

<210> SEQ ID NO 130
<211> LENGTH: 42

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 130
cacaaggaga ctgccatgta tagcctgcgt atttatgtgg cg                      42

<210> SEQ ID NO 131
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 131
gtctcctgtg tgaaattagg catagggttc aaacagcagg caggcg                  46

<210> SEQ ID NO 132
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 132
cacaaggaga ctgccatggg ttttagtcct gccttttatg cgtg                    44

<210> SEQ ID NO 133
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 133
gtctcctgtg tgaaattaca ggggaaacgc ttcaaacagc agactc                  46

<210> SEQ ID NO 134
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 134
cacaaggaga ctgccatgga actgaccctg acgagtctga gcccg                   45

<210> SEQ ID NO 135
<211> LENGTH: 46
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Primer

<400> SEQUENCE: 135
gtctcctgtg tgaaattagc ggcggttact catcttcatg ccatcc            46

<210> SEQ ID NO 136
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 136
cacaaggaga ctgccatgtg taccatcatt agcgtcaatc atc               43

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 137
gtctcctgtg tgaaattaga cgtagggctt aaacagcaga ttggc             45

<210> SEQ ID NO 138
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 138
cacaaggaga ctgccatggc gagtgcggtc ccctgagta gtacg              45

<210> SEQ ID NO 139
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 139
gtctcctgtg tgaaattaac tactcagcag gggcgtaaaa aacaggg           47

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 140
cacaaggaga ctgccatgcg tgagagcctg agcagtagca gtagc                45

<210> SEQ ID NO 141
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 141
gtctcctgtg tgaaattaac taaagcacag tttgatattc ggac                 44

<210> SEQ ID NO 142
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 142
ggcagtctcc ttgtgtgaaa ttgttatccg ctca                            34

<210> SEQ ID NO 143
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 143
tttcacacag gagactgcca tggattttcc ccagc                           35

<210> SEQ ID NO 144
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 144
atgtccaccg ccgtgccctc tatgcccact acccaaaaat g                    41

<210> SEQ ID NO 145
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 145
gcaggtcgac tctagctatt tgttgcgctg gatgatgtaa tc                   42

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Primer

<400> SEQUENCE: 146
ggtacccggg gatcctctag agatcgttta gatccgaagg                40

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Primer

<400> SEQUENCE: 147
cacggcggtg gacattgtat gtcctcctgg acttcgtggt                40

<210> SEQ ID NO 148
<211> LENGTH: 8564
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DNA encoding pVK9-P0480-optAaLINS-ispA*

<400> SEQUENCE: 148
gaggtctgcc tcgtgaagaa ggtgttgctg actcatacca ggcctgaatc gccccatcat    60
ccagccagaa agtgagggag ccacggttga tgagagcttt gttgtaggtg acggggatc   120
ttttctacgg ggtctgacgc tcagtggaac gaaaactcac gttaagggat tttggtcatg   180
agattatcaa aaaggatcat gcgagcaacc tccataagat cagctaggcg atctttggga   240
gcagtccttg tcgcgttacg aggtgagccg gtggggaacc gttagctgcc tatggtgtga   300
gcccccctag agagcttcaa gagcaatcag cccgacctag aaaggaggcc aagagagaga   360
cctacggggg gaaccgtttt ctgcctacga gatgggcaca ttactgggaa gctttacggc   420
gtcctcgtgg aagttcaatg cccgcagact aagtgctct attcacgtc tgacgtgaca    480
cgctaaattc agacatagct tcattgattg tcggccacga gccagtctct ccctcaacag   540
tcataaacca acctgcaatg gtcaagcgat ttccttagc tttcctagct tgtcgttgac    600
tggacttagc tagttttct cgctgtgctc gggcgtactc actgtttggg tctttccagc    660
gttctgcggc cttttaccg ccacgtcttc ccatagtggc cagagctttt cgccctcggc    720
tgctctgcgt ctctgtctga cgagcaggga cgactggctg gcctttagcg acgtagccgc   780
gcacacgtcg cgccatcgtc tggcggtcac gcatcggcgg cagatcaggc tcacggccgt   840
ctgctccgac cgcctgagcg acggtgtagg cacgctcgta ggcgtcgatg atcttggtgt   900
cttttaggcg ctcaccagcc gcttttaact ggtatcccac agtcaaagcg tggcgaaaag   960
ccgtctcatc acgggcggca cgccctggag cagtccagag gacacggacg ccgtcgatca  1020
gctctccaga cgcttcagcg gcgctcggca ggcttgcttc aagcgtggca agtgcttttg  1080

-continued

```
cttccgcagt ggcttttctt gccgcttcga tacgtgcccg tccgctagaa aactcctgct  1140
catagcgttt tttaggtttt tctgtgcctg agatcatgcg agcaacctcc ataagatcag  1200
ctaggcgatc cacgcgattg tgctgggcat gccagcggta cgcggtggga tcgtcggaga  1260
cgtgcagtgg ccaccggctc agcctatgtg aaaaagcctg gtcagcgccg aaaacgcggg  1320
tcatttcctc ggtcgttgca gccagcaggc gcatattcgg gctgctcatg cctgctgcgg  1380
catacaccgg atcaatgagc cagatgagct ggcatttccc gctcagtgga ttcacgccga  1440
tccaagctgg cgcttttttcc aggcgtgccc agcgctccaa aatcgcgtag acctcggggt  1500
ttacgtgctc gattttcccg ccggcctggt ggctcggcac atcaatgtcc aggacaagca  1560
cggctgcgtg ctgcgcgtgc gtcagagcaa catactggca ccgggcaagc gattttgaac  1620
caactcggta taacttcggc tgtgtttctc ccgtgtccgg gtctttgatc caagcgctgg  1680
cgaagtcgcg ggtcttgctg ccctggaaat tttctctgcc caggtgagcg aggaattcgc  1740
ggcggtcttc gctcgtccag ccacgtgatc gcagcgcgag ctcggatgg gtgtcgaaca  1800
gatcagcgga aaatttccag gccggtgtgt caatgtctcg tgaatccgct agagtcattt  1860
ttgagcgctt tctcccaggt ttggactggg ggttagccga cgccctgtga gttaccgctc  1920
acggggcgtt caacattttt caggtattcg tgcagcttat cgcttcttgc cgcctgtgcg  1980
cttttcgac gcgcgacgct gctgccgatt cggtgcaggt ggtggcggcg ctgacacgtc  2040
ctgggcggcc acggccacac gaaacgcggc atttacgatg tttgtcatgc ctgcgggcac  2100
cgcgccacga tcgcggataa ttctcgctgc cgcttccagc tctgtgacga ccatggccaa  2160
aatttcgctc gggggacgca cttccagcgc catttgcgac ctagccgcct ccagctcctc  2220
ggcgtggcgt ttgttggcgc gctcgcggct ggctgcggca cgacacgcat ctgagcaata  2280
ttttgcgcgc cgtcctcgcg ggtcaggccg gggaggaatc aggccaccgc agtaggcgca  2340
actgattcga tcctccacta ctgtgcgtcc tcctggcgct gccgagcacg cagctcgtca  2400
gccagctcct caagatccgc cacgagagtt ctaggtcgc tcgcggcact ggcccagtct  2460
cgtgatgctg gcgcgtccgt cgtatcgaga gctcggaaaa atccgatcac cgttttttaaa  2520
tcgacggcag catcgagcgc gtcggactcc agcgcgacat cagagagatc catagctgat  2580
gattcgggcc aattttggta cttcgtcgtg aaggtcatga caccattata acgaacgttc  2640
gttaaagttt ttggcggaaa atcacgcggc acgaaaattt tcacgaagcg ggactttgcg  2700
cagctcaggg gtgctaaaaa ttttgtatcg cacttgattt ttccgaaaga cagattatct  2760
gcaaacggtg tgtcgtattt ctggcttggt ttttaaaaaa tctggaatcg aaaatttgcg  2820
gggcgaccga gaagtttttt acaaaaggca aaaacttttt cgggatcagc taggcgatcc  2880
acgcgattgt gctgggcatg ccagcggtac gcggtgggat cgtcggagac gtgcagtggc  2940
caccggctca gcctatgtga aaaagcctgg tcagcgccga aaacgcgggt catttcctcg  3000
gtcgttgcag ccagcaggcg catattcggg ctgctcatgc ctgctgcggc atacaccgga  3060
tcggaccagt tggtgatttt gaacttttgc tttgccacgg aacggtctgc gttgtcggga  3120
agatgcgtga tctgatcctt caactcagca aaagttcgat ttattcaaca agccacgtt  3180
gtgtctcaaa atctctgatg ttacattgca caagataaaa atatatcatc atgaacaata  3240
aaactgtctg cttacataaa cagtaataca agggggtgtta tgagccatat tcaacgggaa  3300
acgtcttgct cgaagccgcg attaaattcc aacatggatg ctgatttata tgggtataaa  3360
tgggctcgcg ataatgtcgg gcaatcaggt gcgacaatct atcgattgta tgggaagccc  3420
gatgcgccag agttgtttct gaaacatggc aaaggtagcg ttgccaatga tgttacagat  3480
```

-continued

```
gagatggtca gactaaactg gctgacggaa tttatgcctc ttccgaccat caagcatttt    3540
atccgtactc ctgatgatgc atggttactc accactgcga tccccgggaa aacagcattc    3600
caggtattag aagaatatcc tgattcaggt gaaaatattg ttgatgcgct ggcagtgttc    3660
ctgcgccggt tgcattcgat tcctgtttgt aattgtcctt ttaacagcga tcgcgtattt    3720
cgtctcgctc aggcgcaatc acgaatgaat aacggtttgg ttgatgcgag tgattttgat    3780
gacgagcgta atggctggcc tgttgaacaa gtctggaaag aaatgcataa gcttttgcca    3840
ttctcaccgg attcagtcgt cactcatggt gatttctcac ttgataacct tattttttgac   3900 gagggggaaat aataggttg tattgatgtt ggacgagtcg gaatcgcaga ccgataccag    3960
gatcttgcca tcctatggaa ctgcctcggt gagttttctc cttcattaca gaaacggctt    4020
tttcaaaaat atggtattga taatcctgat atgaataaat tgcagtttca tttgatgctc    4080
gatgagtttt tctaatcaga attggttaat tggttgtaac actggcagag cattacgctg    4140
acttgacggg acggcggctt tgttgaataa atcgcattcg ccattcaggc tgcgcaactg    4200
ttgggaaggg cgatcggtgc gggcctcttc gctattacgc cagctggcga aggggggatg    4260
tgctgcaagg cgattaagtt gggtaacgcc agggttttcc cagtcacgac gttgtaaaac    4320
gacggccagt gaattcgagc tcggtacccg gggatcctct agagatcgtt tagatccgaa    4380
ggaaaacgtc gaaaagcaat ttgcttttcg acgccccacc ccgcgcgttt tagcgtgtca    4440
gtagacgcgt agggtaagtg gggtagcggc ttgttagata tcttgaaatc ggctttcaac    4500
agcattgatt tcgatgtatt tagctggccg ttaccctgcg aatgtccaca gggtagctgg    4560
tagtttgaaa atcaacgccg ttgcccttag gattcagtaa ctggcacatt ttgtaatgcg    4620
ctagatctgt gtgcccagtc ttccaggctg cttatcacag tgaaagcaaa accaattcgt    4680
ggctgcgaaa gtcgtagcca ccacgaagtc caggaggaca tacaatgtcc accgccgtgc    4740
cctctatgcc cactacccaa aaatggtcta ttaccgaaga cttagccttt attagcaatc    4800
ccagcaaaca acataatcac caaaccggct accggatttt tagtgacgaa ttttacctga    4860
aacatgaaaa caaattgaaa gatgtgcggc gcgccttgcg tgaagttgaa gaaacccccc    4920
tggaaggctt ggtgatgatt gacactttac agcggctggg tattgattac cactttcaag    4980
gcgaaattgg tgccttgtta cagaaacaac agcgcattag tacctgtgac tatcccgaac    5040
atgatttgtt tgaagtgagc actcgctttc gtctgttgcg tcaagaaggt cacaatgtgc    5100
ccgccgacgt ttttaataac tttcgcgata agaagggcg ttttaaatct gaactgtccc    5160
gggatattcg cggattgatg tccttatacg aagccagtca actgagcatt caggggaag    5220 acatttggga tcaagccgct gacttttcca gtcagttact gtctggatgg gccaccaatt    5280
tagatcatca ccaagcccgt ctggtgcgga acgctttgac ccatccctac cacaaaagtc    5340
tggccacttt tatggctcgc aactttaact acgattgcaa agggcaaaac ggatgggtga    5400
ataacctgca ggaattggcc aaaatggatt taaccatggt tcaaagtatg catcagaaag    5460
aagtgctgca agttagccag tggtggaaag gcgggggatt ggccaatgaa ctgaaattgg    5520
tgcgcaacca acccttgaaa tggtatatgt ggcccatggc cgctttaacc gatcccggt     5580 tttctgaaga acgcgtggaa ttgactaaac ccatttcctt tatttacatt attgatgaca    5640 ttttgacgt ttatggcacc ttagaagaat taaccctgtt tactgatgcc gtgaatcggt     5700
gggaattaac tgctgttgaa cagctgcccg actacatgaa aatttgtttt aaagccttgt    5760
acgatattac caacgaaatt gcttacaaaa tttacaaaaa acatgggcgc aaccccattg    5820
```

```
atagtttacg tcggacttgg gccagcttat gcaatgcttt tctgaagaa  gccaaatggt    5880
ttgctagtgg caatttgccc aaagccgaag aatacctgaa aaacgggatt attagctctg    5940
gaatgcatgt ggttaccgtg cacatgtttt tcttgttagg cggttgtttt actgaagaat    6000
ccgtgaattt ggttgatgaa catgccggca ttacctccag tattgctact attttgcgtt    6060
tatctgatga cttaggttcc gccaaagatg aagaccaaga tggctatgac ggtagctact    6120
tggaatgtta cctgaaagat cataaaggta gctctgtgga aaatgcccgt gaagaagtta    6180
ttcggatgat ttccgatgct tggaaacgct tgaatgaaga atgcttattt cccaacccct    6240
tttctgccac ctttcgcaaa gggtccttaa atattgctcg tatggtgccc ctgatgtaca    6300
gttacgatga caaccataac ctgcccattc tggaagaaca catgaaaacc atgttgtatg    6360
attccagtag ctaatttcac acaggagact gccatggatt ttccccagca gctggaagcc    6420
tgcgtgaaac aggccaacca ggccctgagc cgctttatcg ccccccctgcc ctttcagaac    6480
accccgtgg tggaaaccat gcagtacggc gccctgctgg cggcaaacg cctgcgcccc    6540
tttctggtgt acgccaccgg ccacatgttt ggcgtgagca ccaacaccct ggatgccccc    6600
gccgccgccg tggaatgcat ccacgcctac tttctgatcc acgatgatct gcccgccatg    6660
gatgatgatg atctgcgccg cggcctgccc acctgccacg tgaaatttgg cgaagccaac    6720
gccatcctgg ccggcgatgc cctgcagacc ctggccttta gcatcctgag cgatgccgat    6780
atgcccgaag tgagcgatcg cgatcgcatc agcatgatca cgaactggc cagcgccagc    6840
ggcatcgccg gcatgtgcgg cggccaggcc ctggatctgg atgccgaagg caaacacgtg    6900
cccctggatg ccctggaacg catccaccgc cacaaaaccg cgcccctgat ccgcgccgcc    6960
gtgcgcctgg gcgccctgag cgccggcgat aaaggccgcc gcgccctgcc cgtgctggat    7020
aaatacgccg aaagcatcgg cctggccttt caggtgcagg atgatatcct ggatgtggtg    7080
ggcgataccg ccaccctggg caaacgccag ggcgccgatc agcagctggg caaaagcacc    7140
tacccccgcc tgctgggcct ggaacaggcc cgcaaaaaag cccgcgatct gatcgatgat    7200
gcccgccaga gcctgaaaca gctggccgaa cagagcctgg ataccagcgc cctggaagcc    7260
ctggccgatt acatcatcca gcgcaacaaa tagctagagt cgacctgcag gcatgcaagc    7320
ttggcgtaat catggtcata gctgtttcct gtgtgaaatt gttatccgct cacaattcca    7380
cacaacatac gagccggaag cataaagtgt aaagcctggg gtgcctaatg agtgagctaa    7440
ctcacattaa ttgcgttgcg ctcactgccc gctttccagt cgggaaacct gtcgtgccag    7500
ctgcattaat gaatcggcca acgcgcgggg agaggcggtt tgcgtattgg cgaacttttg    7560
ctgagttgaa ggatcagatc acgcatcttc ccgacaacgc agaccgttcc gtggcaaagc    7620
aaaagttcaa aatcagtaac cgtcagtgcc gataagttca agttaaaacc tggtgttgat    7680
accaacattg aaacgctgat cgaaaacgcg ctgaaaacg ctgctgaatg tgcgagcttc    7740
ttccgcttcc tcgctcactg actcgctgcg ctcggtcgtt cggctgcggc gagcggtatc    7800
agctcactca aaggcggtaa tacggttatc cacagaatca ggggataacg caggaaagaa    7860
catgtgagca aaaggccagc aaaaggccag gaaccgtaaa aaggccgcgt tgctggcgtt    7920
tttccatagg ctccgccccc ctgacgagca tcacaaaaat cgacgctcaa gtcagaggtg    7980
gcgaaacccg acaggactat aaagatacca ggcgtttccc cctggaagct ccctcgtgcg    8040
ctctcctgtt ccgaccctgc cgcttaccgg atacctgtcc gcctttctcc cttcgggaag    8100
cgtggcgctt tctcaatgct cacgctgtag gtatctcagt tcggtgtagg tcgttcgctc    8160
caagctgggc tgtgtgcacg aaccccccgt tcagcccgac cgctgcgcct tatccggtaa    8220
```

```
ctatcgtctt gagtccaacc cggtaagaca cgacttatcg ccactggcag cagccactgg    8280
taacaggatt agcagagcga ggtatgtagg cggtgctaca gagttcttga agtggtggcc    8340
taactacggc tacactagaa ggacagtatt tggtatctgc gctctgctga agccagttac    8400
cttcggaaaa agagttggta gctcttgatc cggcaaacaa accaccgctg gtagcggtgg    8460 ttttttttgtt tgcaagcagc agattacgcg cagaaaaaaa ggatctcaag aagatccttt    8520 gatctttct acggggtctg acgctcagtg aacgatccg tcga                       8564
```

<210> SEQ ID NO 149
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer

<400> SEQUENCE: 149

```
tctagagtcg acgtcccctg ttgacaatta atcatcggct cgtataatgt gtgga          55
```

<210> SEQ ID NO 150
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 150

```
tccaatgtga ggttttagct actggaatca tacaacatgg ttttcatgtg ttct           54
```

<210> SEQ ID NO 151
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 151

```
aaggaattat aaccaaatgt ccaccgccgt gccctctatg cccactaccc aaaaatg        57
```

<210> SEQ ID NO 152
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 152

```
gatggggaag tttaggctag cctatttgtt gcgctggatg atgtaatcgg ccagg          55
```

<210> SEQ ID NO 153
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Primer

<400> SEQUENCE: 153
ggaggattgg gttaccctca gtgtg                                          25

<210> SEQ ID NO 154
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 154
cgccatatca atcccaacgc tctgg                                          25

<210> SEQ ID NO 155
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 155
ggaatattaa gcttggtacc atgtccaccg ccgtgccctc tatg                     44

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 156
gtggatccga gctcggtacc ctatttgttg cgctggatga tg                       42

<210> SEQ ID NO 157
<211> LENGTH: 609
<212> TYPE: PRT
<213> ORGANISM: Solanum lycopersicum

<400> SEQUENCE: 157

Met Val Ser Ile Leu Ser Asn Ile Gly Met Met Val Val Thr Phe Lys
1               5                   10                  15

Arg Pro Ser Leu Phe Thr Ser Leu Arg Arg Arg Ser Ala Asn Asn Ile
            20                  25                  30

Ile Ile Thr Lys His Ser His Pro Ile Ser Thr Thr Arg Arg Ser Gly
        35                  40                  45

Asn Tyr Lys Pro Thr Met Trp Asp Phe Gln Phe Ile Gln Ser Leu His
    50                  55                  60

Asn Pro Tyr Glu Gly Asp Lys Tyr Met Lys Arg Leu Asn Lys Leu Lys
65                  70                  75                  80

Lys Glu Val Lys Lys Met Met Met Thr Val Glu Gly Ser His Asp Glu
                85                  90                  95

```
Glu Leu Glu Lys Leu Glu Leu Ile Asp Asn Leu Glu Arg Leu Gly Val
            100                 105                 110

Ser Tyr His Phe Lys Asp Glu Ile Met Gln Ile Met Arg Ser Ile Asn
            115                 120                 125

Ile Asn Ile Asn Ile Ala Pro Pro Asp Ser Leu Tyr Thr Thr Ala Leu
            130                 135                 140

Lys Phe Arg Leu Leu Arg Gln His Gly Phe His Ile Ser Gln Asp Ile
145                 150                 155                 160

Leu Asn Asp Phe Lys Asp Glu Asn Gly Asn Leu Lys Gln Ser Ile Cys
                165                 170                 175

Lys Asp Thr Lys Asp Ile Leu Asn Ser Ser Lys Asp Glu His Asp Asn
            180                 185                 190

Leu Lys Gln Ser Thr Cys Asn Asn Thr Lys Gly Leu Leu Lys Leu Tyr
            195                 200                 205

Glu Ala Ser Phe Leu Ser Ile Glu Asn Glu Ser Phe Leu Arg Asn Thr
            210                 215                 220

Thr Lys Ser Thr Leu Ala His Leu Met Arg Tyr Val Asp Gln Asn Arg
225                 230                 235                 240

Cys Gly Glu Glu Asp Asn Met Ile Val Glu Leu Val Val His Ala Leu
                245                 250                 255

Glu Leu Pro Arg His Trp Met Val Pro Arg Leu Glu Thr Arg Trp Tyr
            260                 265                 270

Ile Ser Ile Tyr Glu Arg Met Ser Asn Ala Asn Pro Leu Leu Leu Glu
            275                 280                 285

Leu Ala Lys Leu Asp Phe Asn Ile Val Gln Ala Thr His Gln Gln Asp
            290                 295                 300

Leu Arg Ile Leu Ser Arg Trp Trp Lys Asn Thr Gly Leu Ala Glu Lys
305                 310                 315                 320

Leu Pro Phe Ser Arg Asp Ile Leu Val Glu Asn Met Phe Trp Ala Val
                325                 330                 335

Gly Ala Leu Phe Glu Pro Gln His Ser Tyr Phe Arg Arg Leu Ile Thr
            340                 345                 350

Lys Val Ile Val Phe Ile Ser Ile Ile Asp Asp Ile Tyr Asp Val Tyr
            355                 360                 365

Gly Thr Leu Asp Glu Leu Glu Leu Phe Thr Leu Ala Ile Gln Arg Trp
            370                 375                 380

Asp Thr Lys Ala Met Glu Gln Leu Pro Asp Tyr Met Lys Val Cys Tyr
385                 390                 395                 400

Leu Ala Leu Ile Asn Ile Ile Asn Glu Val Ala Tyr Glu Val Leu Lys
                405                 410                 415

Asn His Asp Ile Asn Val Leu Pro Tyr Leu Thr Lys Ser Trp Ala Asp
            420                 425                 430

Leu Cys Lys Ser Tyr Leu Gln Glu Ala Lys Trp Tyr His Asn Gly Tyr
            435                 440                 445

Lys Pro Asn Leu Glu Glu Tyr Met Asp Asn Ala Arg Ile Ser Ile Gly
            450                 455                 460

Val Pro Met Val Leu Val His Ser Leu Phe Leu Val Thr Asn Gln Ile
465                 470                 475                 480

Thr Lys Glu Ala Leu Asp Ser Leu Thr Asn Tyr Pro Asp Ile Ile Arg
                485                 490                 495

Trp Ser Ala Thr Ile Phe Arg Leu Asn Asp Asp Leu Gly Thr Ser Ser
            500                 505                 510
```

```
Asp Glu Leu Lys Arg Gly Asp Val Ser Lys Ser Ile Gln Cys Tyr Met
            515                 520                 525

Asn Glu Lys Gly Ala Ser Glu Glu Ala Ile Glu His Ile Glu Phe
    530                 535                 540

Leu Ile Gln Glu Thr Trp Glu Ala Met Asn Thr Ala Gln Ser Lys Asn
545                 550                 555                 560

Ser Pro Leu Ser Glu Thr Phe Ile Glu Val Ala Lys Asn Ile Thr Lys
                565                 570                 575

Ala Ser His Phe Met Tyr Leu His Ser Asp Val Lys Ser Ser Ile Ser
                580                 585                 590

Lys Ile Leu Phe Glu Pro Ile Ile Ile Ser Asn Val Ala Phe Ala Leu
            595                 600                 605

Lys

<210> SEQ ID NO 158
<211> LENGTH: 594
<212> TYPE: PRT
<213> ORGANISM: Backhousia citriodora

<400> SEQUENCE: 158

Met Ala Leu Pro Ala Leu Phe Gly Ser Ser Leu Pro Ser Ser Ile Arg
1               5                   10                  15

His Asn Gln Pro Ser Leu Phe Ser Phe Arg His Pro Arg Phe Cys Ser
            20                  25                  30

Ser Ser Ser Ser Ala Ser Phe Ser Ser Gln Phe Ile Leu Cys Ala Ser
                35                  40                  45

Lys Thr Gly Asp Gln Glu Ile Val Arg Arg Ser Ala Asn Trp Gln Pro
    50                  55                  60

Ser Val Trp Asp Tyr Asp Tyr Val Gln Ser Leu Thr Val Asp Tyr Thr
65                  70                  75                  80

Glu Asp Lys Tyr Thr Lys Gln Val Gln Arg Leu Lys Glu Glu Val Lys
                85                  90                  95

Gly Leu Phe Asp Arg Glu Met Lys Gln Val Ala Lys Leu Glu Phe Ile
            100                 105                 110

Asp Val Val Gln Arg Leu Gly Leu Gly Tyr His Phe Lys Thr Glu Ile
            115                 120                 125

Lys Ile Ala Leu Ser Ser Ile His Asn Asn Thr Glu Asp Ala Gln Leu
    130                 135                 140

Ser Asn Asp Leu Tyr Ala Ala Ser Leu Arg Phe Arg Leu Leu Arg Gln
145                 150                 155                 160

Tyr Gly Cys Asn Val Gln Gln Asp Val Phe Gln Arg Phe Met Asn Lys
                165                 170                 175

Thr Gly Thr Phe Lys Glu Ser Leu Asn Lys Asp Val Lys Gly Ile Leu
            180                 185                 190

Gly Leu Tyr Glu Ala Ser Phe His Gly Met Glu Gly Glu Thr Val Leu
            195                 200                 205

Asp Glu Ala Trp Asn Phe Ala Ser Lys His Leu Lys Asp Leu Asn Leu
    210                 215                 220

Asp Glu Val Pro Thr Asn Leu Ala Ser Asn Val Ser His Ala Leu Asp
225                 230                 235                 240

Met Pro Ile His Trp Arg Pro Asn Arg Leu Glu Ala Arg Trp Phe Met
                245                 250                 255

Asp Met Tyr Glu Lys Gln Gln Asp Leu Ile Pro Ser Leu Leu Arg Leu
            260                 265                 270
```

```
Ala Lys Leu Asp Phe Asn Ile Val Gln Ser Ile His Arg Lys Glu Val
            275                 280                 285

Ser Asn Leu Ala Arg Trp Trp Val Glu Leu Gly Ala Asn Lys Met Thr
        290                 295                 300

Phe Phe Arg Asp Arg Leu Val Glu Ser Tyr Phe Trp Ser Cys Ile Leu
305                 310                 315                 320

Val Phe Glu Pro Gln Tyr Thr Asp Phe Arg Glu Leu Asn Thr Arg Ile
                325                 330                 335

Ala Cys Met Ala Thr Leu Ile Asp Val Tyr Asp Ile Tyr Gly Thr
            340                 345                 350

Pro Glu Glu Leu Glu Leu Leu Thr Asp Phe Ile Leu Arg Trp Asp Ile
            355                 360                 365

Thr Asp Ile Asp Lys Leu Pro Pro Thr Ile Arg Asn Gly Phe Met Ala
370                 375                 380

Leu Tyr Asn Thr Thr Asn Lys Val Gly Tyr Arg Thr Met Thr Lys Arg
385                 390                 395                 400

Gly Ile Asn Pro Ile Pro Tyr Leu Arg Lys Leu Trp Gly Asp Glu Cys
                405                 410                 415

Lys Ala Asp Met Lys Glu Val His Trp Phe Asn Asn Gly Ile Lys Pro
                420                 425                 430

Thr Leu Lys Glu Tyr Met Asp Val Ala Val Asp Ser Ile Gly Gly Leu
            435                 440                 445

Ile Leu Leu Leu Asn Ser Tyr Phe Leu Thr Thr Asp Tyr Leu Thr Glu
            450                 455                 460

Glu Gly Leu Asn Tyr Val Ser Lys Ile Pro Ser Val Met His Ser Ser
465                 470                 475                 480

Ala Gln Ile Phe Arg Phe Asn Asp Asp Leu Ser Thr Ser Ser His Glu
                485                 490                 495

Leu Ala Arg Gly Asp Asn Ser Lys Ala Leu Glu Cys Tyr Met Asn Glu
            500                 505                 510

Thr Gly Ala Ser Glu Glu Ile Ala Arg Glu His Ile Arg His Leu Val
            515                 520                 525

Arg Glu Thr Trp Lys Lys Met Asn Lys Glu Val Phe Glu Asp Tyr Pro
530                 535                 540

Phe Ser Gly Phe Gly Pro Phe Leu Ser Ala Cys Leu Asn Leu Ala Arg
545                 550                 555                 560

Ala Ser His Cys Phe Tyr Glu Tyr Gly Asp Gly Tyr Gly Leu Pro Asp
                565                 570                 575

His Gln Thr Arg Asp His Leu Ala Ser Thr Ile Phe Gly Ser Val Ser
            580                 585                 590

Leu Asp

<210> SEQ ID NO 159
<211> LENGTH: 567
<212> TYPE: PRT
<213> ORGANISM: Artemisia annua

<400> SEQUENCE: 159

Gly Asn Ala Tyr Met Arg Ile Tyr Ser Thr Lys Thr Thr Arg Ile Thr
1               5                   10                  15

Ala Asn Ala Thr Val Asn Ala Ala Asp Thr His Val Arg Arg Ser Ala
            20                  25                  30

Asn Tyr Lys Pro Ser Ser Trp Ser Phe Asp His Ile Gln Ser Leu Ser
        35                  40                  45
```

```
Ser Lys Tyr Thr Gly Asp Asp Tyr Val Ala Arg Ala Asn Thr Leu Lys
    50              55                  60
Asp Ala Val Lys Thr Met Ile Arg Lys Ser Gly Asn Ser Leu Arg Thr
65              70                  75                  80
Leu Glu Leu Val Asp Glu Leu Gln Arg Leu Gly Ile Ser Tyr Leu Phe
                85                  90                  95
Glu Glu Glu Ile Ser Asn Leu Leu Glu Thr Ile Tyr Tyr Asn Tyr Tyr
            100                 105                 110
Lys Phe Pro Glu Asn Trp Asn Lys Ile Asn Leu Asn Leu Lys Ala Leu
            115                 120                 125
Gly Phe Arg Leu Leu Arg Gln His Gly Tyr His Val Pro Gln Glu Ile
130                 135                 140
Phe Leu Asn Phe Lys Asp Lys Asn Gln Asn Leu Asn Ser Tyr Leu Leu
145                 150                 155                 160
Asn Asp Val Val Glu Met Leu Asn Leu Tyr Glu Ala Ser Tyr His Ser
                165                 170                 175
Phe Glu Asp Glu Ser Ile Leu Asp Asp Ala Arg Asp Ile Thr Thr Lys
            180                 185                 190
Tyr Leu Lys Glu Ser Leu Glu Lys Ile Asp Gly Ser Ile Phe Ser Ser
            195                 200                 205
Val Thr His Ala Leu Glu Gln Pro Leu His Trp Arg Val Pro Arg Val
210                 215                 220
Glu Ala Lys Trp Phe Ile Glu Leu Tyr Glu Lys Lys Asn Gly Met Ser
225                 230                 235                 240
Pro Thr Leu Val Glu Leu Ala Lys Leu Asp Phe Asp Met Val Gln Ala
                245                 250                 255
Ile His Leu Glu Asp Leu Lys His Ala Ser Arg Trp Trp Arg Asp Thr
            260                 265                 270
Ser Trp Asp Thr Lys Leu Thr Phe Ala Arg Asp Leu Ile Val Glu Asn
            275                 280                 285
Phe Leu Trp Thr Ile Gly Phe Ser Tyr Leu Pro Asn Phe Ser Arg Gly
290                 295                 300
Arg Arg Thr Ile Thr Lys Val Ala Val Met Ile Thr Thr Leu Asp Asp
305                 310                 315                 320
Val Tyr Asp Val Phe Gly Thr Leu Gly Glu Leu Glu Gln Phe Thr Asp
                325                 330                 335
Val Ile Asn Arg Trp Asp Ile Lys Ala Ile Glu Gln Leu Pro Asp Tyr
            340                 345                 350
Met Lys Ile Cys Phe Leu Gly Leu Tyr Lys Ser Ile Asn Asp Ile Thr
            355                 360                 365
His Glu Thr Leu Ala Asn Lys Gly Phe Leu Ile Leu Pro Tyr Leu Lys
370                 375                 380
Lys Ala Trp Ala Asp Leu Cys Lys Ala Tyr Leu Val Glu Ala Gln Trp
385                 390                 395                 400
Tyr His Arg Gly His Ile Pro Thr Leu Asn Glu Tyr Leu Asp Asn Ala
                405                 410                 415
Cys Val Ser Ile Ser Gly Pro Val Ala Leu Met His Val His Phe Leu
            420                 425                 430
Thr Ser Val Ser Ser Ile Glu Glu Ile His Gln Cys Ile Gln Arg Thr
            435                 440                 445
Glu Asn Ile Val His Tyr Val Ser Leu Ile Phe Arg Leu Ala Asp Asp
450                 455                 460
Leu Gly Thr Ser Leu Gly Glu Met Glu Arg Gly Asp Thr Leu Lys Ser
```

```
    465                 470                 475                 480
Ile Gln Leu His Met His Glu Thr Gly Ala Thr Glu Pro Glu Ala Arg
                485                 490                 495

Ser Tyr Ile Lys Leu Leu Ile Asn Lys Thr Trp Lys Lys Leu Asn Lys
                500                 505                 510

Glu Arg Ala Thr Val Asn Ser Glu Ser Ser Gln Glu Phe Ile Asp Tyr
                515                 520                 525

Ala Thr Asn Leu Val Arg Met Ala Gln Phe Met Tyr Gly Glu Gly Asp
                530                 535                 540

Glu Asp Phe Gly Leu Asp Val Ile Lys Ser His Val Leu Ser Leu Leu
545                 550                 555                 560

Phe Thr Pro Ile Gln Gly Ile
                565

<210> SEQ ID NO 160
<211> LENGTH: 583
<212> TYPE: PRT
<213> ORGANISM: Artemisia annua

<400> SEQUENCE: 160

Met Ala Ser Ile Ser Leu Phe Pro Tyr Ser Ile Leu Lys Gln Thr Ser
1               5                   10                  15

Pro Leu Ala Arg Gly Thr Ala Tyr Asn Arg Ile Tyr Ser Thr Lys Thr
                20                  25                  30

Thr Gly Ile Thr Val Asp Val Ala Glu Ser His Val Arg Arg Ser Ala
                35                  40                  45

Asn Tyr Glu Pro Ser Ser Trp Ser Phe Asp His Ile Gln Ser Leu Ser
        50                  55                  60

Ser Lys Tyr Thr Gly Asp Asp Cys Val Ala Arg Ala Asn Thr Leu Lys
65                  70                  75                  80

Glu Ser Val Lys Thr Met Ile Arg Lys Glu Gly Asn Leu Leu Arg Thr
                85                  90                  95

Leu Glu Leu Val Asp Glu Leu Gln Arg Leu Gly Ile Ser Tyr Leu Phe
                100                 105                 110

Glu Gly Glu Ile Ser Asn Leu Leu Glu Thr Ile Tyr Tyr Asn His Tyr
                115                 120                 125

Lys Phe Pro Glu Lys Trp Asn Lys Phe Asp Leu Asn Leu Lys Ala Leu
        130                 135                 140

Gly Phe Arg Leu Leu Arg Gln His Gly Tyr His Val Pro Gln Glu Ile
145                 150                 155                 160

Phe Leu Asn Phe Lys Asp Lys Asn Gln Asn Leu Asn Ser Tyr Leu Leu
                165                 170                 175

Glu Asp Val Val Gly Met Leu Asn Leu Tyr Glu Ala Ser Tyr His Ser
                180                 185                 190

Phe Glu Asp Glu Ser Ile Leu Thr Glu Ala Arg Asp Ile Ala Thr Lys
                195                 200                 205

Tyr Leu Lys Ala Ser Leu Glu Lys Ile Asp Gly Ser Ile Leu Ser Leu
        210                 215                 220

Val Ser His Ala Leu Asp Asn Arg Leu His Trp Arg Val Pro Arg Val
225                 230                 235                 240

Glu Ser Lys Trp Phe Ile Glu Val Tyr Glu Lys Arg Val Gly Ala Ser
                245                 250                 255

Pro Thr Leu Ile Glu Leu Ala Lys Leu Asp Phe Asp Met Val Gln Ala
                260                 265                 270
```

```
Ile His Leu Glu Asp Leu Lys His Ala Ser Arg Trp Trp Arg Asn Thr
            275                 280                 285

Ser Trp Asp Thr Lys Leu Thr Phe Ala Arg Asp Met Leu Val Glu Asn
        290                 295                 300

Phe Leu Trp Thr Val Gly Phe Ser Tyr Leu Pro Asn Phe Ser His Gly
305                 310                 315                 320

Arg Arg Thr Ile Thr Lys Val Ala Ala Met Ile Thr Thr Leu Asp Asp
                325                 330                 335

Val Tyr Asp Val Phe Gly Thr Leu Glu Leu Glu Gln Phe Thr Asp
            340                 345                 350

Val Ile Asn Arg Trp Asp Ile Lys Ala Ile Glu Gln Leu Pro Asp Tyr
        355                 360                 365

Met Lys Ile Cys Phe Phe Gly Leu Tyr Asn Ser Ile Asn Asp Ile Thr
370                 375                 380

Tyr Glu Thr Leu Ala Thr Lys Gly Phe Leu Ile Leu Pro Tyr Ile Lys
385                 390                 395                 400

Lys Ala Trp Ala Asp Leu Cys Lys Ser Tyr Leu Val Glu Ala Gln Trp
                405                 410                 415

Tyr His Arg Gly His Ile Pro Thr Leu Asn Glu Tyr Leu Asp Asn Ala
            420                 425                 430

Cys Val Ser Ile Ser Gly Pro Val Ala Leu Met His Val His Phe Leu
        435                 440                 445

Thr Ser Val Ser Ser Thr Lys Glu Ile His His Cys Ile Glu Arg Thr
        450                 455                 460

Gln Asn Ile Val Arg Tyr Val Ser Leu Ile Phe Arg Leu Thr Asp Asp
465                 470                 475                 480

Leu Gly Thr Ser Leu Gly Glu Met Glu Arg Gly Asp Thr Leu Lys Ser
                485                 490                 495

Ile Gln Leu Tyr Met His Glu Thr Gly Ala Thr Glu Pro Glu Ala Arg
            500                 505                 510

Ser Tyr Ile Lys Ser Leu Ile Asp Lys Thr Trp Lys Lys Leu Asn Lys
        515                 520                 525

Glu Arg Ala Ile Val Ser Ser Glu Ser Ser Arg Glu Phe Ile Asp Tyr
        530                 535                 540

Ala Thr Asn Leu Ala Arg Met Ala His Phe Met Tyr Gly Glu Gly Asp
545                 550                 555                 560

Glu Asp Phe Arg Leu Asp Val Ile Lys Ser His Val Ser Ser Leu Leu
                565                 570                 575

Phe Thr Pro Ile Gln Gly Ile
            580

<210> SEQ ID NO 161
<211> LENGTH: 574
<212> TYPE: PRT
<213> ORGANISM: Actinidia arguta

<400> SEQUENCE: 161

Met Ala Ser Phe Asn Arg Phe Cys Val Ser Ser Leu Leu Ala Pro Asn
1               5                   10                  15

Asn Ser Pro Gln Ile Ser Asn Ala Pro Arg Ser Thr Ala Val Pro Ser
            20                  25                  30

Met Pro Thr Thr Gln Lys Trp Ser Ile Thr Glu Asp Leu Ala Phe Ile
        35                  40                  45

Ser Asn Pro Ser Lys Gln His Asn His Gln Thr Gly Tyr Arg Ile Phe
    50                  55                  60
```

-continued

```
Ser Asp Glu Phe Tyr Leu Lys His Glu Asn Lys Leu Lys Asp Val Arg
 65                  70                  75                  80

Arg Ala Leu Arg Glu Val Glu Glu Thr Pro Leu Glu Gly Leu Val Met
                 85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Gln Arg Ile Ser Thr Cys Asp Tyr
            115                 120                 125

Pro Glu His Asp Leu Phe Glu Val Ser Thr Arg Phe Arg Leu Leu Arg
            130                 135             140

Gln Glu Gly His Asn Val Pro Ala Asp Val Phe Asn Asn Phe Arg Asp
145                 150                 155                 160

Lys Glu Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
            195                 200                 205

Thr Asn Leu Asp His His Gln Ala Arg Leu Val Arg Asn Ala Leu Thr
210                 215                 220

His Pro Tyr His Lys Ser Leu Ala Thr Phe Met Ala Arg Asn Phe Asn
225                 230                 235                 240

Tyr Asp Cys Lys Gly Gln Asn Gly Trp Val Asn Asn Leu Gln Glu Leu
                245                 250                 255

Ala Lys Met Asp Leu Thr Met Val Gln Ser Met His Gln Lys Glu Val
            260                 265                 270

Leu Gln Val Ser Gln Trp Trp Lys Gly Arg Gly Leu Ala Asn Glu Leu
            275                 280                 285

Lys Leu Val Arg Asn Gln Pro Leu Lys Trp Tyr Met Trp Pro Met Ala
290                 295                 300

Ala Leu Thr Asp Pro Arg Phe Ser Glu Glu Arg Val Glu Leu Thr Lys
305                 310                 315                 320

Pro Ile Ser Phe Ile Tyr Ile Ile Asp Asp Ile Phe Asp Val Tyr Gly
                325                 330                 335

Thr Leu Glu Glu Leu Thr Leu Phe Thr Asp Ala Val Asn Arg Trp Glu
            340                 345                 350

Leu Thr Ala Val Glu Gln Leu Pro Asp Tyr Met Lys Ile Cys Phe Lys
            355                 360                 365

Ala Leu Tyr Asp Ile Thr Asn Glu Ile Ala Tyr Lys Ile Tyr Lys Lys
            370                 375                 380

His Gly Arg Asn Pro Ile Asp Ser Leu Arg Arg Thr Trp Ala Ser Leu
385                 390                 395                 400

Cys Asn Ala Phe Leu Glu Glu Ala Lys Trp Phe Ala Ser Gly Asn Leu
                405                 410                 415

Pro Lys Ala Glu Glu Tyr Leu Lys Asn Gly Ile Ile Ser Ser Gly Met
            420                 425                 430

His Val Val Thr Val His Met Phe Phe Leu Leu Gly Gly Cys Phe Thr
            435                 440                 445

Glu Glu Ser Val Asn Leu Val Asp Glu His Ala Gly Ile Thr Ser Ser
            450                 455                 460

Ile Ala Thr Ile Leu Arg Leu Ser Asp Asp Leu Gly Ser Ala Lys Asp
465                 470                 475                 480
```

Glu Asp Gln Asp Gly Tyr Asp Gly Ser Tyr Leu Glu Cys Tyr Leu Lys
                485                 490                 495

Asp His Lys Gly Ser Ser Val Glu Asn Ala Arg Glu Glu Val Ile Arg
            500                 505                 510

Met Ile Ser Asp Ala Trp Lys Arg Leu Asn Glu Glu Cys Leu Phe Pro
            515                 520                 525

Asn Pro Phe Ser Ala Thr Phe Arg Lys Gly Ser Leu Asn Ile Ala Arg
530                 535                 540

Met Val Pro Leu Met Tyr Ser Tyr Asp Asp Asn His Asn Leu Pro Ile
545                 550                 555                 560

Leu Glu Glu His Met Lys Thr Met Leu Tyr Asp Ser Ser Ser
                565                 570

<210> SEQ ID NO 162
<211> LENGTH: 574
<212> TYPE: PRT
<213> ORGANISM: Actinidia polygama

<400> SEQUENCE: 162

Met Ala Ser Phe His Arg Phe Cys Val Ser Ser Leu Leu Val Pro Asn
1               5                   10                  15

Asn Ser Pro Gln Ile Ser Asn Ala Tyr Arg Ala Pro Ala Val Pro Ser
            20                  25                  30

Met Pro Thr Thr Gln Lys Trp Ser Ile Thr Glu Asp Leu Ala Phe Ile
        35                  40                  45

Ser Asn Pro Ser Lys Gln His Asn His Gln Thr Gly Tyr Arg Thr Phe
    50                  55                  60

Ser Asp Glu Phe Tyr Val Lys Arg Glu Lys Lys Leu Lys Asp Val Arg
65                  70                  75                  80

Arg Ala Leu Arg Glu Val Glu Glu Thr Pro Leu Glu Gly Leu Val Met
                85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Gln Arg Lys Ser Lys Cys Asp Tyr
        115                 120                 125

Pro Glu His Asp Leu Phe Glu Val Ser Thr Arg Phe Arg Leu Leu Arg
    130                 135                 140

Gln Glu Gly His Asn Val Pro Ala Asp Val Phe Asn His Phe Arg Asp
145                 150                 155                 160

Lys Lys Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
        195                 200                 205

Thr Asn Pro Asp His His Gln Ala Arg Leu Val Arg Asn Ala Leu Thr
    210                 215                 220

His Pro Tyr His Lys Ser Leu Ala Thr Phe Thr Ala Arg Asn Phe His
225                 230                 235                 240

Tyr Asp Cys Lys Gly Gln Asn Gly Trp Val Asn Asn Leu Gln Glu Leu
                245                 250                 255

Ala Lys Met Asp Leu Thr Val Val Gln Ser Met His Gln Lys Glu Val
            260                 265                 270

Leu Gln Val Ser Gln Trp Trp Lys Asp Arg Gly Leu Ala Asn Glu Leu
        275                 280                 285

-continued

```
Lys Leu Val Arg Asn Gln Pro Leu Lys Trp Tyr Met Trp Pro Met Ala
    290                 295                 300
Ala Leu Thr Asp Pro Arg Phe Ser Glu Glu Arg Val Glu Leu Thr Lys
305                 310                 315                 320
Pro Ile Ser Phe Ile Tyr Ile Ile Asp Ile Phe Asp Val Tyr Gly
                325                 330                 335
Thr Leu Glu Glu Leu Thr Leu Phe Thr Asp Ala Val Asn Arg Trp Glu
                340                 345                 350
Leu Thr Ala Val Glu Gln Leu Pro Asp Tyr Met Lys Val Cys Phe Lys
        355                 360                 365
Ala Leu Tyr Asp Ile Thr Asn Glu Ile Ala Tyr Lys Ile Tyr Lys Lys
    370                 375                 380
His Gly Trp Asn Pro Ile Asp Ser Leu Arg Arg Met Trp Ala Ser Leu
385                 390                 395                 400
Cys Asn Ala Phe Leu Val Glu Ala Lys Trp Phe Ala Ser Gly His Leu
                405                 410                 415
Pro Lys Ala Glu Glu Tyr Leu Lys Asn Gly Ile Ile Ser Ser Gly Met
                420                 425                 430
His Val Val Thr Val His Met Phe Phe Leu Leu Gly Gly Cys Phe Thr
        435                 440                 445
Asp Glu Ser Val Asn Leu Val Asp Glu His Ala Gly Ile Thr Ser Ser
    450                 455                 460
Ile Ala Thr Ile Leu Arg Leu Ser Asp Asp Leu Gly Ser Ala Lys Asp
465                 470                 475                 480
Glu Asp Gln Asp Gly Tyr Asp Gly Ser Tyr Val Glu Tyr Tyr Leu Lys
                485                 490                 495
Asp His Lys Gly Ser Ser Val Gly Asn Ala Arg Glu Glu Val Ile Arg
                500                 505                 510
Met Ile Ser Asp Ala Trp Lys Arg Leu Asn Glu Glu Cys Leu Ser Pro
        515                 520                 525
Asn Pro Phe Ser Ala Thr Phe Arg Lys Gly Cys Leu Asn Ile Ala Arg
    530                 535                 540
Met Val Pro Leu Met Tyr Ser Tyr Asp Asp Asn His Asn Leu Pro Leu
545                 550                 555                 560
Leu Glu Glu His Met Lys Ala Met Leu Tyr Asp Ser Ser Ser
                565                 570

<210> SEQ ID NO 163
<211> LENGTH: 604
<212> TYPE: PRT
<213> ORGANISM: Perilla frutescens

<400> SEQUENCE: 163

Met Ser Ser Met Arg Ile Tyr Val Ala Ile Met Lys Lys Pro Ser Val
1               5                   10                  15
Lys His Val Asp Tyr Val Asp Lys Lys Ala Ser Lys Pro Ser Trp Arg
                20                  25                  30
Val Ser Ser Ser Ala Thr Ala Gly Leu Arg Ala Ser Ser Ser Leu Gln
        35                  40                  45
Leu Asp Val Lys Lys Pro Ala Asp Glu Ile Leu Thr Ala Arg Arg Ser
    50                  55                  60
Gly Asn Tyr Gln Pro Ser Leu Trp Asp Phe Asn Tyr Leu Gln Ser Leu
65                  70                  75                  80
Asn Thr Thr His Tyr Lys Glu Glu Arg His Leu Lys Arg Glu Ala Glu
```

```
                    85                  90                  95
Leu Ile Glu Gln Val Lys Met Leu Leu Asp Glu Glu Met Gly Ala Val
            100                 105                 110

Gln Lys Leu Asp Leu Val Asp Asp Leu Lys Asn Leu Gly Leu Ser Tyr
            115                 120                 125

Phe Phe Glu Asp Gln Ile Lys Gln Ile Leu Thr Phe Ile Tyr Asn Glu
            130                 135                 140

His Glu Cys Phe Arg Ser Asn Val Glu Ala Lys Glu Arg Asp Leu Tyr
145                 150                 155                 160

Phe Thr Ala Leu Gly Phe Arg Leu Leu Arg Gln His Gly Phe Gln Val
                165                 170                 175

Ser Gln Glu Val Phe Asp Cys Phe Lys Asn Glu Glu Gly Ser Asp Phe
            180                 185                 190

Lys Ala Ser Leu Gly Asp Asp Thr Lys Gly Leu Val Gln Leu Tyr Glu
            195                 200                 205

Ala Ser Phe Leu Leu Arg Glu Gly Glu Asp Thr Leu Glu Leu Ala Arg
210                 215                 220

Gln Tyr Ala Thr Lys Phe Leu Gln Lys Lys Val Asp His Glu Leu Ile
225                 230                 235                 240

Asp Asp Asp Ser Asn Leu Leu Ser Trp Ile Arg His Ser Leu Glu Ile
                245                 250                 255

Pro Leu His Trp Arg Ile Gln Arg Leu Glu Ala Arg Trp Phe Leu Asp
            260                 265                 270

Ala Tyr Ala Thr Arg His Asp Val Asn Pro Ile Ile Leu Glu Leu Ala
            275                 280                 285

Lys Leu Asp Phe Asn Ile Ile Gln Ala Thr Gln Gln Glu Glu Leu Lys
290                 295                 300

Asp Leu Ser Arg Trp Trp Asn Ser Thr Cys Leu Val Glu Lys Leu Pro
305                 310                 315                 320

Phe Val Arg Asp Arg Leu Val Glu Ser Tyr Phe Trp Ala Ile Ala Leu
                325                 330                 335

Phe Glu Pro His Gln Tyr Gly Tyr His Arg Lys Ile Ala Ala Lys Ile
            340                 345                 350

Ile Thr Leu Ile Thr Ser Leu Asp Asp Val Tyr Asp Ile Tyr Gly Thr
            355                 360                 365

Leu Asp Glu Leu Gln Leu Phe Thr Asp Ala Ile Gln Arg Trp Asp Thr
370                 375                 380

Glu Ser Ile Ser Arg Leu Ala Tyr Tyr Met Gln Leu Phe Tyr Met Val
385                 390                 395                 400

Leu Tyr Asn Phe Val Ser Glu Leu Ala Tyr Asp Gly Leu Lys Glu Lys
                405                 410                 415

Gly Phe Ile Thr Ile Pro Tyr Leu Gln Arg Ser Trp Ala Asp Leu Val
            420                 425                 430

Glu Ala Tyr Leu Lys Glu Ala Lys Trp Phe Tyr Asn Gly Tyr Thr Pro
            435                 440                 445

Ser Met Glu Glu Tyr Leu Asn Asn Ala Tyr Ile Ser Ile Gly Ala Thr
            450                 455                 460

Pro Val Ile Ser Gln Val Phe Phe Thr Leu Ala Thr Ser Ile Asp Lys
465                 470                 475                 480

Pro Val Ile Glu Ser Leu Tyr Glu Tyr His Arg Ile Leu Arg Leu Ser
                485                 490                 495

Gly Met Leu Val Arg Leu Pro Asp Asp Leu Gly Thr Ser Pro Phe Glu
            500                 505                 510
```

```
Met Lys Arg Gly Asp Val Pro Lys Thr Ile Glu Leu Tyr Met Lys Glu
            515                 520                 525

Arg Asn Ala Thr Glu Ile Glu Ala Gln Glu His Val Arg Phe Leu Ile
            530                 535                 540

Arg Glu Ala Trp Arg Glu Met Asn Thr Ala Thr Ala Ala Ala Asp Cys
545                 550                 555                 560

Pro Phe Thr Asp Asp Leu Val Ala Ala Ala Asn Leu Gly Arg Ala
                565                 570                 575

Ala Gln Phe Met Tyr Leu Asp Gly Asp Gly Asn His Ser Gln Leu His
                580                 585                 590

Gln Arg Ile Ala Ser Leu Leu Phe Glu Pro Tyr Ala
            595                 600

<210> SEQ ID NO 164
<211> LENGTH: 603
<212> TYPE: PRT
<213> ORGANISM: Perilla setoensis

<400> SEQUENCE: 164

Met Ser Ser Met Arg Thr Tyr Val Ala Ile Met Lys Lys Pro Ser Val
1               5                   10                  15

Glu His Val Asp Asn Val Asp Lys Lys Ala Ser Lys Pro Ser Trp Arg
                20                  25                  30

Val Ser Leu Ser Ala Gly Leu Arg Ser Ser Cys Ser Leu Gln Leu Glu
            35                  40                  45

Val Lys Pro Ala Asp Gln Ile Leu Thr Ala Arg Arg Ser Gly Asn Tyr
50                  55                  60

Gln Pro Ser Leu Trp Asp Phe Asn Tyr Leu Gln Ser Leu Asn Thr Thr
65                  70                  75                  80

His Tyr Lys Glu Val Arg His Leu Lys Arg Glu Ala Glu Leu Ile Glu
                85                  90                  95

Gln Val Lys Met Leu Leu Glu Glu Met Glu Ala Val Gln Gln Leu
                100                 105                 110

Glu Leu Val Asp Asp Leu Lys Asn Leu Gly Leu Ser Tyr Phe Phe Glu
            115                 120                 125

Asp Gln Ile Lys Gln Ile Leu Thr Phe Ile Tyr Asn Glu His Lys Cys
        130                 135                 140

Phe His Ser Asn Ser Ile Ile Glu Ala Glu Ile Arg Asp Leu Tyr
145                 150                 155                 160

Phe Thr Ala Leu Gly Phe Arg Leu Leu Arg Gln His Gly Phe Gln Ile
                165                 170                 175

Ser Gln Glu Val Phe Asp Cys Phe Lys Asn Glu Glu Gly Ser Asp Phe
            180                 185                 190

Lys Ala Arg Leu Gly Asp Asp Thr Lys Gly Leu Leu Gln Leu Tyr Glu
        195                 200                 205

Ala Ser Phe Leu Leu Arg Glu Gly Glu Asp Thr Leu Glu Leu Ala Arg
    210                 215                 220

Gln Tyr Ala Thr Lys Phe Leu Gln Lys Val Asp His Glu Leu Ile
225                 230                 235                 240

Asp Asp Asn Asn Leu Leu Ser Trp Ile Leu His Ser Leu Glu Ile Pro
                245                 250                 255

Leu His Trp Arg Ile Gln Arg Leu Glu Ala Arg Trp Phe Leu Asp Ala
            260                 265                 270

Tyr Ala Ser Arg Arg Asp Met Asn Gln Ile Ile Leu Glu Leu Ala Lys
```

```
              275                 280                 285
Leu Asp Phe Asn Ile Ile Gln Ala Thr Gln Gln Glu Leu Lys Asp
    290                 295                 300
Leu Ser Arg Trp Trp Lys Ser Ser Cys Leu Ala Glu Lys Leu Pro Phe
305                 310                 315                 320
Val Arg Asp Arg Leu Val Glu Ser Tyr Phe Trp Ala Ile Ala Leu Phe
                325                 330                 335
Glu Pro His Gln Tyr Gly Tyr His Arg Lys Ile Ala Ala Lys Ile Ile
                340                 345                 350
Thr Leu Ile Thr Ser Leu Asp Asp Val Tyr Asp Ile Tyr Gly Thr Leu
                355                 360                 365
Asp Glu Leu Gln Leu Phe Thr Asp Ala Ile Gln Arg Trp Asp Thr Glu
    370                 375                 380
Ser Ile Ser Arg Leu Pro Tyr Tyr Met Gln Leu Phe Tyr Met Val Leu
385                 390                 395                 400
Tyr Asn Phe Val Pro Arg Leu Ala Tyr Asp Gly Leu Lys Glu Lys Gly
                405                 410                 415
Phe Ile Thr Ile Pro Tyr Leu Gln Arg Ser Trp Ala Asp Leu Val Glu
                420                 425                 430
Ala Tyr Leu Lys Glu Ala Lys Trp Tyr Tyr Asn Gly Tyr Thr Pro Ser
                435                 440                 445
Met Glu Glu Tyr Leu Asn Asn Ala Tyr Ile Ser Ile Gly Ala Thr Pro
    450                 455                 460
Val Ile Ser Gln Val Phe Phe Thr Leu Ala Thr Ser Ile Asp Lys Pro
465                 470                 475                 480
Val Ile Asp Ser Leu Tyr Glu Tyr His Arg Ile Leu Arg Leu Ser Gly
                485                 490                 495
Ile Leu Val Arg Leu Pro Asp Asp Leu Gly Thr Ser Pro Phe Glu Met
                500                 505                 510
Lys Arg Gly Asp Val Pro Lys Ala Ile Gln Leu Tyr Met Lys Glu Arg
                515                 520                 525
Asn Ala Thr Glu Ile Glu Ala Gln Glu His Val Arg Phe Leu Ile Arg
    530                 535                 540
Glu Ala Trp Lys Glu Met Asn Thr Ala Thr Ala Ala Val Asp Cys Pro
545                 550                 555                 560
Phe Thr Asp Asp Leu Val Thr Ala Ala Asn Leu Gly Arg Ala Ala
                565                 570                 575
Gln Phe Met Tyr Leu Asp Gly Asp Gly Asn His Ser Gln Leu His Gln
                580                 585                 590
Arg Ile Ala Cys Leu Leu Phe Glu Pro Tyr Ala
        595                 600

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Phe or Tyr
<220> FEATURE:
```

```
<221> NAME/KEY: MOD_RES
<222> LOCATION: (5)..(5)
<223> OTHER INFORMATION: Asp or Tyr
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 165

Asp Asp Xaa Xaa Xaa Xaa Xaa Gly
1               5

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Arg or Trp
<220> FEATURE:
<221> NAME/KEY: MOD_RES
<222> LOCATION: (12)..(12)
<223> OTHER INFORMATION: Leu or Phe

<400> SEQUENCE: 166

Xaa Leu Xaa Xaa Xaa Xaa Leu Xaa Phe Xaa Leu Xaa Arg
1               5                   10

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Asp or Asn
<220> FEATURE:
<221> NAME/KEY: MOD_RES
<222> LOCATION: (6)..(6)
<223> OTHER INFORMATION: Leu or Ile
<220> FEATURE:
<221> NAME/KEY: MOD_RES
<222> LOCATION: (7)..(7)
<223> OTHER INFORMATION: Any amino acid
```

-continued

```
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 167

Arg Xaa Xaa Xaa Asp Xaa Xaa Xaa Xaa Xaa Glu Xaa Xaa Xaa Gly
1               5                   10                  15

<210> SEQ ID NO 168
<211> LENGTH: 41
<212> TYPE: PRT
<213> ORGANISM: Citrus unshiu

<400> SEQUENCE: 168

Tyr Ile Ile Asp Asp Ile Phe Asp Val Tyr Gly Thr Leu Asp Glu Leu
1               5                   10                  15

Ile Leu Phe Thr Glu Thr Ile Thr Arg Trp Asp Leu Ala Ala Met Gly
            20                  25                  30

Gln Leu Pro Glu Tyr Met Lys Ile Cys
        35                  40

<210> SEQ ID NO 169
<211> LENGTH: 41
<212> TYPE: PRT
<213> ORGANISM: Vitis vinifera

<400> SEQUENCE: 169

Tyr Ile Ile Asp Asp Ile Phe Asp Val His Gly Thr Leu Asp Glu Leu
1               5                   10                  15

Thr Leu Phe Thr Glu Ala Val Asn Arg Trp Asp Ile Ala Ala Phe Glu
            20                  25                  30

Thr Leu Pro Asn Tyr Met Lys Ile Cys
        35                  40

<210> SEQ ID NO 170
<211> LENGTH: 41
<212> TYPE: PRT
<213> ORGANISM: Ocimum basilicum

<400> SEQUENCE: 170

Tyr Val Ile Asp Asp Ile Phe Asp Thr Tyr Gly Lys Met Asp Glu Leu
1               5                   10                  15

Ile Leu Phe Thr Asp Ala Ile Arg Arg Trp Asp Leu Glu Ala Met Glu
            20                  25                  30

Gly Leu Pro Glu Tyr Met Lys Ile Cys
        35                  40

<210> SEQ ID NO 171
<211> LENGTH: 41
<212> TYPE: PRT
<213> ORGANISM: Malus domestica

<400> SEQUENCE: 171

Tyr Leu Ile Asp Asp Ile Phe Asp Val Tyr Gly Thr Leu Asp Glu Leu
1               5                   10                  15
```

<210> SEQ ID NO 172
<211> LENGTH: 41
<212> TYPE: PRT
<213> ORGANISM: Perilla frutescens

<400> SEQUENCE: 172

Thr Ser Leu Asp Asp Val Tyr Asp Ile Tyr Gly Thr Leu Asp Glu Leu
1               5                   10                  15

Gln Leu Phe Thr Asp Ala Ile Gln Arg Trp Asp Thr Glu Ser Ile Ser
            20                  25                  30

Arg Leu Pro Tyr Tyr Met Gln Leu Phe
        35                  40

<210> SEQ ID NO 173
<211> LENGTH: 41
<212> TYPE: PRT
<213> ORGANISM: Vitis vinifera

<400> SEQUENCE: 173

Thr Ala Ile Asp Asp Met Tyr Asp Ile Tyr Gly Ser Pro Asp Glu Leu
1               5                   10                  15

Arg Arg Phe Thr Asp Ala Val Asn Arg Trp Asp Thr Glu Ala Leu Val
            20                  25                  30

Asp Leu Pro Asp Tyr Met Lys Ile Cys
        35                  40

<210> SEQ ID NO 174
<211> LENGTH: 41
<212> TYPE: PRT
<213> ORGANISM: Citrus unshiu

<400> SEQUENCE: 174

Tyr Ile Ile Asp Asp Ile Phe Tyr Val Cys Gly Ala Leu Asp Ala Leu
1               5                   10                  15

Thr Leu Phe Thr Glu Pro Ile Asn Arg Trp Asp Leu Gly Asp Ile Asp
            20                  25                  30

Gln Leu Pro Glu Tyr Met Lys Ile Cys
        35                  40

<210> SEQ ID NO 175
<211> LENGTH: 41
<212> TYPE: PRT
<213> ORGANISM: Arabidopsis thaliana

<400> SEQUENCE: 175

Thr Thr Ile Asp Asp Ile Tyr Asp Ile Tyr Gly Thr Leu Glu Glu Leu
1               5                   10                  15

Gln Leu Phe Thr Val Ala Phe Glu Asn Trp Asp Ile Asn Arg Leu Asp
            20                  25                  30

Glu Leu Pro Glu Tyr Met Arg Leu Cys
        35                  40

<210> SEQ ID NO 176
<211> LENGTH: 41
<212> TYPE: PRT

<213> ORGANISM: Arabidopsis thaliana

<400> SEQUENCE: 176

Tyr Val Ile Asp Asp Ile Phe Asp Val Tyr Gly Glu Leu Glu Leu
1               5                   10                  15

Thr Ile Phe Thr Arg Val Val Glu Arg Trp Asp His Lys Gly Leu Lys
            20                  25                  30

Thr Leu Pro Lys Tyr Met Arg Val Cys
        35                  40

<210> SEQ ID NO 177
<211> LENGTH: 41
<212> TYPE: PRT
<213> ORGANISM: Mentha citrata

<400> SEQUENCE: 177

Thr Ala Leu Asp Asp Val Tyr Asp Ile Tyr Gly Thr Leu Asp Glu Leu
1               5                   10                  15

Gln Leu Phe Thr His Val Ile Arg Arg Trp Asp Thr Glu Ser Ala Thr
            20                  25                  30

Gln Leu Pro Tyr Tyr Leu Gln Leu Phe
        35                  40

<210> SEQ ID NO 178
<211> LENGTH: 41
<212> TYPE: PRT
<213> ORGANISM: Citrus unshiu

<400> SEQUENCE: 178

Ser Ile Ile Asp Asp Ile Tyr Asp Ala Tyr Gly Thr Ile Glu Glu Leu
1               5                   10                  15

Glu Leu Phe Ala Thr Ala Ile Glu Arg Trp Asp Leu Ser Ala Ile Asp
            20                  25                  30

Leu Leu Pro Glu Tyr Met Lys Leu Cys
        35                  40

<210> SEQ ID NO 179
<211> LENGTH: 41
<212> TYPE: PRT
<213> ORGANISM: Lavandula angustifolia

<400> SEQUENCE: 179

Thr Ser Leu Asp Asp Val Tyr Asp Ile Tyr Gly Thr Leu Asp Glu Leu
1               5                   10                  15

Gln Leu Phe Thr Asn Leu Phe Glu Arg Trp Asp Asn Ala Ser Ile Gly
            20                  25                  30

Arg Leu Pro Glu Tyr Leu Gln Leu Phe
        35                  40

<210> SEQ ID NO 180
<211> LENGTH: 41
<212> TYPE: PRT
<213> ORGANISM: Clarkia breweri

<400> SEQUENCE: 180

Thr Val Ala Asp Asp Phe Phe Asp Val Glu Gly Ser Met Val Asp Leu
1               5                   10                  15

Glu Lys Leu Thr Asp Ala Val Arg Arg Trp Asp Ala Glu Gly Leu Gly
            20                  25                  30

Ser His Ser Lys Thr Ile Phe Glu Ala

<210> SEQ ID NO 181
<211> LENGTH: 29
<212> TYPE: PRT
<213> ORGANISM: Malus domestica

<400> SEQUENCE: 181

Asp Leu His Glu Val Ala Leu Arg Phe Arg Leu Leu Arg Gln His Gly
1               5                   10                  15

Tyr Phe Val Ser Asp Asp Val Phe Asn Asn Phe Lys Asn
            20                  25

<210> SEQ ID NO 182
<211> LENGTH: 29
<212> TYPE: PRT
<213> ORGANISM: Perilla frutescens

<400> SEQUENCE: 182

Asp Leu Tyr Phe Thr Ala Leu Gly Phe Arg Leu Leu Arg Gln His Gly
1               5                   10                  15

Phe Gln Val Ser Gln Glu Val Phe Asp Cys Phe Lys Asn
            20                  25

<210> SEQ ID NO 183
<211> LENGTH: 29
<212> TYPE: PRT
<213> ORGANISM: Vitis vinifera

<400> SEQUENCE: 183

Asp Leu Tyr Glu Val Ala Leu Arg Phe Arg Leu Leu Arg Gln Glu Gly
1               5                   10                  15

Tyr His Val Pro Ala Asp Val Phe Asn Asn Phe Lys Asn
            20                  25

<210> SEQ ID NO 184
<211> LENGTH: 29
<212> TYPE: PRT
<213> ORGANISM: Citrus unshiu

<400> SEQUENCE: 184

Asp Leu Gln Glu Val Ala Leu Arg Phe Arg Leu Leu Arg Gln Gln Gly
1               5                   10                  15

Tyr Tyr Val Ser Ala Asp Val Phe Asn Arg Phe Arg Asn
            20                  25

<210> SEQ ID NO 185
<211> LENGTH: 29
<212> TYPE: PRT
<213> ORGANISM: Lavandula angustifolia

<400> SEQUENCE: 185

Asp Leu Tyr Phe Thr Ala Leu Gly Phe Arg Leu Phe Arg Gln His Gly
1               5                   10                  15

Phe Lys Val Ser Gln Glu Val Phe Asp Arg Phe Lys Asn
            20                  25

<210> SEQ ID NO 186
<211> LENGTH: 29
<212> TYPE: PRT
<213> ORGANISM: Mentha citrata

<400> SEQUENCE: 186

```
Asp Leu His Phe Thr Ser Leu Gly Phe Arg Leu Leu Arg Gln His Gly
1               5                   10                  15

Phe Asn Val Ser Gln Gly Val Phe Asp Cys Phe Lys Asn
            20                  25
```

<210> SEQ ID NO 187
<211> LENGTH: 29
<212> TYPE: PRT
<213> ORGANISM: Citrus unshiu

<400> SEQUENCE: 187

```
Asp Leu Gln Glu Val Ala Leu Arg Phe Arg Leu Leu Arg Gln Glu Gly
1               5                   10                  15

Tyr Tyr Val Pro Ala Asp Met Phe Asn Asn Phe Arg Ile
            20                  25
```

<210> SEQ ID NO 188
<211> LENGTH: 29
<212> TYPE: PRT
<213> ORGANISM: Vitis vinifera

<400> SEQUENCE: 188

```
Asp Leu Ser Thr Thr Ala Leu Arg Phe Arg Leu Leu Arg Gln His Gly
1               5                   10                  15

Tyr Pro Val Ser Ser Glu Val Phe Asp Gln Phe Arg Ser
            20                  25
```

<210> SEQ ID NO 189
<211> LENGTH: 29
<212> TYPE: PRT
<213> ORGANISM: Arabidopsis thaliana

<400> SEQUENCE: 189

```
Asp Leu His Ala Thr Ala Leu Glu Phe Arg Leu Phe Arg Gln His Gly
1               5                   10                  15

Phe Asn Val Ser Glu Asp Val Phe Asp Val Phe Met Glu
            20                  25
```

<210> SEQ ID NO 190
<211> LENGTH: 29
<212> TYPE: PRT
<213> ORGANISM: Citrus unshiu

<400> SEQUENCE: 190

```
Glu Leu Tyr Tyr Ile Ser Leu His Phe Arg Leu Leu Arg Gln Asn Gly
1               5                   10                  15

Tyr Lys Ile Ser Ala Asp Val Phe Asn Ser Phe Lys Asp
            20                  25
```

<210> SEQ ID NO 191
<211> LENGTH: 29
<212> TYPE: PRT
<213> ORGANISM: Arabidopsis thaliana

<400> SEQUENCE: 191

```
Asp Leu His Glu Ile Ala Leu Arg Phe Arg Leu Leu Arg Gln Glu Gly
1               5                   10                  15

His Tyr Val Gln Glu Asn Lys Lys Gly Gly Phe Lys Asp
            20                  25
```

<210> SEQ ID NO 192

-continued

```
<211> LENGTH: 29
<212> TYPE: PRT
<213> ORGANISM: Ocimum basilicum

<400> SEQUENCE: 192

Asp Leu Phe Thr Ala Ala Leu Arg Phe Arg Leu Leu Arg His Asn Gly
1               5                   10                  15

Ile Gln Val Thr Pro Glu Ile Phe Leu Lys Phe Lys Asp
            20                  25

<210> SEQ ID NO 193
<211> LENGTH: 29
<212> TYPE: PRT
<213> ORGANISM: Clarkia breweri

<400> SEQUENCE: 193

Glu Leu Tyr Arg Asp Ser Leu Ala Phe Trp Leu Leu Arg Val Asn Asn
1               5                   10                  15

His Trp Val Ser Pro Ser Ile Phe Cys Trp Phe Leu Asp
            20                  25

<210> SEQ ID NO 194
<211> LENGTH: 32
<212> TYPE: PRT
<213> ORGANISM: Citrus unshiu

<400> SEQUENCE: 194

Glu Ile Ala Lys Lys Asp Phe Asn Met Val Gln Ala Leu His Gln Lys
1               5                   10                  15

Glu Ile Val Gln Val Thr Lys Trp Trp Lys Asp Leu Gly Leu Thr Lys
            20                  25                  30

<210> SEQ ID NO 195
<211> LENGTH: 32
<212> TYPE: PRT
<213> ORGANISM: Vitis vinifera

<400> SEQUENCE: 195

Glu Leu Ala Lys Ala Asp Phe Asn Met Val Gln Ser Ile His Gln Gln
1               5                   10                  15

Glu Leu Leu Gln Ile Ser Lys Trp Trp Gln Asp Arg Gly Leu Ala Glu
            20                  25                  30

<210> SEQ ID NO 196
<211> LENGTH: 32
<212> TYPE: PRT
<213> ORGANISM: Arabidopsis thaliana

<400> SEQUENCE: 196

Glu Phe Ala Lys Ile Asp Phe Asn Ile Val Gln Ala Ile His Gln Glu
1               5                   10                  15

Glu Leu Lys Asn Val Ser Ser Trp Trp Met Glu Thr Gly Leu Gly Lys
            20                  25                  30

<210> SEQ ID NO 197
<211> LENGTH: 32
<212> TYPE: PRT
<213> ORGANISM: Perilla frutescens

<400> SEQUENCE: 197

Glu Leu Ala Lys Leu Asp Phe Asn Ile Ile Gln Ala Thr Gln Gln Glu
1               5                   10                  15
```

Glu Leu Lys Asp Leu Ser Arg Trp Trp Lys Ser Thr Cys Leu Ala Glu
            20                  25                  30

<210> SEQ ID NO 198
<211> LENGTH: 32
<212> TYPE: PRT
<213> ORGANISM: Lavandula angustifolia

<400> SEQUENCE: 198

Glu Leu Ala Lys Leu Asn Phe Asn Ile Val Gln Ala Thr Gln Gln Glu
1               5                   10                  15

Glu Leu Lys Ala Leu Ser Arg Trp Trp Ser Ser Leu Gly Leu Ala Glu
            20                  25                  30

<210> SEQ ID NO 199
<211> LENGTH: 32
<212> TYPE: PRT
<213> ORGANISM: Malus domestica

<400> SEQUENCE: 199

Thr Val Ala Lys Thr Asp Leu Asn Met Val Gln Ser Leu His Gln Lys
1               5                   10                  15

Glu Val Ala Gln Val Ser Lys Trp Lys Glu Leu Gly Leu Cys Lys
            20                  25                  30

<210> SEQ ID NO 200
<211> LENGTH: 32
<212> TYPE: PRT
<213> ORGANISM: Ocimum basilicum

<400> SEQUENCE: 200

Glu Leu Ala Ile Leu Asp Tyr Asn Gln Val Gln Ala Gln His Gln Ser
1               5                   10                  15

Glu Leu Thr Glu Ile Thr Arg Trp Trp Lys Gln Leu Gly Leu Val Glu
            20                  25                  30

<210> SEQ ID NO 201
<211> LENGTH: 32
<212> TYPE: PRT
<213> ORGANISM: Mentha citrata

<400> SEQUENCE: 201

Glu Leu Ala Lys Leu Asp Phe Asn Ile Ile Gln Ala Thr Gln Gln Glu
1               5                   10                  15

Glu Leu Lys Asp Leu Ser Arg Trp Trp Asn Asp Ser Ser Leu Pro Gln
            20                  25                  30

<210> SEQ ID NO 202
<211> LENGTH: 32
<212> TYPE: PRT
<213> ORGANISM: Citrus unshiu

<400> SEQUENCE: 202

Glu Leu Ala Asn Met Asp Phe Lys Leu Val Gln Ser Leu His Gln Lys
1               5                   10                  15

Glu Ile Val Gln Ile Ser Ser Trp Trp Arg Glu Leu Gly Leu Ala Lys
            20                  25                  30

<210> SEQ ID NO 203
<211> LENGTH: 32
<212> TYPE: PRT
<213> ORGANISM: Vitis vinifera -continued

<400> SEQUENCE: 203

Glu Leu Ala Lys Leu Asp Tyr Asn Leu Val Gln Ser Ser Tyr Gln Thr
1               5                   10                  15

Glu Leu Lys Glu Leu Thr Arg Trp Trp Thr Asp Leu Gly Phe Lys Glu
            20                  25                  30

<210> SEQ ID NO 204
<211> LENGTH: 32
<212> TYPE: PRT
<213> ORGANISM: Citrus unshiu

<400> SEQUENCE: 204

Thr Phe Ala Met Leu Asp Phe Asn Ile Leu Gln Lys Gln His Gln Glu
1               5                   10                  15

Glu Leu Arg Asp Ile Val Arg Trp Trp Lys Asn Phe Asp Val Pro Asn
            20                  25                  30

<210> SEQ ID NO 205
<211> LENGTH: 32
<212> TYPE: PRT
<213> ORGANISM: Arabidopsis thaliana

<400> SEQUENCE: 205

Arg Val Ala Glu Ile Asp Ser Ile Arg Leu Lys Ser Leu Thr Gln Gly
1               5                   10                  15

Glu Met Ser Gln Thr Phe Lys Trp Trp Thr Glu Leu Gly Leu Glu Lys
            20                  25                  30

<210> SEQ ID NO 206
<211> LENGTH: 32
<212> TYPE: PRT
<213> ORGANISM: Clarkia breweri

<400> SEQUENCE: 206

Gln Leu Ala Val Lys Asn Tyr Thr Leu Arg Gln Leu Val Tyr Arg Asp
1               5                   10                  15

Glu Leu Ala Glu Val Glu Arg Trp Ser Lys Glu Arg Gly Leu Cys Asp
            20                  25                  30

<210> SEQ ID NO 207
<211> LENGTH: 27
<212> TYPE: PRT
<213> ORGANISM: Citrus unshiu

<400> SEQUENCE: 207

Glu Glu Tyr Leu Glu Asn Gly Ile Val Ser Ser Gly Val His Leu Val
1               5                   10                  15

Leu Val His Ile Phe Phe Leu Leu Gly His Gly
            20                  25

<210> SEQ ID NO 208
<211> LENGTH: 27
<212> TYPE: PRT
<213> ORGANISM: Malus domestica

<400> SEQUENCE: 208

Glu Glu Tyr Leu Lys Asn Gly Ile Ile Ser Ser Gly Val Asn Val Val
1               5                   10                  15

Met Val His Ile Phe Phe Leu Leu Gly Glu Gly
            20                  25

<210> SEQ ID NO 209
<211> LENGTH: 27
<212> TYPE: PRT
<213> ORGANISM: Vitis vinifera

<400> SEQUENCE: 209

His Glu Tyr Leu Lys Asn Gly Val Ile Ser Ser Gly Val His Val Val
1               5                   10                  15

Leu Val His Leu Phe Phe Leu Leu Gly His Gly
            20                  25

<210> SEQ ID NO 210
<211> LENGTH: 27
<212> TYPE: PRT
<213> ORGANISM: Citrus unshiu

<400> SEQUENCE: 210

Glu Glu Tyr Leu Arg Asn Gly Ile Glu Ser Ser Gly Val His Val Ala
1               5                   10                  15

Leu Ala His Phe Phe Phe Leu Leu Gly His Gly
            20                  25

<210> SEQ ID NO 211
<211> LENGTH: 27
<212> TYPE: PRT
<213> ORGANISM: Arabidopsis thaliana

<400> SEQUENCE: 211

Glu Glu Tyr Met Lys Asn Gly Val Val Ser Ser Gly Val His Leu Val
1               5                   10                  15

Met Leu His Ala Tyr Ile Leu Leu Gly Glu Glu
            20                  25

<210> SEQ ID NO 212
<211> LENGTH: 27
<212> TYPE: PRT
<213> ORGANISM: Ocimum basilicum

<400> SEQUENCE: 212

Glu Glu Tyr Ile Glu Asn Gly Ala Ser Thr Val Gly Ala Tyr Met Val
1               5                   10                  15

Leu Val His Leu Phe Phe Leu Ile Gly Glu Gly
            20                  25

<210> SEQ ID NO 213
<211> LENGTH: 27
<212> TYPE: PRT
<213> ORGANISM: Vitis vinifera

<400> SEQUENCE: 213

Asp Glu Tyr Leu Ser Asn Ala Trp Thr Ser Val Gly Gly Pro Ala Ala
1               5                   10                  15

Met Val His Ala Tyr Phe Leu Met Gly Cys Ala
            20                  25

<210> SEQ ID NO 214
<211> LENGTH: 27
<212> TYPE: PRT
<213> ORGANISM: Lavandula angustifolia

<400> SEQUENCE: 214

Glu Glu Tyr Phe Asp Asn Ala Phe Met Thr Ile Gly Ala Pro Pro Val
1               5                   10                  15

Leu Ser Gln Ala Tyr Phe Thr Leu Gly Ser Ser
            20                  25

<210> SEQ ID NO 215
<211> LENGTH: 27
<212> TYPE: PRT
<213> ORGANISM: Perilla frutescens

<400> SEQUENCE: 215

Glu Glu Tyr Leu Asn Asn Ala Tyr Ile Ser Ile Gly Ala Thr Pro Val
1               5                   10                  15

Ile Ser Gln Val Phe Phe Thr Leu Ala Thr Ser
            20                  25

<210> SEQ ID NO 216
<211> LENGTH: 27
<212> TYPE: PRT
<213> ORGANISM: Mentha citrata

<400> SEQUENCE: 216

Glu Glu Tyr Leu Asn Tyr Ala Ser Ile Thr Ile Gly Ala Pro Ala Val
1               5                   10                  15

Ile Ser Gln Ile Tyr Phe Met Leu Ala Lys Ser
            20                  25

<210> SEQ ID NO 217
<211> LENGTH: 27
<212> TYPE: PRT
<213> ORGANISM: Arabidopsis thaliana

<400> SEQUENCE: 217

Glu Glu Tyr Met Gln Asn Ala Arg Ile Ser Ile Ser Ser Pro Thr Ile
1               5                   10                  15

Phe Val His Phe Tyr Cys Val Phe Ser Asp Gln
            20                  25

<210> SEQ ID NO 218
<211> LENGTH: 27
<212> TYPE: PRT
<213> ORGANISM: Clarkia breweri

<400> SEQUENCE: 218

Asp Val Tyr Leu Gly Asn Ala Met Thr Ser Ile Ala Ala His Thr Met
1               5                   10                  15

Val Leu Thr Ala Ser Cys Leu Leu Gly Pro Gly
            20                  25

<210> SEQ ID NO 219
<211> LENGTH: 27
<212> TYPE: PRT
<213> ORGANISM: Citrus unshiu

<400> SEQUENCE: 219

Glu Glu Tyr Met Arg Val Ala Leu Leu Ser Cys Gly Tyr Leu Leu Leu
1               5                   10                  15

Ser Thr Ser Ser Phe Leu Gly Met Glu Asp Ile
            20                  25

<210> SEQ ID NO 220
<211> LENGTH: 27
<212> TYPE: PRT
<213> ORGANISM: Malus domestica

```
<400> SEQUENCE: 220

Ile Ile Ser Ser Thr Ala Ala Ile Leu Arg Leu Trp Asp Asp Leu Gly
1               5                   10                  15

Ser Ala Lys Asp Glu Asn Gln Asp Gly Asp
            20                  25

<210> SEQ ID NO 221
<211> LENGTH: 27
<212> TYPE: PRT
<213> ORGANISM: Vitis vinifera

<400> SEQUENCE: 221

Ile Ile Ser Ser Thr Ala Ala Ile Leu Arg Leu Trp Asp Asp Leu Gly
1               5                   10                  15

Ser Ala Lys Asp Glu Asn Gln Asp Gly His Asp
            20                  25

<210> SEQ ID NO 222
<211> LENGTH: 27
<212> TYPE: PRT
<213> ORGANISM: Citrus unshiu

<400> SEQUENCE: 222

Ile Ile Ser Ser Thr Ala Thr Ile Leu Arg Leu Trp Asp Asp Leu Gly
1               5                   10                  15

Ser Ala Lys Asp Glu Asn Gln Glu Gly Lys Asp
            20                  25

<210> SEQ ID NO 223
<211> LENGTH: 27
<212> TYPE: PRT
<213> ORGANISM: Arabidopsis thaliana

<400> SEQUENCE: 223

Ile Val Ser Ser Ala Ala Thr Ile Leu Arg Leu Trp Asp Asp Leu Gly
1               5                   10                  15

Ser Ala Lys Asp Glu Asn Gln Asp Gly Thr Asp
            20                  25

<210> SEQ ID NO 224
<211> LENGTH: 27
<212> TYPE: PRT
<213> ORGANISM: Perilla frutescens

<400> SEQUENCE: 224

Ile Leu Arg Leu Ser Gly Met Leu Val Arg Leu Pro Asp Asp Leu Gly
1               5                   10                  15

Thr Ser Pro Phe Glu Met Lys Arg Gly Asp Val
            20                  25

<210> SEQ ID NO 225
<211> LENGTH: 27
<212> TYPE: PRT
<213> ORGANISM: Mentha citrata

<400> SEQUENCE: 225

Ile Ile Arg Leu Ser Gly Met Leu Val Arg Leu Pro Asp Asp Leu Gly
1               5                   10                  15

Thr Leu Pro Phe Glu Met Lys Arg Gly Asp Val
            20                  25
```

<210> SEQ ID NO 226
<211> LENGTH: 27
<212> TYPE: PRT
<213> ORGANISM: Citrus unshiu

<400> SEQUENCE: 226

Ile Val Ser Ser Val Ala Thr Ile Leu Arg Ile Trp Asp Asp Leu Gly
1               5                   10                  15

Ser Ala Lys Asp Glu Asn Gln Gly Gly Lys Asp
            20                  25

<210> SEQ ID NO 227
<211> LENGTH: 27
<212> TYPE: PRT
<213> ORGANISM: Lavandula angustifolia

<400> SEQUENCE: 227

Ile Leu Arg Val Ser Gly Met Leu Val Arg Leu Pro Asp Asp Leu Gly
1               5                   10                  15

Thr Ser Ser Phe Glu Met Glu Arg Gly Asp Val
            20                  25

<210> SEQ ID NO 228
<211> LENGTH: 27
<212> TYPE: PRT
<213> ORGANISM: Citrus unshiu

<400> SEQUENCE: 228

Ile Val Gln Ala Ser Ser Ile Ile Cys Arg Leu Met Asp Asp Ile Val
1               5                   10                  15

Ser His Lys Phe Glu Gln Gln Arg Gly His Val
            20                  25

<210> SEQ ID NO 229
<211> LENGTH: 27
<212> TYPE: PRT
<213> ORGANISM: Ocimum basilicum

<400> SEQUENCE: 229

Pro Phe Ser Ala Ala Gly Arg Ile Phe Arg Leu Trp Asp Asp Leu Gly
1               5                   10                  15

Thr Ser Gln Glu Glu Glu Arg Gly Asp Met
            20                  25

<210> SEQ ID NO 230
<211> LENGTH: 27
<212> TYPE: PRT
<213> ORGANISM: Arabidopsis thaliana

<400> SEQUENCE: 230

Val Val Arg Cys Ser Ser Ser Val Phe Arg Leu Ala Asn Asp Leu Val
1               5                   10                  15

Thr Ser Pro Asp Glu Leu Ala Arg Gly Asp Val
            20                  25

<210> SEQ ID NO 231
<211> LENGTH: 27
<212> TYPE: PRT
<213> ORGANISM: Vitis vinifera

<400> SEQUENCE: 231

Leu Leu Tyr Trp Ser Ser Leu Ile Thr Arg Leu Ser Asp Asp Leu Gly

```
1               5                  10                 15
Thr Ser Leu Ala Glu Ile Ala Arg Gly Asp Val
              20                  25

<210> SEQ ID NO 232
<211> LENGTH: 27
<212> TYPE: PRT
<213> ORGANISM: Clarkia breweri

<400> SEQUENCE: 232

Ile Thr Ser Leu Leu Met Val Leu Thr Arg Leu Leu Asn Asp Ile Gln
1               5                  10                 15

Ser Tyr Leu Lys Glu Glu Asp Glu Gly Lys Ile
              20                  25
```